US010301390B2

(12) United States Patent
Coyle et al.

(10) Patent No.: US 10,301,390 B2
(45) Date of Patent: *May 28, 2019

(54) ANTI-IFNAR1 ANTIBODIES WITH REDUCED FC LIGAND AFFINITY

(71) Applicant: ASTRAZENECA AB, Sodertalje (SE)

(72) Inventors: Anthony Coyle, Boston, MA (US); Peter Kiener, Potomac, MD (US); Herren Wu, Boyds, MD (US); Ricardo Cibotti, Bethesda, MD (US)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 15/971,127

(22) Filed: May 4, 2018

(65) Prior Publication Data
US 2018/0244791 A1     Aug. 30, 2018

Related U.S. Application Data

(63) Continuation of application No. 15/711,197, filed on Sep. 21, 2017, now Pat. No. 9,988,459, which is a continuation of application No. 12/866,579, filed as application No. PCT/US2009/033358 on Feb. 6, 2009, now abandoned.

(60) Provisional application No. 61/049,970, filed on May 2, 2008, provisional application No. 61/034,618, filed on Mar. 7, 2008, provisional application No. 61/006,962, filed on Feb. 8, 2008.

(51) Int. Cl.
*C07H 21/00* (2006.01)
*C07K 16/28* (2006.01)
*A61K 39/00* (2006.01)

(52) U.S. Cl.
CPC .... *C07K 16/2866* (2013.01); *A61K 2039/505* (2013.01); *C07K 2299/00* (2013.01); *C07K 2317/24* (2013.01); *C07K 2317/71* (2013.01); *C07K 2317/732* (2013.01); *C07K 2317/734* (2013.01); *C07K 2317/76* (2013.01)

(58) Field of Classification Search
None
See application file for complete search history.

(56) References Cited

U.S. PATENT DOCUMENTS

| 5,624,821 A | 4/1997 | Winter et al. |
| 5,648,260 A | 7/1997 | Winter et al. |
| 6,194,551 B1 | 2/2001 | Idusogie et al. |
| 9,988,459 B2 * | 6/2018 | Coyle ............... C07K 16/2866 |
| 2003/0219433 A1 | 11/2003 | Hansen et al. |
| 2004/0132101 A1 | 7/2004 | Lazar et al. |
| 2005/0226876 A1 | 10/2005 | Graus et al. |
| 2006/0029601 A1 | 2/2006 | Cardarelli et al. |

FOREIGN PATENT DOCUMENTS

| EP | 1707627 A1 | 4/2006 |
| WO | WO9429351 | 6/1994 |
| WO | WO2006002177 | 1/2006 |
| WO | WO2006036291 A2 | 4/2006 |

OTHER PUBLICATIONS

Armour, K. L., et al., 2003, "Differential Binding to Human FcgammaRIIa and FcgammaRIIb Receptors by Human IgG Wildtype and Mutant Antibodies," Molecular Immunology, vol. 40, pp. 585-593.
Radaev et al., 2001, "The Structure of a Human Type III Fcgamma Receptor in Complex with Fc," J. Biol. Chem., vol. 276, pp. 16469-16477.
Shields et al., 2001, "High Resolution Mapping of the Binding Site on Human IgG1 for FcgammaRI, FcgammaRII, and FcRn and Design of IgG1 Variants with Improved Binding to the FcgammaR," J. Biol. Chem., vol. 276, pp. 6591-6604.
Holm, et al. (Mol. Immunol. Feb. 2007; 44 (6): 1075-1084).
Medical Immunology (ed. Virella, Gabriel, pp. 131-132, 2005).
Mariuzza et al. (Annu. Rev. Biophys. Biophys. Chem. 1987; 16: 139-159).
Gussow et al. (Methods in Enzymology. 1991; 203: 99-121).
Rudikoff et al. (Proc. Natl. Acad. Sci. USA 1982 vol. 79: p. 1979-1983).
MacCallum et al. (J. Mol. Biol. Oct. 11, 1996; 262 (5): 732-745).
Armour, K.L., et al., "The contrasting IgG-binding interactions of human and herpes simplex virus Fc receptors," Biochemical Society Transactions, 30(4): 495-500 (2002).
Canfield, S.M., et al., "The Binding Affinity of Human IgG for its High Affinity FC Receptor Is Determined by Multiple Amino Acids in the CH2 Domain and Is Modulated by the Hinge Region," J. Exp. Med., 173:1483-1491 (1991).

* cited by examiner

*Primary Examiner* — Brad Duffy

(57) ABSTRACT

The invention provides anti-IFNAR1 antibodies with reduced affinity for Fc receptors and/or ligands and methods of making and using such antibodies.

3 Claims, 54 Drawing Sheets

Figure 7:
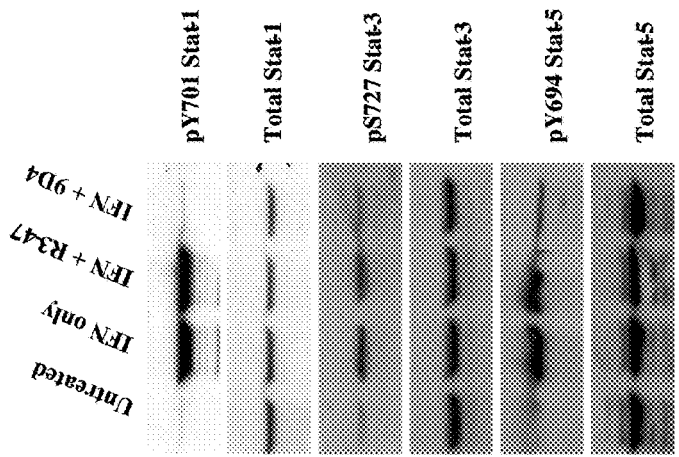

Specification includes a Sequence Listing.

Figure 1A

Anti-IFNAR 3F11 VH

```
1    Q   V   Q   L   Q   Q   W   G   A   G   L   L   K   P   S   E   T   L
     CAG GTG CAG CTA CAG CAG TGG GGC GCA GGA CTG TTG AAG CCT TCT GAG ACC CTG
                                                         ─────────────────────
                                                                CDR1
55   S   L   T   C   A   V   Y   G   G   S   F   S   G   Y   F   W   S   W
     TCC CTC ACC TGC GCT GTC TAT GGT GGG TCC TTC AGT GGT TAT TTC TGG AGC TGG
     ─────                                                    ─────────────────
                                                                    CDR2
109  I   R   Q   P   P   G   K   G   L   E   W   I   G   E   I   D   H   S
     ATC CGC CAG CCC CCA GGG AAG GGG CTG GAG TGG ATT GGG GAA ATC GAT CAC AGT
         ─────────────
          CDR2
163  G   K   T   N   Y   N   P   S   L   K   S   R   V   T   I   S   V   D
     GGA AAG ACC AAC TAC AAT CCG TCC CTC AAG AGT CGA GTT ACC ATA TCA GTA GAC
217  T   S   K   N   Q   V   S   L   K   L   S   S   V   T   A   A   D   T
     ACG TCC AAG AAC CAG GTC TCC CTG AAG CTG AGC TCT GTG ACC GCC GCG GAC ACG
271  A   V   Y   Y   C   A   R   E   S   K   Y   Y   F   G   L   D   V   W
     GCT GTG TAT TAC TGT GCG AGA GAA AGC AAG TAC TAC TTC GGT TTG GAC GTC TGG
                                     ───────────────────────────────────────
                                                      CDR3
325  G   Q   G   T   T   V   T   V   S
     GGC CAA GGG ACC ACG GTC ACC GTC TCA
```

Figure 1B

Anti-IFNAR 3F11 VK

```
     A   I   Q   L   T   Q   S   P   S   S   L   S   A   S   V   G   D   R
1    GCC ATC CAG TTG ACC CAG TCT CCA TCC TCC CTG TCT GCA TCT GTA GGA GAC AGA

V   T   I   T   C   R   A   S   Q   G   I   Y   S   V   L   A   W   Y
55   GTC ACC ATC ACT TGC CGG GCA AGT CAG GGC ATT TAC AGT GTT TTA GCC TGG TAT
                         ─────────────CDR1─────────────

Q   Q   K   P   G   K   A   P   K   L   L   I   Y   D   A   S   R   L
109  CAG CAG AAA CCA GGG AAA ACT CCT AAG CTC CTG ATC TAT GAT GCC TCC CGT TTG
                                          ────────CDR2────────

E   S   G   V   P   S   R   F   S   G   S   G   S   G   T   D   F   T
163  GAA AGT GGG GTC CCA TCA AGG TTC AGC GGC AGT GGA TCT GGG ACA GAT TTC ACT

L   T   I   S   S   L   Q   P   E   D   F   A   T   Y   Y   C   Q   Q
217  CTC ACC ATC AGC AGC CTG CAG CCT GAA GAT TTT GCA ACT TAT TAC TGT CAA CAG
                                                              ──────CDR3

F   N   S   Y   I   T   F   G   Q   G   T   R   L   E   I   K
271  TTT AAT AGT TAC ATC ACC TTC GGC CAA GGG ACA CGA CTG GAG ATT AAA
     ────CDR3────
```

Figure 2A

Anti-IFNAR 4G5 VH

```
  1  Q   V   L   Q   Q   W   G   A   G   L   L   K   P   S   E   T   L
     CAG GTG CTA CAG CAG TGG GGC GCA GGA CTG TTG AAG CCT TCG GAG ACC CTG

55  S   L   T   C   A   V   Y   G   G   S   F   S   N   Y   W   S   W
     TCC CTC ACC TGC GCT GTC TAT GGT GGG TCC TTC AGT AAT TAC TGG AGC TGG
                                              CDR1

109  I   R   Q   P   P   G   K   G   L   E   W   I   G   E   I   L   S
     ATC CGC CAG CCC CCA GGG AAG GGG CTG GAG TGG ATT GGG GAA ATC CTT AGT
                     CDR2

163  G   S   T   N   Y   N   P   S   L   K   S   R   V   T   I   S   V   D
     GGA AGC ACC AAC TAC AAC CCG TCC CTC AAG AGT CGA GTC ACC ATA TCA GTA GAC
                                                                  CDR2

217  T   S   K   N   Q   F   S   L   N   L   T   S   V   T   A   A   D   T
     ACG TCC AAG AAC CAG TTC TCC CTG AAC CTG ACC TCT GTG ACC GCC GCG GAC ACG

271  A   V   Y   Y   C   A   R   E   S   K   W   G   Y   Y   F   D   S   W
     GCT GTG TAT TAC TGT GCG AGA GAG TCT AAA TGG GGT TAC TAC TTT GAC TCC TGG
                                                CDR3

325  G   Q   G   T   L   V   T   V   S   S
     GGC CAG GGA ACC CTG GTC ACC GTC TCC TCA
```

Figure 2B

Anti-IFNAR 4G5 VK

```
  1  A   I   Q   L   T   Q   S   P   S   S   L   S   A   S   V   G   D   R
     GCC ATC CAG TTG ACC CAG TCT CCA TCC TCC TTG TCT GCA TCT GTA GGA GAC AGA
                                     ─────────────────────────────
                                              CDR1

55  V   T   I   T   C   R   A   T   Q   D   I   S   I   A   L   V   W   Y
     GTC ACC ATC ACT TGC CGG GCA ACT CAG GAC ATT AGC ATT GCT TTA GTC TGG TAT
     ─────────────────────────────────
                                                                       ─────
                                                                        CDR2

109  Q   Q   K   P   G   K   A   P   E   L   L   I   Y   D   A   S   G   L
     CAG CAG AAA CCA GGG AAA GCT CCT GAG CTC CTG ATC TAT GAT GCC TCC GGT TTG
     ──
     CDR2

163  G   S   G   V   P   S   R   F   S   G   S   G   S   G   T   D   F   T
     GGA AGT GGG GTC CCA TCA AGG TTC AGC GGC AGT GGA TCT GGC ACA GAT TTC ACT

217  L   T   I   S   S   L   Q   P   E   D   F   A   T   Y   Y   C   Q   Q
     CTC ACC ATC AGC AGC CTG CAG CCT GAA GAT TTT GCA ACT TAT TAC TGT CAA CAG
                                                                 ─────────────
                                                                     CDR3

271  F   N   S   Y   P   Y   T   F   G   Q   G   T   K   L   E   I   K
     TTT AAT AGT TAC CCG TAC ACT TTT GGC CAG GGG ACC AAG CTG GAG ATC AAA
     ─────────────────────
       CDR3
```

Figure 3A

Anti-IFNAR 11E2 VH

```
       E   V   Q   L   V   Q   S   G   A   E   V   K   K   P   G   E   S   L
  1    GAG GTG CAG CTG GTG CAG TCT GGA GCA GAG GTG AAA AAG CCC GGG GAG TCT CTG

CDR1
       K   I   S   C   K   G   S   G   Y   I   F   T   N   Y   W   I   A   W
 55    AAG ATC TCC TGT AAG GGT TCT GGA TAC ATC TTT ACC AAT TAC TGG ATC GCC TGG

CDR2
       V   R   Q   M   P   G   K   G   L   E   S   M   G   I   I   Y   P   G
109    GTG CGC CAG ATG CCC GGT AAA GGC CTG GAG TCG ATG GGG ATC ATC TAT CCT GGT

CDR2
       D   S   D   I   R   Y   S   P   S   F   Q   G   Q   V   T   I   S   A
163    GAC TCT GAT ATC AGA TAC AGC CCG TCC TTC CAA GGC CAG GTC ACC ATC TCA GCC

D   K   S   I   T   A   Y   L   Q   W   S   S   L   K   A   S   D
217    GAC AAG TCC ATC ACC GCC TAC CTG CAG TGG AGC AGT CTG AAG GCC TCA GAC

CDR3
       T   A   M   Y   Y   C   A   R   H   D   I   E   G   F   D   Y   W   G
271    ACC GCC ATG TAT TAC TGT GCG AGA CAT GAC ATT GAG GGG TTT GAC TAC TGG GGC

R   G   T   L   V   T   V   S   S
325    CGG GGA ACC CTG GTC ACC GTC TCC TCA
```

Figure 3B

Anti-IFNAR 11E2 VK

```
     E   I   V   L   T   Q   S   P   G   T   L   S   L   S   P   G   E   R
1    GAA ATT GTG TTG ACG CAG TCT CCA GGC ACC CTG TCT TTG TCT CCA GGG GAA AGA
                                         ─────────────────────────────────
                                                       CDR1

A   T   L   S   C   R   A   S   Q   S   V   S   S   S   F   F   A   W
55   GCC ACC CTC TCC TGC AGG GCC AGT CAG AGT GTT AGC AGC AGC TTC TTC GCC TGG
     ────────────────────────────────────────────────────────────────────
                                                                        CDR2

Y   Q   Q   K   P   G   Q   A   P   R   L   L   I   Y   G   A   S   S
109  TAC CAG CAG AAA CCT GGC CAG GCT CCC AGG CTC CTC ATC TAT GGT GCA TCC AGC
                                                  ─────────────────────────
                                                   CDR2

R   A   T   G   I   P   D   R   L   S   G   S   G   S   G   T   D   F
163  AGG GCC ACT GGC ATC CCA GAC AGG TTA AGT GGC AGT GGG TCT GGG ACA GAC TTC
                                                                       CDR3
                                                                       ────

T   L   T   I   T   R   L   E   P   E   D   F   A   V   Y   Y   C   Q
217  ACT CTC ACC ATC ACC AGA CTG GAG CCT GAA GAT TTT GCA GTG TAT TAC TGT CAG
     ────────────────────────────────────────────────────────────────────

Q   Y   D   S   S   A   I   T   F   G   Q   G   T   R   L   E   I   K
271  CAG TAT GAT AGC TCA GCG ATC ACC TTC GGC CAA GGG ACA CGA CTG GAG ATT AAA
         ───────────────────────────
                  CDR3
```

Figure 4A

Anti-IFNAR 9D4 VH

```
      E   V   Q   L   V   Q   S   G   A   E   V   K   K   P   G   E   S   L
  1   GAG GTG CAG CTG GTG CAG TCT GGA GCA GAG GTG AAA AAG CCC GGG GAG TCT CTG

K   I   S   C   K   G   S   G   Y   I   F   T   N   Y   W   I   A   W
                                                           ─────CDR1─────
 55   AAG ATC TCC TGT AAG GGT TCT GGA TAC ATC TTT ACC AAC TAC TGG ATC GCC TGG

V   R   Q   M   P   G   K   G   L   E   S   M   G   I   I   Y   P   G
                                                           ─────CDR2
109   GTG CGC CAG ATG CCC GGT AAA GGC CTG GAG TCG ATG GGG ATC ATC TAT CCT GGT

D   S   D   I   R   Y   S   P   S   F   Q   G   Q   V   T   I   S   A
      ─────CDR2
163   GAC TCT GAT ATC AGA TAC AGT CCC TCC TTC CAA GGC CAG GTC ACC ATC TCA GCC

D   K   S   I   T   T   A   Y   L   Q   W   S   S   L   K   A   S   D
217   GAC AAG TCC ATC ACC ACC GCC TAC CTG CAG TGG AGC AGT CTG AAG GCC TCA GAC

T   A   M   Y   Y   C   A   R   H   D   I   E   G   F   D   Y   W   G
                                   ─────────────CDR3
271   ACC GCC ATG TAT TAC TGT GCG AGA CAT GAC ATA GAG GGG TTT GAC TAC TGG GGC

R   G   T   L   V   T   V   S   S
325   CGG GGA ACC CTG GTC ACC GTC TCC TCA
```

Figure 4B

Anti-IFNAR 9D4 VK

```
  1   E   I   V   L   T   Q   S   P   G   T   L   S   L   S   P   G   E   R
      GAA ATT GTG TTG ACG CAG TCT CCA GGC ACC CTG TCT TTG TCT CCA GGG GAA AGA
                                                      ────────CDR1────────
 55   A   T   L   S   C   R   A   S   Q   S   V   S   S   S   F   F   A   W
      GCC ACC CTC TCC TGC AGG GCC AGT CAG AGT GTT AGT AGC AGC TTC TTC GCC TGG
      ─────────────────                                               ────CDR2
109   Y   Q   Q   K   P   G   Q   A   P   R   L   L   I   Y   G   A   S   S
      TAC CAG CAG AAA CCT GGC CAG GCT CCC AGG CTC CTC ATC TAT GGT GCA TCC AGC
      ────CDR2────
163   R   A   T   G   I   P   D   R   L   S   G   S   G   S   G   T   D   F
      AGG GCC ACT GGC ATC CCA GAC AGG TTA AGT GGC AGT GGG TCT GGG ACA GAC TTC
                                                                           CDR3
217   T   L   T   I   T   R   L   E   P   E   D   F   A   V   Y   Y   C   Q
      ACT CTC ACC ATC ACC AGA CTG GAG CCT GAA GAT TTT GCA GTG TAT TAC TGT CAG
      ────────CDR3────────
271   Q   Y   D   S   S   A   I   T   F   G   Q   G   T   R   L   E   I   K
      CAG TAT GAT AGC TCA GCG ATC ACC TTC GGC CAA GGG ACA CGA CTG GAG ATT AAA
```

Figure 5

```
ASTKGPSVFPLAPSSKSTSGGTAALGCLVKDYFPEPVTVSWNSGALTSGVHTFPAVLQSSGLYSLSSVVT    IgG1-unmodified
ASTKGPSVFPLAPSSKSTSGGTAALGCLVKDYFPEPVTVSWNSGALTSGVHTFPAVLQSSGLYSLSSVVT    IgG1-modified
ASTKGPSVFPLAPCSRSTSESTAALGCLVKDYFPEPVTVSWNSGALTSGVHTFPAVLQSSGLYSLSSVVT    IgG4-modified
ASTKGPSVFPLAPCSRSTSESTAALGCLVKDYFPEPVTVSWNSGALTSGVHTFPAVLQSSGLYSLSSVVT    IgG4-unmodified
                                              (228)  (234) (235)
VPSSSLGTQTYICNVNHKPSNTKVDKRVEPKSCDKTHTCPPCPAPELLGGPSVFLFPPKPKDTLMISRTP    IgG1-unmodified
VPSSSLGTQTYICNVNHKPSNTKVDKRVEPKSCDKTHTCPPCPAPEFEGGPSVFLFPPKPKDTLMISRTP    IgG1-modified
VPSSSLGTKTYTCNVDHKPSNTKVDKRVESKYG---PPCPPCPAPEFEGGPSVFLFPPKPKDTLMISRTP    IgG4-modified
VPSSSLGTKTYTCNVDHKPSNTKVDKRVESKYG---PPCPSCPAPEFLGGPSVFLFPPKPKDTLMISRTP    IgG4-unmodified EVTCVVVDVSHEDPEVKFNWYVDGVEVHNAKTKPREEQYNSTYRVVSVLTVLHQDWLNGKEYKCKVSNKA    IgG1-unmodified
EVTCVVVDVSHEDPEVKFNWYVDGVEVHNAKTKPREEQYNSTYRVVSVLTVLHQDWLNGKEYKCKVSNKA    IgG1-modified
EVTCVVVDVSQEDPEVQFNWYVDGVEVHNAKTKPREEQFNSTYRVVSVLTVLHQDWLNGKEYRCKVSNKG    IgG4-modified
EVTCVVVDVSQEDPEVQFNWYVDGVEVHNAKTKPREEQFNSTYRVVSVLTVLHQDWLNGKEYRCKVSNKG    IgG4-unmodified
(331)
LPAPIEKTISKAKGQPREPQVYTLPPSREEMTKNQVSLTCLVKGFYPSDIAVEWESNGQPENNYKTTPPV    IgG1-unmodified
LPASIEKTISKAKGQPREPQVYTLPPSREEMTKNQVSLTCLVKGFYPSDIAVEWESNGQPENNYKTTPPV    IgG1-modified
LPSSIEKTISKAKGQPREPQVYTLPPSQEEMTKNQVSLTCLVKGFYPSDIAVEWESNGQPENNYKTTPPV    IgG4-modified
LPSSIEKTISKAKGQPREPQVYTLPPSQEEMTKNQVSLTCLVKGFYPSDIAVEWESNGQPENNYKTTPPV    IgG4-unmodified LDSDGSFFLYSKLTVDKSRWQQGNVFSCSVMHEALHNHYTQKSLSLSPGK.                       IgG1-unmodified
LDSDGSFFLYSKLTVDKSRWQQGNVFSCSVMHEALHNHYTQKSLSLSPGK.                       IgG1-modified
LDSDGSFFLYSRLTVDKSRWQEGNVFSCSVMHEALHNHYTQKSLSLSLGK.                       IgG4-modified
LDSDGSFFLYSRLTVDKSRWQEGNVFSCSVMHEALHNHYTQKSLSLSLGK                        IgG4-unmodified
```

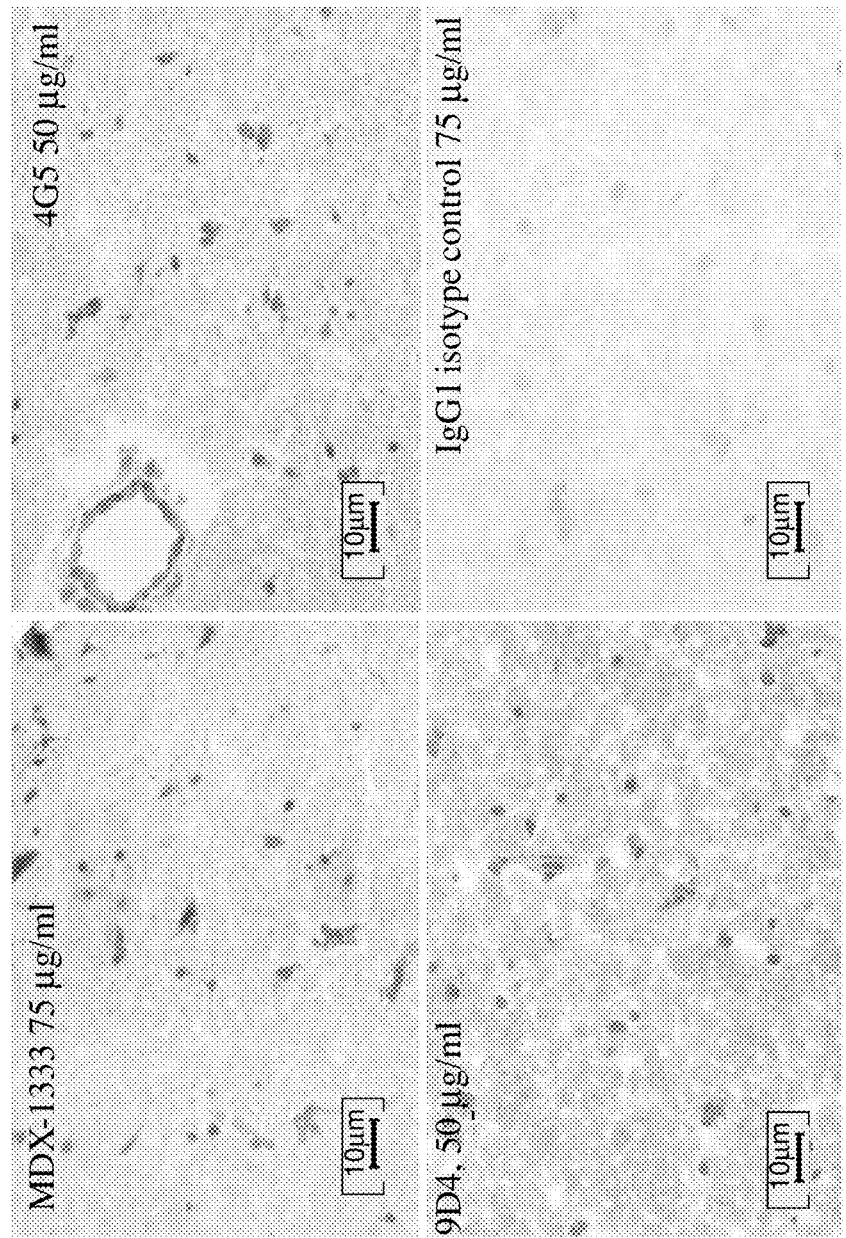

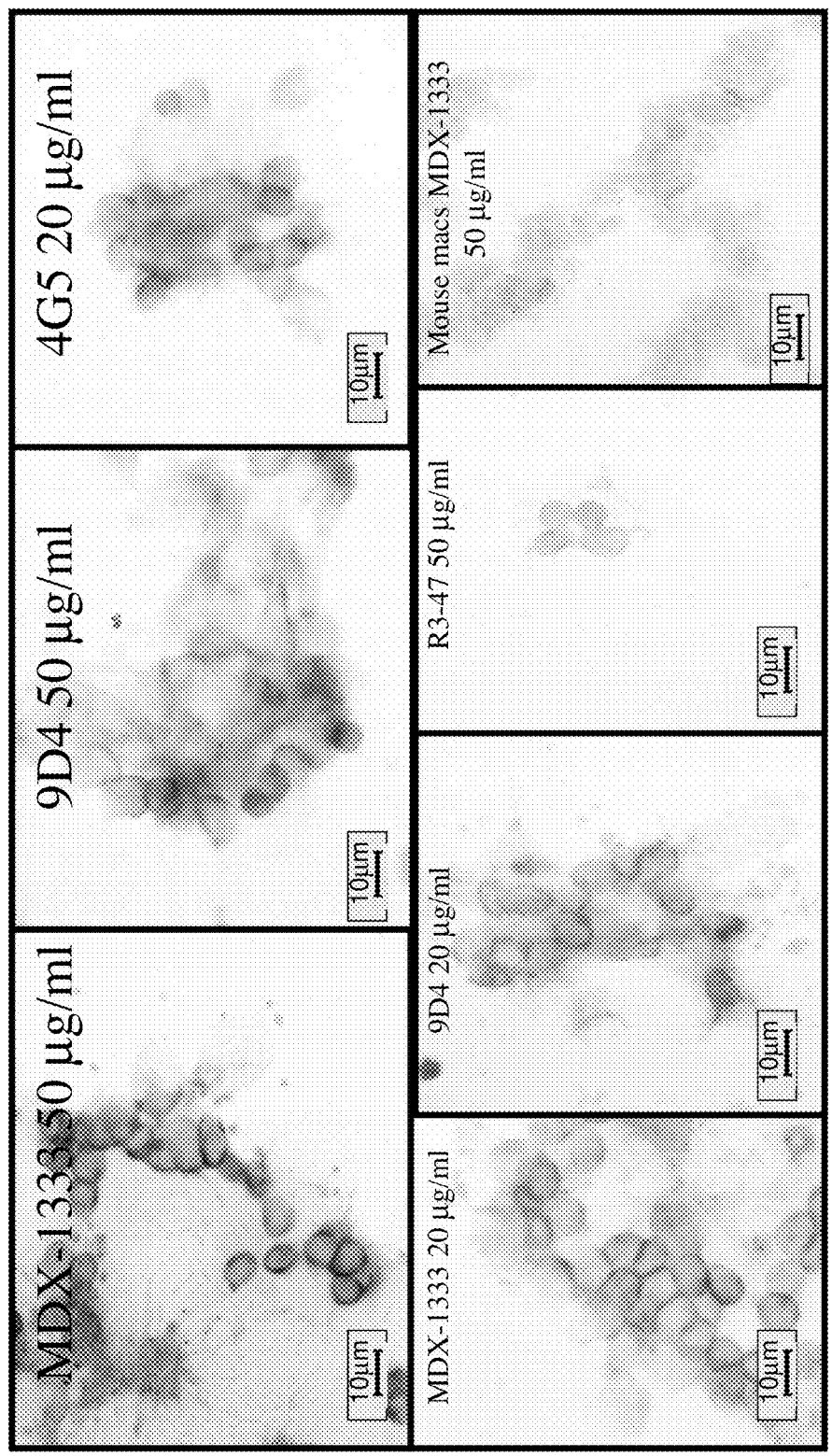

Figure 8

| Donor #190 Type-I IFN concentration (IU/mL) | 9D4 | |
|---|---|---|
| | IC$_{50}$(nM) | Percent Inhibition* |
| 50 | 0.005 | 97 |
| 100 | 0.008 | 98 |
| 500 | 0.04 | 98 |
| 1000 | 0.06 | 99 |
| 2000 | 0.16 | 99 |
| 5000 | 0.5 | 98 |

| Donor #141 Type-I IFN concentration (IU/mL) | 9D4 | |
|---|---|---|
| | IC$_{50}$(nM) | Percent Inhibition* |
| 50 | 0.02 | 99.1 |
| 100 | 0.04 | 99 |
| 500** | 0.2 | 98.6 |
| 1000 | 0.2 | 98 |
| 2000** | 0.9 | 100 |
| 5000** | 2.4 | 100 |

| Donor #237 Type-I IFN concentration (IU/mL) | 9D4 | |
|---|---|---|
| | IC$_{50}$(nM) | Percent Inhibition* |
| 50 | 0.008 | 99 |
| 100 | 0.01 | 99 |
| 500 | 0.04 | 99 |
| 1000 | 0.09 | 98 |
| 2000 | 0.12 | 99 |
| 5000 | 0.65 | 98 |

Figure 9 A, B, C
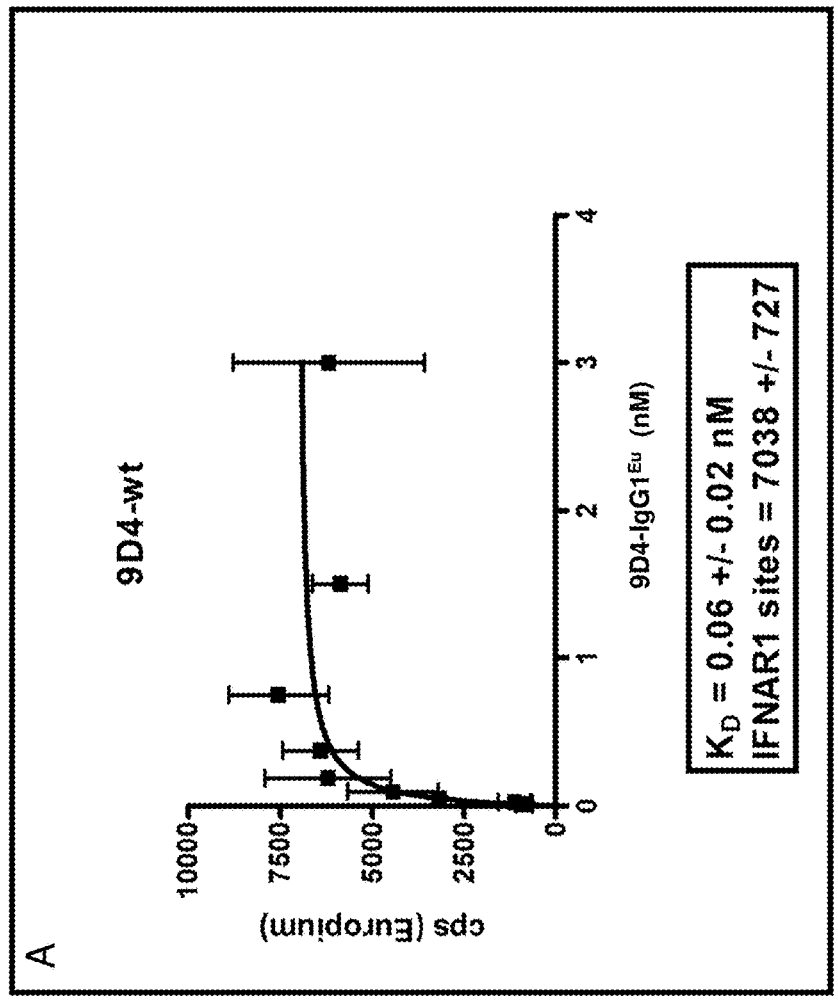

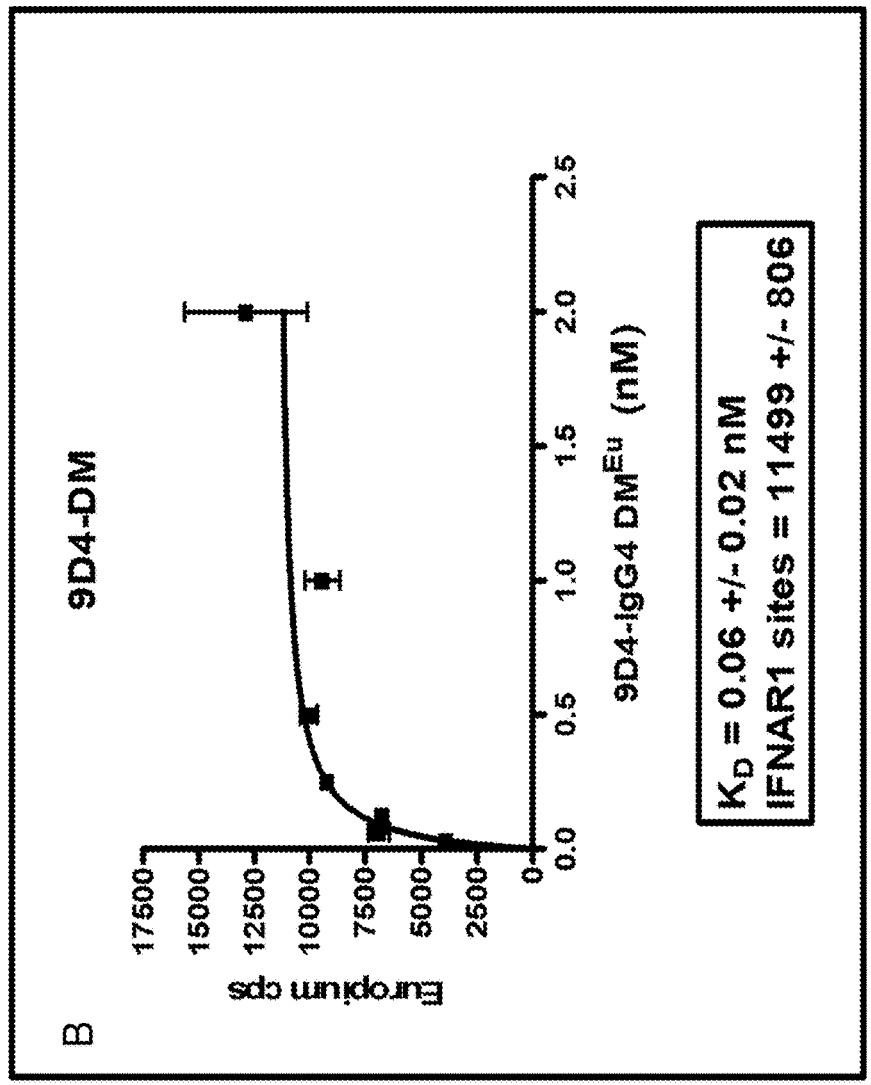
Figure 9 A, B, C continued

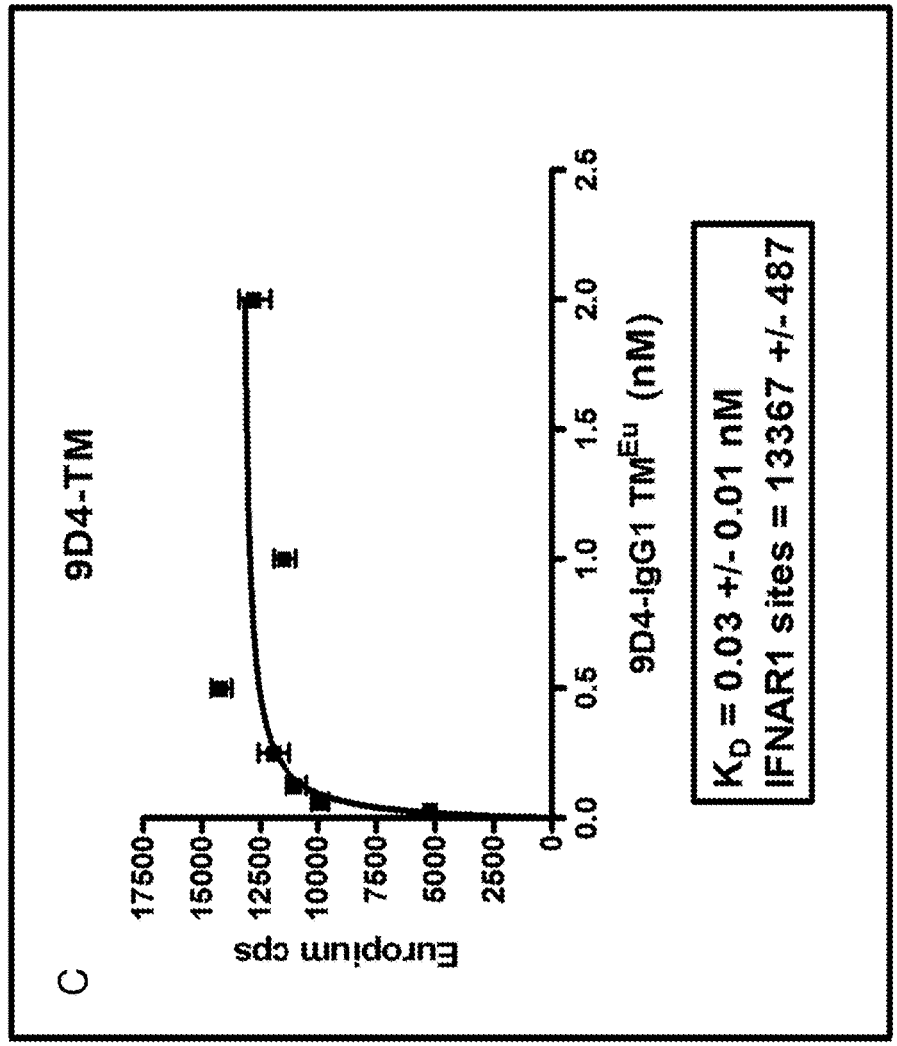
Figure 9 A, B, C continued

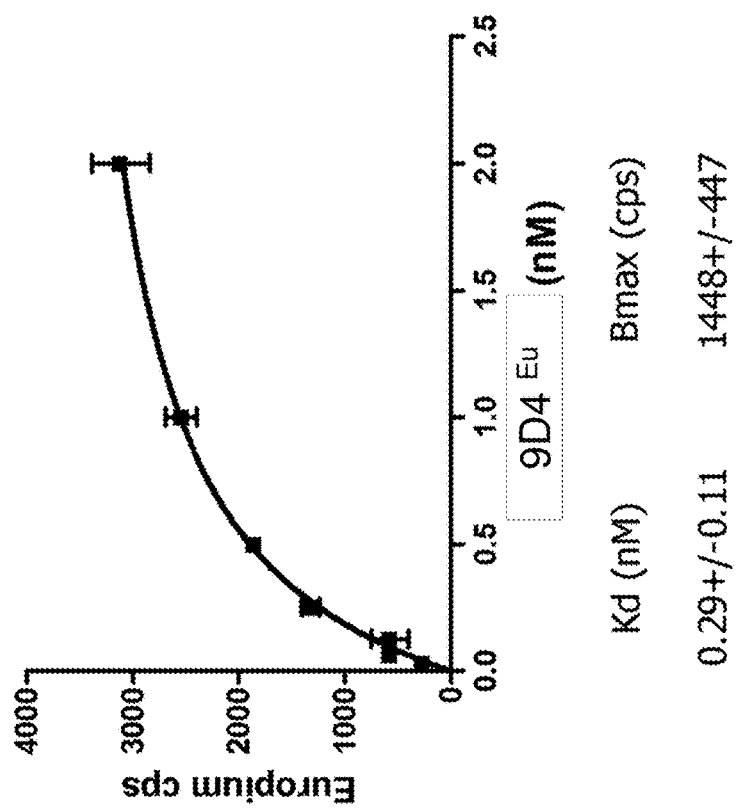

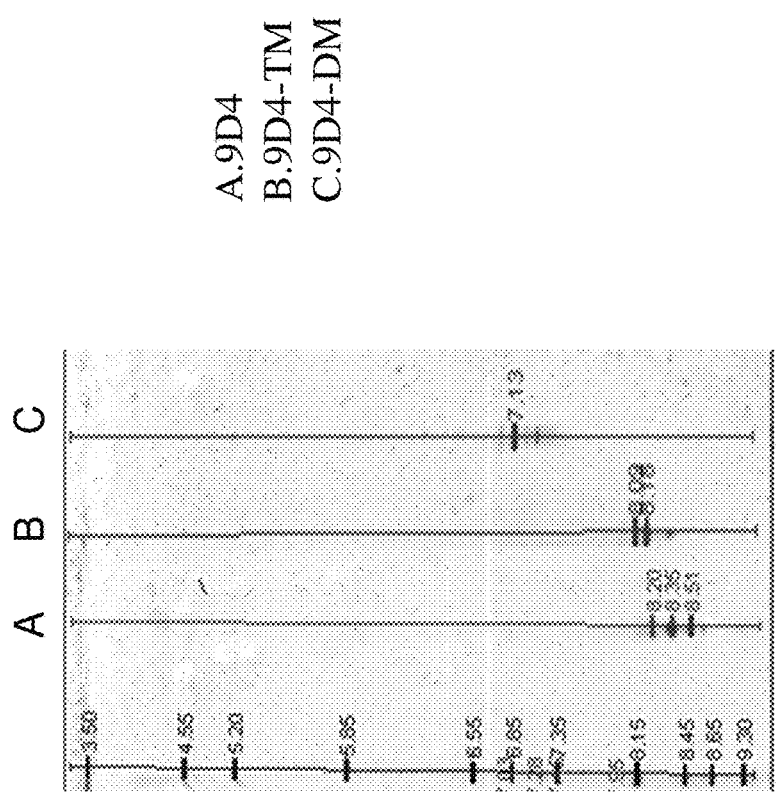

| Exp. # | CD38, % max suppression | IC50 nM | CD123, % max. suppression | IC50 nM |
|---|---|---|---|---|
| 1 | 88% | 0.05 | NC | NC |
| 2 | 100% | 0.05 | 70% | 0.06 |
| 3 | 81% | 0.02 | 64% | 0.04 |
| 4 | 91% | 0.04 | 76% | 0.06 |
| 5 | NC | NC | 72% | 0.06 |

NC: not calculated (no induction).

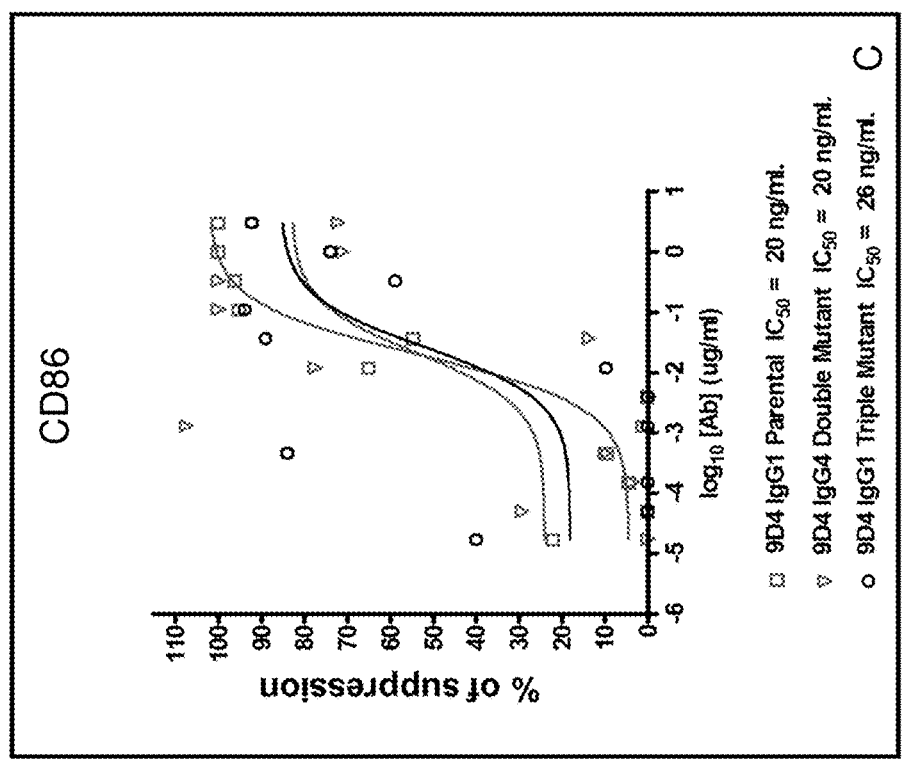

Figure 21, A, B, C
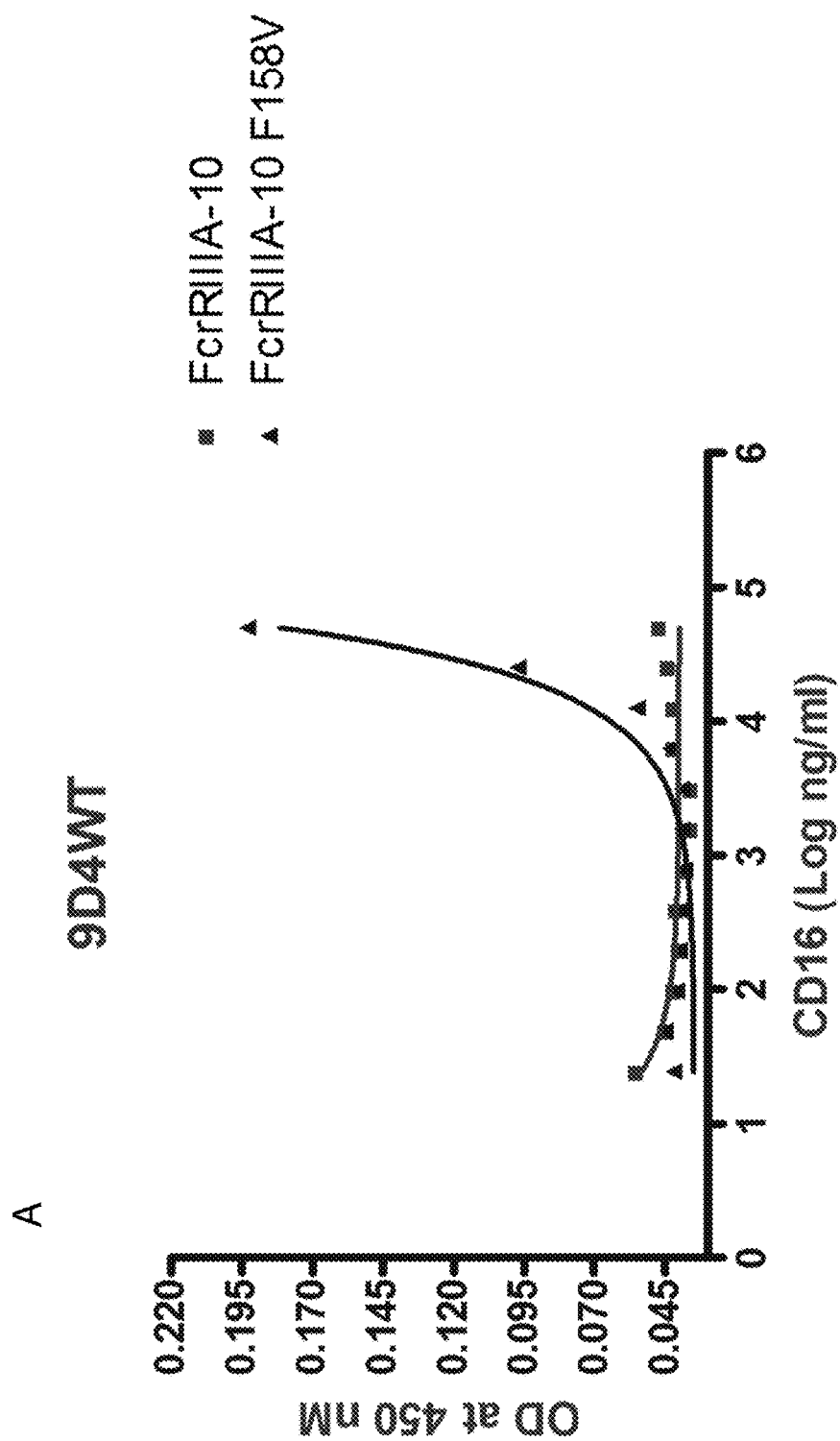

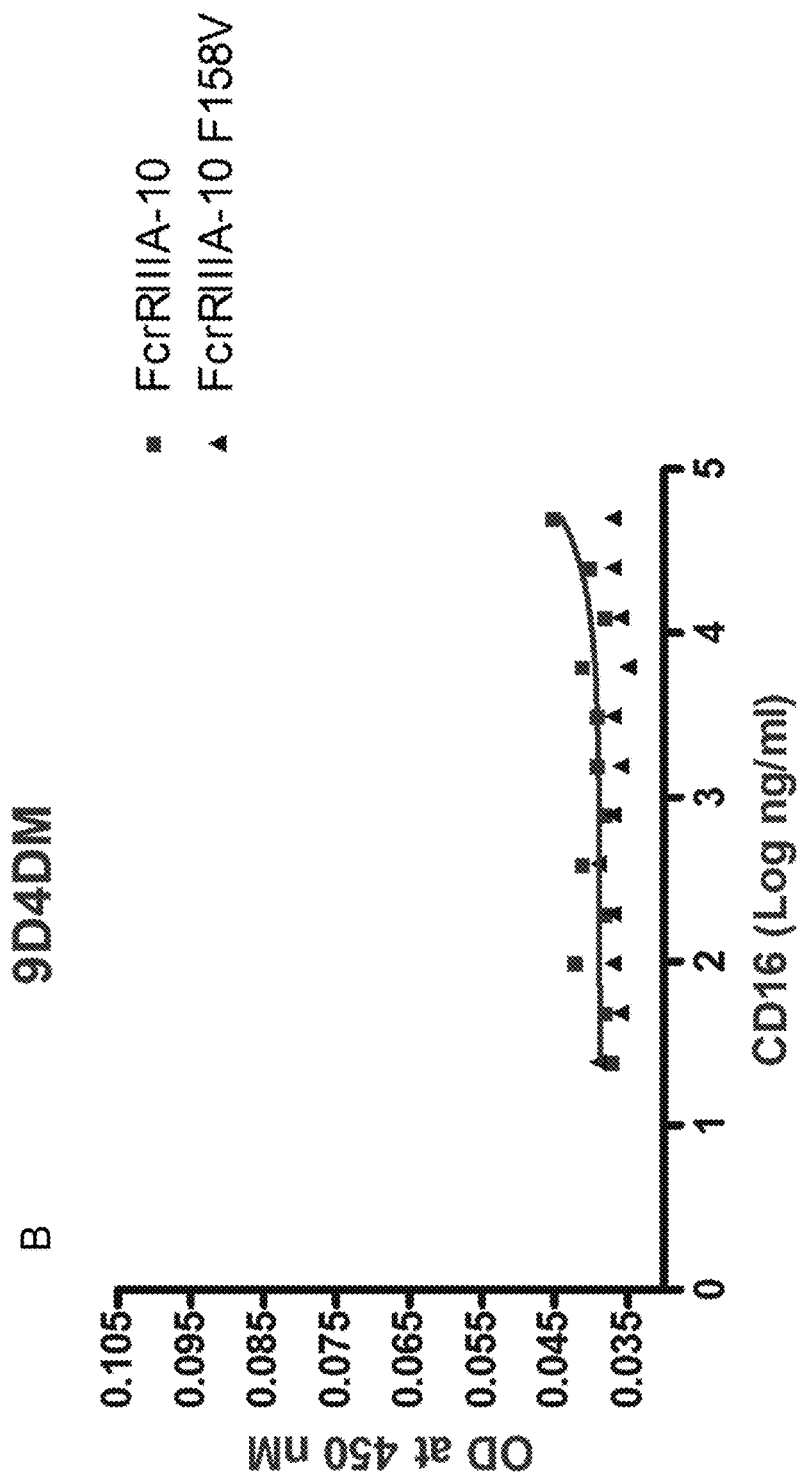
Figure 21, A, B, C continued

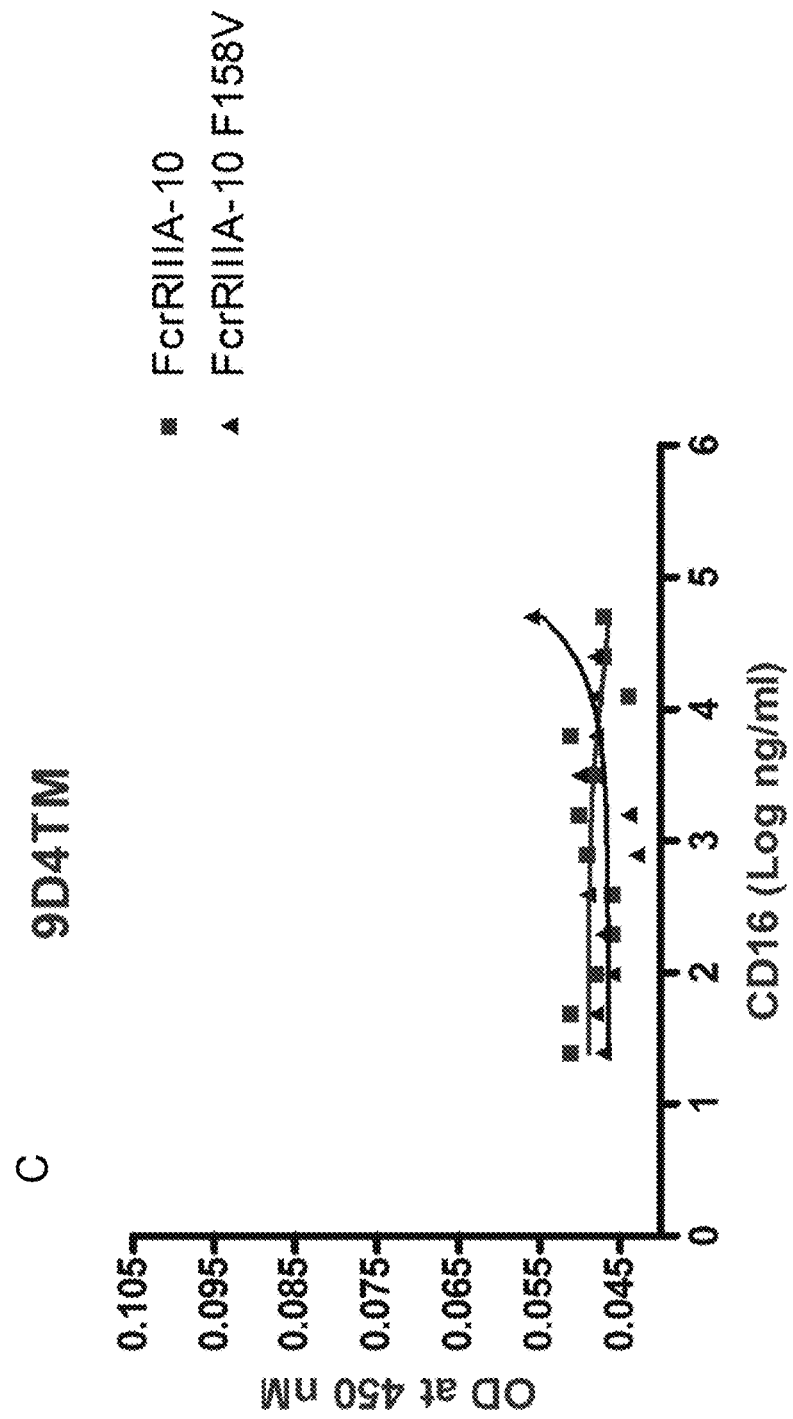
Figure 21, A, B, C continued

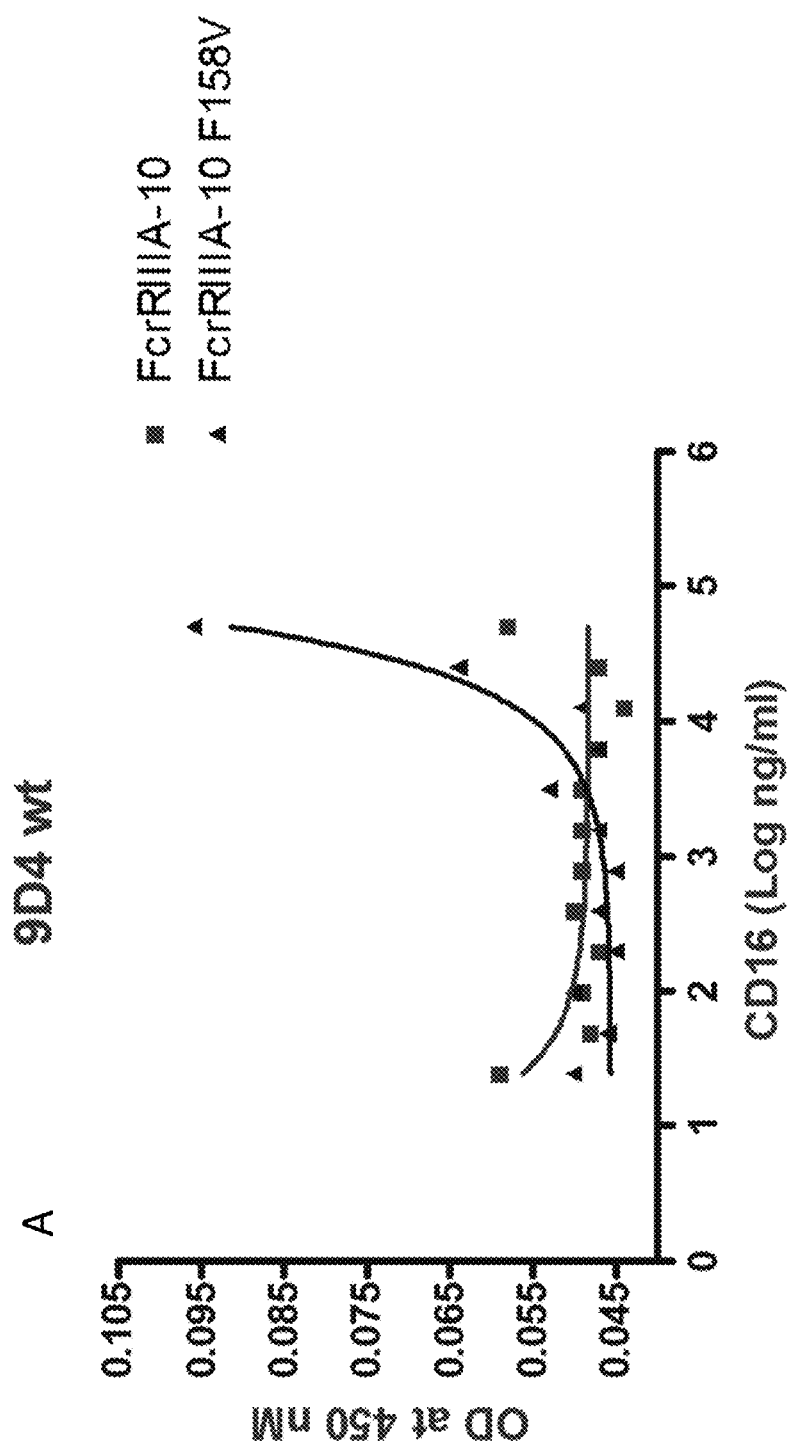

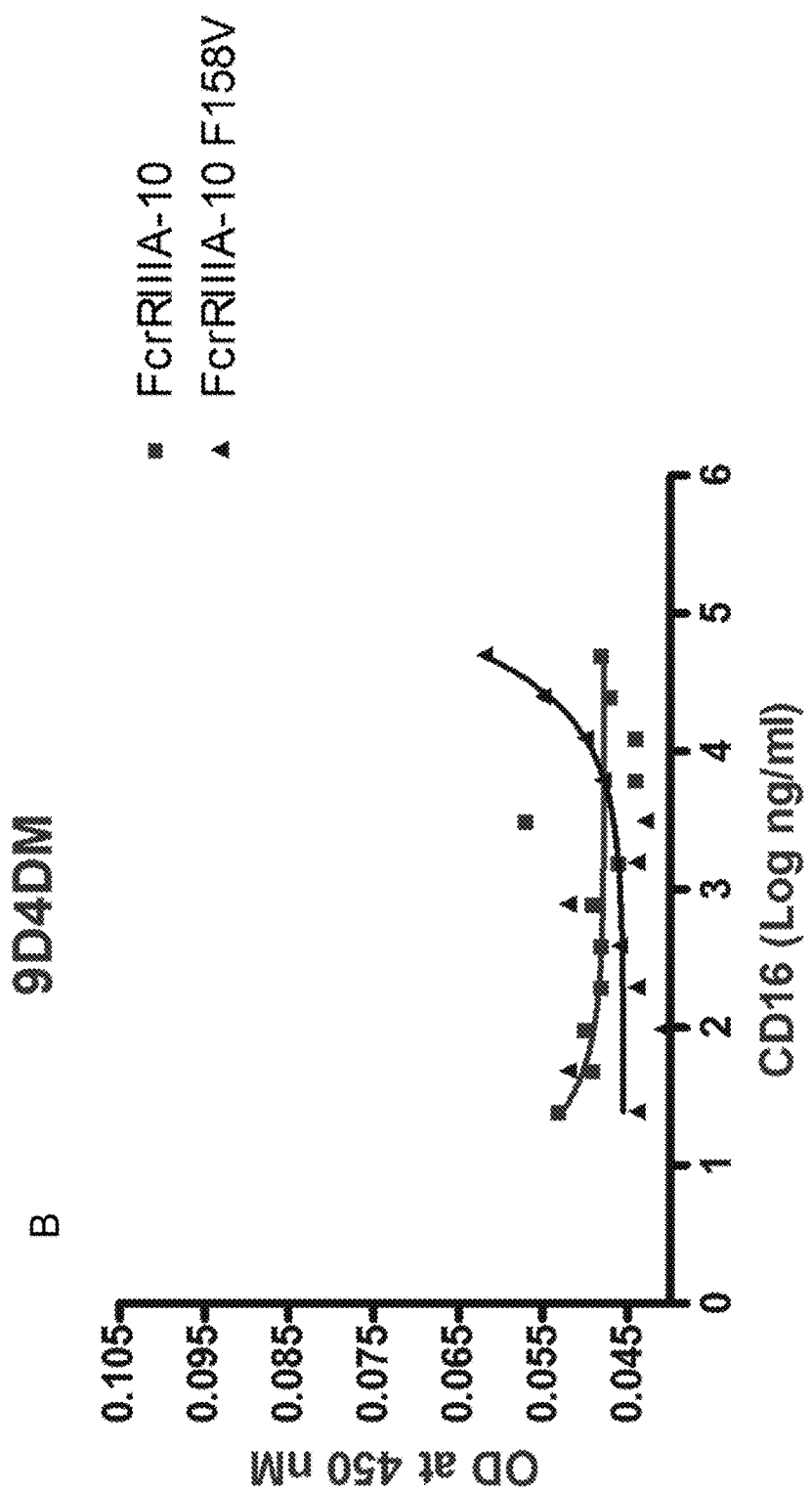
Figure 22, A, B, C continued

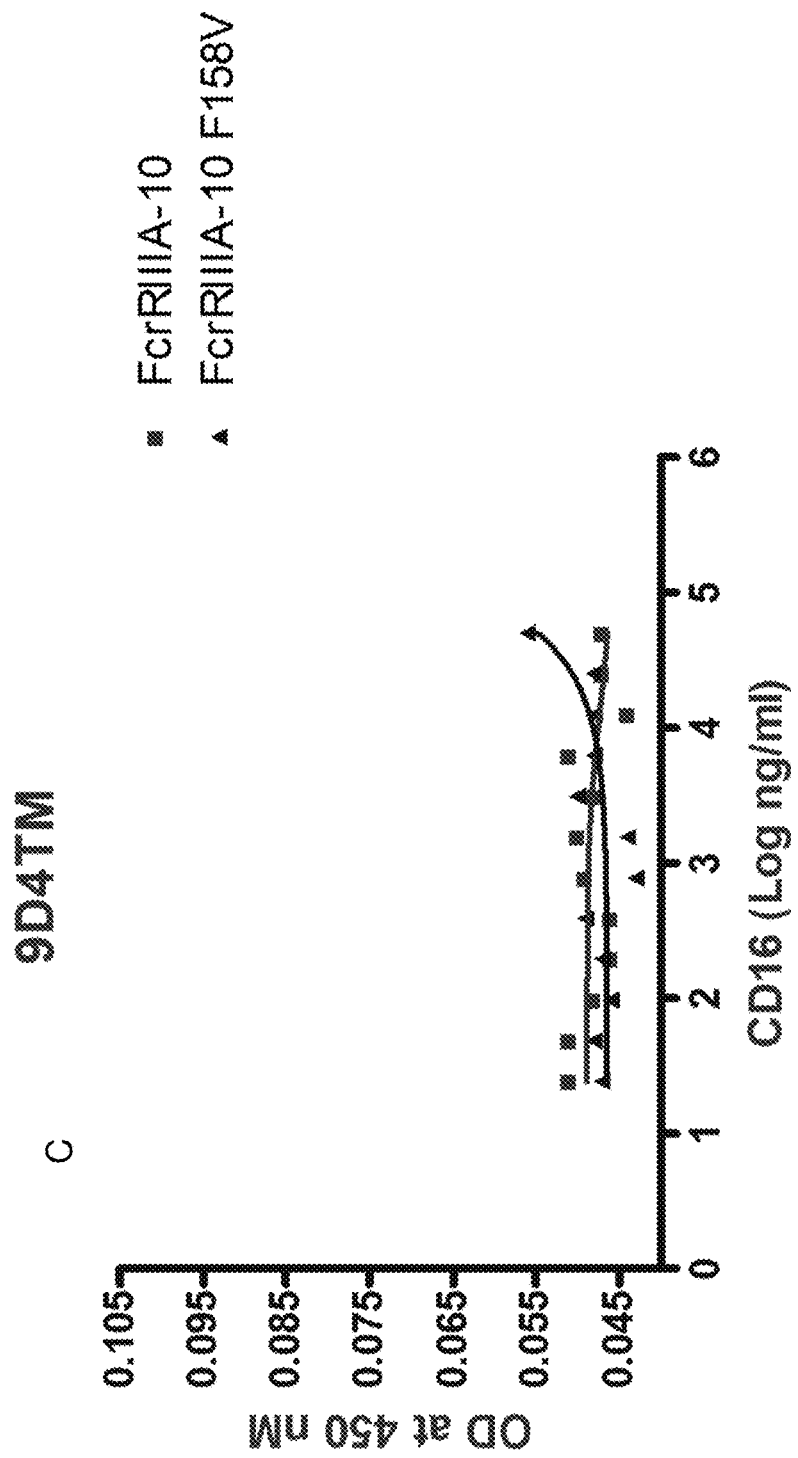

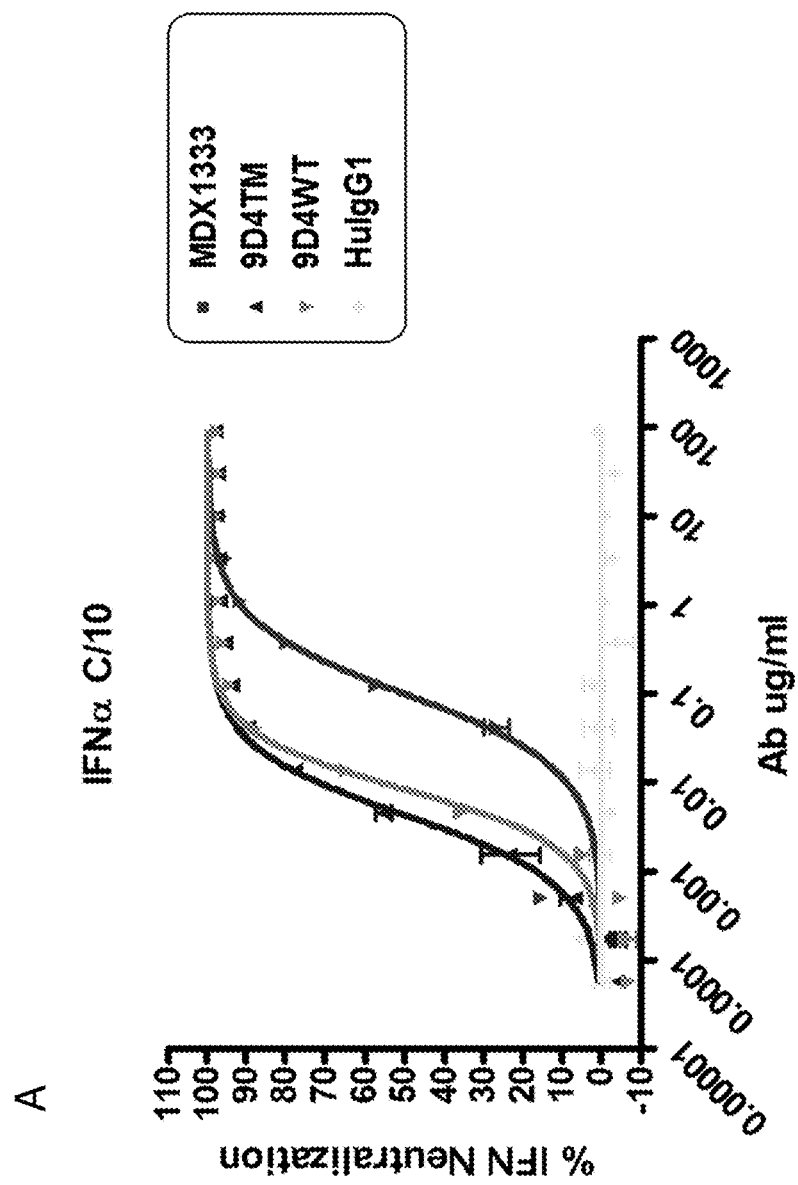
Figure 23 A-E

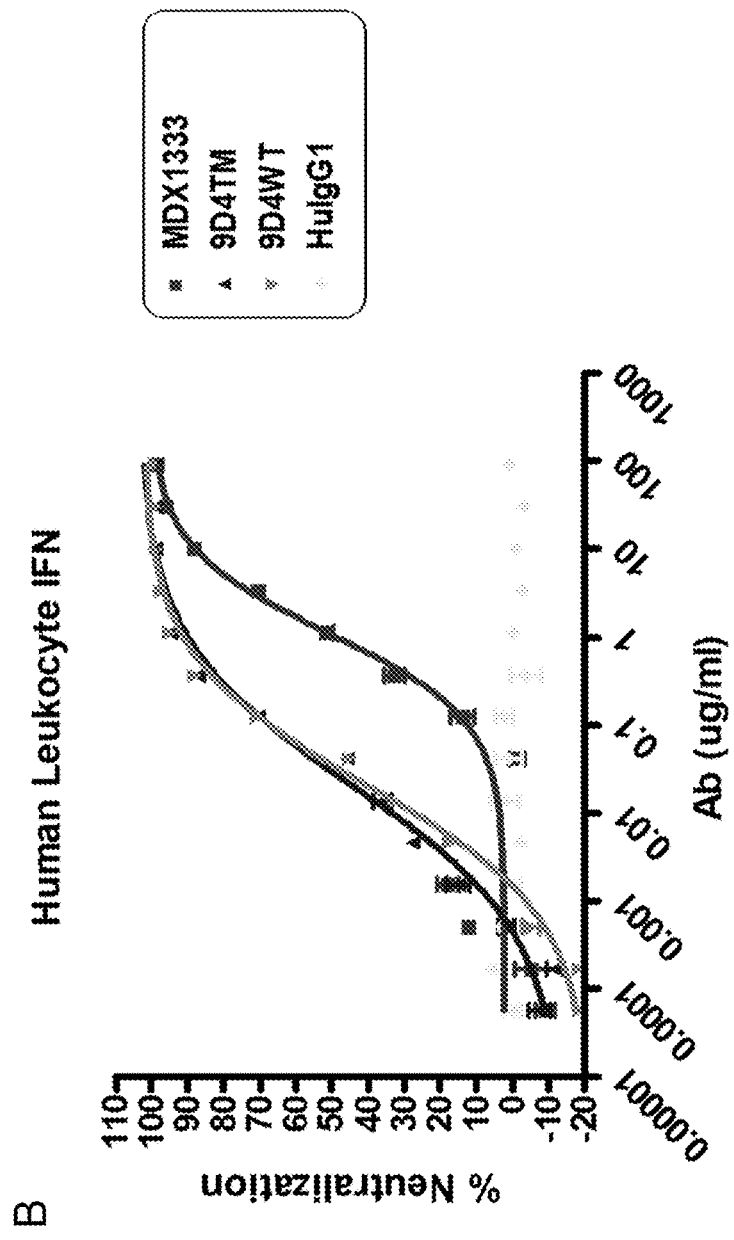
Figure 23 A-E continued

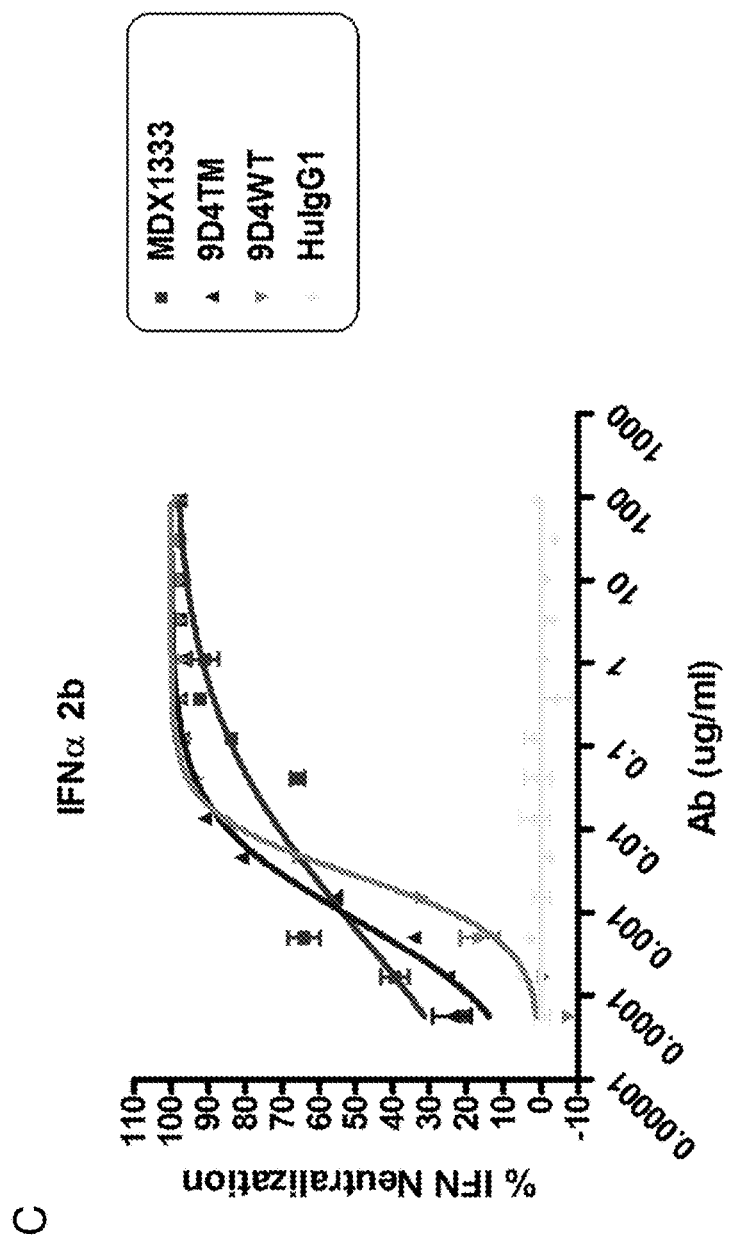
Figure 23 A-E continued

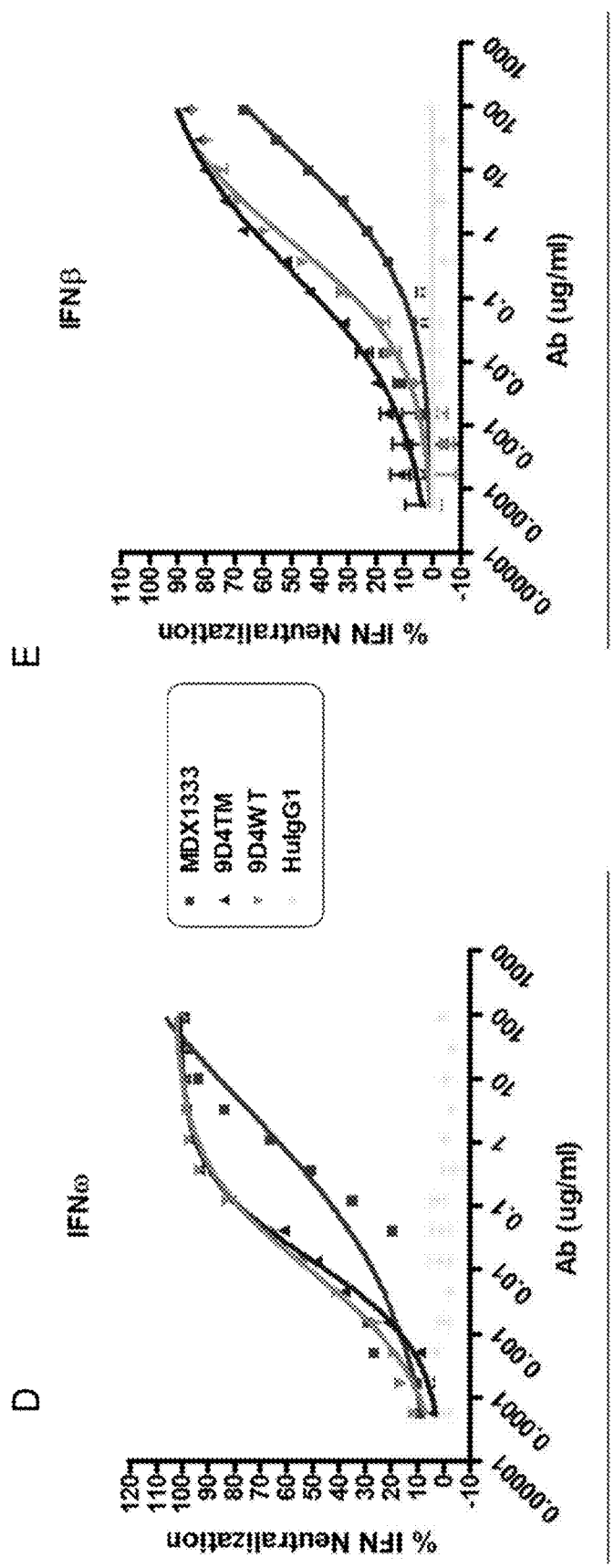
Figure 23 A-E continued

Figure 25 A-D

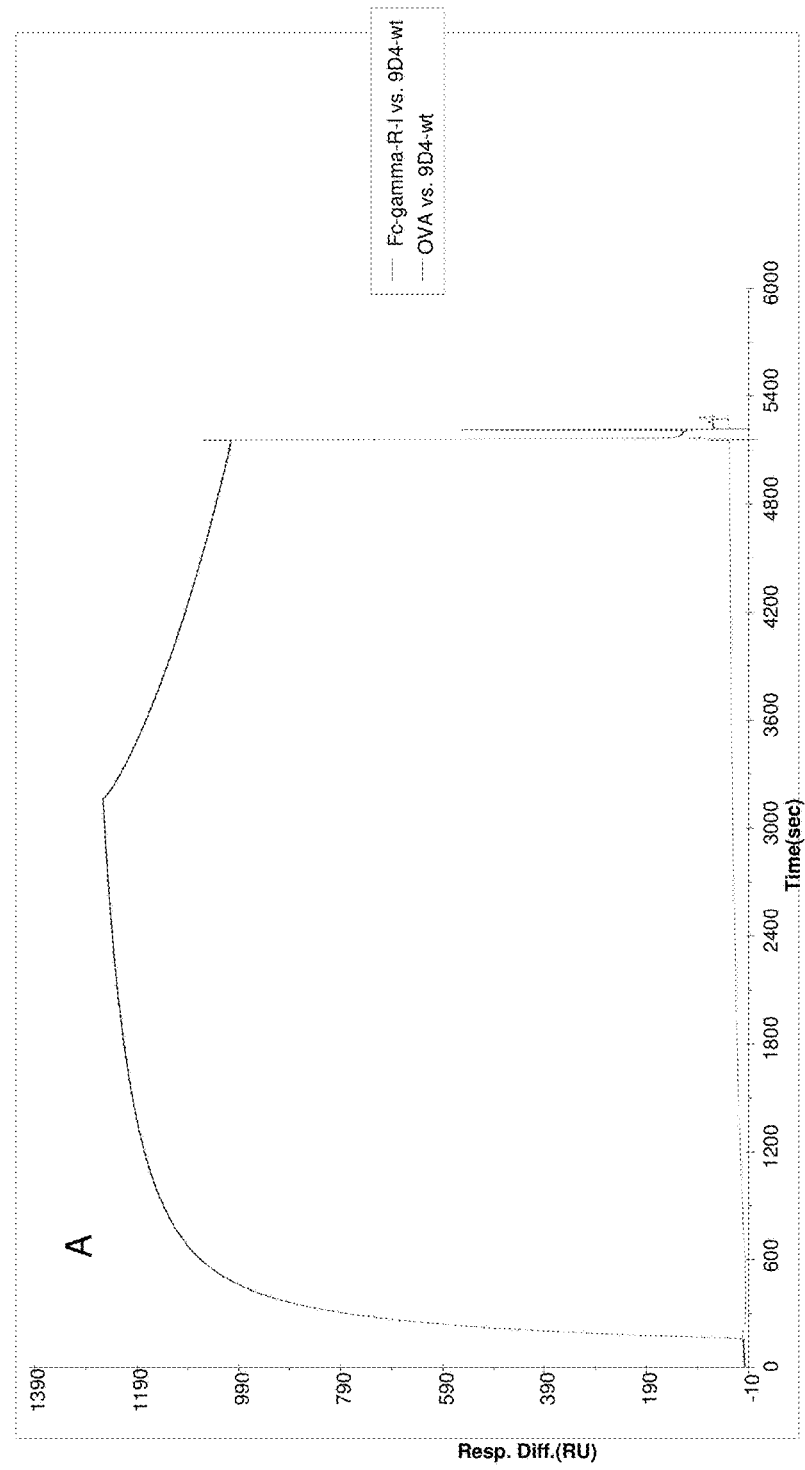
Figure 27 A-C

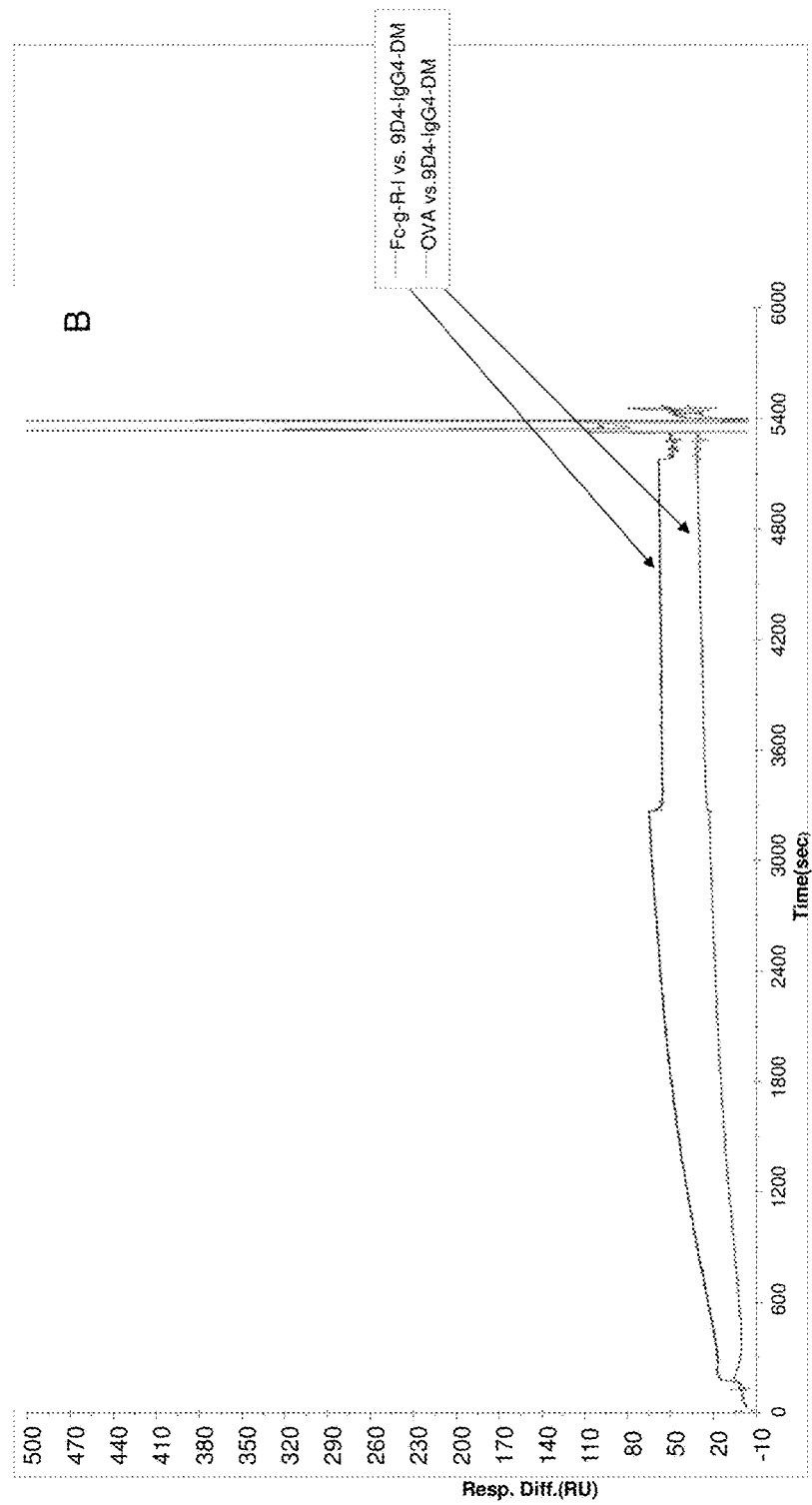
Figure 27 A-C continued

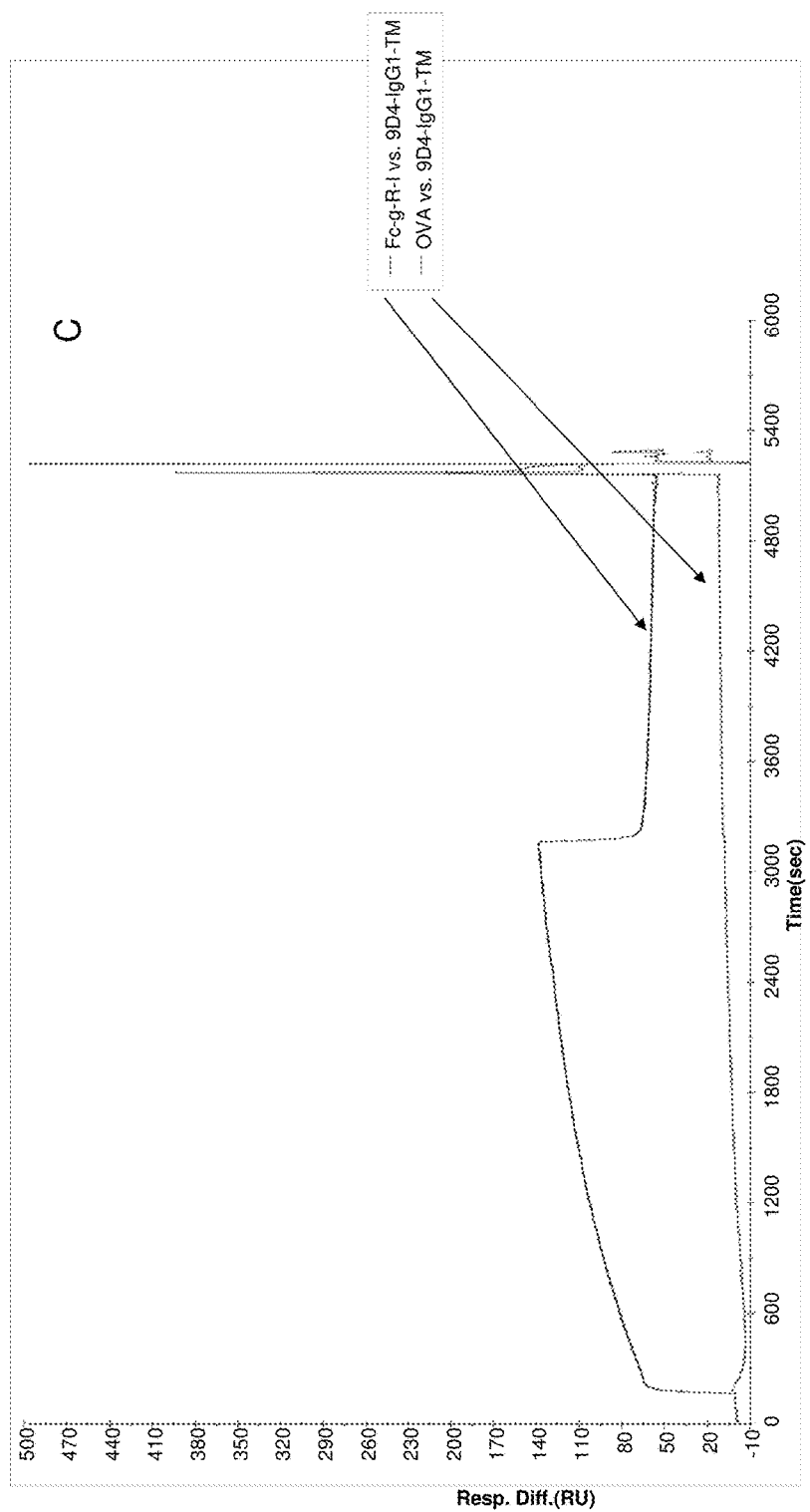
Fig 27 A-C continued

SEQUENCE LISTING

```
<160> NUMBER OF SEQ ID NOS: 54

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 1

Arg Ala Ser Gln Gly Ile Tyr Ser Val Leu Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
                                    peptide construct

<400> SEQUENCE: 2

Asp Ala Ser Arg Leu Glu Ser
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 3

Gln Gln Phe Asn Ser Tyr Ile Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 4

Gly Tyr Phe Trp Ser
1               5

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 5

Glu Ile Asp His Ser Gly Lys Thr Asn Tyr Asn Pro Ser Leu Lys Ser
1               5                   10                  15

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 6

Glu Ser Lys Tyr Tyr Phe Gly Leu Asp Val
1               5                   10

<210> SEQ ID NO 7
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide construct
<220> FEATURE:
<221> NAME/KEY: CDS
<222> LOCATION: (1)..(354)

<400> SEQUENCE: 7 cag gtg cag cta cag cag tgg ggc gca gga ctg ttg aag cct tct gag     48
Gln Val Gln Leu Gln Gln Trp Gly Ala Gly Leu Leu Lys Pro Ser Glu
```

```
acc ctg tcc ctc acc tgc gct gtc tat ggt ggg tcc ttc agt ggt tat      96
Thr Leu Ser Leu Thr Cys Ala Val Tyr Gly Gly Ser Phe Ser Gly Tyr
            20                  25                  30 ttc tgg agc tgg atc cgc cag ccc cca ggg aag ggg ctg gag tgg att     144
Phe Trp Ser Trp Ile Arg Gln Pro Pro Gly Lys Gly Leu Glu Trp Ile
        35                  40                  45 ggg gaa atc gat cac agt gga aag acc aac tac aat ccg tcc ctc aag     192
Gly Glu Ile Asp His Ser Gly Lys Thr Asn Tyr Asn Pro Ser Leu Lys
50                  55                  60 agt cga gtt acc ata tca gta gac acg tcc aag aac cag gtc tcc ctg     240
Ser Arg Val Thr Ile Ser Val Asp Thr Ser Lys Asn Gln Val Ser Leu
65                  70                  75                  80 aag ctg agc tct gtg acc gcc gcg gac acg gct gtg tat tac tgt gcg     288
Lys Leu Ser Ser Val Thr Ala Ala Asp Thr Ala Val Tyr Tyr Cys Ala
                85                  90                  95 aga gaa agc aag tac tac ttc ggt ttg gac gtc tgg ggc caa ggg acc     336
Arg Glu Ser Lys Tyr Tyr Phe Gly Leu Asp Val Trp Gly Gln Gly Thr
            100                 105                 110 acg gtc acc gtc acc tca                                             354
Thr Val Thr Val Thr Ser
        115
```

<210> SEQ ID NO 8
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 8

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Phe Trp Ser Trp Ile Arg Gln Pro Pro Gly Lys Gly Leu Glu Trp Ile
        35                  40                  45

Gly Glu Ile Asp His Ser Gly Lys Thr Asn Tyr Asn Pro Ser Leu Lys
50                  55                  60

Ser Arg Val Thr Ile Ser Val Asp Thr Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Glu Ser Lys Tyr Tyr Phe Gly Leu Asp Val Trp Gly Gln Gly Thr
            100                 105                 110

Thr Val Thr Val Thr Ser
        115
```

<210> SEQ ID NO 9
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide construct
<220> FEATURE:
<221> NAME/KEY: CDS
<222> LOCATION: (1)..(318)

<400> SEQUENCE: 9

```
gcc atc cag ttg acc cag tct cca tcc tcc ctg tct gca tct gta gga    48
Ala Ile Gln Leu Thr Gln Ser Pro Ser Ser Leu Ser Ala Ser Val Gly
1               5                   10                  15 gac aga gtc acc atc act tgc cgg gca agt cag ggc att tac agt gtt    96
Asp Arg Val Thr Ile Thr Cys Arg Ala Ser Gln Gly Ile Tyr Ser Val
            20                  25                  30 tta gcc tgg tat cag cag aaa cca ggg aaa act cct aag ctc ctg atc   144
Leu Ala Trp Tyr Gln Gln Lys Pro Gly Lys Thr Pro Lys Leu Leu Ile
        35                  40                  45 tat gat gcc tcc cgt ttg gaa agt ggg gtc cca tca agg ttc agc ggc   192
Tyr Asp Ala Ser Arg Leu Glu Ser Gly Val Pro Ser Arg Phe Ser Gly
 50                  55                  60 agt gga tct ggg aca gat ttc act ctc acc atc agc agc ctg cag cct   240
Ser Gly Ser Gly Thr Asp Phe Thr Leu Thr Ile Ser Ser Leu Gln Pro
65                  70                  75                  80 gaa gat ttt gca act tat tac tgt caa cag ttt aat agt tac atc acc   288
Glu Asp Phe Ala Thr Tyr Tyr Cys Gln Gln Phe Asn Ser Tyr Ile Thr
                85                  90                  95 ttc ggc caa ggg aca cga ctg gag att aaa                           318
Phe Gly Gln Gly Thr Arg Leu Glu Ile Lys
            100                 105

<210> SEQ ID NO 10
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 10

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Tyr Ser Val
            20                  25                  30

Leu Ala Trp Tyr Gln Gln Lys Pro Gly Lys Thr Pro Lys Leu Leu Ile
        35                  40                  45

Tyr Asp Ala Ser Arg Leu Glu Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Ile Thr
                85                  90                  95

Phe Gly Gln Gly Thr Arg Leu Glu Ile Lys
            100                 105

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 11

Arg Ala Thr Gln Asp Ile Ser Ile Ala Leu Val
1               5                   10

<210> SEQ ID NO 12
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide construct

<400> SEQUENCE: 12

Asp Ala Ser Gly Leu Gly Ser
1               5

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 13

Gln Gln Phe Asn Ser Tyr Pro Tyr Thr
1               5

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 14

Asn Tyr Tyr Trp Ser
1               5

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 15

Glu Ile Ile Leu Ser Gly Ser Thr Asn Tyr Asn Pro Ser Leu Lys Ser
1               5                   10                  15

<210> SEQ ID NO 16
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 16

Glu Ser Lys Trp Gly Tyr Tyr Phe Asp Ser
1               5                   10

<210> SEQ ID NO 17
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide construct
<220> FEATURE:
<221> NAME/KEY: CDS
<222> LOCATION: (1)..(354)

<400> SEQUENCE: 17
```

| | | | | | | | | | | | | | | | |
|---|---|---|---|---|---|---|---|---|---|---|---|---|---|---|---|
| cag | gtg | cag | cta | cag | cag | tgg | ggc | gca | gga | ctg | ttg | aag | cct | tcg | gag | 48 |
| Gln | Val | Gln | Leu | Gln | Gln | Trp | Gly | Ala | Gly | Leu | Leu | Lys | Pro | Ser | Glu | |
| 1 | | | | 5 | | | | | 10 | | | | | 15 | | |

| | | | | | | | | | | | | | | | |
|---|---|---|---|---|---|---|---|---|---|---|---|---|---|---|---|
| acc | ctg | tcc | ctc | acc | tgc | gct | gtc | tat | ggt | ggg | tcc | ttc | agt | aat | tac | 96 |
| Thr | Leu | Ser | Leu | Thr | Cys | Ala | Val | Tyr | Gly | Gly | Ser | Phe | Ser | Asn | Tyr | |
| | | | 20 | | | | | 25 | | | | | 30 | | | |

| | | | | | | | | | | | | | | | |
|---|---|---|---|---|---|---|---|---|---|---|---|---|---|---|---|
| tac | tgg | agc | tgg | atc | cgc | cag | ccc | cca | ggg | aag | ggg | ctg | gag | tgg | att | 144 |
| Tyr | Trp | Ser | Trp | Ile | Arg | Gln | Pro | Pro | Gly | Lys | Gly | Leu | Glu | Trp | Ile | |
| | | 35 | | | | | 40 | | | | | 45 | | | | |

| | | | | | | | | | | | | | | | |
|---|---|---|---|---|---|---|---|---|---|---|---|---|---|---|---|
| ggg | gaa | atc | att | ctt | agt | gga | agc | acc | aac | tac | aac | ccg | tcc | ctc | aag | 192 |
| Gly | Glu | Ile | Ile | Leu | Ser | Gly | Ser | Thr | Asn | Tyr | Asn | Pro | Ser | Leu | Lys | |
| 50 | | | | | 55 | | | | | 60 | | | | | | |

| | | | | | | | | | | | | | | | |
|---|---|---|---|---|---|---|---|---|---|---|---|---|---|---|---|
| agt | cga | gtc | acc | ata | tca | gta | gac | acg | tcc | aag | aac | cag | ttc | tcc | ctg | 240 |
| Ser | Arg | Val | Thr | Ile | Ser | Val | Asp | Thr | Ser | Lys | Asn | Gln | Phe | Ser | Leu | |
| 65 | | | | 70 | | | | | 75 | | | | | 80 | | |

| | | | | | | | | | | | | | | | |
|---|---|---|---|---|---|---|---|---|---|---|---|---|---|---|---|
| aac | ctg | acc | tct | gtg | acc | gcc | gcg | gac | acg | gct | gtg | tat | tac | tgt | gcg | 288 |
| Asn | Leu | Thr | Ser | Val | Thr | Ala | Ala | Asp | Thr | Ala | Val | Tyr | Tyr | Cys | Ala | |
| | | | | 85 | | | | | 90 | | | | | 95 | | |

| | | | | | | | | | | | | | |
|---|---|---|---|---|---|---|---|---|---|---|---|---|---|
| aga | gag | tct | aaa | tgg | ggt | tac | tac | ttt | gac | tcc | tgg | ggc | cag | gga | acc | 336 |
| Arg | Glu | Ser | Lys | Trp | Gly | Tyr | Tyr | Phe | Asp | Ser | Trp | Gly | Gln | Gly | Thr | |
| | | | 100 | | | | | 105 | | | | | 110 | | | |

| | | | | | |
|---|---|---|---|---|---|
| ctg | gtc | acc | gtc | tcc | tca | 354 |
| Leu | Val | Thr | Val | Ser | Ser | |
| | | | 115 | | | |

<210> SEQ ID NO 18
<211> LENGTH: 118
<212> TYPE: PRT
<213> ORGANISM: Artificial Sequence
<220> FEATURE:
<223> OTHER INFORMATION: Description of Artificial Sequence: Synthetic
polypeptide construct

<400> SEQUENCE: 18

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Asn Tyr
            20                  25                  30

Tyr Trp Ser Trp Ile Arg Gln Pro Pro Gly Lys Gly Leu Glu Trp Ile
        35                  40                  45

Gly Glu Ile Ile Leu Ser Gly Ser Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Asn Leu Thr Ser Val Thr Ala Ala Asp Thr Ala Val Tyr Tyr Cys Ala
                85                  90                  95

Arg Glu Ser Lys Trp Gly Tyr Tyr Phe Asp Ser Trp Gly Gln Gly Thr
            100                 105                 110

Leu Val Thr Val Ser Ser
        115

<210> SEQ ID NO 19
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide construct
<220> FEATURE:
<221> NAME/KEY: CDS
<222> LOCATION: (1)..(321)

<400> SEQUENCE: 19

```
gcc atc cag ttg acc cag tct cca tcc tcc ctg tct gca tct gta gga      48
Ala Ile Gln Leu Thr Gln Ser Pro Ser Ser Leu Ser Ala Ser Val Gly
1               5                   10                  15 gac aga gtc acc atc act tgc cgg gca act cag gac att agc att gct      96
Asp Arg Val Thr Ile Thr Cys Arg Ala Thr Gln Asp Ile Ser Ile Ala
            20                  25                  30 tta gtc tgg tat cag cag aaa cca ggg aaa gct cct gag ctc ctg atc     144
Leu Val Trp Tyr Gln Gln Lys Pro Gly Lys Ala Pro Glu Leu Leu Ile
        35                  40                  45 tat gat gcc tcc ggt ttg gga agt ggg gtc cca tca agg ttc agc ggc     192
Tyr Asp Ala Ser Gly Leu Gly Ser Gly Val Pro Ser Arg Phe Ser Gly
    50                  55                  60 agt gga tct ggc aca gat ttc act ctc acc atc agc agc ctg cag cct     240
Ser Gly Ser Gly Thr Asp Phe Thr Leu Thr Ile Ser Ser Leu Gln Pro
65                  70                  75                  80 gaa gat ttt gca act tat tac tgt caa cag ttt aat agt tac ccg tac     288
Glu Asp Phe Ala Thr Tyr Tyr Cys Gln Gln Phe Asn Ser Tyr Pro Tyr
                85                  90                  95 act ttt ggc cag ggg acc aag ctg gag atc aaa                         321
Thr Phe Gly Gln Gly Thr Lys Leu Glu Ile Lys
            100                 105
```

<210> SEQ ID NO 20
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 20

```
Ala Ile Gln Leu Thr Gln Ser Pro Ser Ser Leu Ser Ala Ser Val Gly
1               5                   10                  15

Asp Arg Val Thr Ile Thr Cys Arg Ala Thr Gln Asp Ile Ser Ile Ala
            20                  25                  30

Leu Val Trp Tyr Gln Gln Lys Pro Gly Lys Ala Pro Glu Leu Leu Ile
        35                  40                  45

Tyr Asp Ala Ser Gly Leu Gly Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Tyr
                85                  90                  95

Thr Phe Gly Gln Gly Thr Lys Leu Glu Ile Lys
            100                 105
```

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 21

```
Arg Ala Ser Gln Ser Val Ser Ser Ser Phe Phe Ala
1               5                   10
```

<210> SEQ ID NO 22
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 22

Gly Ala Ser Ser Arg Ala Thr
1               5

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 23

Gln Gln Tyr Tyr Asp Ser Ser Ala Ile Thr
1               5                   10

<210> SEQ ID NO 24
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 24

Asn Tyr Trp Ile Ala
1               5

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 25

Ile Ile Tyr Pro Gly Asp Ser Asp Ile Arg Tyr Ser Pro Ser Phe Gln
1               5                   10                  15

Gly

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 26

His Asp Ile Glu Gly Phe Asp Tyr
1               5

<210> SEQ ID NO 27
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide construct
<220> FEATURE:
<221> NAME/KEY: CDS
```

<222> LOCATION: (1)..(351)

<400> SEQUENCE: 27

```
gag gtg cag ctg gtg cag tct gga gca gag gtg aaa aag ccc ggg gag      48
Glu Val Gln Leu Val Gln Ser Gly Ala Glu Val Lys Lys Pro Gly Glu
1               5                   10                  15 tct ctg aag atc tcc tgt aag ggt tct gga tac atc ttt acc aat tac      96
Ser Leu Lys Ile Ser Cys Lys Gly Ser Gly Tyr Ile Phe Thr Asn Tyr
            20                  25                  30 tgg atc gcc tgg gtg cgc cag atg ccc ggt aaa ggc ctg gag tcg atg     144
Trp Ile Ala Trp Val Arg Gln Met Pro Gly Lys Gly Leu Glu Ser Met
        35                  40                  45 ggg atc atc tat cct ggt gac tct gat atc aga tac agc ccg tcc ttc     192
Gly Ile Ile Tyr Pro Gly Asp Ser Asp Ile Arg Tyr Ser Pro Ser Phe
    50                  55                  60 caa ggc cag gtc acc atc tca gcc gac aag tcc atc acc acc gcc tac     240
Gln Gly Gln Val Thr Ile Ser Ala Asp Lys Ser Ile Thr Thr Ala Tyr
65                  70                  75                  80 ctg cag tgg agc agt ctg aag gcc tca gac acc gcc atg tat tac tgt     288
Leu Gln Trp Ser Ser Leu Lys Ala Ser Asp Thr Ala Met Tyr Tyr Cys
                85                  90                  95 gcg aga cat gac ata gag ggg ttt gac tac tgg ggc cgg gga acc ctg     336
Ala Arg His Asp Ile Glu Gly Phe Asp Tyr Trp Gly Arg Gly Thr Leu
            100                 105                 110 gtc acc gtc tcc tca                                                 351
Val Thr Val Ser Ser
        115
```

<210> SEQ ID NO 28
<211> LENGTH: 117
<212> TYPE: PRT
<213> ORGANISM: Artificial Sequence
<220> FEATURE:
<223> OTHER INFORMATION: Description of Artificial Sequence: Synthetic polypeptide construct

<400> SEQUENCE: 28

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ile Phe Thr Asn Tyr
            20                  25                  30

Trp Ile Ala Trp Val Arg Gln Met Pro Gly Lys Gly Leu Glu Ser Met
        35                  40                  45

Gly Ile Ile Tyr Pro Gly Asp Ser Asp Ile Arg Tyr Ser Pro Ser Phe
    50                  55                  60

Gln Gly Gln Val Thr Ile Ser Ala Asp Lys Ser Ile Thr Thr Ala Tyr
65                  70                  75                  80

Leu Gln Trp Ser Ser Leu Lys Ala Ser Asp Thr Ala Met Tyr Tyr Cys
                85                  90                  95

Ala Arg His Asp Ile Glu Gly Phe Asp Tyr Trp Gly Arg Gly Thr Leu
            100                 105                 110

Val Thr Val Ser Ser
        115
```

<210> SEQ ID NO 29
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide construct

```
<220> FEATURE:
<221> NAME/KEY: CDS
<222> LOCATION: (1)..(324)

<400> SEQUENCE: 29 gaa att gtg ttg acg cag tct cca ggc acc ctg tct ttg tct cca ggg      48
Glu Ile Val Leu Thr Gln Ser Pro Gly Thr Leu Ser Leu Ser Pro Gly
1               5                   10                  15 gaa aga gcc acc ctc tcc tgc agg gcc agt cag agt gtt agc agc agc      96
Glu Arg Ala Thr Leu Ser Cys Arg Ala Ser Gln Ser Val Ser Ser Ser
            20                  25                  30 ttc ttc gcc tgg tac cag cag aaa cct ggc cag gct ccc agg ctc ctc     144
Phe Phe Ala Trp Tyr Gln Gln Lys Pro Gly Gln Ala Pro Arg Leu Leu
        35                  40                  45 atc tat ggt gca tcc agc agg gcc act ggc atc cca gac agg tta agt     192
Ile Tyr Gly Ala Ser Ser Arg Ala Thr Gly Ile Pro Asp Arg Leu Ser
    50                  55                  60 ggc agt ggg tct ggg aca gac ttc act ctc acc atc acc aga ctg gag     240
Gly Ser Gly Ser Gly Thr Asp Phe Thr Leu Thr Ile Thr Arg Leu Glu
65                  70                  75                  80 cct gaa gat ttt gca gtg tat tac tgt cag cag tat gat agc tca gcg     288
Pro Glu Asp Phe Ala Val Tyr Tyr Cys Gln Gln Tyr Asp Ser Ser Ala
                85                  90                  95 atc acc ttc ggc caa ggg aca cga ctg gag att aaa                     324
Ile Thr Phe Gly Gln Gly Thr Arg Leu Glu Ile Lys
            100                 105

<210> SEQ ID NO 30
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 30

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Phe Phe Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Leu Ser
    50                  55                  60

Gly Ser Gly Ser Gly Thr Asp Phe Thr Leu Thr Ile Thr Arg Leu Glu
65                  70                  75                  80

Pro Glu Asp Phe Ala Val Tyr Tyr Cys Gln Gln Tyr Asp Ser Ser Ala
                85                  90                  95

Ile Thr Phe Gly Gln Gly Thr Arg Leu Glu Ile Lys
            100                 105

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 31

Arg Ala Ser Gln Ser Val Ser Ser Ser Phe Phe Ala
1               5                   10
```

```
<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 32

Gly Ala Ser Ser Arg Ala Thr
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 33

Gln Gln Tyr Asp Ser Ser Ala Ile Thr
1               5

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 34

Asn Tyr Trp Ile Ala
1               5

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 35

Ile Ile Tyr Pro Gly Asp Ser Asp Ile Arg Tyr Ser Pro Ser Phe Gln
1               5                   10                  15

Gly

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide construct

<400> SEQUENCE: 36

His Asp Ile Glu Gly Phe Asp Tyr
1               5

<210> SEQ ID NO 37
<211> LENGTH: 351
<212> TYPE: DNA
<213> ORGANISM: Artificial Sequence
<220> FEATURE:
```

<223> OTHER INFORMATION: Description of Artificial Sequence: Synthetic
      polynucleotide construct
<220> FEATURE:
<221> NAME/KEY: CDS
<222> LOCATION: (1)..(351)

<400> SEQUENCE: 37

```
gag gtg cag ctg gtg cag tct gga gca gag gtg aaa aag ccc ggg gag      48
Glu Val Gln Leu Val Gln Ser Gly Ala Glu Val Lys Lys Pro Gly Glu
1               5                   10                  15 tct ctg aag atc tcc tgt aag ggt tct gga tac atc ttt acc aac tac      96
Ser Leu Lys Ile Ser Cys Lys Gly Ser Gly Tyr Ile Phe Thr Asn Tyr
            20                  25                  30 tgg atc gcc tgg gtg cgc cag atg ccc ggt aaa ggc ctg gag tcg atg     144
Trp Ile Ala Trp Val Arg Gln Met Pro Gly Lys Gly Leu Glu Ser Met
        35                  40                  45 ggg atc atc tat cct ggt gac tct gat atc aga tac agc ccg tcc ttc     192
Gly Ile Ile Tyr Pro Gly Asp Ser Asp Ile Arg Tyr Ser Pro Ser Phe
    50                  55                  60 caa ggc cag gtc acc atc tca gcc gac aag tcc atc acc acc gcc tac     240
Gln Gly Gln Val Thr Ile Ser Ala Asp Lys Ser Ile Thr Thr Ala Tyr
65                  70                  75                  80 ctg cag tgg agc agt ctg aag gcc tca gac acc gcc atg tat tac tgt     288
Leu Gln Trp Ser Ser Leu Lys Ala Ser Asp Thr Ala Met Tyr Tyr Cys
                85                  90                  95 gcg aga cat gac ata gag ggg ttt gac tac tgg ggc cgg gga acc ctg     336
Ala Arg His Asp Ile Glu Gly Phe Asp Tyr Trp Gly Arg Gly Thr Leu
            100                 105                 110 gtc acc gtc tcc tca                                                  351
Val Thr Val Ser Ser
        115
```

<210> SEQ ID NO 38
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 38

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ile Phe Thr Asn Tyr
            20                  25                  30

Trp Ile Ala Trp Val Arg Gln Met Pro Gly Lys Gly Leu Glu Ser Met
        35                  40                  45

Gly Ile Ile Tyr Pro Gly Asp Ser Asp Ile Arg Tyr Ser Pro Ser Phe
    50                  55                  60

Gln Gly Gln Val Thr Ile Ser Ala Asp Lys Ser Ile Thr Thr Ala Tyr
65                  70                  75                  80

Leu Gln Trp Ser Ser Leu Lys Ala Ser Asp Thr Ala Met Tyr Tyr Cys
                85                  90                  95

Ala Arg His Asp Ile Glu Gly Phe Asp Tyr Trp Gly Arg Gly Thr Leu
            100                 105                 110

Val Thr Val Ser Ser
        115
```

<210> SEQ ID NO 39
<211> LENGTH: 324
<212> TYPE: DNA

<213> ORGANISM: Artificial Sequence
<220> FEATURE:
<223> OTHER INFORMATION: Description of Artificial Sequence: Synthetic
      polynucleotide construct
<220> FEATURE:
<221> NAME/KEY: CDS
<222> LOCATION: (1)..(324)

<400> SEQUENCE: 39

```
gaa att gtg ttg acg cag tct cca ggc acc ctg tct ttg tct cca ggg      48
Glu Ile Val Leu Thr Gln Ser Pro Gly Thr Leu Ser Leu Ser Pro Gly
1               5                   10                  15 gaa aga gcc acc ctc tcc tgc agg gcc agt cag agt gtt agc agc agc      96
Glu Arg Ala Thr Leu Ser Cys Arg Ala Ser Gln Ser Val Ser Ser Ser
                20                  25                  30 ttc ttc gcc tgg tac cag cag aaa cct ggc cag gct ccc agg ctc ctc     144
Phe Phe Ala Trp Tyr Gln Gln Lys Pro Gly Gln Ala Pro Arg Leu Leu
            35                  40                  45 atc tat ggt gca tcc agc agg gcc act ggc atc cca gac agg tta agt     192
Ile Tyr Gly Ala Ser Ser Arg Ala Thr Gly Ile Pro Asp Arg Leu Ser
        50                  55                  60 ggc agt ggg tct ggg aca gac ttc act ctc acc atc acc aga ctg gag     240
Gly Ser Gly Ser Gly Thr Asp Phe Thr Leu Thr Ile Thr Arg Leu Glu
65                  70                  75                  80 cct gaa gat ttt gca gtg tat tac tgt cag cag tat gat agc tca gcg     288
Pro Glu Asp Phe Ala Val Tyr Tyr Cys Gln Gln Tyr Asp Ser Ser Ala
                85                  90                  95 atc acc ttc ggc caa ggg aca cga ctg gag att aaa                     324
Ile Thr Phe Gly Gln Gly Thr Arg Leu Glu Ile Lys
                100                 105
```

<210> SEQ ID NO 40
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 40

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Phe Phe Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Leu Ser
        50                  55                  60

Gly Ser Gly Ser Gly Thr Asp Phe Thr Leu Thr Ile Thr Arg Leu Glu
65                  70                  75                  80

Pro Glu Asp Phe Ala Val Tyr Tyr Cys Gln Gln Tyr Asp Ser Ser Ala
                85                  90                  95

Ile Thr Phe Gly Gln Gly Thr Arg Leu Glu Ile Lys
                100                 105
```

<210> SEQ ID NO 41
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 41

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 42
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 42

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Phe Glu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Ser Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

```
Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 43
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide construct

<400> SEQUENCE: 43
cgtgcccagc acctgaattc gagggggggac cgtcagtctt c                    41

<210> SEQ ID NO 44
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide construct

<400> SEQUENCE: 44
gaagactgac ggtccccccct cgaattcagg tgctgggcac g                    41

<210> SEQ ID NO 45
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide construct

<400> SEQUENCE: 45
ccaacaaagc cctcccagcc tccatcgaga aaaccatctc c                     41

<210> SEQ ID NO 46
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide construct

<400> SEQUENCE: 46
ggagatggtt ttctcgatgg aggctgggag ggctttgttg g                     41

<210> SEQ ID NO 47
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide construct
```

<400> SEQUENCE: 47
ggtcccccat gcccaccatg cccagcacct g    31

<210> SEQ ID NO 48
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide construct

<400> SEQUENCE: 48
caggtgctgg gcatggtggg catgggggac c    31

<210> SEQ ID NO 49
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide construct

<400> SEQUENCE: 49
ccagcacctg agttcgaggg gggaccatca gtc    33

<210> SEQ ID NO 50
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide construct

<400> SEQUENCE: 50
gactgatggt cccccctcga actcaggtgc tgg    33

<210> SEQ ID NO 51
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 51

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys

```
                130                 135                 140
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Ala Ser Ile Glu Lys Thr Ile Ser Lys Ala Lys Gly
                210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 52
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 52

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Phe Glu Gly Gly Pro Ser Val Phe Leu Phe Pro Pro
            115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Ser Ile Glu Lys Thr Ile Ser Lys Ala Lys Gly
    210                 215                 220
Gln Pro Arg Glu Pro Gln Val Tyr Thr Leu Pro Pro Ser Arg Glu Glu
225                 230                 235                 240
Met Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 53
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 53

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Ser Leu Gly Thr Lys Thr
65                  70                  75                  80
Tyr Thr Cys Asn Val Asp His Lys Pro Ser Asn Thr Lys Val Asp Lys
                85                  90                  95
Arg Val Glu Ser Lys Tyr Gly Pro Pro Cys Pro Pro Cys Pro Ala Pro
            100                 105                 110
Glu Phe Glu Gly Gly Pro Ser Val Phe Leu Phe Pro Pro Lys Pro Lys
        115                 120                 125
Asp Thr Leu Met Ile Ser Arg Thr Pro Glu Val Thr Cys Val Val Val
    130                 135                 140
Asp Val Ser Gln Glu Asp Pro Glu Val Gln Phe Asn Trp Tyr Val Asp
145                 150                 155                 160
Gly Val Glu Val His Asn Ala Lys Thr Lys Pro Arg Glu Glu Gln Phe
                165                 170                 175
Asn Ser Thr Tyr Arg Val Val Ser Val Leu Thr Val Leu His Gln Asp
            180                 185                 190
```

```
Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 54
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide construct

<400> SEQUENCE: 54

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220
```

```
                  210                215                220
Glu Pro Gln Val Tyr Thr Leu Pro Pro Ser Gln Glu Met Thr Lys
225                 230                235                240

Asn Gln Val Ser Leu Thr Cys Leu Val Lys Gly Phe Tyr Pro Ser Asp
                245                250                255

Ile Ala Val Glu Trp Glu Ser Asn Gly Gln Pro Glu Asn Asn Tyr Lys
                260                265                270

Thr Thr Pro Pro Val Leu Asp Ser Asp Gly Ser Phe Phe Leu Tyr Ser
            275                280                285

Arg Leu Thr Val Asp Lys Ser Arg Trp Gln Glu Gly Asn Val Phe Ser
            290                295                300

Cys Ser Val Met His Glu Ala Leu His Asn His Tyr Thr Gln Lys Ser
305                 310                315                320

Leu Ser Leu Ser Leu Gly Lys
                325
```

ANTI-IFNAR1 ANTIBODIES WITH REDUCED FC LIGAND AFFINITY

This application is a continuation of U.S. application Ser. No. 15/711,197 filed Sep. 21, 2017, said application Ser. No. 15/711,197 is continuation of U.S. application Ser. No. 12/866,579 filed on Nov. 9, 2010, said application Ser. No. 12/866,579 is a U.S. National Stage application of International Application No. PCT/US2009/033358, filed Feb. 6, 2009, said Application No. PCT/US2009/033358 claims benefit under 35 U.S.C. § 119(e) of the following U.S. Provisional Application Nos. 61/006,962 filed Feb. 8, 2008, 61/034,618 filed Mar. 7, 2007, and 61/049,970 filed May 2, 2008. Each of the above listed applications is incorporated by reference herein in its entirety for all purposes.

REFERENCE TO THE SEQUENCE LISTING

This application incorporates by reference a Sequence Listing submitted with this application as text file entitled IFNAR-US-110-CNT_SEQUENCE_LISTING.txt created on Sep. 14, 2017, and having a size of 48,534 kilobytes.

1. FIELD OF THE INVENTION

The present invention relates to isolated antibodies and compositions specific for the interferon alpha receptor 1 (IFNAR1) with reduced affinity for Fc ligands. The invention also comprises nucleic acids encoding such antibodies, complementary nucleic acids, vectors, host cells, and methods of making and using thereof, including therapeutic compositions, formulations, administrations and devices.

2. BACKGROUND OF THE INVENTION 2.1 Interferons:

Type I interferons (IFN) (IFNα, IFNβ, IFNω, IFN-τ) are a family of structurally related cytokines having antiviral, antitumor and immunomodulatory effects (Hardy et al. (2001) Blood 97:473; Cutrone and Langer (2001) J. Biol. Chem. 276:17140). The human IFNα locus includes two subfamilies. The first subfamily consists of 14 non-allelic genes and 4 pseudogenes having at least 80% homology. The second subfamily, αII or omega (ω), contains 5 pseudogenes and 1 functional gene which exhibits 70% homology with the IFNα genes (Weissmann and Weber (1986) Prog. Nucl. Acid Res. Mol. Biol., 33:251-300). The subtypes of IFNα have different specific activities but they possess the same biological spectrum (Streuli et al. (1981) Proc. Natl. Acad. Sci. USA 78:2848) and have the same cellular receptor (Agnet M. et al. in "Interferon 5" Ed. I. Gresser p. 1-22, Academic Press, London 1983). Interferon alpha subtypes have been identified with the following nomenclature: IFNα 1, 2a, 2b, 4, 4b, 5, 6, 7, 8, 10, 14, 16, 17, and 21.

The interferon β (IFNβ) is encoded by a single gene, which has approximately 50% homology with the IFNα genes.

Interferon γ, which is produced by activated lymphocytes, does not possess any homology with the alpha/beta interferons and it does not react with their receptor.

2.1.1 Interferon Receptors:

All human type 1 interferons bind to a cell surface receptor (IFN alpha receptor, IFNAR) consisting of two transmembrane proteins, IFNAR1 and IFNAR2 (Uze et. al. (1990) Cell 60:225; Novick et al. (1994) Cell 77:391). IFNAR1 is essential for high affinity binding and differential specificity of the IFNAR complex (Cutrone et al. 2001 J. Bio Chem 276(20):17140-8) While functional differences for each of the type I IFN subtypes have not been identified, it is thought that each may exhibit different interactions with the IFNAR receptor components leading to potentially diverse signaling outcomes (Cook et al. (1996) J. Biol. Chem. 271:13448). In particular, studies utilizing mutant forms of IFNAR1 and IFNAR2 suggested that alpha and beta interferons signal differently through the receptor by interacting differentially with respective chains (Lewerenz et al. (1998) J. Mol. Biol. 282:585).

2.1.2 Function of Interferons:

Early functional studies of type I IFNs focused on innate defense against viral infections (Haller et al. (1981) J. Exp. Med. 154:199; Lindenmann et al. (1981) Methods Enzymol. 78:181). More recent studies, however, implicate type I IFNs as potent immunoregulatory cytokines in the adaptive immune response. Specifically, type I IFNs have been shown to facilitate differentiation of naïve T cells along the Th1 pathway (Brinkmann et al. (1993) J. Exp. Med. 178:1655), to enhance antibody production (Finkelman et al. (1991) J. Exp. Med. 174:1179) and to support the functional activity and survival of memory T cells (Santini et al. (2000) J. Exp. Med. 191:1777; Tough et al. (1996) Science 272:1947).

Recent work by a number of groups suggests that IFNα may enhance the maturation or activation of dendritic cells (DCs) (Santini, et al. (2000) J. Exp. Med. 191:1777; Luft et al. (1998) J. Immunol. 161:1947; Luft et al. (2002) Int. Immunol. 14:367; Radvanyi et al. (1999) Scand. J. Immunol. 50:499). Furthermore, increased expression of type I interferons has been described in numerous autoimmune diseases (Foulis et al. (1987) Lancet 2:1423; Hooks et al. (1982) Arthritis Rheum. 25:396; Hertzog et al. (1988) Clin. Immunol. Immunopathol. 48:192; Hopkins and Meager (1988) Clin. Exp. Immunol. 73:88; Arvin and Miller (1984) Arthritis Rheum. 27:582). The most studied examples of this are insulin-dependent diabetes mellitus (IDDM) (Foulis (1987)) and systemic lupus erythematosus (SLE) (Hooks (1982)), which are associated with elevated levels of IFNα, and rheumatoid arthritis (RA) (Hertzog (1988), Hopkins and Meager (1988), Arvin and Miller (1984)), in which IFNβ may play a more significant role.

Moreover, administration of interferon α has been reported to exacerbate underlying disease in patients with psoriasis and multiple sclerosis and to induce an SLE like syndrome in patients without a previous history of autoimmune disease. Interferon α has also been shown to induce glomerulonephritis in normal mice and to accelerate the onset of the spontaneous autoimmune disease of NZB/W mice. Further, IFNα therapy has been shown in some cases to lead to undesired side effects, including fever and neurological disorders. Hence there are pathological situations in which inhibition of Type I IFN activity may be beneficial to the patient and a need exists for agents effective in inhibiting Type I IFN activity.

2.1.3 Antibody Effector Functions:

The Fc region of an antibody interacts with a number of ligands (also referred herein as "Fc ligands" which include but are not limited to agents that specifically bind to the Fc region of antibodies, such as Fc receptors and C1q) including Fc receptors and C1q, imparting an array of important functional capabilities referred to as effector functions. The Fc receptors mediate communication between antibodies and the cellular arm of the immune system (Raghavan et al., 1996, Annu Rev Cell Dev Biol 12:181-220; Ravetch et al., 2001, Annu Rev Immunol 19:275-290). In humans this protein family includes FcγRI (CD64), including isoforms FcγRIA, FcγRIB, and FcγRIC; FcγRII (CD32), including isoforms FcγRIIA, FcγRIIB, and FcγRIIC; and FcγRIII (CD16), including isoforms FcγRIIIA and FcγRIIIB (Jefferis et al., 2002, Immunol Lett 82:57-65). These receptors typically have an extracellular domain that mediates binding to Fc, a membrane spanning region, and an intracellular domain that may mediate some signaling event within the cell. These receptors are expressed in a variety of immune cells including monocytes, macrophages, neutrophils, dendritic cells, eosinophils, mast cells, platelets, B cells, large granular lymphocytes, Langerhans' cells, natural killer (NK) cells, and T cells. Formation of the Fc/FcγR complex recruits these effector cells to sites of bound antigen, typically resulting in signaling events within the cells and important subsequent immune responses such as release of inflammation mediators, B cell activation, endocytosis, phagocytosis, and cytotoxic attack. The ability to mediate cytotoxic and phagocytic effector functions is a potential mechanism by which antibodies destroy targeted cells. The cell-mediated reaction wherein nonspecific cytotoxic cells that express FcγRs recognize bound antibody on a target cell and subsequently cause lysis of the target cell is referred to as antibody dependent cell-mediated cytotoxicity (ADCC) (Raghavan et al., 1996, Annu Rev Cell Dev Biol 12:181-220; Ghetie et al., 2000, Annu Rev Immunol 18:739-766; Ravetch et al., 2001, Annu Rev Immunol 19:275-290). The cell-mediated reaction wherein nonspecific cytotoxic cells that express FcγRs recognize bound antibody on a target cell and subsequently cause phagocytosis of the target cell is referred to as antibody dependent cell-mediated phagocytosis (ADCP). In addition, an overlapping site on the Fc region of the molecule also controls the activation of a cell independent cytotoxic function mediated by complement, otherwise known as complement dependent cytotoxicity (CDC).

2.1.4 The Different Types of Human FcγR:

Human FcγRs are divided into three distinct classes: FcγRI (CD64), FcγRII (CD32) and FcγRIII (CD16). FcγRI is a high affinity receptor ($K_a$: $10^{-8}$-$10^{-9}$ $M^{-1}$) and binds both immune complexes and monomeric IgG molecules while the Fc receptors FcγRII and FcγRIII exhibit lower affinities ($<10^{-7}$ $M^{-1}$ and $2-3\times10^{-7}$ respectively) (Gessner J. E. et al., 1998, Annn Hematology 76:231-48). Signaling through the FcγRs is either through an immunoreceptor tyrosine-based activation motif (ITAM) or immunoreceptor tyrosine-based inhibitory motif (ITIM) for all the transmembrane receptors (Presta 2006, Adv Drug Deli Rev 58:640-656).

The 72 kDa extracellular glycoprotein FcγRI is mainly expressed on myeloid cells such as monocytes, macrophages CD4+ progenitor cells and may elicit the ADCC, endocytosis, and phagocytosis responses (Siberil et al. 2006, J Immunol Lett 106:111-118).

The 40 kDa FcγRII group of receptors (A, B and C isoforms) exhibit extracellular domains but do not contain active signal transduction domains. These receptors propagate signals through phosphorylation of a cytoplasmic tail domain (Amigorena S. et al., 1992 Science. 256:1808-12). The FcγRIIA is mainly expressed on monocytes, macrophages, neutrophils, and platelets whereas the FcγRIIC receptor has only been identified on NK cells. These two receptors have been shown to initiate ADCC, endocytosis, phagocytosis and inflammatory mediator release (Cassel et al. 1993. Mol Immunol 30:451-60). By contrast, the FcγRIIB (B1 and B2 types) receptors are expressed on B cells, Mast cells, basophils, monocytes, macrophages and dendritic cells and has been shown to downregulate the immune response triggered by the A and C isoforms.

The 50 kDa FcγRIIIA, expressed on NK cells, monocytes, macrophages and a subset of T lymphocytes where it activates ADCC, phagocytosis, endocytosis and cytokine release (Gessner et al.). The FcγRIIIB isoforms is a glycosyl-phosphatidylinositol (GPI) anchored peripheral membrane protein involved in the degranulation and the production of reactive oxygen intermediates (Salmon J. E. et al. 1995 J Clin Inves 95:2877-85).

IgG molecules also exhibit differential isotype specificity for FcγRs. IgG3 molecules bind strongly to all FcγR isoforms. IgG1, the most prevalent isoforms in the blood binds to all FcγRs albeit with a lower affinity for the FcγRIIA/B isoforms. IgG4 is an intermediate binder to FcγR1 and a weak binder to FcγRIIB. Finally, IgG2 binds only weakly to one allelic form of FcγRIIA (FcγRIIA-H131) (Siberil et al. 2006, J Immunol Lett 106:111-118).

2.1.5 Complement

The complement inflammatory cascade is a part of the innate immune response and is crucial to the ability for an individual to ward off infection. Another important Fc ligand is the complement protein C1q. Fc binding to C1q mediates a process called complement dependent cytotoxicity (CDC) (reviewed in Ward et al., 1995, *Ther Immunol* 2:77-94). C1q is capable of binding six antibodies, although binding to two IgGs is sufficient to activate the complement cascade. C1q forms a complex with the C1r and C1s serine proteases to form the C1 complex of the complement pathway.

2.1.6 Regions and Amino-acid Residues of IgG Involved in FcγR Binding

The mapping of human IgG binding sites to different FcγR has been studied extensively. These studies, based on genetically altered IgG molecules have identified a short continuous stretch of amino acid residues (234-238) of the N-terminus part of the CH2 domain as being directly involved in the binding to all FcγRs. Additionally, residues 268, 297, 327 and 329 may impact binding to a subset of FcγRs. Also, multiple residues located in the CH2 and CH3 domains also contribute to FcγR binding (Canfield S M. et al., 1991 J Exp Med 173:1483-91, Chappel M S. Et al. 1991, Proc Nat Acad Sci USA 888:9036-40, Gergely J. et al. 1990 FASEB J 4:3275-83).

2.2 Antibody Therapeutic Related Toxicity

In many circumstances, the binding and stimulation of effector functions mediated by the Fc region of immunoglobulins is highly beneficial, however, in certain instances it may be more advantageous to decrease or eliminate effector function. This is particularly true for those antibodies designed to deliver a drug (e.g., toxins and isotopes) to the target cell where the Fc/FcγR mediated effector functions bring healthy immune cells into the proximity of the deadly payload, resulting in depletion of normal lymphoid tissue along with the target cells (Hutchins et al., 1995, PNAS USA 92:11980-11984; White et al., 2001, Annu Rev Med 52:125-145). In these cases the use of antibodies that poorly recruit complement or effector cells would be of tremendous benefit (see for example, Wu et al., 2000, Cell Immunol 200:16-26; Shields et al., 2001, J. Biol Chem 276:6591-6604; U.S. Pat. Nos. 6,194,551; 5,885,573 and PCT publication WO 04/029207).

In other instances, for example, where blocking the interaction of a widely expressed receptor with its cognate ligand is the objective, it would be advantageous to decrease or eliminate all antibody effector function to reduce unwanted toxicity. Also, in the instance where a therapeutic antibody exhibited promiscuous binding across a number of human tissues it would be prudent to limit the targeting of effector function to a diverse set of tissues to limit toxicity. Although there are certain subclasses of human immunoglobulins that lack specific effector functions, there are no known naturally occurring immunoglobulins that lack all effector functions. An alternate approach would be to engineer or mutate the critical residues in the Fc region that are responsible for effector function. For examples see PCT publications WO2006076594, WO199958572, US20060134709, WO2006047350, WO2006053301, and U.S. Pat. No. 5,624,821 each of which are incorporated by reference in their entireties.

The use of monoclonal antibodies in the treatment of many disease states has been well documented. With the myriad of effector functions that an antibody can trigger, one of the requirements of antibody therapeutics is that they are targeted specifically to a target of interest. For example, but not limited to, the specificity of a target tissue is analyzed by examining the immunohistochemistry (IHC) of a tissue of interest. It is important that the therapeutic only bind to tissues that contain a target of interest. Failure to do so could result in higher toxicity of the antibody therapeutic due to inappropriate activation of effector function elicited at the non-targeted site. If the effector function could be diminished or ablated, the danger of the widespread binding of the therapeutic could be avoided. With all these considerations, there is an unmet need for antibodies with reduced or ablated affinity for at least one Fc ligand responsible for facilitating effector function. Such antibodies would be of particular benefit for use in the treatment of chronic inflammatory and autoimmune conditions.

Citation or discussion of a reference herein shall not be construed as an admission that such is prior art to the present invention.

3. BRIEF DESCRIPTION OF THE FIGURES

For the purpose of illustrating the invention, there are depicted in the drawings certain embodiments on the invention. However, the invention is not limited to the precise arrangements and instrumentalities of the embodiments depicted in the drawings.

FIG. 1A. Nucleic acid (SEQ ID No:7) and amino acid (SEQ ID No:8) sequence alignment of 3F11 VH with the CDR regions are indicated by the overline.

FIG. 1B. Nucleic acid (SEQ ID No:9) and amino acid (SEQ ID No:10) sequence alignment of 3F11 VK with the CDR regions outlined are indicated by the overline.

FIG. 2A. Nucleic acid (SEQ ID No:17) and amino acid (SEQ ID No:18) sequence alignment of 4G5 VH with the CDR regions outlined are indicated by the overline.

FIG. 2B. Nucleic acid (SEQ ID No:19) and amino acid (SEQ ID No:20) sequence alignment of 4G5 VK with the CDR regions outlined are indicated by the overline.

FIG. 3A. Nucleic acid (SEQ ID No:27) and amino acid (SEQ ID No:28) sequence alignment of 11E2 VH with the CDR regions outlined are indicated by the overline.

FIG. 3B. Nucleic acid (SEQ ID No:29) and amino acid (SEQ ID No:30) sequence alignment of 11E2 VK with the CDR regions outlined are indicated by the overline.

FIG. 4A. Nucleic acid (SEQ ID No:37) and amino acid (SEQ ID No:38) sequence alignment of 9D4 VH with the CDR regions outlined are indicated by the overline.

FIG. 4B. Nucleic acid (SEQ ID No:39) and amino acid (SEQ ID No:40) sequence alignment of 9D4 VK with the CDR regions outlined are indicated by the overline.

FIG. 5. Amino acid sequence alignment of heavy chain constant regions for 9D4. Arrows indicate amino acid substitutions (unmodified to modified) to increase stability and reduce affinity to at least one Fc ligand.

FIG. 6A. Immunohistochemical staining profile of human cerebrum tissue treated with various anti-IFNAR1 antibodies. The 9D4 antibody exhibits a lower staining profile when incubated with human cerebrum tissue compared to 4G5 and MDX-1333 antibodies.

FIG. 6B. Immunohistochemical staining profile of human monocytes treated with various anti-IFNAR1 antibodies. As a positive control, various anti-IFNAR1 antibodies were tested for reactivity to human monocytes.

FIG. 7. The anti-IFNAR1 antibody 9D4 inhibits IFNα signaling in a cell based STAT activation assay. Treatment with antibody 9D4 inhibits STAT1/3/4 tyrosine phosphorylation in response to stimulation with interferon alpha as determined by Western Blot analysis with commercially available STAT antibodies.

FIG. 8. Anti-IFNAR1 antibodies block signaling of various concentrations of pDC Cell derived Type I IFNs. Presented are the IC50 values for antibody 9D4 blocking IFN signaling in a luciferase reporter assay utilizing type I IFN supernatants purified from 3 independent donors. Included are the relative amounts of IFNα, IFNβ, and IFNω in each purified type I interferon supernatant.

FIGS. 9 A, B, C. Anti-IFNAR1 antibodies 9D4, 9D4-DM (Double Mutant), and 9D4-TM (Triple Mutant) exhibit similar binding characteristics. Presented are data representing the unmodified 9D4 antibody along with 2 modified antibodies, 9D4-DM and 9D4-TM. The modified antibodies exhibit similar IFNAR1 binding characteristics to the unmodified antibody.

Figure 10A:
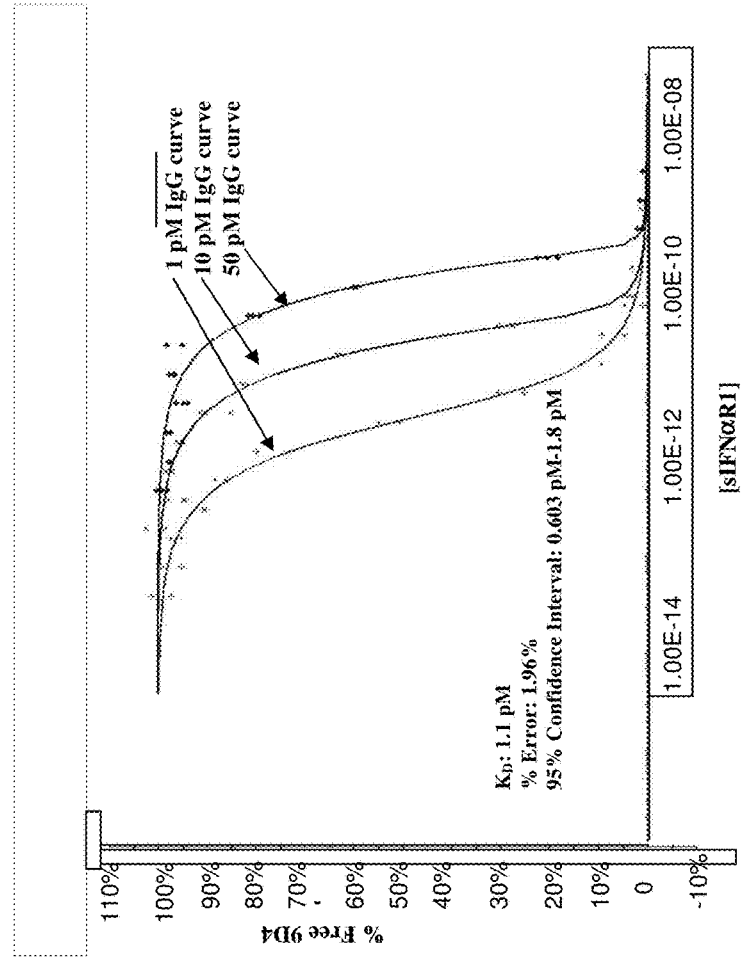

FIG. 10A. The anti-IFNAR1 antibody 9D4 binds soluble interferon alpha receptor (sIFNαR1). Presented are equilibrium binding data that demonstrate dose dependent binding of 9D4 to soluble interferon alpha receptor.

FIG. 10B. Determination of the Kd of 9D4 on human PBMCs. Presented is the dissociation constant determination of 9D4 measured by binding to human PBMCs.

Figure 11:
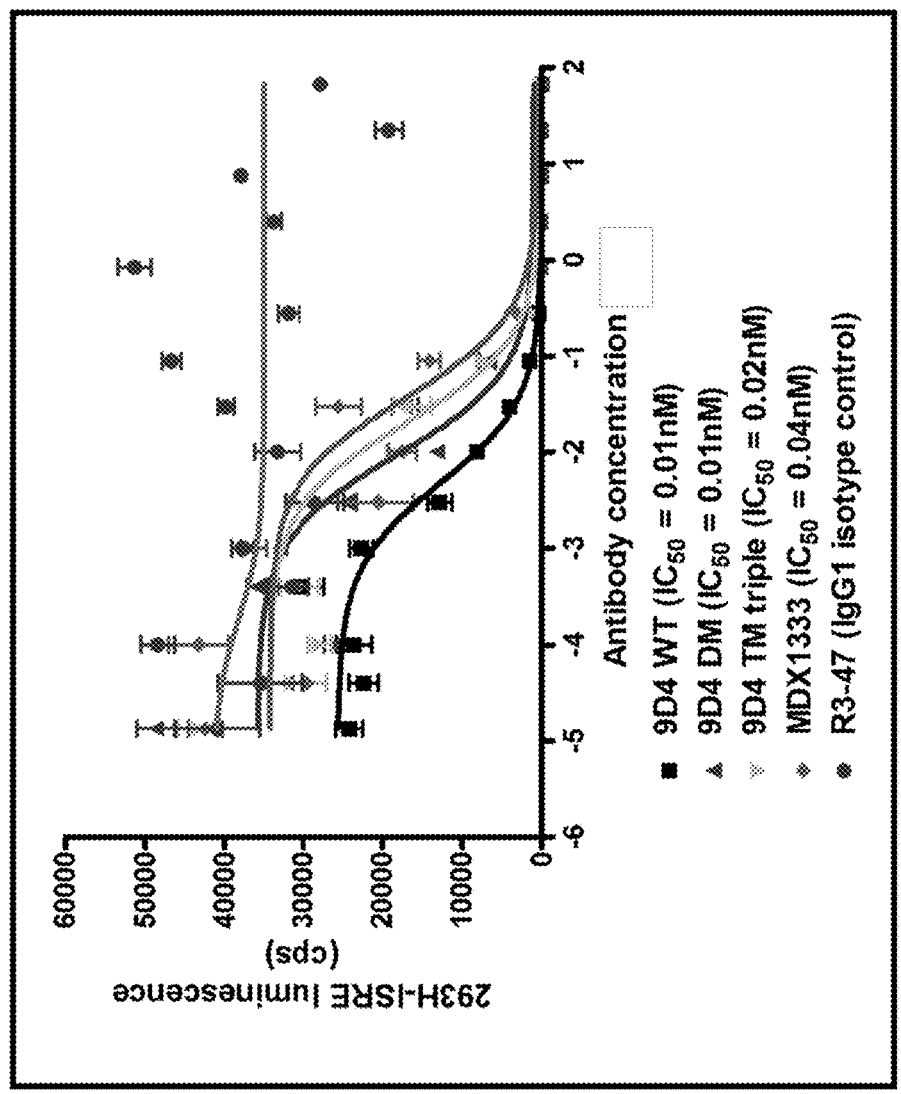

FIG. 11. Anti-IFNAR1 antibodies inhibit IFNα induced signaling in a luciferase reporter assay. Anti-IFNAR1 antibodies including unmodified and modified antibodies demonstrate similar IC50 values for blocking Leukocyte IFN signaling in a luciferase reporter assay system.

FIG. 12A. Determination of the isoelectric point of 9D4 (unmodified) and modified 9D4 antibodies. Presented is an IEF gel documenting the relative pI values for the 9D4 WT (unmodified), 9D4-DM, and 9D4-TM antibodies.

Figure 12B:
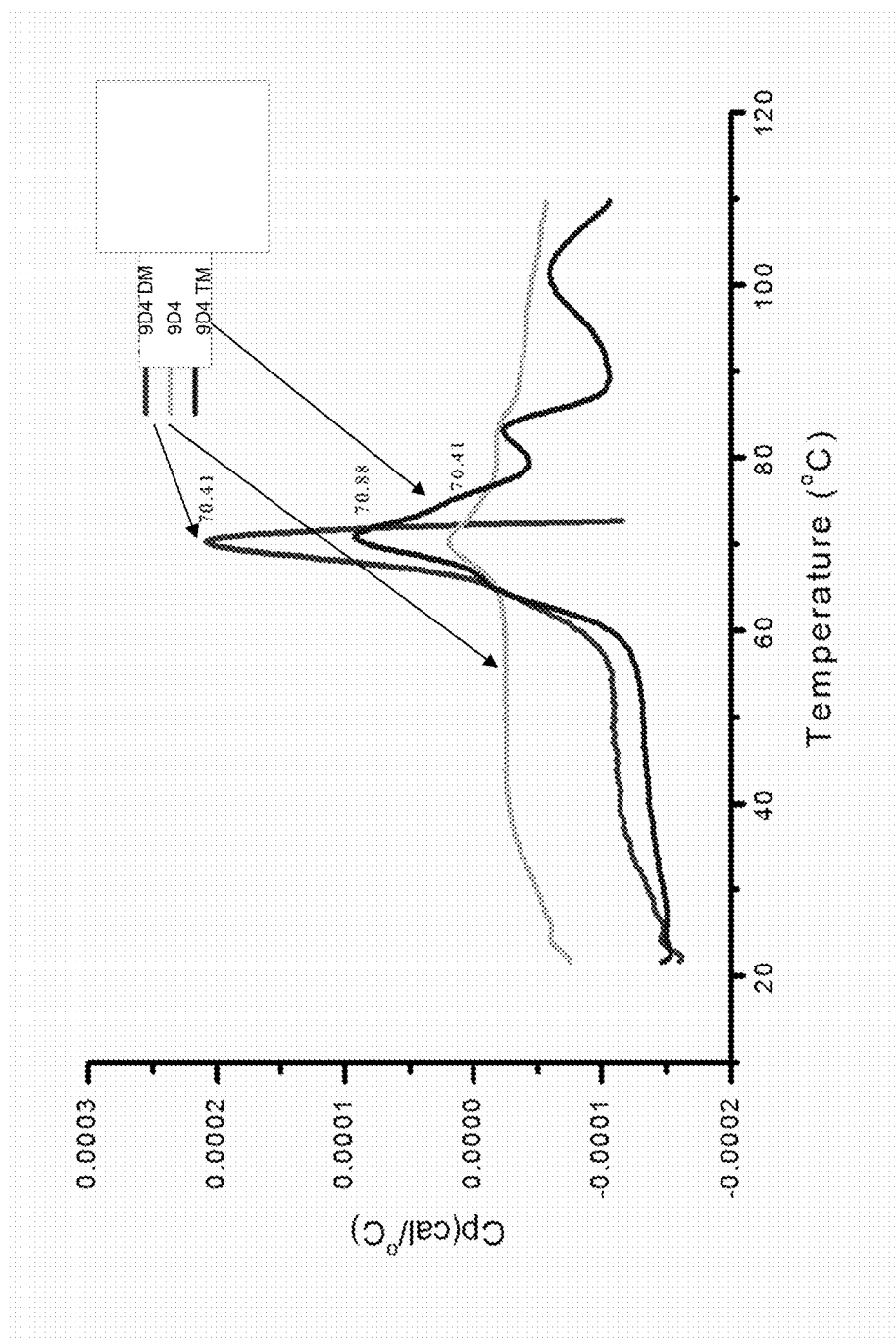

FIG. 12B. Determination of the thermal melting temperatures of 9D4 (unmodified) and modified 9D4 antibodies. Presented here is a melt cure documenting the relative melting temperatures (Tm) for the 9D4, 9D4-DM, and 9D4-TM antibodies.

Figure 13:
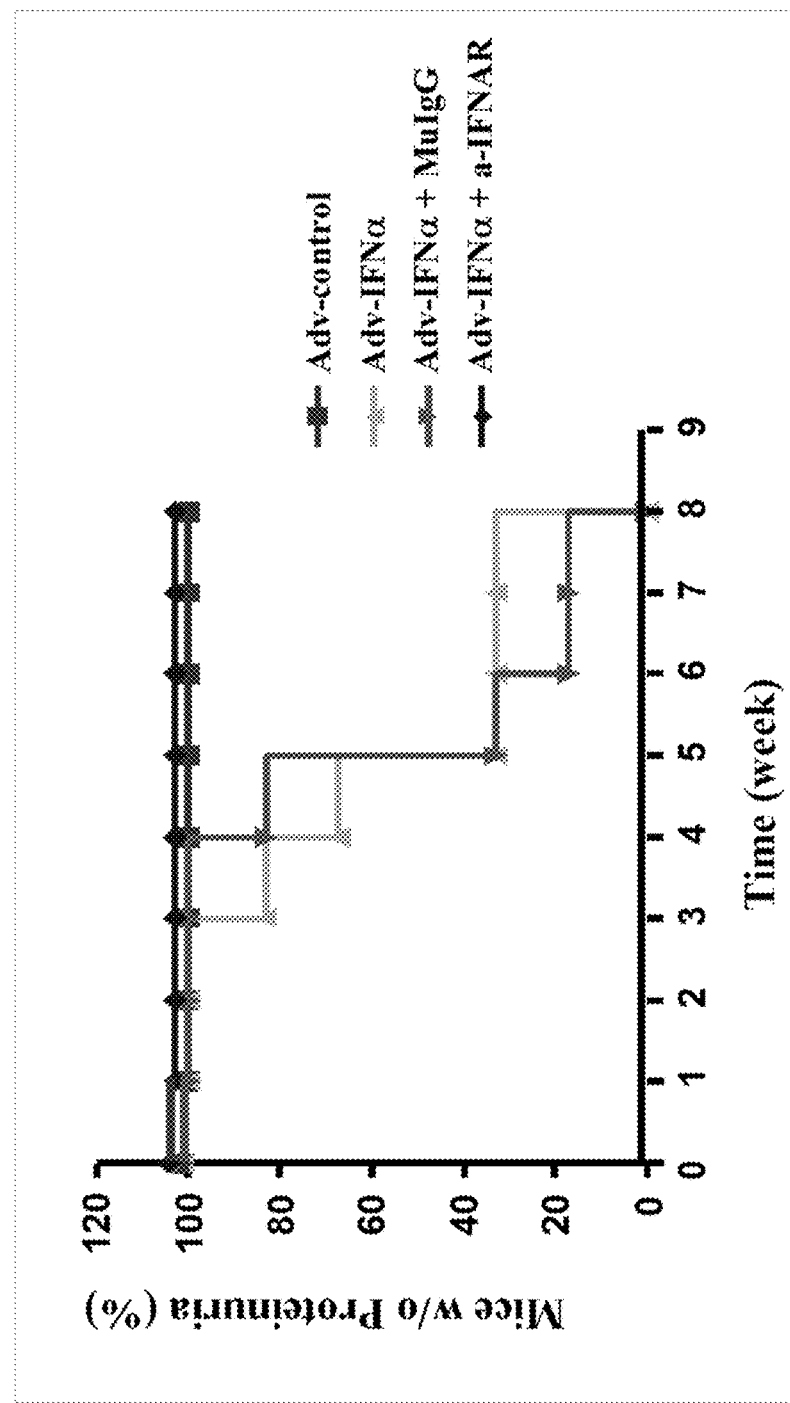

FIG. 13. Prophylactic treatment with anti-IFNAR antibodies blocks Adv-IFNα induced proteinuria. Mice treated with control vector, Adv-IFNα, Adv-IFNα+isotype control pretreatment, and Adv-IFNα+anti-IFNAR pretreatment were analyzed for proteinuria over 9 weeks. Mice pretreated with anti-IFNAR did not exhibit proteinuria after IFNα challenge.

Figure 14:
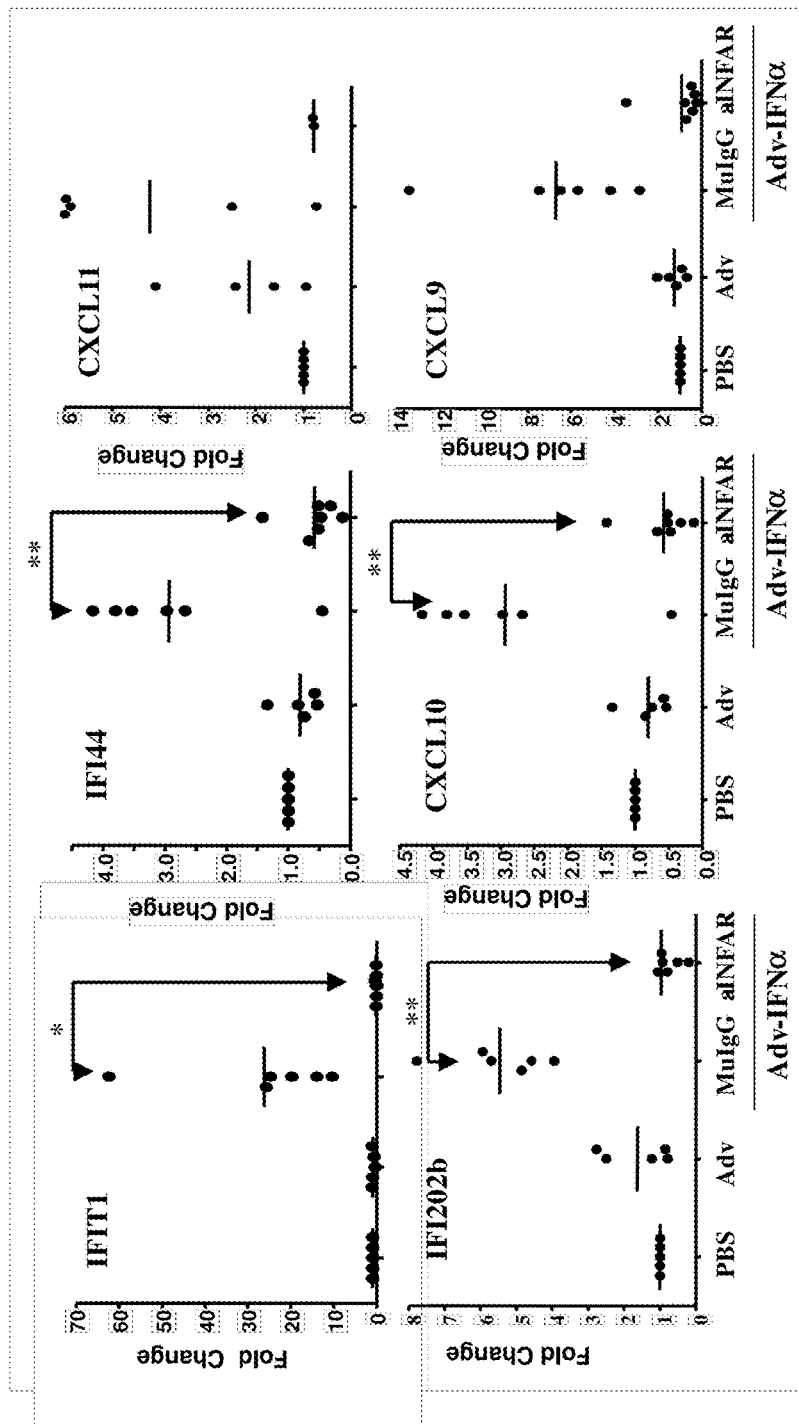

FIG. 14. Prophylactic treatment with anti-IFNAR antibodies blocks the upregulation of IFNα responsive genes (IFIT1, IFI44, CXCL11, IFI202b, CXCL19, CXCL9) in blood. Mice pre-treated with anti-IFNAR antibodies did not exhibit not upregulated selected IFNα responsive genes upon challenge with adenovirus encoded IFN alpha as compared to mice pretreated with control virus, PBS, or isotype IgG controls. Presented are the relative expression of six genes known to be responsive to IFNα in blood samples taken from mice 3 weeks post IFNα induction by infection with Adv-IFNα.

Figure 15:
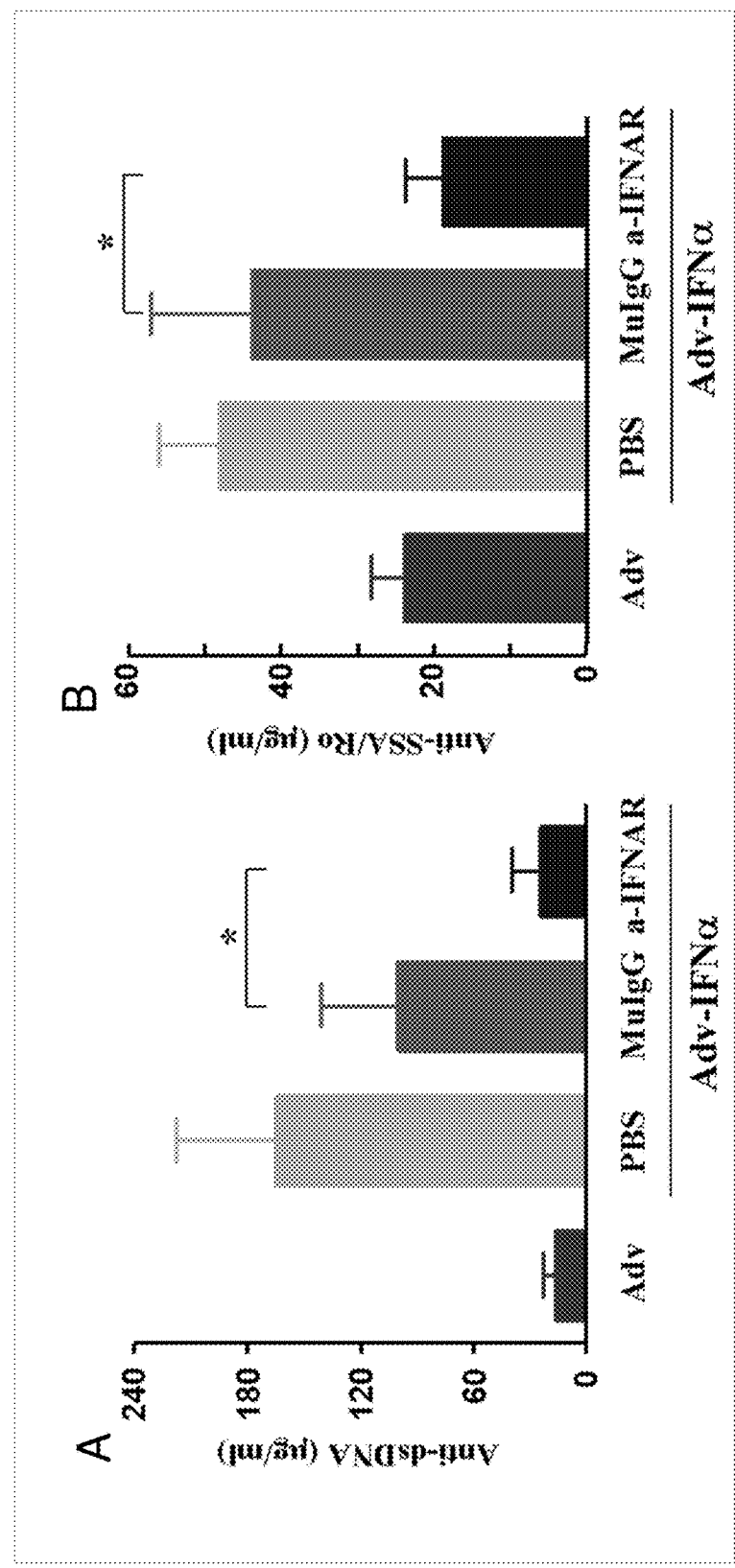

FIGS. 15 A, B. Prophylactic treatment with anti-IFNAR antibodies blocks IFNα induced autoantibody production. Mice pre-treated with anti-IFNAR antibodies did not exhibit elevated autoantibody production upon challenge with adenovirus encoded IFNα as compared to mice pretreated with control virus, PBS or isotype IgG controls. Presented are the concentrations of anti-dsDNA and anti-SSA/Ro in blood samples taken from mice 6 weeks post IFNα induction by infection with Adv-IFNα.

Figure 16:
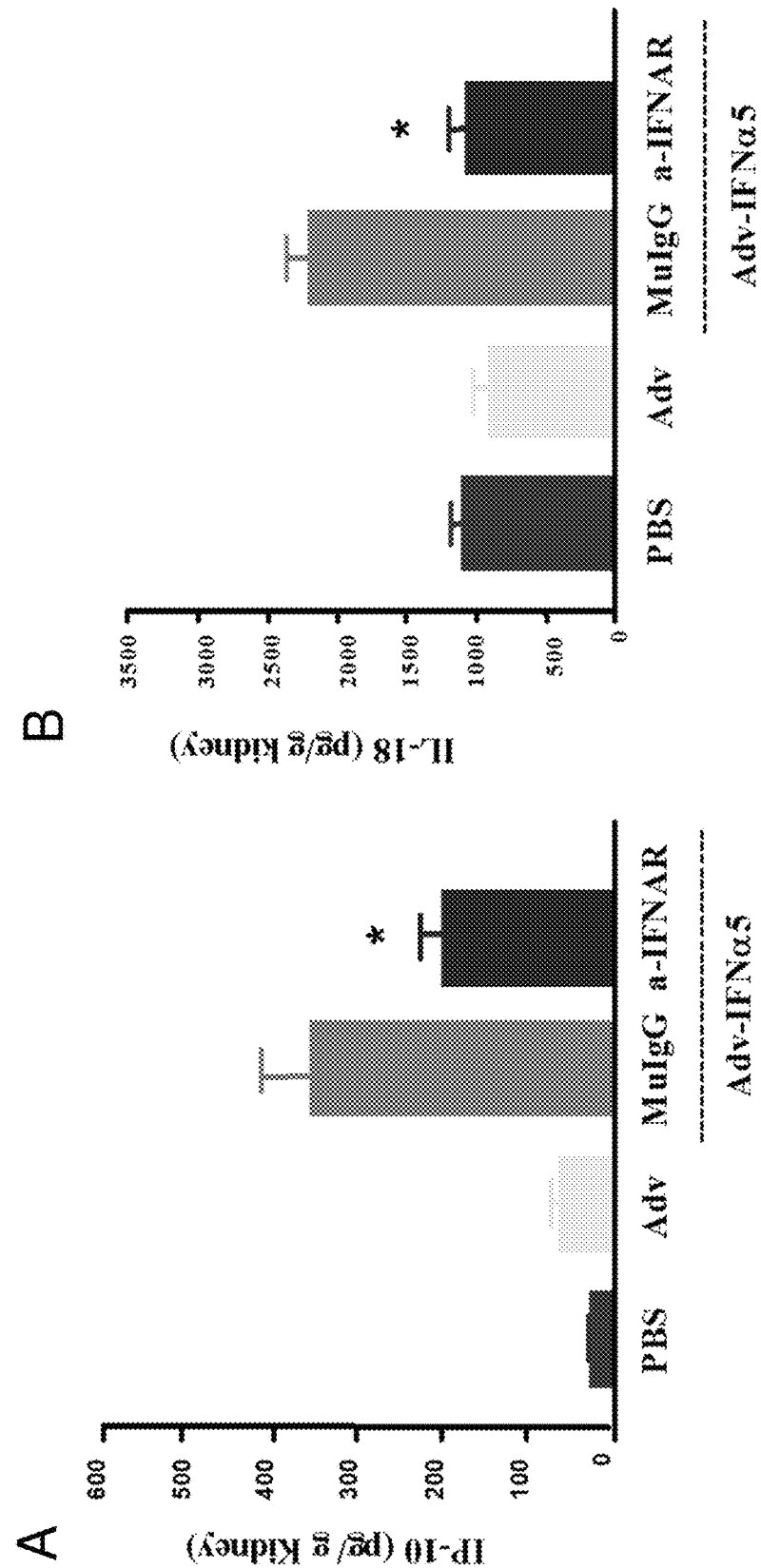

FIGS. 16 A, B. Prophylactic treatment with anti-IFNAR antibodies blocks the upregulation of cytokines in the kidney. Mice pretreated with anti-IFNAR antibodies did not exhibit upregulated cytokines in the kidney upon challenge with adenovirus encoded IFNα5 as compared to mice pretreated with, control virus, PBS or isotype IgG controls. Presented are the measurement of IP-10, and IL-18 levels in kidney samples taken from mice 6 weeks post IFNα induction by infection with Adv-IFNα5.

Figure 17:
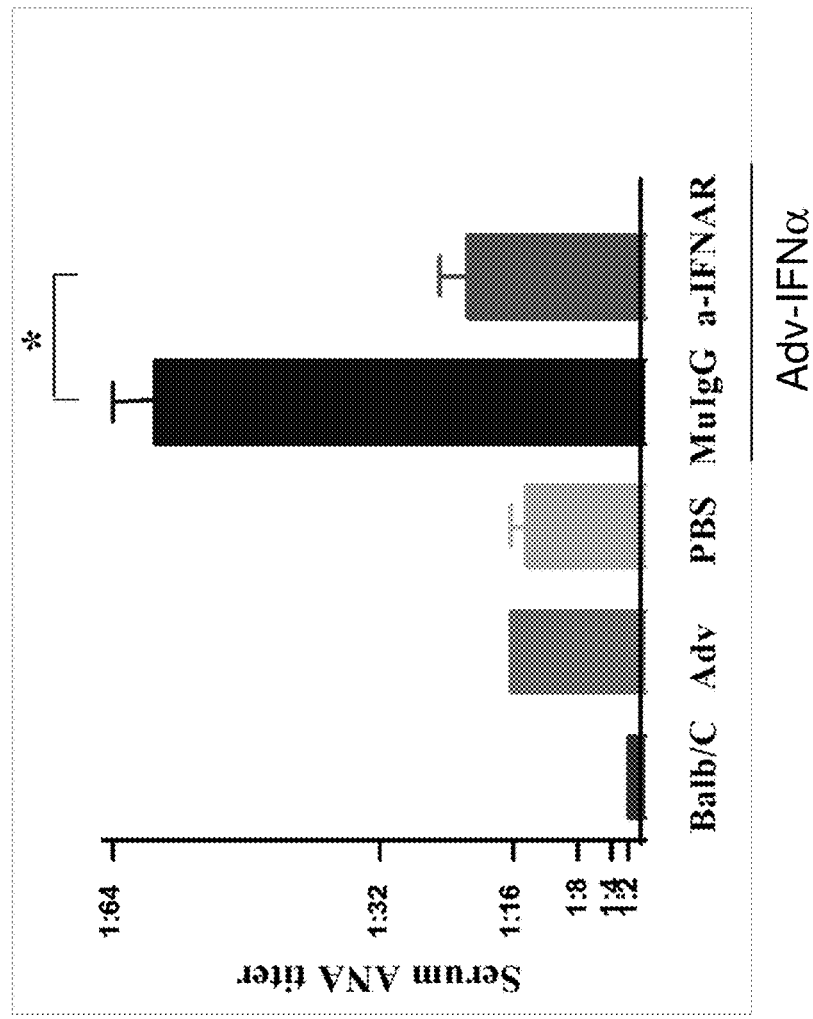

FIG. 17. Prophylactic treatment with anti-IFNAR antibodies blocks IFN induced autoantibody production. Presented here are the relative titers of anti-nuclear antigen (ANA) antibodies from mouse serum. Mice pretreated with anti-IFNAR antibodies exhibited lower ANA serum titers after IFN challenge than mice pretreated with control virus, PBS, or isotype control.

FIG. 18. Antibody mediated inhibition of SLE plasma mediated Dendritic cell development. Presented are the results of 5 individual experiments in which IFN derived from SLE patients was incubated in the presence of anti-IFNAR1 antibody 9D4 and subsequently added to human monocytes. The presence of anti-IFNAR1 antibody 9D4 inhibited the ability of IFN derived from SLE patients to induce the dendritic cell markers CD38 and CD123 in differentiating monocytes.

Figure 19:
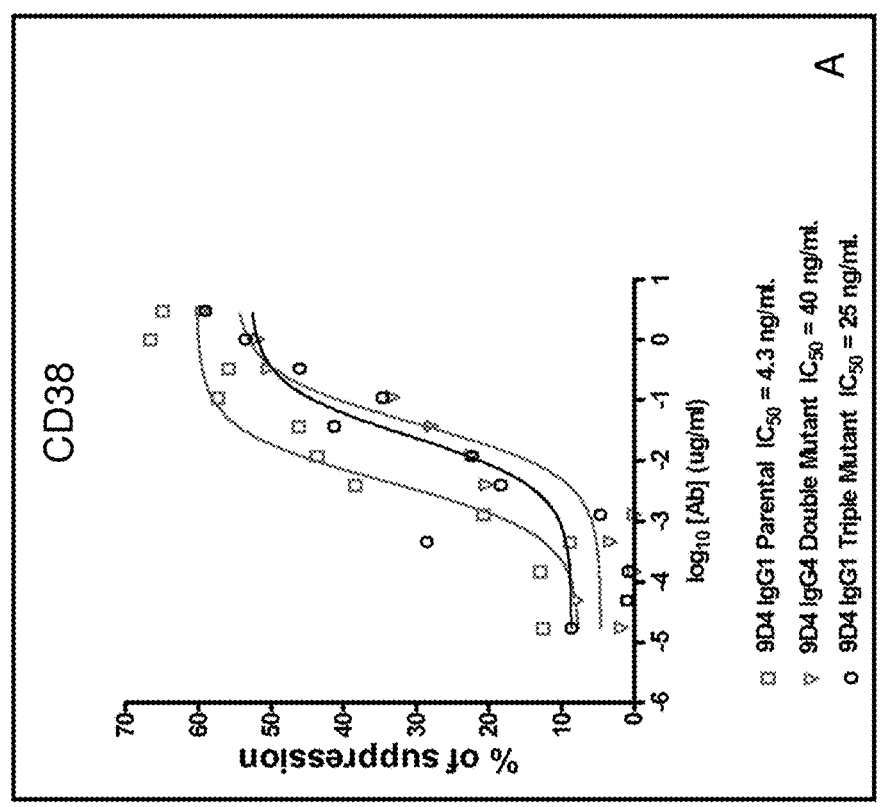
Figure 19:
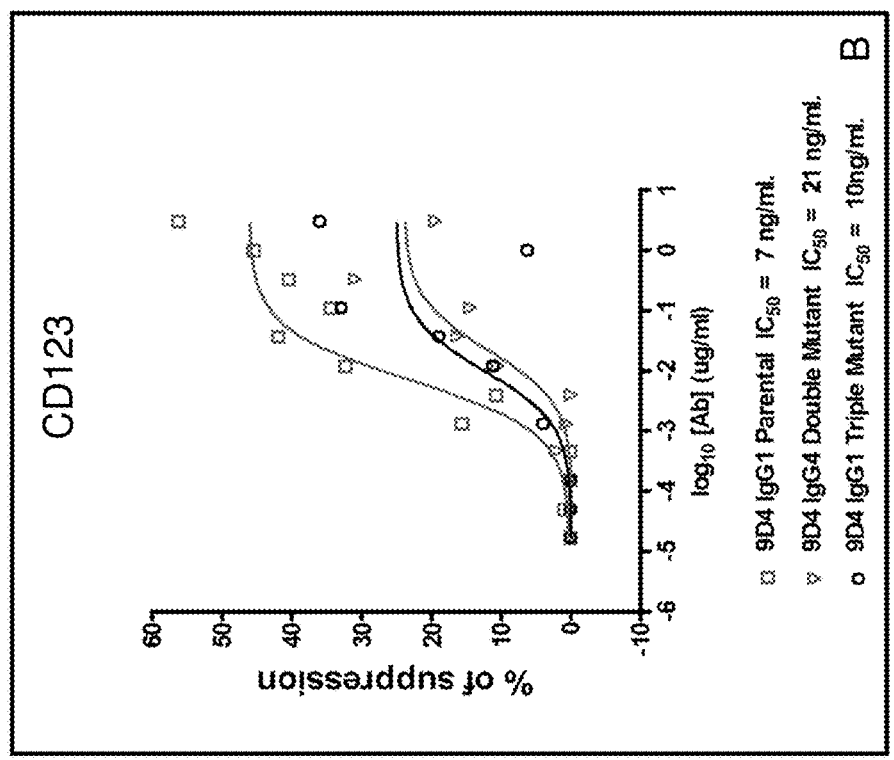

FIG. 19. Anti-IFNAR1 antibodies suppress the expression of CD38, CD123 and CD86 in monocytes stimulated with Leukocyte Interferon. As measured by percent suppression of control stimulated expression, anti-IFNAR1 antibodies 9D4, 9D4-DM and 9D4-TM exhibited similar inhibition profiles for the expression of CD38, CD123 and CD86 in differentiating monocytes.

Figure 20:
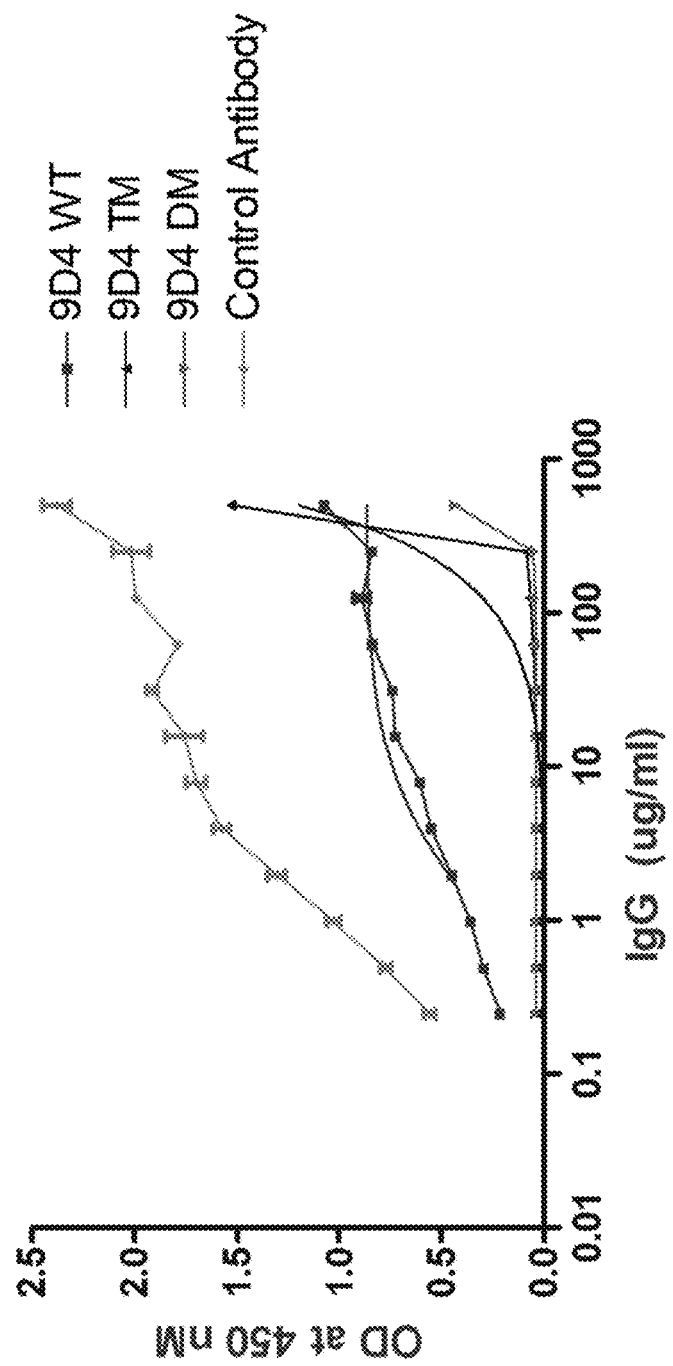

FIG. 20. Modified anti-IFNAR1 antibodies exhibit decreased binding to the Fc receptor FcγRI as compared to unmodified anti-IFNAR1 antibodies. Anti-IFNAR1 antibodies 9D4 (unmodified), 9D4-DM (modified) and 9D4-TM (modified) were analyzed for the ability to bind to plate bound FcγRI in an ELISA experiment. As a positive control for Fc receptor binding, an unrelated unmodified antibody was used (control antibody).

FIG. 21, A, B, C. Modified anti-IFNAR1 antibodies exhibit decreased binding to the Fc receptor FcγRIIIA as compared to unmodified anti-IFNAR1 antibodies. Plate bound unmodified anti-IFNAR1 antibody 9D4(A) and modified anti-IFNAR1 antibodies 9D4-DM (B) and 9D4-TM(C) were analyzed for the ability to bind free FcγRIIIA in an ELISA experimental format.

FIG. 22, A, B, C. Modified anti-IFNAR1 antibodies exhibit decreased binding to the Fc receptor FcγRIIIA. Free unmodified anti-IFNAR1 antibody 9D4(A) and modified anti-IFNAR1 antibodies 9D4-DM(B) and 9D4-TM(C) were analyzed for the ability to bind plate bound FcγRIIIA in an ELISA experimental format.

FIGS. 23 A-E. Neutralization of IFN subtypes in SLE patient serum. As measured by reporter assay, anti-IFNAR1 antibodies MDX-1333, 9D4-WT and 9D4-TM inhibited IFN mediated signaling of α10 (A), Leukocyte interferon (B), α2b (C), ω (D), and (E).

Figure 24:
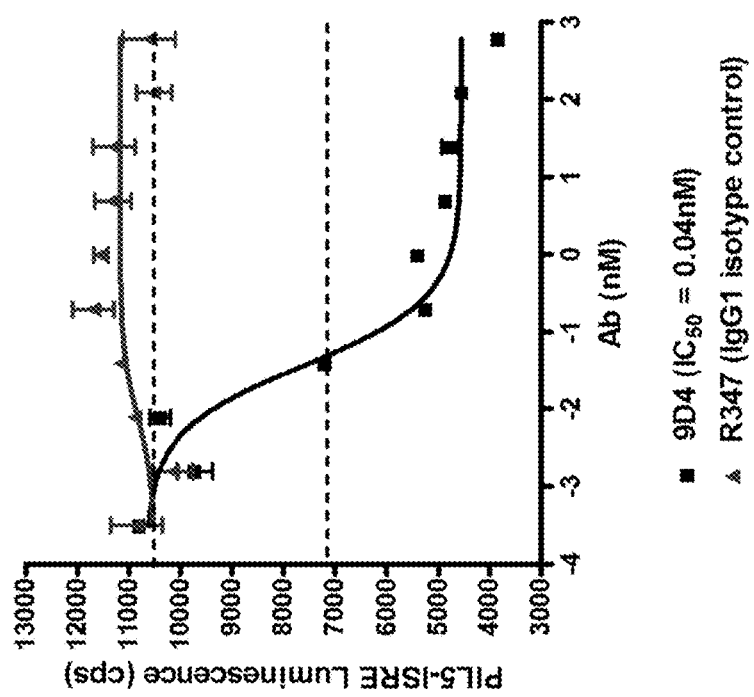

FIG. 24. Anti-IFNAR1 antibodies neutralize type I interferon from SLE patients. By reporter assay, the anti-IFNAR1 antibody, 9D4, inhibited type I interferon mediated signaling as compared to a control, unrelated antibody.

Figure 25:
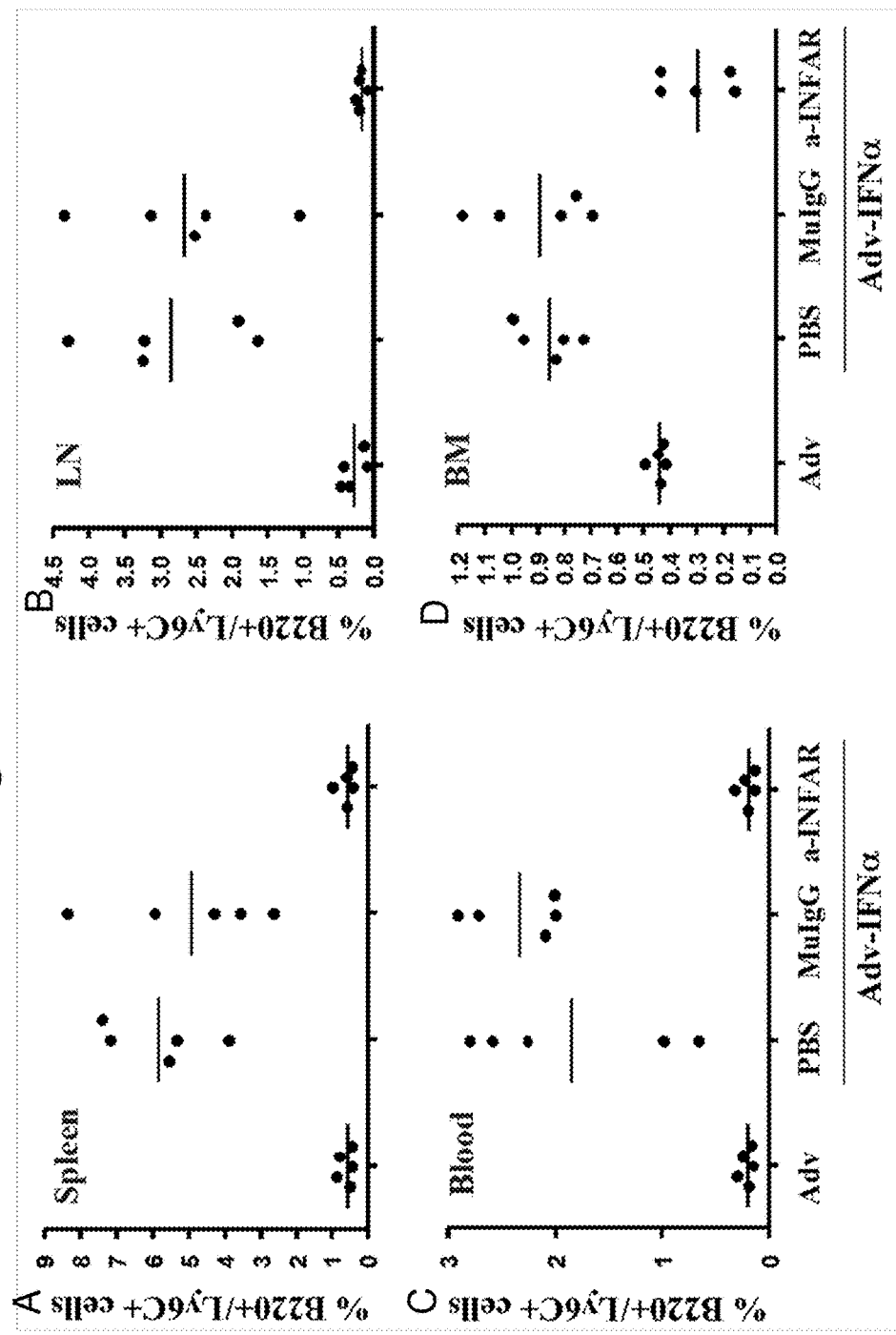

FIGS. 25 A-D. Anti-IFNAR antibodies suppress the IFNα induced pDC population in PBMC's. Anti-IFNAR antibodies blocked the elevation of pDC cells measured by cell surface epitope expression, induced by ectopic adenoviral induced expression of interferon alpha in spleen (A), lymph nodes (B), peripheral blood (C) and bone marrow (D).

Figure 26:
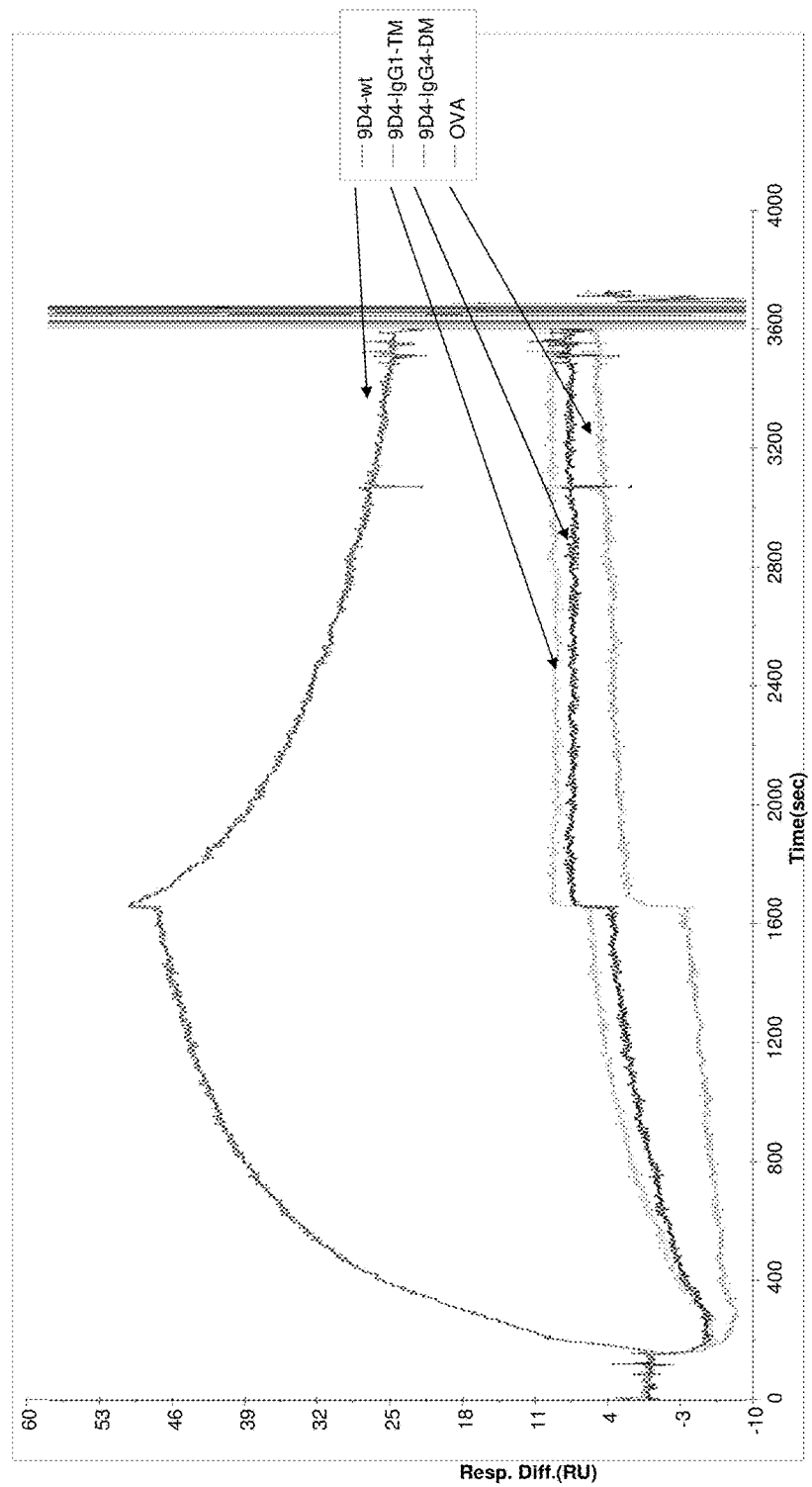

FIG. 26. Binding analysis of anti-IFNAR1 antibodies 9D4-WT, 9D4-DM, and 9D4-TM to the Fc receptor FcγRI was determined by BIACore analysis. Briefly, anti-IFNAR1 antibodies were immobilized and free FcγRI was added to measure affinity. As demonstrated by the tracing, the modified antibodies, 9D4-DM, and 9D4-TM exhibited lower affinities to the free FcγRI as compared to the unmodified 9D4-WT antibody.

FIGS. 27 A-C. Binding analysis of anti-IFNAR1 antibodies 9D4-WT, 9D4-DM, and 9D4-TM to the Fc receptor FcγR1 was determined by BiaCore analysis. Briefly, free anti-IFNAR1 antibodies were passed over immobilized FcγRI to measure affinity. As demonstrated by the tracing, the modified antibodies 9D4-DM (B), and 9D4-TM (C) exhibited lower affinities to the bound FcγRI as compared to the unmodified 9D4-WT (A) antibody.

Figure 28:
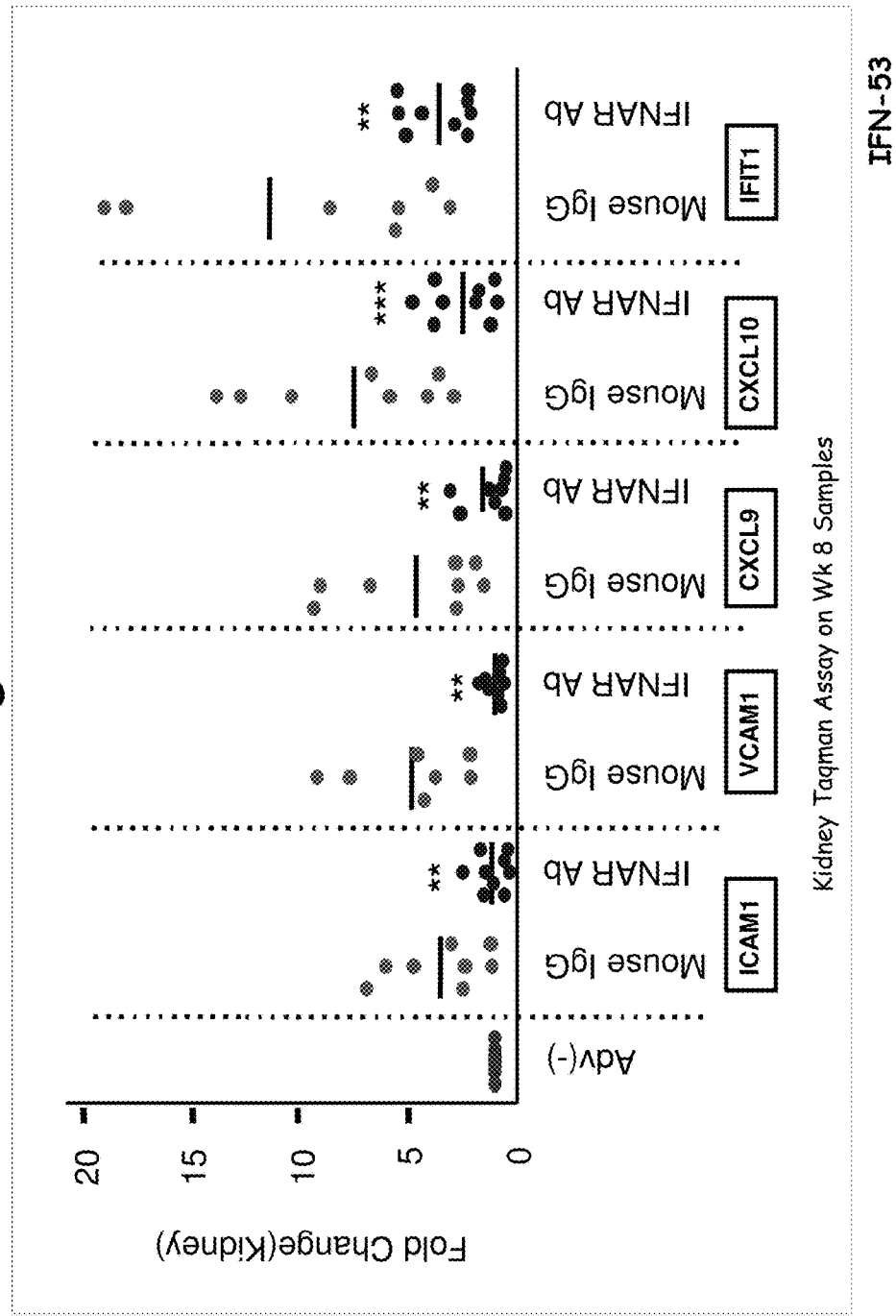

FIG. 28. Anti-IFNAR antibodies inhibit IFNα responsive gene induction in the kidney. Briefly, in the accelerated lupus mouse model, treatment with anti-IFNAR antibodies blocks induction in the kidney of six genes (ICAM1, VCAM1, CXCL9, CXCL10, and IFIT1) mediated by the ectopically expression of IFNα compared to control mice as measured by a Taqman assay.

Figure 29:
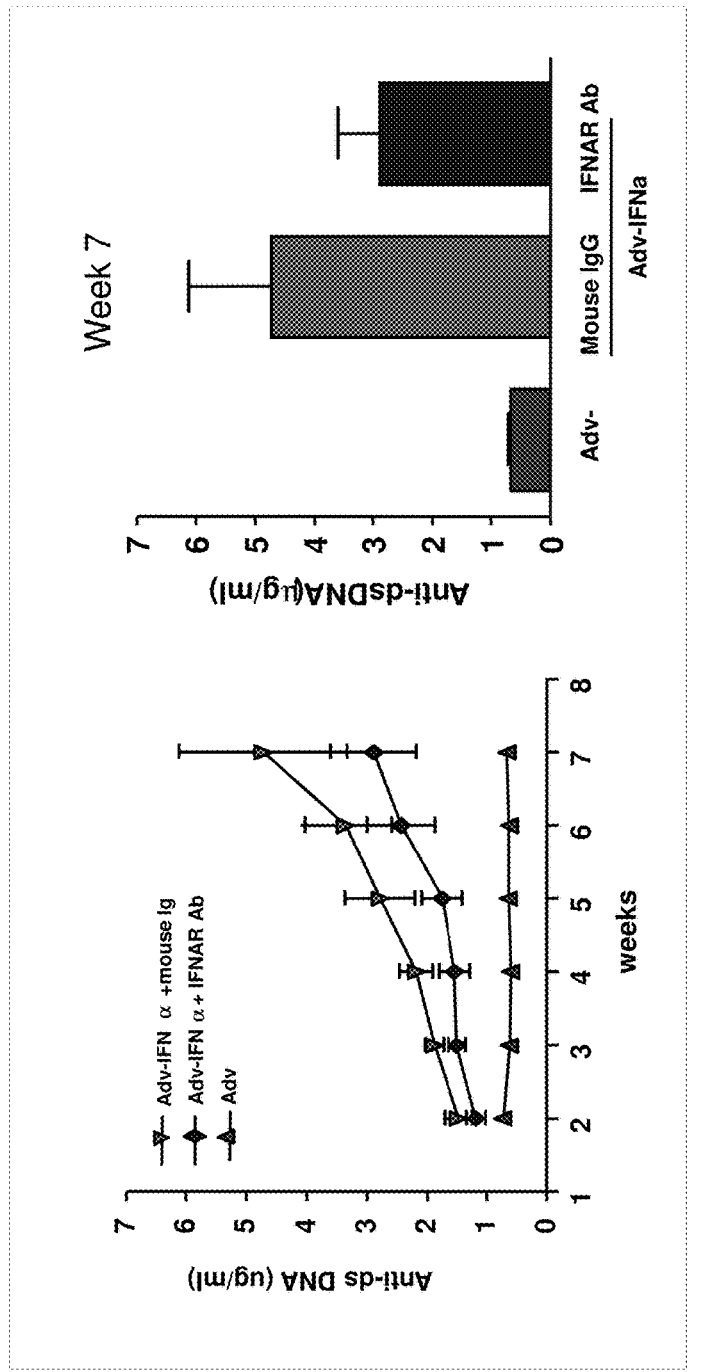

FIG. 29. Anti-IFNAR antibodies inhibit the production of anti-ds DNA antibodies in the accelerated lupus mouse model. Briefly, mice ectopically expressing IFNα and treated with anti-IFNAR antibodies did not accumulate anti-ds DNA antibodies to the same level as mice similarly infected and treated with an IgG control antibody.

Figure 30:
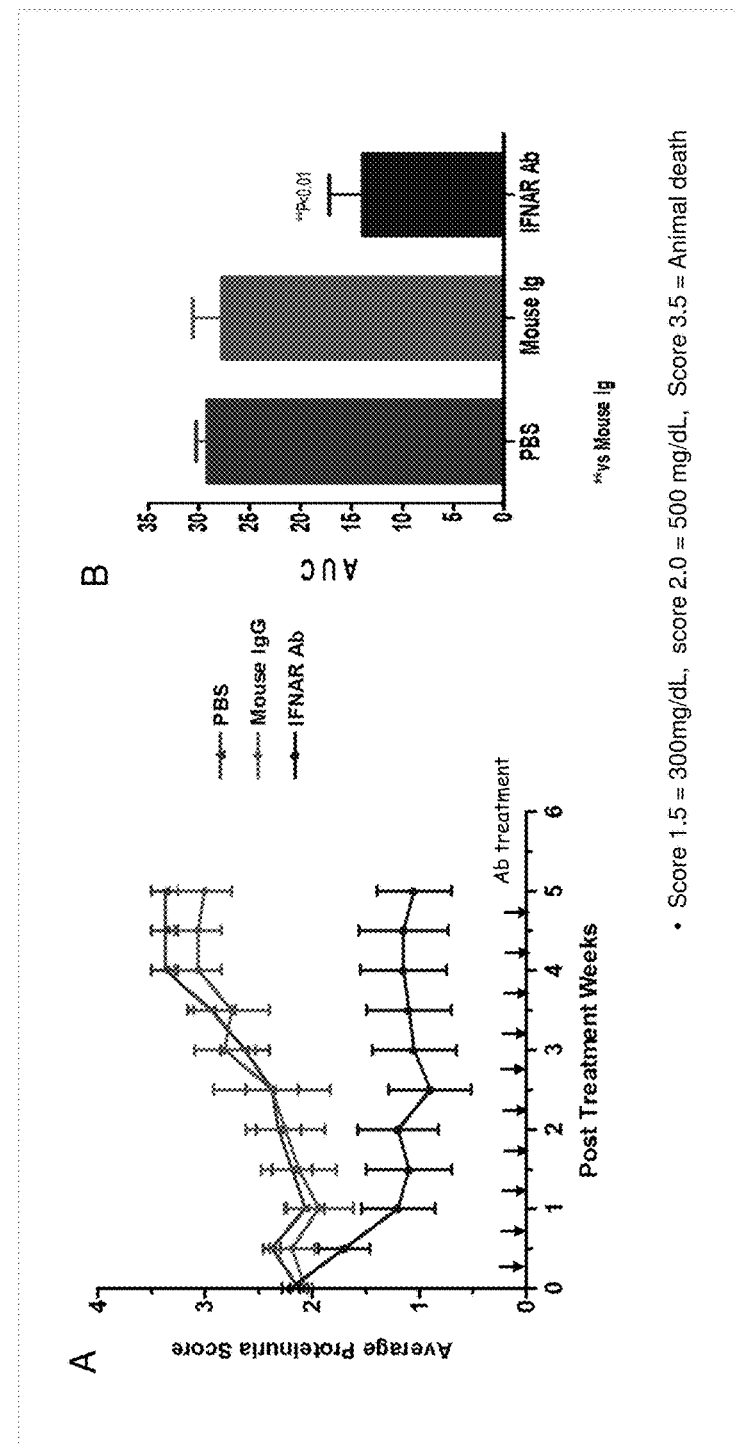

FIG. 30. Anti-IFNAR antibodies are able to reduce proteinuria in a therapeutic setting of the accelerated lupus mouse model. (A) Briefly, mice ectopically expressing IFNα developed Lupus like symptoms, such as proteinuria. In a therapeutic study, anti-IFNAR antibodies were administered to mice once a threshold proteinuria score was reached. Anti-IFNAR antibodies, PBS, or control IgG were administered semi-weekly over a 5 week time course. The anti-IFNAR antibody treated group exhibited decreased severity of proteinuria during the experiment compared to PBS only or control IgG treated groups.

Figure 31:
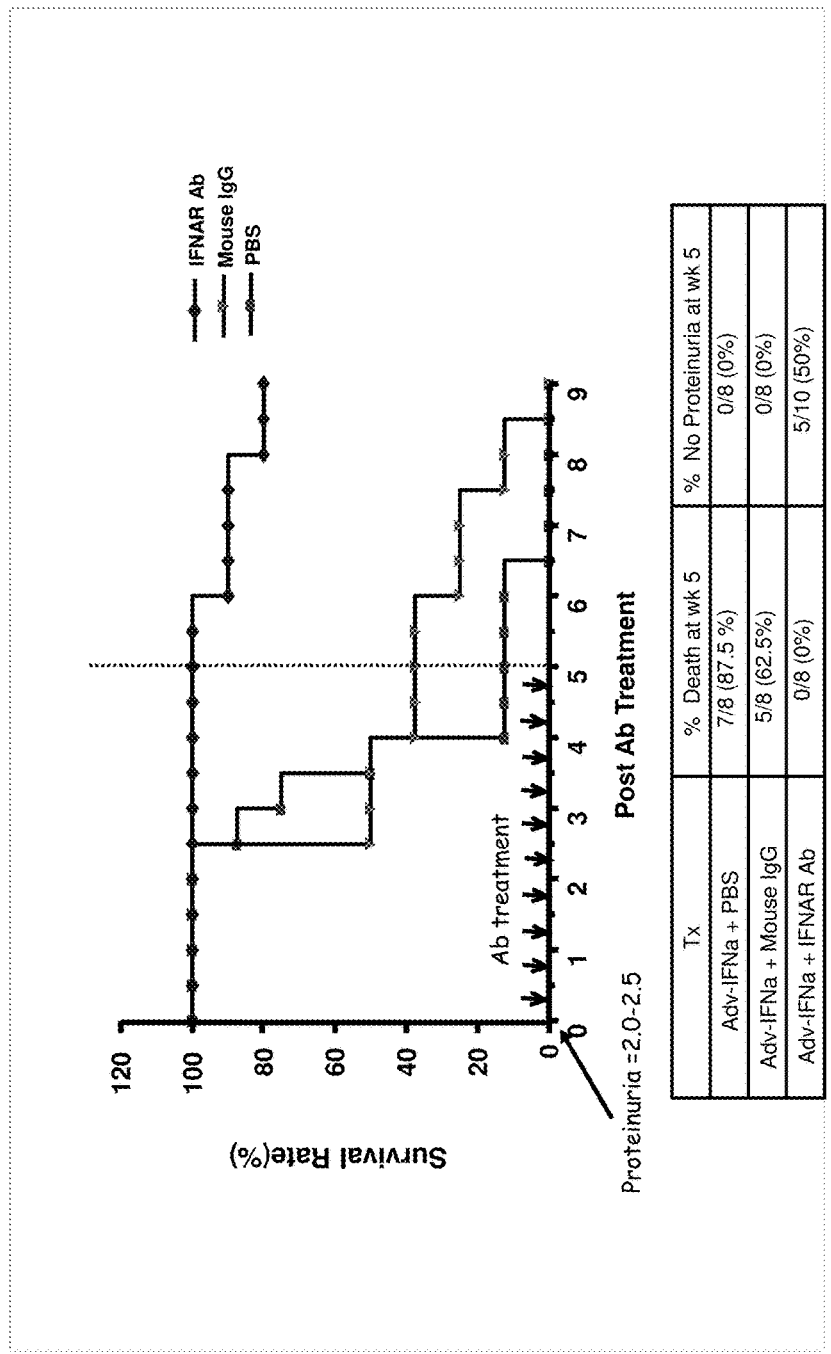

FIG. 31. Anti-IFNAR antibodies are able to increase survival in a therapeutic setting of the accelerated lupus mouse model. (A) Briefly, mice ectopically expressing IFNα had a reduced survival rate at about 8 weeks after developing Lupus-like symptoms such as proteinuria. In the therapeutic study, anti-IFNAR antibodies were administered to mice once a threshold proteinuria score was reached. Anti-IFNAR antibodies, PBS, or control IgG were administered semi-weekly over a 5 week time course. After the five weeks, antibody treatment was stopped and the mortality tracked for all three treatment groups. The anti-IFNAR antibody treated group exhibited a much lower rate of mortality than the PBS alone, or control IgG groups, which both exhibited complete mortality by 9 weeks.

Figure 32:
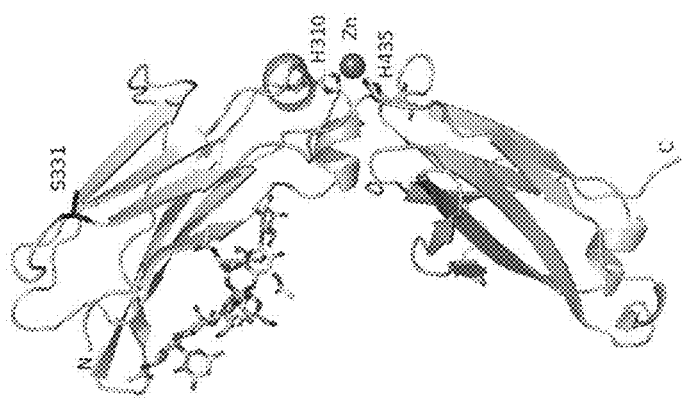

FIG. 32. Representation of the asymmetric unit contents of the crystals of Fc-TM that comprises L234F/L235E/P331S mutations. The mutation P331 is indicated in red. One zinc ion is chelated by two spatially close Histidine residues. The carbohydrate residues attached to 297 were modeled according to their electron density.

Figure 33:
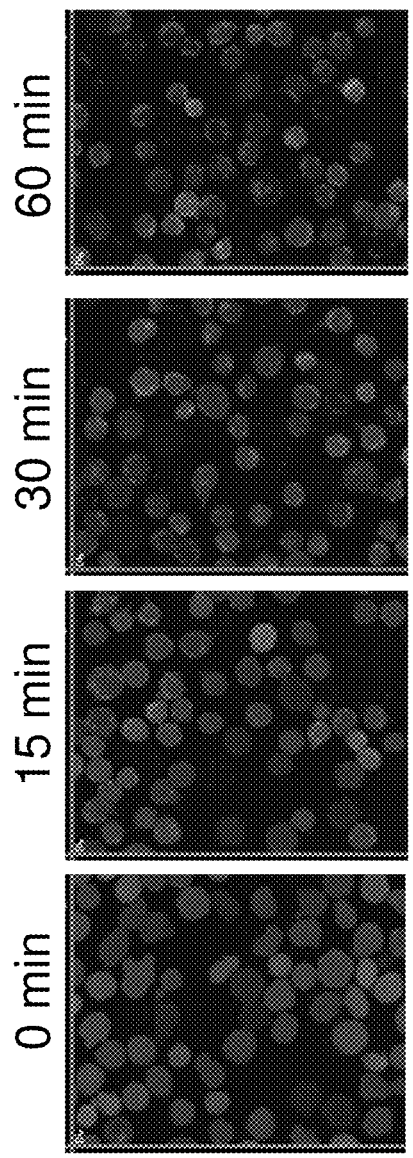

FIG. 33. Kinetic images demonstrate 9D4-TM internalization. THP-1 cells were stained with 1 µM CFSE in a 37° C. $CO_2$ incubator for 10 min followed by 1 µg/ml of Alexa647-9D4-TM on ice for 1 hr. After removal of unbound the cells were incubated at 37° C. for the times indicated (0, 15, 30 and 60 minutes) and the images of cells were taken.

Figure 34:
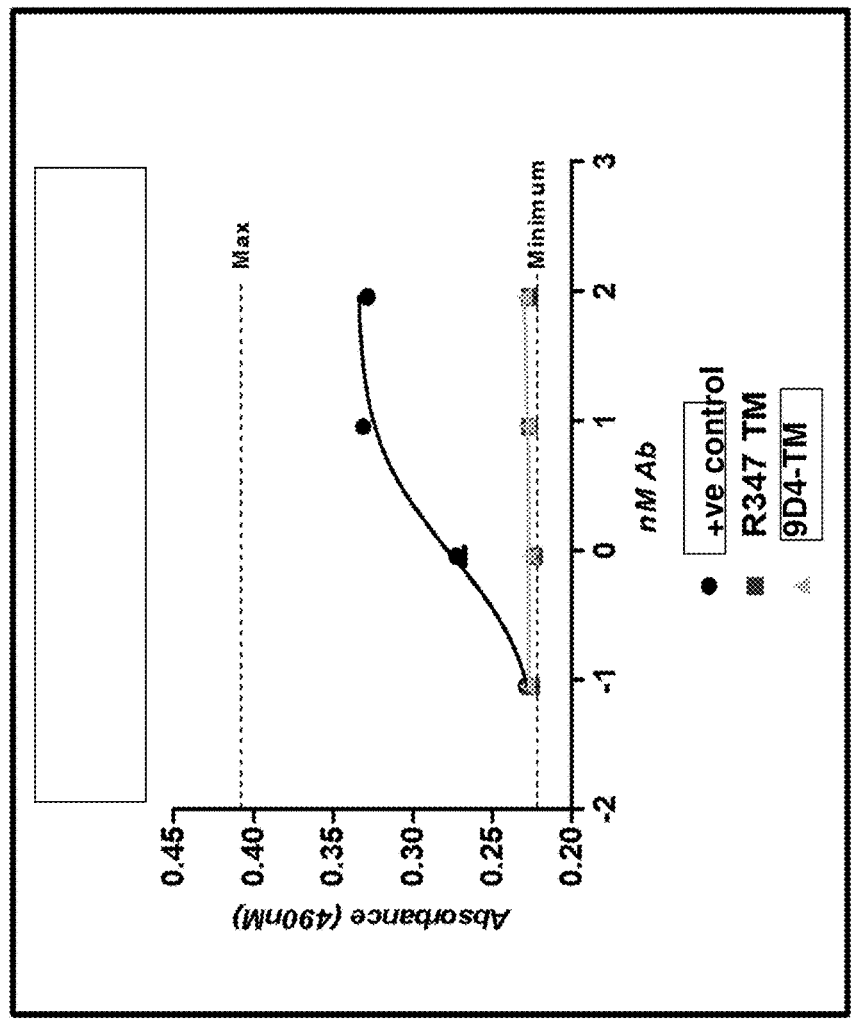

FIG. 34. The anti-IFNAR1 antibody, 9D4-TM does not exhibit CDC activity in an in vitro assay. Presented in this panel are the results from a CDC assay to determine the ability of the 9D4-TM antibody to elicit CDC activity. As presented, the 9D4-TM antibody did not exhibit any CDC activity as compared to the positive control antibody. CDC activity was also undetectable for an unrelated control antibody, R347. Briefly, cells expressing IFNAR1 antigen were incubated with either the positive control antibody, 9D4-TM, or R347. After a series of washes, freshly prepared human serum was added. Complement dependent cytotoxicity (CDC) was measured using a LDH release assay.

4. TERMINOLOGY

The terms "interferon alpha", "IFNα", "IFNa", "IFNA" and "IFN alpha" are used interchangeably and intended to refer to IFN alpha proteins encoded by a functional gene of the interferon alpha gene locus with 75% or greater sequence identity to IFN alpha 1 (GenBank accession number NP_076918 or protein encoded by GenBank accession number NM_024013). Examples of IFN alpha subtypes include IFN alpha 1, alpha 2a, alpha 2b, alpha 4, alpha 4b alpha 5, alpha 6, alpha 7, alpha 8, alpha 10, alpha 13, alpha 14, alpha 16, alpha 17 and alpha 21. The terms "interferon alpha", "IFNα", and "IFN alpha" are intended to encompass recombinant forms of the various IFN alpha subtypes, as well as naturally occurring preparations that comprise IFN alpha proteins, such as leukocyte IFN and lymphoblastoid IFN.

The terms "Interferon alpha receptor-1,", "IFNAR1" "IFNAR-1," and "IFNAR-1 antigen" are used interchangeably, and include variants, isoforms, species homologs of human IFNAR-1, and analogs having at least one common epitope with IFNAR-1. Accordingly, human antibodies of the invention may, in certain embodiments, cross-react with IFNAR-1 from species other than human, or other proteins which are structurally related to human IFNAR-1 (e.g., human IFNAR-1 homologs). In other embodiments, the antibodies may be completely specific for human IFNAR-1 and not exhibit species or other types of cross-reactivity. The complete cDNA sequence of human IFNAR-1 has the Genbank accession number NM_000629.

As used herein, the term "conservative sequence modifications" is intended to include amino acid modifications that do not affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. For example, one or more amino acids of a similar polarity act as functional equivalents and result in a silent alteration within the amino acid sequence of the peptide. Substitutions that are charge neutral and which replace a residue with a smaller residue may also be considered "conservative substitutions" even if the residues are in different groups (e.g., replacement of phenylalanine with the smaller isoleucine). Families of amino acid residues having similar side chains have been defined in the art. Several non-limiting examples of families of conservative amino acid substitutions are shown in Table 1.

TABLE 1

Families of Conservative Amino Acid Substitutions

| Family | Amino Acids |
| --- | --- |
| non-polar | Trp, Phe, Met, Leu, Ile, Val, Ala, Pro |
| Uncharged polar | Gly, Ser, Thr, Asn, Gln, Tyr, Cys |
| acidic/negatively charged | Asp, Glu |
| basic/positively charged | Arg, Lys, His |
| Beta-branched | Thr, Val, Ile |
| residues that influence chain orientation | Gly, Pro |
| Aromatic | Trp, Tyr, Phe, His |

5. DETAILED DESCRIPTION

In contrast to previous teachings, the inventors have found that anti-IFNAR1 antibodies with reduced or ablated effector function are desired for the treatment of chronic autoimmune and/or inflammatory diseases. Previously, antibodies directed against IFNAR1 were developed with the understanding that effector function would play a role in mediating treatment or at least moderation of a chronic autoimmune and/or inflammatory disease state (see, for example U.S. Publication No. 20060029601 or PCT publication No. WO06002177). With this concept, many of the previous teachings directed the artisan to identify anti-IFNAR1 antibodies with strong effector function and to further enhance the effector function by increasing the affinity of the antibody for Fc receptors (e.g., FcRn, FcγRIIIa, FcγRIIb) and/or the complement protein C1q. These resultant effector function-enhanced anti-IFNAR1 antibodies were thought to be advantageous in the treatment of disease states.

In contrast to this previous understanding, the present invention describes anti-IFNAR1 antibodies with reduced or ablated effector function (such as ADCC and/or CDC). Through tissue cross-reactivity studies, it was surprisingly found that anti-IFNAR1 antibodies with strong or enhanced effector function displayed a propensity for unwanted toxicity due to the prevalence of staining of anti-IFNAR1 on non-target tissues. This toxicity would result from the non-specific activation of ADCC and/or CDC at inappropriate sites. To reduce of or eliminate this unwanted toxicity, the inventors recognized the need to reduce effector function of polypeptides comprising an Fc region.

Accordingly, one aspect of the invention encompasses modified antibodies or other polypeptides comprising the Fc region of an antibody, comprising the addition, substitution, or deletion of at least one amino acid residue to the Fc region resulting in reduced or ablated affinity for at least one Fc ligand (referred to herein as "modified antibodies of the invention", "modified antibodies" or "antibodies of the invention"). The Fc region interacts with a number of ligands including but not limited to Fc Receptors (e.g., FcRn, FcγRIIIa, FcγRIIb), the complement protein C1q, and other molecules such as proteins A and G. These interactions are essential for a variety of effector functions and downstream signaling events including, but not limited to, antibody dependent cell-mediated cytotoxicity (ADCC) and complement dependent cytotoxicity (CDC). Accordingly, in certain embodiments the modified antibodies of the invention have reduced or ablated affinity for an Fc ligand responsible for facilitating effector function compared to an antibody having the same amino acid sequence as the antibody of the invention but not comprising the addition, substitution, or deletion of at least one amino acid residue to the Fc region (also referred to herein as an "unmodified antibody"). In certain embodiments, antibodies of the invention comprise at least one or more of the following properties: reduced or ablated effector (ADCC and/or CDC) function, reduced or ablated binding to Fc receptors, or reduced or ablated toxicities. More specifically, embodiments of the invention provide anti-IFNAR1 antibodies with reduced affinity for Fc receptors (e.g., FcRn, FcγRIIIa, FcγRIIb) and/or the complement protein C1q.

In one embodiment, antibodies of the invention comprise an Fc region comprising at least one addition, substitution, or deletion of an amino acid residue selected from the positions consisting of: 234, 235, and 331, wherein the numbering system of the constant region is that of the EU index as set forth in Kabat et al. (1991, NIH Publication 91-3242, National Technical Information Service, Springfield, Va.). In a specific embodiment, antibodies of the invention comprise an Fc region comprising at least one amino acid substitution selected from the group consisting of: L234F, L235E, and P331S, wherein the first letter and number represent the unmodified amino acid and its position and the second letter represents the substituted amino acid at said position.

In another embodiment, antibodies of the invention further comprise an Fc region comprising at least one addition, substitution, or deletion of an amino acid residue that is correlated with increased stability of the antibody. In one embodiment, the addition, substitution, or deletion of an amino acid residue is at position 228 of the Fc region, wherein the numbering system of the constant region is that of the EU index as set forth in Kabat et al. In a specific embodiment, antibodies of the invention comprise an Fc region comprising an amino acid substitution at position 228, wherein the substitution is a serine residue. In another specific embodiment, antibodies of the invention of the IgG4 subtype comprise an amino acid substitution of serine at position 228 of the Fc region. In other embodiments, antibodies of the invention already comprise a serine residue at position 228 of the Fc region; in such embodiments, no modification is required. In alternative embodiments, antibodies of the invention do not require modification of residue 228 of the Fc region or already comprise serine at said position.

In another embodiment, antibodies of the invention may be any of any class (for example, but not limited to IgG, IgM, and IgE). In certain embodiments, antibodies of the invention are members of the IgG class of antibodies. In a specific embodiment, antibodies of the invention are of the IgG1 subclass. In another specific embodiment, antibodies of the invention are of the IgG1 subclass and comprise the following amino acid substitutions: 234F, 235E and 331S of the Fc region. In alternate embodiments, antibodies of the invention are of the IgG4 subclass. In a specific embodiment, antibodies of the invention are of the IgG4 subclass and comprise the following amino acid substitutions: S228P and L235E of the Fc region.

In certain embodiments, the modified antibodies of the present invention may be produced by combining a variable domain, or fragment thereof; with an Fc domain comprising one or more of the amino acid substitutions disclosed herein. In other embodiments modified antibodies of the invention may be produced by modifying an Fc domain-containing antibody by introducing one or more of the amino acid substitutions residues into the Fc domain.

5.1 Reduced Binding to Fc Ligands

One skilled in the art will understand that antibodies of the invention may have altered (relative to an unmodified antibody) FcγR and/or C1q binding properties (examples of binding properties include but are not limited to, binding specificity, equilibrium dissociation constant ($K_D$), dissociation and association rates ($K_{off}$ and $K_{on}$ respectively), binding affinity and/or avidity) and that certain alterations are more or less desirable. It is known in the art that the equilibrium dissociation constant ($K_D$) is defined as $k_{off}/k_{on}$. One skilled in the art can determine which kinetic parameter is most important for a given antibody application. For example, a modification that reduces binding to one or more positive regulator (e.g., FcγRIIIA) and/or enhanced binding to an inhibitory Fc receptor (e.g., FcγRIIB) would be suitable for reducing ADCC activity. Accordingly, the ratio of binding affinities (e.g., equilibrium dissociation constants ($K_D$)) can indicate if the ADCC activity of an antibody of the invention is enhanced or decreased. Additionally, a modification that reduces binding to C1q would be suitable for reducing or eliminating CDC activity.

The affinities and binding properties of an Fc region for its ligand, may be determined by a variety of in vitro assay methods (biochemical or immunological based assays) known in the art for determining Fc-FcγR interactions, i.e., specific binding of an Fc region to an FcγR including but not limited to, equilibrium methods (e.g., enzyme-linked immunoabsorbent assay (ELISA) or radioimmunoassay (RIA)), or kinetics (e.g., BIACORE® analysis), and other methods such as indirect binding assays, competitive inhibition assays, fluorescence resonance energy transfer (FRET), gel electrophoresis and chromatography (e.g., gel filtration). These and other methods may utilize a label on one or more of the components being examined and/or employ a variety of detection methods including but not limited to chromogenic, fluorescent, luminescent, or isotopic labels. A detailed description of binding affinities and kinetics can be found in Paul, W. E., ed., Fundamental Immunology, $4^{th}$ Ed., Lippincott-Raven, Philadelphia (1999).

In one embodiment, antibodies of the invention exhibit reduced binding affinity for one or more Fc receptors including, but not limited to FcγRI (CD64) including isoforms FcγRIA, FcγRIB, and FcγRIC; FcγR11 (CD32 including isoforms FcγRITA, FcγRIIB, and FcγRIIC); and FcγRIII (CD16, including isoforms FcγRIIIA and FcγRIIIB) as compared to an unmodified antibody. In certain embodiments, antibodies of the invention do not comprise a concomitant increase in binding the FcγRIIB receptor as compared to an unmodified (for example, containing a wild type Fc region) antibody.

In one embodiment, antibodies of the invention exhibit decreased affinities to FcγRI relative to an unmodified antibody. In another embodiment, antibodies of the invention exhibit affinities for FcγRI receptor that are at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold less than an unmodified antibody.

In another embodiment, antibodies of the invention exhibit affinity for FcγRI receptor that are at least 90%, at least 80%, at least 70%, at least 60%, at least 50%, at least 40%, at least 30%, at least 20%, at least 10%, or at least 5% less than an unmodified antibody.

In one embodiment, antibodies of the invention exhibit decreased affinity for the FcγRIIIA receptor relative to an unmodified antibody. In another embodiment, antibodies of the invention exhibit affinities for FcγRIIIA receptor that are at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold less than an unmodified antibody.

In another embodiment, antibodies of the invention exhibit affinities for FcγRIIIA receptor that are at least 90%, at least 80%, at least 70%, at least 60%, at least 50%, at least 40%, at least 30%, at least 20%, at least 10%, or at least 5% less than an unmodified antibody.

It is understood in the art that the F158V allelic variant of the FcγRIIIA receptor has altered binding characteristics to antibodies. In one embodiment, antibodies of the invention bind with decreased affinities to FcγRIIIA (F158V) relative to an unmodified antibody. In another embodiment, antibodies of the invention exhibit affinities for FcγRIIIA (F158V) receptor that are at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold less than that of an unmodified antibody. In another embodiment, antibodies of the invention exhibit affinities for the FcγRIIIA (F158V) receptor that are at least 90%, at least 80%, at least 70%, at least 60%, at least 50%, at least 40%, at least 30%, at least 20%, at least 10%, or at least 5% less than an unmodified antibody.

In another embodiment, antibodies of the invention exhibit increased affinities for the FcγRIIB receptor as compared to unmodified antibody. In another embodiment, antibodies of the invention exhibit affinities for the FcγRIIB receptor that are unchanged or increased by at least at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold than that of an unmodified antibody. In another embodiment, antibodies of the invention exhibit affinities for the FcγRIIB receptor that are increased by at least 5%, at least 10%, at least 20%, at least 30%, at least 40%, at least 50%, at least 60%, at least 70%, at least 80%, at least 90%, or at least 95% than an unmodified antibody.

In another embodiment, antibodies of the invention exhibit affinities for the FcγRI, FcγRIIIA, or FcγRIIIA (F158V) receptors that are between about 100 nM to about 100 μM, or about 100 nM to about 10 μM, or about 100 nM to about 1 μM, or about 1 nM to about 100 μM, or about 10 nM to about 100 μM, or about 1 μM to about 100 μM, or about 10 μM to about 100 μM. In certain embodiments, antibodies of the invention exhibit affinities for the FcγRI, FcγRIIIA, or FcγRIIIA (F158V) receptors that are greater than 1 μM, greater than 5 μM, greater than 10 μM, greater than 25 μM, greater than 50 μM, or greater than 100 μM.

In another embodiment, antibodies of the invention exhibit affinities for the FcγRIIB receptor that are between about 100 nM to about 100 μM, or about 100 nM to about 10 μM, or about 100 nM to about 1 μM, or about 1 nM to about 100 μM, or about 10 nM to about 100 μM, or about 1 μM to about 100 μM, or about 10 μM to about 100 μM. In certain embodiments, antibodies of the invention exhibit affinities for the FcγR1, FcγRIIIA, or FcγRIIIA (F158V) receptors that are less than 100 μM, less than 50 μM, less than 10 μM, less than 5 μM, less than 2.5 μM, less than 1 μM, or less than 100 nM, or less than 10 nM.

In another embodiment, antibodies of the invention exhibit affinities for the FcγRIIB receptor that are between about 100 nM to about 100 μM, or about 100 nM to about 10 μM, or about 100 nM to about 1 μM, or about 1 nM to about 100 μM, or about 10 nM to about 100 μM, or about 1 μM to about 100 μM, or about 10 μM to about 100 μM. In certain embodiments, antibodies of the invention exhibit affinities for the FcγR1, FcγRIIIA, or FcγRIIIA (F158V) receptors that are less than 100 μM, less than 50 μM, less than 10 μM, less than 5 μM, less than 2.5 μM, less than 1 μM, or less than 100 nM, or less than 10 nM.

5.2 Reduced ADCC Activity

It is well known in the art that antibodies are capable of directing the attack and destruction of targeted antigen through multiple processes collectively known in the art as antibody effector functions. One of these processes, known as "antibody-dependent cell-mediated cytotoxicity" or "ADCC" refers to a form of cytotoxicity in which secreted Ig bound onto Fc receptors (FcRs) present on certain cytotoxic cells (e.g., Natural Killer (NK) cells, neutrophils, and macrophages) enables these cytotoxic effector cells to bind specifically to an antigen-bearing target cell and subsequently kill the target cell with cytotoxins. Specific high-affinity IgG antibodies directed to the surface of target cells "arm" the cytotoxic cells and are required for such killing. Lysis of the target cell is extracellular, requires direct cell-to-cell contact, and does not involve complement. Another process encompassed by the term effector function is complement dependent cytotoxicity (hereinafter referred to as "CDC") which refers to a biochemical event of antibody-mediated target cell destruction by the complement system. The complement system is a complex system of proteins found in normal blood plasma that combines with antibodies to destroy pathogenic bacteria and other foreign cells.

The ability of any particular antibody to mediate lysis of the target cell by ADCC can be assayed. To assess ADCC activity an antibody of interest is added to target cells in combination with immune effector cells, which may be activated by the antigen antibody complexes resulting in cytolysis of the target cell. Cytolysis is generally detected by the release of label (e.g. radioactive substrates, fluorescent dyes or natural intracellular proteins) from the lysed cells. Useful effector cells for such assays include peripheral blood mononuclear cells (PBMC) and Natural Killer (NK) cells. Specific examples of in vitro ADCC assays are described in Wisecarver et al., 1985 79:277-282; Bruggemann et al., 1987, *J Exp Med* 166:1351-1361; Wilkinson et al., 2001, *J Immunol Methods* 258:183-191; Patel et al., 1995 *J Immunol Methods* 184:29-38. Alternatively, or additionally, ADCC activity of the antibody of interest may be assessed in vivo, e.g., in an animal model such as that disclosed in Clynes et al., 1998, PNAS USA 95:652-656.

It is contemplated that antibodies of the invention are characterized by in vitro functional assays for determining one or more FcγR mediated effector cell functions. In certain embodiments, antibodies of the invention have similar binding properties and effector cell functions in in vivo models (such as those described and disclosed herein) as those in in vitro based assays. However, the present invention does not exclude antibodies of the invention that do not exhibit the desired phenotype in in vitro based assays but do exhibit the desired phenotype in vivo.

In one embodiment, antibodies of the invention exhibit decreased ADCC activities as compared to an unmodified antibody. In another embodiment, antibodies of the invention exhibit ADCC activities that are at least 2 fold, or at least 3 fold, or at least 5 fold or at least 10 fold or at least 50 fold or at least 100 fold less than that of an unmodified antibody. In still another embodiment, antibodies of the invention exhibit ADCC activities that are reduced by at least 10%, or at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% relative to an unmodified antibody. In certain embodiments, antibodies of the invention have no detectable ADCC activity. In specific embodiments, the reduction and/or ablatement of ADCC activity may be attributed to the reduced affinity antibodies of the invention exhibit for Fc ligands and/or receptors.

5.3 Reduced CDC Activity

The complement activation pathway is initiated by the binding of the first component of the complement system (C1q) to a molecule, an antibody for example, complexed with a cognate antigen. To assess complement activation, a CDC assay, e.g. as described in Gazzano-Santoro et al., 1996, *J. Immunol. Methods*, 202:163, may be performed.

In one embodiment, antibodies of the invention exhibit decreased affinities to C1q relative to an unmodified antibody. In another embodiment, antibodies of the invention exhibit affinities for C1q receptor that are at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold less than an unmodified antibody.

In another embodiment, antibodies of the invention exhibit affinities for C1q that are at least 90%, at least 80%, at least 70%, at least 60%, at least 50%, at least 40%, at least 30%, at least 20%, at least 10%, or at least 5% less than an unmodified antibody.

In another embodiment, antibodies of the invention exhibit affinities for C1q that are between about 100 nM to about 100 μM, or about 100 nM to about 10 μM, or about 100 nM to about 1 μM, or about 1 nM to about 100 μM, or about 10 nM to about 100 μM, or about 1 μM to about 100 μM, or about 10 μM to about 100 μM. In certain embodiments, antibodies of the invention exhibit affinities for C1q that are greater than 1 μM, greater than 5 μM, greater than 10 μM, greater than 25 μM, greater than 50 μM, or greater than 100 μM.

In one embodiment, antibodies of the invention exhibit decreased CDC activities as compared to an unmodified antibody. In another embodiment, antibodies of the invention exhibit CDC activities that are at least 2 fold, or at least 3 fold, or at least 5 fold or at least 10 fold or at least 50 fold or at least 100 fold less than that of an unmodified antibody. In still another embodiment, antibodies of the invention exhibit CDC activities that are reduced by at least 10%, or at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% relative to an unmodified antibody. In certain embodiments, antibodies of the invention exhibit no detectable CDC activities. In specific embodiments, the reduction and/or ablatement of CDC activity may be attributed to the reduced affinity antibodies of the invention exhibit for Fc ligands and/or receptors.

5.4 Reduced Antibody Related Toxicity

It is understood in the art that biological therapies may have adverse toxicity issues associated with the complex nature of directing the immune system to recognize and attack unwanted cells and/or targets. When the recognition and/or the targeting for attack do not take place where the treatment is required, consequences such as adverse toxicity may occur. For example, antibody staining of non-targeted tissues may be indicative of potential toxicity issues.

In one embodiment, antibodies of the invention exhibit reduced staining of non-targeted tissues as compared to an unmodified antibody. In another embodiment, antibodies of the invention exhibit reduced staining of non-targeted tissues that are at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold less than that of an unmodified antibody. In another embodiment, antibodies of the invention exhibit reduced staining of non-targeted tissues that are reduced by at least 10%, or at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% relative to an unmodified antibody.

In one embodiment, antibodies of the invention exhibit a reduced antibody related toxicity as compared to an unmodified antibody. In another embodiment, antibodies of the invention exhibit toxicities that are at least 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold less than that of an unmodified antibody. In another embodiment, antibodies of the invention exhibit toxicities that are reduced by at least 10%, or at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% relative to an unmodified antibody.

5.5 Internalizing Antibodies

Antibodies of the invention may bind to cell-surface antigens that may internalize, further carrying the antibodies into the cell. Once inside the cell, the antibodies may be released into the cytoplasm, targeted to a specific compartment, or recycled to the cell surface. In some embodiments, the antibodies of the invention bind to a cell-surface antigen that internalizes. In other embodiments, antibodies of the invention may be targeted to specific organelles or compartments of the cell. In yet other embodiments, the antibodies of the invention may be recycled to the cell surface or periphery after internalization. In a specific embodiment, the antibody of the invention is specific for IFNAR1.

Internalization of antibodies may be measured by art-accepted techniques such as those presented in Example 34.

In some embodiments, the extent of internalization is represented as a percentage of total antibody bound to cells. In other embodiments, the extent of antibody internalization is represented as a comparison to a non-specific control antibody. In other embodiments, the extent of antibody internalization is represented as a comparison to an antibody that binds a cell-surface antigen that does not internalize. In yet other embodiments, the extent of antibody internalization is correlated with the degradation of the antibody. In yet other embodiments, the extent of antibody internalization is represented as a ratio of cytoplasmic versus cell surface staining.

In one embodiment, the antibodies of the invention once bound, internalize into cells wherein internalization is at least about 10%, at least about 20%, at least about 30%, at least about 40%, at least about 50%, at least about 60%, at least about 70%, at least about 80%, or at least about 90%, at least about 100%, at least about 110%, at least about 130%, at least about 140%, at least about 150%, at least about 160%, or at least about 170% more than a non-specific control antibody.

In another embodiment, the antibodies of the invention once bound, internalize into cells wherein internalization is 1-10%, 10-20%, 20-30%, 30-40%, 40-50%, 50-60%, 60-70%, 70-80%, 80-90%, 90-100%, 100-110%, 110-120%, 120-130%, 130-140%, 140-150%, 150-160%, 160-170% more than a non-specific control antibody.

In another embodiment, the antibodies of the invention once bound, internalize into cells wherein internalization is 1-10%, 10-20%, 20-30%, 30-40%, 40-50%, 50-60%, 60-70%, 70-80%, 80-90%, 90-100%, 100-110%, 110-120%, 120-130%, 130-140%, 140-150%, 150-160%, 160-170% more than control antibodies as determined by the internalization assay using a secondary antibody.

5.6 Three-Dimensional Structure of a Human Fc Region

The present invention also provide crystalline forms of a human IgG Fc region, wherein the human Fc region, designated as Fc-TM, comprises amino acid substitutions of L234F, L235E and P331S as numbered by the EU index as set forth in Kabat and exhibits reduced or ablated effector (ADCC and/or CDC) function, reduced or ablated binding to Fc receptors, and/or reduced or ablated toxicities. In certain embodiments, the crystals are characterized by an orthorhombic space group C222$_1$ with unit cell of a=50.18, b=147.30 and c=75.47. In certain embodiments, the crystals are of diffraction quality to permit the determination of the three-dimensional X-ray diffraction structure of the crystalline polypeptide(s) to high resolution, preferably to a resolution of greater than about 3 Å, typically in the range of about 2 Å to about 3 Å.

The present invention further provides the high-resolution three-dimensional structures and atomic structure coordinates of the Fc-TM crystals. The specific methods used to obtain crystals and structure coordinates are provided in the examples, infra.

The atomic structure coordinates of crystalline Fc-TM, obtained from the C222$_1$ form of the crystal to 2.3 Å resolution, are listed in Table 6. All residues at positions 236 to 445 could be traced in the electron density and no electron density was observed for hinge residues prior to position 236, including the L234F and L235E mutations. The electron density at position 331 corresponded to serine.

The overall three-dimensional structure of Fe-TM was very similar to previously reported structures of unliganded human Fc regions (Deisenhofer, (1981). Biochemistry, 20, 2361-2370; Krapp et al., (2003). J. Mol. Biol. 325, 979-989; Matsumiya et al., (2007). J. Mol. Biol. 368, 767-779; Oganesyan et al., (2007) Molecular Immunology, Dec. 11, 2007, in press). When considered individually, Fc-TM C$_H$2 and C$_H$3 domains showed great structural conservation and rigidity when compared with other unliganded, unmutated human Fc structures.

The structure information can be used in a variety of computation or computer-based methods to screen, design or identify anti-IFNAR antibodies that have alter biological properties. For example, the crystals and structure coordinates obtained therefrom can be used to screen, design or identify amino acid additions, substitutions or deletions in Fc region that result in reduced or ablated binding to Fc receptors, reduced or ablated effector (ADCC and/or CDC) function, or reduced or ablated toxicitics.

Once an antibody has been designed or selected by the above methods, its effector function, binding to Fc receptors, or toxicities may be tested and optimized by any methods known to those of skill in the art. Exemplary methods are described in sections 5.1-5.4 above.

The present invention also encompasses anti-IFNAR1 antibodies that are designed or selected by the use of the structure information of Fc-TM and that exhibit the desired biological activities. In some embodiments, such antibodies comprise an Fc region with the mutations of L234F, L235E, and P331S. In some embodiments, such antibodies comprise an Fc region with one or more addition, substitution, or deletion of an amino acid residue other than amino acid residues 234, 235, and 331.

5.7 Anti-IFNAR1 Antibodies

In one embodiment, antibodies of the invention are specific for (i.e. specifically bind) IFNAR1. Such antibodies may also be referred to herein as "anti-IFNAR1 antibodies of the invention." In another embodiment, antibodies of the invention are specific for human IFNAR1. In another embodiment, the anti-IFNAR1 antibodies of the invention may cross-react with IFNAR1 from species other than human, or other proteins which are structurally related to human IFNAR1 (for example, human IFNAR1 homologs). In other embodiments, the anti-IFNAR1 antibodies of the invention may be specific for human IFNAR1 only and not exhibit species or other types of cross-reactivity.

In one embodiment, the anti-IFNAR1 antibodies of the invention exhibit reduced binding affinities for Fc ligands and have at least one of the following properties: reduced or ablated effector (ADCC and/or CDC) function, reduced or ablated binding to Fc ligands, or reduced or ablated toxicities as compared to an unmodified antibody.

In one embodiment, anti-IFNAR1 antibodies of the invention comprise the addition, substitution or deletion of at least one amino acid residue selected from the group consisting of: L234F, L235E, and P331S. In a specific embodiment, the anti-IFNAR1 antibodies of the invention comprise the amino acid substitutions: L234F, L235E, and P331S of the Fc region. In a specific embodiment, an anti-IFNAR1 antibody of the invention is an IgG isotype antibody.

In another embodiment, anti-IFNAR1 antibodies of the invention are of the IgG4 subclass. In yet another embodiment, anti-IFNAR1 IgG4 antibodies of the invention comprise the amino acid substitution L235E of the Fc region. In another embodiment, the anti-IFNAR1 IgG4 antibodies of the invention also comprise an amino acid change that is correlated with increased stability. In a specific embodiment, anti-IFNAR1 IgG4 antibodies of the invention further comprise the amino acid substitution S228P of the Fc region.

In another embodiment, anti-IFNAR1 antibodies of the invention exhibit reduced or ablated binding affinities for Fc receptors (for example, but not limited to FcγRI (CD64), including isoforms FcγRIA, FcγRIB, and FcγRIC; FcγRII (CD32), including isoforms FcγRIIA, FcγRIIB, and FcγRIIC; and FcγRIII (CD16), including isoforms FcγRIIIA and FcγRIIB) as compared to an unmodified antibody. In a specific embodiment, the anti-IFNAR 1 antibodies of the invention exhibit decreased affinities to FcγR1 relative to an unmodified antibody. In another specific embodiment, the anti-IFNAR1 antibodies of the invention exhibit decreased affinities for the FcγRIIIA receptor relative to an unmodified antibody. In another specific embodiment, the anti-IFNAR1 antibodies of the invention bind with decreased affinities to the F158V allele of FcγRIIIA relative to an unmodified antibody.

In another embodiment, anti-IFNAR1 antibodies of the invention exhibit reduced or ablated binding affinities for C1q as compared to an unmodified antibody. In a specific embodiment, the anti-IFNAR 1 antibodies of the invention exhibit decreased affinities to FcγRI relative to an unmodified antibody.

In one embodiment, anti-IFNAR1 antibodies of the invention exhibit reduced or ablated effector function. In a specific embodiment, anti-IFNAR1 antibodies of the invention exhibit reduced or ablated ADCC and/or CDC activity. In another specific embodiment, the anti-IFNAR1 antibodies of the invention exhibit reduced or ablated toxicity.

5.7.1 Anti-IFNAR1 Antibody Sequences

In one embodiment, the amino acid sequences of the heavy chain variable regions and/or light chain variable regions of the anti-IFNAR1 antibodies of the invention are provided herein as FIGS. 1A, 2A, 3A, 4A and FIGS. 1B, 2B, 3B, 4B respectively. In another embodiment, the polynucleotide sequence encoding the heavy chain variable and light chain variable regions of the anti-IFNAR1 antibodies of the invention are provided herein as FIGS. 1A, 2A, 3A, 4A and FIGS. 1B, 2B, 3B, 4B respectively.

In another embodiment, selected sequences of anti-IFNAR1 antibodies of the invention can be found in U.S. Pat. No. 5,919,453, U.S. patent application Ser. Nos. 10/831,459, 10/182,058, 11/157,494, and 11/521,102 each of which are incorporated by reference in their entireties for all purposes. In an alternative embodiment, the sequences of the anti-IFNAR1 antibodies of the invention do not comprise the sequences found in U.S. Pat. No. 5,919,453, U.S. patent application Ser. Nos. 10/831,459, 10/182,058, 11/157,494, and 11/521,102.

In other embodiments, antibodies of the invention are disclosed in U.S. Patent Provisional Applications Ser. Nos. 60/842,925, filed Sep. 8, 2006, 60/866,917; filed Nov. 22, 2006; 60/911,397, filed Apr. 12, 2007; 60/915,309, filed May 22, 2007; U.S. patent application Ser. No. 11/852,106, filed Sep. 7, 2007; and PCT Application Serial No. US2007/07791, filed Sep. 7, 2007, each of which are incorporated in its entirety for all purposes.

In one embodiment, anti-IFNAR1 antibodies of the invention also include antibodies that comprise an amino acid sequence of a variable heavy chain and/or variable light chain that is at least 45%, at least 50%, at least 55%, at least 60%, at least 65%, at least 70%, at least 75%, at least 80%, at least 85%, at least 90%, at least 95%, or at least 99% identical to the amino acid sequence of the variable heavy chain and/or light chain of the 3F11, 11E2, 4G5, and 9D4 antibodies (see FIGS. 1-4 for sequences).

It will be understood that the complementarity determining regions (CDRs) residue numbers referred to herein are those of Kabat et al. (1991, NIH Publication 91-3242, National Technical Information Service, Springfield, Va.). Specifically, residues 24-34 (CDR1), 50-56 (CDR2) and 89-97 (CDR3) in the light chain variable domain and 31-35 (CDR1), 50-65 (CDR2) and 95-102 (CDR3) in the heavy chain variable domain. Note that CDRs vary considerably from antibody to antibody (and by definition will not exhibit homology with the Kabat consensus sequences). Maximal alignment of framework residues frequently requires the insertion of "spacer" residues in the numbering system, to be used for the Fv region. It will be understood that the CDRs referred to herein are those of Kabat et al. supra. In addition, the identity of certain individual residues at any given Kabat site number may vary from antibody chain to antibody chain due to interspecies or allelic divergence.

In one embodiment, the anti-IFNAR1 antibodies of the invention comprise at least one VH CDR having an amino acid sequence of any one of the VH CDRs listed in Table 2. In another embodiment, the anti-IFNAR1 antibodies of the invention comprise at least one VL CDR having an amino acid sequence of any one of the VL CDRs listed in Table 2. In other embodiments, the anti-IFNAR1 antibodies of the invention comprise one or more of the VH CDRs and one or more of the VL CDRs listed in Table 2. In still other embodiments, the anti-IFNAR1 antibodies of the invention comprise any combination of the VH CDRs and VL CDRs listed in Table 2. In another embodiment, the anti-IFNAR1 antibodies of the invention may comprise at least 1, or at least 2, or at least 3, or at least 4, or at least 5, or at least 6 CDRs selected from Table 2. In another embodiment, anti-IFNAR1 antibodies of the invention may comprise a VH domain and/or a VL domain each comprising 1, 2 or 3 CDRs. In another embodiment, the anti-IFNAR1 antibodies of the invention may comprise a VH further comprising 1, 2, or 3 heavy chain CDRs (CDRH#) listed in Table 2. In another embodiment, the anti-IFNAR1 antibodies of the invention may comprise a VL further comprising 1, 2, or 3 light chain CDRs (CDRL#) listed in Table 2.

In a specific embodiment, the anti-IFNAR1 antibodies of the invention comprise the CDRs of antibody 3F11 (see for example Table 2). In another specific embodiment, the anti-IFNAR1 antibodies of the invention comprise the CDRs of antibody 4G5 (see for example Table 2). In another specific embodiment, the anti-IFNAR1 antibodies of the invention comprise the CDRs of antibody 11E2 (see for example Table 2). In yet another specific embodiment, the anti-IFNAR1 antibodies of the invention comprise the CDRs of antibody 9D4 (see for example Table 2).

TABLE 2

Anti-IFNAR1 antibody CDR sequences

| Antibody | CDR | Sequence | Seq ID No: |
|---|---|---|---|
| 3F11 | CDRL1 | RASQGIYSVLA | 1 |
| 3F11 | CDRL2 | DASRLES | 2 |
| 3F11 | CDRL3 | QQFNSYIT | 3 |
| 3F11 | CDRH1 | GYFWS | 4 |
| 3F11 | CDRH2 | EIDHSGKTNYNPSLKS | 5 |
| 3F11 | CDRH3 | ESKYYFGLDV | 6 |
| 4G5 | CDRL1 | RATQDISIALV | 11 |
| 4G5 | CDRL2 | DASGLGS | 12 |
| 4G5 | CDRL3 | QQFNSYPYT | 13 |

TABLE 2-continued

Anti-IFNAR1 antibody CDR sequences

| Antibody | CDR | Sequence | Seq ID No: |
|---|---|---|---|
| 4G5 | CDRH1 | NYYWS | 14 |
| 4G5 | CDRH2 | EIILSGSTNYNPSLKS | 15 |
| 4G5 | CDRH3 | ESKWGYYFDS | 16 |
| 11E2 | CDRL1 | RASQSVSSSFFA | 21 |
| 11E2 | CDRL2 | GASSRAT | 22 |
| 11E2 | CDRL3 | QQYYDSSAIT | 23 |
| 11E2 | CDRH1 | NYWIA | 24 |
| 11E2 | CDRH2 | IIYPGDSDIRYSPSFQG | 25 |
| 11E2 | CDRH3 | HDIEGFDY | 26 |
| 9D4 | CDRL1 | RASQSVSSSFFA | 31 |
| 9D4 | CDRL2 | GASSRAT | 32 |
| 9D4 | CDRL3 | QQYDSSAIT | 33 |
| 9D4 | CDRH1 | NYWIA | 34 |
| 9D4 | CDRH2 | IIYPGDSDIRYSPSFQG | 35 |
| 9D4 | CDRH3 | HDIEGFDY | 36 |

In one embodiment, anti-IFNAR1 antibodies of the invention comprise an amino acid sequence of a variable heavy chain and/or variable light chain that comprises at least 1, at least 2, at least 3, at least 4, at least 5, at least 10, at least 15, or at least 20 amino acid substitutions, additions, or deletions as compared to the variable heavy chains and/or light chains represented in FIG. 1, 2, 3, or 4. In another embodiment, anti-IFNAR1 antibodies of the invention comprise one or more CDRs with at least 1, at least 2, at least 3, at least 4, at least 5, or at least 10 amino acid substitutions, deletions, or additions of one or more CDRs listed in Table 2.

In another embodiment, anti-IFNAR1 antibodies of the invention comprise antibodies encoded by a polynucleotide sequence that hybridizes to the nucleotide sequence represented in FIG. 1, 2, 3, or 4 under stringent conditions. In another embodiment, anti-IFNAR1 antibodies of the invention comprise one or more CDRs encoded by a nucleotide sequence that hybridizes under stringent conditions to the nucleotide sequence of one or more CDRs listed in FIG. 1, 2, 3, or 4. Stringent hybridization conditions include, but are not limited to, hybridization to filter-bound DNA in 6× sodium chloride/sodium citrate (SSC) at about 45° C. followed by one or more washes in 0.2×SSC/0.1% SDS at about 50-65° C., highly stringent conditions such as hybridization to filter-bound DNA in 6×SSC at about 45° C. followed by one or more washes in 0.1×SSC/0.2% SDS at about 60° C., or any other stringent hybridization conditions known to those skilled in the art (see, for example, Ausubel, F. M. et al., eds. 1989 Current Protocols in Molecular Biology, vol. 1, Green Publishing Associates, Inc. and John Wiley and Sons, Inc., NY at pages 6.3.1 to 6.3.6 and 2.10.3). In another embodiment, anti-IFNAR1 antibodies of the invention include, but are not limited to antibodies encoded by a polynucleotide sequence that is at least 70%, at least 80%, at least 85%, at least 90%, at least 95%, at least 96%, at least 97%, at least 98%, or at least 99% identical to a polynucleotide sequence encoding antibodies 3F11, 11E2, 4G5, or 9D4 (see FIGS. 1-4).

5.7.2 Anti-IFNAR1 Binding Affinity

In certain embodiments, the anti-IFNAR1 antibodies of the invention exhibit a high binding affinity for IFNAR1. In a specific embodiment, anti-IFNAR1 antibodies of the invention exhibit association rate ($k_{on}$) of at least $10^5 M^{-1} s^{-1}$, at least $5 \times 10^5 M^{-1} s^{-1}$, at least $10^6 M^{-1} s^{-1}$, at least $5 \times 10^6 M^{-1} s^{-1}$, at least $10^7 M^{-1} s^{-1}$, at least $5 \times 10^7 M^{-1} s^{-1}$, or at least $10^8 M^{-1} s^{-1}$. In another embodiment, anti-IFNAR1 antibodies of the invention exhibit a $k_{on}$ of at least $2 \times 10^5 M^{-1} s^{-1}$, at least $5 \times 10^5 M^{-1} s^{-1}$, at least $10^6 M^{-1} s^{-1}$, at least $5 \times 10^6 M^{-1} s^{-1}$, at least $10^7 M^{-1} s^{-1}$, at least $5 \times 10^7 M^{-1} s^{-1}$, or at least $10^8 M^{-1} s^{-1}$.

In another embodiment, anti-IFNAR1 antibodies of the invention exhibit a dissociation rate ($k_{off}$) of less than $10^{-1} s^{-1}$, less than $5 \times 10^{-1} s^{-1}$, less than $10^{-2} s^{-1}$, less than $5 \times 10^{-2} s^{-1}$, less than $10^{-3} s^{-1}$, less than $5 \times 10^{-1} s^{-1}$, less than $10^{-4} s^{-1}$, less than $5 \times 10^{-4} s^{-1}$, less than $10^{-5} s^{-1}$, less than $5 \times 10^{-5} s^{-1}$, less than $10^{-6} s^{-1}$, less than $5 \times 10^{-6} s^{-1}$, less than $10^{-7} s^{-1}$, less than $5 \times 10^{-7} s^{-1}$, less than $10^{-8} s^{-1}$, less than $5 \times 10^{-8} s^{-1}$, less than $10^{-9} s^{-1}$, less than $5 \times 10^{-9} s^{-1}$, or less than $10^{-10} s^{-1}$. In another embodiment, anti-IFNAR1 antibodies of the invention exhibit a $k_{off}$ of less than $5 \times 10^{-4} s^{-1}$, less than $10^{-5} s^{-1}$, less than $5 \times 10^{-5} s^{-1}$, less than $10^{-6} s^{-1}$, less than $5 \times 10^{-6} s^{-1}$, less than $10^{-7} s^{-1}$, less than $5 \times 10^{-7} s^{-1}$, less than $10^{-8} s^{-1}$, less than $5 \times 10^{-8} s^{-1}$, less than $10^{-9} s^{-1}$, less than $5 \times 10^{-9} s^{-1}$, or less than $10^{-10} s^{-1}$.

In another embodiment, anti-IFNAR1 antibodies of the invention exhibit an affinity constant or $K_a$ ($k_{on}/k_{off}$) of at least $10^2 M^{-1}$, at least $5 \times 10^2 M^{-1}$, at least $10^3 M^{-1}$, at least $5 \times 10^3 M^{-1}$, at least $10^4 M^{-1}$, at least $5 \times 10^4 M^{-1}$, at least $10^5 M^{-1}$, at least $5 \times 10^5 M^{-1}$, at least $10^6 M^{-1}$, at least $5 \times 10^6 M^{-1}$, at least $10^7 M^{-1}$, at least $5 \times 10^7 M^{-1}$, at least $10^8 M^{-1}$, at least $5 \times 10^8 M^{-1}$, at least $10^9 M^{-1}$, at least $5 \times 10^9 M^{-1}$, at least $10^{10} M^{-1}$, at least $5 \times 10^1 M^{-1}$, at least $10^{11} M^-$, at least $5 \times 10^{11} M^{-1}$, at least $10^{12} M^{-1}$, at least $5 \times 10^{12} M$, at least $10^{13} M^{-1}$, at least $5 \times 10^{13} M^{-1}$, at least $10^{14} M^{-1}$, at least $5 \times 10^{14} M^{-1}$, at least $10^{15} M^{-1}$, or at least $5 \times 10^{15} M^{-1}$.

In another embodiment, anti-IFNAR1 antibodies of the invention exhibit a dissociation constant or $K_d$ ($k_{off}/k_{on}$) of less than $10^2 M$, less than $5 \times 10^2 M$, less than $10^3 M$, less than $5 \times 10^{-3} M$, less than $10^{-4} M$, less than $5 \times 10^{-4} M$, less than $10^{-5} M$, less than $5 \times 10^{-5} M$, less than 10 M, less than $5 \times 10^{-6} M$, less than $10^{-7} M$, less than $5 \times 10^{-7} M$, less than $10^{-8} M$, less than $5 \times 10^{-8} M$, less than $10^{-9} M$, less than $5 \times 10^{-9} M$, less than $10^{-10} M$, less than $5 \times 10^{-10} M$, less than $10^{-11} M$, less than $5 \times 10^{-11} M$, less than $10^{-12} M$, less than $5 \times 10^{-12} M$, less than $10^{-13} M$, less than $5 \times 10^{-13} M$, less than $10^{-14} M$, less than $5 \times 10^{-14} M$, less than $10^{-15} M$, or less than $5 \times 10^{-15} M$.

5.7.3 Interferon Alpha Subtype Specificity

In one embodiment, the anti-IFNAR1 antibodies of the invention exhibit the ability to block binding to IFNAR1 and/or neutralize the biological activity of one ore more Type I interferon (IFN) including, but not limited to, IFNα, IFNβ, and IFNω. Binding of IFNα subtypes can be determined by routine competition assays such as that described in Antibodies: A Laboratory Manual, CSHL. In another embodiment, the anti-IFNAR1 antibodies of the invention exhibit the ability to block binding to IFNAR1 and/or neutralize the biological activity of, including but not limited to, IFNα, IFNβ, and IFNω. In another embodiment, the anti-IFNAR1 antibodies of the invention exhibit the ability to block binding to IFNAR1 and/or neutralize the biological activity of one or more subtypes of IFNα including, but not limited to, IFNα subtypes 1, 2a, 2b, 4, 4b, 5, 6, 7, 8, 10, 14, 16, 17, and 21. In another embodiment, the anti-IFNAR1 antibodies of the invention exhibit the ability to block binding to IFNAR1 and/or neutralize the biological activity of all subtypes of IFNα. In this context, anti-IFNAR1 antibodies of the invention exhibit the ability to block the binding of and/or neutralize the biological activity of IFNα subtypes IFNα 1, 2a, 2b, 4, 4b, 5, 6, 7, 8, 10, 14, 16, 17, and 21. In one embodiment, anti-IFNAR1 antibodies of the invention do not exhibit the ability to block binding to IFNAR1 and/or neutralize the biological activity of one or more subtypes of IFNα including, but not limited to, IFNα subtypes 1, 2a, 2b, 4, 4b, 5, 6, 7, 8, 10, 14, 16, 17, and 21. In a specific embodiment, anti-IFNAR1 antibodies of the invention exhibit the ability to block binding to IFNAR1 and/or neutralize the biological activity all IFNα subtypes except IFNα21.

In another embodiment, the anti-IFNAR1 antibodies of the invention exhibit the ability to block binding to IFNAR1 and/or neutralize the biological activity of at least 1, at least 2, at least 3, at least 4, at least 5, at least 6, at least 7, at least 8, at least 9, at least 10, at least 11, at least 12, or at least 13 of the following IFNα subtypes: 1, 2a, 2b, 4, 4b, 5, 6, 7, 8, 10, 14, 16, 17, and 21. In an alternative embodiment, the anti-IFNAR1 antibodies of the invention do not exhibit the ability to block binding to IFNAR1 and/or neutralize the biological activity of at least 1, at least 2, at least 3, at least 4, at least 5, at least 6, at least 7, at least 8, at least 9, at least 10, at least 11, at least 12, or at least 13 of the following IFNα subtypes: 1, 2a, 2b, 4, 4b, 5, 6, 7, 8, 10, 14, 16, 17, and 21.

In other embodiments, the anti-IFNAR1 antibodies of the invention exhibit the ability to block binding to IFNAR1 and/or neutralize the biological activity of non-naturally occurring type I-like interferons. Such non-naturally occurring type I-like interferons, or hybrid type I-like interferons represent molecules that have been altered from their naturally occurring structures by recombinant or synthetic techniques. Hybrid interferons, as described in U.S. Pat. No. 7,232,563, represent a molecular replacement of various segments of a naturally occurring interferon structure to create a molecule that has increased potency and/or reduced toxicity.

In other embodiments, the anti-IFNAR1 antibodies of the invention exhibit the ability to block binding to IFNAR1 and/or neutralize the biological activity of mutated type I interferons. Mutated type I interferons are described in U.S. Pat. Nos. 6,299,870 and 6,300,474 which are incorporated by reference in their entireties.

In yet other embodiments, the anti-IFNAR1 antibodies of the invention exhibit the ability to block binding to IFNAR1 and/or neutralize the biological activity of type I-like interferons derived from other animal species. Such type I-like interferons are isolated from chicken, cat, mouse, rat, rabbit, goat, horse or other animal species. In specific embodiments, human type I interferons are isolated from cells derived from chicken, cat, mouse, rat, rabbit, goat, horse or other animal species. In other embodiments, human type I interferons entail different glycosylation patterns when derived from chicken, cat, mouse, rat, rabbit, goat, horse or other animal species. Further discussion of interferons from other animal species can be found in WIPO publication No. WO06099451A3 which is hereby incorporated by reference.

For the purpose of the present invention, the ability of anti-IFNAR1 antibodies of the invention to neutralize the activity of IFNα, can be monitored, for example, in a Kinase Receptor Activation (KIRA) Assay as described in WO 95/14930, published Jun. 1, 1995, by measuring the ability of a candidate antibody to reduce tyrosine phosphorylation (resulting from ligand binding) of the IFNAR1/R2 receptor complex.

Alternatively, or optionally, for the purpose of the present invention, the ability of anti-IFNAR1 antibodies of the invention to neutralize the elicitation of a cellular response by IFNα may be tested by monitoring the neutralization of the antiviral activity of IFNα, as described by Kawade, J. Interferon Res. 1:61 70 (1980), or Kawade and Watanabe, J. Interferon Res. 4:571 584 (1984), or Yousefi, et al., Am. J. Clin. Pathol. 83: 735 740 (1985), or by testing the ability of anti-IFNAR1 antibodies of the invention to neutralize the ability of IFNα to activate the binding of the signaling molecule, interferon-stimulated factor 3 (ISGF3), to an oligonucleotide derived from the interferon-stimulated response element (ISRE), in an electrophoretic mobility shift assay, as described by Kurabayashi et al., Mol. Cell Biol., 15: 6386 (1995).

In one embodiment, anti-IFNAR1 antibodies of the invention exhibit the ability to inhibit at least one IFNα mediated function of the IFNAR1 receptor. In one embodiment, the anti-IFNAR1 antibodies of the invention inhibit the activity of the IFNAR1 receptor in response to IFNα or subtypes thereof by at least about 60%, at least about 70%, at least about 75%, at least about 80%, at least about 85%, at least about 90%, at least about 95%, or at least about 99%. In another embodiment, the anti-IFNAR1 antibodies of the invention inhibit the activity of the IFNAR1 receptor in response to IFNα or subtypes thereof as measured by the KIRA assay described above by at least about 60%, at least about 70%, at least about 75%, at least about 80%, at least about 85%, at least about 90%, at least about 95%, or at least about 99%. In another embodiment, the anti-IFNAR1 antibodies of the invention inhibit the activity of the IFNAR1 receptor in response to IFNα or subtypes thereof as measured by the binding of the signaling molecule, interferon-stimulated factor 3 (ISGF3), to an oligonucleotide derived from the interferon-stimulated response element (ISRE), in an electrophoretic mobility shift assay, as described by Kurabayashi et al., Mol. Cell Biol., 15: 6386 (1995) by at least about 60%, at least about 70%, at least about 75%, at least about 80%, at least about 85%, at least about 90%, at least about 95%, or at least about 99%. In another embodiment, the anti-IFNAR1 antibodies of the invention inhibit the activity of the IFNAR1 receptor in response to IFNα or subtypes thereof as measured by an assay known in the art by at least about 60%, at least about 70%, at least about 75%, at least about 80%, at least about 85%, at least about 90%, at least about 95%, or at least about 99%.

In another embodiment, anti-IFNAR1 antibodies of the invention exhibit the ability to neutralize the anti-viral properties of IFNα or subtypes thereof. In one embodiment, the anti-IFNAR1 antibodies of the invention neutralize at least about 60%, at least about 70%, at least about 75%, at least about 80%, at least about 85%, at least about 90%, at least about 95%, or at least about 99% of the anti-viral activity of IFNα or subtypes thereof, as determined by the anti-viral assay of Kawade (1980), or Yousefi (1985). In an alternative embodiment, anti-IFNAR1 antibodies of the invention do not neutralize the anti-viral properties of IFNα or subtypes thereof.

For the purpose of the present invention, the ability of anti-IFNAR1 antibodies of the invention to block the binding of IFNα or subtypes thereof to IFNAR1 can be determined by a routine competition assay such as that described in Antibodies: A Laboratory Manual, Cold Spring Harbor Laboratory, Ed Harlow and David Lane (1988). In one embodiment, the anti-IFNAR1 antibodies of the invention exhibit the ability to block or inhibit binding of the following IFNα subtypes: 1, 2, 4, 5, 8, 10, and 21 to IFNAR1. In another embodiment, the anti-IFNAR1 antibodies of the invention exhibit the ability to block ore inhibit binding of: at least 1, at least 2, at least 3, at least 4, at least 5, at least 6, or at least 7 of the following IFNα subtypes: 1, 2, 4, 5, 8, 10, and 21 to IFNAR1.

Antibodies of the invention may act on IFNAR to regulate IFN-I responsive genes. IFN-I responsive genes have been identified in US Patent Applications entitled "IFN alpha-induced Pharmacodynamic Markers" with the following serial numbers; 60/873,008, filed Dec. 6, 2006; 60/907,762, filed Apr. 16, 2007; 60/924,584, filed May 21, 2007; 60/960,187, filed Sep. 19, 2007; 60/966,176, filed Nov. 5, 2007 and PCT application serial number PCT/US2007/02494, filed Dec. 6, 2007 each of which are incorporated by reference in their entireties.

5.7.4 Antibodies

Antibodies of the invention may include monoclonal antibodies, multispecific antibodies, human antibodies, humanized antibodies, camelized antibodies, chimeric antibodies, single-chain Fvs (scFv), disulfide-linked Fvs (sdFv), and anti-idiotypic (anti-Id) antibodies, and epitope-binding fragments of any of the above. In particular, antibodies include immunoglobulin molecules and immunologically active fragments of immunoglobulin molecules, i.e., molecules that contain an antigen binding site, these fragments may or may not be fused to another immunoglobulin domain including but not limited to, an Fc region or fragment thereof. As outlined herein, the terms "antibody" and "antibodies" specifically include the modified antibodies described herein. Immunoglobulin molecules can be of any type (e.g., IgG, IgE, IgM, IgD, IgA and IgY), class (e.g., IgG1, IgG2, IgG3, IgG4, IgA1 and IgA2) or subclass. Antibodies of the invention can be of any isotype. In one embodiment, antibodies of the invention are of the IgG1, IgG2, IgG3 or IgG4 isotype. Antibodies of the invention can be full-length antibodies comprising variable and constant regions, or they can be antigen-binding fragments thereof, such as a single chain antibody.

The term "antigen-binding fragment" of an antibody (or simply "antibody fragment"), as used herein, refers to one or more fragments of an antibody that retain the ability to specifically bind to an antigen (e.g., IFNAR1). It has been shown that the antigen-binding function of an antibody can be performed by fragments of a full-length antibody.

Examples of binding fragments encompassed within the term "antigen-binding fragment" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies.

In other embodiments, the invention provides fusion proteins (hereinafter referred to as "fusion proteins of the invention") comprising a modified Fc region with reduced or ablated affinity for an Fc ligand responsible for facilitating effector function compared to an Fc region having the same amino acid sequence as the fusion protein of the invention but not comprising the addition, substitution, or deletion of at least one amino acid residue to the Fc region.

In some embodiments, fusion proteins of the invention may comprise a peptide, polypeptide, protein scaffold, scFv, dsFv, diabody, Tandab, or an antibody mimetic fused to a modified Fc region. In some embodiments, fusion proteins of the invention comprise a linker region connecting the peptide, polypeptide, protein scaffold, scFv, dsFv, diabody, Tandab, or an antibody mimetic to the modified Fc region. The use of naturally occurring as well as artificial peptide linkers to connect polypeptides into novel linked fusion polypeptides is well known in the literature (Hallewell et al. (1989), J. Biol. Chem. 264, 5260-5268; Alfthan et al. (1995), Protein Eng. 8, 725-731; Robinson & Sauer (1996), Biochemistry 35, 109-116; Khandekar et al. (1997), J. Biol. Chem. 272, 32190-32197; Fares et al. (1998), Endocrinology 139, 2459-2464; Smallshaw et al. (1999), Protein Eng. 12, 623-630; U.S. Pat. No. 5,856,456).

In one embodiment, fusion proteins of the invention comprise an Fc region comprising at least one addition, substitution, or deletion of an amino acid residue selected from the group consisting of: 234, 235, and 331, wherein the numbering system of the constant region is that of the EU index as set forth in Kabat et al. (1991, NIH Publication 91-3242, National Technical Information Service, Springfield, Va.). In a specific embodiment, fusion proteins of the invention comprise an Fc region comprising at least one amino acid residue selected from the group consisting of: L234F, L235E, and P331S.

In another embodiment, fusion proteins of the invention further comprise an Fc region comprising at least one addition, substitution, or deletion of an amino acid residue that is correlated with increased stability of the fusion protein. In one embodiment, the addition, substitution, or deletion of an amino acid residue is at position 228 of the Fc region, wherein the numbering system of the constant region is that of the EU index as set forth in Kabat et al. (supra). In a specific embodiment, fusion proteins of the invention comprise an Fc region comprising an amino acid substitution at position 228, wherein the substitution is a serine residue.

In some embodiments, the antibodies or fusion proteins of the present invention comprise one or more engineered glycoforms, i.e., a carbohydrate composition that is covalently attached to a molecule comprising an Fc region. Engineered glycoforms may be useful for a variety of purposes, including but not limited to reducing effector function. Engineered glycoforms may be generated by any method known to one skilled in the art, for example by using engineered or variant expression strains, by co-expression with one or more enzymes, for example DI N-acetylglucosaminyltransferase III (GnTI11), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al, 1999, *Nat. Biotechnol* 17:176-180; Davies et al., 20017 *Biotechnol Bioeng* 74:288-294; Shields et al, 2002, *J Biol Chem* 277:26733-26740; Shinkawa et al., 2003, *J Biol Chem* 278:3466-3473) U.S. Pat. No. 6,602,684; U.S. Ser. Nos. 10/277,370; 10/113,929; PCT WO 00/61739A1; PCT WO 01/292246A1; PCT WO 02/311140A1; PCT WO 02/30954A1; Potillegent™ technology (Biowa, Inc. Princeton, N.J.); GlycoMAb™ glycosylation engineering technology (GLYCART biotechnology AG, Zurich, Switzerland); each of which is incorporated herein by reference in its entirety. See, e.g., WO 00061739; EA01229125; US 20030115614; Okazaki et al., 2004, *JMB*, 336: 1239-49 each of which is incorporated herein by reference in its entirety.

5.7.5 Antibody Conjugates

The present invention encompasses the use of antibodies or fragments thereof conjugated or fused to one or more moieties, including but not limited to, peptides, polypeptides, proteins, fusion proteins, nucleic acid molecules, small molecules, mimetic agents, synthetic drugs, inorganic molecules, and organic molecules.

The present invention encompasses the use of antibodies or fragments thereof recombinantly fused or chemically conjugated (including both covalent and non-covalent conjugations) to a heterologous protein or polypeptide (or fragment thereof, to a polypeptide of at least 10, at least 20, at least 30, at least 40, at least 50, at least 60, at least 70, at least 80, at least 90 or at least 100 amino acids) to generate fusion proteins. The fusion does not necessarily need to be direct, but may occur through linker sequences. For example, antibodies may be used to target heterologous polypeptides to particular cell types, either in vitro or in vivo, by fusing or conjugating the antibodies to antibodies specific for particular cell surface receptors. Antibodies fused or conjugated to heterologous polypeptides may also be used in in vitro immunoassays and purification methods using methods known in the art. See e.g., International publication No. WO 93/21232; European Patent No. EP 439,095; Naramura et al., 1994, Immunol. Lett. 39:91-99; U.S. Pat. No. 5,474,981; Gillies et al., 1992, PNAS 89:1428-1432; and Fell et al., 1991, J. Immunol. 146:2446-2452, which are incorporated by reference in their entireties.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793; 5,811,238; 5,830,721; 5,834,252; and 5,837,458, and Patten et al., 1997, Curr. Opinion Biotechnol. 8:724-33; Harayama, 1998, Trends Biotechnol. 16(2):76-82; Hansson, et al., 1999, J. Mol. Biol. 287:265-76; and Lorenzo and Blasco, 1998, Biotechniques 24(2):308-313 (each of these patents and publications are hereby incorporated by reference in its entirety). Antibodies or fragments thereof, or the encoded antibodies or fragments thereof, may be modified by being subjected to random mutagenesis by error-prone PCR, random nucleotide insertion or other methods prior to recombination. One or more portions of a polynucleotide encoding an antibody or antibody fragment, which portions specifically bind to IFNAR1 may be recombined with one or more components, motifs, sections, parts, domains, fragments, etc. of one or more heterologous molecules.

Moreover, the antibodies or fragments thereof can be fused to marker sequences, such as a peptide to facilitate purification. In other embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., 1984, Cell 37:767) and the "Flag" tag.

In other embodiments, antibodies of the present invention or fragments, analogs or derivatives thereof conjugated to a diagnostic or detectable agent. Such antibodies can be useful for monitoring or prognosing the development or progression of an inflammatory disorder as part of a clinical testing procedure, such as determining the efficacy of a particular therapy. Such diagnosis and detection can be accomplished by coupling the antibody to detectable substances including, but not limited to various enzymes, such as but not limited to horseradish peroxidase, alkaline phosphatase, beta-galactosidase, or acetylcholinesterase; prosthetic groups, such as but not limited to streptavidin/biotin and avidin/biotin; fluorescent materials, such as but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as but not limited to iodine ($^{131}$I, $^{125}$I, $^{123}$I, $^{121}$I), carbon ($^{14}$C), sulfur ($^{35}$S), tritium ($^{3}$H), indium ($^{115}$In, $^{113}$In, $^{112}$In $^{111}$In), and technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Tin; positron emitting metals using various positron emission tomographies, non-radioactive paramagnetic metal ions, and molecules that are radiolabelled or conjugated to specific radioisotopes.

Techniques for conjugating therapeutic moieties to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56. (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radio labeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119-58.

Alternatively, an antibody can be conjugated to a second antibody to form an antibody heteroconjugate as described by Segal in U.S. Pat. No. 4,676,980, which is incorporated herein by reference in its entirety.

The therapeutic moiety or drug conjugated to an antibody or fragment thereof that specifically binds to IFNAR1 should be chosen to achieve the desired prophylactic or therapeutic effect(s) for a particular disorder in a subject. A clinician or other medical personnel should consider the following when deciding on which therapeutic moiety or drug to conjugate to an antibody or fragment thereof that specifically binds to IFNAR1: the nature of the disease, the severity of the disease, and the condition of the subject.

5.7.6 Methods of Producing Antibodies

The antibodies or fragments thereof can be produced by any method known in the art for the synthesis of antibodies, in particular, by chemical synthesis or by recombinant expression techniques.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and known in the art. Briefly, mice can be immunized with IFNAR1 and once an immune response is detected, e.g., antibodies specific for IFNAR1 are detected in the mouse serum, the mouse spleen is harvested and splenocytes isolated. The splenocytes are then fused by well known techniques to any suitable mycloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, monoclonal antibodies can be generated by culturing a hybridoma cell secreting an antibody of the invention wherein the hybridoma is generated by fusing splenocytes isolated from a mouse immunized with IFNAR1 with myeloma cells and then screening the hybridomas resulting from the fusion for hybridoma clones that secrete an antibody able to bind IFNAR1.

Antibody fragments which recognize specific IFNAR1 epitopes may be generated by any technique known to those of skill in the art. For example, Fab and F(ab')$_2$ fragments of the invention may be produced by proteolytic cleavage of immunoglobulin molecules, using enzymes such as papain (to produce Fab fragments) or pepsin (to produce F(ab')$_2$ fragments). F(ab')$_2$ fragments contain the variable region, the light chain constant region and the CH1 domain of the heavy chain. Further, the antibodies of the present invention can also be generated using various phage display methods known in the art.

In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of lymphoid tissues). The DNA encoding the VH and VL domains are recombined together with an scFv linker by PCR and cloned into a phagemid vector (e.g., p CANTAB 6 or pComb 3 HSS). The vector is electroporated in E. coli and the E. coli is infected with helper phage. Phage used in these methods are typically filamentous phage including fd and M13 and the VH and VL domains are usually recombinantly fused to either the phage gene III or gene VIII. Phage expressing an antigen binding domain that binds to the IFNAR1 epitope of interest can be selected or identified with antigen, e.g., using labeled antigen or antigen bound or captured to a solid surface or bead. Examples of phage display methods that can be used to make the antibodies of the present invention include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; International Application No. PCT/GB91/01134; International Publication Nos. WO 90/02809, WO 91/10737, WO 92/01047, WO 92/18619, WO 93/11236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')2 fragments can also be employed using methods known in the art such as those disclosed in International Publication No. WO 92/22324; Mullinax et al., 1992, BioTechniques 12(6):864-869; Sawai et al., 1995, AJRI 34:26-34; and Better et al., 1988, Science 240:1041-1043 (said references incorporated by reference in their entireties).

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g. the human gamma 4 constant region, and the PCR amplified VL domains can be cloned into vectors expressing a VL constant region, e.g., human kappa or lambda constant regions. In certain embodiments, the vectors for expressing the VH or VL domains comprise an EF-1alpha promoter, a secretion signal, a cloning site for the variable domain, constant domains, and a selection marker such as neomycin. The VH and VL domains may also be cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

For some uses, including in vivo use of antibodies in humans and in vitro detection assays, it may be advantageous to use human or chimeric antibodies. Completely human antibodies are particularly desirable for therapeutic treatment of human subjects. Human antibodies can be made by a variety of methods known in the art including phage display methods described above using antibody libraries derived from human immunoglobulin sequences. Sec also U.S. Pat. Nos. 4,444,887 and 4,716,111; and International Publication Nos. WO 98/46645, WO 98/50433, WO 98/24893, WO98/16654, WO 96/34096, WO 96/33735, and WO 91/10741; each of which is incorporated herein by reference in its entirety.

A chimeric antibody is a molecule in which different portions of the antibody are derived from different immunoglobulin molecules. Methods for producing chimeric antibodies are known in the art. See e.g., Morrison, 1985, Science 229:1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,311,415, which are incorporated herein by reference in their entirety.

A humanized antibody is an antibody or fragment thereof which is capable of binding to a predetermined antigen and which comprises a framework region having substantially the amino acid sequence of a human immunoglobulin and a CDR having substantially the amino acid sequence of a non-human immunoglobulin. A humanized antibody comprises substantially all of at least one, and typically two, variable domains (Fab, Fab', F(ab)$_2$, Fabc, Fv) in which all or substantially all of the CDR regions correspond to those of a non-human immunoglobulin (i.e., donor antibody) and all or substantially all of the framework regions are those of a human immunoglobulin consensus sequence. In certain instances, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD; IgA and IgE, and any isotype, including IgG1, IgG2, IgG3 and IgG4. Usually the constant domain is a complement fixing constant domain where it is desired that the humanized antibody exhibit: cytotoxic activity and the class is typically IgG$_1$. Where such cytotoxic activity is not desirable, the constant domain may be of the IgG$_2$ class. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental framework region (FR) and CDR sequences, more often 90%, and possibly greater than 95%. Humanized antibody can be produced using variety of techniques known in the art, including but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973), chain shuffling (U.S. Pat. No. 5,565,332), and techniques disclosed in, e.g., U.S. Pat. Nos. 6,407,213, 5,766,886, WO 9317105, Tan et al., J. Immunol. 169:1119-25 (2002), Caldas et al., Protein Eng. 13(5):353-60 (2000), Morea et al., Methods 20(3):267-79 (2000), Baca et al., J. Biol. Chem. 272(16):10678-84 (1997), Roguska et al., Protein Eng. 9(14895-904 (1996), Couto et al., Cancer Res. 55 (23 Supp):5973s-5977s (1995), Couto et al., Cancer Res. 55(8):1717-22 (1995), Sandhu J S, Gene 150(2):409-10 (1994), and Pedersen et al., J. Mol. Biol. 235(3):959-73 (1994). Often, framework residues in the framework regions will be substituted with the corresponding residue from the CDR donor antibody to alter or improve antigen binding. These framework substitutions are identified by methods known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature 332:323, which are incorporated herein by reference in their entireties.)

5.7.7 Polynucleotides Encoding an Antibody

The invention also encompass polynucleotides that hybridize under high stringency, intermediate or lower stringency hybridization conditions, e.g., as defined above, to polynucleotides that encode an antibody of the invention.

The polynucleotides may be obtained, and the nucleotide sequence of the polynucleotides determined, by any method known in the art. Since the amino acid sequences of the antibodies are known, nucleotide sequences encoding these antibodies can be determined using methods known in the art, i.e., nucleotide codons known to encode particular amino acids are assembled in such a way to generate a nucleic acid that encodes the antibody or fragment thereof of the invention. Such a polynucleotide encoding the antibody maybe assembled from chemically synthesized oligonucleotides (e.g., as described in Kutmejer et al., 1994, BioTechniques 17:242), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, usually poly A+RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method known in the art.

Once the nucleotide sequence of the antibody is determined, the nucleotide sequence of the antibody may be manipulated using methods known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, one or more of the CDRs is inserted within framework regions using routine recombinant DNA techniques. The framework regions may be naturally occurring or consensus framework regions, and in certain instances human framework regions (see, e.g., Chothia et al., 1998, J. Mol. Biol. 278: 457-479 for a listing of human framework regions). Optionally, the polynucleotide generated by the combination of the framework regions and CDRs encodes an antibody that specifically binds to IFNAR1. Optionally, one or more amino acid substitutions may be made within the framework regions, and, in certain instances, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In specific embodiments, antibodies of the invention are encoded by polynucleotide sequences exemplified in FIGS. 1-4. In other specific embodiments, polynucleotides of the invention encode antibodies comprising light chain and heavy chain constant regions corresponding to SEQ ID Nos: 41 and 42 respectively. In yet other specific embodiments, polynucleotides of the invention encode antibodies comprising heavy chain constant regions corresponding to SEQ ID No: 42 with an allowance for allelic variation wherein the variation is at least one or more residue selected from the group consisting of positions 214, 221, 356, and 358 as defined by the EU index numbering system.

5.7.8 Recombinant Expression of an Antibody

Recombinant expression of an antibody of the invention, derivative, analog or fragment thereof, (e.g., a heavy or light chain of an antibody of the invention or a portion thereof or a single chain antibody of the invention), requires construction of an expression vector containing a polynucleotide that encodes the antibody. Once a polynucleotide encoding an antibody molecule or a heavy or light chain of an antibody, or portion thereof (but not necessarily containing the heavy or light chain variable domain), of the invention has been obtained, the vector for the production of the antibody molecule may be produced by recombinant DNA technology using techniques known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, a heavy or light chain of an antibody, a heavy or light chain variable domain of an antibody or a portion thereof, or a heavy or light chain CDR, operably linked to a promoter. Such vectors may include the nucleotide sequence encoding the constant region of the antibody molecule (see, e.g., International Publication No. WO 86/05807; International Publication No. WO 89/01036; and U.S. Pat. No. 5,122,464) and the variable domain of the antibody maybe cloned into such a vector for expression of the entire heavy, the entire light chain, or both the entire heavy and light chains.

The expression vector is transferred to a host cell by conventional techniques and the transfected cells are then cultured by conventional techniques to produce an antibody of the invention. Thus, the invention includes host cells containing a polynucleotide encoding an antibody of the invention or fragments thereof, or a heavy or light chain thereof, or portion thereof, or a single chain antibody of the invention, operably linked to a heterologous promoter. In other embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention (see, e.g., U.S. Pat. No. 5,807,715). Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli* and *B. subtilis*) transformed with recombinant bacteriophage DNA, plasmid DNA or cosmid DNA expression vectors containing antibody coding sequences; yeast (e.g., *Saccharomyces* and *Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g. Ti plasmid) containing antibody coding sequences; or mammalian cell systems (e.g., COS, CHO, BHK, 293, NSO, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In certain embodiments bacterial cells such as *Escherichia coli*, and in other embodiments, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., 1986, Gene 45:101; and Cockett et al., 1990, Bio/Technology 8:2). In a specific embodiment, the expression of nucleotide sequences encoding antibodies or fragments thereof which specifically bind to IFNAR1 is regulated by a constitutive promoter, inducible promoter or tissue specific promoter.

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., 1983, EMBO 12:1791), in which the antibody coding sequence may be ligated individually into the vector in frame with the lac Z coding region so that a fusion protein is produced; pIN vectors (Inouye & Inouye, 1985, Nucleic Acids Res. 13:3101-3109; Van Heeke & Schuster, 1989, J. Biol. Chem. 24:5503-5509); and the like. pGEX vectors may also be used to express foreign polypeptides as fusion proteins with glutathione 5-transferase (GST). In general, such fusion proteins are soluble and can easily be purified from lysed cells by adsorption and binding to matrix glutathione agarose beads followed by elution in the presence of free glutathione. The pGEX vectors are designed to include thrombin or factor Xa protease cleavage sites so that the cloned target gene product can be released from the GST moiety.

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, 1984, Proc. Natl. Acad. Sci. USA 8 1:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, Methods in Enzymol. 153:516-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, HeLa, COS, MDCK, 293, 3T3, W138, BT483, Hs578T, HTB2, BT2O and T47D, NSO (a murine myeloma cell line that does not endogenously produce any immunoglobulin chains), CRL7O3O and HsS78Bst cells.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compositions that interact directly or indirectly with the antibody molecule.

A number of selection systems may be used, including but not limited to, the herpes simplex virus thymidine kinase (Wigler et al., 1977, Cell 11:223), hypoxanthineguanine phosphoribosyltransferase (Szybalska & Szybalski, 1992, Proc. Natl. Acad. Sci. USA 48:202), and adenine phosphoribosyltransferase (Lowy et al., 1980, Cell 22:8-17) genes can be employed in tk–, hgprt– or aprt– cells, respectively. Also, antimetabolite resistance can be used as the basis of selection for the following genes: dhfr, which confers resistance to methotrexate (Wigler et al., 1980, Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62: 191-217; May, 1993, TIB TECH 11(5):155-2 15); and hygro, which confers resistance to hygromycin (Santerre et al., 1984, Gene 30:147). Methods commonly known in the art of recombinant DNA technology may be routinely applied to select the desired recombinant clone, and such methods are described, for example, in Ausubel et al. (eds.), Current Protocols in Molecular Biology, John Wiley & Sons, N Y (1993); Kriegler, Gene Transfer and Expression, A Laboratory Manual, Stockton Press, N Y (1990); and in Chapters 12 and 13, Dracopoli et al. (eds), Current Protocols in Human Genetics, John Wiley & Sons, N Y (1994); Colberre-Garapin et al., 1981, J. Mol. Biol. 150: 1, which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., 1983, Mol. Cell. Biol. 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, 1986, Nature 322:52; and Kohler, 1980, Proc. Natl. Acad. Sci. USA 77:2 197). The coding sequences for the heavy and light chains may comprise cDNA or genomic DNA.

Once an antibody molecule of the invention has been produced by recombinant expression, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies of the present invention or fragments thereof may be fused to heterologous polypeptide sequences described herein or otherwise known in the art to facilitate purification.

5.8 Scalable Production of Antibodies

In an effort to obtain large quantities, antibodies of the invention may be produced by a scalable process (hereinafter referred to as "scalable process of the invention"). In some embodiments, antibodies may be produced by a scalable process of the invention in the research laboratory that may be scaled up to produce the antibodies of the invention in analytical scale bioreactors (for example, but not limited to 5 L, 10 L, 15 L, 30 L, or 50 L bioreactors). In other embodiments, the antibodies may be produced by a scalable process of the invention in the research laboratory that may be scaled up to produce the antibodies of the invention in production scale bioreactors (for example, but not limited to 75 L, 100 L, 150 L, 300 L, or 500 L). In some embodiments, the scalable process of the invention results in little or no reduction in production efficiency as compared to the production process performed in the research laboratory. In other embodiments, the scalable process of the invention produces antibodies at production efficiency of about 10 mg/L, about 20 m/L, about 30 mg/L, about 50 mg/L, about 75 mg/L, about 100 mg/L, about 125 mg/L, about 150 mg/L, about 175 mg/L, about 200 mg/L, about 250 mg/L, about 300 mg/L or higher. In other embodiments, fusion proteins may be produced by scalable processes of the invention.

In other embodiments, the scalable process of the invention produces antibodies at production efficiency of at least about 10 mg/L, at least about 20 m/L, at least about 30 mg/L, at least about 50 mg/L, at least about 75 mg/L, at least about 100 mg/L, at least about 125 mg/L, at least about 150 mg/L, at least about 175 mg/L, at least about 200 mg/L, at least about 250 mg/L, at least about 300 mg/L or higher.

In other embodiments, the scalable process of the invention produces antibodies at production efficiency from about 10 mg/L to about 300 mg/L, from about 10 mg/L to about 250 mg/L, from about 10 mg/L to about 200 mg/L, from about 10 mg/L to about 175 mg/L, from about 10 mg/L to about 150 mg/L, from about 10 mg/L to about 100 mg/L, from about 20 mg/L to about 300 mg/L, from about 20 mg/L to about 250 mg/L, from about 20 mg/L to about 200 mg/L, from 20 mg/L to about 175 mg/L, from about 20 mg/L to about 150 mg/L, from about 20 mg/L to about 125 mg/L, from about 20 mg/L to about 100 mg/L, from about 30 mg/L to about 300 mg/L, from about 30 mg/L to about 250 mg/L, from about 30 mg/L to about 200 mg/L, from about 30 mg/L to about 175 mg/L, from about 30 mg/L to about 150 mg/L, from about 30 mg/L to about 125 mg/L, from about 30 mg/L to about 100 mg/L, from about 50 mg/L to about 300 mg/L, from about 50 mg/L to about 250 mg/L, from about 50 mg/L to about 200 mg/L, from 50 mg/L to about 175 mg/L, from about 50 mg/L to about 150 mg/L, from about 50 mg/L to about 125 mg/L, or from about 50 mg/L to about 100 mg/L.

5.8.1 Further Methods of Engineering Antibodies

In another embodiment, an Fc hinge region of an antibody of the invention is mutated to decrease the biological half life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, an antibody is modified to increase its biological half life. Various approaches are possible. For example, one or more of the following mutations can be introduced: T252L, T254S, T256F, as described in U.S. Pat. No. 6,277,375. In another embodiment, one or more of the following mutations can be introduced: M252Y, S254T, T256E, as described in U.S. Pat. No. 7,083,784. Alternatively, to increase the biological half life, the antibody can be modified within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In other embodiments, an Fc region is modified by replacing at least one amino acid residue with a different amino acid residue to reduce the effector function(s) of the antibody. For example, one or more amino acids selected from amino acid residues 234, 235, 236, 237, 297, 318, 320 and 322 can be replaced with a different amino acid residue such that the antibody has reduced affinity for an effector ligand but retains the antigen-binding ability of the parent antibody. The effector ligand to which affinity is reduced can be, for example, an Fc receptor or the C1 component of complement. This approach is described in further detail in U.S. Pat. Nos. 5,624,821 and 5,648,260, both by Winter et al.

In another example, one or more amino acids selected from amino acid residues 329, 331 and 322 can be replaced with a different amino acid residue such that the antibody has reduced C1q binding and/or reduced or abolished complement dependent cytotoxicity (CDC). This approach is described in further detail in U.S. Pat. No. 6,194,551 by Idusogie et al.

In another example, one or more amino acid residues within amino acid positions 231 and 239 are modified to thereby reduce the ability of the antibody to fix complement. This approach is described further in PCT Publication WO 94/29351 by Bodmer et al.

In yet another embodiment, an Fc region of an antibody of the invention is further modified to decrease the ability of the antibody to mediate antibody dependent cellular cytotoxicity (ADCC) and/or to decrease the affinity of the antibody for an Fcγreceptor by modifying one or more amino acids at the following positions: 238, 239, 248, 249, 252, 254, 255, 256, 258, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072 by Presta.

Another modification of the antibodies herein that is contemplated by the invention is pegylation. An antibody can be pegylated to, for example, increase the biological (e.g., serum) half life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. In certain instances, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to antibodies of the invention. See for example, EP 0 154 316 by Nishimura et al. and EP 0 401 384 by Ishikawa et al.

Thus, in another aspect of the invention, the structural features of anti-IFNAR1 antibodies, for example, but not limited to 3F11, 4G5, 11E2, and 9D4, are used to create structurally related anti-IFNAR1 antibodies that retain at least one functional property of antibodies of the invention, such as binding to IFNAR1. For example, one or more CDR regions of 3F11, 4G5, 11E2, or 9D4, or mutations thereof, can be combined recombinantly with known framework regions and/or other CDRs to create additional, recombinantly-engineered, anti-IFNAR1 antibodies of the invention, as discussed above. Other types of modifications include those described in the previous section. The starting material for the engineering method is one or more of the $V_H$ and/or $V_L$ sequences provided herein, or one or more CDR regions thereof. To create the engineered antibody, it is not necessary to actually prepare (i.e., express as a protein) an antibody having one or more of the $V_H$ and/or $V_L$ sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

5.9 Compositions

In another aspect, the present invention provides compositions containing one or a combination of monoclonal antibodies, or fusion proteins comprising an Fc region thereof, as described herein, formulated together with a carrier. Such compositions may include one or a combination of (e.g., two or more different) antibodies, fusion proteins, immunoconjugates or bispecific molecules of the invention. In some embodiments, such compositions are physiologically tolerable and as such are suitable for administration to a subject (also referred to as a "pharmaceutical composition of the invention." For example, pharmaceutical compositions of the invention may comprise a combination of antibodies (or immunoconjugates or bispecifics) that bind to different epitopes on the target antigen or that have complementary activities.

In another embodiment, compositions of the invention may include one or more pharmaceutically acceptable salts. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

In another embodiment, compositions of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in contemplated compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

In another embodiment, compositions of the invention may also contain adjuvants such as preservatives, wetting agents, emulsifying agents and dispersing agents. Prevention of presence of microorganisms may be ensured both by sterilization procedures and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions. Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be suitable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

In one embodiment, compositions (e.g., liquid formulations) of the invention are pyrogen-free formulations which are substantially free of endotoxins and/or related pyrogenic substances. Endotoxins include toxins that are confined inside a microorganism and are released when the microorganisms are broken down or die. Pyrogenic substances also include fever-inducing, thermostable substances (glycoproteins) from the outer membrane of bacteria and other microorganisms. Both of these substances can cause fever, hypotension and shock if administered to humans. Due to the potential harmful effects, it is advantageous to remove even low amounts of endotoxins from intravenously administered pharmaceutical drug solutions. The Food & Drug Administration ("FDA") has set an upper limit of 5 endotoxin units (EU) per dose per kilogram body weight in a single one hour period for intravenous drug applications (The United States Pharmacopeial Convention, Pharmacopeial Forum 26 (1):223 (2000)). When therapeutic proteins are administered in amounts of several hundred or thousand milligrams per kilogram body weight, as can be the case with monoclonal antibodies, it is advantageous to remove even trace amounts of endotoxin. In one embodiment, endotoxin and pyrogen levels in the composition are less then 10 EU/mg, or less then 5 EU/mg, or less then 1 EU/mg, or less then 0.1 EU/mg, or less then 0.01 EU/mg, or less then 0.001 EU/mg. In another embodiment, endotoxin and pyrogen levels in the composition are less then about 10 EU/mg, or less then about 5 EU/mg, or less then about 1 EU/mg, or less then about 0.1 EU/mg, or less then about 0.01 EU/mg, or less then about 0.001 EU/mg.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, also from about 0.1 percent to about 70 percent, also from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of an antibody, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Dosage regimens for an anti-IFNAR1 antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

Alternatively, an antibody of fusion protein may be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and usually until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A therapeutically effective dosage of an anti-IFNAR1 antibody of the invention results in a decrease in severity of disease symptoms, an increase in frequency and duration of disease symptom-free periods, or a prevention of impairment or disability due to the disease affliction. In the case of, for example, Systemic Lupus Erythematosus (SLE), a therapeutically effective dose may prevent further deterioration of physical symptoms associated with SLE, such as, for example, pain, fatigue or weakness. A therapeutically effective dose may also prevent or delays onset of SLE, such as may be desired when early or preliminary signs of the disease are present. Likewise it includes delaying chronic progression associated with SLE. Laboratory tests utilized in the diagnosis of SLE include chemistries, hematology, serology and radiology. Accordingly, any clinical or biochemical assay that monitors any of the foregoing may be used to determine whether a particular treatment is a therapeutically effective dose for treating SLE. One of ordinary skill in the art would be able to determine such amounts based on such factors as the subject's size, the severity of the subject's symptoms, and the particular composition or route of administration selected.

A composition of the present invention can be administered via one or more routes of administration using one or more of a variety of methods known in the art. As will be appreciated by the skilled artisan, the route and/or mode of administration will vary depending upon the desired results. Selected routes of administration for antibodies of the invention include intravenous, intramuscular, intradermal, intraperitoneal, subcutaneous, spinal or other parenteral routes of administration, for example by injection or infusion. Parenteral administration may represent modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in another embodiment, a therapeutic composition of the invention can be administered with a needleless hypodermic injection device, such as the devices disclosed in U.S. Pat. No. 5,399,163; 5,383,851; 5,312,335; 5,064,413; 4,941,880; 4,790,824; or 4,596,556. Examples of well-known implants and modules useful in the present invention include: U.S. Pat. No. 4,487,603, which discloses an implantable microinfusion pump for dispensing medication at a controlled rate; U.S. Pat. No. 4,486,194, which discloses a therapeutic device for administering medicants through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, antibodies of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

5.10 Diagnostic Uses

In other embodiments, antibodies of the present invention have in vitro and in vivo diagnostic and therapeutic utilities. For example, these molecules can be administered to cells in culture, e.g. in vitro or ex vivo, or in a subject, e.g., in vivo, to treat, prevent or diagnose a variety of disorders.

In one embodiment, antibodies of the invention can be used to detect levels of IFNAR1, or levels of cells that express IFNAR1. This can be achieved, for example, by contacting a sample (such as an in vitro sample) and a control sample with the anti-IFNAR1 antibody under conditions that allow for the formation of a complex between the antibody and IFNAR1. Any complexes formed between the antibody and IFNAR1 are detected and compared in the sample and the control. For example, standard detection methods, well-known in the art, such as ELISA and flow cytometric assays, can be performed using the compositions of the invention.

Accordingly, in one aspect, the invention further provides methods for detecting the presence of IFNAR1 (e.g., human IFNAR1 antigen) in a sample, or measuring the amount of IFNAR1, comprising contacting the sample, and a control sample, with antibodies of the invention, or an antigen binding portion thereof, which specifically binds to IFNAR1, under conditions that allow for formation of a complex between the antibody or portion thereof and IFNAR1. The formation of a complex is then detected, wherein a difference in complex formation between the sample compared to the control sample is indicative of the presence of IFNAR1 in the sample.

5.11 Therapeutic Applications

IFNAR1 is part of the cellular receptor for Type 1 interferons, and Type I interferons are known to be immunoregulatory cytokines that are involved in T cell differentiation, antibody production and activity and survival of memory T cells. Moreover, increased expression of Type I interferons has been described in numerous autoimmune diseases, in HIV infection, in transplant rejection and in graft versus host disease (GVHD). Accordingly, the anti-IFNAR1 antibodies of the invention or fragments thereof, which inhibit the functional activity of Type I interferons, can be used in a variety of clinical indications involving aberrant or undesired Type I interferon activity. The invention encompasses methods of preventing, treating, maintaining, ameliorating, or inhibiting a Type I interferon-mediated disease or disorder, wherein the methods comprise administering antibodies, or antigen-binding portions thereof, of the invention.

Specific examples of autoimmune conditions in which antibodies of the invention can be used include, but are not limited to, the following: systemic lupus erythematosus (SLE), insulin dependent diabetes mellitus (IDDM), inflammatory bowel disease (IBD) (including Crohn's Disease, Ulcerative Colitis and Celiac's Disease), multiple sclerosis (MS), psoriasis, autoimmune thyroiditis, rheumatoid arthritis (RA) and glomerulonephritis. Furthermore, the antibody compositions of the invention can be used for inhibiting or preventing transplant rejection or in the treatment of graft versus host disease (GVHD) or in the treatment of HIV infection/AIDS.

High levels of IFNα have been observed in the serum of patients with systemic lupus erythematosus (SLE) (see e.g., Kim et al. (1987) Clin. Exp. Immunol. 70:562-569). Moreover, administration of IFNα, for example in the treatment of cancer or viral infections, has been shown to induce SLE (Garcia-Porrua et al. (1998) Clin. Exp. Rheumatol. 16:107-108). Accordingly, in another embodiment, anti-IFNAR1 antibodies of the invention can be used in the treatment of SLE by administering the antibody to a subject in need of treatment.

Other methods of treating SLE are described in U.S. Patent Applications entitled "Methods of treating SLE" with the following Ser. Nos. 60/907,767, filed Apr. 16, 07; 60/966,174, filed Nov. 5, 2007 and PCT application serial number PCT/US2007/02494, filed Dec. 9, 2007 each of which are incorporated by reference in their entireties.

IFNα also has been implicated in the pathology of Type I diabetes. For example, the presence of immunoreactive IFNα in pancreatic beta cells of Type I diabetes patients has been reported (Foulis et al. (1987) Lancet 2:1423-1427). Prolonged use of IFNα in anti-viral therapy also has been shown to induce Type I diabetes (Waguri et al. (1994) Diabetes Res. Clin. Pract. 23:33-36). Accordingly, in another embodiment, the anti-IFNAR1 antibodies or fragments thereof of the invention can be used in the treatment of Type I diabetes by administering the antibody to a subject in need of treatment. The antibody can be used alone or in combination with other anti-diabetic agents, such as insulin.

Antibodies to IFNAR1 have been shown to be effective in an animal model of inflammatory bowel disease (see U.S. Patent Application 60/465,155). Thus, the anti-IFNAR1 antibodies or fragments thereof of the invention can be used in the treatment of inflammatory bowel disease (IBD), including ulcerative colitis and Crohn's disease, by administering the antibody to a subject in need of treatment.

Treatment with IFNα has also been observed to induce autoimmune thyroiditis (Monzani et al. (2004) Clin. Exp. Med. 3:199-210; Prummel and Laurberg (2003) Thyroid 13:547-551). Accordingly, in another embodiment, anti-IFNAR1 antibodies of the invention can be used in the treatment of autoimmune thyroid disease, including autoimmune primary hypothyroidism, Graves Disease, Hashimoto's thyroiditis and destructive thyroiditis with hypothyroidism, by administering an antibody of the invention to a subject in need of treatment. Antibodies of the invention can be used alone or in combination with other agents or treatments, such as anti-thyroid drugs, radioactive iodine and subtotal thyroidectomy.

High levels of IFNα also have been observed in the circulation of patients with HIV infection and its presence is a predictive marker of AIDS progression (DeStefano et al. (1982) J. Infec. Disease 146:451; Vadhan-Raj et al. (1986) Cancer Res. 46:417). Thus, in another embodiment, anti-IFNAR1 antibodies of the invention may be used in the treatment of HIV infection or AIDS by administering the antibody of the invention to a subject in need of treatment. In another embodiment, antibodies of the invention can be used alone or in combination with other anti-HIV agents, such as nucleoside reverse transcriptase inhibitors, non-nucleoside reverse transcriptase inhibitors, protease inhibitors and fusion inhibitors.

Antibodies to IFNAR1 have been demonstrated to be effective in inhibiting allograft rejection and prolonging allograft survival (see e.g., Tovey et al. (1996) J. Leukoc. Biol. 59:512-517; Benizri et al. (1998) J. Interferon Cytokine Res. 18:273-284). Accordingly, the anti-IFNAR1 antibodies of the invention also can be used in transplant recipients to inhibit allograft rejection and/or prolong allograft survival. The invention provides a method of inhibiting transplant rejection by administering anti-IFNAR1 antibodies of the invention to a transplant recipient in need of treatment. Examples of tissue transplants that can be treated include, but are not limited to, liver, lung, kidney, heat, small bowel, and pancreatic islet cells, as well as the treatment of graft versus host disease (GVHD). Antibodies of the invention can be used alone or in combination with other agents for inhibiting transplant rejection, such as immunosuppressive agents (e.g., cyclosporine, azathioprine, methylprednisolone, prednisolone, prednisone, mycophenolate mofetil, sirilimus, rapamycin, tacrolimus), anti-infective agents (e.g., acyclovir, clotrimazole, ganciclovir, nystatin, trimethoprim-sulfarnethoxazole), diuretics (e.g., bumetanide, furosemide, metolazone) and ulcer medications (e.g., cimetidine, famotidine, lansoprazole, omeprazole, ranitidine, sucralfate).

In other specific embodiments, the invention provides methods of administering and using compositions and antibodies of the invention to treat and prevent a wide range of inflammatory conditions including both chronic and acute conditions, such as, but not limited to, appendicitis, peptic, gastric and duodenal ulcers, peritonitis, pancreatitis, ulcerative, pseudomembranous, acute and ischemic colitis, diverticulitis, epiglottitis, achalasia, cholangitis, cholecystitis, hepatitis, Crohn's disease, enteritis, Whipple's disease, asthma, allergy, anaphylactic shock, immune complex disease, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, pneumoultramicroscopicsilicovolcanoconiosis, alvealitis, bronchiolitis, pharyngitis, pleurisy, sinusitis, influenza, respiratory syncytial virus infection, herpes infection, HIV infection, hepatitis B virus infection, hepatitis C virus infection, disseminated bacteremia, Dengue fever, candidiasis, malaria, filariasis, amebiasis, hydatid cysts, burns, dermatitis, dermatomyositis, sunburn, urticaria, warts, wheals, vasulitis, angiitis, endocarditis, arteritis, atherosclerosis, thrombophlebitis, pericarditis, myocarditis, myocardial ischemia, periarteritis nodosa, rheumatic fever, Alzheimer's disease, celiac disease, congestive heart failure, restenosis, COPD adult respiratory distress syndrome, meningitis, encephalitis, multiple sclerosis, cerebral infarction, cerebral embolism, Guillame-Barre syndrome, neuritis, neuralgia, spinal cord injury, paralysis, uveitis, arthritides, arthralgias, osteomyelitis, fascitis, Paget's disease, gout, periodontal disease, rheumatoid arthritis, synovitis, myasthenia gravis, thryoiditis, systemic lupus erythematosus, Goodpasture's syndrome, Behcets's syndrome, allograft rejection, graft-versus-host disease, Type I diabetes, ankylosing spondylitis, Berger's disease, Retier's syndrome, and Hodgkins disease.

In another embodiment, methods of administration and compositions of antibodies of the invention may be useful in the prevention, treatment, amelioration of symptoms associated with the following conditions or disease states:

Graves's disease, Hashimoto's thyroiditis, Crohn's disease, psoriasis, psoriatic arthritis, sympathetic opthalmitis, autoimmune oophoritis, autoimmune orchitis, autoimmune lymphoproliferative syndrome, antiphospholipid syndrome. Sjogren's syndrome, sclerodeima, Addison's disease, polyendocrine deficiency syndrome, Guillan-Barre syndrome, immune thrombocytopenic purpura, pernicious anemia, myasthenia gravis, primary biliary cirrhosis, mixed connective tissue disease, vitiligo, autoimmune uveitis, autoimmune hemolytic anemia, autoimmune thrombopocytopenia, celiac disease, dermatitis herpetiformis, autoimmune hepatitis, pemphigus, pemphigus vulgaris, pemphigus foliaceus, bullous pemphigoid, autoimmune myocarditis, autoimmune vasculitis, alopecia areata, autoimmune artherosclerosis, Behcet's disease, autoimmune myelopathy, autoimmune hemophelia, autoimmune interstitial cystitis, autoimmune diabetes isipidus, autoimmune endometriosis, relapsing polychondritis, ankylosing spondylitis, autoimmune urticaria, dermatomyositis, Miller-Fisher syndrome, IgA nephropathy, goodpastures syndrome, and herpes gestationis.

In another embodiment, methods of administration and compositions of antibodies of the invention may be useful in the prevention, treatment, amelioration of symptoms associated with Sjogren's syndrome. Sjögren's syndrome is an autoimmune disorder in which immune cells attack and destroy the exocrine glands that produce tears and saliva. It is named after Swedish ophthalmologist Henrik Sjögren (1899-1986), who first described it. Sjögren's syndrome is also associated with rheumatic disorders such as rheumatoid arthritis, and it is rheumatoid factor positive in 90 percent of cases. The hallmark symptoms of the disorder are dry mouth and dry eyes. In addition, Sjögren's syndrome may cause skin, nose, and vaginal dryness, and may affect other organs of the body, including the kidneys, blood vessels, lungs, liver, pancreas, and brain. Nine out of ten Sjögren's patients are women and the average age of onset is late 40s, although Sjögren's occurs in all age groups in both women and men. It is estimated to strike as many as 4 million people in the United States alone making it the second most common autoimmune rheumatic disease.

Myositis is general condition characterized by inflammation of skeletal muscle or voluntary muscle. Muscle inflammation may be caused by an allergic reaction, exposure to a toxic substance or medicine, another disease such as cancer or rheumatoid conditions, or a virus or other infectious agent. The chronic inflammatory myopathies are idiopathic, meaning they have no known cause. They are understood to be autoimmune disorders, in which the body's white blood cells (that normally fight disease) attack blood vessels, normal muscle fibers, and connective tissue in organs, bones, and joints.

Polymyositis affects skeletal muscles (involved with making movement) on both sides of the body. It is rarely seen in persons under age 18; most cases are in patients between the ages of 31 and 60. In addition to symptoms listed above, progressive muscle weakness leads to difficulty swallowing, speaking, rising from a sitting position, climbing stairs, lifting objects, or reaching overhead. Patients with polymyositis may also experience arthritis, shortness of breath, and heart arrhythmias.

Dermatomyositis is characterized by a skin rash that precedes or accompanies progressive muscle weakness. The rash looks patchy, with bluish-purple or red discolorations, and characteristically develops on the eyelids and on muscles used to extend or straighten joints, including knuckles, elbows, heels, and toes. Red rashes may also occur on the face, neck, shoulders, upper chest, back, and other locations, and there may be swelling in the affected areas. The rash sometimes occurs without obvious muscle involvement. Adults with dermatomyositis may experience weight loss or a low-grade fever, have inflamed lungs, and be sensitive to light. Adult dermatomyositis, unlike polymyositis, may accompany tumors of the breast, lung, female genitalia, or bowel. Children and adults with dermatomyositis may develop calcium deposits, which appear as hard bumps under the skin or in the muscle (called calcinosis). Calcinosis most often occurs 1-3 years after disease onset but may occur many years later. These deposits are seen more often in childhood dermatomyositis than in dermatomyositis that begins in adults. Dermatomyositis may be associated with collagen-vascular or autoimmune diseases.

Inclusion body myositis (IBM) is characterized by progressive muscle weakness and wasting. IBM is similar to polymyositis but has its own distinctive features. The onset of muscle weakness is generally gradual (over months or years) and affects both proximal and distal muscles. Muscle weakness may affect only one side of the body. Small holes called vacuoles are seen in the cells of affected muscle fibers. Falling and tripping are usually the first noticeable symptoms of IBM. For some patients the disorder begins with weakness in the wrists and fingers that causes difficulty with pinching, buttoning, and gripping objects. There may be weakness of the wrist and finger muscles and atrophy (thinning or loss of muscle bulk) of the forearm muscles and quadricep muscles in the legs. Difficulty swallowing occurs in approximately half of IBM cases. Symptoms of the disease usually begin after the age of 50, although the disease can occur earlier. Unlike polymyositis and dermatomyositis, IBM occurs more frequently in men than in women.

Juvenile myositis has some similarities to adult dermatomyositis and polymyositis. It typically affects children ages 2 to 15 years, with symptoms that include proximal muscle weakness and inflammation, edema (an abnormal collection of fluids within body tissues that causes swelling), muscle pain, fatigue, skin rashes, abdominal pain, fever, and contractures (chronic shortening of muscles or tendons around joints, caused by inflammation in the muscle tendons, which prevents the joints from moving freely). Children with juvenile myositis may also have difficulty swallowing and breathing, and the heart may be affected. Approximately 20 to 30 percent of children with juvenile dermatomyositis develop calcinosis. Juvenile patients may not show higher than normal levels of the muscle enzyme creatine kinase in their blood but have higher than normal levels of other muscle enzymes.

Accordingly, in other embodiments, antibodies of the invention may be useful in the prevention, treatment, or amelioration of myositis, inflammatory myositis, idiopathic myositis, polymyositis, dermatomyositis, inclusion body myositis (IBM), juvenile myositis or symptoms associated with these conditions.

In another embodiment, antibodies of the invention may be useful in the prevention, treatment, or amelioration of symptoms associated with vasculitis.

Antibodies of the invention may be useful for the treatment of scleroderma. Methods of treating Scleroderma are described in a U.S. patent application entitled "Methods Of Treating Scleroderma" with an application serial number of 60/996,175, filed on Nov. 5, 2007 and PCT Application No. PCT/US2008/82481 are incorporated by reference in their entireties for all purposes.

In another embodiment, antibodies of the invention may be useful in the prevention, treatment, or amelioration of symptoms associated with sarcoidosis. Sarcoidosis (also called sarcoid or Besnier-Boeck disease) is an immune system disorder characterized by non-necrotizing granulomas (small inflammatory nodules). Virtually any organ can be affected; however, granulomas most often appear in the lungs or the lymph nodes. Symptoms can occasionally appear suddenly but usually appear gradually. When viewing X-rays of the lungs, sarcoidosis can have the appearance of tuberculosis or lymphoma.

Also within the scope of the invention are kits comprising the compositions (e.g., anti-IFNAR1 antibodies) of the invention and instructions for use. The kit can further contain a least one additional reagent, or one or more additional antibodies of the invention (e.g., an antibody having a complementary activity which binds to an epitope on the target antigen distinct from the first antibody). Kits typically include a label indicating the intended use of the contents of the kit. The term label includes any writing, or recorded material supplied on or with the kit, or which otherwise accompanies the kit.

5.12 Combinations

Compositions of the invention also can be administered in combination therapy, such as, combined with other agents. For example, the combination therapy can include an anti-IFNAR1 antibody of the present invention combined with at least one other immunosuppressent.

In some methods, two or more monoclonal antibodies with different binding specificities are administered simultaneously, in which case the dosage of each antibody administered falls within the ranges indicated. The antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 μg/ml and in some methods about 25-300 μg/ml.

When antibodies to IFNAR1 are administered together with another agent, the two can be administered in either order or simultaneously. For example, an anti-IFNAR1 antibody of the invention can be used in combination with one or more of the following agents: drugs containing mesalamine (including sulfasalazine and other agents containing 5-aminosalicylic acid (5-ASA), such as olsalazine and balsalazide), non-steroidal anti-inflammatory drugs (NSAIDs), analgesics, corticosteroids (e.g., predinisone, hydrocortisone), TNF-inhibitors (including adalimumab (HUMIRA®), etanercept (ENBREL®) and infliximab (REMICADE®)), immunosuppressants (such as 6-mercaptopurine, azathioprine and cyclosporine A), and antibiotics anti-IFNα antibody, anti-IFNγ receptor antibody, and soluble IFNγ receptor. Furthermore, an anti-IFNAR1 antibody of invention can be used in combination with a Flt3 ligand antagonist (see e.g., U.S. Application No. 2002/0160974).

In other embodiments, the compositions of the invention may also include agents useful in the treatment of SLE. Such agents include analgesics, corticosteroids (e.g., predinisone, hydrocortisone), immunosuppressants (such as cyclophosphamide, azathioprine, and methotrexate), antimalarials (such as hydroxychloroquine) and biologic drugs that inhibit the production of dsDNA antibodies (e.g., LJP 394).

5.13 Equivalents

Those skilled in the art will recognize, or be able to ascertain using no more than routine experimentation, many equivalents to embodiments of the invention described herein.

All publications, patents and patent applications mentioned in this specification are herein incorporated by reference into the specification to the same extent as if each individual publication, patent or patent application was specifically and individually indicated to be incorporated herein by reference.

In addition, the following U.S. provisional patent applications No. 61/006,962 filed Feb. 8, 2008, 61/034,618 filed Mar. 7, 2007, and 61/049,970 filed May 2, 2008 are hereby incorporated by reference herein in its entirety for all purposes.

5.14 Specific Embodiments

1. A modified IgG class monoclonal antibody specific for IFNAR1, wherein said antibody comprises in the Fc region at least one amino acid substitution selected from the group consisting of L234F, L235E, and P331S, as numbered by the EU index as set forth in Kabat and wherein said antibody exhibits reduced affinity for at least one Fc ligand compared to an unmodified antibody.
2. The antibody of embodiment 1, wherein, said antibody is an IgG1 or IgG4 subclass.
3. The antibody of embodiment 2, wherein said antibody is an IgG1 class molecule.
4. The antibody of embodiment 3, wherein said antibody comprises an amino acid substitution of P331S.
5. The antibody of embodiment 3, wherein said antibody comprises the amino acid substitutions: L234F and L235E.
6. The antibody of embodiment 3, wherein said antibody comprises the amino acid substitutions: L234F, L235E and P331S.
7. The antibody of embodiment 3 wherein, said antibody is an IgG4 class molecule.
8. The antibody of embodiment 7 wherein, said antibody comprises an amino acid substitution of L235E of the Fc region.
9. The antibody of embodiment 7, wherein, said antibody further comprises in the Fc region amino acid substitution S228P.
10. The antibody of any of embodiments 1-9 wherein, said antibody comprises at least one complementarity determining region (CDR) selected from Table 2.
11. The antibody of any of embodiments 1-10, wherein, said antibody comprises:
    a. a human heavy chain variable region CDR1 comprising Seq ID NO: 31;
    b. a human heavy chain variable region CDR2 comprising Seq ID NO: 32;
    c. a human heavy chain variable region CDR3 comprising Seq ID NO: 33;
    d. a human light chain variable region CDR1 comprising Seq ID NO: 34;
    e. a human light chain variable region CDR2 comprising Seq ID NO: 35; and
    f. a human light chain variable region CDR3 comprising Seq ID NO: 36.
12. The antibody of any of embodiments 1-10, wherein, said antibody comprises:
    a. a human heavy chain variable region CDR1 comprising Seq ID NO: 1;
    b. a human heavy chain variable region CDR2 comprising Seq ID NO: 2;
    c. a human heavy chain variable region CDR3 comprising Seq ID NO: 3;
    d. a human light chain variable region CDR1 comprising Seq ID NO: 4;

e. a human light chain variable region CDR2 comprising Seq ID NO: 5; and
f. a human light chain variable region CDR3 comprising Seq ID NO: 6.
13. The antibody of any of embodiments 1-10, wherein, said antibody comprises: a. a human heavy chain variable region CDR1 comprising Seq ID NO: 11;
b. a human heavy chain variable region CDR2 comprising Seq ID NO: 12;
c. a human heavy chain variable region CDR3 comprising Seq ID NO: 13;
d. a human light chain variable region CDR1 comprising Seq ID NO: 14;
e. a human light chain variable region CDR2 comprising Seq ID NO: 15; and
f. a human light chain variable region CDR3 comprising Seq ID NO: 16.
14. The antibody of any of embodiments 1-10, wherein, said antibody comprises:
a. a human heavy chain variable region CDR1 comprising Seq ID NO: 21;
b. a human heavy chain variable region CDR2 comprising Seq ID NO: 22;
c. a human heavy chain variable region CDR3 comprising Seq ID NO: 23;
d. a human light chain variable region CDR1 comprising Seq ID NO: 24;
e. a human light chain variable region CDR2 comprising Seq ID NO: 25; and
f. a human light chain variable region CDR3 comprising Seq ID NO: 26.
15. The antibody of any of embodiments 1-10, wherein, said antibody comprises:
a. a human heavy chain variable region comprising the amino acid sequence of Seq ID No: 38; and
b. a human light chain variable region comprising the amino acid sequence of Seq ID No: 40.
16. The antibody of any of embodiments 1-10, wherein, said antibody comprises:
a. a human heavy chain variable region comprising the amino acid sequence of Seq ID No: 8; and
b. a human light chain variable region comprising the amino acid sequence of Seq ID No: 10.
17. The antibody of any of embodiments 1-10, wherein, said antibody comprises:
a. a human heavy chain variable region comprising the amino acid sequence of Seq ID No: 18; and
b. a human light chain variable region comprising the amino acid sequence of Seq ID No: 20.
18. The antibody of any of embodiments 1-10, wherein, said antibody comprises:
a. a human heavy chain variable region comprising the amino acid sequence of Seq ID No: 28; and
b. a human light chain variable region comprising the amino acid sequence of Seq ID No: 30.
19. The antibody of any of embodiments 1-18, wherein, said antibody comprises the light chain constant region sequence of Seq ID No: 41.
20. The antibody of any of embodiments 1-18, wherein, said antibody comprises the heavy chain constant region of Seq ID No: 42.
21. The antibody of any of embodiments 1-18, wherein, said antibody comprises the light chain constant region having the amino acid sequence of SEQ ID No:41 and the heavy chain constant region having the amino acid sequence of Seq ID No: 42.
22. The antibody of any of embodiments 19-21, wherein, said antibody comprises a heavy chain amino acid sequence comprising allelic variation, wherein said allelic variation is at least one or more positions selected from the group consisting of 214, 221, 356 and 358 as defined by the EU index numbering system.
23. The antibody of any of the preceding embodiments wherein, said antibody is selected from the group consisting of: human antibody, humanized antibody, chimeric antibody, intrabody, and a synthetic antibody.
24. An isolated nucleic acid comprising a polynucleotide sequence encoding the antibody of any of the preceding embodiments.
25. The nucleic acid of embodiment 24 wherein, said nucleic acid is a replicable vector.
26. The nucleic acid of embodiment 25 wherein, said polynucleotide sequence is operably linked to a promoter.
27. A host cell comprising or transformed with the vector of embodiment 25 or 26.
28. A transgenic mouse comprising human immunoglobulin heavy and light chain transgenes, wherein the mouse expresses the antibody of any of embodiments 1-23.
29. A hybridoma prepared from the mouse of embodiment 28 wherein the hybridoma produces said antibody.
30. A pharmaceutical composition comprising the antibody of any of the embodiments 1-23, and a pharmaceutically acceptable excipient.
31. A method of treating a condition or a disease associated with an immune disorder, comprising administering to a subject in need thereof an effective amount of the composition of embodiment 30.
32. The method of embodiment 31 wherein said disease is a type I interferon mediated disease.
33. The method of embodiment 32 wherein said type I interferon is interferon alpha.
34. The method of embodiment 33 wherein said type I interferon mediated disease is associated with the type I interferon receptor.
35. The method of embodiment 31, wherein said disease or disorder is HIV infection of AIDS.
36. The method of embodiment 31, wherein said disease or disorder is systemic lupus erythematosus.
37. The method of embodiment 31, wherein said disease or disorder is Sjogren's syndrome.
38. The method of embodiment 31, wherein said disease or disorder is myositis.
39. The method of embodiment 31, wherein said disease or disorder is inflammatory myositis.
40. The method of embodiment 31, wherein said disease or disorder is polymyositis.
41. The method of embodiment 31, wherein said disease or disorder is dermatomyositis.
42. The method of embodiment 31, wherein said disease or disorder is inclusion body myositis.
43. The method of embodiment 31, wherein said disease or disorder is juvenile myositis.
44. The method of embodiment 31, wherein said disease or disorder is idiopathic inflammatory myositis.
45. The method of embodiment 31, wherein said disease or disorder is vasculitis.
46. The method of embodiment 31, wherein said disease or disorder is sarcoidosis.
47. The method of embodiment 31, wherein said disease or disorder is selected from the group consisting of: inflammatory bowel disease, multiple sclerosis, autoimmune thyroiditis, rheumatoid arthritis, insulin dependent diabetes mellitus, glomerulonephritis, and graft versus host disease.
48. The method of embodiment 31, wherein said disease or disorder is psoriasis or conditions resulting thereof.
49. The method of embodiment 31, wherein said disease or disorder is transplant rejection or graft versus host disease.
50. The method of embodiment 31 wherein said disease or disorder is selected from the group consisting of: Grave's disease, Hashimoto's thyroiditis, Crohn's disease, psoriasis, psoriatic arthritis, sympathetic opthalmitis, autoimmune oophoritis, autoimmune orchitis, autoimmune lymphoproliferative syndrome, antiphospholipid syndrome. Sjogren's syndrome, scleroderma, Addison's disease, polyendocrine deficiency syndrome, Guinan-Barre syndrome, immune thrombocytopenic purpura, pernicious anemia, myasthenia gravis, primary biliary cirrhosis, mixed connective tissue disease, vitiligo, autoimmune uveitis, autoimmune hemolytic anemia, autoimmune thrombopocytopenia, celiac disease, dermatitis herpetiformis, autoimmune hepatitis, pemphigus, pemphigus vulgaris, pemphigus foliaceus, bullous pemphigoid, autoimmune myocarditis, autoimmune vasculitis, alopecia areata, autoimmune artherosclerosis, Behcet's disease, autoimmune myelopathy, autoimmune hemophelia, autoimmune interstitial cystitis, autoimmune diabetes isipidus, autoimmune endometriosis, relapsing polychondritis, ankylosing spondylitis, autoimmune urticaria, dermatomyositis, Miller-Fisher syndrome, IgA nephropathy, goodpastures syndrome, and herpes gestationis.
51. The method of any of embodiments 31-50, further comprising administering at least one agent selected from the group consisting of: phototherapy, corticosteroids, prednisone, NSAIDS, plasmapheresis, immunosuppressants, methotrexate, retinoic acid, tioguanine, mycophenolate mofetil, fumaric esters, cyclophosphamide, azathioprine, cyclosporine, and immunoglobulins.
52. The method of any of embodiments 31-51 further comprising administering at least one agent selected from the group consisting of: alefacept (AMEVIVE™), etanercept (ENBREL®), adalimumab (HUMIRA®), infliximab (REMICADE®), belimumab (LYMPHOSTATB™), rituxumab (RITUXAN®), and efalizumab (RAPTIVA®).
53. A crystal comprising a human IgG Fc region, wherein the human IgG Fc region comprises at least one amino acid substitution selected from the group consisting of L234F, L235E, and P331S, as numbered by the EU index as set forth in Kabat and wherein said fragment exhibits reduced affinity for at least one Fc ligand compared to an unmodified Fc region.
54. The crystal of Embodiment 53, wherein the human IgG Fc region comprises the amino acid substitutions L234F, L235E and P331S.
55. The crystal of Embodiment 53, which is diffraction quality.
56. The crystal of Embodiment 53, which is a native crystal.
57. The crystal of Embodiment 53, which is characterized by an orthorhombic unit cell of a=50.18±0.2 Å, b=147.30±0.2 Å, and c=75.47±0.2 Å.
58. The crystal of Embodiment 53, which has a space group of $C222_1$.
59. A modified monoclonal antibody, wherein said antibody comprises in the Fc region the amino acid substitutions L234F, L235E, and P331S, as numbered by the EU index as set forth in Kabat and wherein said antibody exhibits reduced affinity for at least one Fc ligand compared to an unmodified antibody.
60. A fusion protein comprising a modified Fc region, wherein said Fc region comprises the amino acid substitutions L234F, L235E, and P331S, as numbered by the EU index as set forth in Kabat and wherein said Fc region exhibits reduced affinity for at least one Fc ligand compared to an Fc region.
61. A method of making the antibody of any of embodiments 1-23 or 59.
62. The antibody of any of embodiments 1-23 or 59, wherein said antibody is an internalizing antibody.
63. The fusion protein of embodiment 60, wherein said fusion protein is an internalizing fusion protein.
64. The fusion protein of embodiment 63, wherein said fusion protein specifically binds IFNAR1.
65. The antibody of any of embodiments 1-23, 59, or 62, wherein said antibody exhibits reduced or ablated antibody dependent cell-mediated cytotoxicity (ADCC) as compared to said unmodified antibody.
66. The antibody of any of embodiments 1-23, 59, or 62, wherein said antibody exhibits reduced or ablated complement mediated cytotoxicity (CDC) as compared to said unmodified antibody.
67. The antibody of any of embodiments 1-23, 59, or 62, wherein said antibody exhibits reduced or ablated ADCC and CDC as compared to said unmodified antibody.

5.15 Sequences

```
Light Chain constant region
                                         (SEQ ID No: 41)
RTVAAPSVFIFPPSDEQLKSGTASVVCLLNNEYPREAKVQWKVDNALQSG

NSQESVTEQDSKDSTYSLSSTLTLSKADYEKHKVYACEVTHQGLSSPVTK

SENRGEC

Heavy Chain constant region
                                         (SEQ ID No: 42)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPEFEGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPASIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK
```

6. EXAMPLES

The invention is now described with reference to the following examples. These examples are provided for the purpose of illustration only and the invention should in no way be construed as being limited to these examples but rather should be construed to encompass any and all variations which become evident as a result of the teachings provided herein.

6.1 Example 1: IHC Profile of Multiple Anti-IFNAR1 Antibodies

Purpose: To evaluate the IHC profile of anti-IFNAR1 antibodies on a diverse set of tissues.

Methods: Immunohistochemistry techniques to study antibody binding characteristics are readily known in the art and for example, could be performed by isolating the desired cells or tissues and preparing them for microscopy by standard fixation and mounting techniques.

Mouse Macrophages: A cell suspension was spun down to form a loose pellet. The pellet was frozen in OCT freezing medium to form a block. Slide sections were cut to 5 microns thickness, soaked in acetone for 10 minutes and allowed to dry with dessicant overnight. Prior to use, the slides were dipped into 10% neutral buffered formalin for 10 sec and washed 3× in buffer (1×TBS with 0.01% Tween20).

Human Monocytes: A cell suspension was smeared/spotted directly onto slides. The slides were allowed to dry overnight and then soaked in Acetone for 10 min and allowed to air dry. Prior to use, slides were dipped into 10% neutral buffered formalin for 10 secs and washed 3× in buffer (1×TBS with 0.01% Tween20).

Human Cerebrum and Cardiac Tissue: Tissue samples from donors were frozen in OCT freezing medium to form a block. Slide sections were cut to 5 micron thickness, soaked in acetone for 10 minutes and allowed to dry with dessicant overnight. Prior to use, the slides were dipped into 10% neutral buffered formalin for 10 sec and washed 3× in buffer (1×TBS with 0.01% Tween 20).

Antibody labeling: Antibodies were conjugated to biotin by the following protocol. Approximately 500 µg of antibody was mixed with a 20 fold excess of biotin and incubated for 2 hours in the dark at 4° C. After the 2 hour incubation, the antibody/biotin mix was applied to a pre-equilibrated PD10 column with 1×PBS. Subsequently, the biotin conjugated antibodies were concentrated to a desired concentration using an YM-30 Centricon concentration tube.

Slide staining: After washing in buffer, slides were treated to quench endogenous peroxidases by treatment with a solution of Glucose Oxidase (1 U/ml, Sigma G0543), B-D (+) Glucose (10 mM, Sigma G5250), Sodium Azide (1 mM, Sigma, 58032) for 1 hour at room temperature. Slides were then rinsed in wash buffer (1×TBS with 0.01% Tween 20). Slides were placed in a protein block solution (1x PBS pH7.2, 0.5% casein (N-Z amine, Sigma C0626), 1% BSA (Sigma A7906), 1.5% Normal Goat serum (Jackson Labs #005-000-001) for 30 min at room temperature. Biotinylated antibody (see above) was applied to the slides by dilution into the protein block solution. Incubation of the slides with the biotinylated antibody was performed at room temperature for 2 hours. Slides were rinsed 3× in wash buffer (1×TBS, 0.01% Tween 20). Antibody detection was performed using a Vectastain Kit (Vector Laboratories). Slides were washed and counterstained with hematoxylin. Slides were dehydrated and mounted with coverslips prior to viewing.

Results: Presented in FIG. 6A are the results of an IHC analysis of Human cerebrum tissue stained with various anti-IFNAR1 and control antibodies. The antibodies MDX-1333 (75 µg/ml) and 4G5 (50 µg/ml) exhibited strong staining of the cerebrum tissue as exemplified by the brown/dark staining seen throughout the samples. Antibody 9D4 (50 µg/ml) did not stain the human cerebrum tissue sample as well as MDX-1333 and 4G5 as demonstrated by the reduced brown/dark staining throughout the sample. An IgG1 isotype control was included to demonstrate that binding specificity of the individual antibodies.

Presented in FIG. 6B are the results of an IHC analysis of monocytes stained with various anti-IFNAR1 and control antibodies. The antibodies MDX-1333 (50 and 20 µg/ml), 4G5 (50 µg/ml) and 9D4 (50 and 20 µg/ml) all exhibited prominent staining on human monocytes as demonstrated by the brown/dark staining of the samples. The isotype control antibody R3-47 (50 µg/ml) did not exhibit prominent staining on human monocytes. In addition, MDX-1333(50 µg/ml) did not stain purified mouse macrophages.

Conclusions: In IHC study the anti-IFNAR1 antibody 9D4 exhibited a lower level of staining as compared to other anti-IFNAR1 antibodies such as MDX-1333 and 4G5.

6.2 Example 2: Generation of Antibody 9D4 TM

The modified anti-IFNAR1 antibody designated "9D4-TM" was generated through the following procedure;

Human γ1 Fc was cloned and engineered from human PBLs by first isolating total RNA, transcribing cDNA, and PCR amplifying the constant regions with gene-specific primers containing restriction sites Apa I and EcoRI for cloning into the mammalian vector PEE6. The triple mutant (TM) includes three amino acid changes in human IgG to decrease ADCC effector function (L234F, L235E, and P331S). TM was engineered using human IgG1 (KOL) as a template, and utilizing site-directed mutagenesis (Quick-Change XL, Stratagene) to encode three residue changes in the Fc. Sequence of the mutagenic primers used to encode the L234F/L235E/P331S changes were as follows:

```
MD1056 =
                                          (SEQ ID NO: 43)
5' cgtgcccagcacctgaaTtcGAgggggggaccgtcagtcttc
3' L234F, L235E forward MD1057 =
                                          (SEQ ID NO: 44)
5' gaagactgacggtcceccaCgaAttcaggtgctgggcacg
3' L234F, L235E reverse MD1058 =
                                          (SEQ ID NO: 45)
5' ccaacaaagccctcccagccTccatcgagaaaaccatctcc
3' P331S forward MD1059 =
                                          (SEQ ID NO: 46)
5' ggagatggttttctcgatggAggctgggagggctttgttgg
3' P331S reverse
```

Clones encoding the 9D4-TM antibody were sequenced to confirm the triple mutations, and resolved on the ABI3100 genetic analyzer.

6.3 Example 3: Generation of Antibody 9D4 DM

The modified anti-IFNAR1 antibody designated "9D4-DM" was generated through the following procedure;

Human γ4 Fc was cloned and engineered from human PBLs by first isolating total RNA, transcribing cDNA, and PCR amplifying the constant regions with gene-specific primers containing restriction sites Apa I and EcoRI for cloning into the mammalian vector PEE6.

The double mutant (DM) consists of two mutations in human IgG4 Fc: S228P and L235E. Mutagenic primers to encode DM include:

```
MD1060 =
                                          (SEQ ID NO: 47)
5' ggtcccccatgcccaCcatgcccagcacctg 3'
hinge S228P forward MD1061 =
                                          (SEQ ID NO: 48)
5' caggtgctgggcatgGtgggcatgggggacc 3'
hinge S228P reverse MD1062 =
                                          (SEQ ID NO: 49)
5' ccagcaectgagttcGAggggggaccatcagtc 3'
IgG4 L234F, L235E forward
```

```
MD1063 =
                                  (SEQ ID NO: 50)
5' gactgatggtccccccTCgaactcaggtgctgg 3'
IgG4 L234F, L235E reverse
```

Clones encoding the 9D4-DM antibody were sequenced to confirm the encoded changes, and resolved on the ABI3100 genetic analyzer.

6.4 Example 4 Anti-IFNAR1 Antibodies Inhibit IFN Mediated STAT Phosphorylation

Purpose: To establish the ability of the anti-IFNAR1 antibody 9D4-TM to inhibit IFN mediated STAT phosphorylation in peripheral blood mononuclear cells.

Methods: Peripheral blood mononuclear cells were purified from healthy human donors using LSM media (MP Biomedical, Solon Ohio). PBMCs were quantified and seeded at $10^6$ cell per condition per well. Antibodies were added at 10 µg/mL to appropriate well and incubated at 37° C., 5% $CO_2$ for 10 minutes. After pre-incubation with antibodies, recombinant human IFNα2a (PBL Biomedical, Piscataway N.J.) or human plasmacytoid dendritic cell-derived IFN (see below for generation of PDCs derived type-I IFN supernatants) was added to appropriate wells at 100 or 500 IU/mL for 20 minutes. Cells were spun at 1200 rpm for 5 minutes and washed with sterile 1×PBS. After one additional spin, PBS was removed and cells were lysed using mammalian protein extraction reagent (Pierce, Rockford Ill.) supplemented with 300 µL of 1× phosphatase inhibitor cocktails 1 and 2 (Sigma, St. Louis Mo.) and 1× protease inhibitor (Roche Biomedical, Nutley N.J.). Lysates were incubated for 10 minutes on an orbital shaker to ensure complete lysis, transferred to microfuge tubes and spun at 14000 rpm to remove cellular debris. NuPAGE sample buffer (Invitrogen, Carlsbad Calif.) and dTT (Sigma, St. Louis Mo.) were added to lysates for a final concentration of 1× and all samples were denatured in a heat block at 100° C. for approximately 10 minutes. 15 µL of each sample was added to NuPage 10% Bis-tris polyacrylamide gel (Invitrogen, Carlsbad Calif.) in NuPAGE MES SDS running buffer supplemented with 1× NuPAGE antioxidant buffer. Samples were run at 180V for 30 minutes for separation of protein bands. Proteins were then transferred to a nitrocellulose membrane and blots were blocked with 1×PBS (Gibco BRL, Carlsbad Calif.) containing 5% BSA (Sigma, St. Louis Mo.) overnight at 4° C. Blocking media was subsequently removed and 0.2 µg/mL anti-STAT1, anti-STAT1 pY701, or 1:1000 dilution of β-Actin antibodies (Cell Signaling Technology, Danvers Mass.) were added to appropriate blots and incubated overnight at 4° C. Blots were washed 3× in 1×TBS with 0.05% Tween20 (Sigma, St. Louis Mo.). 1:2500 diluted, HRP conjugated anti-rabbit secondary antibody was added to blots and incubated for 1 hr at room temperature. Blots were washed as described before and 3 mL of a 1:1 mixture of Pico Supersignal West reagent (Pierce, Rockford Ill.) was added to each blot for 1 minute. Blots were drained, excess reagent was removed and bands were visualized using a Kodak X-omat 1000A Processor.

Results: Presented in FIG. 7. are the results of a STAT activation assay in which cells stimulated with Leukocyte IFN in the presence or absence of anti-IFNAR1 antibodies. In the absence of antibodies, leukocyte interferon stimulates the phosphorylation of STAT isoforms 1, 3 and 5. Incubation of cells with 9D4-TM antibody inhibits the phosphorylation mediated by treatment with leukocyte interferon. Cells treated with the isotype control antibody R3-47 do not exhibit inhibition of STAT phosphorylation in response to stimulation with leukocyte interferon.

Conclusions: The results in FIG. 7 demonstrate that 9D4-TM is capable of inhibiting responses to IFNα such as the induction of STAT phosphorylation in peripheral blood mononuclear cells.

6.5 Example 5: Anti-IFNAR1 Antibodies Inhibit Type I IFN Signaling

Purpose: Using purified Type I IFN from pDC cells, a reporter assay was used to test the ability of anti-IFNAR1 antibodies to block Type I IFN signaling.

Methods: Plasmacytoid dendritic cells (PDCs) were isolated from whole blood of healthy donors using a lymphocyte separation media (MP Biomedical, Solon Ohio) followed by positive selection using CD304 (BDCA-4/Neuropilin-1) MicroBead Kit (Milteny Biotec, Auburn Calif.). Purified PDCs were then cultured at $1 \times 10^6$ cells/mL in RPMI 1640 supplemented with 10% FBS (Gibco BRL) and 6 µg/mL CpGA (InVivogen, San Diego Calif.). Supernatants were harvested and clarified after 20 hours in culture and type-I IFN was quantified using a stably transfected HEK293-ISRE reporter cell line against a standard curve of human leukocyte IFN (PBL Biomedical, Piscataway N.J.).

pDCs from three healthy human donors were used to generate human pDC-derived type-I interferon supernatants, as described above. HEK293 (ATCC, Manassas Va.) cells were stably transfected with pHTS-ISRE reported plasmid (Biomyx Technology, San Diego Calif.) and were maintained in DMEM supplemented with 10% FBS, 1×NEAA, and 700 µg/mL G418 (Invitrogen, Carlsbad Calif.). Cells were seeded at a concentration of 80,000 cells per well in Optilix white/clear 96 well plates (VWR, West Chester Pa.). Appropriate concentrations of antibodies (611-0.00004 nM) were added to each well followed by addition of appropriate concentrations of human PDC-derived type-I interferon supernatants. Cells, IFN, and antibodies were incubated overnight at 37° C., 5% $CO_2$ and amplification of the luciferase protein was evaluated by lysing the cells with Cell Culture Lysis reagent and visualization using the Luciferase Assay System (Promega, Madison Wis.). Signal was measured in cps and IC50 values were generated.

Results: Type I IFN supernatants were harvested from pDC cells derived from three individual donors. In a Luciferase reporter assay, incubation of anti-IFNAR1 antibodies inhibited the signaling ability of various concentrations of Type I IFN supernatant (FIG. 8).

Conclusions: These results demonstrate that anti-IFNAR1 antibodies are capable of inhibiting Type I IFN mediated signaling as measured by reporter assay activity.

6.6 Example 6: Modified Anti-IFNAR1 Antibodies Exhibit Similar Binding Characteristics to the Parental Unmodified Antibody Purpose: To investigate the IFNAR1 binding characteristics of modified antibodies as compared to parental unmodified versions. Represented in FIG. 9 are the binding affinity curves for 9D4, 9D4DM, and 9D4TM. The binding constants (Kd) for the 9D4, 9D4DM, and 9D4TM anti-IFNAR1 antibodies were determined from the binding curves.

Methods: 200,000 HEK 293F cells were seeded in a round bottom, 96-well plate using 50 µL RPMI 1640 media supplemented with 10% FBS. Europium-labeled 9D4-TM was prepared under contract by PerkinElmer Life and Analytical Sciences. To measure non-specific Europium signal, 25 µL of 100-fold excess unlabeled, serially diluted anti-IFNAR1 antibodies were added to appropriate wells of the 96 well for 5-10 minutes prior to the addition of labeled 9D4-TM. 25 µL of europium conjugated, serially diluted antibody was then added to appropriate wells and cells and antibodies were agitated gently at room temperature for 1-2 hours. After binding incubation, 150 µL of cell media was added to all wells and plates were spun at 1200 rpm for 5 minutes at room temperature. Plates were quickly decanted and 250 µL cell media was added to all wells. Spins and washes were repeated for a total of 3 washes. Cells were then resuspended in 100 µL cell media. 50 µL of resuspended cells were transferred to 200 µL of DELPHIA enhancement solution (PerkinElmer) in a DELPHIA yellow microtiter plate and Europium emission was measured on a Victor2 Multilabel reader (PerkinElmer). Signal was measured in cps and $K_d$ values and $B_{max}$ values were generated using GraphPad Prism 4 analysis software.

Results: The data represented in FIG. 9 demonstrates that the modified antibodies 9D4-TM and 9D4-DM exhibit similar binding affinities for IFNAR1 (9D4=0.06+/−0.02 nM, 9D4-DM=0.06+/−0.02 nM, 9D4-TM=0.03+/−0.01 nM) to the parental unmodified antibody.

Conclusions: The data presented in this example demonstrates that the modified antibodies share similar IFNAR1 binding characteristics with the parental unmodified antibodies.

6.7 Example 7: Equilibrium Binding Assay Data for 9D4-TM Vs. sIFNαRI

Purpose: To determine equilibrium binding data for 9D4-TM using soluble IFNAR1 (srIFNAR1)

Methods: srIFNAR1 ligand was coated onto UltraLink® Biosupport beads (PIERCE, Rockford, Ill.) at concentrations of 5 µg/mL and 50 µg/mL in coating buffer (50 mM sodium carbonate buffer, pH9) for a period of 1-2 days at 4° C. Coated beads were then separated (gentle pulse spin) from unreacted ligand solution, and gently rocked in block buffer (1 mL 1M Tris, pH8, containing BSA at 10 mg/mL) for about 15 min at room temperature (RT). After this, the bead slurry was again spun to remove the blocking solution, and then the block step was repeated for about 2 hrs at RT using a fresh aliquot of block buffer. Following the blocking step, the coated beads were stored at 4° C. until used. Prior to use, the srIFNAR1-coated beads were transferred to a bead vial, resuspended in 27 mLs of instrument run buffer (PBS, pH7.4—0.02% NaN3), then attached to the KinExA 3000 instrument.

All equilibrium binding constants ($K_D$) were obtained from measurements made on a KinExA 3000 instrument (Sapidyne Instruments, Boise, Id.). Briefly, 9D4-TM IgG was prepared at 1 pM, 10 pM and 50 pM and dispensed into three series of tubes. This range of IgG concentrations was designed to permit measurements to be made at under both receptor- and $K_D$-controlled conditions. Two-fold serial dilutions of srIFNAR1 ligand were then titrated across these IgG solutions, at concentrations ranging from 19.5 fM-1 nM. Based on the vendor-supplied, theory curve simulations available through the software (Sapidyne Instruments, Boise, Id.), these equilibration mixtures were incubated anywhere from 2-6 days at RT. At the end of this time, signal-testing experiments were conducted to determine the appropriate run conditions. Detection of free antibody was made possible using a species-specific, Cy5-labeled secondary antibody reagent (Cy5 AffiniPure F(ab')2 Fragment Goat Anti-Human IgG, Part #109-176-097, Jackson ImmunoResearch Laboratories), employed at 0.1, 1.0 or 2.0 µg/mL of PBS, pH7.4-0.02% NaN3 containing BSA at 1 mg/mL. Data obtained from the experiments were then simultaneously fitted using the software provided n-Curve analysis feature to obtain the reported binding constant ($K_D$).

Results: Depicted in FIG. 10A are the binding curves for three concentrations of 9D4-TM (1 pM, 10 pM, and 50 pM) with sIFNαRI. Data obtained from at least three independent experiments were fitted to a software derived binding curve to establish a relative $K_D$ for 9D4-TM. The $K_D$ of 9D4-TM in this binding assay was determined to be 1.1 pM with a 95% confidence interval of 0.603 pM-1.8 pM. The percentage error of the $K_D$ determination of 1.1 pM was 1.96%. The Kon and Koff for 9D4-TM was also determined to be $7 \times 10^6 +/- 1.3 \times 10^6$ $S^{-1}$ and $7.7 \times 10^{-6} +/- 1.57 \times 10^{-6}$ 1/Ms respectively (data not shown).

Conclusions: The modified anti-IFNAR1 antibody 9D4=TM exhibits a very low $K_D$ of approximately 1.1 pM, for sIFNAR1 as determined by the KinExa assay.

6.8 Example 8: Determination of Binding Affinity of 9D4-TM on Human PBMCs

Purpose: To determine the binding affinity on human PBMC's

Methods: Peripheral blood mononuclear cells were purified from healthy human donors using LSM media (MP Biomedical, Solon Ohio). Cells were counted and 200,000 cells were seeded in a round bottom, 96-well plate using 50 µL RPMI 1640 media supplemented with 10% FBS. Europium-labeled 9D4-TM was prepared under contract by PerkinElmer Life and Analytical Sciences. To measure non-specific europium signal, 25 µL of 100-fold excess unlabeled, serially diluted 9D4-TM was added to appropriate wells of the 96 well for 5-10 minutes prior to the addition of labeled 9D4-TM. 25 µL of europium conjugated, serially diluted 9D4-TM was then added to appropriate wells and cells and antibodies were agitated gently at room temperature for 1-2 hours. After binding incubation, 150 µL of cell media was added to all wells and plates were spun at 1200 rpm for 5 minutes at room temperature. Plates were quickly decanted and 250 µL cell media was added to all wells. Spins and washes were repeated for a total of 3 washes. Cells were then resuspended in 100 µL cell media. 50 µL of resuspended cells were transferred to 200 µL of DELPHIA enhancement solution (PerkinElmer) in a DELPHIA yellow microtiter plate and Europium emission was measured on a Victor2 Multilabel reader (PerkinElmer). Signal was measured in cps and Kd values and B max values were generated using GraphPad Prism 4 analysis software.

Results: Using the affinity measurements documented in FIG. 10B. it was determined that the Kd for 9D4-TM binding to human PBMCs was 0.29 nM+/−0.11 nM with the number of binding sites determined to be 1448+/−447. Using a similar approach, the affinity binding constant for cynomologus monkey IFNAR was determined to be 0.65+/−0.42 nM with the number of binding sites determined to be 648+/−204 (data not shown).

Conclusions: The results presented in FIG. 10B demonstrate that 9D4-TM binds specifically and with high affinity to human PBMCs.

6.9 Example 9: The Modified Anti-IFNAR1 Antibodies Exhibit Similar Potency with the Parental Unmodified Antibody Purpose: To demonstrate that modified anti-IFNAR2 antibodies (i.e. anti-IFNAR1 antibodies with reduced Fc ligand affinity) exhibit similar potency with the parental unmodified antibodies.

Methods: The Luciferase Reporter assay system used in this example has been previously described above (See Example 3). Antibodies to IFNAR1 used in this example include 9D4, 9D4-DM, 9D4-TM, MDX-1333. Included is a control antibody R3-47.

Results: Using the Luciferase reporter system, IC50 values were generated for the various anti-IFNAR1 antibodies described above (See FIG. 11A). The anti-IFNAR1 antibody 9D4 (0.01 nM) and the modified antibodies, such as 9D4-DM (0.01 nM) and 9D4-TM (0.02 nM) each elicit a similar IC50 value in the reporter assay demonstrating that they exhibit a similar potency. Another anti-IFNAR1 antibody, MDX1333 (0.04 nM) also exhibits a similar potency to the unmodified 9D4 antibody. The isotype control does not inhibit Type I IFN mediated signaling in this Luciferase reporter assay.

Conclusions: Modified anti-IFNAR1 antibodies share similar potencies to the unmodified versions as demonstrated by IC50 values generated in a Luciferase Reporter assay system designed to quantify IFN signaling events.

6.10 Example 10: 9D4-TM Inhibits the Activity of Multiple Type I Interferon Alpha Isoforms Purpose: To demonstrate that 9D4-TM inhibits signaling attributed to specific and multiple interferon alpha isoforms.

Methods: The Luciferase Reporter assay system used in this example has been previously described above (See Example 5).

Results: The IC50 values for the 9D4-TM mediated inhibition of Type I interferon activity are presented in Table 4.

TABLE 4

IC50 values for 9D4-TM mediated inhibition of Type I interferon activity

| Type I Interferon | 9D4-TM IC50 (nM) |
|---|---|
| IFN-α2b | 0.07 +/− 0.01 |
| IFN-α2a | 0.3 +/− 0.2 |
| IFN-α6 | 0.04 +/− 0.01 |
| IFN-α16 | 0.02 +/− 0.03 |
| IFN-α8 | 0.03 +/− 0.04 |
| IFN-α10 | 0.01 +/− 0.01 |
| Leukocyte Interferon | 0.01 +/− 0.01 |
| IFN-α17 | 0.04 +/− 0.03 |
| IFN-α14 | 0.02 +/− 0.01 |
| IFN-α1 | 0.004 +/− 0.01 |
| IFN-α21 | 0.01 +/− 0.002 |
| IFN-α7 | 0.04 +/− 0.01 |
| IFN-α4b | 0.02 +/− 0.01 |
| IFN-β1 | 6.8 +/− 9.4 |
| IFN-ω | 0.1 +/− 0 |

As shown, 9D4-TM exhibits IC50 values in the sub-nanomolar range for multiple interferon alpha isoforms, leukocyte interferon, and interferon omega.

Conclusions: The modified anti-IFNAR1 antibody 9D4-TM demonstrates the ability to inhibit the signaling attributed to multiple specific interferon alpha subtypes as well as leukocyte interferon alpha in a reporter assay 6.11 Example 11: Isoelectric Point Determination of 9D4, 9D4DM and 9D4TM Purpose: To evaluate the biophysical characteristics of the parental unmodified antibody 9D4 in comparison to the modified antibodies 9D4-DM and 9D4-TM.

Methods: Native Isoelectric Focusing Polyacrylamide Gel Electrophoresis (IEF-PAGE) analysis was performed as follows: Pre-cast ampholine gels (Amersham Biosciences, pI range 3.5-9.5) were loaded with 8 μg of protein. Protein samples were dialyzed in 10 mM Histidine pH-6 before loading on the gel. Broad range pI marker standards (Amersham, pI range 3-10, 8 μL) were used to determine relative pI for the Mabs. Electrophoresis was performed at 1500 V, 50 mA for 105 minutes. The gel was fixed for 45 minutes using a Sigma fixing solution (5×) diluted with purified water to 1×. Staining was performed overnight at room temperature using Simply Blue stain (Invitrogen). Destaining was carried out with a solution that consisted of 25% ethanol, 8% acetic acid and 67% purified water. Isoelectric points were determined using a Bio-Rad GS-800 Densitometer with Quantity One Imaging Software.

Results: Depicted in FIG. 12A is the isoelectric point (pI) determination for antibodies 9D4WT, 9D4DM, and 9D4TM. Samples of the antibodies were run according to the methods above and exhibited the following characteristics. The 9D4 WT antibody exhibited prominent protein bands corresponding to 8.2, 8.35 and 8.51. The 9D4 DM antibody exhibited a single prominent protein band corresponding to 7.13. The 9D4 TM antibody exhibited prominent protein bands corresponding to 8.09 and 8.18.

Conclusions: As presented in this Example, the modified antibodies 9D4-DM and 9D4-TM exhibit very similar biophysical characteristics (pI) to the parental unmodified antibody 9D4.

6.12 Example 12: Thermostability of 9D4, 9D4-DM and 9D4-TM

Purpose: To evaluate the biophysical characteristics of the parental unmodified antibody 9D4 in comparison to the modified antibodies 9D4-DM and 9D4-TM.

Methods: Differential Scanning calorimetry was performed as follows: thermal melting temperatures ($T_m$) were measured with a VP-DSC (MicroCal, LLC) using a scan rate of 1.0° C./min and a temperature range of 20-110° C. A filter period of 8 seconds was used along with a 15 minute pre-scan. Samples were prepared by dialysis into 10 mM Histidine-HCl, pH 6 using Pierce dialysis cassettes (3.5 kD). Mab concentrations were 0.14 mg/ml, 0.79 mg/ml, and 0.64 mg/ml as determined by $A_{280}$. Melting temperatures were determined following manufacturer procedures using Origin software supplied with the system. Briefly, multiple baselines were run with buffer in both the sample and reference cell to establish thermal equilibrium. After the baseline was subtracted from the sample thermogram, the data were concentration normalized.

Results: The antibodies 9D4, 9D4-DM, 9D4-TM were subjected to differential scanning calorimetry as detailed above with the results presented in FIG. 12B. Each of the antibodies studied exhibited similar melting temperatures in the assay. Specifically, the antibodies exhibited the following melting temperatures; 9D4 WT=70.41° C., 9D4-DM=70.41° C., and 9D4-TM=70.88° C.

Conclusions: As presented in this Example, the modified antibodies 9D4-DM and 9D4-TM exhibit very similar biophysical characteristics ($T_m$) to the parental unmodified antibody 9D4.

6.13 Example 13: Surrogate Anti-IFNAR Antibodies Protect Mice from IFNα Induced Proteinuria Purpose: To demonstrate that anti-IFNAR antibodies protect mice from induced proteinuria in a model of SLE.

Methods: Female NZB/W F1 mice were purchased from Jackson Labs and housed in pathogen-free barrier facility. The recombinant adenovirus vector containing the mouse IFNα subtype 5 cDNA under the control of the CMV promoter/enhancer (Adv-mIFNα5) was used to induce early lupus in these mice. Mice (8 mice/group) were treated at 8-11 wk of age with a single i.v. injection of $0.3\times10^{10}$ Adv-mIFNα5 viral particles (vp). Controls received the same amount of control Adv particles. In some experiments, mice were injected with gradual doses of Adv-mIFNα5 ranging from $0.01\times10^{10}$ to $1.0\times10^{10}$ vp/mouse. To test the efficacy of anti-IFNAR1, mice were treated with successive 5 daily i.p. dosing of antibody at 10 mg/kg starting at the time of Adv delivery. For proteinuria, urine was tested using a dipstick (Chemstrip 2 GP; Roche Diagnostics). Proteinuria scored as 1 for levels of 30 mg/dl, 2 for 100 mg/dl, and 3 for levels ≥500 mg/dl. Mice were considered to have proteinuria if two consecutive urine samples scored 2 or higher.

Results: The results of the adenovirus infected mice treated with anti-IFNAR1 antibodies are presented in FIG. 13. Mice infected with Adv-mIFNα5 exhibit proteinuria with an onset of about 3 weeks. Infected mice treated with control mouse IgG antibody are not protected from the onset of proteinuria over the course of the experiment as demonstrated by an onset of proteinuria of about 4 weeks. Mice treated with anti-IFNAR antibodies do not show evidence of proteinuria throughout the 8 week time course. Mice treated with an adenovirus control show no proteinuria over the experimental time course.

Conclusions: Taken together, the data in this example demonstrates that the presence of anti-IFNAR antibodies is protective against adv-IFN induced proteinuria in an in vivo mouse model.

6.14 Example 14: Anti-IFNAR Antibodies Block Type I IFN Induced Gene Regulation

Purpose: To demonstrate that anti-IFNAR1 antibodies inhibit or reduce Type I interferon gene regulation in a mouse model of SLE.

Methods: Mice from the experimental procedures described in Example 13 also provided samples for analysis in this example. RNA was prepared from tissues using RLT lysis buffer (Qiagen). For solid tissues (kidney, spleen, skin), no more than 50 mg of tissue was used for RNA processing each time. Samples were placed in lysis buffer and lysing matrix A (Qbiogene), and processed for 30 sec at 4.5 m/s using Fastprep24 homogenizer instrument (Thermo Electron Corporation, Waltham, Mass.). For PBMC, whole blood samples were centrifuged and the pellet was lysed in RLT buffer. Upon lysis, samples were snap frozen at −80° C. until further processed. To isolate RNA, thawed tissue lysates were first processed using Qiashredder spin columns, then equal volumes of 70% ethanol were added to the tissue lysates and RNA was purified using Rneasy mini spin column kits according to the manufacturer's instruction.

cDNA was generated from 3 μg of RNA using SuperScript III reverse transcriptase and oligo d(T) as described in the manufacturer's protocol (Invitrogen, Corp. Carlsbad, Calif.). Samples of cDNA were diluted in nuclease-free water and stored at −80° C.

Expression levels of selected genes were measured by real-time PCR TaqMan® analysis using the ABI 7900HT Fast Real-time PCR system (Applied Biosystems, Foster City, Calif.). Housekeeping gene β-actin was used for endogenous control. Reaction mixtures had a final volume of 20 μl consisting of 1 μl of cDNA, 2 μl of 20× primers and probes (TaqMan® Gene Expression Assays, Applied Biosystems) and 18 μl of diluted TaqMan® Fast Universal PCR Master Mix. Amplification conditions were: 20 seconds at 95° C., 50 cycles of 1 second at 95° C. and 20 seconds at 60° C. CT values range from 0 to 50, with the latter number assumed to represent no product formation. Quantification of gene expression was performed using the comparative CT method (Sequence Detector User Bulletin 2; Applied Biosystems) and reported as the fold difference relative to the housekeeping gene.

Results: Type I interferon ectopically expressed in mice (See example 13) leads to induction of a number of genes. Presented in FIG. 14 are the fold changes of six Type I interferon responsive genes in the different populations of mice used in this experiment. Specifically, genes IFIT1, IFI44, IFI202b, CXCL9, CXCL10, and CXCL11 are all induced in the mice ectopically expressing IFNα and treated with nonspecific Mouse IgG. Mice ectopically expressing IFNα and treated with anti-IFNAR antibodies do not show any induction of the six Type I interferon responsive genes. As a control to demonstrate specificity of the adenovirally encoded IFNα, mice treated with PBS, or control adenovirus do not show any induction of these 6 genes. These results demonstrate that the administration of anti-IFNAR antibodies can block the gene induction response to IFN alpha in an in vivo mouse model.

Conclusions: Anti-IFNAR antibodies can block the regulation of Type 1 responsive genes in mouse model of SLE.

6.15 Example 15: Anti-IFNAR Antibodies Block the Production of Anti-dsDNA and Anti-SSA/Ro (Anti-Nuclear Antigen) Antibodies Induced by Type I Interferon Purpose: To demonstrate the ability of anti-IFNAR antibodies to block the production of anti-nuclear antibodies, such as anti-dsDNA and anti-SSa/Ro induced by Type I interferon in a mouse model of SLE.

Methods: Mice were prepared and treated as described in Example 13. Serum anti-dsDNA autoantibody levels were assessed by ELISA. Briefly, ELISA plates pretreated with poly (L-lysine) (100 μg/ml) were coated with calf thymus activated DNA (5 μg/ml in carbonate-bicarbonate buffer) (SIGMA). After overnight incubation at 4° C., plates were blocked with PBS/10% FCS. Sera (1/200 dilution) were incubated for 30 minutes at room temperature. Bound IgG was detected with peroxidase-conjugated goat anti-mouse IgG (1/4000) (KPL) added to the plates for 30 min. Binding was measured by adding TMB substrate (KPL) and stop solution (KPL), and the OD was read at 450 nm. A mouse anti-ds DNA IgG standard in serum was run in serial dilution (from 625 ng/ml) (Alpha Diagnostic) on each plate to allow standardization. Serum anti-SSA/Ro autoantibody levels were measured by ELISA (Alpha Diagnostic) following the manufacturer's instructions.

Results: Type I interferon ectopically expressed in mice (See Example 13) leads to accumulation of anti-dsDNA and anti-SSA/Ro antibodies. Presented in FIG. 15 are the relative quantities of anti-dsDNA (A) and anti-SSA/Ro (B) antibodies in the different populations of mice (control adenovirus, Adv-IFNα+PBS, Adv-IFNα+MuIgG, and Adv-IFNα+Anti-IFNAR) as measured by ELISA. Control adenovirus infected mice show little accumulation of anti-dsDNA or anti-SSA/Ro antibodies in this experiment. Mice infected with adenovirus encoding IFNα and treated with PBS accumulate anti-dsDNA and anti-SSA/Ro antibodies. Adv-IFNα infected mice treated with anti-IFNAR antibodies acquire less anti-dsDNA and anti-SSA/Ro antibodies than Adv-IFNα infected mice treated with non-specific IgG. These results demonstrate that treatment with anti-IFNAR antibodies inhibits the accumulation of anti-dsDNA and anti-SSA/Ro antibodies in response to ectopically expressed Type I IFN.

6.16 Example 16: Anti-IFNAR Antibodies Block the Production of IP-10 and IL-18 Induced by Type I Interferon Purpose: To demonstrate the ability of anti-IFNAR antibodies to block the accumulation of IFNα induced cytokines in a mouse model of SLE.

Methods: Mice from the experimental procedures described in Example 13 also provided samples for analysis in this example. Serum levels of cytokines were measured by ELISA (R&D systems) following the manufacturer's instructions.

Results: Type I interferon ectopically expressed in mice (See Example 13) leads to accumulation of IP-10 and IL-18 cytokines. Presented in FIG. 16 are the relative quantities of IP-10 (A) and IL-18 (B) in the different populations of mice (PBS, control adenovirus, Adv-IFNα+MuIgG, and Adv-IFNα+Anti-IFNAR) as measured by ELISA. Type I interferon ectopically expressed in mice (See Example 12) leads to accumulation of the cytokines, IP-10 and IL-18. Control adenovirus infected mice show little accumulation of IP-10 (A) or IL-18 (B) cytokines in this experiment. Adv-IFNα infected mice treated with anti-IFNAR antibodies accumulate less IP-10 and IL-18 cytokines than Adv-IFNα infected mice treated with non-specific IgG. These results demonstrate that treatment with anti-IFNAR antibodies inhibits the accumulation of the cytokines IP-10 and IL-18 in response to ectopically expressed Type I IFN.

Conclusions: Anti-IFNAR antibodies are able to block the accumulation of IFNα induced cytokines in a mouse model of SLE.

6.17 Example 17: Anti-IFNAR Antibodies Block the Production of ANA (Anti-Nuclear Antibodies) Induced by Type I Interferon Purpose: To demonstrate the ability of anti-IFNAR antibodies to block the accumulation of IFNα induced antinuclear antibodies in a mouse model of SLE.

Methods: Mice from the experimental procedures described in Example 13 also provided samples for analysis in this example. Antinuclear antibody (ANA) levels were measured by ANA test kit (Antibodies Incorporated) with Hcp-2 stabilized substrate and mitotic figures following the manufacturer's instruction. Serum was serially diluted and incubated with the Hep-2 cells on slides and the bound antinuclear antibody was detected by Hi-FITC labeled goat anti-mouse IgG (H+L) (Antibodies Incorporated). The titer of ANA is defined as the serum dilution factor where the ANA is no longer detectable.

Results: Type 1 interferon ectopically expressed in mice (See Example 13) leads to accumulation of anti-ANA antibodies. Presented in FIG. 17 is the serum titer of anti-ANA antibodies in the different populations of mice (no virus, control adenovirus, Adv-IFNα+PBS, Adv-IFNα+MuIgG, and Adv-IFNα+Anti-IFNAR) as measured by serial dilution staining on HEP2 cells. Control adenovirus infected mice show little accumulation of anti-ANA antibodies in this experiment. Mice infected with adenovirus encoding IFNα and treated with PBS accumulate anti-ANA antibodies. Adv-IFNα infected mice treated with anti-IFNAR antibodies acquire less anti-ANA antibodies than Adv-IFNα infected mice treated with non-specific IgG. These results demonstrate that treatment with anti-IFNAR antibodies inhibits the accumulation of anti-ANA antibodies in response to ectopically expressed Type I IFN.

Conclusions: Anti-IFNAR antibodies are able to block the accumulation of anti-nuclear antibodies induced by IFNα in a mouse model of SLE.

6.18 Example 18: Antibody Inhibition of SLE Plasma Mediated Dendritic Cell Development Purpose: SLE plasma induces dendritic cell development from normal human monocytes. In this example, the purified monoclonal antibody 9D4-TM was tested for the inhibition of dendritic cell development, as assessed by the ability of the antibodies to inhibit the induction of the cell surface markers CD38, and CD123 by SLE plasma.

Methods: The methods have been previously described in US Patent Application No. 20006/0029601 and is hereby incorporated by reference in its entirety. Essentially, the experiments were conducted as follows: A 25 ml buffy coat was diluted four-fold with phosphate buffered saline (PBS). The sample was separated into 4×50 ml conical tubes, and 15 ml of lymphocyte separation medium (ICN Biomedicals) was layered underneath. After a 30 minute spin at 500 g, the buffy layer containing the peripheral blood mononuclear cells (PBMCs) was removed and washed with PBS. Cells were resuspended in culture media containing 1% heat inactivated human serum at $4 \times 10^6$ cells/ml. Monocytes were isolated by incubating PBMCs ($2.0 \times 10^7$ cells/5 ml/25 cm$^2$ flask) for 1.5 hours at 37° C. in culture media and then washing away non-adherent cells twice. For induction of monocyte maturation, the cells were incubated with medium containing 25% human plasma from healthy volunteers or from patients with SLE. Antibody blocking studies were conducted by adding 30 µg/ml of anti-IFNAR1 antibody or isotype control, IgG1, to the culture. The cells were incubated for 4 days, washed with PBS, and treated with 1:5000 Versene for 10 minutes at 37° C. When necessary, the cells were detached by gentle cell scraping before being washed and analyzed. Each culture was resuspended in staining medium (Hanks's Balanced Salt Solution with 0.2% sodium bicarbonate, 0.01% sodium azide, 0.1 mM EDTA, 20 mM HEPES, and 2% fetal calf serum) and separated equally into six wells of a V bottom 96 well plate. The cells were pulse-spun at 2100 rpm on a Sorvall RTH-750 rotor, and resuspended in 25 µl of staining media. One microgram of specific phycoerythrin conjugated antibody was added to each well and incubated on ice for 45 minutes. The cells were washed three times, resuspended in 200 µl of 2% paraformaldehyde in PBS, and analyzed by flow cytometry with the Becton Dickinson FACScalibur. Gates were drawn on the forward v side scatter graph to remove contaminating cells from the analysis.

Results: In this experiment, the differentiation of human monocytes to dendritic cells in response to IFN derived from the plasma of SLE patients blocked by treatment with 9D4-TM was measured by surface expression of two dendritic cell markers, CD38 and CD123. In FIG. 18. multiple serum samples from SLE patients failed to increase the surface expression of CD38 and CD123 in the presence of 9D4-TM. The IC50 values for 9D4-TM varied from 0.02 nM to 0.06 nM for both CD38 and CD123.

Conclusions: The anti-IFNAR1 antibody 9D4-TM was able to block the ability of IFNα derived form SLE patients to induce pDC maturation as measured by cell surface marker expression.

6.19 Example 19: Anti-IFNAR Antibodies Suppress the Expression of CD38, CD123 and CD86 in Monocytes Stimulated with Leukocyte-IFN Purpose: In this example, the antibodies 9D4, 9D4-DM and 9D4 TM were tested for the inhibition of dendritic cell development, as assessed by the ability of the antibodies to inhibit the induction of the cell surface markers CD38, and CD123 by Leukocyte IFN.

Methods: Monocytes were isolated from whole blood of healthy donors using a lymphocyte separation media (MP Biomedical, Solon Ohio) followed by positive selection using Monocyte Isolation kit II (Milteny Biotec, Auburn Calif.). Purified monocytes were then cultured at $1 \times 10^6$ cells/mL in RPMI 1640 supplemented with 10% FBS (Gibco BRL). Serially diluted antibodies were prepared at final concentrations of 3 µg/mL-20 pg/mL in media and were added to appropriate wells of cells. After pre-incubation of approximately 5 minutes, 100 IU/mL of human leukocyte IFN (PBL Biomedical, Piscataway N.J.) was added to appropriate wells and cultures were incubated at 37° C., 5% $CO_2$ for 48 hours after which surface expression of CD38 and CD123 evaluated. Briefly, cells were pelleted at 1200 rpm for 5 minutes and culture media was removed from monolayers by aspiration followed by one wash 1× with sterile PBS. PBS was removed and 1 mL sterile cell dissociation buffer (Gibco BRL, Carlsbad Calif.) or 0.05% trypsin (Invitrogen, Carlsbad Calif.) was added to wells to remove cells from monolayers. After 5 minutes and brief agitation, equal volumes of RPMI 1640 supplemented with 10% FBS was added to each well, followed by two series of centrifugation and washes with sterile PBS. 50 µL of 1×PBS supplemented with 5% BSA (Sigma, St. Louis Mo.) and 10 µg/mL whole human IgG (Jackson ImmunoResearch Laboratories, West Grove Pa.) was added to each well for blocking of non-specific Fc antibody binding and incubated for 10 minutes at room temperature. 50 µL of 1×PBS supplemented with 5% BSA and PE-anti human CD123 and FITC-anti human CD38 antibodies (Becton Dickinson, Franklin Lakes N.J.) were added to appropriate wells and incubated for 30 minutes on ice. Cells were washed once in 1×PBS supplemented with 5% BSA and surface protein expression was measured on a BD LSRII (Becton Dickinson, Franklin Lakes N.J.).

Results: Presented in FIG. 19 are the suppression curves of CD38 (A), CD123 (B), and CD86(C) expression exhibited by leukocyte-IFN stimulated PBMCs incubated with anti-IFNAR antibodies 9D4, 9D4DM, and 9D4TM. For each CD molecule, the anti-IFNAR antibodies elicited similar suppression curves which were utilized to generate IC50 values. For CD38 expression on PBMCs stimulated with leukocyte-IFN (A), the anti-IFNAR antibodies elicited IC50 values as follows: 9D4=4.3 ng/ml, 9D4DM=40 ng/ml, 9D4TM=25 ng/ml. For CD123 expression on PBMCs stimulated with leukocyte-IFN (B), the anti-IFNAR antibodies elicited IC50 values as follows: 9D4=7 ng/ml, 9D4DM=21 ng/ml, 9D4TM=10 ng/ml. For CD86 expression on PBMCs stimulated with leukocyte-IFN (C), the anti-IFNAR antibodies elicited IC50 values as follows: 9D4=20 ng/ml, 9D4DM=20 ng/ml, 9D4TM=26 ng/ml.

Conclusions: The results in this Example demonstrate that antibodies of the invention, 9D4-DM and 9D4-TM exhibit similar suppression curves of IFN induction of pDC cell surface markers as compared to the parental 9D4 antibody.

6.20 Example 20: Modified Anti-IFNAR1 Antibodies Exhibit Decreased Binding to the Fc Receptor FcγRI Purpose: To demonstrate the reduced binding of a specific Fc receptor to modified anti-IFNAR1 antibodies.

Methods: The binding activity of modified antibodies 9D4-DM and 9D4-TM to human FcγRI (CD64) was evaluated by ELISA. FcγRI in PBS (pH7.4) was coated at 25 µl/well in a microtiter plate (Costar cat. 3690) at the concentration of 20 µg/ml over night at 4° C. After washing and blocking with 4% milk 1 hr at room temperature, the biotinylated 9D4, 9D4TM, 9D4DM and control antibodies were added into the previously blocked plate and incubated at 37° C. for an hour, starting at 500 µg/ml and then in two fold serial dilution. The plate was washed with PBS (pH7.4) containing 0.05% of Tween 20 and 25 µl of HRP conjugated Avidin was added to each well. After an hour incubation at 37° C., the plates were washed again and 50 µl/well of substrate—SureBlue TMB peroxidase (KPL cat. 52-00-03) was added. The reaction was stopped with 50 µl of 0.2M $H_2SO_4$ after 5-10 minutes development. The ELISA signal was read at 450 nM.

Results: In an ELISA based binding assay (FIG. 20), Modified anti-IFNAR1 antibodies 9D4DM and 9D4TM exhibited lower binding affinities to the FcγRI that the unmodified 9D4WT antibody as well as the control antibody.

Conclusions: These results demonstrate that the modified anti-IFNAR1 antibodies 9D4-DM and 9D4-TM elicit a lower affinity for the Fc receptor FcγRI as compared to the unmodified 9D4 antibody. The lowered affinity for the FcγRI receptor would lead to a lower induction of ADCC.

6.21 Example 21: The Fc Receptor FcγRIIIA Exhibits Reduced Binding to the Modified Anti-IFNAR1 Antibodies Purpose: To demonstrate the reduced binding of a specific Fc receptor to the modified anti-IFNAR1 antibodies 9D4-DM and 9D4-TM as compared to the unmodified anti-IFNAR1 antibody 9D4.

Methods: Fifty µg/ml of 9D4, 9D4TM, and 9D4DM antibodies diluted in PBS were coated on Immunlon IV microtiter plate over night at 4° C. After washing and blocking with 4% milk 1 hr at room temperature FcγRIIIA variants 158F (low affinity) and 158V (high affinity) with Flag tag were added to the wells of the blocked plate, starting at 50 µg/ml then in two-fold serial dilution. The plate was washed one hour later and incubated with biotin conjugated anti Flag antibody (Sigma) at 2 µg/ml. After washing 25 µl of HRP conjugated Avidin was added to each well. The unbound materials were removed by washing one hour after incubation. The binding signal was detected with the substrate TMB.

Results: The results from an ELISA based binding assay between anti-IFNAR1 antibodies (9D4WT, 9D4DM, and 9D4TM) and the high and low affinity Fc receptor FcγRIIIA are presented in FIGS. 21(A, B, C). In FIG. 21(A) 9D4WT antibodies coated on the ELISA plate efficiently bind the high affinity FcγRIIIA receptor at concentrations greater than 3 ng/ml while there is limited binding of the low affinity FcγRIIIA receptor at all concentrations tested. In FIG. 21(B) Modified 9D4DM antibodies coated on the ELISA plate do not efficiently bind the high or low affinity FcγRIIIA receptors at any concentrations tested. Likewise, in FIG. 21(C) Modified 9D4TM antibodies coated on the ELISA plate do not efficiently bind the high or low affinity FcγRIIIA receptors at any concentrations tested.

Conclusions: These results suggest that the modified anti-IFNAR1 antibodies 9D4-DM and 9D4-TM have a decreased affinity for the FcγRIIIA receptor as compared to the unmodified anti-IFNAR1 antibody 9D4. Additionally, the decreased affinity for the specific Fc receptor could lead to a decrease in ADCC effector function.

6.22 Example 22: The Modified Antibodies 9D4DM and 9D4TM Exhibit Reduced Binding for the Fc Receptor FcγRIIIA Purpose: To demonstrate the reduced binding of a specific Fc receptor to modified antibodies 9D4DM and 9D4TM.

Methods: Fifty µg/ml of FcγRIIIA variants (FcγRIIIA-10 158F and FcγRIIIA-10 158V) in PBS were coated on Immunlon IV microtiter plate over night at 4° C. After washing and blocking with 4% milk 1 hr at room temperature biotinylated 9D4, 9D4TM, and 9D4DM antibodies were added to the wells of the blocked plate at 100 µg/mL. The plate was washed one hour later and incubated with HRP conjugated Avidin. The unbound materials were removed by washing one hr after incubation. The binding signal was detected with the substrate TMB.

Results: The results from an ELISA based binding assay between the high and low affinity Fc receptors FcγRIIIA and anti-IFNAR1 antibodies (9D4WT, 9D4DM, and 9D4TM) are presented in FIGS. 22(A, B, C). In FIG. 22(A) the unmodified anti-IFNAR1 antibody 9D4, at concentrations greater than 3 ng/ml, efficiently binds the high affinity FcγRIIIA receptor immobilized on the ELISA plate, whereas the antibody demonstrates limited binding to the immobilized low affinity FcγRIIIA receptor at all concentrations tested. In FIG. 22(B) the modified anti-IFNAR1 antibody 9D4DM does not efficiently bind the immobilized high or low affinity FcγRIIIA receptors at any concentrations tested compared to the unmodified 9D4WT anti-IFNAR1 antibody. Likewise, in FIG. 22(C) the modified anti-IFNAR1 antibody 9D4TM does not efficiently bind the immobilized high or low affinity FcγRIIIA receptors at any concentrations tested compared to the unmodified 9D4WT anti-IFNAR1 antibody.

Conclusions: This Example demonstrates that the modified antibodies 9D4DM and 9D4TM, exhibit decreased affinity for the Fc receptor, FcγRIIIA as compared to the parental unmodified 9D4 antibody. This reduced affinity could lead to a decrease in FcγRIIIA mediated ADCC effector function as compared to the parental antibody.

6.23 Example 23: Neutralization of IFNs Subtypes by Anti-IFNAR1 Antibodies

Purpose: To demonstrate the ability of the anti-IFNAR1 antibodies MDX-1333, 9D4WT, and 9D4TM to neutralize specific IFNα subtypes in a reporter assay Methods: Reporter assays for IFNα neutralization have been well documented in the art. In this example, IFNα neutralization is measured by a HiL3 based reporter assay. An example of how a IFNα neutralization assay using HiL3 cells as a reporter is as follows: A human hepatoma cell line HiL3 was transfected with a plasmid containing an IFNα stimulated response element-luciferase (ISRE-Luc), and a neomycin resistance gene. These cells were kindly provided by Dr Michael Tovey (CNRS, Paris, France). Hil3, 30,000 cells/well, was cultured in white reflective 96 well plates (DYNEX Microlite) and grown overnight in Dulbecco's modified Eagle's medium containing 10% fetal bovine serum and 1 mg/ml G418 (+penicillin/streptomycin/L-glutamine). After this incubation, various forms of interferon were added and the plates were cultured for 18 hours. The reaction was terminated by adding 10 ml of lysis buffer to luciferase substrate vial (Luc Lite Plus kit, Perkin-Elmer); 100 μl of this substrate solution was added to each well and read on Top Count for 10 minutes (10 minutes waiting in the dark, then 1 second read/well). The counts per second (cps) at each IFN concentration were determined and the IFN concentration or cps in each sample was calculated from the IFN titration curve using Prism software (San Diego, Calif.) with linear regression parameters.

Results: The neutralization capacity for anti-IFNAR1 antibodies for various IFN species in a HiL3 reporter assay is presented in FIGS. 23 (A-E). The anti-IFNAR1 antibodies MDX-1333, 9D4WT and 9D4TM inhibit multiple Type I interferon subtypes with similar potency. The anti-IFNAR1 antibodies MDX-1333, 9D4WT and 9D4TM neutralize IFNα10 (A) with IC50 values of 0.09880 μg/ml, 0.008345 μg/ml, and 0.004287 μg/ml respectively. The anti-IFNAR1 antibodies MDX-1333, 9D4WT and 9D4TM neutralize Human Leukocyte TEN (B) with IC50 values of 1.121 μg/ml, 0.02104 μg/ml, and 0.02120 μg/ml respectively. The anti-IFNAR1 antibodies MDX-1333, 9D4WT and 9D4TM neutralize IFNα 2b (C) with IC50 values of 0.0006462 μg/ml, 0.002789 μg/ml, and 0.0008279 μg/ml respectively. The anti-IFNAR1 antibodies MDX-1333, 9D4WT and 9D4TM neutralize IFNω (D) with IC50 values of 5.323 μg/ml, 0.01015 μg/ml, and 0.01423 μg/ml respectively. The anti-IFNAR1 antibodies MDX-1333, 9D4WT and 9D4TM neutralize IFNβ (E) with IC50 values of 18.97 μg/ml, 0.7403 μg/ml, and 0.2611 μg/ml respectively.

Conclusions: These results indicate that the anti-IFNAR1 antibodies MDX-1333, 9D4WT (unmodified) and 9D4TM (modified) exhibit similar neutralization specificity and capacity for multiple Type I interferons.

6.24 Example 24: Anti-IFNAR1 Antibodies Neutralize Type I IFN in Plasma from SLE Patients Purpose: To demonstrate the ability of anti-IFNAR1 antibodies to neutralize Type I IFN in plasma isolated from SLE patients as measured by a report assay.

Methods: Stably transfected PIL-5 ISRE cells were maintained in RPMI 1640+1× Pen-strep-glutamine+10% FBS and seeded at 100,000 cells per well in Optilix white/clear 96 well plates (VWR, West Chester Pa.). Antibodies were titrated added to appropriate wells for a final concentration ranging from 90 μg/mL-60 pg/mL. Type-I interferon positive human SLE patient serum samples were added to each well for a final serum percentage of 50% per well. Cells, IFN, and antibodies were incubated overnight at 37° C., 5% $CO_2$. After overnight incubation, cells were pelleted briefly at 1200 rpm for 5 minutes and amplification of the luciferase protein was evaluated by lysing the cells with Cell Culture Lysis reagent and visualization using the Luciferase Assay System (Promega, Madison Wis.). Signal was measured in cps and IC50 curves were generated using GraphPad Prism 4 analysis software.

Results: 9D4-TM neutralizes Type I interferons in SLE patient plasma. The results from a neutralization assay of Type I interferons in SLE patient plasma is presented in FIG. 24. Neutralization of Type I interferon contained in the SLE patient plasma sample is specifically neutralized with 9D4-TM versus an Isotype control at increasing antibody concentrations. Specifically, 9D4-TM exhibits an IC50 of 0.04 nM for neutralization of Type I interferons in this plasma sample taken from an SLE patient.

Conclusions: This result suggests that the modified anti-IFNAR1 antibody 9D4-TM has the capacity to effectively neutralize Type I interferon in SLE patients.

6.25 Example 25: Anti-IFNAR Antibodies Suppress the IFNα Induced pDC Population in PBMCs Purpose: To demonstrate the ability of anti-IFNAR antibodies to suppress the accumulation of pDC cells in the peripheral blood of mice from a model of SLE.

Methods: Mice from the experimental procedures described in Example 13 also provided samples for analysis in this example. PBMCs were isolated from Spleen, Lymph Nodes, Bone Marrow and Peripheral Blood using standard isolation techniques and stained for the B220 and Ly6C surface markers. Isolated PBMCs were analyzed by FACS and double positive (B220 and Ly6C) cells were scored as pDC cells and the relative populations are represented in FIG. 25.

Results: As represented in FIG. 25, ectopic expression of IFNα triggers an increase in pDC cells within the PBMCs isolated from spleen (A), lymph nodes (B), blood (C), and bone marrow (D) in the presence of PBS or mouse non-specific IgG. Mice treated with anti-IFNAR antibodies do not accumulate pDC cells in response to IFN-alpha. Mice treated with control Adenovirus do not accumulate pDCs in the PBMC population.

Conclusions: These results suggest that anti-IFNAR antibodies specifically block the IFNαα induced upregulation of pDC cells.

6.26 Example 26: Modified Anti-IFNAR1 Antibodies Exhibit Lower Binding Affinities to Fc Receptors Purpose: To evaluate the relative binding affinities of the modified anti-IFNAR1 antibodies 9D4-DM and 9D4-TM with the parental unmodified antibody 9D4 to various Fc receptors.

Methods: All experiments were performed on a BIAcore 3000 instrument (BIAcore, Inc., Uppsala, Sweden). In a typical experiment 1 µM solutions of 9D4 IgGs were used to immobilize anywhere from ~7000 RUs–~11,000 RUs of protein onto CM5 sensor chip surfaces using a standard amino coupling protocol (BIAcore, Inc.). Separately, a blank surface was also prepared on each chip using the identical protocol, minus the protein. This blank surface was used as a reference cell throughout the experiment, and served to correct for both non-specific binding and certain housekeeping artifacts. For the test-binding experiments, FcγRI was prepared at 20 nM in HBS-EP buffer (BIAcore, Inc., consisting of the following: 10 mM HEPES buffer, pH7.4, 150 mM NaCl, 3 mM EDTA, and 0.005% P20. Between FcγRI injections, the IgG surface was regenerated with a 1 min. injection of 5 mM HCl. Sensorgram overlays were generated using the BIAevaluation 4.1 software (BIAcore, Inc, Uppsala, Sweden).

Results: The anti-IFNAR1 antibody 9D4 and modified anti-IFNAR1 antibodies 9D4-TM and 9D4-DM were tested for binding affinity to immobilized FcγRI protein in a BIAcore assay format. As depicted in FIG. 26, the anti-IFNAR1 antibody 9D4 exhibits a high affinity for the immobilized FcγRI. The binding of the anti-IFNAR1 antibody 9D4 to FcγRI is specific as the similar assay run with ovalbumin exhibits very little affinity for the immobilized receptor. The modified anti-IFNAR1 antibodies 9D4-TM and 9D4-DM exhibit a lower affinity of the immobilized receptor FcγR1 compared to the unmodified 9D4 anti-IFNAR1 antibody.

Conclusions: The resultant lower affinities for FcγRI exhibited by the modified anti-IFNAR1 antibodies 9D4-TM and 9D4-DM suggest that these antibodies would have a diminished capacity to activate ADCC in vivo.

6.27 Example 27: Fc Receptors Exhibit Reduced Binding Affinities to Modified Anti-IFNAR1 Antibodies Purpose: To evaluate the relative binding affinities of various Fc receptors to the modified anti-IFNAR1 antibodies 9D4-DM and 9D4-TM and the parental unmodified anti-IFNAR1 antibody 9D4.

Methods: Surface Plasmon Resonance Measurements

All experiments were performed on a BIAcore 3000 instrument (BIAcore, Inc., Uppsala, Sweden). In a typical experiment a 1 µM solution of FcγR1 was used to immobilize anywhere from ~7000 RUs–~11,000 RUs of protein onto CM5 sensor chip surfaces using a standard amino coupling protocol (BIAcore, Inc.). Separately, a blank surface was also prepared on each chip using the identical protocol, minus the protein. This blank surface was used as a reference cell throughout the experiment, and served to correct for both non-specific binding and certain housekeeping artifacts. For the test-binding experiments, antibodies were prepared at 333 nM in HBS-EP buffer (BIAcore, Inc., consisting of the following: 10 mM HEPES buffer, pH7.4, 150 mM NaCl, 3 mM EDTA, and 0.005% P20. Between antibody injections, the FcγRI surface was regenerated with a 1 min. injection of 3M MgCl2. Sensorgram overlays were generated using the BIAevaluation 4.1 software (BIAcore, Inc, Uppsala, Sweden).

Results: The anti-IFNAR1 antibodies 9D4, 9D4-TM and 9D4-DM were immobilized and incubated with soluble FcγRI. Binding affinity of the soluble FcγRI receptor to each of the anti-IFNAR1 antibodies were measured in a BIAcore assay and the resultant tracings are represented in FIGS. 27 A, B, C. The FcγRI bound the immobilized anti-IFNAR1 antibody 9D4 with a high affinity as represented in FIG. 27A. This interaction was highly specific as soluble ovalbumin did not show any binding to the immobilized anti-IFNAR1 antibody 9D4. The modified antibodies 9D4-TM and 9D4-DM do not bind the FcγRI as strongly as the wild type unmodified 9D4 antibody. In FIG. 27B, the modified anti-IFNAR1 antibody 9D4-DM was immobilized and incubated with either soluble FcγR1 or ovalbumin. The FcγRI exhibited a low binding affinity for the immobilized 9D4-DM antibody. This binding affinity is similar to the non-specific interaction seen with soluble ovalbumin. In FIG. 27C, the modified anti-IFNAR1 antibody 9D4-TM was immobilized and incubated with either soluble FcγRI or ovalbumin. The FcγRI exhibited a low binding affinity for the immobilized 9D4-TM antibody. This binding affinity is similar to the non-specific interaction seen with soluble ovalbumin.

Conclusions: The lower affinities exhibited by the Fc receptor FcγRI for the immobilized modified anti-IFNAR1 antibodies 9D4-DM and 9D4-TM over the unmodified anti-IFNAR1 antibody 9D4 suggests that the modified antibodies would exhibit a lower capacity to elicit an ADCC response.

6.28 Example 28: Anti-IFNAR Antibodies Block IFNα Responsive Gene Induction

Purpose: To demonstrate the ability of anti-IFNAR antibodies to block the induction of IFNα responsive genes in a mouse model of SLE.

Methods: Mice from the experimental procedures described in Example 13 also provided samples for analysis in this example. After 8 weeks into the experiment the mice were sacrificed and kidney tissue was removed. No more than 50 mg of tissue was used for RNA extraction using RLT lysis buffer (Qiagen). Samples were placed in lysis buffer and lysing matrix A (Qbiogene), and processed for 30 sec at 4.5 m/s using Fastprep24 homogenizer instrument (Thermo Electron Corporation, Waltham, Mass.). To isolate RNA, thawed tissue lysates were first processed using Qiashredder spin columns, then equal volumes of 70% ethanol were added to the tissue lysates and RNA was purified using Rneasy mini spin column kits according to the manufacturer's instruction. cDNA was generated from 3 μg of RNA using SuperScript III reverse transcriptase and oligo d(T) as described in the manufacturer's protocol (Invitrogen, Corp. Carlsbad, Calif.). Samples of cDNA were diluted in nuclease-free water and stored at −80° C.

Expression levels of selected genes were measured by real-time PCR TaqMan® analysis using the ABI 7900HT Fast Real-time PCR system (Applied Biosystems, Foster City, Calif.). Housekeeping gene β-actin was used for endogenous control. Reaction mixtures had a final volume of 20 μl consisting of 1 μl of cDNA, 2 μl of 20× primers and probes (TaqMan® Gene Expression Assays, Applied Biosystems) and 18 μl of diluted TaqMan® Fast Universal PCR Master Mix. Amplification conditions were: 20 seconds at 95° C., 50 cycles of 1 second at 95° C. and 20 seconds at 60° C. CT values range from 0 to 50, with the latter number assumed to represent no product formation. Quantification of gene expression was performed using the comparative CT method (Sequence Detector User Bulletin 2; Applied Biosystems) and reported as the fold difference relative to the housekeeping gene.

Results: Presented in FIG. 28 are the results from a comparative expression analysis in the kidney of 6 genes induced by interferon alpha after 8 weeks in an accelerated lupus mouse model. Mice ectopically expressing interferon alpha were treated with mouse IgG or anti-IFNAR antibodies. After 8 weeks, the mice treated with control IgG demonstrated a high induction of IFNα responsive genes namely ICAM1, VCAM1, CXCL9, CXCL10, and IFIT1. Mice treated with anti-IFNAR antibodies did not show induction of IFNα responsive genes after 8 weeks.

Conclusions: In the accelerated lupus mouse model treatment with anti-IFNAR antibodies blocks induction in the kidney of six genes (ICAM1, VCAM1, CXCL9, CXCL10, and IFIT1) mediated by the ectopically expression of IFN-alpha compared to control mice as measured by a Taqman assay. These results demonstrate that anti-IFNAR antibodies are capable of blocking IFNα mediated signaling in a SLE mouse model.

6.29 Example 29: Anti-IFNAR Antibodies Inhibit Accumulation of Autoantibodies in Serum Purpose: To demonstrate the ability of anti-IFNAR antibodies to inhibit the accumulation of autoantibodies in serum of mice in an SLE model.

Methods: Mice from the experimental procedures described in Example 13 also provided samples for analysis in this example. Whole blood samples were taken at 1 week intervals from week 2-7 of the regimen. Serum anti-dsDNA autoantibody levels were assessed by ELISA. Briefly, ELISA plates pretreated with poly (L-lysine) (100 μg/ml) were coated with calf thymus activated DNA (5 μg/ml in carbonate-bicarbonate buffer) (SIGMA). After overnight incubation at 4° C., plates were blocked with PBS/10% FCS. Sera (1/200 dilution) were incubated for 30 minutes at room temperature. Bound IgG was detected with peroxidase-conjugated goat anti-mouse IgG (1/4000) (KPL) added to the plates for 30 min. Binding was measured by adding TMB substrate (KPL) and stop solution (KPL), and the OD was read at 450 nm. A mouse anti-ds DNA IgG standard in serum was run in serial dilution (from 625 ng/ml) (Alpha Diagnostic) on each plate to allow standardization.

Results: Presented in FIG. 29 are the results from the ELISA based analysis of the levels of anti-ds DNA antibodies in mouse serum during an accelerated lupus mouse model time course. Mice ectopically expressing IFNα were treated with anti-IFNAR antibodies or mouse IgG control antibodies during an 7 week regimen. The mice treated with anti-IFNAR antibodies did not accumulate anti-dsDNA antibodies at the same rate or to the same extent of mice treated with control IgG antibodies. Mice infected with control adenovirus did not develop anti-ds DNA antibodies over the time course.

Conclusions: These results demonstrate that anti-IFNAR antibodies reduced the accumulation of anti-dsDNA antibodies in response to elevated levels of IFN alpha.

6.30 Example 30: Anti-IFNAR Antibodies Reduce Proteinuria in the Accelerated Lupus Mouse Model Purpose: To demonstrate the ability of anti-IFNAR antibodies to reduce established proteinuria (therapeutic setting) in the SLE mouse model.

Methods: Mice from the experimental procedures described in Example 13 also provided samples for analysis in this example. However, in a therapeutic approach, mice were allowed to develop proteinuria as a symptom of Lupus before application of the antibodies. Specifically, mice were allowed to develop a proteinuria score of 2.0-2.5 as described previously. Once the threshold level of proteinuria was passed, a treatment regimen of semi-weekly doses of PBS, control IgG or anti-IFNAR antibodies was conducted for 5 additional weeks. At semi-weekly intervals urine samples were tested and given a proteinuria score.

Results: Presented in FIG. 30A are the results from a therapeutic study of anti-IFNAR antibodies reducing the proteinuria score of mice from an accelerated lupus model Briefly, mice were allowed to develop proteinuria at which time, the cohort was either given PBS, control IgG or anti-IFNAR antibodies as treatment. As documented within the figure, the proteinuria score decreased for only the group receiving anti-IFNAR antibodies. The mice receiving PBS or control IgG as treatment continued to increase the proteinuria score over time. (B) An analysis of the area under the curve for the results over the five weeks determined that the anti-IFNAR antibody treated group differed from the PBS alone or IgG control groups, both of which were very similar.

Conclusions: These results demonstrate that anti-IFNAR antibodies could be used in a therapeutic setting of SLE.

6.31 Example 31: Anti-IFNAR Antibodies Reduce Mortality in the Accelerated Lupus Mouse Model Purpose: To demonstrate the ability of anti-IFNAR antibodies to reduce mortality in a therapeutic setting of the SLE lupus mouse model.

Methods: Mice from the experimental procedures described in Example 30 also provided samples for analysis in this example. In a therapeutic approach, mice were allowed to develop proteinuria as a symptom of Lupus before application of the antibodies. Specifically, mice were allowed to develop a proteinuria score of 2.0-2.5 as described previously. Once the threshold level of proteinuria was passed, a treatment regimen of semi-weekly doses of PBS, control IgG or anti-IFNAR antibodies was conducted for 5 additional weeks. Overall mortality was tracked for an additional 4 weeks.

Results: Presented in FIG. 31 are the mortality rates from a therapeutic study of anti-IFNAR antibodies in an accelerated lupus model Briefly, mice were allowed to develop proteinuria at which time, the cohort was either given PBS, control IgG or anti-IFNAR antibodies as treatment. Mice treated with anti-IFNAR antibodies exhibited no mortality at week 5, whereas mice treated with PBS or control IgG exhibited mortality rates of 87.5% and 62.5% respectively. Additionally, over the nine week study, anti-IFNAR treated animals exhibited a high survival rate compared to PBS or control IgG treated animals.

Conclusions: The results in this Example demonstrate that anti-IFNAR antibodies can decrease the mortality associated with Lupus.

6.32 Example 32: Absence of 9D4-TM Mediated ADCC Activity

Purpose: To verify that 9D4-TM is unable to induce ADCC activity, due to its poor binding affinity to FcγR1 and FcγRIIIA a series of experiments were conducted.

Methods: 293F target cells were labeled with DiO cell label (Invitrogen, experiments I & II) and combined with unlabeled effectors PBMCs (for 4h at 37° C., in the absence or presence 10 μg/ml of 9D4-TM, human IgG1 isotype negative control R3-47, 9D4-WT or anti-EphA2 antibody used as a positive control. Lysis of target cells was evaluated by measuring $DiO^+/PI^+$ (propidium iodide) double positive staining. Effector-target ratio=50-1, percent of lysis was calculated according to the formula: [(percent of double positive staining in the presence of antibodies−percent of double positive staining in media alone)/(percent of double positive staining in the presence of lysis buffer−percent of double positive staining in media alone)]. One hundred percent of lysis was achieved by adding lysis buffer (Promega).

Alternatively, 293F target cells were incubated with cells from a transgenic NK cell line stably expressing FcγRIIIA (experiment III) for 4h at 37° C., in the absence or presence 10 μg/ml of 9D4-TM, human IgG1 isotype negative control R3-47, 9D4-wt or anti-EphA2 antibody used as a positive control. Effector-target ratio=4–1 and percent of lysis was calculated according to the formula: 100×(Experimental–Effector Spontaneous–Target Spontaneous)/(Target Maximum–Target Spontaneous).

On experiments I & II (PBMCs-293H ratio=50-1), percent of lysis was calculated according to the formula: [(percent of double positive staining in the presence of antibodies–percent of double positive staining in media alone)/(percent of double positive staining in the presence of lysis buffer–percent of double positive staining in media alone)]. On experiment III (Transgenic NK cell line expressing FcγIIIA-293H ratio=4-1), percent of lysis was calculated according to the formula: 100×(Experimental–Effector Spontaneous–Target Spontaneous)/(Target Maximum–Target Spontaneous).

Results: The modified antibody 9D4-TM or the unmodified antibody 9D4-WT exhibited no detectable ADCC activity on 293F cells over that observed with the R3-47 antibody, (Table 4). In contrast, the positive control antibody, an anti-EphA2 antibody, caused a two-fold increase in cytotoxicity over background level. These results confirm that 9D4-TM cannot mediate ADCC on IFNAR1 expressing targets.

TABLE 5

Evaluation of ADCC activity of Anti-IFNAR1 antibodies.

| Antibodies | Exp. I % of target lysis | Exp. II % of target lysis | Exp. III % of target lysis |
|---|---|---|---|
| Positive control: Anti-EphA2 | 33 ± 4 | 36 ± 1 | 43.4 ± 0.5 |
| Negative control: R3-47 | 14 ± 1 | 18 ± 3 | 18.1 ± 1.1 |
| 9D4-WT | 14 ± 2 | 20 ± 2 | 17.5 ± 1.6 |
| 9D-TM | 14 ± 2 | 20 ± 2 | ND |

Exp. I/II/III: experiments I/II/III.
ND: not done.

Conclusions: These results demonstrate that modified anti-IFNAR1 antibody 9D4-TM does not stimulate detectable ADCC activity directed at IFNAR1 expressing target cells.

6.33 Example 33: Three-Dimensional Structures of Human Fc Region Comprising L234F/L235E/P331S Mutations Purpose: To determine the three-dimensional structures of human IgG1 Fc region comprising L234F/L235E/P331S mutations (Fc-TM).

Methods: Purification of Fc-TM: The human Fc/TM fragment was obtained from the enzymatic cleavage of 9D4-TM. Digestion was carried out using immobilized ficin according to the manufacturer's instructions (Pierce). Purification was first performed on HiTrap Protein A columns according to the manufacturer's instructions (GE Healthcare, Piscataway, N.J.). After dialysis in 50 mM NaOAc/pH 5.2, the protein solution was applied to a HiTrap SP HP column (GE Healthcare) and collected in the flow through. The flow through was loaded onto a HiTrap Q column (GE Healthcare) and eluted in a NaCl gradient to yield a homogenous Fc/TM preparation, as judged by reducing and non-reducing SDS-PAGE. Fc-TM SDS-PAGE profile showed the presence of only one band around 25 kDa or 50 kDa under reducing or non reducing conditions, respectively. This observation clearly demonstrated the presence of at least one interchain disulfide bond at positions C226 and/or C229. Consequently, mutated 'downstream' residues F234 and E235 were present in the polypeptide chain comprising the crystal.

Crystallization of Fc-TM: Purified Fc-TM was concentrated to about 5 mg/ml using a Centricon concentrator (Millipore, Billerica Mass., 30 KDa cutoff). Crystallization conditions were identified using the commercial screens from Hampton Research (Hampton Research, Aliso Viejo, Calif.), Emerald BioSystems (Emerald BioSystems, Inc., Bainbridge Island, Wash.) and Molecular Dimensions (Molecular Dimensions Inc., Apopka, Fla.). Each screen yielded several potentially usable crystallization conditions. Upon optimization, diffraction-quality crystals were obtained from 0.2 M Zinc acetate, 0.1 M Imidazole-Malate, pH 8.0, 5% PEG 3350, 5% glycerol at protein concentration of 2.0 mg/ml. Under these conditions, well-shaped crystals with three dimensions ranging from 0.1 to 0.2 mm grew in 2-3 days.

Data Collection: Diffraction data were collected from a single crystal at the Center for Advanced Research in Biotechnology (CARB, University of Maryland Biotechnology Institute, Rockville, Md.) using a Rigaku MicroMax™ 007 rotating anode generator with an R-AXIS IV++ imaging plate (Rigaku/MSC, The Woodlands, Tex.). Prior to cooling, the crystal was kept for a few minutes in its growth solution supplemented with 20% glycerol. The crystal was then cooled to 105 kelvins with an X-stream 2000 Cryogenic cooler (Rigaku/MSC). Diffraction of up to 2.3 Å was achieved after one round of annealing as described (Oganesyan et al., 2007). Diffraction data comprising 234 images were collected using an oscillation range of 0.5°, a crystal/detector distance of 200 mm and an exposure time of 600 s. Data were integrated and scaled using the HKL 2000 software (Otwinowski & Minor, 1997).

Structure Determination: Molecular replacement, refinement, and electron density calculation were carried out using the CCP4 (Collaborative Computational Project) program suite. The C-face centered orthorhombic crystal had a 58% solvent content and $V_M$ of 2.9, assuming one Fc polypeptide in the asymmetric unit of the cell. The crystal structure of Fc/TM was determined by molecular replacement and refined at 2.3 Å resolution. The human Fc structure corresponding to PDB ID number 2DTQ (Matsumiya et al., (2007) J. Mol. Biol. 368:767-779) was used as the model because of its high resolution and unliganded state. In particular, the $C_H2$ and $C_H3$ domains were considered separately to minimize any bias in terms of the domains relative conformation. Data up to 3.0 Å were used for the molecular replacement problem using Phaser (McCoy et al., (2005) Acta Cryst. D61, 458-464). After refinement of the solutions, the final LL-gain and the Z-score were 1192 and 31, respectively. Weighted electron density calculated with FWT/PHWT at 3.0 Å showed a good match with the model with the exception of some loops in the $C_H2$ and $C_H3$ domains. Strong positive difference electron density calculated with DELFWT/PHDELWT was visible in the expected place of N-linked carbohydrate residues attached to N297. There was no density present for any hinge residue preceding that at position 236, a result presumably attributable to the high flexibility of this region. It is noted that only two previously described unliganded human Fc structures could reveal positions 234 and 235 (2DTQ/2DTS; Matsumiya et al., (2007) J. Mol. Biol. 368:767-779). Likewise, residues at positions 446 and 447 could not be visualized. The residue at position 331 was first modeled as an alanine.

Several alternating rounds of refinement with 'Refmac 5' (Murshudov et al., (1997) Acta Cryst. D53, 240-255) and manual building using the "0" graphics software (Jones et al., (1991) Acta Cryst. A47, 110-119) converged with $R_{factor}$ of 21.6 and Free $R_{factor}$ of 27.5 for data up to 2.3 Å resolution. After the first round of refinement, the electron density allowed placement of the carbohydrates as well as substitution by a serine residue at position 331. At later stages of refinement, the model was analyzed using the TLS Motion Determination (TLSMD) program running on its web Server (Painter et al. (2006). J. Appl. Cryst. 39, 109-111; Painter et al. (2006) Acta Cryst. D62, 439-450). Further refinement was then carried out with Refmac 5 in TLS and restrained refinement mode using five distinct groups of residues (236-324, 325-341, 342-358, 359-403 and 404-445). Zinc ions present in the crystallization buffer were detected in the electron density and modeled as such when the coordination sphere and distance permitted. In particular, one zinc ion was found coordinated by H310 and H435. Another was coordinated by H285 and H268 of the symmetry related polypeptide. Two others were bound to E318 and E345. In all cases, water molecules completed the expected tetrahedral coordination sphere of the zinc ions. The carbohydrate moiety was modeled according to its electron density and the final model contained nine sugar residues, essentially as described by us in the context of another human Fc structure (Oganesyan et al., (2007) Molecular Immunology, Dec. 11, 2007, in press). The final model contained 75 solvent molecules. Crystallographic data and refinement statistics are given in Table 6.

TABLE 6

X-Ray data collection and model refinement statistics.

| | |
|---|---|
| Wavelength, Å | 1.54 |
| Resolution, Å | 36.83-2.30 (2.38-2.30) [a] |
| Space group | $C222_1$ |
| Cell parameters, Å | 50.18, 147.30, 75.47 |
| Total reflections | 54,409 |
| Unique reflections | 12,617 |
| Average redundancy | 4.31 (2.72) [a] |
| Completeness, % | 98.3 (90.0) [a] |
| $R_{merge}$ | 0.062 (0.300) [a] |
| I/σ(I) | 13.0 (3.3) [a] |
| R factor/Free R factor | 0.216/0.275 |
| RMSD bonds, Å | 0.012 |
| RMSD angles, ° | 1.48 |
| Residues in most favored region of {φ, ψ} space, % | 89.9 |

TABLE 6-continued

X-Ray data collection and model refinement statistics.

| | |
|---|---|
| Residues in additionally allowed region of {φ, ψ} space, % | 10.1 |
| Number of protein atoms | 1678 |
| Number of non-protein atoms | 189 |
| B factor (Model/Wilson), Å² | 43/40 |

[a] Values in parentheses correspond to the highest resolution shell

Results: Fc-TM crystallized in space group $C222_1$ with one polypeptide in the asymmetric unit (FIG. 32). The crystal diffracted to 2.3 Å resolution, and exhibited a relatively high average mosaicity of 1.26°. This high mosaicity appeared to be a property of both cooled and non-cooled crystals. All residues at positions 236 to 445 could be traced in the electron density and no electron density was observed for hinge residues prior to position 236, thus rendering the L234F and L235E mutations invisible. The electron density at position 331 corresponded to serine.

The atomic coordinates and experimental structure factors of Fc-TM have been deposited with the Protein Data Bank under accession number 3C2S.

The overall three-dimensional structure of Fc-TM was very similar to previously reported structures of unliganded human Fc regions (Deisenhofer, (1981). Biochemistry, 20: 2361-2370; Krapp et al., (2003). J. Mol. Biol. 325, 979-989; Matsumiya et al., (2007). J. Mol. Biol. 368:767-779; Oganesyan et al., (2007) Molecular Immunology, Dec. 11, 2007, in press). More precisely, the human Fc structures corresponding to PDB ID numbers 1H3W (Krapp et al., (2003). J. Mol. Biol. 325:979-989) and 2QL1 (Oganesyan et al., (2007) Molecular Immunology, Dec. 11, 2007, In the press) were closest to Fc-TM in terms of cell parameters, asymmetric unit content, space group and packing. When considered individually, Fc-TM $C_H2$ and $C_H3$ domains showed great structural conservation and rigidity when compared with other unliganded, unmutated human Fc structures. For instance, rms coordinate displacements of Cα atoms were 0.6 and 0.4 Å for the $C_H2$ and $C_H3$ domains, respectively, when superimposing Fc-TM with chain A of PDB ID number 2DTQ (Matsumiya et al., (2007). J. Mol. Biol. 368, 767-779).

Table 7 following below, provides the atomic structure coordinates of Fc-TM. The following abbreviations are used in Table 7

"Atom Type" refers to the element whose coordinates are provided. The first letter in the column defines the element.

"A.A." refers to amino acid.

"X, Y and Z" provide the Cartesian coordinates of the element.

"B" is a thermal factor that measures movement of the atom around its atomic center.

"OCC" refers to occupancy, and represents the percentage of time the atom type occupies the particular coordinate. OCC values range from 0 to 1, with 1 being 100%.

TABLE 7

The atomic structure coordinates of Fc-TM

| | | | |
|---|---|---|---|
| REMARK | 3 | | |
| REMARK | 3 | REFINEMENT. | |
| REMARK | 3 | PROGRAM | : REFMAC 5.2.0019 |
| REMARK | 3 | AUTHORS | : MURSHUDOV, VAGIN, DODSON |
| REMARK | 3 | | |
| REMARK | 3 | REFINEMENT TARGET: MAXIMUM LIKELIHOOD | |
| REMARK | 3 | | |
| REMARK | 3 | DATA USED IN REFINEMENT. | |
| REMARK | 3 | RESOLUTION RANGE HIGH | (ANGSTROMS) : 2.30 |
| REMARK | 3 | RESOLUTION RANGE LOW | (ANGSTROMS) : 30.00 |

TABLE 7-continued

The atomic structure coordinates of Fc-TM

| REMARK | 3 | DATA CUTOFF | (SIGMA(F)) : NONE |
|---|---|---|---|
| REMARK | 3 | COMPLETENESS FOR RANGE | (%) : 98.43 |
| REMARK | 3 | NUMBER OF REFLECTIONS | : 11994 |
| REMARK | 3 | | |
| REMARK | 3 | FIT TO DATA USED IN REFINEMENT. | |
| REMARK | 3 | CROSS-VALIDATION METHOD | : THROUGHOUT |
| REMARK | 3 | FREE R VALUE TEST SET SELECTION | : RANDOM |
| REMARK | 3 | R VALUE (WORKING + TEST SET) : 0.21928 | |
| REMARK | 3 | R VALUE (WORKING SET) : 0.21637 | |
| REMARK | 3 | FREE R VALUE | : 0.27541 |
| REMARK | 3 | FREE R VALUE TEST SET SIZE (%) : 4.9 | |
| REMARK | 3 | FREE R VALUE TEST SET COUNT | : 619 |
| REMARK | 3 | | |
| REMARK | 3 | FIT IN THE HIGHEST RESOLUTION BIN. | |
| REMARK | 3 | TOTAL NUMBER OF BINS USED | : 20 |
| REMARK | 3 | BIN RESOLUTION RANGE HIGH | : 2.300 |
| REMARK | 3 | BIN RESOLUTION RANGE LOW | : 2.360 |
| REMARK | 3 | REFLECTION IN BIN (WORKING SET) : 794 | |
| REMARK | 3 | BIN COMPLETENESS (WORKING + TEST) (%) : 89.74 | |
| REMARK | 3 | BIN R VALUE (WORKING SET) : 0.242 | |
| REMARK | 3 | BIN FREE R VALUE SET COUNT | : 46 |
| REMARK | 3 | BIN FREE R VALUE | : 0.342 |
| REMARK | 3 | | |
| REMARK | 3 | NUMBER OF NON-HYDROGEN ATOMS USED IN REFINEMENT. | |
| REMARK | 3 | ALL ATOMS | : 1867 |
| REMARK | 3 | | |
| REMARK | 3 | B VALUES. | |
| REMARK | 3 | FROM WILSON PLOT (A**2) : NULL | |
| REMARK | 3 | MEAN B VALUE (OVERALL, A**2) : 43.320 | |
| REMARK | 3 | OVERALL ANISOTROPIC B VALUE. | |
| REMARK | 3 | B11 (A**2) : −3.83 | |
| REMARK | 3 | B22 (A**2) : 0.96 | |
| REMARK | 3 | B33 (A**2) : 2.88 | |
| REMARK | 3 | B12 (A**2) : 0.00 | |
| REMARK | 3 | B13 (A**2) : 0.00 | |
| REMARK | 3 | B23 (A**2) : 0.00 | |
| REMARK | 3 | | |
| REMARK | 3 | ESTIMATED OVERALL COORDINATE ERROR. | |
| REMARK | 3 | ESU BASED ON R VALUE (A): 0.327 | |
| REMARK | 3 | ESU BASED ON FREE R VALUE (A): 0.256 | |
| REMARK | 3 | ESU BASED ON MAXIMUM LIKELIHOOD (A): 0.194 | |
| REMARK | 3 | ESU FOR B VALUES BASED ON MAXIMUM LIKELIHOOD (A**2): 14.024 | |
| REMARK | 3 | | |
| REMARK | 3 | CORRELATION COEFFICIENTS. | |
| REMARK | 3 | CORRELATION COEFFICIENT FO-FC : 0.941 | |
| REMARK | 3 | CORRELATION COEFFICIENT FO-FC FREE : 0.898 | |
| REMARK | 3 | | |
| REMARK | 3 | RMS DEVIATIONS FROM IDEAL VALUES COUNT RMS WEIGHT | |
| REMARK | 3 | BOND LENGTHS REFINED ATOMS (A): 1845 ; 0.012 ; 0.022 | |
| REMARK | 3 | BOND ANGLES REFINED ATOMS (DEGREES): 2527 ; 1.482 ; 2.032 | |
| REMARK | 3 | TORSION ANGLES, PERIOD 1 (DEGREES): 209 ; 6.172 ; 5.000 | |
| REMARK | 3 | TORSION ANGLES, PERIOD 2 (DEGREES): 76 ;33.844 ;25.000 | |
| REMARK | 3 | TORSION ANGLES, PERIOD 3 (DEGREES): 295 ;17.124 ;15.000 | |
| REMARK | 3 | TORSION ANGLES, PERIOD 4 (DEGREES): 6 ;20.037 ;15.000 | |
| REMARK | 3 | CHIRAL-CENTER RESTRAINTS (A**3): 302 ; 0.085 ; 0.200 | |
| REMARK | 3 | GENERAL PLANES REFINED ATOMS (A): 1323 ; 0.005 ; 0.020 | |
| REMARK | 3 | NON-BONDED CONTACTS REFINED ATOMS (A): 714 ; 0.202 ; 0.200 | |
| REMARK | 3 | NON-BONDED TORSION REFINED ATOMS (A): 1211 ; 0.311 ; 0.200 | |
| REMARK | 3 | H-BOND (X...Y) REFINED ATOMS (A): 85 ; 0.168 ; 0.200 | |
| REMARK | 3 | POTENTIAL METAL-ION REFINED ATOMS (A): 1 ; 0.013 ; 0.200 | |
| REMARK | 3 | SYMMETRY VDW REFINED ATOMS (A): 45 ; 0.267 ; 0.200 | |
| REMARK | 3 | SYMMETRY H-BOND REFINED ATOMS (A): 10 ; 0.166 ; 0.200 | |
| REMARK | 3 | | |
| REMARK | 3 | ISOTROPIC THERMAL FACTOR RESTRAINTS. COUNT RMS WEIGHT | |
| REMARK | 3 | MAIN-CHAIN BOND REFINED ATOMS (A**2): 1090 ; 0.502 ; 1.500 | |
| REMARK | 3 | MAIN-CHAIN ANGLE REFINED ATOMS (A**2): 1737 ; 0.773 ; 2.000 | |
| REMARK | 3 | SIDE-CHAIN BOND REFINED ATOMS (A**2): 850 ; 1.312 ; 3.000 | |
| REMARK | 3 | SIDE-CHAIN ANGLE REFINED ATOMS (A**2): 790 ; 2.117 ; 4.500 | |
| REMARK | 3 | | |
| REMARK | 3 | NCS RESTRAINTS STATISTICS | |
| REMARK | 3 | NUMBER OF NCS GROUPS : NULL | |
| REMARK | 3 | | |
| REMARK | 3 | | |
| REMARK | 3 | TLS DETAILS | |
| REMARK | 3 | NUMBER OF TLS GROUPS : 5 | |
| REMARK | 3 | ATOM RECORD CONTAINS RESIDUAL B FACTORS ONLY | |
| REMARK | 3 | | |
| REMARK | 3 | TLS GROUP : 1 | |

TABLE 7-continued

The atomic structure coordinates of Fc-TM

| REMARK | 3 | NUMBER OF COMPONENTS GROUP : | 1 | | | |
|---|---|---|---|---|---|---|
| REMARK | 3 | COMPONENTS          C   SSSEQI   TO   C   SSSEQI | | | | |
| REMARK | 3 | RESIDUE RANGE :     A    236          A    324 | | | | |
| REMARK | 3 | ORIGIN FOR THE GROUP (A): | 8.3389 | 24.1913 | −4.5478 | |
| REMARK | 3 | T TENSOR | | | | |
| REMARK | 3 | T11:    0.0215 T22:    0.0920 | | | | |
| REMARK | 3 | T33:    0.3541 T12:    0.0433 | | | | |
| REMARK | 3 | T13:   −0.0938 T23:   −0.3463 | | | | |
| REMARK | 3 | L TENSOR | | | | |
| REMARK | 3 | L11:    5.5174 L22:    6.9851 | | | | |
| REMARK | 3 | L33:    1.3110 L12:    0.6985 | | | | |
| REMARK | 3 | L13:   −0.3877 L23:    1.4474 | | | | |
| REMARK | 3 | S TENSOR | | | | |
| REMARK | 3 | S11:    0.0024 S12:   −0.9714 S13:    1.6061 | | | | |
| REMARK | 3 | S21:    0.4006 S22:    0.0112 S23:   −0.5043 | | | | |
| REMARK | 3 | S31:   −0.2230 S32:   −0.0083 S33:   −0.0136 | | | | |
| REMARK | 3 | | | | | |
| REMARK | 3 | TLS GROUP :    2 | | | | |
| REMARK | 3 | NUMBER OF COMPONENTS GROUP :   1 | | | | |
| REMARK | 3 | COMPONENTS          C   SSSEQI   TO   C   SSSEQI | | | | |
| REMARK | 3 | RESIDUE RANGE:      A    325          A    341 | | | | |
| REMARK | 3 | ORIGIN FOR THE GROUP (A): | 6.2355 | 28.7737 | −13.4151 | |
| REMARK | 3 | T TENSOR | | | | |
| REMARK | 3 | T11:    0.4194 T22:    0.0438 | | | | |
| REMARK | 3 | T33:    0.6367 T12:    0.0309 | | | | |
| REMARK | 3 | T13:   −0.1209 T23:   −0.1743 | | | | |
| REMARK | 3 | L TENSOR | | | | |
| REMARK | 3 | L11:    2.0696 L22:    7.3867 | | | | |
| REMARK | 3 | L33:    3.9900 L12:    0.5828 | | | | |
| REMARK | 3 | L13:   −0.3193 L23:    2.0049 | | | | |
| REMARK | 3 | S TENSOR | | | | |
| REMARK | 3 | S11:   −0.3128 S12:   −0.3347 S13:    1.6116 | | | | |
| REMARK | 3 | S21:   −0.6048 S22:    0.4400 S23:    0.4114 | | | | |
| REMARK | 3 | S31:   −1.6055 S32:    0.0271 S33:   −0.1271 | | | | |
| REMARK | 3 | | | | | |
| REMARK | 3 | TLS GROUP :    3 | | | | |
| REMARK | 3 | NUMBER OF COMPONENTS GROUP :   1 | | | | |
| REMARK | 3 | COMPONENTS          C   SSSEQI   TO   C   SSSEQI | | | | |
| REMARK | 3 | RESIDUE RANGE:      A    342          A    358 | | | | |
| REMARK | 3 | ORIGIN FOR THE GROUP (A): | 19.6741 | −9.9102 | −17.8082 | |
| REMARK | 3 | T TENSOR | | | | |
| REMARK | 3 | T11:    0.0147 T22:   −0.0558 | | | | |
| REMARK | 3 | T33:    0.2412 T12:    0.0130 | | | | |
| REMARK | 3 | T13:   −0.0465 T23:    0.0419 | | | | |
| REMARK | 3 | L TENSOR | | | | |
| REMARK | 3 | L11:    5.9397 L22:    3.4770 | | | | |
| REMARK | 3 | L33:    1.3027 L12:   −0.2675 | | | | |
| REMARK | 3 | L13:   −2.7731 L23:    0.2922 | | | | |
| REMARK | 3 | S TENSOR | | | | |
| REMARK | 3 | S11:    0.1902 S12:    0.1053 S13:   −2.1005 | | | | |
| REMARK | 3 | S21:   −0.2927 S22:   −0.5125 S23:   −0.3505 | | | | |
| REMARK | 3 | S31:    0.2359 S32:   −0.0277 S33:    0.3223 | | | | |
| REMARK | 3 | | | | | |
| REMARK | 3 | TLS GROUP :    4 | | | | |
| REMARK | 3 | NUMBER OF COMPONENTS GROUP :   1 | | | | |
| REMARK | 3 | COMPONENTS          C   SSSEQI   TO   C   SSSEQI | | | | |
| REMARK | 3 | RESIDUE RANGE:      A    359          A    403 | | | | |
| REMARK | 3 | ORIGIN FOR THE GROUP (A): | 21.2651 | −3.5914 | −12.2859 | |
| REMARK | 3 | T TENSOR | | | | |
| REMARK | 3 | T11:   −0.1689 T22:   −0.0639 | | | | |
| REMARK | 3 | T33:   −0.1638 T12:    0.0043 | | | | |
| REMARK | 3 | T13:    0.0241 T23:    0.0801 | | | | |
| REMARK | 3 | L TENSOR | | | | |
| REMARK | 3 | L11:   12.4510 L22:    2.7911 | | | | |
| REMARK | 3 | L33:    2.9332 L12:    0.0470 | | | | |
| REMARK | 3 | L13:    0.1119 L23:   −0.2768 | | | | |
| REMARK | 3 | S TENSOR | | | | |
| REMARK | 3 | S11:   −0.1346 S12:   −1.2217 S13:   −1.1281 | | | | |
| REMARK | 3 | S21:    0.1580 S22:    0.0409 S23:   −0.1830 | | | | |
| REMARK | 3 | S31:    0.0059 S32:    0.2154 S33:    0.0937 | | | | |
| REMARK | 3 | | | | | |
| REMARK | 3 | TLS GROUP :    5 | | | | |
| REMARK | 3 | NUMBER OF COMPONENTS GROUP :   1 | | | | |
| REMARK | 3 | COMPONENTS          C   SSSEQI   TO   C   SSSEQI | | | | |
| REMARK | 3 | RESIDUE RANGE:      A    404          A    445 | | | | |
| REMARK | 3 | ORIGIN FOR THE GROUP (A): | 19.4718 | −9.7512 | −9.1313 | |
| REMARK | 3 | T TENSOR | | | | |
| REMARK | 3 | T11:   −0.0158 T22:    0.1994 | | | | |

TABLE 7-continued

The atomic structure coordinates of Fc-TM

| REMARK | 3 | | T33: | | 0.1938 | T12: | | 0.0293 | | | | |
|---|---|---|---|---|---|---|---|---|---|---|---|---|
| REMARK | 3 | | T13: | | 0.0582 | T23: | | 0.3819 | | | | |
| REMARK | 3 | | L TENSOR | | | | | | | | | |
| REMARK | 3 | | L11: | | 13.1107 | L22: | | 0.0678 | | | | |
| REMARK | 3 | | L33: | | 1.6932 | L12: | | 0.9209 | | | | |
| REMARK | 3 | | L13: | | −1.5605 | L23: | | −0.0412 | | | | |
| REMARK | 3 | | S TENSOR | | | | | | | | | |
| REMARK | 3 | | S11: | | −0.1532 | S12: | | −2.3239 | S13: | | −2.6014 | |
| REMARK | 3 | | S21: | | −0.0410 | S22: | | −0.1484 | S23: | | −0.1293 | |
| REMARK | 3 | | S31: | | 0.3788 | S32: | | 0.2592 | S33: | | 0.3017 | |
| REMARK | 3 | | | | | | | | | | | |
| REMARK | 3 | | | | | | | | | | | |
| REMARK | 3 | | BULK SOLVENT MODELLING. | | | | | | | | | |
| REMARK | 3 | | METHOD USED : MASK | | | | | | | | | |
| REMARK | 3 | | PARAMETERS FOR MASK CALCULATION | | | | | | | | | |
| REMARK | 3 | | VDW PROBE RADIUS | | : | 1.20 | | | | | | |
| REMARK | 3 | | ION PROBE RADIUS | | : | 0.80 | | | | | | |
| REMARK | 3 | | SHRINKAGE RADIUS | | : | 0.80 | | | | | | |
| REMARK | 3 | | | | | | | | | | | |
| REMARK | 3 | | OTHER REFINEMENT REMARKS: NULL | | | | | | | | | |
| REMARK | 3 | | | | | | | | | | | |
| SSBOND | 1 | CYS | A | 321 | | CYS | A | 261 | | | | |
| SSBOND | 2 | CYS | A | 425 | | CYS | A | 367 | | | | |
| LINK | | C1 | NAG C | 1 | | | 1.439 | | ND2 | ASN A | 297 | |
| NAG-ASN | | | | | | | | | | | | |
| CISPEP | 1 | TYR | A | 373 | | PRO | A | 374 | | | | 0.00 |
| LINK | | | NAG C | 1 | | | | | | NAG C | 2 | |
| BETA1-4 | | | | | | | | | | | | |
| LINK | | | NAG C | 2 | | | | | | BMA C | 3 | |
| BETA1-4 | | | | | | | | | | | | |
| LINK | | | BMA C | 3 | | | | | | MAN C | 4 | |
| ALPHA1-3 | | | | | | | | | | | | |
| LINK | | | MAN C | 4 | | | | | | NAG C | 5 | |
| BETA1-2 | | | | | | | | | | | | |
| LINK | | | BMA C | 3 | | | | | | MAN C | 7 | |
| ALPHA1-6 | | | | | | | | | | | | |
| LINK | | | MAN C | 7 | | | | | | NAG C | 8 | |
| BETA1-2 | | | | | | | | | | | | |
| LINK | | | NAG C | 8 | | | | | | GAL C | 9 | |
| BETA1-4 | | | | | | | | | | | | |
| LINK | | | NAG C | 1 | | | | | | FUC C | 11 | |
| ALPHA1-6 | | | | | | | | | | | | |
| MODRES | | NAG C | | 1 | NAG-b-D | | | | | | | |
| RENAME | | | | | | | | | | | | |
| MODRES | | NAG C | | 2 | NAG-b-D | | | | | | | |
| RENAME | | | | | | | | | | | | |
| MODRES | | MAN C | | 4 | MAN-a-D | | | | | | | |
| RENAME | | | | | | | | | | | | |
| MODRES | | NAG C | | 5 | NAG-b-D | | | | | | | |
| RENAME | | | | | | | | | | | | |
| MODRES | | MAN C | | 7 | MAN-a-D | | | | | | | |
| RENAME | | | | | | | | | | | | |
| MODRES | | NAG C | | 8 | NAG-b-D | | | | | | | |
| RENAME | | | | | | | | | | | | |
| MODRES | | GAL C | | 9 | GAL-b-D | | | | | | | |
| RENAME | | | | | | | | | | | | |
| MODRES | | FUC C | | 11 | FUC-a-L | | | | | | | |
| RENAME | | | | | | | | | | | | |
| CRYST1 | 50.178 | 147.301 | | 75.473 | 90.00 | 90.00 | 90.00 | C | 2 | 2 | 21 | |
| SCALE1 | | 0.019929 | 0.000000 | | 0.000000 | | | 0.00000 | | | | |
| SCALE2 | | 0.000000 | 0.006789 | | 0.000000 | | | 0.00000 | | | | |
| SCALE3 | | 0.000000 | 0.000000 | | 0.013250 | | | 0.00000 | | | | |
| ATOM | 1 | N | GLY | A | 236 | | 18.122 | 39.286 | −14.907 | 1.00 | 50.67 | N |
| ANISOU | 1 | N | GLY | A | 236 | 6366 | 6478 | 6407 | 30 | −8 | −27 | N |
| ATOM | 2 | CA | GLY | A | 236 | | 17.938 | 40.336 | −13.862 | 1.00 | 50.37 | C |
| ANISOU | 2 | CA | GLY | A | 236 | 6370 | 6447 | 6319 | 23 | 15 | 16 | C |
| ATOM | 3 | C | GLY | A | 236 | | 17.092 | 39.872 | −12.683 | 1.00 | 50.35 | C |
| ANISOU | 3 | C | GLY | A | 236 | 6337 | 6451 | 6340 | 0 | 7 | 36 | C |
| ATOM | 4 | O | GLY | A | 236 | | 17.603 | 39.755 | −11.559 | 1.00 | 50.77 | O |
| ANISOU | 4 | O | GLY | A | 236 | 6425 | 6518 | 6346 | −19 | −27 | 64 | O |
| ATOM | 5 | N | GLY | A | 237 | | 15.805 | 39.607 | −12.942 | 1.00 | 49.94 | N |
| ANISOU | 5 | N | GLY | A | 237 | 6294 | 6360 | 6321 | −7 | 22 | 32 | N |
| ATOM | 6 | CA | GLY | A | 237 | | 14.821 | 39.264 | −11.889 | 1.00 | 48.94 | C |
| ANISOU | 6 | CA | GLY | A | 237 | 6194 | 6188 | 6211 | 20 | 42 | 32 | C |
| ATOM | 7 | C | GLY | A | 237 | | 15.074 | 37.906 | −11.254 | 1.00 | 48.37 | C |
| ANISOU | 7 | C | GLY | A | 237 | 6128 | 6107 | 6142 | 17 | 76 | 5 | C |
| ATOM | 8 | O | GLY | A | 237 | | 16.078 | 37.256 | −11.568 | 1.00 | 48.88 | O |
| ANISOU | 8 | O | GLY | A | 237 | 6209 | 6156 | 6205 | 47 | 90 | −11 | O |

TABLE 7-continued

The atomic structure coordinates of Fc-TM

| | | | | | | | | | | | | |
|---|---|---|---|---|---|---|---|---|---|---|---|---|
| ATOM | 9 | N | PRO | A | 238 | 14.186 | 37.462 | −10.336 | 1.00 | 47.63 | | N |
| ANISOU | 9 | N | PRO | A | 238 | 6027 | 5985 | 6082 | 15 | 57 | −17 | N |
| ATOM | 10 | CA | PRO | A | 238 | 14.432 | 36.144 | −9.746 | 1.00 | 46.76 | | C |
| ANISOU | 10 | CA | PRO | A | 238 | 5926 | 5876 | 5964 | 31 | 25 | −22 | C |
| ATOM | 11 | CB | PRO | A | 238 | 13.327 | 36.008 | −8.686 | 1.00 | 46.65 | | C |
| ANISOU | 11 | CB | PRO | A | 238 | 5911 | 5868 | 5945 | 11 | −23 | 3 | C |
| ATOM | 12 | CG | PRO | A | 238 | 12.878 | 37.422 | −8.404 | 1.00 | 46.85 | | C |
| ANISOU | 12 | CG | PRO | A | 238 | 5930 | 5861 | 6007 | 30 | 38 | 0 | C |
| ATOM | 13 | CD | PRO | A | 238 | 12.974 | 38.083 | −9.771 | 1.00 | 47.56 | | C |
| ANISOU | 13 | CD | PRO | A | 238 | 6038 | 5947 | 6084 | 21 | 63 | −44 | C |
| ATOM | 14 | C | PRO | A | 238 | 14.308 | 35.056 | −10.800 | 1.00 | 46.45 | | C |
| ANISOU | 14 | C | PRO | A | 238 | 5899 | 5823 | 5925 | 31 | 3 | −16 | C |
| ATOM | 15 | O | PRO | A | 238 | 13.803 | 35.311 | −11.898 | 1.00 | 46.74 | | O |
| ANISOU | 15 | O | PRO | A | 238 | 5942 | 5884 | 5930 | 50 | −21 | −25 | O |
| ATOM | 16 | N | SER | A | 239 | 14.806 | 33.868 | −10.471 | 1.00 | 46.09 | | N |
| ANISOU | 16 | N | SER | A | 239 | 5876 | 5767 | 5868 | 24 | 12 | −30 | N |
| ATOM | 17 | CA | SER | A | 239 | 14.710 | 32.689 | −11.333 | 1.00 | 45.35 | | C |
| ANISOU | 17 | CA | SER | A | 239 | 5783 | 5670 | 5778 | −8 | 43 | −6 | C |
| ATOM | 18 | CB | SER | A | 239 | 16.093 | 32.273 | −11.833 | 1.00 | 45.44 | | C |
| ANISOU | 18 | CB | SER | A | 239 | 5822 | 5669 | 5773 | 12 | 73 | −51 | C |
| ATOM | 19 | OG | SER | A | 239 | 16.516 | 33.126 | −12.892 | 1.00 | 46.53 | | O |
| ANISOU | 19 | OG | SER | A | 239 | 6055 | 5754 | 5871 | 22 | 122 | 1 | O |
| ATOM | 20 | C | SER | A | 239 | 14.112 | 31.580 | −10.496 | 1.00 | 44.68 | | C |
| ANISOU | 20 | C | SER | A | 239 | 5695 | 5601 | 5679 | 8 | 13 | 0 | C |
| ATOM | 21 | O | SER | A | 239 | 14.492 | 31.423 | −9.338 | 1.00 | 44.81 | | O |
| ANISOU | 21 | O | SER | A | 239 | 5689 | 5655 | 5681 | 51 | 18 | 72 | O |
| ATOM | 22 | N | VAL | A | 240 | 13.161 | 30.845 | −11.077 | 1.00 | 43.99 | | N |
| ANISOU | 22 | N | VAL | A | 240 | 5587 | 5491 | 5634 | −1 | 45 | 2 | N |
| ATOM | 23 | CA | VAL | A | 240 | 12.474 | 29.760 | −10.386 | 1.00 | 43.00 | | C |
| ANISOU | 23 | CA | VAL | A | 240 | 5453 | 5401 | 5482 | −1 | 37 | −22 | C |
| ATOM | 24 | CB | VAL | A | 240 | 10.932 | 29.909 | −10.474 | 1.00 | 43.13 | | C |
| ANISOU | 24 | CB | VAL | A | 240 | 5481 | 5408 | 5496 | 8 | 59 | −20 | C |
| ATOM | 25 | CG1 | VAL | A | 240 | 10.217 | 28.789 | −9.696 | 1.00 | 42.84 | | C |
| ANISOU | 25 | CG1 | VAL | A | 240 | 5433 | 5309 | 5533 | 54 | −34 | −15 | C |
| ATOM | 26 | CG2 | VAL | A | 240 | 10.519 | 31.239 | −9.927 | 1.00 | 43.46 | | C |
| ANISOU | 26 | CG2 | VAL | A | 240 | 5572 | 5367 | 5572 | −2 | 12 | 0 | C |
| ATOM | 27 | C | VAL | A | 240 | 12.868 | 28.427 | −10.986 | 1.00 | 42.45 | | C |
| ANISOU | 27 | C | VAL | A | 240 | 5377 | 5353 | 5396 | −10 | 11 | −1 | C |
| ATOM | 28 | O | VAL | A | 240 | 12.936 | 28.272 | −12.207 | 1.00 | 42.69 | | O |
| ANISOU | 28 | O | VAL | A | 240 | 5376 | 5426 | 5419 | −44 | 62 | −24 | O |
| ATOM | 29 | N | PHE | A | 241 | 13.128 | 27.468 | −10.108 | 1.00 | 41.87 | | N |
| ANISOU | 29 | N | PHE | A | 241 | 5300 | 5311 | 5296 | −10 | 1 | −22 | N |
| ATOM | 30 | CA | PHE | A | 241 | 13.405 | 26.097 | −10.498 | 1.00 | 40.91 | | C |
| ANISOU | 30 | CA | PHE | A | 241 | 5188 | 5170 | 5185 | −31 | −20 | −52 | C |
| ATOM | 31 | CB | PHE | A | 241 | 14.884 | 25.757 | −10.294 | 1.00 | 41.14 | | C |
| ANISOU | 31 | CB | PHE | A | 241 | 5199 | 5228 | 5204 | −15 | −44 | −34 | C |
| ATOM | 32 | CG | PHE | A | 241 | 15.799 | 26.534 | −11.203 | 1.00 | 41.60 | | C |
| ANISOU | 32 | CG | PHE | A | 241 | 5289 | 5240 | 5274 | −81 | 3 | −5 | C |
| ATOM | 33 | CD1 | PHE | A | 241 | 16.448 | 27.682 | −10.744 | 1.00 | 41.55 | | C |
| ANISOU | 33 | CD1 | PHE | A | 241 | 5248 | 5213 | 5326 | −52 | 1 | −15 | C |
| ATOM | 34 | CE1 | PHE | A | 241 | 17.271 | 28.424 | −11.601 | 1.00 | 40.85 | | C |
| ANISOU | 34 | CE1 | PHE | A | 241 | 5052 | 5159 | 5308 | −21 | −14 | −18 | C |
| ATOM | 35 | CZ | PHE | A | 241 | 17.448 | 28.019 | −12.917 | 1.00 | 40.46 | | C |
| ANISOU | 35 | CZ | PHE | A | 241 | 5124 | 5094 | 5154 | −75 | 22 | −43 | C |
| ATOM | 36 | CE2 | PHE | A | 241 | 16.792 | 26.872 | −13.391 | 1.00 | 42.17 | | C |
| ANISOU | 36 | CE2 | PHE | A | 241 | 5259 | 5419 | 5342 | 51 | 84 | −27 | C |
| ATOM | 37 | CD2 | PHE | A | 241 | 15.978 | 26.143 | −12.537 | 1.00 | 41.34 | | C |
| ANISOU | 37 | CD2 | PHE | A | 241 | 5253 | 5148 | 5303 | −103 | 60 | −23 | C |
| ATOM | 38 | C | PHE | A | 241 | 12.493 | 25.189 | −9.716 | 1.00 | 40.07 | | C |
| ANISOU | 38 | C | PHE | A | 241 | 5090 | 5072 | 5061 | −21 | −17 | −53 | C |
| ATOM | 39 | O | PHE | A | 241 | 12.175 | 25.475 | −8.572 | 1.00 | 40.18 | | O |
| ANISOU | 39 | O | PHE | A | 241 | 5110 | 5045 | 5111 | −37 | −101 | −113 | O |
| ATOM | 40 | N | LEU | A | 242 | 12.044 | 24.109 | −10.356 | 1.00 | 39.75 | | N |
| ANISOU | 40 | N | LEU | A | 242 | 5035 | 5028 | 5040 | 6 | 13 | −59 | N |
| ATOM | 41 | CA | LEU | A | 242 | 11.017 | 23.235 | −9.794 | 1.00 | 38.92 | | C |
| ANISOU | 41 | CA | LEU | A | 242 | 4944 | 4899 | 4942 | 2 | 21 | −61 | C |
| ATOM | 42 | CB | LEU | A | 242 | 9.663 | 23.546 | −10.438 | 1.00 | 38.70 | | C |
| ANISOU | 42 | CB | LEU | A | 242 | 4941 | 4864 | 4898 | −18 | 4 | −84 | C |
| ATOM | 43 | CG | LEU | A | 242 | 8.396 | 22.862 | −9.936 | 1.00 | 38.46 | | C |
| ANISOU | 43 | CG | LEU | A | 242 | 4855 | 4805 | 4951 | 71 | −15 | −74 | C |
| ATOM | 44 | CD1 | LEU | A | 242 | 8.085 | 23.234 | −8.504 | 1.00 | 37.91 | | C |
| ANISOU | 44 | CD1 | LEU | A | 242 | 4727 | 4827 | 4849 | 50 | −49 | −62 | C |
| ATOM | 45 | CD2 | LEU | A | 242 | 7.275 | 23.271 | −10.825 | 1.00 | 38.22 | | C |
| ANISOU | 45 | CD2 | LEU | A | 242 | 4846 | 4868 | 4806 | 137 | −149 | −134 | C |
| ATOM | 46 | C | LEU | A | 242 | 11.409 | 21.793 | −10.021 | 1.00 | 39.20 | | C |
| ANISOU | 46 | C | LEU | A | 242 | 4972 | 4961 | 4959 | −11 | 13 | −31 | C |
| ATOM | 47 | O | LEU | A | 242 | 11.605 | 21.361 | −11.149 | 1.00 | 39.40 | | O |
| ANISOU | 47 | O | LEU | A | 242 | 5021 | 4924 | 5024 | −24 | 63 | −55 | O |

TABLE 7-continued

The atomic structure coordinates of Fc-TM

| ATOM | 48 | N | PHE | A | 243 | 11.510 | 21.044 | −8.936 | 1.00 | 39.65 | | N |
|---|---|---|---|---|---|---|---|---|---|---|---|---|
| ANISOU | 48 | N | PHE | A | 243 | 4992 | 5044 | 5028 | 12 | −12 | −43 | N |
| ATOM | 49 | CA | PHE | A | 243 | 12.230 | 19.792 | −8.968 | 1.00 | 39.97 | | C |
| ANISOU | 49 | CA | PHE | A | 243 | 5044 | 5044 | 5099 | −24 | −2 | −51 | C |
| ATOM | 50 | CB | PHE | A | 243 | 13.404 | 19.823 | −7.970 | 1.00 | 40.13 | | C |
| ANISOU | 50 | CB | PHE | A | 243 | 5022 | 5064 | 5162 | −8 | 40 | −26 | C |
| ATOM | 51 | CG | PHE | A | 243 | 14.424 | 20.876 | −8.279 | 1.00 | 41.34 | | C |
| ANISOU | 51 | CG | PHE | A | 243 | 5170 | 5154 | 5381 | −72 | 6 | −95 | C |
| ATOM | 52 | CD1 | PHE | A | 243 | 14.319 | 22.156 | −7.719 | 1.00 | 42.25 | | C |
| ANISOU | 52 | CD1 | PHE | A | 243 | 5360 | 5249 | 5441 | 34 | −36 | −90 | C |
| ATOM | 53 | CE1 | PHE | A | 243 | 15.269 | 23.146 | −8.016 | 1.00 | 41.11 | | C |
| ANISOU | 53 | CE1 | PHE | A | 243 | 5158 | 5065 | 5394 | −69 | 72 | −88 | C |
| ATOM | 54 | CZ | PHE | A | 243 | 16.321 | 22.865 | −8.888 | 1.00 | 41.69 | | C |
| ANISOU | 54 | CZ | PHE | A | 243 | 5217 | 5205 | 5418 | −88 | −1 | −97 | C |
| ATOM | 55 | CE2 | PHE | A | 243 | 16.435 | 21.587 | −9.458 | 1.00 | 42.21 | | C |
| ANISOU | 55 | CE2 | PHE | A | 243 | 5279 | 5206 | 5551 | −93 | 135 | −80 | C |
| ATOM | 56 | CD2 | PHE | A | 243 | 15.487 | 20.603 | −9.154 | 1.00 | 42.21 | | C |
| ANISOU | 56 | CD2 | PHE | A | 243 | 5308 | 5220 | 5508 | −31 | 66 | −136 | C |
| ATOM | 57 | C | PHE | A | 243 | 11.275 | 18.673 | −8.648 | 1.00 | 40.06 | | C |
| ANISOU | 57 | C | PHE | A | 243 | 5009 | 5104 | 5107 | −37 | −10 | −64 | C |
| ATOM | 58 | O | PHE | A | 243 | 10.462 | 18.809 | −7.729 | 1.00 | 39.94 | | O |
| ANISOU | 58 | O | PHE | A | 243 | 4936 | 5131 | 5107 | −18 | −13 | −92 | O |
| ATOM | 59 | N | PRO | A | 244 | 11.369 | 17.561 | −9.405 | 1.00 | 40.05 | | N |
| ANISOU | 59 | N | PRO | A | 244 | 5036 | 5044 | 5138 | −26 | 19 | −78 | N |
| ATOM | 60 | CA | PRO | A | 244 | 10.474 | 16.436 | −9.204 | 1.00 | 39.94 | | C |
| ANISOU | 60 | CA | PRO | A | 244 | 5074 | 5000 | 5099 | −2 | 16 | −66 | C |
| ATOM | 61 | CB | PRO | A | 244 | 10.819 | 15.510 | −10.373 | 1.00 | 40.24 | | C |
| ANISOU | 61 | CB | PRO | A | 244 | 5091 | 5057 | 5139 | −22 | 19 | −62 | C |
| ATOM | 62 | CG | PRO | A | 244 | 12.252 | 15.834 | −10.700 | 1.00 | 40.53 | | C |
| ANISOU | 62 | CG | PRO | A | 244 | 5047 | 5064 | 5287 | −14 | −26 | −70 | C |
| ATOM | 63 | CD | PRO | A | 244 | 12.334 | 17.315 | −10.494 | 1.00 | 40.31 | | C |
| ANISOU | 63 | CD | PRO | A | 244 | 5051 | 5061 | 5203 | −28 | −12 | −57 | C |
| ATOM | 64 | C | PRO | A | 244 | 10.810 | 15.760 | −7.881 | 1.00 | 39.34 | | C |
| ANISOU | 64 | C | PRO | A | 244 | 5004 | 4929 | 5012 | 10 | −25 | −82 | C |
| ATOM | 65 | O | PRO | A | 244 | 11.848 | 16.049 | −7.315 | 1.00 | 39.44 | | O |
| ANISOU | 65 | O | PRO | A | 244 | 5071 | 4916 | 4996 | 11 | −14 | −147 | O |
| ATOM | 66 | N | PRO | A | 245 | 9.943 | 14.861 | −7.397 | 1.00 | 38.79 | | N |
| ANISOU | 66 | N | PRO | A | 245 | 4967 | 4861 | 4907 | 1 | −10 | −50 | N |
| ATOM | 67 | CA | PRO | A | 245 | 10.374 | 14.051 | −6.266 | 1.00 | 38.61 | | C |
| ANISOU | 67 | CA | PRO | A | 245 | 4913 | 4858 | 4895 | −18 | −64 | −80 | C |
| ATOM | 68 | CB | PRO | A | 245 | 9.108 | 13.286 | −5.850 | 1.00 | 38.29 | | C |
| ANISOU | 68 | CB | PRO | A | 245 | 4913 | 4765 | 4870 | −17 | −31 | −43 | C |
| ATOM | 69 | CG | PRO | A | 245 | 7.963 | 13.883 | −6.657 | 1.00 | 38.73 | | C |
| ANISOU | 69 | CG | PRO | A | 245 | 4943 | 4859 | 4914 | −8 | −25 | −82 | C |
| ATOM | 70 | CD | PRO | A | 245 | 8.576 | 14.533 | −7.845 | 1.00 | 38.57 | | C |
| ANISOU | 70 | CD | PRO | A | 245 | 4919 | 4821 | 4912 | 41 | −48 | −19 | C |
| ATOM | 71 | C | PRO | A | 245 | 11.490 | 13.073 | −6.621 | 1.00 | 38.77 | | C |
| ANISOU | 71 | C | PRO | A | 245 | 4914 | 4890 | 4926 | −38 | −52 | −39 | C |
| ATOM | 72 | O | PRO | A | 245 | 11.863 | 12.917 | −7.800 | 1.00 | 37.94 | | O |
| ANISOU | 72 | O | PRO | A | 245 | 4774 | 4779 | 4862 | −114 | −92 | −2 | O |
| ATOM | 73 | N | LYS | A | 246 | 12.028 | 12.430 | −5.589 | 1.00 | 39.37 | | N |
| ANISOU | 73 | N | LYS | A | 246 | 4984 | 4983 | 4991 | −16 | −60 | −30 | N |
| ATOM | 74 | CA | LYS | A | 246 | 12.931 | 11.318 | −5.796 | 1.00 | 39.82 | | C |
| ANISOU | 74 | CA | LYS | A | 246 | 5023 | 5058 | 5050 | 14 | −26 | −33 | C |
| ATOM | 75 | CB | LYS | A | 246 | 13.669 | 10.947 | −4.509 | 1.00 | 40.23 | | C |
| ANISOU | 75 | CB | LYS | A | 246 | 5091 | 5073 | 5120 | 18 | −39 | −40 | C |
| ATOM | 76 | CG | LYS | A | 246 | 14.888 | 11.842 | −4.290 | 1.00 | 41.46 | | C |
| ANISOU | 76 | CG | LYS | A | 246 | 5178 | 5330 | 5245 | −27 | 39 | 8 | C |
| ATOM | 77 | CD | LYS | A | 246 | 15.623 | 12.015 | −5.627 | 1.00 | 45.52 | | C |
| ANISOU | 77 | CD | LYS | A | 246 | 5812 | 5935 | 5546 | 66 | −16 | −88 | C |
| ATOM | 78 | CE | LYS | A | 246 | 16.445 | 13.285 | −5.737 | 1.00 | 46.82 | | C |
| ANISOU | 78 | CE | LYS | A | 246 | 5686 | 5640 | 6463 | −111 | −80 | −47 | C |
| ATOM | 79 | NZ | LYS | A | 246 | 16.762 | 13.502 | −7.165 | 1.00 | 46.41 | | N |
| ANISOU | 79 | NZ | LYS | A | 246 | 5883 | 6214 | 5535 | 18 | 173 | 183 | N |
| ATOM | 80 | C | LYS | A | 246 | 12.159 | 10.148 | −6.374 | 1.00 | 39.48 | | C |
| ANISOU | 80 | C | LYS | A | 246 | 4992 | 5034 | 4975 | 21 | −27 | −32 | C |
| ATOM | 81 | O | LYS | A | 246 | 11.088 | 9.797 | −5.861 | 1.00 | 39.69 | | O |
| ANISOU | 81 | O | LYS | A | 246 | 5028 | 5127 | 4923 | 65 | −62 | −106 | O |
| ATOM | 82 | N | PRO | A | 247 | 12.697 | 9.540 | −7.448 | 1.00 | 39.18 | | N |
| ANISOU | 82 | N | PRO | A | 247 | 4951 | 5000 | 4932 | 33 | −13 | −12 | N |
| ATOM | 83 | CA | PRO | A | 247 | 12.000 | 8.478 | −8.161 | 1.00 | 38.92 | | C |
| ANISOU | 83 | CA | PRO | A | 247 | 4924 | 4959 | 4905 | 51 | −17 | −16 | C |
| ATOM | 84 | CB | PRO | A | 247 | 13.085 | 7.878 | −9.054 | 1.00 | 38.79 | | C |
| ANISOU | 84 | CB | PRO | A | 247 | 4920 | 4940 | 4877 | 55 | 8 | −7 | C |
| ATOM | 85 | CG | PRO | A | 247 | 14.014 | 8.985 | −9.285 | 1.00 | 38.59 | | C |
| ANISOU | 85 | CG | PRO | A | 247 | 4889 | 4914 | 4858 | 19 | 11 | −18 | C |
| ATOM | 86 | CD | PRO | A | 247 | 14.021 | 9.809 | −8.040 | 1.00 | 39.18 | | C |
| ANISOU | 86 | CD | PRO | A | 247 | 4973 | 4976 | 4934 | 18 | 3 | −6 | C |

TABLE 7-continued

The atomic structure coordinates of Fc-TM

| | | | | | | | | | | | | |
|---|---|---|---|---|---|---|---|---|---|---|---|---|
| ATOM | 87 | C | PRO | A | 247 | 11.450 | 7.425 | −7.230 | 1.00 | 38.87 | | C |
| ANISOU | 87 | C | PRO | A | 247 | 4936 | 4933 | 4896 | 54 | 4 | −38 | C |
| ATOM | 88 | O | PRO | A | 247 | 10.303 | 7.039 | −7.385 | 1.00 | 38.56 | | O |
| ANISOU | 88 | O | PRO | A | 247 | 4878 | 4910 | 4862 | 97 | 6 | −34 | O |
| ATOM | 89 | N | LYS | A | 248 | 12.246 | 6.970 | −6.261 | 1.00 | 38.99 | | N |
| ANISOU | 89 | N | LYS | A | 248 | 4950 | 4955 | 4907 | 43 | 4 | −29 | N |
| ATOM | 90 | CA | LYS | A | 248 | 11.781 | 5.891 | −5.389 | 1.00 | 38.78 | | C |
| ANISOU | 90 | CA | LYS | A | 248 | 4934 | 4936 | 4863 | 41 | −23 | −10 | C |
| ATOM | 91 | CB | LYS | A | 248 | 12.937 | 5.021 | −4.850 | 1.00 | 39.27 | | C |
| ANISOU | 91 | CB | LYS | A | 248 | 5026 | 4978 | 4917 | 7 | −18 | −25 | C |
| ATOM | 92 | CG | LYS | A | 248 | 13.648 | 5.482 | −3.580 | 1.00 | 36.38 | | C |
| ANISOU | 92 | CG | LYS | A | 248 | 4760 | 4251 | 4810 | 413 | −171 | 220 | C |
| ATOM | 93 | CD | LYS | A | 248 | 14.700 | 4.434 | −3.086 | 1.00 | 40.67 | | C |
| ANISOU | 93 | CD | LYS | A | 248 | 5196 | 5302 | 4953 | −77 | 72 | −121 | C |
| ATOM | 94 | CE | LYS | A | 248 | 14.061 | 3.085 | −2.711 | 1.00 | 35.80 | | C |
| ANISOU | 94 | CE | LYS | A | 248 | 4447 | 4475 | 4680 | 291 | −218 | 261 | C |
| ATOM | 95 | NZ | LYS | A | 248 | 15.004 | 2.044 | −2.179 | 1.00 | 40.36 | | N |
| ANISOU | 95 | NZ | LYS | A | 248 | 5159 | 5539 | 4635 | −366 | 221 | −488 | N |
| ATOM | 96 | C | LYS | A | 248 | 10.799 | 6.352 | −4.312 | 1.00 | 38.61 | | C |
| ANISOU | 96 | C | LYS | A | 248 | 4939 | 4906 | 4825 | 14 | −19 | −2 | C |
| ATOM | 97 | O | LYS | A | 248 | 10.063 | 5.550 | −3.775 | 1.00 | 38.84 | | O |
| ANISOU | 97 | O | LYS | A | 248 | 5003 | 4972 | 4783 | 16 | −22 | −36 | O |
| ATOM | 98 | N | ASP | A | 249 | 10.750 | 7.655 | −4.033 | 1.00 | 38.44 | | N |
| ANISOU | 98 | N | ASP | A | 249 | 4875 | 4955 | 4772 | 44 | 3 | −16 | N |
| ATOM | 99 | CA | ASP | A | 249 | 9.691 | 8.181 | −3.171 | 1.00 | 37.92 | | C |
| ANISOU | 99 | CA | ASP | A | 249 | 4847 | 4859 | 4700 | 48 | −19 | 22 | C |
| ATOM | 100 | CB | ASP | A | 249 | 9.970 | 9.633 | −2.774 | 1.00 | 38.25 | | C |
| ANISOU | 100 | CB | ASP | A | 249 | 4896 | 4868 | 4767 | 11 | 7 | 17 | C |
| ATOM | 101 | CG | ASP | A | 249 | 10.882 | 9.741 | −1.587 | 1.00 | 38.86 | | C |
| ANISOU | 101 | CG | ASP | A | 249 | 5031 | 4871 | 4860 | 18 | 23 | 22 | C |
| ATOM | 102 | OD1 | ASP | A | 249 | 11.024 | 8.755 | −0.860 | 1.00 | 41.27 | | O |
| ANISOU | 102 | OD1 | ASP | A | 249 | 5480 | 5121 | 5080 | 125 | 28 | −54 | O |
| ATOM | 103 | OD2 | ASP | A | 249 | 11.457 | 10.815 | −1.352 | 1.00 | 41.70 | | O |
| ANISOU | 103 | OD2 | ASP | A | 249 | 5332 | 5260 | 5250 | −57 | 123 | 4 | O |
| ATOM | 104 | C | ASP | A | 249 | 8.325 | 8.043 | −3.853 | 1.00 | 36.93 | | C |
| ANISOU | 104 | C | ASP | A | 249 | 4734 | 4748 | 4547 | 24 | −9 | 14 | C |
| ATOM | 105 | O | ASP | A | 249 | 7.300 | 7.842 | −3.198 | 1.00 | 36.04 | | O |
| ANISOU | 105 | O | ASP | A | 249 | 4654 | 4626 | 4413 | 57 | −57 | 34 | O |
| ATOM | 106 | N | THR | A | 250 | 8.338 | 8.136 | −5.182 | 1.00 | 36.24 | | N |
| ANISOU | 106 | N | THR | A | 250 | 4619 | 4672 | 4477 | 50 | −15 | 16 | N |
| ATOM | 107 | CA | THR | A | 250 | 7.131 | 7.982 | −5.982 | 1.00 | 35.08 | | C |
| ANISOU | 107 | CA | THR | A | 250 | 4477 | 4569 | 4283 | 0 | 2 | 47 | C |
| ATOM | 108 | CB | THR | A | 250 | 7.233 | 8.753 | −7.345 | 1.00 | 35.01 | | C |
| ANISOU | 108 | CB | THR | A | 250 | 4440 | 4538 | 4324 | 26 | 1 | 31 | C |
| ATOM | 109 | OG1 | THR | A | 250 | 7.969 | 7.992 | −8.287 | 1.00 | 33.57 | | O |
| ANISOU | 109 | OG1 | THR | A | 250 | 4192 | 4584 | 3978 | 26 | −86 | 100 | O |
| ATOM | 110 | CG2 | THR | A | 250 | 7.901 | 10.112 | −7.157 | 1.00 | 34.29 | | C |
| ANISOU | 110 | CG2 | THR | A | 250 | 4178 | 4535 | 4312 | −61 | −10 | 167 | C |
| ATOM | 111 | C | THR | A | 250 | 6.674 | 6.521 | −6.163 | 1.00 | 34.51 | | C |
| ANISOU | 111 | C | THR | A | 250 | 4501 | 4473 | 4136 | 12 | 33 | −4 | C |
| ATOM | 112 | O | THR | A | 250 | 5.499 | 6.269 | −6.443 | 1.00 | 33.70 | | O |
| ANISOU | 112 | O | THR | A | 250 | 4487 | 4349 | 3968 | −15 | 94 | −34 | O |
| ATOM | 113 | N | LEU | A | 251 | 7.570 | 5.569 | −5.940 | 1.00 | 34.49 | | N |
| ANISOU | 113 | N | LEU | A | 251 | 4464 | 4483 | 4158 | −14 | 57 | −24 | N |
| ATOM | 114 | CA | LEU | A | 251 | 7.288 | 4.145 | −6.229 | 1.00 | 35.46 | | C |
| ANISOU | 114 | CA | LEU | A | 251 | 4591 | 4519 | 4360 | −36 | 56 | 39 | C |
| ATOM | 115 | CB | LEU | A | 251 | 8.416 | 3.552 | −7.084 | 1.00 | 34.39 | | C |
| ANISOU | 115 | CB | LEU | A | 251 | 4522 | 4286 | 4258 | −37 | 43 | 44 | C |
| ATOM | 116 | CG | LEU | A | 251 | 8.640 | 4.234 | −8.448 | 1.00 | 32.40 | | C |
| ANISOU | 116 | CG | LEU | A | 251 | 4144 | 4197 | 3968 | −25 | 0 | −41 | C |
| ATOM | 117 | CD1 | LEU | A | 251 | 9.950 | 3.850 | −9.025 | 1.00 | 31.29 | | C |
| ANISOU | 117 | CD1 | LEU | A | 251 | 4008 | 4153 | 3728 | 70 | −120 | 25 | C |
| ATOM | 118 | CD2 | LEU | A | 251 | 7.538 | 3.937 | −9.435 | 1.00 | 30.02 | | C |
| ANISOU | 118 | CD2 | LEU | A | 251 | 3862 | 3832 | 3709 | −19 | 204 | 164 | C |
| ATOM | 119 | C | LEU | A | 251 | 6.967 | 3.247 | −4.999 | 1.00 | 36.71 | | C |
| ANISOU | 119 | C | LEU | A | 251 | 4788 | 4688 | 4471 | −34 | 12 | 51 | C |
| ATOM | 120 | O | LEU | A | 251 | 6.530 | 2.097 | −5.126 | 1.00 | 36.26 | | O |
| ANISOU | 120 | O | LEU | A | 251 | 4757 | 4604 | 4414 | −55 | 47 | 142 | O |
| ATOM | 121 | N | MET | A | 252 | 7.187 | 3.791 | −3.816 | 1.00 | 38.60 | | N |
| ANISOU | 121 | N | MET | A | 252 | 5026 | 4943 | 4698 | −27 | 20 | 29 | N |
| ATOM | 122 | CA | MET | A | 252 | 6.895 | 3.102 | −2.566 | 1.00 | 40.29 | | C |
| ANISOU | 122 | CA | MET | A | 252 | 5241 | 5198 | 4870 | 1 | −7 | 44 | C |
| ATOM | 123 | CB | MET | A | 252 | 8.114 | 3.092 | −1.677 | 1.00 | 40.45 | | C |
| ANISOU | 123 | CB | MET | A | 252 | 5226 | 5262 | 4879 | −22 | −28 | −14 | C |
| ATOM | 124 | CG | MET | A | 252 | 9.210 | 2.179 | −2.138 | 1.00 | 42.62 | | C |
| ANISOU | 124 | CG | MET | A | 252 | 5404 | 5525 | 5262 | 48 | 6 | −36 | C |
| ATOM | 125 | SD | MET | A | 252 | 10.657 | 2.547 | −1.165 | 1.00 | 43.78 | | S |
| ANISOU | 125 | SD | MET | A | 252 | 5542 | 5849 | 5244 | 48 | −85 | 63 | S |

TABLE 7-continued

The atomic structure coordinates of Fc-TM

| | | | | | | | | | | | | |
|---|---|---|---|---|---|---|---|---|---|---|---|---|
| ATOM | 126 | CE | MET | A | 252 | 10.140 | 1.837 | 0.396 | 1.00 | 45.33 | | C |
| ANISOU | 126 | CE | MET | A | 252 | 5743 | 5827 | 5653 | −34 | 103 | 102 | C |
| ATOM | 127 | C | MET | A | 252 | 5.829 | 3.879 | −1.874 | 1.00 | 39.26 | | C |
| ANISOU | 127 | C | MET | A | 252 | 5153 | 5083 | 4681 | −6 | −19 | 52 | C |
| ATOM | 128 | O | MET | A | 252 | 6.043 | 5.040 | −1.508 | 1.00 | 39.40 | | O |
| ANISOU | 128 | O | MET | A | 252 | 5246 | 5129 | 4594 | −46 | −43 | 54 | O |
| ATOM | 129 | N | ILE | A | 253 | 4.682 | 3.237 | −1.700 | 1.00 | 39.08 | | N |
| ANISOU | 129 | N | ILE | A | 253 | 5163 | 5016 | 4667 | 12 | −39 | 49 | N |
| ATOM | 130 | CA | ILE | A | 253 | 3.486 | 3.888 | −1.183 | 1.00 | 39.29 | | C |
| ANISOU | 130 | CA | ILE | A | 253 | 5103 | 5050 | 4775 | 29 | 12 | 19 | C |
| ATOM | 131 | CB | ILE | A | 253 | 2.247 | 3.011 | −1.395 | 1.00 | 38.95 | | C |
| ANISOU | 131 | CB | ILE | A | 253 | 5067 | 5028 | 4703 | 31 | 24 | 14 | C |
| ATOM | 132 | CG1 | ILE | A | 253 | 0.953 | 3.823 | −1.205 | 1.00 | 39.49 | | C |
| ANISOU | 132 | CG1 | ILE | A | 253 | 5092 | 5115 | 4795 | 9 | −6 | −38 | C |
| ATOM | 133 | CD1 | ILE | A | 253 | −0.330 | 3.042 | −1.535 | 1.00 | 38.97 | | C |
| ANISOU | 133 | CD1 | ILE | A | 253 | 5004 | 5047 | 4756 | 10 | 47 | 50 | C |
| ATOM | 134 | CG2 | ILE | A | 253 | 2.320 | 1.777 | −0.515 | 1.00 | 39.92 | | C |
| ANISOU | 134 | CG2 | ILE | A | 253 | 5138 | 5135 | 4895 | 40 | −36 | 1 | C |
| ATOM | 135 | C | ILE | A | 253 | 3.622 | 4.327 | 0.280 | 1.00 | 39.88 | | C |
| ANISOU | 135 | C | ILE | A | 253 | 5183 | 5139 | 4829 | 56 | 53 | 44 | C |
| ATOM | 136 | O | ILE | A | 253 | 2.795 | 5.089 | 0.776 | 1.00 | 40.73 | | O |
| ANISOU | 136 | O | ILE | A | 253 | 5278 | 5260 | 4936 | 23 | 76 | 42 | O |
| ATOM | 137 | N | SER | A | 254 | 4.683 | 3.892 | 0.950 | 1.00 | 40.46 | | N |
| ANISOU | 137 | N | SER | A | 254 | 5255 | 5229 | 4888 | 63 | 59 | 23 | N |
| ATOM | 138 | CA | SER | A | 254 | 4.863 | 4.181 | 2.364 | 1.00 | 40.63 | | C |
| ANISOU | 138 | CA | SER | A | 254 | 5276 | 5248 | 4914 | 9 | 50 | −9 | C |
| ATOM | 139 | CB | SER | A | 254 | 5.567 | 3.005 | 3.055 | 1.00 | 40.37 | | C |
| ANISOU | 139 | CB | SER | A | 254 | 5254 | 5212 | 4870 | 59 | 53 | −23 | C |
| ATOM | 140 | OG | SER | A | 254 | 6.984 | 3.119 | 2.972 | 1.00 | 40.90 | | O |
| ANISOU | 140 | OG | SER | A | 254 | 5421 | 5224 | 4893 | −34 | 108 | −21 | O |
| ATOM | 141 | C | SER | A | 254 | 5.628 | 5.488 | 2.550 | 1.00 | 40.97 | | C |
| ANISOU | 141 | C | SER | A | 254 | 5312 | 5271 | 4982 | −19 | 76 | 25 | C |
| ATOM | 142 | O | SER | A | 254 | 5.603 | 6.114 | 3.632 | 1.00 | 41.28 | | O |
| ANISOU | 142 | O | SER | A | 254 | 5346 | 5328 | 5007 | −41 | 116 | 79 | O |
| ATOM | 143 | N | ARG | A | 255 | 6.307 | 5.897 | 1.484 | 1.00 | 41.20 | | N |
| ANISOU | 143 | N | ARG | A | 255 | 5344 | 5362 | 4946 | −17 | 73 | −22 | N |
| ATOM | 144 | CA | ARG | A | 255 | 7.116 | 7.128 | 1.464 | 1.00 | 40.77 | | C |
| ANISOU | 144 | CA | ARG | A | 255 | 5217 | 5295 | 4977 | −30 | 15 | −71 | C |
| ATOM | 145 | CB | ARG | A | 255 | 8.312 | 6.960 | 0.520 | 1.00 | 41.05 | | C |
| ANISOU | 145 | CB | ARG | A | 255 | 5254 | 5318 | 5025 | −26 | 19 | −59 | C |
| ATOM | 146 | CG | ARG | A | 255 | 9.203 | 5.754 | 0.873 | 1.00 | 41.23 | | C |
| ANISOU | 146 | CG | ARG | A | 255 | 5241 | 5314 | 5109 | −16 | −53 | −75 | C |
| ATOM | 147 | CD | ARG | A | 255 | 10.479 | 5.781 | 0.055 | 1.00 | 42.71 | | C |
| ANISOU | 147 | CD | ARG | A | 255 | 5282 | 5481 | 5463 | −20 | −70 | −52 | C |
| ATOM | 148 | NE | ARG | A | 255 | 11.486 | 4.874 | 0.595 | 1.00 | 44.95 | | N |
| ANISOU | 148 | NE | ARG | A | 255 | 5686 | 5632 | 5761 | −23 | −8 | 6 | N |
| ATOM | 149 | CZ | ARG | A | 255 | 12.800 | 5.096 | 0.570 | 1.00 | 44.62 | | C |
| ANISOU | 149 | CZ | ARG | A | 255 | 5581 | 5638 | 5732 | −42 | −75 | 37 | C |
| ATOM | 150 | NH1 | ARG | A | 255 | 13.283 | 6.213 | 0.045 | 1.00 | 44.95 | | N |
| ANISOU | 150 | NH1 | ARG | A | 255 | 5600 | 5866 | 5612 | −153 | −140 | 84 | N |
| ATOM | 151 | NH2 | ARG | A | 255 | 13.632 | 4.205 | 1.093 | 1.00 | 45.14 | | N |
| ANISOU | 151 | NH2 | ARG | A | 255 | 5708 | 5780 | 5660 | 6 | −107 | −75 | N |
| ATOM | 152 | C | ARG | A | 255 | 6.300 | 8.371 | 1.111 | 1.00 | 40.62 | | C |
| ANISOU | 152 | C | ARG | A | 255 | 5207 | 5295 | 4932 | −38 | 26 | −78 | C |
| ATOM | 153 | O | ARG | A | 255 | 5.092 | 8.307 | 0.939 | 1.00 | 41.23 | | O |
| ANISOU | 153 | O | ARG | A | 255 | 5213 | 5455 | 4994 | 0 | −1 | −130 | O |
| ATOM | 154 | N | THR | A | 256 | 6.959 | 9.512 | 1.013 | 1.00 | 40.48 | | N |
| ANISOU | 154 | N | THR | A | 256 | 5221 | 5247 | 4910 | −13 | 43 | −73 | N |
| ATOM | 155 | CA | THR | A | 256 | 6.253 | 10.779 | 0.949 | 1.00 | 40.65 | | C |
| ANISOU | 155 | CA | THR | A | 256 | 5233 | 5241 | 4969 | 29 | 14 | 6 | C |
| ATOM | 156 | CB | THR | A | 256 | 6.265 | 11.522 | 2.350 | 1.00 | 40.92 | | C |
| ANISOU | 156 | CB | THR | A | 256 | 5291 | 5223 | 5035 | 40 | 47 | −14 | C |
| ATOM | 157 | OG1 | THR | A | 256 | 6.218 | 10.571 | 3.438 | 1.00 | 42.34 | | O |
| ANISOU | 157 | OG1 | THR | A | 256 | 5543 | 5436 | 5106 | 142 | 62 | −151 | O |
| ATOM | 158 | CG2 | THR | A | 256 | 5.082 | 12.466 | 2.479 | 1.00 | 41.51 | | C |
| ANISOU | 158 | CG2 | THR | A | 256 | 5386 | 5196 | 5190 | 75 | 11 | 15 | C |
| ATOM | 159 | C | THR | A | 256 | 6.931 | 11.637 | −0.116 | 1.00 | 40.11 | | C |
| ANISOU | 159 | C | THR | A | 256 | 5160 | 5179 | 4899 | 0 | 8 | 30 | C |
| ATOM | 160 | O | THR | A | 256 | 7.896 | 12.347 | 0.183 | 1.00 | 40.28 | | O |
| ANISOU | 160 | O | THR | A | 256 | 5245 | 5223 | 4835 | −24 | 20 | 133 | O |
| ATOM | 161 | N | PRO | A | 257 | 6.448 | 11.568 | −1.366 | 1.00 | 39.60 | | N |
| ANISOU | 161 | N | PRO | A | 257 | 5072 | 5102 | 4872 | −11 | 3 | −7 | N |
| ATOM | 162 | CA | PRO | A | 257 | 7.093 | 12.373 | −2.402 | 1.00 | 39.43 | | C |
| ANISOU | 162 | CA | PRO | A | 257 | 5067 | 5077 | 4836 | 1 | −29 | −23 | C |
| ATOM | 163 | CB | PRO | A | 257 | 6.587 | 11.750 | −3.707 | 1.00 | 39.18 | | C |
| ANISOU | 163 | CB | PRO | A | 257 | 5053 | 5055 | 4778 | 7 | −3 | −63 | C |
| ATOM | 164 | CG | PRO | A | 257 | 5.294 | 11.091 | −3.363 | 1.00 | 39.06 | | C |
| ANISOU | 164 | CG | PRO | A | 257 | 5063 | 5013 | 4764 | −13 | −1 | −34 | C |

TABLE 7-continued

The atomic structure coordinates of Fc-TM

| | | | | | | | | | | | | |
|---|---|---|---|---|---|---|---|---|---|---|---|---|
| ATOM | 165 | CD | PRO | A | 257 | 5.315 | 10.781 | −1.890 | 1.00 | 40.06 | | C |
| ANISOU | 165 | CD | PRO | A | 257 | 5172 | 5085 | 4963 | −7 | 17 | 5 | C |
| ATOM | 166 | C | PRO | A | 257 | 6.744 | 13.855 | −2.321 | 1.00 | 39.42 | | C |
| ANISOU | 166 | C | PRO | A | 257 | 5113 | 5073 | 4792 | −38 | −37 | −56 | C |
| ATOM | 167 | O | PRO | A | 257 | 5.645 | 14.229 | −1.926 | 1.00 | 38.86 | | O |
| ANISOU | 167 | O | PRO | A | 257 | 5152 | 4918 | 4693 | −21 | −22 | −87 | O |
| ATOM | 168 | N | GLU | A | 258 | 7.692 | 14.683 | −2.730 | 1.00 | 40.26 | | N |
| ANISOU | 168 | N | GLU | A | 258 | 5231 | 5155 | 4908 | −57 | −80 | −131 | N |
| ATOM | 169 | CA | GLU | A | 258 | 7.562 | 16.117 | −2.647 | 1.00 | 40.63 | | C |
| ANISOU | 169 | CA | GLU | A | 258 | 5252 | 5182 | 5001 | −31 | −77 | −91 | C |
| ATOM | 170 | CB | GLU | A | 258 | 8.386 | 16.633 | −1.456 | 1.00 | 41.53 | | C |
| ANISOU | 170 | CB | GLU | A | 258 | 5416 | 5269 | 5091 | −15 | −86 | −96 | C |
| ATOM | 171 | CG | GLU | A | 258 | 7.818 | 16.238 | −0.078 | 1.00 | 44.60 | | C |
| ANISOU | 171 | CG | GLU | A | 258 | 5886 | 5562 | 5495 | −57 | 188 | −51 | C |
| ATOM | 172 | CD | GLU | A | 258 | 8.897 | 16.116 | 1.007 | 1.00 | 40.88 | | C |
| ANISOU | 172 | CD | GLU | A | 258 | 4965 | 5716 | 4850 | −392 | −49 | 386 | C |
| ATOM | 173 | OE1 | GLU | A | 258 | 8.594 | 15.520 | 2.079 | 1.00 | 48.80 | | O |
| ANISOU | 173 | OE1 | GLU | A | 258 | 6168 | 6166 | 6208 | 50 | −119 | −284 | O |
| ATOM | 174 | OE2 | GLU | A | 258 | 10.041 | 16.600 | 0.785 | 1.00 | 46.91 | | O |
| ANISOU | 174 | OE2 | GLU | A | 258 | 6298 | 5858 | 5666 | 75 | −119 | −191 | O |
| ATOM | 175 | C | GLU | A | 258 | 8.092 | 16.753 | −3.903 | 1.00 | 40.29 | | C |
| ANISOU | 175 | C | GLU | A | 258 | 5202 | 5119 | 4985 | −31 | −97 | −129 | C |
| ATOM | 176 | O | GLU | A | 258 | 9.072 | 16.292 | −4.477 | 1.00 | 40.44 | | O |
| ANISOU | 176 | O | GLU | A | 258 | 5293 | 5116 | 4956 | −54 | −98 | −185 | O |
| ATOM | 177 | N | VAL | A | 259 | 7.459 | 17.840 | −4.303 | 1.00 | 40.01 | | N |
| ANISOU | 177 | N | VAL | A | 259 | 5143 | 5064 | 4994 | −48 | −92 | −112 | N |
| ATOM | 178 | CA | VAL | A | 259 | 7.948 | 18.670 | −5.392 | 1.00 | 40.26 | | C |
| ANISOU | 178 | CA | VAL | A | 259 | 5155 | 5061 | 5081 | 18 | −77 | −86 | C |
| ATOM | 179 | CB | VAL | A | 259 | 6.797 | 18.967 | −6.381 | 1.00 | 40.32 | | C |
| ANISOU | 179 | CB | VAL | A | 259 | 5194 | 5086 | 5040 | 3 | −70 | −79 | C |
| ATOM | 180 | CG1 | VAL | A | 259 | 7.169 | 20.031 | −7.349 | 1.00 | 39.85 | | C |
| ANISOU | 180 | CG1 | VAL | A | 259 | 5102 | 5046 | 4994 | −46 | −49 | −51 | C |
| ATOM | 181 | CG2 | VAL | A | 259 | 6.390 | 17.682 | −7.103 | 1.00 | 40.01 | | C |
| ANISOU | 181 | CG2 | VAL | A | 259 | 5111 | 5024 | 5065 | 55 | −92 | −113 | C |
| ATOM | 182 | C | VAL | A | 259 | 8.529 | 19.942 | −4.761 | 1.00 | 40.31 | | C |
| ANISOU | 182 | C | VAL | A | 259 | 5146 | 5030 | 5137 | 22 | −59 | −6 | C |
| ATOM | 183 | O | VAL | A | 259 | 7.939 | 20.517 | −3.840 | 1.00 | 39.93 | | O |
| ANISOU | 183 | O | VAL | A | 259 | 5181 | 4910 | 5080 | 30 | −43 | −21 | O |
| ATOM | 184 | N | THR | A | 260 | 9.704 | 20.355 | −5.211 | 1.00 | 40.59 | | N |
| ANISOU | 184 | N | THR | A | 260 | 5198 | 5044 | 5180 | 37 | −40 | 1 | N |
| ATOM | 185 | CA | THR | A | 260 | 10.377 | 21.475 | −4.556 | 1.00 | 40.90 | | C |
| ANISOU | 185 | CA | THR | A | 260 | 5225 | 5103 | 5210 | 17 | −22 | −52 | C |
| ATOM | 186 | CB | THR | A | 260 | 11.722 | 21.052 | −3.918 | 1.00 | 40.60 | | C |
| ANISOU | 186 | CB | THR | A | 260 | 5177 | 5055 | 5191 | 5 | 7 | −62 | C |
| ATOM | 187 | OG1 | THR | A | 260 | 11.488 | 19.986 | −2.986 | 1.00 | 40.40 | | O |
| ANISOU | 187 | OG1 | THR | A | 260 | 5213 | 5077 | 5059 | 47 | 26 | −208 | O |
| ATOM | 188 | CG2 | THR | A | 260 | 12.342 | 22.196 | −3.157 | 1.00 | 40.61 | | C |
| ANISOU | 188 | CG2 | THR | A | 260 | 5192 | 5102 | 5132 | −11 | 38 | 10 | C |
| ATOM | 189 | C | THR | A | 260 | 10.510 | 22.656 | −5.512 | 1.00 | 41.22 | | C |
| ANISOU | 189 | C | THR | A | 260 | 5246 | 5148 | 5267 | −11 | −3 | −54 | C |
| ATOM | 190 | O | THR | A | 260 | 11.068 | 22.527 | −6.598 | 1.00 | 41.63 | | O |
| ANISOU | 190 | O | THR | A | 260 | 5257 | 5264 | 5294 | 15 | 23 | −122 | O |
| ATOM | 191 | N | CYS | A | 261 | 9.943 | 23.795 | −5.109 | 1.00 | 41.33 | | N |
| ANISOU | 191 | N | CYS | A | 261 | 5272 | 5136 | 5296 | −17 | −27 | −88 | N |
| ATOM | 192 | CA | CYS | A | 261 | 10.029 | 25.032 | −5.889 | 1.00 | 41.26 | | C |
| ANISOU | 192 | CA | CYS | A | 261 | 5292 | 5146 | 5237 | −26 | −50 | −63 | C |
| ATOM | 193 | CB | CYS | A | 261 | 8.691 | 25.769 | −5.894 | 1.00 | 40.72 | | C |
| ANISOU | 193 | CB | CYS | A | 261 | 5249 | 5103 | 5116 | −4 | −33 | −99 | C |
| ATOM | 194 | SG | CYS | A | 261 | 8.495 | 27.040 | −7.213 | 1.00 | 41.29 | | S |
| ANISOU | 194 | SG | CYS | A | 261 | 5307 | 4989 | 5391 | −25 | −29 | −151 | S |
| ATOM | 195 | C | CYS | A | 261 | 11.104 | 25.928 | −5.292 | 1.00 | 41.60 | | C |
| ANISOU | 195 | C | CYS | A | 261 | 5340 | 5207 | 5259 | −19 | −18 | −67 | C |
| ATOM | 196 | O | CYS | A | 261 | 11.014 | 26.324 | −4.133 | 1.00 | 42.19 | | O |
| ANISOU | 196 | O | CYS | A | 261 | 5452 | 5297 | 5280 | −24 | −69 | −78 | O |
| ATOM | 197 | N | VAL | A | 262 | 12.121 | 26.234 | −6.084 | 1.00 | 41.65 | | N |
| ANISOU | 197 | N | VAL | A | 262 | 5287 | 5236 | 5301 | −27 | 5 | −70 | N |
| ATOM | 198 | CA | VAL | A | 262 | 13.192 | 27.102 | −5.645 | 1.00 | 41.52 | | C |
| ANISOU | 198 | CA | VAL | A | 262 | 5296 | 5172 | 5305 | −10 | −8 | −79 | C |
| ATOM | 199 | CB | VAL | A | 262 | 14.566 | 26.403 | −5.736 | 1.00 | 41.57 | | C |
| ANISOU | 199 | CB | VAL | A | 262 | 5266 | 5213 | 5312 | −4 | −11 | −73 | C |
| ATOM | 200 | CG1 | VAL | A | 262 | 15.703 | 27.418 | −5.531 | 1.00 | 41.51 | | C |
| ANISOU | 200 | CG1 | VAL | A | 262 | 5318 | 5058 | 5393 | 16 | 35 | −129 | C |
| ATOM | 201 | CG2 | VAL | A | 262 | 14.667 | 25.238 | −4.732 | 1.00 | 40.60 | | C |
| ANISOU | 201 | CG2 | VAL | A | 262 | 5239 | 5053 | 5131 | −58 | −15 | −107 | C |
| ATOM | 202 | C | VAL | A | 262 | 13.230 | 28.375 | −6.493 | 1.00 | 41.97 | | C |
| ANISOU | 202 | C | VAL | A | 262 | 5353 | 5249 | 5344 | −6 | 1 | −62 | C |
| ATOM | 203 | O | VAL | A | 262 | 13.277 | 28.308 | −7.744 | 1.00 | 41.34 | | O |
| ANISOU | 203 | O | VAL | A | 262 | 5297 | 5185 | 5225 | 3 | 27 | −162 | O |

TABLE 7-continued

The atomic structure coordinates of Fc-TM

| | | | | | | | | | | | | | |
|---|---|---|---|---|---|---|---|---|---|---|---|---|---|
| ATOM | 204 | N | VAL | A | 263 | 13.200 | 29.523 | −5.795 | 1.00 | 41.79 | | | N |
| ANISOU | 204 | N | VAL | A | 263 | 5323 | 5198 | 5357 | −8 | 26 | −81 | | N |
| ATOM | 205 | CA | VAL | A | 263 | 13.450 | 30.829 | −6.399 | 1.00 | 41.87 | | | C |
| ANISOU | 205 | CA | VAL | A | 263 | 5331 | 5210 | 5365 | 13 | −1 | −48 | | C |
| ATOM | 206 | CB | VAL | A | 263 | 12.381 | 31.882 | −6.011 | 1.00 | 42.15 | | | C |
| ANISOU | 206 | CB | VAL | A | 263 | 5365 | 5244 | 5407 | −13 | −13 | −29 | | C |
| ATOM | 207 | CG1 | VAL | A | 263 | 12.197 | 32.897 | −7.151 | 1.00 | 41.64 | | | C |
| ANISOU | 207 | CG1 | VAL | A | 263 | 5414 | 5099 | 5308 | −3 | −61 | −36 | | C |
| ATOM | 208 | CG2 | VAL | A | 263 | 11.070 | 31.217 | −5.688 | 1.00 | 41.69 | | | C |
| ANISOU | 208 | CG2 | VAL | A | 263 | 5219 | 5254 | 5366 | 28 | 11 | 9 | | C |
| ATOM | 209 | C | VAL | A | 263 | 14.825 | 31.331 | −5.954 | 1.00 | 42.07 | | | C |
| ANISOU | 209 | C | VAL | A | 263 | 5367 | 5246 | 5371 | −13 | 24 | −47 | | C |
| ATOM | 210 | O | VAL | A | 263 | 15.194 | 31.243 | −4.773 | 1.00 | 42.24 | | | O |
| ANISOU | 210 | O | VAL | A | 263 | 5419 | 5263 | 5365 | −9 | 12 | −77 | | O |
| ATOM | 211 | N | VAL | A | 264 | 15.594 | 31.819 | −6.915 | 1.00 | 42.34 | | | N |
| ANISOU | 211 | N | VAL | A | 264 | 5407 | 5261 | 5417 | −40 | 15 | −20 | | N |
| ATOM | 212 | CA | VAL | A | 264 | 16.912 | 32.371 | −6.640 | 1.00 | 42.34 | | | C |
| ANISOU | 212 | CA | VAL | A | 264 | 5355 | 5321 | 5408 | −44 | −15 | 0 | | C |
| ATOM | 213 | CB | VAL | A | 264 | 18.086 | 31.458 | −7.123 | 1.00 | 42.32 | | | C |
| ANISOU | 213 | CB | VAL | A | 264 | 5369 | 5281 | 5427 | −74 | −22 | 5 | | C |
| ATOM | 214 | CG1 | VAL | A | 264 | 18.307 | 30.333 | −6.151 | 1.00 | 42.89 | | | C |
| ANISOU | 214 | CG1 | VAL | A | 264 | 5398 | 5442 | 5455 | 11 | −96 | 65 | | C |
| ATOM | 215 | CG2 | VAL | A | 264 | 17.862 | 30.926 | −8.536 | 1.00 | 42.03 | | | C |
| ANISOU | 215 | CG2 | VAL | A | 264 | 5346 | 5351 | 5270 | −55 | −7 | 25 | | C |
| ATOM | 216 | C | VAL | A | 264 | 17.003 | 33.756 | −7.271 | 1.00 | 42.94 | | | C |
| ANISOU | 216 | C | VAL | A | 264 | 5419 | 5400 | 5493 | −38 | −13 | 22 | | C |
| ATOM | 217 | O | VAL | A | 264 | 16.131 | 34.135 | −8.077 | 1.00 | 43.29 | | | O |
| ANISOU | 217 | O | VAL | A | 264 | 5396 | 5527 | 5525 | −14 | −27 | 41 | | O |
| ATOM | 218 | N | ASP | A | 265 | 18.057 | 34.500 | −6.918 | 1.00 | 42.97 | | | N |
| ANISOU | 218 | N | ASP | A | 265 | 5466 | 5374 | 5487 | −58 | −15 | −6 | | N |
| ATOM | 219 | CA | ASP | A | 265 | 18.204 | 35.890 | −7.353 | 1.00 | 43.20 | | | C |
| ANISOU | 219 | CA | ASP | A | 265 | 5502 | 5401 | 5511 | −43 | 11 | 9 | | C |
| ATOM | 220 | CB | ASP | A | 265 | 18.142 | 36.018 | −8.889 | 1.00 | 43.15 | | | C |
| ANISOU | 220 | CB | ASP | A | 265 | 5545 | 5394 | 5456 | −50 | −12 | −19 | | C |
| ATOM | 221 | CG | ASP | A | 265 | 19.371 | 35.453 | −9.579 | 1.00 | 44.92 | | | C |
| ANISOU | 221 | CG | ASP | A | 265 | 5679 | 5711 | 5678 | −48 | 12 | −4 | | C |
| ATOM | 222 | OD1 | ASP | A | 265 | 19.303 | 35.191 | −10.803 | 1.00 | 46.63 | | | O |
| ANISOU | 222 | OD1 | ASP | A | 265 | 5857 | 6021 | 5836 | −140 | −10 | −71 | | O |
| ATOM | 223 | OD2 | ASP | A | 265 | 20.411 | 35.263 | −8.906 | 1.00 | 47.21 | | | O |
| ANISOU | 223 | OD2 | ASP | A | 265 | 5935 | 5986 | 6016 | −141 | −96 | −22 | | O |
| ATOM | 224 | C | ASP | A | 265 | 17.117 | 36.728 | −6.695 | 1.00 | 43.08 | | | C |
| ANISOU | 224 | C | ASP | A | 265 | 5496 | 5395 | 5475 | −37 | 49 | −4 | | C |
| ATOM | 225 | O | ASP | A | 265 | 16.547 | 37.636 | −7.313 | 1.00 | 43.22 | | | O |
| ANISOU | 225 | O | ASP | A | 265 | 5505 | 5422 | 5495 | −37 | 102 | 40 | | O |
| ATOM | 226 | N | VAL | A | 266 | 16.787 | 36.397 | −5.449 | 1.00 | 43.36 | | | N |
| ANISOU | 226 | N | VAL | A | 266 | 5544 | 5410 | 5520 | −42 | 9 | −52 | | N |
| ATOM | 227 | CA | VAL | A | 266 | 15.823 | 37.227 | −4.722 | 1.00 | 43.59 | | | C |
| ANISOU | 227 | CA | VAL | A | 266 | 5576 | 5445 | 5541 | −38 | −7 | −62 | | C |
| ATOM | 228 | CB | VAL | A | 266 | 15.117 | 36.476 | −3.564 | 1.00 | 43.62 | | | C |
| ANISOU | 228 | CB | VAL | A | 266 | 5567 | 5440 | 5564 | −36 | −10 | −65 | | C |
| ATOM | 229 | CG1 | VAL | A | 266 | 14.260 | 37.426 | −2.730 | 1.00 | 43.27 | | | C |
| ANISOU | 229 | CG1 | VAL | A | 266 | 5518 | 5469 | 5453 | −20 | −46 | −125 | | C |
| ATOM | 230 | CG2 | VAL | A | 266 | 14.253 | 35.309 | −4.109 | 1.00 | 43.36 | | | C |
| ANISOU | 230 | CG2 | VAL | A | 266 | 5463 | 5462 | 5547 | 25 | −14 | −83 | | C |
| ATOM | 231 | C | VAL | A | 266 | 16.653 | 38.421 | −4.250 | 1.00 | 43.81 | | | C |
| ANISOU | 231 | C | VAL | A | 266 | 5612 | 5461 | 5572 | −40 | −47 | −75 | | C |
| ATOM | 232 | O | VAL | A | 266 | 17.678 | 38.243 | −3.606 | 1.00 | 44.05 | | | O |
| ANISOU | 232 | O | VAL | A | 266 | 5645 | 5485 | 5605 | −62 | −80 | −95 | | O |
| ATOM | 233 | N | SER | A | 267 | 16.252 | 39.625 | −4.629 | 1.00 | 44.16 | | | N |
| ANISOU | 233 | N | SER | A | 267 | 5674 | 5467 | 5637 | −42 | −51 | −55 | | N |
| ATOM | 234 | CA | SER | A | 267 | 17.044 | 40.809 | −4.291 | 1.00 | 44.92 | | | C |
| ANISOU | 234 | CA | SER | A | 267 | 5742 | 5605 | 5720 | −26 | −25 | −27 | | C |
| ATOM | 235 | CB | SER | A | 267 | 16.574 | 42.015 | −5.098 | 1.00 | 44.80 | | | C |
| ANISOU | 235 | CB | SER | A | 267 | 5731 | 5551 | 5737 | −24 | −13 | −6 | | C |
| ATOM | 236 | OG | SER | A | 267 | 15.463 | 42.605 | −4.458 | 1.00 | 44.95 | | | O |
| ANISOU | 236 | OG | SER | A | 267 | 5676 | 5584 | 5816 | 9 | 4 | −13 | | O |
| ATOM | 237 | C | SER | A | 267 | 16.978 | 41.119 | −2.789 | 1.00 | 45.15 | | | C |
| ANISOU | 237 | C | SER | A | 267 | 5807 | 5630 | 5718 | −32 | −6 | −55 | | C |
| ATOM | 238 | O | SER | A | 267 | 16.586 | 40.278 | −1.978 | 1.00 | 45.49 | | | O |
| ANISOU | 238 | O | SER | A | 267 | 5828 | 5712 | 5744 | −51 | 7 | −60 | | O |
| ATOM | 239 | N | HIS | A | 268 | 17.366 | 42.333 | −2.428 | 1.00 | 45.94 | | | N |
| ANISOU | 239 | N | HIS | A | 268 | 5897 | 5755 | 5801 | −37 | −7 | −42 | | N |
| ATOM | 240 | CA | HIS | A | 268 | 17.252 | 42.793 | −1.044 | 1.00 | 46.15 | | | C |
| ANISOU | 240 | CA | HIS | A | 268 | 5932 | 5783 | 5817 | −26 | −11 | −31 | | C |
| ATOM | 241 | CB | HIS | A | 268 | 18.614 | 43.221 | −0.546 | 1.00 | 46.45 | | | C |
| ANISOU | 241 | CB | HIS | A | 268 | 5950 | 5843 | 5855 | −51 | −45 | −21 | | C |
| ATOM | 242 | CG | HIS | A | 268 | 19.575 | 42.093 | −0.372 | 1.00 | 47.75 | | | C |
| ANISOU | 242 | CG | HIS | A | 268 | 6131 | 5941 | 6069 | 30 | −23 | −45 | | C |

TABLE 7-continued

The atomic structure coordinates of Fc-TM

| | | | | | | | | | | | | |
|---|---|---|---|---|---|---|---|---|---|---|---|---|
| ATOM | 243 | ND1 | HIS | A | 268 | 19.941 | 41.617 | 0.869 | 1.00 | 49.83 | | N |
| ANISOU | 243 | ND1 | HIS | A | 268 | 6445 | 6227 | 6259 | 116 | 7 | −9 | N |
| ATOM | 244 | CE1 | HIS | A | 268 | 20.804 | 40.628 | 0.722 | 1.00 | 49.57 | | C |
| ANISOU | 244 | CE1 | HIS | A | 268 | 6470 | 6345 | 6018 | 34 | 60 | −31 | C |
| ATOM | 245 | NE2 | HIS | A | 268 | 21.011 | 40.445 | −0.570 | 1.00 | 49.91 | | N |
| ANISOU | 245 | NE2 | HIS | A | 268 | 6326 | 6330 | 6306 | 20 | −64 | 2 | N |
| ATOM | 246 | CD2 | HIS | A | 268 | 20.257 | 41.354 | −1.276 | 1.00 | 48.94 | | C |
| ANISOU | 246 | CD2 | HIS | A | 268 | 6300 | 6208 | 6085 | 12 | 8 | −40 | C |
| ATOM | 247 | C | HIS | A | 268 | 16.270 | 43.953 | −0.932 | 1.00 | 46.31 | | C |
| ANISOU | 247 | C | HIS | A | 268 | 5952 | 5787 | 5855 | −19 | 8 | −26 | C |
| ATOM | 248 | O | HIS | A | 268 | 15.635 | 44.151 | 0.120 | 1.00 | 46.57 | | O |
| ANISOU | 248 | O | HIS | A | 268 | 6023 | 5813 | 5856 | −91 | 5 | −43 | O |
| ATOM | 249 | N | GLU | A | 269 | 16.140 | 44.701 | −2.032 | 1.00 | 46.57 | | N |
| ANISOU | 249 | N | GLU | A | 269 | 5987 | 5794 | 5912 | 0 | 24 | 16 | N |
| ATOM | 250 | CA | GLU | A | 269 | 15.251 | 45.875 | −2.109 | 1.00 | 46.95 | | C |
| ANISOU | 250 | CA | GLU | A | 269 | 5979 | 5849 | 6010 | 4 | 29 | −27 | C |
| ATOM | 251 | CB | GLU | A | 269 | 15.603 | 46.754 | −3.323 | 1.00 | 46.62 | | C |
| ANISOU | 251 | CB | GLU | A | 269 | 5977 | 5776 | 5960 | −3 | 18 | −3 | C |
| ATOM | 252 | CG | GLU | A | 269 | 17.070 | 46.679 | −3.764 | 1.00 | 47.69 | | C |
| ANISOU | 252 | CG | GLU | A | 269 | 5996 | 5921 | 6202 | −64 | 33 | 27 | C |
| ATOM | 253 | CD | GLU | A | 269 | 17.958 | 47.749 | −3.127 | 1.00 | 50.37 | | C |
| ANISOU | 253 | CD | GLU | A | 269 | 6386 | 6291 | 6460 | −14 | −39 | −64 | C |
| ATOM | 254 | OE1 | GLU | A | 269 | 17.419 | 48.766 | −2.634 | 1.00 | 49.63 | | O |
| ANISOU | 254 | OE1 | GLU | A | 269 | 6277 | 6189 | 6390 | 40 | −9 | −219 | O |
| ATOM | 255 | OE2 | GLU | A | 269 | 19.208 | 47.585 | −3.161 | 1.00 | 51.70 | | O |
| ANISOU | 255 | OE2 | GLU | A | 269 | 6319 | 6463 | 6858 | 16 | −192 | 20 | O |
| ATOM | 256 | C | GLU | A | 269 | 13.797 | 45.428 | −2.211 | 1.00 | 47.24 | | C |
| ANISOU | 256 | C | GLU | A | 269 | 6001 | 5892 | 6054 | 2 | 38 | −55 | C |
| ATOM | 257 | O | GLU | A | 269 | 12.901 | 46.013 | −1.583 | 1.00 | 48.33 | | O |
| ANISOU | 257 | O | GLU | A | 269 | 6161 | 6020 | 6182 | 27 | 66 | −84 | O |
| ATOM | 258 | N | ASP | A | 270 | 13.572 | 44.392 | −3.019 | 1.00 | 47.26 | | N |
| ANISOU | 258 | N | ASP | A | 270 | 6029 | 5892 | 6034 | 10 | 36 | −52 | N |
| ATOM | 259 | CA | ASP | A | 270 | 12.251 | 43.806 | −3.226 | 1.00 | 46.94 | | C |
| ANISOU | 259 | CA | ASP | A | 270 | 5979 | 5862 | 5992 | 11 | 11 | −19 | C |
| ATOM | 260 | CB | ASP | A | 270 | 11.817 | 44.010 | −4.678 | 1.00 | 47.64 | | C |
| ANISOU | 260 | CB | ASP | A | 270 | 6125 | 5924 | 6052 | −10 | 2 | −55 | C |
| ATOM | 261 | CG | ASP | A | 270 | 12.011 | 45.446 | −5.149 | 1.00 | 49.53 | | C |
| ANISOU | 261 | CG | ASP | A | 270 | 6428 | 6106 | 6283 | 5 | 83 | 46 | C |
| ATOM | 262 | OD1 | ASP | A | 270 | 11.562 | 46.383 | −4.426 | 1.00 | 50.58 | | O |
| ANISOU | 262 | OD1 | ASP | A | 270 | 6655 | 6105 | 6455 | 75 | 138 | −47 | O |
| ATOM | 263 | OD2 | ASP | A | 270 | 12.620 | 45.632 | −6.232 | 1.00 | 50.17 | | O |
| ANISOU | 263 | OD2 | ASP | A | 270 | 6461 | 6333 | 6269 | 47 | 198 | −153 | O |
| ATOM | 264 | C | ASP | A | 270 | 12.379 | 42.331 | −2.925 | 1.00 | 46.46 | | C |
| ANISOU | 264 | C | ASP | A | 270 | 5904 | 5821 | 5928 | 4 | 5 | −41 | C |
| ATOM | 265 | O | ASP | A | 270 | 12.490 | 41.528 | −3.852 | 1.00 | 46.73 | | O |
| ANISOU | 265 | O | ASP | A | 270 | 5861 | 5902 | 5992 | 73 | 80 | −3 | O |
| ATOM | 266 | N | PRO | A | 271 | 12.383 | 41.970 | −1.628 | 1.00 | 46.30 | | N |
| ANISOU | 266 | N | PRO | A | 271 | 5872 | 5815 | 5902 | 19 | 9 | −39 | N |
| ATOM | 267 | CA | PRO | A | 271 | 12.735 | 40.625 | −1.182 | 1.00 | 46.38 | | C |
| ANISOU | 267 | CA | PRO | A | 271 | 5878 | 5802 | 5940 | 8 | 8 | −53 | C |
| ATOM | 268 | CB | PRO | A | 271 | 13.321 | 40.873 | 0.207 | 1.00 | 46.74 | | C |
| ANISOU | 268 | CB | PRO | A | 271 | 5927 | 5842 | 5990 | 0 | 20 | −18 | C |
| ATOM | 269 | CG | PRO | A | 271 | 12.532 | 42.082 | 0.732 | 1.00 | 46.35 | | C |
| ANISOU | 269 | CG | PRO | A | 271 | 5868 | 5817 | 5922 | 37 | −13 | −51 | C |
| ATOM | 270 | CD | PRO | A | 271 | 12.074 | 42.863 | −0.487 | 1.00 | 46.34 | | C |
| ANISOU | 270 | CD | PRO | A | 271 | 5887 | 5812 | 5907 | 47 | 16 | −33 | C |
| ATOM | 271 | C | PRO | A | 271 | 11.567 | 39.661 | −1.064 | 1.00 | 46.91 | | C |
| ANISOU | 271 | C | PRO | A | 271 | 5915 | 5843 | 6064 | 16 | 18 | −55 | C |
| ATOM | 272 | O | PRO | A | 271 | 11.751 | 38.464 | −1.297 | 1.00 | 47.80 | | O |
| ANISOU | 272 | O | PRO | A | 271 | 5999 | 5932 | 6231 | 72 | 10 | −41 | O |
| ATOM | 273 | N | GLU | A | 272 | 10.385 | 40.161 | −0.703 | 1.00 | 47.03 | | N |
| ANISOU | 273 | N | GLU | A | 272 | 5924 | 5834 | 6111 | 10 | 9 | −81 | N |
| ATOM | 274 | CA | GLU | A | 272 | 9.255 | 39.289 | −0.375 | 1.00 | 46.90 | | C |
| ANISOU | 274 | CA | GLU | A | 272 | 5899 | 5861 | 6056 | −31 | 2 | −69 | C |
| ATOM | 275 | CB | GLU | A | 272 | 8.199 | 40.002 | 0.480 | 1.00 | 47.05 | | C |
| ANISOU | 275 | CB | GLU | A | 272 | 5905 | 5909 | 6061 | −29 | −1 | −57 | C |
| ATOM | 276 | CG | GLU | A | 272 | 8.736 | 40.972 | 1.528 | 1.00 | 48.65 | | C |
| ANISOU | 276 | CG | GLU | A | 272 | 6104 | 6206 | 6174 | −35 | −24 | −64 | C |
| ATOM | 277 | CD | GLU | A | 272 | 9.674 | 40.329 | 2.566 | 1.00 | 50.71 | | C |
| ANISOU | 277 | CD | GLU | A | 272 | 6405 | 6393 | 6466 | 10 | −66 | 39 | C |
| ATOM | 278 | OE1 | GLU | A | 272 | 9.577 | 39.104 | 2.812 | 1.00 | 51.33 | | O |
| ANISOU | 278 | OE1 | GLU | A | 272 | 6528 | 6257 | 6717 | −21 | 33 | −12 | O |
| ATOM | 279 | OE2 | GLU | A | 272 | 10.509 | 41.074 | 3.139 | 1.00 | 50.98 | | O |
| ANISOU | 279 | OE2 | GLU | A | 272 | 6448 | 6560 | 6361 | −33 | −177 | −55 | O |
| ATOM | 280 | C | GLU | A | 272 | 8.631 | 38.686 | −1.633 | 1.00 | 46.54 | | C |
| ANISOU | 280 | C | GLU | A | 272 | 5881 | 5811 | 5989 | −31 | −30 | −51 | C |
| ATOM | 281 | O | GLU | A | 272 | 8.366 | 39.380 | −2.630 | 1.00 | 47.00 | | O |
| ANISOU | 281 | O | GLU | A | 272 | 5929 | 5827 | 6100 | −69 | −26 | −34 | O |

TABLE 7-continued

The atomic structure coordinates of Fc-TM

| ATOM | 282 | N | VAL | A | 273 | 8.434 | 37.372 | −1.573 | 1.00 | 45.97 | | N |
|---|---|---|---|---|---|---|---|---|---|---|---|---|
| ANISOU | 282 | N | VAL | A | 273 | 5822 | 5768 | 5875 | −28 | −35 | −72 | N |
| ATOM | 283 | CA | VAL | A | 273 | 7.935 | 36.586 | −2.697 | 1.00 | 45.26 | | C |
| ANISOU | 283 | CA | VAL | A | 273 | 5738 | 5675 | 5781 | −15 | −4 | −87 | C |
| ATOM | 284 | CB | VAL | A | 273 | 9.042 | 35.675 | −3.296 | 1.00 | 45.49 | | C |
| ANISOU | 284 | CB | VAL | A | 273 | 5723 | 5777 | 5781 | −37 | 9 | −110 | C |
| ATOM | 285 | CG1 | VAL | A | 273 | 8.629 | 35.110 | −4.669 | 1.00 | 45.42 | | C |
| ANISOU | 285 | CG1 | VAL | A | 273 | 5681 | 5791 | 5783 | −59 | 0 | −59 | C |
| ATOM | 286 | CG2 | VAL | A | 273 | 10.363 | 36.439 | −3.429 | 1.00 | 45.73 | | C |
| ANISOU | 286 | CG2 | VAL | A | 273 | 5844 | 5761 | 5769 | −107 | 2 | −86 | C |
| ATOM | 287 | C | VAL | A | 273 | 6.749 | 35.756 | −2.202 | 1.00 | 44.66 | | C |
| ANISOU | 287 | C | VAL | A | 273 | 5681 | 5592 | 5694 | 0 | 3 | −104 | C |
| ATOM | 288 | O | VAL | A | 273 | 6.687 | 35.353 | −1.029 | 1.00 | 44.72 | | O |
| ANISOU | 288 | O | VAL | A | 273 | 5778 | 5509 | 5704 | 26 | 36 | −129 | O |
| ATOM | 289 | N | LYS | A | 274 | 5.811 | 35.522 | −3.108 | 1.00 | 43.97 | | N |
| ANISOU | 289 | N | LYS | A | 274 | 5556 | 5534 | 5616 | 10 | 13 | −109 | N |
| ATOM | 290 | CA | LYS | A | 274 | 4.568 | 34.833 | −2.807 | 1.00 | 43.21 | | C |
| ANISOU | 290 | CA | LYS | A | 274 | 5485 | 5435 | 5495 | −5 | 21 | −75 | C |
| ATOM | 291 | CB | LYS | A | 274 | 3.407 | 35.759 | −3.179 | 1.00 | 42.77 | | C |
| ANISOU | 291 | CB | LYS | A | 274 | 5436 | 5394 | 5419 | 0 | −19 | −102 | C |
| ATOM | 292 | CG | LYS | A | 274 | 2.050 | 35.407 | −2.597 | 1.00 | 41.82 | | C |
| ANISOU | 292 | CG | LYS | A | 274 | 5335 | 5189 | 5365 | −22 | −50 | −111 | C |
| ATOM | 293 | CD | LYS | A | 274 | 0.997 | 36.393 | −3.092 | 1.00 | 42.08 | | C |
| ANISOU | 293 | CD | LYS | A | 274 | 5342 | 5275 | 5370 | −13 | −1 | −45 | C |
| ATOM | 294 | CE | LYS | A | 274 | 0.899 | 36.385 | −4.614 | 1.00 | 44.59 | | C |
| ANISOU | 294 | CE | LYS | A | 274 | 5681 | 5789 | 5470 | −483 | 152 | −326 | C |
| ATOM | 295 | NZ | LYS | A | 274 | −0.045 | 37.398 | −5.185 | 1.00 | 40.06 | | N |
| ANISOU | 295 | NZ | LYS | A | 274 | 5019 | 4610 | 5590 | 369 | −248 | 81 | N |
| ATOM | 296 | C | LYS | A | 274 | 4.498 | 33.570 | −3.651 | 1.00 | 43.36 | | C |
| ANISOU | 296 | C | LYS | A | 274 | 5514 | 5454 | 5504 | −3 | 30 | −52 | C |
| ATOM | 297 | O | LYS | A | 274 | 4.678 | 33.627 | −4.873 | 1.00 | 43.92 | | O |
| ANISOU | 297 | O | LYS | A | 274 | 5587 | 5567 | 5534 | 35 | 17 | −66 | O |
| ATOM | 298 | N | PHE | A | 275 | 4.229 | 32.431 | −3.024 | 1.00 | 43.43 | | N |
| ANISOU | 298 | N | PHE | A | 275 | 5510 | 5465 | 5523 | 17 | 5 | −41 | N |
| ATOM | 299 | CA | PHE | A | 275 | 4.007 | 31.206 | −3.803 | 1.00 | 43.22 | | C |
| ANISOU | 299 | CA | PHE | A | 275 | 5474 | 5466 | 5480 | 9 | 9 | −42 | C |
| ATOM | 300 | CB | PHE | A | 275 | 4.673 | 30.013 | −3.158 | 1.00 | 43.00 | | C |
| ANISOU | 300 | CB | PHE | A | 275 | 5486 | 5398 | 5452 | 2 | 15 | −33 | C |
| ATOM | 301 | CG | PHE | A | 275 | 6.166 | 30.040 | −3.246 | 1.00 | 43.42 | | C |
| ANISOU | 301 | CG | PHE | A | 275 | 5474 | 5474 | 5547 | 30 | −1 | −25 | C |
| ATOM | 302 | CD1 | PHE | A | 275 | 6.929 | 30.554 | −2.193 | 1.00 | 42.75 | | C |
| ANISOU | 302 | CD1 | PHE | A | 275 | 5315 | 5360 | 5568 | 9 | −25 | −65 | C |
| ATOM | 303 | CE1 | PHE | A | 275 | 8.322 | 30.570 | −2.263 | 1.00 | 42.60 | | C |
| ANISOU | 303 | CE1 | PHE | A | 275 | 5337 | 5322 | 5527 | −92 | −56 | 14 | C |
| ATOM | 304 | CZ | PHE | A | 275 | 8.962 | 30.062 | −3.392 | 1.00 | 42.99 | | C |
| ANISOU | 304 | CZ | PHE | A | 275 | 5390 | 5492 | 5450 | −41 | −24 | −57 | C |
| ATOM | 305 | CE2 | PHE | A | 275 | 8.208 | 29.543 | −4.459 | 1.00 | 43.86 | | C |
| ANISOU | 305 | CE2 | PHE | A | 275 | 5445 | 5657 | 5560 | −71 | 26 | −48 | C |
| ATOM | 306 | CD2 | PHE | A | 275 | 6.818 | 29.538 | −4.379 | 1.00 | 43.43 | | C |
| ANISOU | 306 | CD2 | PHE | A | 275 | 5481 | 5591 | 5428 | 9 | −44 | 3 | C |
| ATOM | 307 | C | PHE | A | 275 | 2.544 | 30.902 | −4.001 | 1.00 | 43.40 | | C |
| ANISOU | 307 | C | PHE | A | 275 | 5526 | 5484 | 5479 | −33 | 19 | −47 | C |
| ATOM | 308 | O | PHE | A | 275 | 1.750 | 30.906 | −3.046 | 1.00 | 44.16 | | O |
| ANISOU | 308 | O | PHE | A | 275 | 5666 | 5605 | 5505 | −26 | 30 | −41 | O |
| ATOM | 309 | N | ASN | A | 276 | 2.177 | 30.660 | −5.252 | 1.00 | 43.24 | | N |
| ANISOU | 309 | N | ASN | A | 276 | 5500 | 5462 | 5466 | −18 | 42 | −22 | N |
| ATOM | 310 | CA | ASN | A | 276 | 0.890 | 30.052 | −5.539 | 1.00 | 43.32 | | C |
| ANISOU | 310 | CA | ASN | A | 276 | 5497 | 5427 | 5532 | −7 | 31 | −42 | C |
| ATOM | 311 | CB | ASN | A | 276 | 0.089 | 30.864 | −6.573 | 1.00 | 42.83 | | C |
| ANISOU | 311 | CB | ASN | A | 276 | 5423 | 5396 | 5453 | 32 | 70 | −1 | C |
| ATOM | 312 | CG | ASN | A | 276 | −0.109 | 32.337 | −6.171 | 1.00 | 43.44 | | C |
| ANISOU | 312 | CG | ASN | A | 276 | 5519 | 5499 | 5487 | 9 | 9 | −16 | C |
| ATOM | 313 | OD1 | ASN | A | 276 | −0.722 | 33.112 | −6.918 | 1.00 | 44.20 | | O |
| ANISOU | 313 | OD1 | ASN | A | 276 | 5682 | 5657 | 5455 | −11 | 91 | 56 | O |
| ATOM | 314 | ND2 | ASN | A | 276 | 0.392 | 32.724 | −4.997 | 1.00 | 44.64 | | N |
| ANISOU | 314 | ND2 | ASN | A | 276 | 5694 | 5621 | 5644 | 84 | −43 | 23 | N |
| ATOM | 315 | C | ASN | A | 276 | 1.193 | 28.629 | −6.021 | 1.00 | 43.23 | | C |
| ANISOU | 315 | C | ASN | A | 276 | 5471 | 5387 | 5567 | 12 | 67 | −36 | C |
| ATOM | 316 | O | ASN | A | 276 | 2.271 | 28.381 | −6.566 | 1.00 | 43.45 | | O |
| ANISOU | 316 | O | ASN | A | 276 | 5468 | 5431 | 5610 | 15 | 74 | −38 | O |
| ATOM | 317 | N | TRP | A | 277 | 0.261 | 27.703 | −5.780 | 1.00 | 43.29 | | N |
| ANISOU | 317 | N | TRP | A | 277 | 5473 | 5373 | 5600 | 17 | 43 | −43 | N |
| ATOM | 318 | CA | TRP | A | 277 | 0.403 | 26.290 | −6.173 | 1.00 | 42.95 | | C |
| ANISOU | 318 | CA | TRP | A | 277 | 5415 | 5377 | 5523 | −6 | 0 | −103 | C |
| ATOM | 319 | CB | TRP | A | 277 | 0.758 | 25.397 | −4.985 | 1.00 | 42.16 | | C |
| ANISOU | 319 | CB | TRP | A | 277 | 5263 | 5304 | 5451 | 28 | −4 | −65 | C |
| ATOM | 320 | CG | TRP | A | 277 | 2.183 | 25.417 | −4.469 | 1.00 | 42.99 | | C |
| ANISOU | 320 | CG | TRP | A | 277 | 5406 | 5401 | 5527 | 5 | 23 | −87 | C |

TABLE 7-continued

| The atomic structure coordinates of Fc-TM | | | | | | | | | | | |
|---|---|---|---|---|---|---|---|---|---|---|---|
| ATOM | 321 | CD1 | TRP | A | 277 | 2.657 | 26.129 | −3.398 | 1.00 | 42.90 | C |
| ANISOU | 321 | CD1 | TRP | A | 277 | 5338 | 5415 | 5547 | 10 | −15 | −143 | C |
| ATOM | 322 | NE1 | TRP | A | 277 | 3.990 | 25.862 | −3.194 | 1.00 | 43.36 | N |
| ANISOU | 322 | NE1 | TRP | A | 277 | 5319 | 5500 | 5653 | −54 | −62 | −48 | N |
| ATOM | 323 | CE2 | TRP | A | 277 | 4.405 | 24.949 | −4.125 | 1.00 | 42.25 | C |
| ANISOU | 323 | CE2 | TRP | A | 277 | 5236 | 5343 | 5471 | 68 | 39 | −134 | C |
| ATOM | 324 | CD2 | TRP | A | 277 | 3.289 | 24.634 | −4.943 | 1.00 | 42.84 | C |
| ANISOU | 324 | CD2 | TRP | A | 277 | 5364 | 5403 | 5509 | 30 | 27 | −96 | C |
| ATOM | 325 | CE3 | TRP | A | 277 | 3.455 | 23.715 | −5.991 | 1.00 | 43.02 | C |
| ANISOU | 325 | CE3 | TRP | A | 277 | 5359 | 5403 | 5582 | 49 | −27 | −100 | C |
| ATOM | 326 | CZ3 | TRP | A | 277 | 4.717 | 23.141 | −6.186 | 1.00 | 42.65 | C |
| ANISOU | 326 | CZ3 | TRP | A | 277 | 5369 | 5373 | 5462 | −37 | −12 | −164 | C |
| ATOM | 327 | CH2 | TRP | A | 277 | 5.801 | 23.471 | −5.354 | 1.00 | 42.95 | C |
| ANISOU | 327 | CH2 | TRP | A | 277 | 5324 | 5462 | 5533 | 8 | −25 | −87 | C |
| ATOM | 328 | CZ2 | TRP | A | 277 | 5.668 | 24.376 | −4.322 | 1.00 | 43.40 | C |
| ANISOU | 328 | CZ2 | TRP | A | 277 | 5423 | 5476 | 5590 | −13 | −3 | −46 | C |
| ATOM | 329 | C | TRP | A | 277 | −0.922 | 25.793 | −6.720 | 1.00 | 42.96 | C |
| ANISOU | 329 | C | TRP | A | 277 | 5381 | 5417 | 5524 | 9 | 0 | −104 | C |
| ATOM | 330 | O | TRP | A | 277 | −1.978 | 26.129 | −6.192 | 1.00 | 43.23 | O |
| ANISOU | 330 | O | TRP | A | 277 | 5408 | 5439 | 5576 | −15 | −28 | −119 | O |
| ATOM | 331 | N | TYR | A | 278 | −0.842 | 24.965 | −7.754 | 1.00 | 42.84 | N |
| ANISOU | 331 | N | TYR | A | 278 | 5366 | 5431 | 5478 | 38 | −13 | −101 | N |
| ATOM | 332 | CA | TYR | A | 278 | −1.988 | 24.432 | −8.471 | 1.00 | 42.52 | C |
| ANISOU | 332 | CA | TYR | A | 278 | 5338 | 5365 | 5451 | 19 | −12 | −52 | C |
| ATOM | 333 | CB | TYR | A | 278 | −2.247 | 25.265 | −9.746 | 1.00 | 43.43 | C |
| ANISOU | 333 | CB | TYR | A | 278 | 5419 | 5517 | 5565 | 0 | −11 | −30 | C |
| ATOM | 334 | CG | TYR | A | 278 | −2.307 | 26.769 | −9.500 | 1.00 | 44.08 | C |
| ANISOU | 334 | CG | TYR | A | 278 | 5578 | 5473 | 5695 | 8 | 54 | 0 | C |
| ATOM | 335 | CD1 | TYR | A | 278 | −1.140 | 27.535 | −9.452 | 1.00 | 43.87 | C |
| ANISOU | 335 | CD1 | TYR | A | 278 | 5454 | 5517 | 5694 | 19 | −5 | −65 | C |
| ATOM | 336 | CE1 | TYR | A | 278 | −1.177 | 28.900 | −9.228 | 1.00 | 44.77 | C |
| ANISOU | 336 | CE1 | TYR | A | 278 | 5712 | 5565 | 5732 | 0 | −41 | −53 | C |
| ATOM | 337 | CZ | TYR | A | 278 | −2.395 | 29.528 | −9.019 | 1.00 | 44.46 | C |
| ANISOU | 337 | CZ | TYR | A | 278 | 5561 | 5435 | 5893 | 3 | −8 | −83 | C |
| ATOM | 338 | OH | TYR | A | 278 | −2.429 | 30.889 | −8.788 | 1.00 | 45.34 | O |
| ANISOU | 338 | OH | TYR | A | 278 | 5756 | 5539 | 5929 | 47 | 81 | −4 | O |
| ATOM | 339 | CE2 | TYR | A | 278 | −3.575 | 28.797 | −9.047 | 1.00 | 46.00 | C |
| ANISOU | 339 | CE2 | TYR | A | 278 | 5736 | 5868 | 5872 | 2 | 3 | 28 | C |
| ATOM | 340 | CD2 | TYR | A | 278 | −3.525 | 27.416 | −9.291 | 1.00 | 44.42 | C |
| ANISOU | 340 | CD2 | TYR | A | 278 | 5603 | 5446 | 5827 | 91 | −7 | −3 | C |
| ATOM | 341 | C | TYR | A | 278 | −1.705 | 22.978 | −8.845 | 1.00 | 42.48 | C |
| ANISOU | 341 | C | TYR | A | 278 | 5350 | 5371 | 5416 | −2 | −44 | −14 | C |
| ATOM | 342 | O | TYR | A | 278 | −0.649 | 22.659 | −9.386 | 1.00 | 42.02 | O |
| ANISOU | 342 | O | TYR | A | 278 | 5346 | 5257 | 5361 | 43 | −47 | −56 | O |
| ATOM | 343 | N | VAL | A | 279 | −2.658 | 22.100 | −8.551 | 1.00 | 42.92 | N |
| ANISOU | 343 | N | VAL | A | 279 | 5472 | 5419 | 5416 | −5 | −44 | 20 | N |
| ATOM | 344 | CA | VAL | A | 279 | −2.610 | 20.701 | −8.983 | 1.00 | 42.90 | C |
| ANISOU | 344 | CA | VAL | A | 279 | 5447 | 5421 | 5431 | 20 | −27 | −3 | C |
| ATOM | 345 | CB | VAL | A | 279 | −2.902 | 19.744 | −7.795 | 1.00 | 42.52 | C |
| ANISOU | 345 | CB | VAL | A | 279 | 5413 | 5380 | 5362 | 33 | −38 | −9 | C |
| ATOM | 346 | CG1 | VAL | A | 279 | −2.993 | 18.320 | −8.244 | 1.00 | 41.55 | C |
| ANISOU | 346 | CG1 | VAL | A | 279 | 5177 | 5298 | 5311 | 13 | −94 | 26 | C |
| ATOM | 347 | CG2 | VAL | A | 279 | −1.824 | 19.896 | −6.731 | 1.00 | 42.94 | C |
| ANISOU | 347 | CG2 | VAL | A | 279 | 5406 | 5427 | 5483 | 79 | 6 | 17 | C |
| ATOM | 348 | C | VAL | A | 279 | −3.633 | 20.546 | −10.115 | 1.00 | 43.47 | C |
| ANISOU | 348 | C | VAL | A | 279 | 5510 | 5501 | 5503 | −5 | −32 | −11 | C |
| ATOM | 349 | O | VAL | A | 279 | −4.840 | 20.532 | −9.876 | 1.00 | 43.83 | O |
| ANISOU | 349 | O | VAL | A | 279 | 5537 | 5526 | 5589 | −14 | −44 | −13 | O |
| ATOM | 350 | N | ASP | A | 280 | −3.133 | 20.472 | −11.348 | 1.00 | 43.97 | N |
| ANISOU | 350 | N | ASP | A | 280 | 5575 | 5537 | 5591 | 11 | −28 | −30 | N |
| ATOM | 351 | CA | ASP | A | 280 | −3.963 | 20.499 | −12.557 | 1.00 | 44.09 | C |
| ANISOU | 351 | CA | ASP | A | 280 | 5575 | 5525 | 5649 | 5 | −64 | −42 | C |
| ATOM | 352 | CB | ASP | A | 280 | −4.869 | 19.252 | −12.634 | 1.00 | 44.22 | C |
| ANISOU | 352 | CB | ASP | A | 280 | 5608 | 5545 | 5645 | 17 | −30 | 9 | C |
| ATOM | 353 | CG | ASP | A | 280 | −4.151 | 18.026 | −13.197 | 1.00 | 43.82 | C |
| ANISOU | 353 | CG | ASP | A | 280 | 5606 | 5434 | 5609 | −22 | −32 | −26 | C |
| ATOM | 354 | OD1 | ASP | A | 280 | −3.283 | 18.156 | −14.086 | 1.00 | 43.76 | O |
| ANISOU | 354 | OD1 | ASP | A | 280 | 5538 | 5390 | 5698 | −27 | 32 | −141 | O |
| ATOM | 355 | OD2 | ASP | A | 280 | −4.474 | 16.915 | −12.756 | 1.00 | 43.89 | O |
| ANISOU | 355 | OD2 | ASP | A | 280 | 5597 | 5469 | 5609 | −7 | 1 | −1 | O |
| ATOM | 356 | C | ASP | A | 280 | −4.786 | 21.799 | −12.756 | 1.00 | 44.61 | C |
| ANISOU | 356 | C | ASP | A | 280 | 5619 | 5577 | 5751 | 16 | −59 | −63 | C |
| ATOM | 357 | O | ASP | A | 280 | −5.887 | 21.761 | −13.314 | 1.00 | 45.34 | O |
| ANISOU | 357 | O | ASP | A | 280 | 5661 | 5665 | 5897 | 54 | −94 | −85 | O |
| ATOM | 358 | N | GLY | A | 281 | −4.254 | 22.941 | −12.318 | 1.00 | 44.62 | N |
| ANISOU | 358 | N | GLY | A | 281 | 5615 | 5564 | 5774 | 9 | −33 | −63 | N |
| ATOM | 359 | CA | GLY | A | 281 | −4.920 | 24.239 | −12.522 | 1.00 | 43.93 | C |
| ANISOU | 359 | CA | GLY | A | 281 | 5546 | 5506 | 5639 | 43 | −15 | −9 | C |

TABLE 7-continued

The atomic structure coordinates of Fc-TM

| | | | | | | | | | | | |
|---|---|---|---|---|---|---|---|---|---|---|---|
| ATOM | 360 | C | GLY | A | 281 | −5.889 | 24.672 | −11.425 | 1.00 | 44.05 | C |
| ANISOU | 360 | C | GLY | A | 281 | 5544 | 5513 | 5679 | 30 | −12 | 3 | C |
| ATOM | 361 | O | GLY | A | 281 | −6.548 | 25.727 | −11.535 | 1.00 | 44.55 | O |
| ANISOU | 361 | O | GLY | A | 281 | 5577 | 5596 | 5754 | 17 | 20 | −60 | O |
| ATOM | 362 | N | VAL | A | 282 | −5.968 | 23.871 | −10.367 | 1.00 | 43.31 | N |
| ANISOU | 362 | N | VAL | A | 282 | 5472 | 5421 | 5561 | 14 | −8 | 19 | N |
| ATOM | 363 | CA | VAL | A | 282 | −6.851 | 24.121 | −9.241 | 1.00 | 43.04 | C |
| ANISOU | 363 | CA | VAL | A | 282 | 5464 | 5380 | 5508 | 26 | −25 | −11 | C |
| ATOM | 364 | CB | VAL | A | 282 | −7.691 | 22.860 | −8.916 | 1.00 | 43.44 | C |
| ANISOU | 364 | CB | VAL | A | 282 | 5511 | 5459 | 5536 | 37 | 4 | −16 | C |
| ATOM | 365 | CG1 | VAL | A | 282 | −8.661 | 23.101 | −7.753 | 1.00 | 44.12 | C |
| ANISOU | 365 | CG1 | VAL | A | 282 | 5583 | 5557 | 5621 | 14 | 21 | −60 | C |
| ATOM | 366 | CG2 | VAL | A | 282 | −8.442 | 22.350 | −10.169 | 1.00 | 42.54 | C |
| ANISOU | 366 | CG2 | VAL | A | 282 | 5348 | 5334 | 5481 | 10 | −71 | 16 | C |
| ATOM | 367 | C | VAL | A | 282 | −5.948 | 24.480 | −8.073 | 1.00 | 43.28 | C |
| ANISOU | 367 | C | VAL | A | 282 | 5520 | 5394 | 5528 | 31 | −9 | 0 | C |
| ATOM | 368 | O | VAL | A | 282 | −4.938 | 23.807 | −7.830 | 1.00 | 43.32 | O |
| ANISOU | 368 | O | VAL | A | 282 | 5586 | 5392 | 5480 | −4 | −7 | 0 | O |
| ATOM | 369 | N | GLU | A | 283 | −6.269 | 25.552 | −7.361 | 1.00 | 43.39 | N |
| ANISOU | 369 | N | GLU | A | 283 | 5533 | 5428 | 5524 | 46 | −30 | −15 | N |
| ATOM | 370 | CA | GLU | A | 283 | −5.332 | 26.039 | −6.359 | 1.00 | 43.99 | C |
| ANISOU | 370 | CA | GLU | A | 283 | 5588 | 5513 | 5614 | 39 | −27 | −44 | C |
| ATOM | 371 | CB | GLU | A | 283 | −5.541 | 27.527 | −6.015 | 1.00 | 44.14 | C |
| ANISOU | 371 | CB | GLU | A | 283 | 5616 | 5518 | 5637 | 22 | −32 | −77 | C |
| ATOM | 372 | CG | GLU | A | 283 | −4.233 | 28.237 | −5.566 | 1.00 | 45.14 | C |
| ANISOU | 372 | CG | GLU | A | 283 | 5698 | 5626 | 5824 | 1 | −30 | −88 | C |
| ATOM | 373 | CD | GLU | A | 283 | −4.371 | 29.755 | −5.272 | 1.00 | 45.52 | C |
| ANISOU | 373 | CD | GLU | A | 283 | 5808 | 5640 | 5847 | 63 | −22 | −79 | C |
| ATOM | 374 | OE1 | GLU | A | 283 | −5.169 | 30.449 | −5.936 | 1.00 | 45.98 | O |
| ANISOU | 374 | OE1 | GLU | A | 283 | 5903 | 5748 | 5817 | 168 | −129 | −128 | O |
| ATOM | 375 | OE2 | GLU | A | 283 | −3.643 | 30.256 | −4.381 | 1.00 | 45.87 | O |
| ANISOU | 375 | OE2 | GLU | A | 283 | 5852 | 5692 | 5885 | 80 | −99 | −213 | O |
| ATOM | 376 | C | GLU | A | 283 | −5.379 | 25.129 | −5.137 | 1.00 | 43.97 | C |
| ANISOU | 376 | C | GLU | A | 283 | 5562 | 5548 | 5597 | 37 | −9 | −38 | C |
| ATOM | 377 | O | GLU | A | 283 | −6.407 | 24.499 | −4.844 | 1.00 | 44.59 | O |
| ANISOU | 377 | O | GLU | A | 283 | 5634 | 5595 | 5712 | 35 | 51 | −49 | O |
| ATOM | 378 | N | VAL | A | 284 | −4.236 | 24.998 | −4.479 | 1.00 | 43.75 | N |
| ANISOU | 378 | N | VAL | A | 284 | 5529 | 5540 | 5552 | 44 | −36 | −57 | N |
| ATOM | 379 | CA | VAL | A | 284 | −4.120 | 24.176 | −3.273 | 1.00 | 43.31 | C |
| ANISOU | 379 | CA | VAL | A | 284 | 5511 | 5464 | 5480 | 32 | −24 | −78 | C |
| ATOM | 380 | CB | VAL | A | 284 | −3.476 | 22.788 | −3.586 | 1.00 | 43.18 | C |
| ANISOU | 380 | CB | VAL | A | 284 | 5470 | 5449 | 5488 | 12 | −27 | −98 | C |
| ATOM | 381 | CG1 | VAL | A | 284 | −4.052 | 22.210 | −4.898 | 1.00 | 43.69 | C |
| ANISOU | 381 | CG1 | VAL | A | 284 | 5545 | 5529 | 5525 | 52 | −3 | −77 | C |
| ATOM | 382 | CG2 | VAL | A | 284 | −1.955 | 22.880 | −3.689 | 1.00 | 42.77 | C |
| ANISOU | 382 | CG2 | VAL | A | 284 | 5474 | 5424 | 5350 | 28 | −8 | −121 | C |
| ATOM | 383 | C | VAL | A | 284 | −3.295 | 25.000 | −2.284 | 1.00 | 43.29 | C |
| ANISOU | 383 | C | VAL | A | 284 | 5540 | 5456 | 5451 | 58 | 2 | −99 | C |
| ATOM | 384 | O | VAL | A | 284 | −2.599 | 25.934 | −2.685 | 1.00 | 43.04 | O |
| ANISOU | 384 | O | VAL | A | 284 | 5517 | 5406 | 5431 | 65 | 12 | −172 | O |
| ATOM | 385 | N | HIS | A | 285 | −3.359 | 24.658 | −1.005 | 1.00 | 43.83 | N |
| ANISOU | 385 | N | HIS | A | 285 | 5611 | 5536 | 5504 | 66 | −17 | −98 | N |
| ATOM | 386 | CA | HIS | A | 285 | −2.861 | 25.567 | 0.027 | 1.00 | 44.27 | C |
| ANISOU | 386 | CA | HIS | A | 285 | 5668 | 5587 | 5565 | 87 | −30 | −55 | C |
| ATOM | 387 | CB | HIS | A | 285 | −4.050 | 26.282 | 0.698 | 1.00 | 44.73 | C |
| ANISOU | 387 | CB | HIS | A | 285 | 5756 | 5646 | 5593 | 75 | −33 | −36 | C |
| ATOM | 388 | CG | HIS | A | 285 | −4.976 | 26.958 | −0.275 | 1.00 | 44.92 | C |
| ANISOU | 388 | CG | HIS | A | 285 | 5649 | 5723 | 5694 | 77 | −25 | −31 | C |
| ATOM | 389 | ND1 | HIS | A | 285 | −4.656 | 28.136 | −0.918 | 1.00 | 44.58 | N |
| ANISOU | 389 | ND1 | HIS | A | 285 | 5612 | 5609 | 5716 | 66 | −65 | −20 | N |
| ATOM | 390 | CE1 | HIS | A | 285 | −5.646 | 28.483 | −1.724 | 1.00 | 45.27 | C |
| ANISOU | 390 | CE1 | HIS | A | 285 | 5786 | 5744 | 5667 | 95 | 17 | −124 | C |
| ATOM | 391 | NE2 | HIS | A | 285 | −6.598 | 27.573 | −1.625 | 1.00 | 43.43 | N |
| ANISOU | 391 | NE2 | HIS | A | 285 | 5469 | 5597 | 5434 | 28 | 51 | −17 | N |
| ATOM | 392 | CD2 | HIS | A | 285 | −6.199 | 26.603 | −0.735 | 1.00 | 44.79 | C |
| ANISOU | 392 | CD2 | HIS | A | 285 | 5612 | 5701 | 5703 | 19 | 85 | −129 | C |
| ATOM | 393 | C | HIS | A | 285 | −1.950 | 24.866 | 1.049 | 1.00 | 44.64 | C |
| ANISOU | 393 | C | HIS | A | 285 | 5770 | 5605 | 5584 | 68 | −24 | −62 | C |
| ATOM | 394 | O | HIS | A | 285 | −1.415 | 25.503 | 1.966 | 1.00 | 44.57 | O |
| ANISOU | 394 | O | HIS | A | 285 | 5789 | 5585 | 5561 | 88 | −2 | −76 | O |
| ATOM | 395 | N | ASN | A | 286 | −1.729 | 23.565 | 0.843 | 1.00 | 44.50 | N |
| ANISOU | 395 | N | ASN | A | 286 | 5789 | 5535 | 5584 | 80 | −9 | −57 | N |
| ATOM | 396 | CA | ASN | A | 286 | −0.962 | 22.747 | 1.781 | 1.00 | 44.26 | C |
| ANISOU | 396 | CA | ASN | A | 286 | 5730 | 5533 | 5553 | 67 | −12 | −83 | C |
| ATOM | 397 | CB | ASN | A | 286 | −1.450 | 21.295 | 1.735 | 1.00 | 44.27 | C |
| ANISOU | 397 | CB | ASN | A | 286 | 5748 | 5527 | 5545 | 38 | 6 | −34 | C |
| ATOM | 398 | CG | ASN | A | 286 | −1.216 | 20.635 | 0.373 | 1.00 | 44.25 | C |
| ANISOU | 398 | CG | ASN | A | 286 | 5821 | 5469 | 5519 | 47 | −24 | −56 | C |

TABLE 7-continued

The atomic structure coordinates of Fc-TM

| | | | | | | | | | | | | |
|---|---|---|---|---|---|---|---|---|---|---|---|---|
| ATOM | 399 | OD1 | ASN | A | 286 | −1.410 | 21.255 | −0.676 | 1.00 | 43.91 | | O |
| ANISOU | 399 | OD1 | ASN | A | 286 | 5808 | 5508 | 5364 | 5 | −68 | −229 | O |
| ATOM | 400 | ND2 | ASN | A | 286 | −0.803 | 19.376 | 0.391 | 1.00 | 44.62 | | N |
| ANISOU | 400 | ND2 | ASN | A | 286 | 5770 | 5592 | 5590 | 125 | 0 | −53 | N |
| ATOM | 401 | C | ASN | A | 286 | 0.568 | 22.816 | 1.625 | 1.00 | 44.26 | | C |
| ANISOU | 401 | C | ASN | A | 286 | 5738 | 5529 | 5547 | 68 | −18 | −77 | C |
| ATOM | 402 | O | ASN | A | 286 | 1.286 | 22.107 | 2.322 | 1.00 | 45.01 | | O |
| ANISOU | 402 | O | ASN | A | 286 | 5800 | 5597 | 5702 | 141 | −25 | −4 | O |
| ATOM | 403 | N | ALA | A | 287 | 1.077 | 23.681 | 0.750 | 1.00 | 43.66 | | N |
| ANISOU | 403 | N | ALA | A | 287 | 5666 | 5502 | 5421 | 51 | −13 | −117 | N |
| ATOM | 404 | CA | ALA | A | 287 | 2.530 | 23.836 | 0.631 | 1.00 | 43.65 | | C |
| ANISOU | 404 | CA | ALA | A | 287 | 5588 | 5531 | 5464 | 78 | −35 | −99 | C |
| ATOM | 405 | CB | ALA | A | 287 | 2.881 | 24.633 | −0.594 | 1.00 | 43.62 | | C |
| ANISOU | 405 | CB | ALA | A | 287 | 5586 | 5509 | 5477 | 102 | −29 | −107 | C |
| ATOM | 406 | C | ALA | A | 287 | 3.178 | 24.463 | 1.879 | 1.00 | 43.97 | | C |
| ANISOU | 406 | C | ALA | A | 287 | 5604 | 5597 | 5503 | 92 | −43 | −106 | C |
| ATOM | 407 | O | ALA | A | 287 | 2.539 | 25.238 | 2.598 | 1.00 | 43.85 | | O |
| ANISOU | 407 | O | ALA | A | 287 | 5569 | 5635 | 5454 | 105 | −67 | −115 | O |
| ATOM | 408 | N | LYS | A | 288 | 4.453 | 24.128 | 2.104 | 1.00 | 44.17 | | N |
| ANISOU | 408 | N | LYS | A | 288 | 5627 | 5595 | 5558 | 72 | −23 | −103 | N |
| ATOM | 409 | CA | LYS | A | 288 | 5.217 | 24.563 | 3.272 | 1.00 | 44.18 | | C |
| ANISOU | 409 | CA | LYS | A | 288 | 5625 | 5588 | 5572 | 29 | −45 | −99 | C |
| ATOM | 410 | CB | LYS | A | 288 | 5.689 | 23.352 | 4.080 | 1.00 | 44.81 | | C |
| ANISOU | 410 | CB | LYS | A | 288 | 5699 | 5701 | 5626 | 40 | −42 | −150 | C |
| ATOM | 411 | CG | LYS | A | 288 | 4.593 | 22.555 | 4.792 | 1.00 | 46.48 | | C |
| ANISOU | 411 | CG | LYS | A | 288 | 5865 | 5903 | 5892 | −76 | 11 | −29 | C |
| ATOM | 412 | CD | LYS | A | 288 | 4.200 | 23.232 | 6.110 | 1.00 | 49.09 | | C |
| ANISOU | 412 | CD | LYS | A | 288 | 6127 | 6301 | 6221 | −126 | 134 | −75 | C |
| ATOM | 413 | CE | LYS | A | 288 | 2.938 | 22.633 | 6.718 | 1.00 | 52.04 | | C |
| ANISOU | 413 | CE | LYS | A | 288 | 6488 | 6709 | 6575 | 43 | −23 | −39 | C |
| ATOM | 414 | NZ | LYS | A | 288 | 1.723 | 22.869 | 5.865 | 1.00 | 52.37 | | N |
| ANISOU | 414 | NZ | LYS | A | 288 | 6568 | 6732 | 6598 | 74 | −80 | 19 | N |
| ATOM | 415 | C | LYS | A | 288 | 6.420 | 25.342 | 2.794 | 1.00 | 44.20 | | C |
| ANISOU | 415 | C | LYS | A | 288 | 5613 | 5591 | 5587 | 58 | −50 | −120 | C |
| ATOM | 416 | O | LYS | A | 288 | 7.391 | 24.752 | 2.339 | 1.00 | 44.44 | | O |
| ANISOU | 416 | O | LYS | A | 288 | 5687 | 5545 | 5650 | 97 | −149 | −161 | O |
| ATOM | 417 | N | THR | A | 289 | 6.354 | 26.670 | 2.864 | 1.00 | 44.16 | | N |
| ANISOU | 417 | N | THR | A | 289 | 5601 | 5569 | 5607 | 51 | −24 | −106 | N |
| ATOM | 418 | CA | THR | A | 289 | 7.461 | 27.508 | 2.418 | 1.00 | 44.15 | | C |
| ANISOU | 418 | CA | THR | A | 289 | 5612 | 5539 | 5620 | 39 | 5 | −85 | C |
| ATOM | 419 | CB | THR | A | 289 | 6.970 | 28.884 | 1.928 | 1.00 | 44.07 | | C |
| ANISOU | 419 | CB | THR | A | 289 | 5583 | 5531 | 5628 | 43 | 0 | −85 | C |
| ATOM | 420 | OG1 | THR | A | 289 | 5.785 | 28.708 | 1.148 | 1.00 | 44.05 | | O |
| ANISOU | 420 | OG1 | THR | A | 289 | 5591 | 5462 | 5685 | 41 | 30 | −182 | O |
| ATOM | 421 | CG2 | THR | A | 289 | 8.017 | 29.571 | 1.057 | 1.00 | 43.05 | | C |
| ANISOU | 421 | CG2 | THR | A | 289 | 5481 | 5379 | 5495 | 32 | 70 | −140 | C |
| ATOM | 422 | C | THR | A | 289 | 8.492 | 27.654 | 3.538 | 1.00 | 44.68 | | C |
| ANISOU | 422 | C | THR | A | 289 | 5698 | 5604 | 5673 | 42 | 1 | −63 | C |
| ATOM | 423 | O | THR | A | 289 | 8.134 | 27.775 | 4.699 | 1.00 | 44.31 | | O |
| ANISOU | 423 | O | THR | A | 289 | 5702 | 5521 | 5612 | 66 | 10 | −51 | O |
| ATOM | 424 | N | LYS | A | 290 | 9.774 | 27.609 | 3.180 | 1.00 | 45.81 | | N |
| ANISOU | 424 | N | LYS | A | 290 | 5825 | 5733 | 5846 | 14 | −29 | −52 | N |
| ATOM | 425 | CA | LYS | A | 290 | 10.851 | 27.684 | 4.165 | 1.00 | 46.81 | | C |
| ANISOU | 425 | CA | LYS | A | 290 | 5945 | 5856 | 5982 | 13 | −25 | −36 | C |
| ATOM | 426 | CB | LYS | A | 290 | 12.115 | 26.942 | 3.676 | 1.00 | 47.41 | | C |
| ANISOU | 426 | CB | LYS | A | 290 | 6028 | 5957 | 6026 | 13 | 4 | −53 | C |
| ATOM | 427 | CG | LYS | A | 290 | 11.847 | 25.624 | 2.921 | 1.00 | 48.57 | | C |
| ANISOU | 427 | CG | LYS | A | 290 | 6220 | 6021 | 6211 | −2 | 67 | −25 | C |
| ATOM | 428 | CD | LYS | A | 290 | 11.104 | 24.615 | 3.765 | 1.00 | 51.96 | | C |
| ANISOU | 428 | CD | LYS | A | 290 | 6717 | 6409 | 6614 | 73 | 185 | 3 | C |
| ATOM | 429 | CE | LYS | A | 290 | 9.953 | 24.034 | 2.979 | 1.00 | 49.11 | | C |
| ANISOU | 429 | CE | LYS | A | 290 | 6138 | 6223 | 6296 | −248 | 15 | 22 | C |
| ATOM | 430 | NZ | LYS | A | 290 | 9.085 | 23.115 | 3.801 | 1.00 | 53.79 | | N |
| ANISOU | 430 | NZ | LYS | A | 290 | 6802 | 6907 | 6729 | 208 | −33 | −113 | N |
| ATOM | 431 | C | LYS | A | 290 | 11.172 | 29.147 | 4.440 | 1.00 | 46.84 | | C |
| ANISOU | 431 | C | LYS | A | 290 | 5963 | 5877 | 5957 | 0 | −26 | −24 | C |
| ATOM | 432 | O | LYS | A | 290 | 11.011 | 29.996 | 3.549 | 1.00 | 47.40 | | O |
| ANISOU | 432 | O | LYS | A | 290 | 5986 | 5914 | 6109 | 0 | −16 | −3 | O |
| ATOM | 433 | N | PRO | A | 291 | 11.592 | 29.457 | 5.681 | 1.00 | 46.94 | | N |
| ANISOU | 433 | N | PRO | A | 291 | 5985 | 5900 | 5950 | −14 | −59 | −1 | N |
| ATOM | 434 | CA | PRO | A | 291 | 12.091 | 30.804 | 5.994 | 1.00 | 46.84 | | C |
| ANISOU | 434 | CA | PRO | A | 291 | 5974 | 5891 | 5931 | −18 | −52 | −2 | C |
| ATOM | 435 | CB | PRO | A | 291 | 12.554 | 30.682 | 7.462 | 1.00 | 46.82 | | C |
| ANISOU | 435 | CB | PRO | A | 291 | 5971 | 5895 | 5921 | −11 | −80 | −5 | C |
| ATOM | 436 | CG | PRO | A | 291 | 12.624 | 29.199 | 7.753 | 1.00 | 46.92 | | C |
| ANISOU | 436 | CG | PRO | A | 291 | 6015 | 5881 | 5931 | −28 | −125 | 7 | C |
| ATOM | 437 | CD | PRO | A | 291 | 11.585 | 28.578 | 6.870 | 1.00 | 47.19 | | C |
| ANISOU | 437 | CD | PRO | A | 291 | 6015 | 5909 | 6005 | −25 | −71 | 32 | C |

TABLE 7-continued

The atomic structure coordinates of Fc-TM

| | | | | | | | | | | | | |
|---|---|---|---|---|---|---|---|---|---|---|---|---|
| ATOM | 438 | C | PRO | A | 291 | 13.261 | 31.147 | 5.075 | 1.00 | 46.64 | | C |
| ANISOU | 438 | C | PRO | A | 291 | 5925 | 5886 | 5910 | 5 | −30 | −4 | C |
| ATOM | 439 | O | PRO | A | 291 | 14.133 | 30.296 | 4.863 | 1.00 | 47.04 | | O |
| ANISOU | 439 | O | PRO | A | 291 | 5987 | 5882 | 6001 | 31 | −44 | −33 | O |
| ATOM | 440 | N | ARG | A | 292 | 13.264 | 32.364 | 4.520 | 1.00 | 46.46 | | N |
| ANISOU | 440 | N | ARG | A | 292 | 5884 | 5850 | 5915 | 18 | −40 | −33 | N |
| ATOM | 441 | CA | ARG | A | 292 | 14.214 | 32.738 | 3.462 | 1.00 | 46.02 | | C |
| ANISOU | 441 | CA | ARG | A | 292 | 5853 | 5808 | 5821 | 13 | −28 | −46 | C |
| ATOM | 442 | CB | ARG | A | 292 | 13.794 | 34.046 | 2.798 | 1.00 | 46.45 | | C |
| ANISOU | 442 | CB | ARG | A | 292 | 5904 | 5847 | 5896 | 2 | −27 | −71 | C |
| ATOM | 443 | CG | ARG | A | 292 | 13.611 | 35.259 | 3.741 | 1.00 | 47.04 | | C |
| ANISOU | 443 | CG | ARG | A | 292 | 6025 | 5960 | 5886 | 9 | −27 | −61 | C |
| ATOM | 444 | CD | ARG | A | 292 | 13.483 | 36.560 | 2.938 | 1.00 | 47.13 | | C |
| ANISOU | 444 | CD | ARG | A | 292 | 6000 | 5923 | 5984 | −61 | −73 | −30 | C |
| ATOM | 445 | NE | ARG | A | 292 | 12.698 | 37.551 | 3.667 | 1.00 | 47.83 | | N |
| ANISOU | 445 | NE | ARG | A | 292 | 6097 | 5602 | 6472 | −52 | 16 | −335 | N |
| ATOM | 446 | CZ | ARG | A | 292 | 13.127 | 38.770 | 4.014 | 1.00 | 57.33 | | C |
| ANISOU | 446 | CZ | ARG | A | 292 | 7795 | 7019 | 6967 | 93 | −377 | 229 | C |
| ATOM | 447 | NH1 | ARG | A | 292 | 14.348 | 39.183 | 3.676 | 1.00 | 49.57 | | N |
| ANISOU | 447 | NH1 | ARG | A | 292 | 5617 | 6420 | 6794 | −337 | 306 | 19 | N |
| ATOM | 448 | NH2 | ARG | A | 292 | 12.320 | 39.589 | 4.688 | 1.00 | 48.78 | | N |
| ANISOU | 448 | NH2 | ARG | A | 292 | 5976 | 6056 | 6501 | 282 | 328 | −326 | N |
| ATOM | 449 | C | ARG | A | 292 | 15.654 | 32.829 | 3.962 | 1.00 | 46.46 | | C |
| ANISOU | 449 | C | ARG | A | 292 | 5866 | 5923 | 5862 | 7 | −4 | −68 | C |
| ATOM | 450 | O | ARG | A | 292 | 15.881 | 33.227 | 5.111 | 1.00 | 46.71 | | O |
| ANISOU | 450 | O | ARG | A | 292 | 5920 | 5996 | 5831 | 8 | 24 | −119 | O |
| ATOM | 451 | N | GLU | A | 293 | 16.617 | 32.446 | 3.108 | 1.00 | 46.36 | | N |
| ANISOU | 451 | N | GLU | A | 293 | 5854 | 5928 | 5831 | 24 | −8 | −73 | N |
| ATOM | 452 | CA | GLU | A | 293 | 18.053 | 32.436 | 3.465 | 1.00 | 46.15 | | C |
| ANISOU | 452 | CA | GLU | A | 293 | 5799 | 5867 | 5867 | 0 | −8 | −62 | C |
| ATOM | 453 | CB | GLU | A | 293 | 18.639 | 31.019 | 3.384 | 1.00 | 46.12 | | C |
| ANISOU | 453 | CB | GLU | A | 293 | 5824 | 5830 | 5866 | 1 | −58 | 0 | C |
| ATOM | 454 | CG | GLU | A | 293 | 17.798 | 29.901 | 3.963 | 1.00 | 47.34 | | C |
| ANISOU | 454 | CG | GLU | A | 293 | 5940 | 5960 | 6085 | −28 | −21 | −38 | C |
| ATOM | 455 | CD | GLU | A | 293 | 18.535 | 28.556 | 3.942 | 1.00 | 47.14 | | C |
| ANISOU | 455 | CD | GLU | A | 293 | 5934 | 5957 | 6020 | 39 | −105 | −55 | C |
| ATOM | 456 | OE1 | GLU | A | 293 | 19.338 | 28.315 | 4.865 | 1.00 | 49.59 | | O |
| ANISOU | 456 | OE1 | GLU | A | 293 | 6438 | 6317 | 6085 | 42 | −160 | 10 | O |
| ATOM | 457 | OE2 | GLU | A | 293 | 18.316 | 27.742 | 3.006 | 1.00 | 48.92 | | O |
| ANISOU | 457 | OE2 | GLU | A | 293 | 6228 | 6211 | 6148 | −49 | −12 | −85 | O |
| ATOM | 458 | C | GLU | A | 293 | 18.833 | 33.336 | 2.514 | 1.00 | 45.36 | | C |
| ANISOU | 458 | C | GLU | A | 293 | 5761 | 5721 | 5752 | −18 | −34 | −35 | C |
| ATOM | 459 | O | GLU | A | 293 | 18.457 | 33.457 | 1.355 | 1.00 | 45.82 | | O |
| ANISOU | 459 | O | GLU | A | 293 | 5815 | 5803 | 5791 | −15 | 0 | −122 | O |
| ATOM | 460 | N | GLU | A | 294 | 19.926 | 33.938 | 2.994 | 1.00 | 45.28 | | N |
| ANISOU | 460 | N | GLU | A | 294 | 5733 | 5714 | 5756 | −18 | −2 | −11 | N |
| ATOM | 461 | CA | GLU | A | 294 | 20.712 | 34.932 | 2.222 | 1.00 | 44.87 | | C |
| ANISOU | 461 | CA | GLU | A | 294 | 5685 | 5636 | 5725 | −25 | −11 | −35 | C |
| ATOM | 462 | CB | GLU | A | 294 | 21.091 | 36.145 | 3.107 | 1.00 | 44.81 | | C |
| ANISOU | 462 | CB | GLU | A | 294 | 5705 | 5615 | 5706 | −20 | −7 | −42 | C |
| ATOM | 463 | CG | GLU | A | 294 | 21.392 | 37.439 | 2.323 | 1.00 | 44.23 | | C |
| ANISOU | 463 | CG | GLU | A | 294 | 5601 | 5551 | 5653 | −69 | −25 | −17 | C |
| ATOM | 464 | CD | GLU | A | 294 | 22.111 | 38.531 | 3.140 | 1.00 | 44.89 | | C |
| ANISOU | 464 | CD | GLU | A | 294 | 5751 | 5638 | 5664 | −73 | 2 | −26 | C |
| ATOM | 465 | OE1 | GLU | A | 294 | 22.680 | 39.462 | 2.517 | 1.00 | 44.05 | | O |
| ANISOU | 465 | OE1 | GLU | A | 294 | 5729 | 5440 | 5566 | −143 | 73 | −204 | O |
| ATOM | 466 | OE2 | GLU | A | 294 | 22.116 | 38.473 | 4.393 | 1.00 | 46.43 | | O |
| ANISOU | 466 | OE2 | GLU | A | 294 | 5939 | 5975 | 5726 | −261 | −49 | 46 | O |
| ATOM | 467 | C | GLU | A | 294 | 21.976 | 34.325 | 1.586 | 1.00 | 44.97 | | C |
| ANISOU | 467 | C | GLU | A | 294 | 5700 | 5636 | 5749 | −24 | −23 | −39 | C |
| ATOM | 468 | O | GLU | A | 294 | 22.738 | 33.611 | 2.247 | 1.00 | 45.23 | | O |
| ANISOU | 468 | O | GLU | A | 294 | 5722 | 5641 | 5823 | 4 | −34 | −91 | O |
| ATOM | 469 | N | GLN | A | 295 | 22.211 | 34.628 | 0.315 | 1.00 | 45.12 | | N |
| ANISOU | 469 | N | GLN | A | 295 | 5687 | 5686 | 5771 | −24 | 0 | −36 | N |
| ATOM | 470 | CA | GLN | A | 295 | 23.288 | 33.972 | −0.424 | 1.00 | 45.81 | | C |
| ANISOU | 470 | CA | GLN | A | 295 | 5768 | 5739 | 5898 | 0 | −23 | −34 | C |
| ATOM | 471 | CB | GLN | A | 295 | 22.770 | 33.466 | −1.772 | 1.00 | 45.40 | | C |
| ANISOU | 471 | CB | GLN | A | 295 | 5746 | 5699 | 5802 | 14 | −9 | −34 | C |
| ATOM | 472 | CG | GLN | A | 295 | 21.458 | 32.654 | −1.658 | 1.00 | 45.05 | | C |
| ANISOU | 472 | CG | GLN | A | 295 | 5671 | 5623 | 5819 | 25 | −48 | 39 | C |
| ATOM | 473 | CD | GLN | A | 295 | 21.627 | 31.319 | −0.930 | 1.00 | 50.11 | | C |
| ANISOU | 473 | CD | GLN | A | 295 | 6357 | 6206 | 6473 | −225 | −440 | −126 | C |
| ATOM | 474 | OE1 | GLN | A | 295 | 22.456 | 30.493 | −1.319 | 1.00 | 46.51 | | O |
| ANISOU | 474 | OE1 | GLN | A | 295 | 5639 | 5846 | 6183 | 244 | 39 | −244 | O |
| ATOM | 475 | NE2 | GLN | A | 295 | 20.831 | 31.098 | 0.119 | 1.00 | 44.53 | | N |
| ANISOU | 475 | NE2 | GLN | A | 295 | 5399 | 5954 | 5566 | −128 | 161 | −70 | N |
| ATOM | 476 | C | GLN | A | 295 | 24.555 | 34.838 | −0.580 | 1.00 | 46.43 | | C |
| ANISOU | 476 | C | GLN | A | 295 | 5854 | 5802 | 5984 | 26 | 12 | 5 | C |

TABLE 7-continued

| The atomic structure coordinates of Fc-TM | | | | | | | | | | | |
|---|---|---|---|---|---|---|---|---|---|---|---|
| ATOM | 477 | O | GLN | A | 295 | 24.486 | 36.076 | −0.703 | 1.00 | 47.58 | O |
| ANISOU | 477 | O | GLN | A | 295 | 6015 | 5902 | 6161 | 59 | 10 | −25 | O |
| ATOM | 478 | N | TYR | A | 296 | 25.714 | 34.187 | −0.561 | 1.00 | 46.40 | N |
| ANISOU | 478 | N | TYR | A | 296 | 5836 | 5823 | 5968 | 44 | 40 | 12 | N |
| ATOM | 479 | CA | TYR | A | 296 | 26.988 | 34.887 | −0.681 | 1.00 | 46.22 | C |
| ANISOU | 479 | CA | TYR | A | 296 | 5850 | 5807 | 5904 | 6 | 0 | −13 | C |
| ATOM | 480 | CB | TYR | A | 296 | 28.136 | 33.947 | −0.299 | 1.00 | 46.54 | C |
| ANISOU | 480 | CB | TYR | A | 296 | 5879 | 5805 | 5997 | 11 | 21 | −4 | C |
| ATOM | 481 | CG | TYR | A | 296 | 28.369 | 33.809 | 1.199 | 1.00 | 46.10 | C |
| ANISOU | 481 | CG | TYR | A | 296 | 5899 | 5814 | 5802 | −12 | 36 | 13 | C |
| ATOM | 482 | CD1 | TYR | A | 296 | 27.454 | 33.149 | 2.015 | 1.00 | 46.85 | C |
| ANISOU | 482 | CD1 | TYR | A | 296 | 5952 | 5814 | 6034 | 41 | 56 | −47 | C |
| ATOM | 483 | CE1 | TYR | A | 296 | 27.676 | 33.022 | 3.393 | 1.00 | 47.39 | C |
| ANISOU | 483 | CE1 | TYR | A | 296 | 6047 | 6058 | 5900 | 5 | −74 | 8 | C |
| ATOM | 484 | CZ | TYR | A | 296 | 28.836 | 33.551 | 3.951 | 1.00 | 46.56 | C |
| ANISOU | 484 | CZ | TYR | A | 296 | 5965 | 5924 | 5799 | −82 | 4 | 31 | C |
| ATOM | 485 | OH | TYR | A | 296 | 29.080 | 33.427 | 5.309 | 1.00 | 47.47 | O |
| ANISOU | 485 | OH | TYR | A | 296 | 6193 | 5903 | 5937 | −47 | −8 | −40 | O |
| ATOM | 486 | CE2 | TYR | A | 296 | 29.756 | 34.202 | 3.145 | 1.00 | 47.62 | C |
| ANISOU | 486 | CE2 | TYR | A | 296 | 5995 | 5884 | 6215 | 36 | 51 | −59 | C |
| ATOM | 487 | CD2 | TYR | A | 296 | 29.520 | 34.324 | 1.786 | 1.00 | 45.57 | C |
| ANISOU | 487 | CD2 | TYR | A | 296 | 5830 | 5826 | 5658 | 6 | −68 | 15 | C |
| ATOM | 488 | C | TYR | A | 296 | 27.193 | 35.501 | −2.083 | 1.00 | 46.49 | C |
| ANISOU | 488 | C | TYR | A | 296 | 5907 | 5803 | 5951 | 6 | −4 | 3 | C |
| ATOM | 489 | O | TYR | A | 296 | 28.292 | 35.440 | −2.666 | 1.00 | 46.50 | O |
| ANISOU | 489 | O | TYR | A | 296 | 5897 | 5779 | 5989 | −14 | −14 | −11 | O |
| ATOM | 490 | N | ASN | A | 297 | 26.119 | 36.064 | −2.631 | 1.00 | 46.88 | N |
| ANISOU | 490 | N | ASN | A | 297 | 5965 | 5855 | 5991 | 17 | −15 | −17 | N |
| ATOM | 491 | CA | ASN | A | 297 | 26.216 | 36.949 | −3.792 | 1.00 | 47.71 | C |
| ANISOU | 491 | CA | ASN | A | 297 | 6085 | 5986 | 6055 | 26 | −38 | −12 | C |
| ATOM | 492 | CB | ASN | A | 297 | 26.142 | 36.169 | −5.117 | 1.00 | 48.85 | C |
| ANISOU | 492 | CB | ASN | A | 297 | 6260 | 6139 | 6160 | 64 | 0 | −11 | C |
| ATOM | 493 | CG | ASN | A | 297 | 24.947 | 35.221 | −5.195 | 1.00 | 50.92 | C |
| ANISOU | 493 | CG | ASN | A | 297 | 6460 | 6440 | 6445 | −63 | 58 | −1 | C |
| ATOM | 494 | OD1 | ASN | A | 297 | 24.216 | 35.028 | −4.220 | 1.00 | 52.42 | O |
| ANISOU | 494 | OD1 | ASN | A | 297 | 6674 | 6584 | 6659 | 87 | 34 | −103 | O |
| ATOM | 495 | ND2 | ASN | A | 297 | 24.768 | 34.605 | −6.370 | 1.00 | 56.08 | N |
| ANISOU | 495 | ND2 | ASN | A | 297 | 7171 | 7114 | 7021 | −39 | −31 | −25 | N |
| ATOM | 496 | C | ASN | A | 297 | 25.188 | 38.088 | −3.729 | 1.00 | 47.37 | C |
| ANISOU | 496 | C | ASN | A | 297 | 6034 | 5962 | 6003 | 2 | −36 | −28 | C |
| ATOM | 497 | O | ASN | A | 297 | 24.879 | 38.733 | −4.748 | 1.00 | 47.54 | O |
| ANISOU | 497 | O | ASN | A | 297 | 6064 | 5970 | 6028 | −37 | −68 | −27 | O |
| ATOM | 498 | N | SER | A | 298 | 24.679 | 38.332 | −2.516 | 1.00 | 47.02 | N |
| ANISOU | 498 | N | SER | A | 298 | 5921 | 5925 | 6017 | 5 | −15 | −17 | N |
| ATOM | 499 | CA | SER | A | 298 | 23.797 | 39.477 | −2.220 | 1.00 | 46.71 | C |
| ANISOU | 499 | CA | SER | A | 298 | 5868 | 5873 | 6005 | −26 | −29 | 0 | C |
| ATOM | 500 | CB | SER | A | 298 | 24.415 | 40.801 | −2.693 | 1.00 | 46.68 | C |
| ANISOU | 500 | CB | SER | A | 298 | 5861 | 5857 | 6015 | −11 | −30 | 45 | C |
| ATOM | 501 | OG | SER | A | 298 | 25.715 | 40.961 | −2.150 | 1.00 | 48.13 | O |
| ANISOU | 501 | OG | SER | A | 298 | 6019 | 6020 | 6244 | −95 | −25 | −12 | O |
| ATOM | 502 | C | SER | A | 298 | 22.395 | 39.255 | −2.792 | 1.00 | 46.18 | C |
| ANISOU | 502 | C | SER | A | 298 | 5828 | 5812 | 5906 | −33 | −31 | 13 | C |
| ATOM | 503 | O | SER | A | 298 | 21.852 | 40.082 | −3.545 | 1.00 | 46.36 | O |
| ANISOU | 503 | O | SER | A | 298 | 5846 | 5850 | 5918 | −31 | −40 | 43 | O |
| ATOM | 504 | N | THR | A | 299 | 21.810 | 38.137 | −2.365 | 1.00 | 45.58 | N |
| ANISOU | 504 | N | THR | A | 299 | 5776 | 5728 | 5815 | −47 | −20 | 0 | N |
| ATOM | 505 | CA | THR | A | 299 | 20.634 | 37.558 | −2.982 | 1.00 | 45.03 | C |
| ANISOU | 505 | CA | THR | A | 299 | 5757 | 5632 | 5719 | −42 | −23 | −30 | C |
| ATOM | 506 | CB | THR | A | 299 | 21.118 | 36.736 | −4.229 | 1.00 | 45.29 | C |
| ANISOU | 506 | CB | THR | A | 299 | 5793 | 5664 | 5749 | −38 | −58 | −30 | C |
| ATOM | 507 | OG1 | THR | A | 299 | 20.498 | 37.203 | −5.433 | 1.00 | 46.45 | O |
| ANISOU | 507 | OG1 | THR | A | 299 | 5934 | 5743 | 5972 | 21 | −92 | −8 | O |
| ATOM | 508 | CG2 | THR | A | 299 | 20.931 | 35.249 | −4.066 | 1.00 | 45.09 | C |
| ANISOU | 508 | CG2 | THR | A | 299 | 5820 | 5677 | 5634 | −42 | −57 | −34 | C |
| ATOM | 509 | C | THR | A | 299 | 19.994 | 36.667 | −1.895 | 1.00 | 44.73 | C |
| ANISOU | 509 | C | THR | A | 299 | 5717 | 5578 | 5700 | −68 | −31 | −58 | C |
| ATOM | 510 | O | THR | A | 299 | 20.734 | 36.055 | −1.103 | 1.00 | 44.52 | O |
| ANISOU | 510 | O | THR | A | 299 | 5722 | 5570 | 5623 | −99 | −47 | −90 | O |
| ATOM | 511 | N | TYR | A | 300 | 18.656 | 36.609 | −1.809 | 1.00 | 44.50 | N |
| ANISOU | 511 | N | TYR | A | 300 | 5713 | 5554 | 5640 | −37 | 1 | −53 | N |
| ATOM | 512 | CA | TYR | A | 300 | 18.007 | 35.534 | −1.007 | 1.00 | 44.78 | C |
| ANISOU | 512 | CA | TYR | A | 300 | 5706 | 5632 | 5674 | −53 | 22 | −106 | C |
| ATOM | 513 | CB | TYR | A | 300 | 16.841 | 36.048 | −0.117 | 1.00 | 45.79 | C |
| ANISOU | 513 | CB | TYR | A | 300 | 5829 | 5719 | 5847 | −42 | 30 | −116 | C |
| ATOM | 514 | CG | TYR | A | 300 | 17.195 | 37.233 | 0.822 | 1.00 | 47.96 | C |
| ANISOU | 514 | CG | TYR | A | 300 | 6051 | 6119 | 6052 | 4 | 19 | −11 | C |
| ATOM | 515 | CD1 | TYR | A | 300 | 17.216 | 38.547 | 0.337 | 1.00 | 46.79 | C |
| ANISOU | 515 | CD1 | TYR | A | 300 | 6033 | 5674 | 6069 | −83 | −3 | −132 | C |

TABLE 7-continued

The atomic structure coordinates of Fc-TM

| ATOM | 516 | CE1 | TYR | A | 300 | 17.531 | 39.614 | 1.158 | 1.00 | 47.40 | | C |
|---|---|---|---|---|---|---|---|---|---|---|---|---|
| ANISOU | 516 | CE1 | TYR | A | 300 | 6116 | 6018 | 5876 | −35 | 4 | −148 | C |
| ATOM | 517 | CZ | TYR | A | 300 | 17.834 | 39.387 | 2.495 | 1.00 | 47.96 | | C |
| ANISOU | 517 | CZ | TYR | A | 300 | 6083 | 6090 | 6048 | 47 | −15 | 45 | C |
| ATOM | 518 | OH | TYR | A | 300 | 18.148 | 40.465 | 3.318 | 1.00 | 46.29 | | O |
| ANISOU | 518 | OH | TYR | A | 300 | 6171 | 5754 | 5662 | −44 | −150 | −180 | O |
| ATOM | 519 | CE2 | TYR | A | 300 | 17.804 | 38.096 | 3.006 | 1.00 | 47.39 | | C |
| ANISOU | 519 | CE2 | TYR | A | 300 | 6071 | 5825 | 6109 | 49 | −44 | −39 | C |
| ATOM | 520 | CD2 | TYR | A | 300 | 17.490 | 37.029 | 2.170 | 1.00 | 46.41 | | C |
| ANISOU | 520 | CD2 | TYR | A | 300 | 5977 | 5849 | 5807 | −92 | −119 | −95 | C |
| ATOM | 521 | C | TYR | A | 300 | 17.585 | 34.279 | −1.817 | 1.00 | 44.23 | | C |
| ANISOU | 521 | C | TYR | A | 300 | 5614 | 5568 | 5621 | −41 | 28 | −39 | C |
| ATOM | 522 | O | TYR | A | 300 | 17.452 | 34.291 | −3.056 | 1.00 | 44.14 | | O |
| ANISOU | 522 | O | TYR | A | 300 | 5567 | 5606 | 5598 | −57 | 27 | −81 | O |
| ATOM | 523 | N | ARG | A | 301 | 17.383 | 33.193 | −1.085 | 1.00 | 43.82 | | N |
| ANISOU | 523 | N | ARG | A | 301 | 5560 | 5519 | 5571 | 14 | −13 | −43 | N |
| ATOM | 524 | CA | ARG | A | 301 | 16.918 | 31.936 | −1.647 | 1.00 | 43.57 | | C |
| ANISOU | 524 | CA | ARG | A | 301 | 5505 | 5506 | 5542 | −3 | −7 | −33 | C |
| ATOM | 525 | CB | ARG | A | 301 | 18.004 | 30.864 | −1.516 | 1.00 | 43.36 | | C |
| ANISOU | 525 | CB | ARG | A | 301 | 5504 | 5467 | 5501 | 15 | −47 | −49 | C |
| ATOM | 526 | CG | ARG | A | 301 | 17.592 | 29.478 | −2.000 | 1.00 | 44.07 | | C |
| ANISOU | 526 | CG | ARG | A | 301 | 5519 | 5525 | 5699 | −32 | −46 | −8 | C |
| ATOM | 527 | CD | ARG | A | 301 | 18.816 | 28.611 | −2.243 | 1.00 | 44.34 | | C |
| ANISOU | 527 | CD | ARG | A | 301 | 5415 | 5556 | 5873 | −21 | −27 | −130 | C |
| ATOM | 528 | NE | ARG | A | 301 | 18.503 | 27.319 | −2.846 | 1.00 | 45.93 | | N |
| ANISOU | 528 | NE | ARG | A | 301 | 5462 | 6031 | 5957 | 106 | −48 | −104 | N |
| ATOM | 529 | CZ | ARG | A | 301 | 18.153 | 26.232 | −2.170 | 1.00 | 42.24 | | C |
| ANISOU | 529 | CZ | ARG | A | 301 | 5643 | 5431 | 4975 | −112 | 61 | −40 | C |
| ATOM | 530 | NH1 | ARG | A | 301 | 18.055 | 26.272 | −0.844 | 1.00 | 47.72 | | N |
| ANISOU | 530 | NH1 | ARG | A | 301 | 5737 | 6114 | 6280 | 8 | −101 | −45 | N |
| ATOM | 531 | NH2 | ARG | A | 301 | 17.891 | 25.102 | −2.821 | 1.00 | 46.14 | | N |
| ANISOU | 531 | NH2 | ARG | A | 301 | 5495 | 6132 | 5903 | 156 | 108 | 67 | N |
| ATOM | 532 | C | ARG | A | 301 | 15.674 | 31.523 | −0.876 | 1.00 | 43.64 | | C |
| ANISOU | 532 | C | ARG | A | 301 | 5540 | 5535 | 5503 | 1 | −17 | −7 | C |
| ATOM | 533 | O | ARG | A | 301 | 15.705 | 31.440 | 0.362 | 1.00 | 44.01 | | O |
| ANISOU | 533 | O | ARG | A | 301 | 5675 | 5632 | 5413 | 52 | 3 | 7 | O |
| ATOM | 534 | N | VAL | A | 302 | 14.574 | 31.295 | −1.598 | 1.00 | 43.14 | | N |
| ANISOU | 534 | N | VAL | A | 302 | 5467 | 5424 | 5499 | −21 | −5 | −6 | N |
| ATOM | 535 | CA | VAL | A | 302 | 13.342 | 30.854 | −0.956 | 1.00 | 42.72 | | C |
| ANISOU | 535 | CA | VAL | A | 302 | 5403 | 5315 | 5512 | −37 | 8 | −17 | C |
| ATOM | 536 | CB | VAL | A | 302 | 12.244 | 31.957 | −0.857 | 1.00 | 43.01 | | C |
| ANISOU | 536 | CB | VAL | A | 302 | 5439 | 5350 | 5551 | −47 | 13 | −13 | C |
| ATOM | 537 | CG1 | VAL | A | 302 | 11.403 | 31.739 | 0.404 | 1.00 | 42.56 | | C |
| ANISOU | 537 | CG1 | VAL | A | 302 | 5310 | 5394 | 5466 | −110 | −2 | −109 | C |
| ATOM | 538 | CG2 | VAL | A | 302 | 12.860 | 33.368 | −0.830 | 1.00 | 43.35 | | C |
| ANISOU | 538 | CG2 | VAL | A | 302 | 5471 | 5351 | 5646 | −38 | 32 | −2 | C |
| ATOM | 539 | C | VAL | A | 302 | 12.803 | 29.606 | −1.643 | 1.00 | 42.39 | | C |
| ANISOU | 539 | C | VAL | A | 302 | 5389 | 5308 | 5407 | −33 | −5 | −28 | C |
| ATOM | 540 | O | VAL | A | 302 | 12.657 | 29.560 | −2.863 | 1.00 | 41.88 | | O |
| ANISOU | 540 | O | VAL | A | 302 | 5326 | 5264 | 5320 | −2 | −39 | −30 | O |
| ATOM | 541 | N | VAL | A | 303 | 12.529 | 28.603 | −0.810 | 1.00 | 42.33 | | N |
| ANISOU | 541 | N | VAL | A | 303 | 5387 | 5251 | 5445 | −64 | −2 | −41 | N |
| ATOM | 542 | CA | VAL | A | 303 | 12.107 | 27.279 | −1.230 | 1.00 | 42.18 | | C |
| ANISOU | 542 | CA | VAL | A | 303 | 5328 | 5270 | 5427 | −26 | 30 | −33 | C |
| ATOM | 543 | CB | VAL | A | 303 | 13.036 | 26.184 | −0.605 | 1.00 | 42.24 | | C |
| ANISOU | 543 | CB | VAL | A | 303 | 5310 | 5283 | 5454 | −22 | 24 | −23 | C |
| ATOM | 544 | CG1 | VAL | A | 303 | 12.534 | 24.790 | −0.910 | 1.00 | 41.59 | | C |
| ANISOU | 544 | CG1 | VAL | A | 303 | 5214 | 5202 | 5384 | −38 | 86 | −28 | C |
| ATOM | 545 | CG2 | VAL | A | 303 | 14.501 | 26.353 | −1.073 | 1.00 | 42.85 | | C |
| ANISOU | 545 | CG2 | VAL | A | 303 | 5375 | 5362 | 5542 | −30 | 59 | −55 | C |
| ATOM | 546 | C | VAL | A | 303 | 10.674 | 27.041 | −0.748 | 1.00 | 41.94 | | C |
| ANISOU | 546 | C | VAL | A | 303 | 5300 | 5258 | 5377 | −12 | 27 | −38 | C |
| ATOM | 547 | O | VAL | A | 303 | 10.364 | 27.277 | 0.424 | 1.00 | 42.19 | | O |
| ANISOU | 547 | O | VAL | A | 303 | 5391 | 5257 | 5381 | 11 | 76 | 22 | O |
| ATOM | 548 | N | SER | A | 304 | 9.801 | 26.596 | −1.648 | 1.00 | 41.73 | | N |
| ANISOU | 548 | N | SER | A | 304 | 5238 | 5240 | 5375 | 4 | 30 | −44 | N |
| ATOM | 549 | CA | SER | A | 304 | 8.505 | 26.065 | −1.231 | 1.00 | 41.38 | | C |
| ANISOU | 549 | CA | SER | A | 304 | 5196 | 5202 | 5323 | −26 | 5 | −31 | C |
| ATOM | 550 | CB | SER | A | 304 | 7.339 | 26.861 | −1.831 | 1.00 | 41.38 | | C |
| ANISOU | 550 | CB | SER | A | 304 | 5184 | 5211 | 5327 | −22 | −8 | −54 | C |
| ATOM | 551 | OG | SER | A | 304 | 6.152 | 26.629 | −1.076 | 1.00 | 40.98 | | O |
| ANISOU | 551 | OG | SER | A | 304 | 5221 | 5152 | 5196 | 20 | 16 | −154 | O |
| ATOM | 552 | C | SER | A | 304 | 8.391 | 24.579 | −1.579 | 1.00 | 41.13 | | C |
| ANISOU | 552 | C | SER | A | 304 | 5166 | 5191 | 5269 | −40 | 12 | −60 | C |
| ATOM | 553 | O | SER | A | 304 | 8.646 | 24.190 | −2.718 | 1.00 | 40.85 | | O |
| ANISOU | 553 | O | SER | A | 304 | 5073 | 5198 | 5250 | −55 | −3 | −38 | O |
| ATOM | 554 | N | VAL | A | 305 | 7.992 | 23.779 | −0.583 | 1.00 | 41.00 | | N |
| ANISOU | 554 | N | VAL | A | 305 | 5201 | 5158 | 5219 | −43 | −30 | −25 | N |

TABLE 7-continued

The atomic structure coordinates of Fc-TM

| | | | | | | | | | | | | | |
|---|---|---|---|---|---|---|---|---|---|---|---|---|---|
| ATOM | 555 | CA | VAL | A | 305 | 7.796 | 22.329 | −0.709 | 1.00 | 40.98 | | | C |
| ANISOU | 555 | CA | VAL | A | 305 | 5182 | 5183 | 5204 | −45 | −18 | −47 | | C |
| ATOM | 556 | CB | VAL | A | 305 | 8.559 | 21.550 | 0.407 | 1.00 | 40.91 | | | C |
| ANISOU | 556 | CB | VAL | A | 305 | 5162 | 5158 | 5221 | −31 | −36 | −13 | | C |
| ATOM | 557 | CG1 | VAL | A | 305 | 8.340 | 20.053 | 0.282 | 1.00 | 40.60 | | | C |
| ANISOU | 557 | CG1 | VAL | A | 305 | 5114 | 5164 | 5145 | −82 | −121 | −82 | | C |
| ATOM | 558 | CG2 | VAL | A | 305 | 10.044 | 21.845 | 0.363 | 1.00 | 41.19 | | | C |
| ANISOU | 558 | CG2 | VAL | A | 305 | 5200 | 5121 | 5326 | −85 | −25 | −36 | | C |
| ATOM | 559 | C | VAL | A | 305 | 6.306 | 21.921 | −0.660 | 1.00 | 41.10 | | | C |
| ANISOU | 559 | C | VAL | A | 305 | 5186 | 5211 | 5215 | −36 | −14 | −73 | | C |
| ATOM | 560 | O | VAL | A | 305 | 5.573 | 22.260 | 0.293 | 1.00 | 40.73 | | | O |
| ANISOU | 560 | O | VAL | A | 305 | 5174 | 5103 | 5197 | −37 | 9 | −126 | | O |
| ATOM | 561 | N | LEU | A | 306 | 5.887 | 21.153 | −1.666 | 1.00 | 41.07 | | | N |
| ANISOU | 561 | N | LEU | A | 306 | 5191 | 5259 | 5153 | −10 | −16 | −73 | | N |
| ATOM | 562 | CA | LEU | A | 306 | 4.535 | 20.592 | −1.719 | 1.00 | 40.99 | | | C |
| ANISOU | 562 | CA | LEU | A | 306 | 5188 | 5219 | 5166 | −16 | −40 | −36 | | C |
| ATOM | 563 | CB | LEU | A | 306 | 3.748 | 21.148 | −2.918 | 1.00 | 41.06 | | | C |
| ANISOU | 563 | CB | LEU | A | 306 | 5204 | 5163 | 5234 | −12 | −54 | −29 | | C |
| ATOM | 564 | CG | LEU | A | 306 | 2.268 | 20.728 | −3.008 | 1.00 | 40.75 | | | C |
| ANISOU | 564 | CG | LEU | A | 306 | 5172 | 5155 | 5154 | 53 | −5 | −10 | | C |
| ATOM | 565 | CD1 | LEU | A | 306 | 1.434 | 21.455 | −1.976 | 1.00 | 40.43 | | | C |
| ANISOU | 565 | CD1 | LEU | A | 306 | 5289 | 5183 | 4888 | −31 | −17 | 50 | | C |
| ATOM | 566 | CD2 | LEU | A | 306 | 1.705 | 20.962 | −4.394 | 1.00 | 40.87 | | | C |
| ANISOU | 566 | CD2 | LEU | A | 306 | 5213 | 5177 | 5135 | −17 | −41 | −45 | | C |
| ATOM | 567 | C | LEU | A | 306 | 4.544 | 19.069 | −1.779 | 1.00 | 41.08 | | | C |
| ANISOU | 567 | C | LEU | A | 306 | 5177 | 5234 | 5197 | 40 | −34 | −43 | | C |
| ATOM | 568 | O | LEU | A | 306 | 5.110 | 18.481 | −2.693 | 1.00 | 40.95 | | | O |
| ANISOU | 568 | O | LEU | A | 306 | 5163 | 5223 | 5171 | 14 | −57 | −46 | | O |
| ATOM | 569 | N | THR | A | 307 | 3.895 | 18.438 | −0.807 | 1.00 | 41.54 | | | N |
| ANISOU | 569 | N | THR | A | 307 | 5217 | 5276 | 5288 | 40 | −35 | −55 | | N |
| ATOM | 570 | CA | THR | A | 307 | 3.718 | 17.004 | −0.828 | 1.00 | 42.10 | | | C |
| ANISOU | 570 | CA | THR | A | 307 | 5268 | 5362 | 5363 | 50 | −25 | −59 | | C |
| ATOM | 571 | CB | THR | A | 307 | 3.238 | 16.490 | 0.534 | 1.00 | 42.33 | | | C |
| ANISOU | 571 | CB | THR | A | 307 | 5295 | 5394 | 5391 | 46 | −26 | −62 | | C |
| ATOM | 572 | OG1 | THR | A | 307 | 4.261 | 16.717 | 1.510 | 1.00 | 43.20 | | | O |
| ANISOU | 572 | OG1 | THR | A | 307 | 5387 | 5546 | 5479 | 27 | −27 | −143 | | O |
| ATOM | 573 | CG2 | THR | A | 307 | 2.943 | 15.007 | 0.486 | 1.00 | 42.37 | | | C |
| ANISOU | 573 | CG2 | THR | A | 307 | 5388 | 5344 | 5365 | 25 | −24 | −57 | | C |
| ATOM | 574 | C | THR | A | 307 | 2.738 | 16.624 | −1.946 | 1.00 | 42.61 | | | C |
| ANISOU | 574 | C | THR | A | 307 | 5343 | 5394 | 5449 | 60 | −18 | −56 | | C |
| ATOM | 575 | O | THR | A | 307 | 1.695 | 17.279 | −2.138 | 1.00 | 43.31 | | | O |
| ANISOU | 575 | O | THR | A | 307 | 5405 | 5457 | 5593 | 122 | −38 | −50 | | O |
| ATOM | 576 | N | VAL | A | 308 | 3.092 | 15.590 | −2.705 | 1.00 | 41.88 | | | N |
| ANISOU | 576 | N | VAL | A | 308 | 5290 | 5285 | 5337 | 54 | −5 | −77 | | N |
| ATOM | 577 | CA | VAL | A | 308 | 2.175 | 15.039 | −3.688 | 1.00 | 41.32 | | | C |
| ANISOU | 577 | CA | VAL | A | 308 | 5239 | 5211 | 5250 | 40 | −12 | −42 | | C |
| ATOM | 578 | CB | VAL | A | 308 | 2.772 | 15.033 | −5.136 | 1.00 | 41.12 | | | C |
| ANISOU | 578 | CB | VAL | A | 308 | 5250 | 5192 | 5180 | 37 | −40 | −41 | | C |
| ATOM | 579 | CG1 | VAL | A | 308 | 3.194 | 16.439 | −5.532 | 1.00 | 40.83 | | | C |
| ANISOU | 579 | CG1 | VAL | A | 308 | 5238 | 5210 | 5064 | −11 | −14 | −71 | | C |
| ATOM | 580 | CG2 | VAL | A | 308 | 3.956 | 14.098 | −5.273 | 1.00 | 40.49 | | | C |
| ANISOU | 580 | CG2 | VAL | A | 308 | 5160 | 5093 | 5131 | 11 | −79 | −30 | | C |
| ATOM | 581 | C | VAL | A | 308 | 1.678 | 13.663 | −3.230 | 1.00 | 41.17 | | | C |
| ANISOU | 581 | C | VAL | A | 308 | 5209 | 5209 | 5223 | 41 | −23 | −66 | | C |
| ATOM | 582 | O | VAL | A | 308 | 2.346 | 12.959 | −2.475 | 1.00 | 40.78 | | | O |
| ANISOU | 582 | O | VAL | A | 308 | 5262 | 5123 | 5107 | 24 | −11 | −56 | | O |
| ATOM | 583 | N | LEU | A | 309 | 0.480 | 13.302 | −3.665 | 1.00 | 40.99 | | | N |
| ANISOU | 583 | N | LEU | A | 309 | 5170 | 5164 | 5238 | 33 | −1 | −65 | | N |
| ATOM | 584 | CA | LEU | A | 309 | −0.019 | 11.972 | −3.414 | 1.00 | 40.25 | | | C |
| ANISOU | 584 | CA | LEU | A | 309 | 5082 | 5101 | 5109 | 31 | −12 | −14 | | C |
| ATOM | 585 | CB | LEU | A | 309 | −1.545 | 11.939 | −3.388 | 1.00 | 40.44 | | | C |
| ANISOU | 585 | CB | LEU | A | 309 | 5114 | 5151 | 5098 | 6 | −34 | −12 | | C |
| ATOM | 586 | CG | LEU | A | 309 | −2.214 | 12.728 | −2.261 | 1.00 | 41.27 | | | C |
| ANISOU | 586 | CG | LEU | A | 309 | 5230 | 5236 | 5213 | 32 | −21 | 0 | | C |
| ATOM | 587 | CD1 | LEU | A | 309 | −3.692 | 12.898 | −2.547 | 1.00 | 42.21 | | | C |
| ANISOU | 587 | CD1 | LEU | A | 309 | 5289 | 5393 | 5355 | 41 | −69 | 23 | | C |
| ATOM | 588 | CD2 | LEU | A | 309 | −2.011 | 12.051 | −0.896 | 1.00 | 42.35 | | | C |
| ANISOU | 588 | CD2 | LEU | A | 309 | 5357 | 5365 | 5366 | 17 | −14 | 3 | | C |
| ATOM | 589 | C | LEU | A | 309 | 0.561 | 10.988 | −4.429 | 1.00 | 39.55 | | | C |
| ANISOU | 589 | C | LEU | A | 309 | 4964 | 5033 | 5027 | −2 | −36 | −27 | | C |
| ATOM | 590 | O | LEU | A | 309 | 0.800 | 11.310 | −5.591 | 1.00 | 38.60 | | | O |
| ANISOU | 590 | O | LEU | A | 309 | 4763 | 4962 | 4938 | 33 | −16 | −94 | | O |
| ATOM | 591 | N | HIS | A | 310 | 0.816 | 9.795 | −3.922 | 1.00 | 39.07 | | | N |
| ANISOU | 591 | N | HIS | A | 310 | 4906 | 4954 | 4982 | 4 | −10 | −70 | | N |
| ATOM | 592 | CA | HIS | A | 310 | 1.381 | 8.692 | −4.663 | 1.00 | 38.71 | | | C |
| ANISOU | 592 | CA | HIS | A | 310 | 4886 | 4959 | 4862 | −8 | 4 | −35 | | C |
| ATOM | 593 | CB | HIS | A | 310 | 1.371 | 7.441 | −3.778 | 1.00 | 37.81 | | | C |
| ANISOU | 593 | CB | HIS | A | 310 | 4801 | 4808 | 4757 | 22 | −8 | −14 | | C |

TABLE 7-continued

The atomic structure coordinates of Fc-TM

| ATOM | 594 | CG | HIS | A | 310 | 1.655 | 6.180 | −4.519 | 1.00 | 36.41 | | C |
|---|---|---|---|---|---|---|---|---|---|---|---|---|
| ANISOU | 594 | CG | HIS | A | 310 | 4652 | 4701 | 4480 | −32 | −3 | 59 | C |
| ATOM | 595 | ND1 | HIS | A | 310 | 2.932 | 5.690 | −4.685 | 1.00 | 34.00 | | N |
| ANISOU | 595 | ND1 | HIS | A | 310 | 4396 | 4421 | 4101 | −33 | −38 | −4 | N |
| ATOM | 596 | CE1 | HIS | A | 310 | 2.880 | 4.568 | −5.376 | 1.00 | 34.94 | | C |
| ANISOU | 596 | CE1 | HIS | A | 310 | 4527 | 4316 | 4434 | −5 | −4 | 140 | C |
| ATOM | 597 | NE2 | HIS | A | 310 | 1.614 | 4.314 | −5.667 | 1.00 | 34.85 | | N |
| ANISOU | 597 | NE2 | HIS | A | 310 | 4517 | 4245 | 4480 | 61 | 16 | 113 | N |
| ATOM | 598 | CD2 | HIS | A | 310 | 0.829 | 5.307 | −5.140 | 1.00 | 35.34 | | C |
| ANISOU | 598 | CD2 | HIS | A | 310 | 4432 | 4621 | 4373 | 9 | 62 | 95 | C |
| ATOM | 599 | C | HIS | A | 310 | 0.644 | 8.427 | −5.973 | 1.00 | 38.70 | | C |
| ANISOU | 599 | C | HIS | A | 310 | 4902 | 4960 | 4840 | −15 | −27 | −46 | C |
| ATOM | 600 | O | HIS | A | 310 | 1.277 | 8.305 | −7.027 | 1.00 | 37.82 | | O |
| ANISOU | 600 | O | HIS | A | 310 | 4807 | 4841 | 4722 | −36 | −23 | −44 | O |
| ATOM | 601 | N | GLN | A | 311 | −0.684 | 8.335 | −5.883 | 1.00 | 39.22 | | N |
| ANISOU | 601 | N | GLN | A | 311 | 5005 | 5002 | 4894 | −3 | 19 | −72 | N |
| ATOM | 602 | CA | GLN | A | 311 | −1.541 | 8.052 | −7.037 | 1.00 | 39.83 | | C |
| ANISOU | 602 | CA | GLN | A | 311 | 5068 | 5069 | 4997 | 4 | −14 | −53 | C |
| ATOM | 603 | CB | GLN | A | 311 | −2.941 | 7.575 | −6.615 | 1.00 | 39.64 | | C |
| ANISOU | 603 | CB | GLN | A | 311 | 5050 | 5101 | 4910 | 8 | −4 | −67 | C |
| ATOM | 604 | CG | GLN | A | 311 | −3.814 | 8.592 | −5.859 | 1.00 | 41.81 | | C |
| ANISOU | 604 | CG | GLN | A | 311 | 5349 | 5334 | 5203 | 34 | 4 | 3 | C |
| ATOM | 605 | CD | GLN | A | 311 | −3.637 | 8.590 | −4.319 | 1.00 | 44.78 | | C |
| ANISOU | 605 | CD | GLN | A | 311 | 5943 | 5685 | 5387 | −47 | 37 | −57 | C |
| ATOM | 606 | OE1 | GLN | A | 311 | −2.590 | 8.195 | −3.771 | 1.00 | 43.08 | | O |
| ANISOU | 606 | OE1 | GLN | A | 311 | 5380 | 5867 | 5120 | 97 | −37 | −211 | O |
| ATOM | 607 | NE2 | GLN | A | 311 | −4.681 | 9.036 | −3.622 | 1.00 | 43.39 | | N |
| ANISOU | 607 | NE2 | GLN | A | 311 | 5563 | 5667 | 5256 | 170 | 135 | −45 | N |
| ATOM | 608 | C | GLN | A | 311 | −1.594 | 9.229 | −7.995 | 1.00 | 39.90 | | C |
| ANISOU | 608 | C | GLN | A | 311 | 5049 | 5064 | 5045 | −16 | −7 | −58 | C |
| ATOM | 609 | O | GLN | A | 311 | −1.555 | 9.046 | −9.229 | 1.00 | 40.38 | | O |
| ANISOU | 609 | O | GLN | A | 311 | 5051 | 5083 | 5207 | −72 | 45 | −44 | O |
| ATOM | 610 | N | ASP | A | 312 | −1.642 | 10.431 | −7.425 | 1.00 | 39.64 | | N |
| ANISOU | 610 | N | ASP | A | 312 | 5014 | 5048 | 4998 | −22 | −10 | −70 | N |
| ATOM | 611 | CA | ASP | A | 312 | −1.723 | 11.662 | −8.196 | 1.00 | 39.61 | | C |
| ANISOU | 611 | CA | ASP | A | 312 | 5003 | 5033 | 5013 | −9 | −1 | −80 | C |
| ATOM | 612 | CB | ASP | A | 312 | −1.841 | 12.891 | −7.276 | 1.00 | 39.79 | | C |
| ANISOU | 612 | CB | ASP | A | 312 | 5039 | 5090 | 4987 | −8 | −26 | −109 | C |
| ATOM | 613 | CG | ASP | A | 312 | −3.202 | 13.029 | −6.639 | 1.00 | 40.70 | | C |
| ANISOU | 613 | CG | ASP | A | 312 | 5104 | 5172 | 5186 | −39 | 18 | −131 | C |
| ATOM | 614 | OD1 | ASP | A | 312 | −4.081 | 12.167 | −6.863 | 1.00 | 42.10 | | O |
| ANISOU | 614 | OD1 | ASP | A | 312 | 5286 | 5405 | 5303 | 51 | 91 | −230 | O |
| ATOM | 615 | OD2 | ASP | A | 312 | −3.389 | 14.010 | −5.888 | 1.00 | 43.00 | | O |
| ANISOU | 615 | OD2 | ASP | A | 312 | 5297 | 5347 | 5692 | −20 | 69 | 1 | O |
| ATOM | 616 | C | ASP | A | 312 | −0.518 | 11.833 | −9.091 | 1.00 | 38.73 | | C |
| ANISOU | 616 | C | ASP | A | 312 | 4902 | 4899 | 4914 | 11 | 12 | −121 | C |
| ATOM | 617 | O | ASP | A | 312 | −0.655 | 12.241 | −10.251 | 1.00 | 39.28 | | O |
| ANISOU | 617 | O | ASP | A | 312 | 4946 | 4963 | 5014 | −3 | 85 | −129 | O |
| ATOM | 618 | N | TRP | A | 313 | 0.656 | 11.537 | −8.543 | 1.00 | 37.61 | | N |
| ANISOU | 618 | N | TRP | A | 313 | 4772 | 4760 | 4758 | −8 | 10 | −110 | N |
| ATOM | 619 | CA | TRP | A | 313 | 1.907 | 11.678 | −9.279 | 1.00 | 36.85 | | C |
| ANISOU | 619 | CA | TRP | A | 313 | 4619 | 4730 | 4649 | −7 | −60 | −88 | C |
| ATOM | 620 | CB | TRP | A | 313 | 3.129 | 11.487 | −8.357 | 1.00 | 36.13 | | C |
| ANISOU | 620 | CB | TRP | A | 313 | 4550 | 4680 | 4494 | −8 | −75 | −20 | C |
| ATOM | 621 | CG | TRP | A | 313 | 4.441 | 11.751 | −9.093 | 1.00 | 35.34 | | C |
| ANISOU | 621 | CG | TRP | A | 313 | 4466 | 4697 | 4264 | 43 | −176 | −103 | C |
| ATOM | 622 | CD1 | TRP | A | 313 | 5.343 | 10.827 | −9.512 | 1.00 | 35.07 | | C |
| ANISOU | 622 | CD1 | TRP | A | 313 | 4501 | 4715 | 4109 | −17 | −197 | −29 | C |
| ATOM | 623 | NE1 | TRP | A | 313 | 6.406 | 11.442 | −10.135 | 1.00 | 34.18 | | N |
| ANISOU | 623 | NE1 | TRP | A | 313 | 4463 | 4332 | 4191 | −11 | −148 | 20 | N |
| ATOM | 624 | CE2 | TRP | A | 313 | 6.187 | 12.796 | −10.146 | 1.00 | 35.05 | | C |
| ANISOU | 624 | CE2 | TRP | A | 313 | 4446 | 4707 | 4162 | −75 | −196 | −97 | C |
| ATOM | 625 | CD2 | TRP | A | 313 | 4.954 | 13.028 | −9.497 | 1.00 | 33.56 | | C |
| ANISOU | 625 | CD2 | TRP | A | 313 | 4353 | 4503 | 3893 | −30 | −139 | 4 | C |
| ATOM | 626 | CE3 | TRP | A | 313 | 4.501 | 14.348 | −9.354 | 1.00 | 32.76 | | C |
| ANISOU | 626 | CE3 | TRP | A | 313 | 4229 | 4481 | 3734 | 0 | −202 | 82 | C |
| ATOM | 627 | CZ3 | TRP | A | 313 | 5.279 | 15.377 | −9.862 | 1.00 | 35.07 | | C |
| ANISOU | 627 | CZ3 | TRP | A | 313 | 4469 | 4665 | 4192 | −3 | −238 | 41 | C |
| ATOM | 628 | CH2 | TRP | A | 313 | 6.493 | 15.113 | −10.532 | 1.00 | 34.15 | | C |
| ANISOU | 628 | CH2 | TRP | A | 313 | 4324 | 4418 | 4233 | −22 | −142 | 86 | C |
| ATOM | 629 | CZ2 | TRP | A | 313 | 6.959 | 13.833 | −10.685 | 1.00 | 35.30 | | C |
| ANISOU | 629 | CZ2 | TRP | A | 313 | 4442 | 4682 | 4288 | −11 | −136 | −64 | C |
| ATOM | 630 | C | TRP | A | 313 | 1.998 | 10.709 | −10.457 | 1.00 | 36.14 | | C |
| ANISOU | 630 | C | TRP | A | 313 | 4477 | 4717 | 4537 | 0 | −78 | −55 | C |
| ATOM | 631 | O | TRP | A | 313 | 2.313 | 11.107 | −11.562 | 1.00 | 35.50 | | O |
| ANISOU | 631 | O | TRP | A | 313 | 4328 | 4708 | 4450 | 45 | −104 | −91 | O |
| ATOM | 632 | N | LEU | A | 314 | 1.765 | 9.438 | −10.157 | 1.00 | 35.58 | | N |
| ANISOU | 632 | N | LEU | A | 314 | 4401 | 4613 | 4503 | −13 | −76 | −52 | N |

TABLE 7-continued

The atomic structure coordinates of Fc-TM

| | | | | | | | | | | | |
|---|---|---|---|---|---|---|---|---|---|---|---|
| ATOM | 633 | CA | LEU | A | 314 | 1.729 | 8.348 | −11.105 | 1.00 | 35.56 | C |
| ANISOU | 633 | CA | LEU | A | 314 | 4445 | 4567 | 4497 | 28 | 5 | −28 | C |
| ATOM | 634 | CB | LEU | A | 314 | 1.574 | 7.016 | −10.361 | 1.00 | 35.07 | C |
| ANISOU | 634 | CB | LEU | A | 314 | 4405 | 4507 | 4410 | −12 | 18 | −47 | C |
| ATOM | 635 | CG | LEU | A | 314 | 2.750 | 6.390 | −9.621 | 1.00 | 34.91 | C |
| ANISOU | 635 | CG | LEU | A | 314 | 4444 | 4487 | 4331 | −14 | −28 | −14 | C |
| ATOM | 636 | CD1 | LEU | A | 314 | 2.290 | 5.110 | −8.980 | 1.00 | 35.56 | C |
| ANISOU | 636 | CD1 | LEU | A | 314 | 4432 | 4609 | 4471 | 17 | −104 | −47 | C |
| ATOM | 637 | CD2 | LEU | A | 314 | 3.922 | 6.091 | −10.522 | 1.00 | 34.75 | C |
| ANISOU | 637 | CD2 | LEU | A | 314 | 4491 | 4405 | 4306 | 41 | −118 | −7 | C |
| ATOM | 638 | C | LEU | A | 314 | 0.618 | 8.461 | −12.146 | 1.00 | 35.53 | C |
| ANISOU | 638 | C | LEU | A | 314 | 4500 | 4504 | 4495 | −33 | −16 | −32 | C |
| ATOM | 639 | O | LEU | A | 314 | 0.782 | 7.941 | −13.236 | 1.00 | 35.75 | O |
| ANISOU | 639 | O | LEU | A | 314 | 4455 | 4563 | 4564 | −36 | −3 | 17 | O |
| ATOM | 640 | N | ASN | A | 315 | −0.504 | 9.110 | −11.802 | 1.00 | 35.21 | N |
| ANISOU | 640 | N | ASN | A | 315 | 4478 | 4419 | 4481 | −76 | −52 | −36 | N |
| ATOM | 641 | CA | ASN | A | 315 | −1.580 | 9.402 | −12.763 | 1.00 | 35.05 | C |
| ANISOU | 641 | CA | ASN | A | 315 | 4531 | 4373 | 4411 | −33 | 2 | −57 | C |
| ATOM | 642 | CB | ASN | A | 315 | −2.958 | 9.466 | −12.074 | 1.00 | 35.00 | C |
| ANISOU | 642 | CB | ASN | A | 315 | 4513 | 4349 | 4433 | −40 | −16 | −16 | C |
| ATOM | 643 | CG | ASN | A | 315 | −3.500 | 8.086 | −11.725 | 1.00 | 35.48 | C |
| ANISOU | 643 | CG | ASN | A | 315 | 4451 | 4447 | 4582 | −119 | −42 | −126 | C |
| ATOM | 644 | OD1 | ASN | A | 315 | −3.252 | 7.128 | −12.445 | 1.00 | 33.89 | O |
| ANISOU | 644 | OD1 | ASN | A | 315 | 4226 | 4285 | 4363 | −276 | −266 | −225 | O |
| ATOM | 645 | ND2 | ASN | A | 315 | −4.209 | 7.977 | −10.601 | 1.00 | 34.22 | N |
| ANISOU | 645 | ND2 | ASN | A | 315 | 4214 | 4375 | 4410 | −223 | 34 | −77 | N |
| ATOM | 646 | C | ASN | A | 315 | −1.379 | 10.647 | −13.620 | 1.00 | 34.87 | C |
| ANISOU | 646 | C | ASN | A | 315 | 4516 | 4388 | 4343 | −23 | 1 | −67 | C |
| ATOM | 647 | O | ASN | A | 315 | −2.321 | 11.112 | −14.237 | 1.00 | 34.63 | O |
| ANISOU | 647 | O | ASN | A | 315 | 4549 | 4319 | 4289 | −30 | 41 | −65 | O |
| ATOM | 648 | N | GLY | A | 316 | −0.171 | 11.197 | −13.639 | 1.00 | 35.22 | N |
| ANISOU | 648 | N | GLY | A | 316 | 4517 | 4502 | 4360 | 6 | 3 | −37 | N |
| ATOM | 649 | CA | GLY | A | 316 | 0.165 | 12.331 | −14.516 | 1.00 | 35.71 | C |
| ANISOU | 649 | CA | GLY | A | 316 | 4494 | 4573 | 4500 | −5 | −1 | −46 | C |
| ATOM | 650 | C | GLY | A | 316 | −0.397 | 13.709 | −14.206 | 1.00 | 35.78 | C |
| ANISOU | 650 | C | GLY | A | 316 | 4467 | 4612 | 4516 | −28 | −42 | −50 | C |
| ATOM | 651 | O | GLY | A | 316 | −0.366 | 14.597 | −15.058 | 1.00 | 35.56 | O |
| ANISOU | 651 | O | GLY | A | 316 | 4332 | 4654 | 4522 | −7 | −66 | −97 | O |
| ATOM | 652 | N | LYS | A | 317 | −0.902 | 13.890 | −12.991 | 1.00 | 36.31 | N |
| ANISOU | 652 | N | LYS | A | 317 | 4528 | 4698 | 4570 | −30 | −42 | −59 | N |
| ATOM | 653 | CA | LYS | A | 317 | −1.315 | 15.203 | −12.493 | 1.00 | 37.07 | C |
| ANISOU | 653 | CA | LYS | A | 317 | 4699 | 4780 | 4606 | −7 | −28 | −47 | C |
| ATOM | 654 | CB | LYS | A | 317 | −1.755 | 15.110 | −11.031 | 1.00 | 37.28 | C |
| ANISOU | 654 | CB | LYS | A | 317 | 4696 | 4803 | 4663 | −25 | −9 | −80 | C |
| ATOM | 655 | CG | LYS | A | 317 | −3.033 | 14.325 | −10.813 | 1.00 | 38.63 | C |
| ANISOU | 655 | CG | LYS | A | 317 | 4886 | 4905 | 4884 | −49 | −2 | −35 | C |
| ATOM | 656 | CD | LYS | A | 317 | −3.784 | 14.865 | −9.616 | 1.00 | 39.92 | C |
| ANISOU | 656 | CD | LYS | A | 317 | 4984 | 5172 | 5010 | 19 | 65 | −11 | C |
| ATOM | 657 | CE | LYS | A | 317 | −5.138 | 14.188 | −9.434 | 1.00 | 40.77 | C |
| ANISOU | 657 | CE | LYS | A | 317 | 5161 | 5227 | 5100 | 116 | 79 | −35 | C |
| ATOM | 658 | NZ | LYS | A | 317 | −6.015 | 15.042 | −8.572 | 1.00 | 41.78 | N |
| ANISOU | 658 | NZ | LYS | A | 317 | 5263 | 5525 | 5086 | 124 | 26 | 96 | N |
| ATOM | 659 | C | LYS | A | 317 | −0.180 | 16.214 | −12.629 | 1.00 | 37.17 | C |
| ANISOU | 659 | C | LYS | A | 317 | 4747 | 4823 | 4551 | −27 | −28 | −80 | C |
| ATOM | 660 | O | LYS | A | 317 | 0.980 | 15.859 | −12.440 | 1.00 | 37.06 | O |
| ANISOU | 660 | O | LYS | A | 317 | 4756 | 4804 | 4520 | −34 | 84 | −155 | O |
| ATOM | 661 | N | GLU | A | 318 | −0.525 | 17.462 | −12.941 | 1.00 | 37.60 | N |
| ANISOU | 661 | N | GLU | A | 318 | 4848 | 4817 | 4621 | −12 | −30 | −99 | N |
| ATOM | 662 | CA | GLU | A | 318 | 0.452 | 18.519 | −13.238 | 1.00 | 40.15 | C |
| ANISOU | 662 | CA | GLU | A | 318 | 5164 | 5032 | 5058 | −54 | −30 | −117 | C |
| ATOM | 663 | CB | GLU | A | 318 | 0.052 | 19.263 | −14.523 | 1.00 | 39.10 | C |
| ANISOU | 663 | CB | GLU | A | 318 | 5034 | 4963 | 4859 | −60 | −36 | −45 | C |
| ATOM | 664 | CG | GLU | A | 318 | 0.271 | 18.492 | −15.799 | 1.00 | 41.10 | C |
| ANISOU | 664 | CG | GLU | A | 318 | 5181 | 5159 | 5275 | −19 | 9 | −184 | C |
| ATOM | 665 | CD | GLU | A | 318 | 0.118 | 19.357 | −17.031 | 1.00 | 38.29 | C |
| ANISOU | 665 | CD | GLU | A | 318 | 4479 | 5157 | 4911 | 107 | 25 | 128 | C |
| ATOM | 666 | OE1 | GLU | A | 318 | 1.126 | 19.619 | −17.700 | 1.00 | 46.87 | O |
| ANISOU | 666 | OE1 | GLU | A | 318 | 6088 | 5866 | 5854 | −27 | −89 | −299 | O |
| ATOM | 667 | OE2 | GLU | A | 318 | −0.997 | 19.815 | −17.354 | 1.00 | 46.71 | O |
| ANISOU | 667 | OE2 | GLU | A | 318 | 6297 | 5852 | 5598 | −240 | 197 | −211 | O |
| ATOM | 668 | C | GLU | A | 318 | 0.583 | 19.530 | −12.092 | 1.00 | 38.57 | C |
| ANISOU | 668 | C | GLU | A | 318 | 4938 | 4896 | 4818 | −31 | −53 | −85 | C |
| ATOM | 669 | O | GLU | A | 318 | −0.425 | 20.012 | −11.578 | 1.00 | 38.13 | O |
| ANISOU | 669 | O | GLU | A | 318 | 4923 | 4789 | 4774 | −39 | −135 | −122 | O |
| ATOM | 670 | N | TYR | A | 319 | 1.821 | 19.851 | −11.705 | 1.00 | 38.78 | N |
| ANISOU | 670 | N | TYR | A | 319 | 4998 | 4868 | 4867 | −48 | −21 | −87 | N |
| ATOM | 671 | CA | TYR | A | 319 | 2.079 | 20.701 | −10.529 | 1.00 | 39.04 | C |
| ANISOU | 671 | CA | TYR | A | 319 | 5000 | 4916 | 4916 | −26 | −53 | −60 | C |

TABLE 7-continued

The atomic structure coordinates of Fc-TM

| | | | | | | | | | | | | |
|---|---|---|---|---|---|---|---|---|---|---|---|---|
| ATOM | 672 | CB | TYR | A | 319 | 2.884 | 19.937 | −9.476 | 1.00 | 38.84 | | C |
| ANISOU | 672 | CB | TYR | A | 319 | 4972 | 4905 | 4879 | −26 | −72 | −93 | C |
| ATOM | 673 | CG | TYR | A | 319 | 2.172 | 18.689 | −8.973 | 1.00 | 37.38 | | C |
| ANISOU | 673 | CG | TYR | A | 319 | 4832 | 4650 | 4719 | −86 | 32 | −11 | C |
| ATOM | 674 | CD1 | TYR | A | 319 | 2.258 | 17.460 | −9.673 | 1.00 | 38.12 | | C |
| ANISOU | 674 | CD1 | TYR | A | 319 | 4829 | 4759 | 4893 | 7 | −6 | −24 | C |
| ATOM | 675 | CE1 | TYR | A | 319 | 1.593 | 16.320 | −9.215 | 1.00 | 36.71 | | C |
| ANISOU | 675 | CE1 | TYR | A | 319 | 4646 | 4520 | 4781 | −18 | −157 | −183 | C |
| ATOM | 676 | CZ | TYR | A | 319 | 0.834 | 16.411 | −8.065 | 1.00 | 36.25 | | C |
| ANISOU | 676 | CZ | TYR | A | 319 | 4621 | 4505 | 4646 | −178 | −20 | −20 | C |
| ATOM | 677 | OH | TYR | A | 319 | 0.166 | 15.322 | −7.573 | 1.00 | 39.25 | | O |
| ANISOU | 677 | OH | TYR | A | 319 | 5143 | 5009 | 4759 | 54 | −255 | −66 | O |
| ATOM | 678 | CE2 | TYR | A | 319 | 0.725 | 17.612 | −7.374 | 1.00 | 37.40 | | C |
| ANISOU | 678 | CE2 | TYR | A | 319 | 4648 | 4766 | 4794 | 39 | −30 | −82 | C |
| ATOM | 679 | CD2 | TYR | A | 319 | 1.389 | 18.736 | −7.836 | 1.00 | 36.44 | | C |
| ANISOU | 679 | CD2 | TYR | A | 319 | 4701 | 4522 | 4622 | 68 | −116 | −138 | C |
| ATOM | 680 | C | TYR | A | 319 | 2.745 | 22.028 | −10.889 | 1.00 | 39.24 | | C |
| ANISOU | 680 | C | TYR | A | 319 | 5014 | 4957 | 4938 | −40 | −57 | −97 | C |
| ATOM | 681 | O | TYR | A | 319 | 3.918 | 22.071 | −11.266 | 1.00 | 39.11 | | O |
| ANISOU | 681 | O | TYR | A | 319 | 4977 | 4930 | 4951 | −22 | −85 | −124 | O |
| ATOM | 682 | N | LYS | A | 320 | 1.961 | 23.101 | −10.790 | 1.00 | 39.64 | | N |
| ANISOU | 682 | N | LYS | A | 320 | 5077 | 5012 | 4970 | −1 | −53 | −107 | N |
| ATOM | 683 | CA | LYS | A | 320 | 2.398 | 24.454 | −11.109 | 1.00 | 40.77 | | C |
| ANISOU | 683 | CA | LYS | A | 320 | 5193 | 5147 | 5150 | −23 | −13 | −85 | C |
| ATOM | 684 | CB | LYS | A | 320 | 1.310 | 25.173 | −11.921 | 1.00 | 40.27 | | C |
| ANISOU | 684 | CB | LYS | A | 320 | 5129 | 5063 | 5107 | 21 | −64 | −45 | C |
| ATOM | 685 | CG | LYS | A | 320 | 1.704 | 26.535 | −12.547 | 1.00 | 46.09 | | C |
| ANISOU | 685 | CG | LYS | A | 320 | 6665 | 5282 | 5563 | −484 | 537 | −253 | C |
| ATOM | 686 | CD | LYS | A | 320 | 0.609 | 27.084 | −13.492 | 1.00 | 38.31 | | C |
| ANISOU | 686 | CD | LYS | A | 320 | 4594 | 5097 | 4864 | 287 | −177 | 117 | C |
| ATOM | 687 | CE | LYS | A | 320 | −0.733 | 27.374 | −12.771 | 1.00 | 47.84 | | C |
| ANISOU | 687 | CE | LYS | A | 320 | 6419 | 5509 | 6250 | −354 | 338 | −151 | C |
| ATOM | 688 | NZ | LYS | A | 320 | −1.892 | 27.744 | −13.695 | 1.00 | 37.09 | | N |
| ANISOU | 688 | NZ | LYS | A | 320 | 4077 | 5276 | 4737 | 675 | −795 | 197 | N |
| ATOM | 689 | C | LYS | A | 320 | 2.759 | 25.250 | −9.840 | 1.00 | 40.86 | | C |
| ANISOU | 689 | C | LYS | A | 320 | 5229 | 5123 | 5173 | 18 | −10 | −35 | C |
| ATOM | 690 | O | LYS | A | 320 | 2.030 | 25.259 | −8.843 | 1.00 | 40.72 | | O |
| ANISOU | 690 | O | LYS | A | 320 | 5252 | 5105 | 5111 | 38 | −28 | −57 | O |
| ATOM | 691 | N | CYS | A | 321 | 3.915 | 25.888 | −9.894 | 1.00 | 41.68 | | N |
| ANISOU | 691 | N | CYS | A | 321 | 5350 | 5199 | 5287 | 18 | −5 | −32 | N |
| ATOM | 692 | CA | CYS | A | 321 | 4.373 | 26.788 | −8.860 | 1.00 | 42.24 | | C |
| ANISOU | 692 | CA | CYS | A | 321 | 5408 | 5260 | 5381 | 31 | 1 | −18 | C |
| ATOM | 693 | CB | CYS | A | 321 | 5.763 | 26.361 | −8.379 | 1.00 | 42.35 | | C |
| ANISOU | 693 | CB | CYS | A | 321 | 5400 | 5274 | 5415 | 9 | −9 | −35 | C |
| ATOM | 694 | SG | CYS | A | 321 | 6.500 | 27.426 | −7.128 | 1.00 | 42.58 | | S |
| ANISOU | 694 | SG | CYS | A | 321 | 5484 | 5270 | 5421 | 50 | −14 | −77 | S |
| ATOM | 695 | C | CYS | A | 321 | 4.411 | 28.191 | −9.472 | 1.00 | 42.81 | | C |
| ANISOU | 695 | C | CYS | A | 321 | 5475 | 5310 | 5480 | 8 | 16 | −9 | C |
| ATOM | 696 | O | CYS | A | 321 | 5.156 | 28.422 | −10.460 | 1.00 | 42.92 | | O |
| ANISOU | 696 | O | CYS | A | 321 | 5461 | 5316 | 5528 | 24 | 61 | −9 | O |
| ATOM | 697 | N | LYS | A | 322 | 3.570 | 29.085 | −8.924 | 1.00 | 42.76 | | N |
| ANISOU | 697 | N | LYS | A | 322 | 5459 | 5348 | 5439 | 17 | 33 | −26 | N |
| ATOM | 698 | CA | LYS | A | 322 | 3.565 | 30.511 | −9.287 | 1.00 | 42.86 | | C |
| ANISOU | 698 | CA | LYS | A | 322 | 5437 | 5374 | 5471 | 56 | −15 | 9 | C |
| ATOM | 699 | CB | LYS | A | 322 | 2.147 | 31.078 | −9.435 | 1.00 | 43.24 | | C |
| ANISOU | 699 | CB | LYS | A | 322 | 5551 | 5409 | 5468 | 25 | 18 | −36 | C |
| ATOM | 700 | CG | LYS | A | 322 | 2.064 | 32.254 | −10.426 | 1.00 | 44.33 | | C |
| ANISOU | 700 | CG | LYS | A | 322 | 5694 | 5515 | 5634 | 14 | −35 | −25 | C |
| ATOM | 701 | CD | LYS | A | 322 | 0.634 | 32.831 | −10.569 | 1.00 | 45.76 | | C |
| ANISOU | 701 | CD | LYS | A | 322 | 5744 | 5672 | 5970 | −51 | 35 | −111 | C |
| ATOM | 702 | CE | LYS | A | 322 | 0.468 | 33.530 | −11.933 | 1.00 | 40.52 | | C |
| ANISOU | 702 | CE | LYS | A | 322 | 4781 | 4752 | 5862 | 1225 | −190 | 243 | C |
| ATOM | 703 | NZ | LYS | A | 322 | −0.714 | 34.463 | −12.029 | 1.00 | 52.37 | | N |
| ANISOU | 703 | NZ | LYS | A | 322 | 7085 | 6923 | 5891 | −760 | 97 | −81 | N |
| ATOM | 704 | C | LYS | A | 322 | 4.352 | 31.332 | −8.284 | 1.00 | 42.99 | | C |
| ANISOU | 704 | C | LYS | A | 322 | 5456 | 5381 | 5497 | 1 | 30 | 0 | C |
| ATOM | 705 | O | LYS | A | 322 | 4.196 | 31.206 | −7.065 | 1.00 | 42.73 | | O |
| ANISOU | 705 | O | LYS | A | 322 | 5391 | 5361 | 5482 | 50 | 28 | −24 | O |
| ATOM | 706 | N | VAL | A | 323 | 5.220 | 32.172 | −8.823 | 1.00 | 43.35 | | N |
| ANISOU | 706 | N | VAL | A | 323 | 5501 | 5422 | 5545 | −16 | −11 | 12 | N |
| ATOM | 707 | CA | VAL | A | 323 | 6.125 | 32.979 | −8.025 | 1.00 | 42.78 | | C |
| ANISOU | 707 | CA | VAL | A | 323 | 5428 | 5354 | 5472 | −14 | −20 | −20 | C |
| ATOM | 708 | CB | VAL | A | 323 | 7.586 | 32.528 | −8.212 | 1.00 | 42.83 | | C |
| ANISOU | 708 | CB | VAL | A | 323 | 5397 | 5384 | 5491 | −25 | −20 | 12 | C |
| ATOM | 709 | CG1 | VAL | A | 323 | 8.557 | 33.587 | −7.703 | 1.00 | 41.95 | | C |
| ANISOU | 709 | CG1 | VAL | A | 323 | 5327 | 5304 | 5305 | 17 | −15 | −62 | C |
| ATOM | 710 | CG2 | VAL | A | 323 | 7.811 | 31.192 | −7.509 | 1.00 | 43.44 | | C |
| ANISOU | 710 | CG2 | VAL | A | 323 | 5415 | 5409 | 5681 | 24 | −7 | −27 | C |

TABLE 7-continued

The atomic structure coordinates of Fc-TM

| | | | | | | | | | | | |
|---|---|---|---|---|---|---|---|---|---|---|---|
| ATOM | 711 | C | VAL | A | 323 | 5.942 | 34.423 | −8.432 | 1.00 | 42.81 | C |
| ANISOU | 711 | C | VAL | A | 323 | 5441 | 5360 | 5463 | −14 | −20 | −44 | C |
| ATOM | 712 | O | VAL | A | 323 | 6.102 | 34.796 | −9.621 | 1.00 | 42.57 | O |
| ANISOU | 712 | O | VAL | A | 323 | 5408 | 5357 | 5408 | −89 | 29 | −68 | O |
| ATOM | 713 | N | SER | A | 324 | 5.597 | 35.219 | −7.421 | 1.00 | 42.64 | N |
| ANISOU | 713 | N | SER | A | 324 | 5419 | 5369 | 5414 | −2 | −9 | −59 | N |
| ATOM | 714 | CA | SER | A | 324 | 5.207 | 36.605 | −7.584 | 1.00 | 42.51 | C |
| ANISOU | 714 | CA | SER | A | 324 | 5426 | 5317 | 5408 | −11 | −3 | −71 | C |
| ATOM | 715 | CB | SER | A | 324 | 3.750 | 36.783 | −7.154 | 1.00 | 42.22 | C |
| ANISOU | 715 | CB | SER | A | 324 | 5364 | 5281 | 5394 | 16 | −26 | −72 | C |
| ATOM | 716 | OG | SER | A | 324 | 2.864 | 36.502 | −8.216 | 1.00 | 41.92 | O |
| ANISOU | 716 | OG | SER | A | 324 | 5332 | 5206 | 5387 | 19 | 53 | −145 | O |
| ATOM | 717 | C | SER | A | 324 | 6.104 | 37.522 | −6.760 | 1.00 | 43.07 | C |
| ANISOU | 717 | C | SER | A | 324 | 5479 | 5404 | 5481 | −32 | −10 | −59 | C |
| ATOM | 718 | O | SER | A | 324 | 6.352 | 37.271 | −5.575 | 1.00 | 42.70 | O |
| ANISOU | 718 | O | SER | A | 324 | 5452 | 5352 | 5420 | −41 | −68 | −72 | O |
| ATOM | 719 | N | ASN | A | 325 | 6.571 | 38.596 | −7.396 | 1.00 | 44.33 | N |
| ANISOU | 719 | N | ASN | A | 325 | 5633 | 5581 | 5628 | −43 | 19 | −83 | N |
| ATOM | 720 | CA | ASN | A | 325 | 7.437 | 39.570 | −6.724 | 1.00 | 45.40 | C |
| ANISOU | 720 | CA | ASN | A | 325 | 5802 | 5719 | 5727 | −31 | 13 | −62 | C |
| ATOM | 721 | CB | ASN | A | 325 | 8.886 | 39.074 | −6.668 | 1.00 | 45.78 | C |
| ANISOU | 721 | CB | ASN | A | 325 | 5807 | 5817 | 5767 | −17 | 24 | −48 | C |
| ATOM | 722 | CG | ASN | A | 325 | 9.749 | 39.887 | −5.724 | 1.00 | 47.87 | C |
| ANISOU | 722 | CG | ASN | A | 325 | 6012 | 6087 | 6088 | −56 | −15 | −90 | C |
| ATOM | 723 | OD1 | ASN | A | 325 | 9.252 | 40.493 | −4.758 | 1.00 | 51.73 | O |
| ANISOU | 723 | OD1 | ASN | A | 325 | 6606 | 6613 | 6436 | 43 | 24 | −165 | O |
| ATOM | 724 | ND2 | ASN | A | 325 | 11.055 | 39.898 | −5.986 | 1.00 | 49.10 | N |
| ANISOU | 724 | ND2 | ASN | A | 325 | 6088 | 6256 | 6312 | 27 | 72 | 40 | N |
| ATOM | 725 | C | ASN | A | 325 | 7.379 | 40.924 | −7.396 | 1.00 | 45.82 | C |
| ANISOU | 725 | C | ASN | A | 325 | 5904 | 5749 | 5757 | −16 | 29 | −60 | C |
| ATOM | 726 | O | ASN | A | 325 | 7.568 | 41.032 | −8.624 | 1.00 | 46.11 | O |
| ANISOU | 726 | O | ASN | A | 325 | 5966 | 5817 | 5735 | 8 | 24 | −72 | O |
| ATOM | 727 | N | LYS | A | 326 | 7.106 | 41.945 | −6.581 | 1.00 | 46.40 | N |
| ANISOU | 727 | N | LYS | A | 326 | 5999 | 5832 | 5798 | 6 | 54 | −106 | N |
| ATOM | 728 | CA | LYS | A | 326 | 7.088 | 43.359 | −6.999 | 1.00 | 46.62 | C |
| ANISOU | 728 | CA | LYS | A | 326 | 6011 | 5855 | 5844 | −28 | 75 | −54 | C |
| ATOM | 729 | CB | LYS | A | 326 | 6.596 | 44.250 | −5.847 | 1.00 | 46.66 | C |
| ANISOU | 729 | CB | LYS | A | 326 | 6026 | 5795 | 5908 | −14 | 78 | −87 | C |
| ATOM | 730 | CG | LYS | A | 326 | 5.693 | 43.541 | −4.808 | 1.00 | 46.45 | C |
| ANISOU | 730 | CG | LYS | A | 326 | 6008 | 5829 | 5811 | 1 | 106 | −66 | C |
| ATOM | 731 | CD | LYS | A | 326 | 5.224 | 44.500 | −3.730 | 1.00 | 46.76 | C |
| ANISOU | 731 | CD | LYS | A | 326 | 6052 | 5871 | 5842 | −23 | 128 | −26 | C |
| ATOM | 732 | CE | LYS | A | 326 | 4.627 | 43.755 | −2.527 | 1.00 | 47.92 | C |
| ANISOU | 732 | CE | LYS | A | 326 | 6179 | 6075 | 5951 | −22 | 57 | 57 | C |
| ATOM | 733 | NZ | LYS | A | 326 | 3.645 | 44.615 | −1.795 | 1.00 | 46.79 | N |
| ANISOU | 733 | NZ | LYS | A | 326 | 6086 | 5950 | 5742 | 84 | 143 | 63 | N |
| ATOM | 734 | C | LYS | A | 326 | 8.492 | 43.774 | −7.398 | 1.00 | 47.27 | C |
| ANISOU | 734 | C | LYS | A | 326 | 6099 | 5947 | 5913 | −66 | 66 | −56 | C |
| ATOM | 735 | O | LYS | A | 326 | 9.180 | 44.487 | −6.654 | 1.00 | 48.18 | O |
| ANISOU | 735 | O | LYS | A | 326 | 6284 | 6034 | 5987 | −48 | 39 | −1 | O |
| ATOM | 736 | N | ALA | A | 327 | 8.916 | 43.299 | −8.570 | 1.00 | 48.04 | N |
| ANISOU | 736 | N | ALA | A | 327 | 6153 | 6097 | 6003 | −80 | 76 | −72 | N |
| ATOM | 737 | CA | ALA | A | 327 | 10.266 | 43.501 | −9.120 | 1.00 | 48.25 | C |
| ANISOU | 737 | CA | ALA | A | 327 | 6151 | 6154 | 6027 | −80 | 65 | −43 | C |
| ATOM | 738 | CB | ALA | A | 327 | 11.322 | 42.844 | −8.247 | 1.00 | 48.36 | C |
| ANISOU | 738 | CB | ALA | A | 327 | 6156 | 6153 | 6064 | −60 | 40 | −40 | C |
| ATOM | 739 | C | ALA | A | 327 | 10.305 | 42.901 | −10.522 | 1.00 | 48.66 | C |
| ANISOU | 739 | C | ALA | A | 327 | 6209 | 6190 | 6089 | −90 | 89 | −47 | C |
| ATOM | 740 | O | ALA | A | 327 | 11.017 | 43.403 | −11.396 | 1.00 | 49.36 | O |
| ANISOU | 740 | O | ALA | A | 327 | 6216 | 6343 | 6195 | −143 | 160 | −32 | O |
| ATOM | 741 | N | LEU | A | 328 | 9.531 | 41.834 | −10.732 | 1.00 | 48.61 | N |
| ANISOU | 741 | N | LEU | A | 328 | 6214 | 6128 | 6125 | −66 | 61 | −36 | N |
| ATOM | 742 | CA | LEU | A | 328 | 9.411 | 41.216 | −12.056 | 1.00 | 48.46 | C |
| ANISOU | 742 | CA | LEU | A | 328 | 6198 | 6118 | 6096 | −1 | 44 | −5 | C |
| ATOM | 743 | CB | LEU | A | 328 | 8.993 | 39.743 | −11.934 | 1.00 | 48.19 | C |
| ANISOU | 743 | CB | LEU | A | 328 | 6138 | 6070 | 6100 | 13 | 48 | 9 | C |
| ATOM | 744 | CG | LEU | A | 328 | 10.002 | 38.667 | −11.520 | 1.00 | 48.23 | C |
| ANISOU | 744 | CG | LEU | A | 328 | 6153 | 6038 | 6133 | 9 | 15 | 36 | C |
| ATOM | 745 | CD1 | LEU | A | 328 | 9.283 | 37.550 | −10.802 | 1.00 | 46.88 | C |
| ANISOU | 745 | CD1 | LEU | A | 328 | 5933 | 5924 | 5956 | −6 | 2 | 89 | C |
| ATOM | 746 | CD2 | LEU | A | 328 | 10.797 | 38.134 | −12.728 | 1.00 | 46.84 | C |
| ANISOU | 746 | CD2 | LEU | A | 328 | 6059 | 5772 | 5966 | 30 | −18 | 8 | C |
| ATOM | 747 | C | LEU | A | 328 | 8.377 | 41.962 | −12.905 | 1.00 | 48.82 | C |
| ANISOU | 747 | C | LEU | A | 328 | 6215 | 6170 | 6161 | 42 | 47 | 3 | C |
| ATOM | 748 | O | LEU | A | 328 | 7.346 | 42.391 | −12.370 | 1.00 | 49.39 | O |
| ANISOU | 748 | O | LEU | A | 328 | 6288 | 6214 | 6264 | 62 | 78 | −17 | O |
| ATOM | 749 | N | PRO | A | 329 | 8.627 | 42.096 | −14.233 | 1.00 | 48.99 | N |
| ANISOU | 749 | N | PRO | A | 329 | 6230 | 6210 | 6172 | 52 | 35 | 20 | N |

TABLE 7-continued

| The atomic structure coordinates of Fc-TM | | | | | | | | | | | |
|---|---|---|---|---|---|---|---|---|---|---|---|
| ATOM | 750 | CA | PRO | A | 329 | 7.583 | 42.691 | −15.083 | 1.00 | 48.98 | C |
| ANISOU | 750 | CA | PRO | A | 329 | 6183 | 6202 | 6224 | 38 | 16 | 11 | C |
| ATOM | 751 | CB | PRO | A | 329 | 8.121 | 42.512 | −16.512 | 1.00 | 48.81 | C |
| ANISOU | 751 | CB | PRO | A | 329 | 6180 | 6199 | 6165 | 26 | 5 | 20 | C |
| ATOM | 752 | CG | PRO | A | 329 | 9.255 | 41.473 | −16.402 | 1.00 | 49.03 | C |
| ANISOU | 752 | CG | PRO | A | 329 | 6235 | 6230 | 6164 | 50 | −11 | 24 | C |
| ATOM | 753 | CD | PRO | A | 329 | 9.824 | 41.712 | −15.016 | 1.00 | 49.11 | C |
| ANISOU | 753 | CD | PRO | A | 329 | 6245 | 6228 | 6184 | 54 | 26 | 18 | C |
| ATOM | 754 | C | PRO | A | 329 | 6.275 | 41.925 | −14.898 | 1.00 | 49.47 | C |
| ANISOU | 754 | C | PRO | A | 329 | 6237 | 6232 | 6324 | 32 | 28 | 24 | C |
| ATOM | 755 | O | PRO | A | 329 | 5.199 | 42.555 | −14.828 | 1.00 | 50.19 | O |
| ANISOU | 755 | O | PRO | A | 329 | 6307 | 6296 | 6465 | 82 | 62 | 20 | O |
| ATOM | 756 | N | ALA | A | 330 | 6.386 | 40.588 | −14.815 | 1.00 | 49.21 | N |
| ANISOU | 756 | N | ALA | A | 330 | 6236 | 6180 | 6279 | 31 | 21 | 35 | N |
| ATOM | 757 | CA | ALA | A | 330 | 5.267 | 39.685 | −14.511 | 1.00 | 48.97 | C |
| ANISOU | 757 | CA | ALA | A | 330 | 6221 | 6162 | 6220 | 0 | 15 | 46 | C |
| ATOM | 758 | C | ALA | A | 330 | 5.734 | 38.538 | −13.611 | 1.00 | 48.44 | C |
| ANISOU | 758 | C | ALA | A | 330 | 6145 | 6082 | 6176 | 14 | 16 | 18 | C |
| ATOM | 759 | O | ALA | A | 330 | 6.938 | 38.338 | −13.433 | 1.00 | 48.63 | O |
| ANISOU | 759 | O | ALA | A | 330 | 6183 | 6095 | 6196 | 22 | 6 | 21 | O |
| ATOM | 760 | CB | ALA | A | 330 | 4.638 | 39.170 | −15.796 | 1.00 | 49.45 | C |
| ANISOU | 760 | CB | ALA | A | 330 | 6282 | 6264 | 6242 | −3 | 41 | 22 | C |
| ATOM | 761 | N | SER | A | 331 | 4.774 | 37.789 | −13.057 | 1.00 | 47.86 | N |
| ANISOU | 761 | N | SER | A | 331 | 6127 | 5988 | 6070 | 15 | 23 | 18 | N |
| ATOM | 762 | CA | SER | A | 331 | 5.044 | 36.573 | −12.279 | 1.00 | 47.47 | C |
| ANISOU | 762 | CA | SER | A | 331 | 6076 | 5962 | 5998 | 20 | 52 | −2 | C |
| ATOM | 763 | CB | SER | A | 331 | 3.732 | 35.989 | −11.759 | 1.00 | 47.76 | C |
| ANISOU | 763 | CB | SER | A | 331 | 6111 | 5968 | 6068 | −34 | 62 | −6 | C |
| ATOM | 764 | OG | SER | A | 331 | 3.328 | 36.636 | −10.566 | 1.00 | 49.07 | O |
| ANISOU | 764 | OG | SER | A | 331 | 6264 | 6200 | 6180 | −65 | 112 | −82 | O |
| ATOM | 765 | C | SER | A | 331 | 5.784 | 35.490 | −13.063 | 1.00 | 46.93 | C |
| ANISOU | 765 | C | SER | A | 331 | 6026 | 5870 | 5936 | 45 | 11 | 17 | C |
| ATOM | 766 | O | SER | A | 331 | 5.841 | 35.530 | −14.306 | 1.00 | 46.88 | O |
| ANISOU | 766 | O | SER | A | 331 | 6028 | 5874 | 5910 | 64 | −8 | 49 | O |
| ATOM | 767 | N | ILE | A | 332 | 6.349 | 34.524 | −12.326 | 1.00 | 46.46 | N |
| ANISOU | 767 | N | ILE | A | 332 | 5955 | 5859 | 5838 | 52 | 8 | 10 | N |
| ATOM | 768 | CA | ILE | A | 332 | 6.997 | 33.345 | −12.921 | 1.00 | 45.16 | C |
| ANISOU | 768 | CA | ILE | A | 332 | 5784 | 5664 | 5710 | 32 | 1 | −50 | C |
| ATOM | 769 | CB | ILE | A | 332 | 8.447 | 33.111 | −12.418 | 1.00 | 45.49 | C |
| ANISOU | 769 | CB | ILE | A | 332 | 5827 | 5705 | 5750 | 38 | 30 | −55 | C |
| ATOM | 770 | CG1 | ILE | A | 332 | 9.226 | 34.425 | −12.299 | 1.00 | 45.00 | C |
| ANISOU | 770 | CG1 | ILE | A | 332 | 5746 | 5597 | 5752 | 3 | 1 | −96 | C |
| ATOM | 771 | CD1 | ILE | A | 332 | 10.603 | 34.263 | −11.676 | 1.00 | 44.54 | C |
| ANISOU | 771 | CD1 | ILE | A | 332 | 5753 | 5514 | 5657 | 62 | −2 | −95 | C |
| ATOM | 772 | CG2 | ILE | A | 332 | 9.199 | 32.107 | −13.353 | 1.00 | 46.08 | C |
| ANISOU | 772 | CG2 | ILE | A | 332 | 5899 | 5694 | 5914 | 5 | 5 | −81 | C |
| ATOM | 773 | C | ILE | A | 332 | 6.212 | 32.091 | −12.614 | 1.00 | 45.22 | C |
| ANISOU | 773 | C | ILE | A | 332 | 5786 | 5699 | 5695 | 11 | 19 | −20 | C |
| ATOM | 774 | O | ILE | A | 332 | 5.959 | 31.784 | −11.447 | 1.00 | 45.15 | O |
| ANISOU | 774 | O | ILE | A | 332 | 5742 | 5739 | 5670 | 47 | −18 | −46 | O |
| ATOM | 775 | N | GLU | A | 333 | 5.846 | 31.365 | −13.675 | 1.00 | 45.30 | N |
| ANISOU | 775 | N | GLU | A | 333 | 5774 | 5702 | 5736 | −22 | 17 | 4 | N |
| ATOM | 776 | CA | GLU | A | 333 | 5.198 | 30.059 | −13.561 | 1.00 | 45.04 | C |
| ANISOU | 776 | CA | GLU | A | 333 | 5702 | 5658 | 5752 | 6 | 34 | −3 | C |
| ATOM | 777 | CB | GLU | A | 333 | 3.920 | 30.002 | −14.403 | 1.00 | 45.11 | C |
| ANISOU | 777 | CB | GLU | A | 333 | 5759 | 5677 | 5704 | −3 | 34 | 16 | C |
| ATOM | 778 | CG | GLU | A | 333 | 2.743 | 30.808 | −13.893 | 1.00 | 46.10 | C |
| ANISOU | 778 | CG | GLU | A | 333 | 5802 | 5868 | 5845 | 9 | −6 | 18 | C |
| ATOM | 779 | CD | GLU | A | 333 | 1.567 | 30.734 | −14.839 | 1.00 | 47.62 | C |
| ANISOU | 779 | CD | GLU | A | 333 | 6049 | 5979 | 6064 | −46 | 8 | 80 | C |
| ATOM | 780 | OE1 | GLU | A | 333 | 0.502 | 31.308 | −14.524 | 1.00 | 49.66 | O |
| ANISOU | 780 | OE1 | GLU | A | 333 | 6257 | 6258 | 6355 | 147 | 141 | 19 | O |
| ATOM | 781 | OE2 | GLU | A | 333 | 1.706 | 30.101 | −15.911 | 1.00 | 49.76 | O |
| ANISOU | 781 | OE2 | GLU | A | 333 | 6561 | 6209 | 6136 | 66 | 28 | −65 | O |
| ATOM | 782 | C | GLU | A | 333 | 6.112 | 28.961 | −14.076 | 1.00 | 44.61 | C |
| ANISOU | 782 | C | GLU | A | 333 | 5648 | 5599 | 5700 | −8 | 55 | 47 | C |
| ATOM | 783 | O | GLU | A | 333 | 6.661 | 29.064 | −15.180 | 1.00 | 44.56 | O |
| ANISOU | 783 | O | GLU | A | 333 | 5623 | 5595 | 5712 | −41 | 123 | 71 | O |
| ATOM | 784 | N | LYS | A | 334 | 6.230 | 27.892 | −13.290 | 1.00 | 44.01 | N |
| ANISOU | 784 | N | LYS | A | 334 | 5544 | 5539 | 5638 | 18 | 36 | 50 | N |
| ATOM | 785 | CA | LYS | A | 334 | 6.873 | 26.659 | −13.734 | 1.00 | 42.98 | C |
| ANISOU | 785 | CA | LYS | A | 334 | 5422 | 5388 | 5518 | 15 | 17 | 31 | C |
| ATOM | 786 | CB | LYS | A | 334 | 8.212 | 26.486 | −13.006 | 1.00 | 43.19 | C |
| ANISOU | 786 | CB | LYS | A | 334 | 5438 | 5429 | 5541 | 15 | 10 | 54 | C |
| ATOM | 787 | CG | LYS | A | 334 | 9.342 | 27.415 | −13.491 | 1.00 | 43.78 | C |
| ANISOU | 787 | CG | LYS | A | 334 | 5486 | 5549 | 5597 | −63 | 48 | −57 | C |
| ATOM | 788 | CD | LYS | A | 334 | 9.999 | 26.862 | −14.756 | 1.00 | 47.27 | C |
| ANISOU | 788 | CD | LYS | A | 334 | 6256 | 5959 | 5746 | 137 | −131 | −161 | C |

TABLE 7-continued

The atomic structure coordinates of Fc-TM

| | | | | | | | | | | | | |
|---|---|---|---|---|---|---|---|---|---|---|---|---|
| ATOM | 789 | CE | LYS | A | 334 | 11.210 | 27.670 | −15.180 | 1.00 | 41.47 | | C |
| ANISOU | 789 | CE | LYS | A | 334 | 5573 | 4547 | 5633 | −141 | −13 | 547 | C |
| ATOM | 790 | NZ | LYS | A | 334 | 10.822 | 28.944 | −15.871 | 1.00 | 48.95 | | N |
| ANISOU | 790 | NZ | LYS | A | 334 | 5949 | 6476 | 6171 | −108 | −137 | −288 | N |
| ATOM | 791 | C | LYS | A | 334 | 5.942 | 25.479 | −13.449 | 1.00 | 42.38 | | C |
| ANISOU | 791 | C | LYS | A | 334 | 5339 | 5347 | 5415 | 47 | 18 | 4 | C |
| ATOM | 792 | O | LYS | A | 334 | 5.416 | 25.373 | −12.342 | 1.00 | 41.36 | | O |
| ANISOU | 792 | O | LYS | A | 334 | 5235 | 5235 | 5242 | 88 | 46 | 19 | O |
| ATOM | 793 | N | THR | A | 335 | 5.737 | 24.606 | −14.448 | 1.00 | 42.28 | | N |
| ANISOU | 793 | N | THR | A | 335 | 5315 | 5358 | 5388 | 22 | −3 | 5 | N |
| ATOM | 794 | CA | THR | A | 335 | 4.887 | 23.413 | −14.297 | 1.00 | 42.27 | | C |
| ANISOU | 794 | CA | THR | A | 335 | 5328 | 5336 | 5394 | 20 | −27 | −22 | C |
| ATOM | 795 | CB | THR | A | 335 | 3.669 | 23.442 | −15.297 | 1.00 | 42.66 | | C |
| ANISOU | 795 | CB | THR | A | 335 | 5389 | 5366 | 5451 | 24 | −40 | 7 | C |
| ATOM | 796 | OG1 | THR | A | 335 | 2.797 | 24.540 | −14.973 | 1.00 | 43.84 | | O |
| ANISOU | 796 | OG1 | THR | A | 335 | 5548 | 5558 | 5551 | 61 | −31 | −90 | O |
| ATOM | 797 | CG2 | THR | A | 335 | 2.849 | 22.137 | −15.256 | 1.00 | 42.03 | | C |
| ANISOU | 797 | CG2 | THR | A | 335 | 5251 | 5336 | 5381 | 1 | −34 | 33 | C |
| ATOM | 798 | C | THR | A | 335 | 5.691 | 22.094 | −14.399 | 1.00 | 42.02 | | C |
| ANISOU | 798 | C | THR | A | 335 | 5275 | 5343 | 5344 | 6 | −2 | 3 | C |
| ATOM | 799 | O | THR | A | 335 | 6.591 | 21.962 | −15.233 | 1.00 | 42.24 | | O |
| ANISOU | 799 | O | THR | A | 335 | 5317 | 5422 | 5307 | −6 | 27 | −4 | O |
| ATOM | 800 | N | ILE | A | 336 | 5.364 | 21.130 | −13.536 | 1.00 | 41.53 | | N |
| ANISOU | 800 | N | ILE | A | 336 | 5220 | 5253 | 5307 | −22 | 0 | −2 | N |
| ATOM | 801 | CA | ILE | A | 336 | 6.033 | 19.830 | −13.521 | 1.00 | 41.14 | | C |
| ANISOU | 801 | CA | ILE | A | 336 | 5192 | 5158 | 5280 | −5 | −6 | −31 | C |
| ATOM | 802 | CB | ILE | A | 336 | 7.112 | 19.767 | −12.399 | 1.00 | 41.49 | | C |
| ANISOU | 802 | CB | ILE | A | 336 | 5260 | 5196 | 5307 | 8 | 7 | −66 | C |
| ATOM | 803 | CG1 | ILE | A | 336 | 8.130 | 18.656 | −12.661 | 1.00 | 41.08 | | C |
| ANISOU | 803 | CG1 | ILE | A | 336 | 5207 | 5068 | 5332 | 72 | −8 | −97 | C |
| ATOM | 804 | CD1 | ILE | A | 336 | 9.561 | 19.137 | −12.634 | 1.00 | 40.27 | | C |
| ANISOU | 804 | CD1 | ILE | A | 336 | 5179 | 4874 | 5247 | −8 | −10 | −97 | C |
| ATOM | 805 | CG2 | ILE | A | 336 | 6.480 | 19.580 | −11.011 | 1.00 | 42.34 | | C |
| ANISOU | 805 | CG2 | ILE | A | 336 | 5379 | 5259 | 5448 | −35 | 90 | 0 | C |
| ATOM | 806 | C | ILE | A | 336 | 5.046 | 18.664 | −13.378 | 1.00 | 40.65 | | C |
| ANISOU | 806 | C | ILE | A | 336 | 5139 | 5100 | 5203 | −7 | 0 | −31 | C |
| ATOM | 807 | O | ILE | A | 336 | 4.003 | 18.801 | −12.761 | 1.00 | 41.39 | | O |
| ANISOU | 807 | O | ILE | A | 336 | 5205 | 5207 | 5311 | −38 | −23 | −17 | O |
| ATOM | 808 | N | SER | A | 337 | 5.387 | 17.522 | −13.967 | 1.00 | 39.94 | | N |
| ANISOU | 808 | N | SER | A | 337 | 5084 | 5004 | 5084 | −68 | −53 | −17 | N |
| ATOM | 809 | CA | SER | A | 337 | 4.678 | 16.250 | −13.746 | 1.00 | 38.58 | | C |
| ANISOU | 809 | CA | SER | A | 337 | 4946 | 4829 | 4883 | −42 | −91 | −14 | C |
| ATOM | 810 | CB | SER | A | 337 | 3.495 | 16.104 | −14.717 | 1.00 | 38.30 | | C |
| ANISOU | 810 | CB | SER | A | 337 | 4878 | 4805 | 4869 | −19 | −98 | −9 | C |
| ATOM | 811 | OG | SER | A | 337 | 3.996 | 15.979 | −16.037 | 1.00 | 37.12 | | O |
| ANISOU | 811 | OG | SER | A | 337 | 4890 | 4556 | 4658 | −36 | −329 | 74 | O |
| ATOM | 812 | C | SER | A | 337 | 5.671 | 15.117 | −13.992 | 1.00 | 37.26 | | C |
| ANISOU | 812 | C | SER | A | 337 | 4761 | 4669 | 4727 | −28 | −55 | −53 | C |
| ATOM | 813 | O | SER | A | 337 | 6.763 | 15.356 | −14.454 | 1.00 | 36.64 | | O |
| ANISOU | 813 | O | SER | A | 337 | 4712 | 4560 | 4646 | −72 | −77 | −119 | O |
| ATOM | 814 | N | LYS | A | 338 | 5.259 | 13.888 | −13.696 | 1.00 | 36.86 | | N |
| ANISOU | 814 | N | LYS | A | 338 | 4689 | 4665 | 4651 | 34 | −19 | −58 | N |
| ATOM | 815 | CA | LYS | A | 338 | 5.995 | 12.667 | −14.048 | 1.00 | 36.00 | | C |
| ANISOU | 815 | CA | LYS | A | 338 | 4571 | 4534 | 4570 | −3 | −18 | −52 | C |
| ATOM | 816 | CB | LYS | A | 338 | 5.191 | 11.468 | −13.542 | 1.00 | 35.29 | | C |
| ANISOU | 816 | CB | LYS | A | 338 | 4455 | 4494 | 4457 | 5 | 24 | −42 | C |
| ATOM | 817 | CG | LYS | A | 338 | 5.828 | 10.099 | −13.681 | 1.00 | 33.67 | | C |
| ANISOU | 817 | CG | LYS | A | 338 | 4244 | 4375 | 4173 | 27 | −21 | 32 | C |
| ATOM | 818 | CD | LYS | A | 338 | 4.832 | 8.999 | −13.385 | 1.00 | 30.62 | | C |
| ANISOU | 818 | CD | LYS | A | 338 | 3883 | 4010 | 3741 | 34 | −66 | 1 | C |
| ATOM | 819 | CE | LYS | A | 338 | 3.843 | 8.803 | −14.522 | 1.00 | 29.42 | | C |
| ANISOU | 819 | CE | LYS | A | 338 | 3949 | 3572 | 3656 | 25 | 104 | 81 | C |
| ATOM | 820 | NZ | LYS | A | 338 | 4.576 | 8.396 | −15.745 | 1.00 | 27.21 | | N |
| ANISOU | 820 | NZ | LYS | A | 338 | 3843 | 3118 | 3374 | −83 | −117 | 132 | N |
| ATOM | 821 | C | LYS | A | 338 | 6.258 | 12.571 | −15.572 | 1.00 | 35.50 | | C |
| ANISOU | 821 | C | LYS | A | 338 | 4535 | 4440 | 4512 | −21 | −20 | −80 | C |
| ATOM | 822 | O | LYS | A | 338 | 5.479 | 13.073 | −16.374 | 1.00 | 34.30 | | O |
| ANISOU | 822 | O | LYS | A | 338 | 4439 | 4209 | 4381 | −34 | 4 | −116 | O |
| ATOM | 823 | N | ALA | A | 339 | 7.366 | 11.950 | −15.968 | 1.00 | 35.70 | | N |
| ANISOU | 823 | N | ALA | A | 339 | 4573 | 4471 | 4517 | −35 | −30 | −65 | N |
| ATOM | 824 | CA | ALA | A | 339 | 7.638 | 11.750 | −17.393 | 1.00 | 36.15 | | C |
| ANISOU | 824 | CA | ALA | A | 339 | 4615 | 4521 | 4599 | −15 | −13 | −58 | C |
| ATOM | 825 | CB | ALA | A | 339 | 8.837 | 10.811 | −17.606 | 1.00 | 36.05 | | C |
| ANISOU | 825 | CB | ALA | A | 339 | 4546 | 4589 | 4559 | −45 | −58 | −37 | C |
| ATOM | 826 | C | ALA | A | 339 | 6.373 | 11.204 | −18.084 | 1.00 | 36.01 | | C |
| ANISOU | 826 | C | ALA | A | 339 | 4591 | 4506 | 4583 | −12 | −7 | −66 | C |
| ATOM | 827 | O | ALA | A | 339 | 5.767 | 10.235 | −17.626 | 1.00 | 35.29 | | O |
| ANISOU | 827 | O | ALA | A | 339 | 4495 | 4403 | 4508 | 20 | 0 | −69 | O |

TABLE 7-continued

| The atomic structure coordinates of Fc-TM | | | | | | | | | | | | |
|---|---|---|---|---|---|---|---|---|---|---|---|---|
| ATOM | 828 | N | LYS | A | 340 | 5.957 | 11.871 | −19.150 | 1.00 | 36.06 | | N |
| ANISOU | 828 | N | LYS | A | 340 | 4636 | 4483 | 4580 | −50 | 15 | −31 | N |
| ATOM | 829 | CA | LYS | A | 340 | 4.776 | 11.478 | −19.901 | 1.00 | 36.79 | | C |
| ANISOU | 829 | CA | LYS | A | 340 | 4727 | 4622 | 4626 | −22 | −2 | −23 | C |
| ATOM | 830 | CB | LYS | A | 340 | 4.201 | 12.675 | −20.674 | 1.00 | 37.11 | | C |
| ANISOU | 830 | CB | LYS | A | 340 | 4729 | 4625 | 4746 | −33 | 22 | −34 | C |
| ATOM | 831 | CG | LYS | A | 340 | 3.417 | 13.646 | −19.808 | 1.00 | 38.15 | | C |
| ANISOU | 831 | CG | LYS | A | 340 | 4951 | 4783 | 4759 | −17 | 8 | −23 | C |
| ATOM | 832 | CD | LYS | A | 340 | 3.035 | 14.930 | −20.552 | 1.00 | 38.31 | | C |
| ANISOU | 832 | CD | LYS | A | 340 | 4857 | 4845 | 4852 | −53 | −56 | −11 | C |
| ATOM | 833 | CE | LYS | A | 340 | 2.454 | 15.928 | −19.583 | 1.00 | 39.66 | | C |
| ANISOU | 833 | CE | LYS | A | 340 | 4859 | 5039 | 5171 | 67 | −10 | −26 | C |
| ATOM | 834 | NZ | LYS | A | 340 | 2.557 | 17.333 | −20.080 | 1.00 | 42.09 | | N |
| ANISOU | 834 | NZ | LYS | A | 340 | 5215 | 5411 | 5363 | −28 | 21 | 40 | N |
| ATOM | 835 | C | LYS | A | 340 | 5.120 | 10.297 | −20.833 | 1.00 | 36.19 | | C |
| ANISOU | 835 | C | LYS | A | 340 | 4615 | 4591 | 4545 | 0 | 0 | −14 | C |
| ATOM | 836 | O | LYS | A | 340 | 6.286 | 9.917 | −20.940 | 1.00 | 36.01 | | O |
| ANISOU | 836 | O | LYS | A | 340 | 4613 | 4608 | 4461 | −17 | −8 | −9 | O |
| ATOM | 837 | N | GLY | A | 341 | 4.109 | 9.717 | −21.486 | 1.00 | 35.13 | | N |
| ANISOU | 837 | N | GLY | A | 341 | 4487 | 4443 | 4417 | −7 | 9 | −27 | N |
| ATOM | 838 | CA | GLY | A | 341 | 4.315 | 8.552 | −22.351 | 1.00 | 33.53 | | C |
| ANISOU | 838 | CA | GLY | A | 341 | 4232 | 4341 | 4165 | 28 | −19 | 20 | C |
| ATOM | 839 | C | GLY | A | 341 | 3.679 | 7.281 | −21.845 | 1.00 | 32.52 | | C |
| ANISOU | 839 | C | GLY | A | 341 | 4085 | 4155 | 4114 | 71 | −32 | −34 | C |
| ATOM | 840 | O | GLY | A | 341 | 3.552 | 7.075 | −20.628 | 1.00 | 31.86 | | O |
| ANISOU | 840 | O | GLY | A | 341 | 3925 | 4073 | 4106 | 82 | −44 | −75 | O |
| ATOM | 841 | N | GLN | A | 342 | 3.276 | 6.427 | −22.781 | 1.00 | 31.81 | | N |
| ANISOU | 841 | N | GLN | A | 342 | 4021 | 4126 | 3939 | 78 | −15 | −18 | N |
| ATOM | 842 | CA | GLN | A | 342 | 2.697 | 5.123 | −22.472 | 1.00 | 31.42 | | C |
| ANISOU | 842 | CA | GLN | A | 342 | 4041 | 3988 | 3909 | 45 | −37 | −59 | C |
| ATOM | 843 | CB | GLN | A | 342 | 2.283 | 4.401 | −23.770 | 1.00 | 31.69 | | C |
| ANISOU | 843 | CB | GLN | A | 342 | 4054 | 3993 | 3992 | 79 | −26 | −40 | C |
| ATOM | 844 | CG | GLN | A | 342 | 1.017 | 4.931 | −24.463 | 1.00 | 30.27 | | C |
| ANISOU | 844 | CG | GLN | A | 342 | 4081 | 3823 | 3597 | 2 | −53 | −130 | C |
| ATOM | 845 | CD | GLN | A | 342 | −0.282 | 4.551 | −23.748 | 1.00 | 28.05 | | C |
| ANISOU | 845 | CD | GLN | A | 342 | 3804 | 3406 | 3445 | 149 | −27 | 92 | C |
| ATOM | 846 | OE1 | GLN | A | 342 | −0.345 | 3.562 | −22.997 | 1.00 | 31.57 | | O |
| ANISOU | 846 | OE1 | GLN | A | 342 | 4346 | 4036 | 3611 | 80 | 115 | −150 | O |
| ATOM | 847 | NE2 | GLN | A | 342 | −1.324 | 5.329 | −23.982 | 1.00 | 27.78 | | N |
| ANISOU | 847 | NE2 | GLN | A | 342 | 3742 | 3685 | 3128 | 63 | 86 | 28 | N |
| ATOM | 848 | C | GLN | A | 342 | 3.699 | 4.278 | −21.678 | 1.00 | 31.71 | | C |
| ANISOU | 848 | C | GLN | A | 342 | 4108 | 3972 | 3968 | 2 | −33 | −40 | C |
| ATOM | 849 | O | GLN | A | 342 | 4.828 | 4.083 | −22.128 | 1.00 | 31.42 | | O |
| ANISOU | 849 | O | GLN | A | 342 | 4162 | 3884 | 3891 | −39 | −112 | −23 | O |
| ATOM | 850 | N | PRO | A | 343 | 3.301 | 3.785 | −20.489 | 1.00 | 32.23 | | N |
| ANISOU | 850 | N | PRO | A | 343 | 4160 | 4035 | 4051 | 10 | −31 | −23 | N |
| ATOM | 851 | CA | PRO | A | 343 | 4.181 | 2.960 | −19.638 | 1.00 | 32.69 | | C |
| ANISOU | 851 | CA | PRO | A | 343 | 4213 | 4109 | 4098 | −3 | −4 | 6 | C |
| ATOM | 852 | CB | PRO | A | 343 | 3.380 | 2.837 | −18.349 | 1.00 | 32.19 | | C |
| ANISOU | 852 | CB | PRO | A | 343 | 4159 | 4011 | 4060 | 30 | −13 | 10 | C |
| ATOM | 853 | CG | PRO | A | 343 | 1.964 | 2.866 | −18.832 | 1.00 | 32.66 | | C |
| ANISOU | 853 | CG | PRO | A | 343 | 4242 | 4047 | 4116 | 0 | 21 | −24 | C |
| ATOM | 854 | CD | PRO | A | 343 | 1.968 | 3.940 | −19.879 | 1.00 | 32.17 | | C |
| ANISOU | 854 | CD | PRO | A | 343 | 4181 | 4052 | 3987 | 16 | −21 | −13 | C |
| ATOM | 855 | C | PRO | A | 343 | 4.431 | 1.555 | −20.220 | 1.00 | 33.20 | | C |
| ANISOU | 855 | C | PRO | A | 343 | 4284 | 4187 | 4141 | −16 | −2 | 31 | C |
| ATOM | 856 | O | PRO | A | 343 | 3.523 | 0.944 | −20.760 | 1.00 | 32.66 | | O |
| ANISOU | 856 | O | PRO | A | 343 | 4246 | 4100 | 4061 | −46 | −31 | 42 | O |
| ATOM | 857 | N | ARG | A | 344 | 5.661 | 1.059 | −20.113 | 1.00 | 34.11 | | N |
| ANISOU | 857 | N | ARG | A | 344 | 4385 | 4381 | 4194 | −20 | −12 | 7 | N |
| ATOM | 858 | CA | ARG | A | 344 | 5.966 | −0.318 | −20.495 | 1.00 | 34.88 | | C |
| ANISOU | 858 | CA | ARG | A | 344 | 4443 | 4484 | 4326 | 4 | −8 | −16 | C |
| ATOM | 859 | CB | ARG | A | 344 | 6.837 | −0.389 | −21.766 | 1.00 | 35.47 | | C |
| ANISOU | 859 | CB | ARG | A | 344 | 4420 | 4544 | 4511 | −12 | −30 | −52 | C |
| ATOM | 860 | CG | ARG | A | 344 | 6.369 | 0.413 | −22.984 | 1.00 | 35.46 | | C |
| ANISOU | 860 | CG | ARG | A | 344 | 4558 | 4556 | 4357 | −10 | 103 | −41 | C |
| ATOM | 861 | CD | ARG | A | 344 | 7.187 | −0.019 | −24.224 | 1.00 | 42.30 | | C |
| ANISOU | 861 | CD | ARG | A | 344 | 5121 | 5594 | 5357 | 27 | −186 | −291 | C |
| ATOM | 862 | NE | ARG | A | 344 | 7.453 | 1.068 | −25.179 | 1.00 | 34.97 | | N |
| ANISOU | 862 | NE | ARG | A | 344 | 4759 | 4835 | 3690 | −15 | 779 | 214 | N |
| ATOM | 863 | CZ | ARG | A | 344 | 8.223 | 0.943 | −26.268 | 1.00 | 46.83 | | C |
| ANISOU | 863 | CZ | ARG | A | 344 | 5377 | 6384 | 6029 | −370 | −579 | −303 | C |
| ATOM | 864 | NH1 | ARG | A | 344 | 8.798 | −0.225 | −26.541 | 1.00 | 36.80 | | N |
| ANISOU | 864 | NH1 | ARG | A | 344 | 4533 | 4393 | 5057 | 477 | 227 | −349 | N |
| ATOM | 865 | NH2 | ARG | A | 344 | 8.406 | 1.976 | −27.085 | 1.00 | 32.95 | | N |
| ANISOU | 865 | NH2 | ARG | A | 344 | 4473 | 3988 | 4058 | −185 | 138 | 349 | N |
| ATOM | 866 | C | ARG | A | 344 | 6.652 | −1.014 | −19.326 | 1.00 | 35.55 | | C |
| ANISOU | 866 | C | ARG | A | 344 | 4503 | 4565 | 4439 | −1 | 2 | −55 | C |

TABLE 7-continued

The atomic structure coordinates of Fc-TM

| ATOM | 867 | O | ARG | A | 344 | 7.600 | −0.490 | −18.751 | 1.00 | 35.51 | | O |
|---|---|---|---|---|---|---|---|---|---|---|---|---|
| ANISOU | 867 | O | ARG | A | 344 | 4476 | 4590 | 4426 | 24 | −11 | −37 | O |
| ATOM | 868 | N | GLU | A | 345 | 6.144 | −2.186 | −18.971 | 1.00 | 35.97 | | N |
| ANISOU | 868 | N | GLU | A | 345 | 4588 | 4586 | 4489 | −8 | −41 | −78 | N |
| ATOM | 869 | CA | GLU | A | 345 | 6.656 | −2.995 | −17.880 | 1.00 | 36.16 | | C |
| ANISOU | 869 | CA | GLU | A | 345 | 4630 | 4626 | 4481 | 3 | −56 | −31 | C |
| ATOM | 870 | CB | GLU | A | 345 | 5.668 | −4.114 | −17.573 | 1.00 | 36.66 | | C |
| ANISOU | 870 | CB | GLU | A | 345 | 4710 | 4666 | 4553 | 2 | −39 | −45 | C |
| ATOM | 871 | CG | GLU | A | 345 | 5.939 | −4.802 | −16.249 | 1.00 | 38.92 | | C |
| ANISOU | 871 | CG | GLU | A | 345 | 5030 | 4961 | 4795 | 50 | −70 | 23 | C |
| ATOM | 872 | CD | GLU | A | 345 | 5.466 | −6.244 | −16.197 | 1.00 | 39.25 | | C |
| ANISOU | 872 | CD | GLU | A | 345 | 4949 | 4976 | 4987 | −33 | −88 | 12 | C |
| ATOM | 873 | OE1 | GLU | A | 345 | 6.215 | −7.086 | −15.680 | 1.00 | 41.62 | | O |
| ANISOU | 873 | OE1 | GLU | A | 345 | 5509 | 5056 | 5247 | −30 | 46 | −48 | O |
| ATOM | 874 | OE2 | GLU | A | 345 | 4.360 | −6.544 | −16.660 | 1.00 | 41.29 | | O |
| ANISOU | 874 | OE2 | GLU | A | 345 | 5302 | 5254 | 5132 | 24 | −6 | −54 | O |
| ATOM | 875 | C | GLU | A | 345 | 8.014 | −3.607 | −18.213 | 1.00 | 36.11 | | C |
| ANISOU | 875 | C | GLU | A | 345 | 4648 | 4610 | 4459 | −14 | −51 | −17 | C |
| ATOM | 876 | O | GLU | A | 345 | 8.151 | −4.270 | −19.242 | 1.00 | 35.55 | | O |
| ANISOU | 876 | O | GLU | A | 345 | 4678 | 4510 | 4316 | −23 | −92 | −1 | O |
| ATOM | 877 | N | PRO | A | 346 | 9.029 | −3.396 | −17.338 | 1.00 | 35.96 | | N |
| ANISOU | 877 | N | PRO | A | 346 | 4575 | 4638 | 4446 | −16 | −46 | −18 | N |
| ATOM | 878 | CA | PRO | A | 346 | 10.320 | −4.041 | −17.561 | 1.00 | 35.46 | | C |
| ANISOU | 878 | CA | PRO | A | 346 | 4492 | 4581 | 4399 | 4 | −42 | −18 | C |
| ATOM | 879 | CB | PRO | A | 346 | 11.182 | −3.552 | −16.380 | 1.00 | 35.73 | | C |
| ANISOU | 879 | CB | PRO | A | 346 | 4524 | 4597 | 4452 | 12 | −21 | 4 | C |
| ATOM | 880 | CG | PRO | A | 346 | 10.228 | −3.061 | −15.358 | 1.00 | 35.62 | | C |
| ANISOU | 880 | CG | PRO | A | 346 | 4572 | 4580 | 4380 | 38 | −12 | −22 | C |
| ATOM | 881 | CD | PRO | A | 346 | 9.046 | −2.540 | −16.136 | 1.00 | 35.89 | | C |
| ANISOU | 881 | CD | PRO | A | 346 | 4545 | 4611 | 4479 | −7 | −43 | −41 | C |
| ATOM | 882 | C | PRO | A | 346 | 10.299 | −5.561 | −17.570 | 1.00 | 35.18 | | C |
| ANISOU | 882 | C | PRO | A | 346 | 4416 | 4581 | 4370 | −24 | −79 | −24 | C |
| ATOM | 883 | O | PRO | A | 346 | 9.494 | −6.194 | −16.877 | 1.00 | 34.62 | | O |
| ANISOU | 883 | O | PRO | A | 346 | 4353 | 4580 | 4219 | −12 | −186 | −66 | O |
| ATOM | 884 | N | GLN | A | 347 | 11.219 | −6.120 | −18.349 | 1.00 | 35.18 | | N |
| ANISOU | 884 | N | GLN | A | 347 | 4543 | 4504 | 4317 | −46 | −63 | −72 | N |
| ATOM | 885 | CA | GLN | A | 347 | 11.631 | −7.507 | −18.254 | 1.00 | 35.53 | | C |
| ANISOU | 885 | CA | GLN | A | 347 | 4553 | 4530 | 4414 | 0 | −45 | −78 | C |
| ATOM | 886 | CB | GLN | A | 347 | 11.789 | −8.075 | −19.670 | 1.00 | 36.10 | | C |
| ANISOU | 886 | CB | GLN | A | 347 | 4629 | 4569 | 4515 | 5 | −25 | −114 | C |
| ATOM | 887 | CG | GLN | A | 347 | 10.539 | −7.907 | −20.521 | 1.00 | 37.59 | | C |
| ANISOU | 887 | CG | GLN | A | 347 | 4887 | 4687 | 4707 | 85 | −90 | −113 | C |
| ATOM | 888 | CD | GLN | A | 347 | 10.854 | −7.408 | −21.902 | 1.00 | 40.93 | | C |
| ANISOU | 888 | CD | GLN | A | 347 | 5327 | 5075 | 5147 | −59 | −3 | 9 | C |
| ATOM | 889 | OE1 | GLN | A | 347 | 11.724 | −7.946 | −22.587 | 1.00 | 42.38 | | O |
| ANISOU | 889 | OE1 | GLN | A | 347 | 5289 | 5375 | 5436 | 61 | 68 | 117 | O |
| ATOM | 890 | NE2 | GLN | A | 347 | 10.135 | −6.381 | −22.337 | 1.00 | 41.52 | | N |
| ANISOU | 890 | NE2 | GLN | A | 347 | 5299 | 5090 | 5385 | 92 | −137 | −75 | N |
| ATOM | 891 | C | GLN | A | 347 | 12.969 | −7.538 | −17.513 | 1.00 | 34.81 | | C |
| ANISOU | 891 | C | GLN | A | 347 | 4451 | 4436 | 4337 | −31 | 7 | −68 | C |
| ATOM | 892 | O | GLN | A | 347 | 13.907 | −6.895 | −17.937 | 1.00 | 34.34 | | O |
| ANISOU | 892 | O | GLN | A | 347 | 4438 | 4322 | 4286 | −90 | −26 | −42 | O |
| ATOM | 893 | N | VAL | A | 348 | 13.034 | −8.283 | −16.409 | 1.00 | 34.50 | | N |
| ANISOU | 893 | N | VAL | A | 348 | 4388 | 4352 | 4366 | −33 | 16 | −8 | N |
| ATOM | 894 | CA | VAL | A | 348 | 14.195 | −8.336 | −15.520 | 1.00 | 34.25 | | C |
| ANISOU | 894 | CA | VAL | A | 348 | 4345 | 4345 | 4324 | −31 | 17 | −6 | C |
| ATOM | 895 | CB | VAL | A | 348 | 13.798 | −8.061 | −14.027 | 1.00 | 34.35 | | C |
| ANISOU | 895 | CB | VAL | A | 348 | 4334 | 4344 | 4372 | −35 | 28 | 27 | C |
| ATOM | 896 | CG1 | VAL | A | 348 | 14.988 | −8.250 | −13.096 | 1.00 | 33.51 | | C |
| ANISOU | 896 | CG1 | VAL | A | 348 | 4238 | 4355 | 4138 | −36 | 50 | −12 | C |
| ATOM | 897 | CG2 | VAL | A | 348 | 13.222 | −6.668 | −13.844 | 1.00 | 33.93 | | C |
| ANISOU | 897 | CG2 | VAL | A | 348 | 4281 | 4316 | 4294 | 5 | 17 | −7 | C |
| ATOM | 898 | C | VAL | A | 348 | 14.833 | −9.720 | −15.601 | 1.00 | 34.64 | | C |
| ANISOU | 898 | C | VAL | A | 348 | 4404 | 4383 | 4373 | −32 | 6 | 27 | C |
| ATOM | 899 | O | VAL | A | 348 | 14.156 | −10.730 | −15.359 | 1.00 | 34.49 | | O |
| ANISOU | 899 | O | VAL | A | 348 | 4366 | 4418 | 4317 | −11 | −34 | 44 | O |
| ATOM | 900 | N | TYR | A | 349 | 16.126 | −9.769 | −15.935 | 1.00 | 34.98 | | N |
| ANISOU | 900 | N | TYR | A | 349 | 4437 | 4393 | 4459 | −54 | 12 | 32 | N |
| ATOM | 901 | CA | TYR | A | 349 | 16.835 | −11.040 | −16.125 | 1.00 | 35.60 | | C |
| ANISOU | 901 | CA | TYR | A | 349 | 4504 | 4476 | 4547 | −57 | −29 | 71 | C |
| ATOM | 902 | CB | TYR | A | 349 | 17.128 | −11.334 | −17.612 | 1.00 | 33.85 | | C |
| ANISOU | 902 | CB | TYR | A | 349 | 4148 | 4389 | 4323 | −53 | −206 | −7 | C |
| ATOM | 903 | CG | TYR | A | 349 | 15.930 | −11.322 | −18.532 | 1.00 | 37.15 | | C |
| ANISOU | 903 | CG | TYR | A | 349 | 4880 | 4508 | 4724 | 99 | 192 | −36 | C |
| ATOM | 904 | CD1 | TYR | A | 349 | 14.882 | −12.237 | −18.364 | 1.00 | 33.27 | | C |
| ANISOU | 904 | CD1 | TYR | A | 349 | 4290 | 4016 | 4335 | −10 | −59 | 97 | C |
| ATOM | 905 | CE1 | TYR | A | 349 | 13.785 | −12.242 | −19.206 | 1.00 | 31.99 | | C |
| ANISOU | 905 | CE1 | TYR | A | 349 | 4268 | 3911 | 3974 | 66 | −115 | 123 | C |

TABLE 7-continued

The atomic structure coordinates of Fc-TM

| ATOM | 906 | CZ | TYR | A | 349 | 13.707 | −11.324 | −20.253 | 1.00 | 36.97 | | C |
|---|---|---|---|---|---|---|---|---|---|---|---|---|
| ANISOU | 906 | CZ | TYR | A | 349 | 5013 | 4524 | 4509 | 156 | 357 | −207 | C |
| ATOM | 907 | OH | TYR | A | 349 | 12.592 | −11.340 | −21.085 | 1.00 | 32.56 | | O |
| ANISOU | 907 | OH | TYR | A | 349 | 3951 | 4398 | 4022 | −11 | −218 | −91 | O |
| ATOM | 908 | CE2 | TYR | A | 349 | 14.726 | −10.404 | −20.457 | 1.00 | 31.78 | | C |
| ANISOU | 908 | CE2 | TYR | A | 349 | 4079 | 4051 | 3944 | −130 | 10 | −26 | C |
| ATOM | 909 | CD2 | TYR | A | 349 | 15.850 | −10.416 | −19.605 | 1.00 | 34.01 | | C |
| ANISOU | 909 | CD2 | TYR | A | 349 | 4476 | 4272 | 4172 | 69 | −61 | 92 | C |
| ATOM | 910 | C | TYR | A | 349 | 18.143 | −11.028 | −15.368 | 1.00 | 36.74 | | C |
| ANISOU | 910 | C | TYR | A | 349 | 4676 | 4594 | 4687 | −68 | −58 | 59 | C |
| ATOM | 911 | O | TYR | A | 349 | 18.887 | −10.037 | −15.418 | 1.00 | 37.20 | | O |
| ANISOU | 911 | O | TYR | A | 349 | 4797 | 4592 | 4743 | −80 | −156 | 107 | O |
| ATOM | 912 | N | THR | A | 350 | 18.432 | −12.130 | −14.680 | 1.00 | 37.32 | | N |
| ANISOU | 912 | N | THR | A | 350 | 4742 | 4621 | 4817 | −56 | −66 | 36 | N |
| ATOM | 913 | CA | THR | A | 350 | 19.718 | −12.304 | −14.026 | 1.00 | 38.14 | | C |
| ANISOU | 913 | CA | THR | A | 350 | 4825 | 4721 | 4943 | −21 | −81 | 20 | C |
| ATOM | 914 | CB | THR | A | 350 | 19.559 | −12.839 | −12.597 | 1.00 | 38.40 | | C |
| ANISOU | 914 | CB | THR | A | 350 | 4860 | 4761 | 4966 | −31 | −61 | 7 | C |
| ATOM | 915 | OG1 | THR | A | 350 | 18.731 | −14.018 | −12.598 | 1.00 | 39.46 | | O |
| ANISOU | 915 | OG1 | THR | A | 350 | 4927 | 4782 | 5282 | −54 | −167 | −97 | O |
| ATOM | 916 | CG2 | THR | A | 350 | 18.928 | −11.782 | −11.709 | 1.00 | 37.43 | | C |
| ANISOU | 916 | CG2 | THR | A | 350 | 4800 | 4532 | 4887 | 17 | −112 | −76 | C |
| ATOM | 917 | C | THR | A | 350 | 20.611 | −13.217 | −14.868 | 1.00 | 38.74 | | C |
| ANISOU | 917 | C | THR | A | 350 | 4927 | 4769 | 5022 | 1 | −79 | 18 | C |
| ATOM | 918 | O | THR | A | 350 | 20.123 | −14.185 | −15.444 | 1.00 | 38.86 | | O |
| ANISOU | 918 | O | THR | A | 350 | 4914 | 4739 | 5112 | 8 | −126 | 13 | O |
| ATOM | 919 | N | LEU | A | 351 | 21.898 | −12.871 | −14.979 | 1.00 | 39.30 | | N |
| ANISOU | 919 | N | LEU | A | 351 | 4977 | 4875 | 5078 | 7 | −62 | 40 | N |
| ATOM | 920 | CA | LEU | A | 351 | 22.867 | −13.658 | −15.755 | 1.00 | 40.29 | | C |
| ANISOU | 920 | CA | LEU | A | 351 | 5136 | 5014 | 5156 | 0 | −38 | 5 | C |
| ATOM | 921 | CB | LEU | A | 351 | 23.357 | −12.912 | −17.004 | 1.00 | 40.56 | | C |
| ANISOU | 921 | CB | LEU | A | 351 | 5169 | 5086 | 5156 | −3 | −7 | −12 | C |
| ATOM | 922 | CG | LEU | A | 351 | 22.508 | −11.927 | −17.836 | 1.00 | 41.22 | | C |
| ANISOU | 922 | CG | LEU | A | 351 | 5191 | 5222 | 5247 | −1 | −7 | 19 | C |
| ATOM | 923 | CD1 | LEU | A | 351 | 23.198 | −11.617 | −19.177 | 1.00 | 42.94 | | C |
| ANISOU | 923 | CD1 | LEU | A | 351 | 5594 | 5366 | 5355 | 47 | 57 | −43 | C |
| ATOM | 924 | CD2 | LEU | A | 351 | 21.117 | −12.418 | −18.099 | 1.00 | 41.57 | | C |
| ANISOU | 924 | CD2 | LEU | A | 351 | 5226 | 5213 | 5354 | 23 | −32 | −39 | C |
| ATOM | 925 | C | LEU | A | 351 | 24.076 | −14.028 | −14.888 | 1.00 | 40.94 | | C |
| ANISOU | 925 | C | LEU | A | 351 | 5192 | 5092 | 5268 | 4 | −33 | −14 | C |
| ATOM | 926 | O | LEU | A | 351 | 24.582 | −13.189 | −14.116 | 1.00 | 41.33 | | O |
| ANISOU | 926 | O | LEU | A | 351 | 5233 | 5217 | 5252 | 6 | −14 | 2 | O |
| ATOM | 927 | N | PRO | A | 352 | 24.561 | −15.277 | −15.020 | 1.00 | 41.37 | | N |
| ANISOU | 927 | N | PRO | A | 352 | 5252 | 5155 | 5309 | −9 | −38 | −17 | N |
| ATOM | 928 | CA | PRO | A | 352 | 25.657 | −15.706 | −14.168 | 1.00 | 41.43 | | C |
| ANISOU | 928 | CA | PRO | A | 352 | 5288 | 5166 | 5287 | 4 | −22 | 0 | C |
| ATOM | 929 | CB | PRO | A | 352 | 25.512 | −17.225 | −14.185 | 1.00 | 41.27 | | C |
| ANISOU | 929 | CB | PRO | A | 352 | 5261 | 5141 | 5277 | −45 | −23 | −16 | C |
| ATOM | 930 | CG | PRO | A | 352 | 25.003 | −17.514 | −15.565 | 1.00 | 41.74 | | C |
| ANISOU | 930 | CG | PRO | A | 352 | 5297 | 5231 | 5329 | −13 | −41 | 16 | C |
| ATOM | 931 | CD | PRO | A | 352 | 24.147 | −16.336 | −15.966 | 1.00 | 41.31 | | C |
| ANISOU | 931 | CD | PRO | A | 352 | 5282 | 5099 | 5315 | 6 | 7 | −17 | C |
| ATOM | 932 | C | PRO | A | 352 | 27.006 | −15.272 | −14.759 | 1.00 | 41.59 | | C |
| ANISOU | 932 | C | PRO | A | 352 | 5340 | 5165 | 5297 | −16 | 0 | 11 | C |
| ATOM | 933 | O | PRO | A | 352 | 27.064 | −14.880 | −15.928 | 1.00 | 42.08 | | O |
| ANISOU | 933 | O | PRO | A | 352 | 5477 | 5215 | 5295 | 16 | 16 | −12 | O |
| ATOM | 934 | N | PRO | A | 353 | 28.089 | −15.328 | −13.967 | 1.00 | 41.79 | | N |
| ANISOU | 934 | N | PRO | A | 353 | 5347 | 5197 | 5334 | −44 | 8 | 11 | N |
| ATOM | 935 | CA | PRO | A | 353 | 29.375 | −14.972 | −14.556 | 1.00 | 42.47 | | C |
| ANISOU | 935 | CA | PRO | A | 353 | 5405 | 5319 | 5412 | −10 | 26 | −14 | C |
| ATOM | 936 | CB | PRO | A | 353 | 30.363 | −15.451 | −13.503 | 1.00 | 42.11 | | C |
| ANISOU | 936 | CB | PRO | A | 353 | 5366 | 5274 | 5359 | 6 | 19 | 1 | C |
| ATOM | 937 | CG | PRO | A | 353 | 29.616 | −15.312 | −12.210 | 1.00 | 41.83 | | C |
| ANISOU | 937 | CG | PRO | A | 353 | 5318 | 5207 | 5368 | −12 | 18 | 34 | C |
| ATOM | 938 | CD | PRO | A | 353 | 28.212 | −15.662 | −12.533 | 1.00 | 41.62 | | C |
| ANISOU | 938 | CD | PRO | A | 353 | 5287 | 5204 | 5320 | −37 | 9 | −1 | C |
| ATOM | 939 | C | PRO | A | 353 | 29.664 | −15.642 | −15.914 | 1.00 | 43.38 | | C |
| ANISOU | 939 | C | PRO | A | 353 | 5539 | 5438 | 5506 | −59 | 7 | 0 | C |
| ATOM | 940 | O | PRO | A | 353 | 29.099 | −16.686 | −16.238 | 1.00 | 43.79 | | O |
| ANISOU | 940 | O | PRO | A | 353 | 5568 | 5453 | 5616 | −92 | −13 | 7 | O |
| ATOM | 941 | N | SER | A | 354 | 30.550 | −15.029 | −16.692 | 1.00 | 44.02 | | N |
| ANISOU | 941 | N | SER | A | 354 | 5647 | 5507 | 5570 | −62 | 32 | 25 | N |
| ATOM | 942 | CA | SER | A | 354 | 31.029 | −15.600 | −17.947 | 1.00 | 44.25 | | C |
| ANISOU | 942 | CA | SER | A | 354 | 5684 | 5544 | 5581 | −36 | 2 | 16 | C |
| ATOM | 943 | CB | SER | A | 354 | 31.801 | −14.533 | −18.728 | 1.00 | 43.63 | | C |
| ANISOU | 943 | CB | SER | A | 354 | 5643 | 5426 | 5508 | −42 | 5 | 44 | C |
| ATOM | 944 | OG | SER | A | 354 | 32.102 | −14.957 | −20.044 | 1.00 | 43.43 | | O |
| ANISOU | 944 | OG | SER | A | 354 | 5647 | 5312 | 5541 | −41 | −107 | 63 | O |

TABLE 7-continued

The atomic structure coordinates of Fc-TM

| | | | | | | | | | | | |
|---|---|---|---|---|---|---|---|---|---|---|---|
| ATOM | 945 | C | SER | A | 354 | 31.932 | −16.816 | −17.684 | 1.00 | 44.69 | C |
| ANISOU | 945 | C | SER | A | 354 | 5752 | 5587 | 5640 | −28 | −2 | 53 | C |
| ATOM | 946 | O | SER | A | 354 | 32.576 | −16.911 | −16.628 | 1.00 | 45.23 | O |
| ANISOU | 946 | O | SER | A | 354 | 5780 | 5703 | 5700 | −78 | −15 | 91 | O |
| ATOM | 947 | N | ARG | A | 355 | 31.978 | −17.740 | −18.639 | 1.00 | 45.17 | N |
| ANISOU | 947 | N | ARG | A | 355 | 5825 | 5641 | 5696 | −10 | 22 | 54 | N |
| ATOM | 948 | CA | ARG | A | 355 | 32.923 | −18.860 | −18.570 | 1.00 | 45.90 | C |
| ANISOU | 948 | CA | ARG | A | 355 | 5863 | 5750 | 5824 | 12 | −2 | 65 | C |
| ATOM | 949 | CB | ARG | A | 355 | 32.871 | −19.735 | −19.832 | 1.00 | 46.10 | C |
| ANISOU | 949 | CB | ARG | A | 355 | 5934 | 5737 | 5845 | 20 | 17 | 36 | C |
| ATOM | 950 | CG | ARG | A | 355 | 33.824 | −20.954 | −19.799 | 1.00 | 47.55 | C |
| ANISOU | 950 | CG | ARG | A | 355 | 6059 | 5947 | 6060 | 67 | 78 | 50 | C |
| ATOM | 951 | CD | ARG | A | 355 | 33.145 | −22.221 | −19.262 | 1.00 | 49.46 | C |
| ANISOU | 951 | CD | ARG | A | 355 | 6372 | 5960 | 6459 | −34 | 23 | 14 | C |
| ATOM | 952 | NE | ARG | A | 355 | 34.055 | −23.376 | −19.231 | 1.00 | 51.31 | N |
| ANISOU | 952 | NE | ARG | A | 355 | 6419 | 6227 | 6849 | 47 | 33 | 24 | N |
| ATOM | 953 | CZ | ARG | A | 355 | 33.662 | −24.659 | −19.211 | 1.00 | 49.87 | C |
| ANISOU | 953 | CZ | ARG | A | 355 | 5961 | 6130 | 6856 | 36 | 60 | 63 | C |
| ATOM | 954 | NH1 | ARG | A | 355 | 32.368 | −24.974 | −19.225 | 1.00 | 51.01 | N |
| ANISOU | 954 | NH1 | ARG | A | 355 | 6530 | 6058 | 6792 | −50 | 14 | 64 | N |
| ATOM | 955 | NH2 | ARG | A | 355 | 34.566 | −25.636 | −19.183 | 1.00 | 51.06 | N |
| ANISOU | 955 | NH2 | ARG | A | 355 | 6527 | 6353 | 6518 | −114 | 122 | 111 | N |
| ATOM | 956 | C | ARG | A | 355 | 34.337 | −18.338 | −18.363 | 1.00 | 46.16 | C |
| ANISOU | 956 | C | ARG | A | 355 | 5873 | 5790 | 5874 | 3 | −27 | 85 | C |
| ATOM | 957 | O | ARG | A | 355 | 35.002 | −18.735 | −17.402 | 1.00 | 46.73 | O |
| ANISOU | 957 | O | ARG | A | 355 | 5996 | 5863 | 5893 | 12 | −54 | 137 | O |
| ATOM | 958 | N | GLU | A | 356 | 34.784 | −17.436 | −19.244 | 1.00 | 46.08 | N |
| ANISOU | 958 | N | GLU | A | 356 | 5863 | 5771 | 5872 | 22 | −47 | 101 | N |
| ATOM | 959 | CA | GLU | A | 356 | 36.160 | −16.914 | −19.201 | 1.00 | 45.95 | C |
| ANISOU | 959 | CA | GLU | A | 356 | 5824 | 5716 | 5915 | −12 | −25 | 83 | C |
| ATOM | 960 | CB | GLU | A | 356 | 36.460 | −16.024 | −20.406 | 1.00 | 46.56 | C |
| ANISOU | 960 | CB | GLU | A | 356 | 5923 | 5802 | 5963 | −14 | −29 | 55 | C |
| ATOM | 961 | CG | GLU | A | 356 | 35.478 | −16.076 | −21.574 | 1.00 | 48.71 | C |
| ANISOU | 961 | CG | GLU | A | 356 | 6157 | 6172 | 6178 | −18 | −52 | −43 | C |
| ATOM | 962 | CD | GLU | A | 356 | 35.388 | −14.734 | −22.325 | 1.00 | 44.20 | C |
| ANISOU | 962 | CD | GLU | A | 356 | 5022 | 5601 | 6171 | −315 | −566 | 188 | C |
| ATOM | 963 | OE1 | GLU | A | 356 | 36.355 | −13.927 | −22.227 | 1.00 | 50.80 | O |
| ANISOU | 963 | OE1 | GLU | A | 356 | 6751 | 6418 | 6131 | 327 | 68 | 47 | O |
| ATOM | 964 | OE2 | GLU | A | 356 | 34.348 | −14.493 | −23.006 | 1.00 | 52.20 | O |
| ANISOU | 964 | OE2 | GLU | A | 356 | 7079 | 5919 | 6833 | −107 | 191 | −53 | O |
| ATOM | 965 | C | GLU | A | 356 | 36.487 | −16.133 | −17.917 | 1.00 | 45.96 | C |
| ANISOU | 965 | C | GLU | A | 356 | 5812 | 5714 | 5934 | −1 | −14 | 67 | C |
| ATOM | 966 | O | GLU | A | 356 | 37.654 | −16.022 | −17.533 | 1.00 | 46.16 | O |
| ANISOU | 966 | O | GLU | A | 356 | 5833 | 5670 | 6036 | 10 | −15 | 75 | O |
| ATOM | 967 | N | GLU | A | 357 | 35.465 | −15.585 | −17.259 | 1.00 | 46.00 | N |
| ANISOU | 967 | N | GLU | A | 357 | 5832 | 5718 | 5928 | −5 | −1 | 46 | N |
| ATOM | 968 | CA | GLU | A | 357 | 35.658 | −14.822 | −16.022 | 1.00 | 46.17 | C |
| ANISOU | 968 | CA | GLU | A | 357 | 5858 | 5789 | 5893 | −19 | −29 | 37 | C |
| ATOM | 969 | CB | GLU | A | 357 | 34.500 | −13.832 | −15.807 | 1.00 | 46.20 | C |
| ANISOU | 969 | CB | GLU | A | 357 | 5855 | 5775 | 5922 | −22 | −31 | 25 | C |
| ATOM | 970 | CG | GLU | A | 357 | 34.741 | −12.830 | −14.672 | 1.00 | 46.03 | C |
| ANISOU | 970 | CG | GLU | A | 357 | 5890 | 5813 | 5786 | −3 | 20 | 5 | C |
| ATOM | 971 | CD | GLU | A | 357 | 33.511 | −12.050 | −14.288 | 1.00 | 45.84 | C |
| ANISOU | 971 | CD | GLU | A | 357 | 5810 | 5736 | 5870 | 18 | −15 | 23 | C |
| ATOM | 972 | OE1 | GLU | A | 357 | 32.394 | −12.574 | −14.466 | 1.00 | 47.43 | O |
| ANISOU | 972 | OE1 | GLU | A | 357 | 5997 | 5800 | 6223 | −69 | 19 | 64 | O |
| ATOM | 973 | OE2 | GLU | A | 357 | 33.665 | −10.908 | −13.793 | 1.00 | 47.18 | O |
| ANISOU | 973 | OE2 | GLU | A | 357 | 6018 | 5915 | 5990 | −47 | 69 | 47 | O |
| ATOM | 974 | C | GLU | A | 357 | 35.791 | −15.713 | −14.789 | 1.00 | 46.48 | C |
| ANISOU | 974 | C | GLU | A | 357 | 5902 | 5797 | 5962 | 2 | −60 | 36 | C |
| ATOM | 975 | O | GLU | A | 357 | 36.116 | −15.242 | −13.695 | 1.00 | 46.82 | O |
| ANISOU | 975 | O | GLU | A | 357 | 5954 | 5880 | 5956 | 12 | −81 | 46 | O |
| ATOM | 976 | N | MET | A | 358 | 35.527 | −17.000 | −14.966 | 1.00 | 47.05 | N |
| ANISOU | 976 | N | MET | A | 358 | 5945 | 5879 | 6053 | −19 | −52 | 49 | N |
| ATOM | 977 | CA | MET | A | 358 | 35.559 | −17.963 | −13.864 | 1.00 | 47.74 | C |
| ANISOU | 977 | CA | MET | A | 358 | 6017 | 5957 | 6164 | −17 | −69 | 67 | C |
| ATOM | 978 | CB | MET | A | 358 | 34.728 | −19.192 | −14.238 | 1.00 | 48.21 | C |
| ANISOU | 978 | CB | MET | A | 358 | 6105 | 5944 | 6269 | −34 | −75 | 93 | C |
| ATOM | 979 | CG | MET | A | 358 | 33.208 | −18.945 | −14.199 | 1.00 | 49.31 | C |
| ANISOU | 979 | CG | MET | A | 358 | 6165 | 6106 | 6465 | −8 | −14 | 71 | C |
| ATOM | 980 | SD | MET | A | 358 | 32.552 | −19.075 | −12.527 | 1.00 | 52.44 | S |
| ANISOU | 980 | SD | MET | A | 358 | 6730 | 6476 | 6717 | −163 | 20 | 106 | S |
| ATOM | 981 | CE | MET | A | 358 | 32.822 | −17.454 | −11.834 | 1.00 | 51.39 | C |
| ANISOU | 981 | CE | MET | A | 358 | 6475 | 6527 | 6523 | 47 | −35 | 165 | C |
| ATOM | 982 | C | MET | A | 358 | 36.981 | −18.353 | −13.440 | 1.00 | 47.84 | C |
| ANISOU | 982 | C | MET | A | 358 | 6037 | 5968 | 6170 | −13 | −76 | 65 | C |
| ATOM | 983 | O | MET | A | 358 | 37.261 | −19.524 | −13.131 | 1.00 | 48.04 | O |
| ANISOU | 983 | O | MET | A | 358 | 6128 | 5948 | 6176 | −23 | −92 | 42 | O |

TABLE 7-continued

The atomic structure coordinates of Fc-TM

| | | | | | | | | | | | |
|---|---|---|---|---|---|---|---|---|---|---|---|
| ATOM | 984 | N | THR | A | 359 | 37.855 | −17.348 | −13.399 | 1.00 | 47.68 | N |
| ANISOU | 984 | N | THR | A | 359 | 6033 | 5948 | 6134 | −20 | −77 | 59 | N |
| ATOM | 985 | CA | THR | A | 359 | 39.290 | −17.516 | −13.163 | 1.00 | 47.64 | C |
| ANISOU | 985 | CA | THR | A | 359 | 6020 | 5995 | 6085 | 0 | −63 | 39 | C |
| ATOM | 986 | CB | THR | A | 359 | 40.100 | −17.070 | −14.403 | 1.00 | 47.73 | C |
| ANISOU | 986 | CB | THR | A | 359 | 6003 | 6022 | 6108 | 15 | −50 | 37 | C |
| ATOM | 987 | OG1 | THR | A | 359 | 39.769 | −17.914 | −15.522 | 1.00 | 49.09 | O |
| ANISOU | 987 | OG1 | THR | A | 359 | 6271 | 6170 | 6209 | 91 | −41 | 16 | O |
| ATOM | 988 | CG2 | THR | A | 359 | 41.608 | −17.130 | −14.143 | 1.00 | 48.38 | C |
| ANISOU | 988 | CG2 | THR | A | 359 | 6138 | 6071 | 6172 | −8 | −78 | 7 | C |
| ATOM | 989 | C | THR | A | 359 | 39.722 | −16.691 | −11.958 | 1.00 | 47.42 | C |
| ANISOU | 989 | C | THR | A | 359 | 5966 | 5981 | 6070 | −5 | −71 | 67 | C |
| ATOM | 990 | O | THR | A | 359 | 40.618 | −17.090 | −11.219 | 1.00 | 47.99 | O |
| ANISOU | 990 | O | THR | A | 359 | 6050 | 6064 | 6120 | 6 | −66 | 108 | O |
| ATOM | 991 | N | LYS | A | 360 | 39.081 | −15.545 | −11.763 | 1.00 | 46.86 | N |
| ANISOU | 991 | N | LYS | A | 360 | 5868 | 5926 | 6009 | 11 | −50 | 41 | N |
| ATOM | 992 | CA | LYS | A | 360 | 39.494 | −14.595 | −10.743 | 1.00 | 47.00 | C |
| ANISOU | 992 | CA | LYS | A | 360 | 5889 | 5971 | 5996 | 29 | −30 | 61 | C |
| ATOM | 993 | CB | LYS | A | 360 | 39.110 | −13.153 | −11.142 | 1.00 | 46.95 | C |
| ANISOU | 993 | CB | LYS | A | 360 | 5886 | 5968 | 5983 | 21 | −5 | 46 | C |
| ATOM | 994 | CG | LYS | A | 360 | 38.907 | −12.927 | −12.637 | 1.00 | 47.63 | C |
| ANISOU | 994 | CG | LYS | A | 360 | 5963 | 6082 | 6050 | 61 | −16 | 111 | C |
| ATOM | 995 | CD | LYS | A | 360 | 40.223 | −12.855 | −13.426 | 1.00 | 50.53 | C |
| ANISOU | 995 | CD | LYS | A | 360 | 6261 | 6404 | 6531 | 60 | 21 | 9 | C |
| ATOM | 996 | CE | LYS | A | 360 | 39.961 | −12.875 | −14.932 | 1.00 | 49.77 | C |
| ANISOU | 996 | CE | LYS | A | 360 | 6180 | 6480 | 6250 | 30 | 132 | 33 | C |
| ATOM | 997 | NZ | LYS | A | 360 | 41.160 | −12.482 | −15.751 | 1.00 | 53.54 | N |
| ANISOU | 997 | NZ | LYS | A | 360 | 6756 | 6647 | 6937 | 76 | 9 | −32 | N |
| ATOM | 998 | C | LYS | A | 360 | 38.846 | −15.001 | −9.427 | 1.00 | 47.06 | C |
| ANISOU | 998 | C | LYS | A | 360 | 5905 | 5954 | 6021 | 12 | −44 | 84 | C |
| ATOM | 999 | O | LYS | A | 360 | 38.141 | −16.004 | −9.374 | 1.00 | 47.87 | O |
| ANISOU | 999 | O | LYS | A | 360 | 6011 | 6041 | 6135 | 7 | −64 | 106 | O |
| ATOM | 1000 | N | ASN | A | 361 | 39.081 | −14.239 | −8.368 | 1.00 | 46.80 | N |
| ANISOU | 1000 | N | ASN | A | 361 | 5895 | 5940 | 5944 | 39 | −18 | 64 | N |
| ATOM | 1001 | CA | ASN | A | 361 | 38.505 | −14.578 | −7.076 | 1.00 | 47.13 | C |
| ANISOU | 1001 | CA | ASN | A | 361 | 5932 | 5982 | 5992 | 48 | −3 | 96 | C |
| ATOM | 1002 | CB | ASN | A | 361 | 39.554 | −14.470 | −5.963 | 1.00 | 47.64 | C |
| ANISOU | 1002 | CB | ASN | A | 361 | 5962 | 6070 | 6066 | 49 | −24 | 69 | C |
| ATOM | 1003 | CG | ASN | A | 361 | 40.414 | −13.225 | −6.085 | 1.00 | 48.35 | C |
| ANISOU | 1003 | CG | ASN | A | 361 | 6032 | 6093 | 6242 | 20 | 57 | 53 | C |
| ATOM | 1004 | OD1 | ASN | A | 361 | 39.932 | −12.094 | −5.891 | 1.00 | 50.52 | O |
| ANISOU | 1004 | OD1 | ASN | A | 361 | 6442 | 6402 | 6351 | 180 | 54 | 178 | O |
| ATOM | 1005 | ND2 | ASN | A | 361 | 41.709 | −13.426 | −6.389 | 1.00 | 49.41 | N |
| ANISOU | 1005 | ND2 | ASN | A | 361 | 6268 | 6360 | 6143 | 31 | 14 | 44 | N |
| ATOM | 1006 | C | ASN | A | 361 | 37.271 | −13.744 | −6.746 | 1.00 | 46.75 | C |
| ANISOU | 1006 | C | ASN | A | 361 | 5840 | 5963 | 5960 | 64 | −21 | 151 | C |
| ATOM | 1007 | O | ASN | A | 361 | 36.510 | −14.058 | −5.815 | 1.00 | 47.14 | O |
| ANISOU | 1007 | O | ASN | A | 361 | 5925 | 6049 | 5938 | 101 | −35 | 168 | O |
| ATOM | 1008 | N | GLN | A | 362 | 37.081 | −12.666 | −7.503 | 1.00 | 46.36 | N |
| ANISOU | 1008 | N | GLN | A | 362 | 5775 | 5900 | 5936 | 28 | 11 | 116 | N |
| ATOM | 1009 | CA | GLN | A | 362 | 35.802 | −11.967 | −7.500 | 1.00 | 45.32 | C |
| ANISOU | 1009 | CA | GLN | A | 362 | 5680 | 5745 | 5794 | 29 | −4 | 84 | C |
| ATOM | 1010 | CB | GLN | A | 362 | 35.974 | −10.507 | −7.118 | 1.00 | 45.41 | C |
| ANISOU | 1010 | CB | GLN | A | 362 | 5707 | 5735 | 5811 | 14 | −8 | 83 | C |
| ATOM | 1011 | CG | GLN | A | 362 | 36.150 | −10.334 | −5.621 | 1.00 | 45.58 | C |
| ANISOU | 1011 | CG | GLN | A | 362 | 5724 | 5792 | 5802 | −53 | 11 | 71 | C |
| ATOM | 1012 | CD | GLN | A | 362 | 36.166 | −8.891 | −5.204 | 1.00 | 45.91 | C |
| ANISOU | 1012 | CD | GLN | A | 362 | 5751 | 5817 | 5875 | 17 | 163 | 20 | C |
| ATOM | 1013 | OE1 | GLN | A | 362 | 35.381 | −8.478 | −4.363 | 1.00 | 47.89 | O |
| ANISOU | 1013 | OE1 | GLN | A | 362 | 6152 | 5957 | 6085 | −12 | 83 | 107 | O |
| ATOM | 1014 | NE2 | GLN | A | 362 | 37.063 | −8.105 | −5.797 | 1.00 | 48.21 | N |
| ANISOU | 1014 | NE2 | GLN | A | 362 | 6100 | 5959 | 6259 | 38 | 0 | 10 | N |
| ATOM | 1015 | C | GLN | A | 362 | 35.119 | −12.139 | −8.842 | 1.00 | 44.69 | C |
| ANISOU | 1015 | C | GLN | A | 362 | 5577 | 5712 | 5689 | 45 | 2 | 97 | C |
| ATOM | 1016 | O | GLN | A | 362 | 35.779 | −12.142 | −9.875 | 1.00 | 45.00 | O |
| ANISOU | 1016 | O | GLN | A | 362 | 5562 | 5769 | 5766 | 68 | 40 | 92 | O |
| ATOM | 1017 | N | VAL | A | 363 | 33.799 | −12.329 | −8.807 | 1.00 | 44.15 | N |
| ANISOU | 1017 | N | VAL | A | 363 | 5530 | 5638 | 5605 | 38 | −12 | 83 | N |
| ATOM | 1018 | CA | VAL | A | 363 | 32.983 | −12.486 | −10.023 | 1.00 | 43.03 | C |
| ANISOU | 1018 | CA | VAL | A | 363 | 5413 | 5445 | 5488 | 52 | −6 | 43 | C |
| ATOM | 1019 | CB | VAL | A | 363 | 32.402 | −13.912 | −10.140 | 1.00 | 43.18 | C |
| ANISOU | 1019 | CB | VAL | A | 363 | 5453 | 5459 | 5492 | 67 | 13 | 28 | C |
| ATOM | 1020 | CG1 | VAL | A | 363 | 33.520 | −14.906 | −10.390 | 1.00 | 43.95 | C |
| ANISOU | 1020 | CG1 | VAL | A | 363 | 5470 | 5624 | 5603 | 82 | 29 | 48 | C |
| ATOM | 1021 | CG2 | VAL | A | 363 | 31.600 | −14.302 | −8.882 | 1.00 | 42.30 | C |
| ANISOU | 1021 | CG2 | VAL | A | 363 | 5359 | 5266 | 5446 | 80 | −4 | 36 | C |
| ATOM | 1022 | C | VAL | A | 363 | 31.853 | −11.440 | −10.120 | 1.00 | 42.52 | C |
| ANISOU | 1022 | C | VAL | A | 363 | 5376 | 5398 | 5380 | 63 | −27 | 59 | C |

TABLE 7-continued

The atomic structure coordinates of Fc-TM

| | | | | | | | | | | | | |
|---|---|---|---|---|---|---|---|---|---|---|---|---|
| ATOM | 1023 | O | VAL | A | 363 | 31.447 | −10.834 | −9.104 | 1.00 | 42.81 | | O |
| ANISOU | 1023 | O | VAL | A | 363 | 5403 | 5365 | 5495 | 71 | −45 | 3 | O |
| ATOM | 1024 | N | SER | A | 364 | 31.354 | −11.252 | −11.343 | 1.00 | 41.31 | | N |
| ANISOU | 1024 | N | SER | A | 364 | 5256 | 5207 | 5231 | 62 | −5 | 118 | N |
| ATOM | 1025 | CA | SER | A | 364 | 30.298 | −10.280 | −11.635 | 1.00 | 40.20 | | C |
| ANISOU | 1025 | CA | SER | A | 364 | 5150 | 5057 | 5065 | 36 | −19 | 138 | C |
| ATOM | 1026 | CB | SER | A | 364 | 30.652 | −9.403 | −12.850 | 1.00 | 39.70 | | C |
| ANISOU | 1026 | CB | SER | A | 364 | 5109 | 4974 | 5002 | 54 | −65 | 171 | C |
| ATOM | 1027 | OG | SER | A | 364 | 31.895 | −8.732 | −12.692 | 1.00 | 37.97 | | O |
| ANISOU | 1027 | OG | SER | A | 364 | 5007 | 4675 | 4744 | 119 | −32 | 315 | O |
| ATOM | 1028 | C | SER | A | 364 | 28.962 | −10.967 | −11.868 | 1.00 | 39.95 | | C |
| ANISOU | 1028 | C | SER | A | 364 | 5127 | 5016 | 5034 | 45 | −31 | 160 | C |
| ATOM | 1029 | O | SER | A | 364 | 28.831 | −11.854 | −12.735 | 1.00 | 39.44 | | O |
| ANISOU | 1029 | O | SER | A | 364 | 5142 | 4888 | 4955 | 54 | −17 | 221 | O |
| ATOM | 1030 | N | LEU | A | 365 | 27.981 | −10.554 | −11.071 | 1.00 | 39.87 | | N |
| ANISOU | 1030 | N | LEU | A | 365 | 5068 | 5037 | 5042 | 61 | −21 | 140 | N |
| ATOM | 1031 | CA | LEU | A | 365 | 26.589 | −10.955 | −11.269 | 1.00 | 39.99 | | C |
| ANISOU | 1031 | CA | LEU | A | 365 | 5074 | 5073 | 5045 | 9 | −33 | 86 | C |
| ATOM | 1032 | CB | LEU | A | 365 | 25.924 | −11.321 | −9.937 | 1.00 | 40.04 | | C |
| ANISOU | 1032 | CB | LEU | A | 365 | 5074 | 5098 | 5040 | −11 | −44 | 81 | C |
| ATOM | 1033 | CG | LEU | A | 365 | 26.530 | −12.451 | −9.066 | 1.00 | 40.30 | | C |
| ANISOU | 1033 | CG | LEU | A | 365 | 5182 | 5030 | 5100 | 14 | −46 | 30 | C |
| ATOM | 1034 | CD1 | LEU | A | 365 | 25.665 | −12.646 | −7.874 | 1.00 | 39.40 | | C |
| ANISOU | 1034 | CD1 | LEU | A | 365 | 5149 | 4949 | 4869 | −42 | 31 | 113 | C |
| ATOM | 1035 | CD2 | LEU | A | 365 | 26.697 | −13.782 | −9.784 | 1.00 | 39.06 | | C |
| ANISOU | 1035 | CD2 | LEU | A | 365 | 5102 | 4928 | 4808 | −9 | −43 | 35 | C |
| ATOM | 1036 | C | LEU | A | 365 | 25.801 | −9.848 | −11.985 | 1.00 | 39.79 | | C |
| ANISOU | 1036 | C | LEU | A | 365 | 4994 | 5066 | 5057 | 24 | −48 | 75 | C |
| ATOM | 1037 | O | LEU | A | 365 | 25.823 | −8.677 | −11.582 | 1.00 | 38.88 | | O |
| ANISOU | 1037 | O | LEU | A | 365 | 4910 | 4982 | 4882 | 74 | −17 | 36 | O |
| ATOM | 1038 | N | THR | A | 366 | 25.099 | −10.244 | −13.044 | 1.00 | 39.92 | | N |
| ANISOU | 1038 | N | THR | A | 366 | 5000 | 5095 | 5069 | 45 | −33 | 66 | N |
| ATOM | 1039 | CA | THR | A | 366 | 24.421 | −9.292 | −13.933 | 1.00 | 39.88 | | C |
| ANISOU | 1039 | CA | THR | A | 366 | 4988 | 5034 | 5128 | 11 | −42 | 67 | C |
| ATOM | 1040 | CB | THR | A | 366 | 24.903 | −9.487 | −15.393 | 1.00 | 39.60 | | C |
| ANISOU | 1040 | CB | THR | A | 366 | 4964 | 5029 | 5051 | 11 | −16 | 62 | C |
| ATOM | 1041 | OG1 | THR | A | 366 | 26.320 | −9.308 | −15.459 | 1.00 | 38.90 | | O |
| ANISOU | 1041 | OG1 | THR | A | 366 | 5015 | 4949 | 4816 | −20 | −181 | 162 | O |
| ATOM | 1042 | CG2 | THR | A | 366 | 24.235 | −8.512 | −16.335 | 1.00 | 38.62 | | C |
| ANISOU | 1042 | CG2 | THR | A | 366 | 4770 | 4839 | 5062 | −13 | 46 | 66 | C |
| ATOM | 1043 | C | THR | A | 366 | 22.871 | −9.311 | −13.869 | 1.00 | 39.94 | | C |
| ANISOU | 1043 | C | THR | A | 366 | 4957 | 5035 | 5180 | 37 | −21 | 65 | C |
| ATOM | 1044 | O | THR | A | 366 | 22.232 | −10.335 | −14.103 | 1.00 | 39.93 | | O |
| ANISOU | 1044 | O | THR | A | 366 | 4869 | 5040 | 5262 | 43 | 12 | 60 | O |
| ATOM | 1045 | N | CYS | A | 367 | 22.280 | −8.161 | −13.565 | 1.00 | 39.76 | | N |
| ANISOU | 1045 | N | CYS | A | 367 | 4930 | 5062 | 5115 | 29 | −27 | 86 | N |
| ATOM | 1046 | CA | CYS | A | 367 | 20.852 | −7.960 | −13.805 | 1.00 | 39.32 | | C |
| ANISOU | 1046 | CA | CYS | A | 367 | 4931 | 4985 | 5022 | 26 | −8 | 80 | C |
| ATOM | 1047 | CB | CYS | A | 367 | 20.233 | −7.205 | −12.634 | 1.00 | 39.39 | | C |
| ANISOU | 1047 | CB | CYS | A | 367 | 4944 | 5076 | 4946 | 21 | −2 | 117 | C |
| ATOM | 1048 | SG | CYS | A | 367 | 18.472 | −7.483 | −12.391 | 1.00 | 39.53 | | S |
| ANISOU | 1048 | SG | CYS | A | 367 | 4830 | 5094 | 5094 | 24 | −129 | 170 | S |
| ATOM | 1049 | C | CYS | A | 367 | 20.601 | −7.210 | −15.139 | 1.00 | 38.81 | | C |
| ANISOU | 1049 | C | CYS | A | 367 | 4865 | 4957 | 4923 | 15 | −1 | 46 | C |
| ATOM | 1050 | O | CYS | A | 367 | 21.014 | −6.067 | −15.311 | 1.00 | 38.63 | | O |
| ANISOU | 1050 | O | CYS | A | 367 | 4817 | 5047 | 4814 | 9 | 43 | 133 | O |
| ATOM | 1051 | N | LEU | A | 368 | 19.929 | −7.861 | −16.076 | 1.00 | 38.38 | | N |
| ANISOU | 1051 | N | LEU | A | 368 | 4830 | 4891 | 4859 | 14 | 7 | 46 | N |
| ATOM | 1052 | CA | LEU | A | 368 | 19.456 | −7.190 | −17.282 | 1.00 | 37.80 | | C |
| ANISOU | 1052 | CA | LEU | A | 368 | 4781 | 4779 | 4800 | −21 | 24 | 8 | C |
| ATOM | 1053 | CB | LEU | A | 368 | 19.625 | −8.079 | −18.516 | 1.00 | 37.58 | | C |
| ANISOU | 1053 | CB | LEU | A | 368 | 4733 | 4775 | 4770 | −33 | 5 | 0 | C |
| ATOM | 1054 | CG | LEU | A | 368 | 18.982 | −7.599 | −19.827 | 1.00 | 37.13 | | C |
| ANISOU | 1054 | CG | LEU | A | 368 | 4703 | 4665 | 4738 | −43 | 63 | −35 | C |
| ATOM | 1055 | CD1 | LEU | A | 368 | 19.398 | −6.178 | −20.237 | 1.00 | 34.47 | | C |
| ANISOU | 1055 | CD1 | LEU | A | 368 | 4419 | 4312 | 4366 | −26 | 110 | −219 | C |
| ATOM | 1056 | CD2 | LEU | A | 368 | 19.275 | −8.606 | −20.956 | 1.00 | 37.22 | | C |
| ANISOU | 1056 | CD2 | LEU | A | 368 | 4639 | 4690 | 4810 | −62 | −1 | −69 | C |
| ATOM | 1057 | C | LEU | A | 368 | 17.999 | −6.740 | −17.158 | 1.00 | 37.59 | | C |
| ANISOU | 1057 | C | LEU | A | 368 | 4799 | 4734 | 4747 | −15 | 12 | 21 | C |
| ATOM | 1058 | O | LEU | A | 368 | 17.086 | −7.556 | −17.070 | 1.00 | 38.09 | | O |
| ANISOU | 1058 | O | LEU | A | 368 | 4826 | 4762 | 4883 | 0 | 0 | 19 | O |
| ATOM | 1059 | N | VAL | A | 369 | 17.785 | −5.433 | −17.182 | 1.00 | 36.66 | | N |
| ANISOU | 1059 | N | VAL | A | 369 | 4710 | 4628 | 4590 | −14 | 8 | −31 | N |
| ATOM | 1060 | CA | VAL | A | 369 | 16.437 | −4.899 | −17.150 | 1.00 | 35.51 | | C |
| ANISOU | 1060 | CA | VAL | A | 369 | 4618 | 4432 | 4441 | −32 | 24 | −25 | C |
| ATOM | 1061 | CB | VAL | A | 369 | 16.240 | −3.901 | −15.978 | 1.00 | 35.04 | | C |
| ANISOU | 1061 | CB | VAL | A | 369 | 4579 | 4397 | 4336 | −16 | 9 | −42 | C |

TABLE 7-continued

| The atomic structure coordinates of Fc-TM | | | | | | | | | | | |
|---|---|---|---|---|---|---|---|---|---|---|---|
| ATOM | 1062 | CG1 | VAL | A | 369 | 14.774 | −3.571 | −15.809 | 1.00 | 32.99 | C |
| ANISOU | 1062 | CG1 | VAL | A | 369 | 4372 | 4088 | 4074 | −154 | 64 | −67 | C |
| ATOM | 1063 | CG2 | VAL | A | 369 | 16.828 | −4.445 | −14.690 | 1.00 | 33.45 | C |
| ANISOU | 1063 | CG2 | VAL | A | 369 | 4399 | 4030 | 4280 | −68 | 82 | −84 | C |
| ATOM | 1064 | C | VAL | A | 369 | 16.149 | −4.214 | −18.495 | 1.00 | 35.59 | C |
| ANISOU | 1064 | C | VAL | A | 369 | 4633 | 4477 | 4411 | −5 | 55 | −52 | C |
| ATOM | 1065 | O | VAL | A | 369 | 16.819 | −3.261 | −18.862 | 1.00 | 33.94 | O |
| ANISOU | 1065 | O | VAL | A | 369 | 4433 | 4347 | 4113 | −86 | 75 | 14 | O |
| ATOM | 1066 | N | LYS | A | 370 | 15.142 | −4.699 | −19.212 | 1.00 | 35.68 | N |
| ANISOU | 1066 | N | LYS | A | 370 | 4629 | 4439 | 4486 | 5 | 61 | −52 | N |
| ATOM | 1067 | CA | LYS | A | 370 | 14.862 | −4.155 | −20.524 | 1.00 | 36.56 | C |
| ANISOU | 1067 | CA | LYS | A | 370 | 4733 | 4538 | 4619 | −4 | 54 | −72 | C |
| ATOM | 1068 | CB | LYS | A | 370 | 15.582 | −4.963 | −21.616 | 1.00 | 37.40 | C |
| ANISOU | 1068 | CB | LYS | A | 370 | 4812 | 4631 | 4766 | 21 | 15 | −67 | C |
| ATOM | 1069 | CG | LYS | A | 370 | 14.926 | −6.255 | −22.047 | 1.00 | 38.42 | C |
| ANISOU | 1069 | CG | LYS | A | 370 | 4880 | 4762 | 4953 | −43 | −18 | −43 | C |
| ATOM | 1070 | CD | LYS | A | 370 | 15.576 | −6.722 | −23.346 | 1.00 | 38.00 | C |
| ANISOU | 1070 | CD | LYS | A | 370 | 4710 | 5016 | 4710 | −111 | −78 | −144 | C |
| ATOM | 1071 | CE | LYS | A | 370 | 14.530 | −7.210 | −24.325 | 1.00 | 42.54 | C |
| ANISOU | 1071 | CE | LYS | A | 370 | 5280 | 5298 | 5583 | 88 | 107 | −138 | C |
| ATOM | 1072 | NZ | LYS | A | 370 | 14.737 | −6.578 | −25.665 | 1.00 | 40.11 | N |
| ANISOU | 1072 | NZ | LYS | A | 370 | 5090 | 5259 | 4890 | −7 | 15 | 108 | N |
| ATOM | 1073 | C | LYS | A | 370 | 13.393 | −3.913 | −20.847 | 1.00 | 36.36 | C |
| ANISOU | 1073 | C | LYS | A | 370 | 4750 | 4479 | 4586 | 26 | 55 | −79 | C |
| ATOM | 1074 | O | LYS | A | 370 | 12.496 | −4.426 | −20.174 | 1.00 | 35.86 | O |
| ANISOU | 1074 | O | LYS | A | 370 | 4750 | 4336 | 4537 | 38 | 36 | −46 | O |
| ATOM | 1075 | N | GLY | A | 371 | 13.164 | −3.101 | −21.873 | 1.00 | 36.40 | N |
| ANISOU | 1075 | N | GLY | A | 371 | 4754 | 4514 | 4560 | 14 | 101 | −70 | N |
| ATOM | 1076 | CA | GLY | A | 371 | 11.821 | −2.792 | −22.348 | 1.00 | 36.43 | C |
| ANISOU | 1076 | CA | GLY | A | 371 | 4719 | 4559 | 4561 | 16 | 44 | −51 | C |
| ATOM | 1077 | C | GLY | A | 371 | 10.981 | −1.871 | −21.467 | 1.00 | 36.58 | C |
| ANISOU | 1077 | C | GLY | A | 371 | 4751 | 4566 | 4581 | 22 | 1 | −59 | C |
| ATOM | 1078 | O | GLY | A | 371 | 9.739 | −1.850 | −21.601 | 1.00 | 36.50 | O |
| ANISOU | 1078 | O | GLY | A | 371 | 4704 | 4546 | 4617 | 42 | 12 | −66 | O |
| ATOM | 1079 | N | PHE | A | 372 | 11.624 | −1.118 | −20.566 | 1.00 | 35.97 | N |
| ANISOU | 1079 | N | PHE | A | 372 | 4631 | 4483 | 4552 | −15 | −16 | −47 | N |
| ATOM | 1080 | CA | PHE | A | 372 | 10.853 | −0.250 | −19.635 | 1.00 | 34.98 | C |
| ANISOU | 1080 | CA | PHE | A | 372 | 4543 | 4431 | 4315 | −24 | −65 | −38 | C |
| ATOM | 1081 | CB | PHE | A | 372 | 11.347 | −0.338 | −18.188 | 1.00 | 34.15 | C |
| ANISOU | 1081 | CB | PHE | A | 372 | 4462 | 4305 | 4208 | −30 | −25 | 7 | C |
| ATOM | 1082 | CG | PHE | A | 372 | 12.732 | 0.220 | −17.952 | 1.00 | 31.81 | C |
| ANISOU | 1082 | CG | PHE | A | 372 | 4269 | 4040 | 3776 | 7 | 34 | 78 | C |
| ATOM | 1083 | CD1 | PHE | A | 372 | 12.902 | 1.534 | −17.521 | 1.00 | 29.99 | C |
| ANISOU | 1083 | CD1 | PHE | A | 372 | 4046 | 4049 | 3299 | −75 | 66 | 87 | C |
| ATOM | 1084 | CE1 | PHE | A | 372 | 14.158 | 2.046 | −17.270 | 1.00 | 29.52 | C |
| ANISOU | 1084 | CE1 | PHE | A | 372 | 4091 | 3871 | 3254 | −37 | 73 | 41 | C |
| ATOM | 1085 | CZ | PHE | A | 372 | 15.278 | 1.245 | −17.432 | 1.00 | 30.63 | C |
| ANISOU | 1085 | CZ | PHE | A | 372 | 4204 | 3924 | 3509 | −6 | 99 | 84 | C |
| ATOM | 1086 | CE2 | PHE | A | 372 | 15.126 | −0.073 | −17.842 | 1.00 | 30.13 | C |
| ANISOU | 1086 | CE2 | PHE | A | 372 | 4163 | 4003 | 3281 | −10 | 108 | 120 | C |
| ATOM | 1087 | CD2 | PHE | A | 372 | 13.849 | −0.580 | −18.094 | 1.00 | 29.81 | C |
| ANISOU | 1087 | CD2 | PHE | A | 372 | 4076 | 3919 | 3330 | −84 | 142 | 106 | C |
| ATOM | 1088 | C | PHE | A | 372 | 10.664 | 1.198 | −20.081 | 1.00 | 34.59 | C |
| ANISOU | 1088 | C | PHE | A | 372 | 4487 | 4398 | 4257 | −43 | −112 | −70 | C |
| ATOM | 1089 | O | PHE | A | 372 | 11.487 | 1.745 | −20.787 | 1.00 | 33.11 | O |
| ANISOU | 1089 | O | PHE | A | 372 | 4403 | 4216 | 3961 | −15 | −136 | −82 | O |
| ATOM | 1090 | N | TYR | A | 373 | 9.549 | 1.783 | −19.647 | 1.00 | 34.91 | N |
| ANISOU | 1090 | N | TYR | A | 373 | 4521 | 4486 | 4255 | −49 | −176 | −43 | N |
| ATOM | 1091 | CA | TYR | A | 373 | 9.193 | 3.175 | −19.910 | 1.00 | 35.31 | C |
| ANISOU | 1091 | CA | TYR | A | 373 | 4589 | 4543 | 4284 | −16 | −143 | −35 | C |
| ATOM | 1092 | CB | TYR | A | 373 | 8.567 | 3.358 | −21.307 | 1.00 | 35.68 | C |
| ANISOU | 1092 | CB | TYR | A | 373 | 4580 | 4691 | 4283 | −10 | −157 | −87 | C |
| ATOM | 1093 | CG | TYR | A | 373 | 8.621 | 4.789 | −21.762 | 1.00 | 34.18 | C |
| ANISOU | 1093 | CG | TYR | A | 373 | 4411 | 4534 | 4041 | −21 | −162 | −10 | C |
| ATOM | 1094 | CD1 | TYR | A | 373 | 9.690 | 5.243 | −22.509 | 1.00 | 34.45 | C |
| ANISOU | 1094 | CD1 | TYR | A | 373 | 4413 | 4527 | 4147 | 23 | −212 | −54 | C |
| ATOM | 1095 | CE1 | TYR | A | 373 | 9.774 | 6.554 | −22.912 | 1.00 | 34.42 | C |
| ANISOU | 1095 | CE1 | TYR | A | 373 | 4358 | 4572 | 4148 | −101 | −173 | −16 | C |
| ATOM | 1096 | CZ | TYR | A | 373 | 8.780 | 7.423 | −22.558 | 1.00 | 34.48 | C |
| ANISOU | 1096 | CZ | TYR | A | 373 | 4422 | 4435 | 4243 | −45 | −91 | 0 | C |
| ATOM | 1097 | OH | TYR | A | 373 | 8.873 | 8.715 | −22.969 | 1.00 | 36.84 | O |
| ANISOU | 1097 | OH | TYR | A | 373 | 4769 | 4819 | 4407 | −28 | −199 | 64 | O |
| ATOM | 1098 | CE2 | TYR | A | 373 | 7.702 | 7.007 | −21.797 | 1.00 | 35.52 | C |
| ANISOU | 1098 | CE2 | TYR | A | 373 | 4524 | 4712 | 4258 | 83 | −192 | −76 | C |
| ATOM | 1099 | CD2 | TYR | A | 373 | 7.622 | 5.698 | −21.414 | 1.00 | 33.27 | C |
| ANISOU | 1099 | CD2 | TYR | A | 373 | 4467 | 4373 | 3798 | −92 | −214 | 63 | C |
| ATOM | 1100 | C | TYR | A | 373 | 8.202 | 3.675 | −18.866 | 1.00 | 35.10 | C |
| ANISOU | 1100 | C | TYR | A | 373 | 4544 | 4556 | 4234 | −5 | −101 | 20 | C |

TABLE 7-continued

The atomic structure coordinates of Fc-TM

| | | | | | | | | | | | | |
|---|---|---|---|---|---|---|---|---|---|---|---|---|
| ATOM | 1101 | O | TYR | A | 373 | 7.290 | 2.959 | −18.526 | 1.00 | 35.49 | | O |
| ANISOU | 1101 | O | TYR | A | 373 | 4648 | 4556 | 4281 | −4 | −149 | −115 | O |
| ATOM | 1102 | N | PRO | A | 374 | 8.373 | 4.908 | −18.352 | 1.00 | 34.96 | | N |
| ANISOU | 1102 | N | PRO | A | 374 | 4537 | 4551 | 4194 | 45 | −66 | 59 | N |
| ATOM | 1103 | CA | PRO | A | 374 | 9.466 | 5.844 | −18.520 | 1.00 | 35.26 | | C |
| ANISOU | 1103 | CA | PRO | A | 374 | 4581 | 4561 | 4251 | 42 | −69 | 28 | C |
| ATOM | 1104 | CB | PRO | A | 374 | 8.950 | 7.099 | −17.813 | 1.00 | 35.21 | | C |
| ANISOU | 1104 | CB | PRO | A | 374 | 4553 | 4560 | 4265 | 58 | −42 | 60 | C |
| ATOM | 1105 | CG | PRO | A | 374 | 7.997 | 6.614 | −16.837 | 1.00 | 35.05 | | C |
| ANISOU | 1105 | CG | PRO | A | 374 | 4419 | 4469 | 4428 | 84 | −49 | 79 | C |
| ATOM | 1106 | CD | PRO | A | 374 | 7.309 | 5.495 | −17.527 | 1.00 | 35.26 | | C |
| ANISOU | 1106 | CD | PRO | A | 374 | 4566 | 4516 | 4316 | 65 | −103 | 72 | C |
| ATOM | 1107 | C | PRO | A | 374 | 10.783 | 5.361 | −17.913 | 1.00 | 35.32 | | C |
| ANISOU | 1107 | C | PRO | A | 374 | 4595 | 4588 | 4236 | 62 | −26 | 0 | C |
| ATOM | 1108 | O | PRO | A | 374 | 10.835 | 4.264 | −17.344 | 1.00 | 35.13 | | O |
| ANISOU | 1108 | O | PRO | A | 374 | 4500 | 4669 | 4178 | 31 | −57 | −52 | O |
| ATOM | 1109 | N | SER | A | 375 | 11.825 | 6.180 | −18.055 | 1.00 | 35.27 | | N |
| ANISOU | 1109 | N | SER | A | 375 | 4649 | 4543 | 4206 | 33 | −50 | −18 | N |
| ATOM | 1110 | CA | SER | A | 375 | 13.189 | 5.833 | −17.672 | 1.00 | 35.64 | | C |
| ANISOU | 1110 | CA | SER | A | 375 | 4661 | 4565 | 4316 | 56 | −9 | −5 | C |
| ATOM | 1111 | CB | SER | A | 375 | 14.180 | 6.826 | −18.293 | 1.00 | 35.47 | | C |
| ANISOU | 1111 | CB | SER | A | 375 | 4643 | 4554 | 4277 | 90 | −42 | 37 | C |
| ATOM | 1112 | OG | SER | A | 375 | 14.059 | 8.122 | −17.713 | 1.00 | 35.13 | | O |
| ANISOU | 1112 | OG | SER | A | 375 | 4615 | 4635 | 4097 | −15 | −115 | 99 | O |
| ATOM | 1113 | C | SER | A | 375 | 13.422 | 5.744 | −16.151 | 1.00 | 36.11 | | C |
| ANISOU | 1113 | C | SER | A | 375 | 4725 | 4626 | 4366 | 77 | 20 | 5 | C |
| ATOM | 1114 | O | SER | A | 375 | 14.398 | 5.153 | −15.722 | 1.00 | 35.49 | | O |
| ANISOU | 1114 | O | SER | A | 375 | 4766 | 4553 | 4165 | 116 | 99 | −42 | O |
| ATOM | 1115 | N | ASP | A | 376 | 12.533 | 6.347 | −15.358 | 1.00 | 36.79 | | N |
| ANISOU | 1115 | N | ASP | A | 376 | 4838 | 4675 | 4462 | 79 | 35 | 8 | N |
| ATOM | 1116 | CA | ASP | A | 376 | 12.622 | 6.326 | −13.893 | 1.00 | 37.26 | | C |
| ANISOU | 1116 | CA | ASP | A | 376 | 4809 | 4708 | 4637 | 54 | 59 | −73 | C |
| ATOM | 1117 | CB | ASP | A | 376 | 11.505 | 7.175 | −13.281 | 1.00 | 37.66 | | C |
| ANISOU | 1117 | CB | ASP | A | 376 | 4923 | 4705 | 4679 | 39 | 24 | −73 | C |
| ATOM | 1118 | CG | ASP | A | 376 | 11.316 | 8.474 | −14.010 | 1.00 | 37.98 | | C |
| ANISOU | 1118 | CG | ASP | A | 376 | 5073 | 4681 | 4676 | 103 | 74 | −82 | C |
| ATOM | 1119 | OD1 | ASP | A | 376 | 10.191 | 8.720 | −14.495 | 1.00 | 38.29 | | O |
| ANISOU | 1119 | OD1 | ASP | A | 376 | 5022 | 4872 | 4652 | 110 | 58 | −124 | O |
| ATOM | 1120 | OD2 | ASP | A | 376 | 12.302 | 9.227 | −14.118 | 1.00 | 35.66 | | O |
| ANISOU | 1120 | OD2 | ASP | A | 376 | 4760 | 4253 | 4535 | 135 | 89 | −76 | O |
| ATOM | 1121 | C | ASP | A | 376 | 12.549 | 4.905 | −13.354 | 1.00 | 37.15 | | C |
| ANISOU | 1121 | C | ASP | A | 376 | 4817 | 4718 | 4579 | 80 | 84 | −76 | C |
| ATOM | 1122 | O | ASP | A | 376 | 11.569 | 4.191 | −13.564 | 1.00 | 36.68 | | O |
| ANISOU | 1122 | O | ASP | A | 376 | 4770 | 4615 | 4551 | 97 | 140 | −112 | O |
| ATOM | 1123 | N | ILE | A | 377 | 13.600 | 4.508 | −12.657 | 1.00 | 37.17 | | N |
| ANISOU | 1123 | N | ILE | A | 377 | 4813 | 4723 | 4588 | 72 | 69 | −107 | N |
| ATOM | 1124 | CA | ILE | A | 377 | 13.763 | 3.128 | −12.208 | 1.00 | 37.39 | | C |
| ANISOU | 1124 | CA | ILE | A | 377 | 4797 | 4801 | 4607 | 45 | 40 | −64 | C |
| ATOM | 1125 | CB | ILE | A | 377 | 14.301 | 2.230 | −13.385 | 1.00 | 37.15 | | C |
| ANISOU | 1125 | CB | ILE | A | 377 | 4748 | 4758 | 4609 | 63 | 21 | −92 | C |
| ATOM | 1126 | CG1 | ILE | A | 377 | 14.247 | 0.732 | −13.024 | 1.00 | 36.97 | | C |
| ANISOU | 1126 | CG1 | ILE | A | 377 | 4634 | 4816 | 4597 | 20 | −23 | −72 | C |
| ATOM | 1127 | CD1 | ILE | A | 377 | 14.240 | −0.238 | −14.232 | 1.00 | 36.57 | | C |
| ANISOU | 1127 | CD1 | ILE | A | 377 | 4633 | 4701 | 4559 | 59 | 46 | −11 | C |
| ATOM | 1128 | CG2 | ILE | A | 377 | 15.680 | 2.712 | −13.815 | 1.00 | 35.92 | | C |
| ANISOU | 1128 | CG2 | ILE | A | 377 | 4679 | 4583 | 4385 | 86 | 48 | −83 | C |
| ATOM | 1129 | C | ILE | A | 377 | 14.714 | 3.107 | −11.004 | 1.00 | 37.34 | | C |
| ANISOU | 1129 | C | ILE | A | 377 | 4800 | 4829 | 4556 | 19 | 37 | −66 | C |
| ATOM | 1130 | O | ILE | A | 377 | 15.420 | 4.080 | −10.762 | 1.00 | 37.26 | | O |
| ANISOU | 1130 | O | ILE | A | 377 | 4794 | 4872 | 4491 | 24 | 40 | −63 | O |
| ATOM | 1131 | N | ALA | A | 378 | 14.715 | 2.004 | −10.259 | 1.00 | 37.20 | | N |
| ANISOU | 1131 | N | ALA | A | 378 | 4763 | 4859 | 4511 | 46 | 40 | −67 | N |
| ATOM | 1132 | CA | ALA | A | 378 | 15.600 | 1.828 | −9.108 | 1.00 | 37.25 | | C |
| ANISOU | 1132 | CA | ALA | A | 378 | 4784 | 4835 | 4533 | 7 | 69 | −43 | C |
| ATOM | 1133 | CB | ALA | A | 378 | 14.914 | 2.277 | −7.836 | 1.00 | 36.48 | | C |
| ANISOU | 1133 | CB | ALA | A | 378 | 4699 | 4751 | 4411 | 9 | 47 | −91 | C |
| ATOM | 1134 | C | ALA | A | 378 | 16.010 | 0.362 | −9.005 | 1.00 | 36.92 | | C |
| ANISOU | 1134 | C | ALA | A | 378 | 4754 | 4825 | 4447 | 10 | 95 | −25 | C |
| ATOM | 1135 | O | ALA | A | 378 | 15.193 | −0.530 | −9.200 | 1.00 | 36.27 | | O |
| ANISOU | 1135 | O | ALA | A | 378 | 4740 | 4750 | 4291 | −5 | 121 | −49 | O |
| ATOM | 1136 | N | VAL | A | 379 | 17.279 | 0.120 | −8.715 | 1.00 | 36.82 | | N |
| ANISOU | 1136 | N | VAL | A | 379 | 4725 | 4842 | 4420 | 2 | 94 | 1 | N |
| ATOM | 1137 | CA | VAL | A | 379 | 17.784 | −1.248 | −8.628 | 1.00 | 37.12 | | C |
| ANISOU | 1137 | CA | VAL | A | 379 | 4726 | 4809 | 4568 | −25 | 45 | 13 | C |
| ATOM | 1138 | CB | VAL | A | 379 | 18.544 | −1.709 | −9.905 | 1.00 | 36.60 | | C |
| ANISOU | 1138 | CB | VAL | A | 379 | 4604 | 4751 | 4550 | −2 | 47 | −13 | C |
| ATOM | 1139 | CG1 | VAL | A | 379 | 18.767 | −3.219 | −9.875 | 1.00 | 35.07 | | C |
| ANISOU | 1139 | CG1 | VAL | A | 379 | 4394 | 4622 | 4307 | −46 | −4 | 35 | C |

TABLE 7-continued

The atomic structure coordinates of Fc-TM

| | | | | | | | | | | | |
|---|---|---|---|---|---|---|---|---|---|---|---|
| ATOM | 1140 | CG2 | VAL | A | 379 | 17.795 | −1.317 | −11.182 | 1.00 | 35.08 | C |
| ANISOU | 1140 | CG2 | VAL | A | 379 | 4482 | 4481 | 4363 | 10 | 124 | −1 | C |
| ATOM | 1141 | C | VAL | A | 379 | 18.671 | −1.420 | −7.396 | 1.00 | 38.16 | C |
| ANISOU | 1141 | C | VAL | A | 379 | 4798 | 4927 | 4773 | −24 | 7 | 3 | C |
| ATOM | 1142 | O | VAL | A | 379 | 19.429 | −0.532 | −7.037 | 1.00 | 38.18 | O |
| ANISOU | 1142 | O | VAL | A | 379 | 4785 | 4914 | 4805 | −16 | −25 | 12 | O |
| ATOM | 1143 | N | GLU | A | 380 | 18.537 | −2.590 | −6.782 | 1.00 | 39.23 | N |
| ANISOU | 1143 | N | GLU | A | 380 | 4938 | 5049 | 4919 | −34 | −11 | 35 | N |
| ATOM | 1144 | CA | GLU | A | 380 | 19.132 | −2.979 | −5.521 | 1.00 | 39.91 | C |
| ANISOU | 1144 | CA | GLU | A | 380 | 5001 | 5151 | 5009 | −14 | −15 | 58 | C |
| ATOM | 1145 | CB | GLU | A | 380 | 18.105 | −2.836 | −4.402 | 1.00 | 40.43 | C |
| ANISOU | 1145 | CB | GLU | A | 380 | 5124 | 5190 | 5045 | −5 | −16 | 64 | C |
| ATOM | 1146 | CG | GLU | A | 380 | 18.362 | −1.738 | −3.389 | 1.00 | 42.17 | C |
| ANISOU | 1146 | CG | GLU | A | 380 | 5360 | 5320 | 5342 | 32 | −171 | 80 | C |
| ATOM | 1147 | CD | GLU | A | 380 | 17.614 | −2.017 | −2.100 | 1.00 | 42.78 | C |
| ANISOU | 1147 | CD | GLU | A | 380 | 5158 | 5727 | 5370 | 116 | 5 | 121 | C |
| ATOM | 1148 | OE1 | GLU | A | 380 | 18.231 | −2.566 | −1.163 | 1.00 | 47.83 | O |
| ANISOU | 1148 | OE1 | GLU | A | 380 | 6101 | 6126 | 5945 | −126 | 75 | 20 | O |
| ATOM | 1149 | OE2 | GLU | A | 380 | 16.400 | −1.757 | −2.035 | 1.00 | 44.96 | O |
| ANISOU | 1149 | OE2 | GLU | A | 380 | 5954 | 5476 | 5650 | 139 | −62 | 98 | O |
| ATOM | 1150 | C | GLU | A | 380 | 19.455 | −4.455 | −5.653 | 1.00 | 39.85 | C |
| ANISOU | 1150 | C | GLU | A | 380 | 5002 | 5135 | 5004 | −37 | 4 | 77 | C |
| ATOM | 1151 | O | GLU | A | 380 | 18.764 | −5.188 | −6.373 | 1.00 | 40.25 | O |
| ANISOU | 1151 | O | GLU | A | 380 | 5041 | 5193 | 5055 | −78 | −3 | 155 | O |
| ATOM | 1152 | N | TRP | A | 381 | 20.525 | −4.883 | −4.991 | 1.00 | 39.62 | N |
| ANISOU | 1152 | N | TRP | A | 381 | 4988 | 5103 | 4960 | −22 | 19 | 92 | N |
| ATOM | 1153 | CA | TRP | A | 381 | 20.811 | −6.302 | −4.832 | 1.00 | 39.46 | C |
| ANISOU | 1153 | CA | TRP | A | 381 | 4896 | 5090 | 5004 | 38 | −4 | 35 | C |
| ATOM | 1154 | CB | TRP | A | 381 | 22.186 | −6.672 | −5.399 | 1.00 | 36.87 | C |
| ANISOU | 1154 | CB | TRP | A | 381 | 4655 | 4832 | 4520 | 30 | 23 | −91 | C |
| ATOM | 1155 | CG | TRP | A | 381 | 22.339 | −6.667 | −6.907 | 1.00 | 35.55 | C |
| ANISOU | 1155 | CG | TRP | A | 381 | 4204 | 4698 | 4603 | 56 | −104 | 34 | C |
| ATOM | 1156 | CD1 | TRP | A | 381 | 22.580 | −5.579 | −7.708 | 1.00 | 34.03 | C |
| ANISOU | 1156 | CD1 | TRP | A | 381 | 4124 | 4434 | 4368 | 59 | −71 | −36 | C |
| ATOM | 1157 | NE1 | TRP | A | 381 | 22.702 | −5.972 | −9.020 | 1.00 | 32.72 | N |
| ANISOU | 1157 | NE1 | TRP | A | 381 | 4017 | 4085 | 4329 | 60 | −50 | 143 | N |
| ATOM | 1158 | CE2 | TRP | A | 381 | 22.554 | −7.332 | −9.093 | 1.00 | 33.85 | C |
| ANISOU | 1158 | CE2 | TRP | A | 381 | 3981 | 4555 | 4323 | 111 | −94 | 101 | C |
| ATOM | 1159 | CD2 | TRP | A | 381 | 22.337 | −7.806 | −7.779 | 1.00 | 33.47 | C |
| ANISOU | 1159 | CD2 | TRP | A | 381 | 3886 | 4432 | 4397 | 76 | −69 | 127 | C |
| ATOM | 1160 | CE3 | TRP | A | 381 | 22.170 | −9.179 | −7.580 | 1.00 | 32.88 | C |
| ANISOU | 1160 | CE3 | TRP | A | 381 | 3976 | 4447 | 4068 | −65 | −127 | 39 | C |
| ATOM | 1161 | CZ3 | TRP | A | 381 | 22.231 | −10.030 | −8.681 | 1.00 | 35.44 | C |
| ANISOU | 1161 | CZ3 | TRP | A | 381 | 4009 | 4794 | 4660 | 101 | −42 | 213 | C |
| ATOM | 1162 | CH2 | TRP | A | 381 | 22.435 | −9.520 | −9.972 | 1.00 | 34.99 | C |
| ANISOU | 1162 | CH2 | TRP | A | 381 | 4060 | 4680 | 4552 | 47 | 1 | 121 | C |
| ATOM | 1163 | CZ2 | TRP | A | 381 | 22.611 | −8.179 | −10.191 | 1.00 | 33.99 | C |
| ANISOU | 1163 | CZ2 | TRP | A | 381 | 4025 | 4431 | 4455 | 65 | −84 | 182 | C |
| ATOM | 1164 | C | TRP | A | 381 | 20.740 | −6.654 | −3.337 | 1.00 | 40.26 | C |
| ANISOU | 1164 | C | TRP | A | 381 | 5035 | 5192 | 5067 | 47 | −30 | 55 | C |
| ATOM | 1165 | O | TRP | A | 381 | 20.945 | −5.799 | −2.475 | 1.00 | 39.66 | O |
| ANISOU | 1165 | O | TRP | A | 381 | 4949 | 5140 | 4979 | 133 | −91 | 17 | O |
| ATOM | 1166 | N | GLU | A | 382 | 20.443 | −7.914 | −3.051 | 1.00 | 41.50 | N |
| ANISOU | 1166 | N | GLU | A | 382 | 5218 | 5300 | 5247 | 27 | −21 | 45 | N |
| ATOM | 1167 | CA | GLU | A | 382 | 20.251 | −8.407 | −1.685 | 1.00 | 42.87 | C |
| ANISOU | 1167 | CA | GLU | A | 382 | 5409 | 5466 | 5411 | 39 | −22 | 74 | C |
| ATOM | 1168 | CB | GLU | A | 382 | 18.793 | −8.269 | −1.244 | 1.00 | 43.55 | C |
| ANISOU | 1168 | CB | GLU | A | 382 | 5498 | 5513 | 5534 | 40 | 6 | 64 | C |
| ATOM | 1169 | CG | GLU | A | 382 | 18.342 | −6.887 | −0.771 | 1.00 | 46.25 | C |
| ANISOU | 1169 | CG | GLU | A | 382 | 5998 | 5768 | 5807 | −22 | 21 | 16 | C |
| ATOM | 1170 | CD | GLU | A | 382 | 16.931 | −6.573 | −1.248 | 1.00 | 44.15 | C |
| ANISOU | 1170 | CD | GLU | A | 382 | 5607 | 6334 | 4832 | 111 | 89 | 195 | C |
| ATOM | 1171 | OE1 | GLU | A | 382 | 16.003 | −6.614 | −0.420 | 1.00 | 48.91 | O |
| ANISOU | 1171 | OE1 | GLU | A | 382 | 6266 | 6173 | 6143 | 76 | −184 | −79 | O |
| ATOM | 1172 | OE2 | GLU | A | 382 | 16.748 | −6.330 | −2.470 | 1.00 | 51.39 | O |
| ANISOU | 1172 | OE2 | GLU | A | 382 | 6325 | 6387 | 6814 | −32 | −58 | 41 | O |
| ATOM | 1173 | C | GLU | A | 382 | 20.600 | −9.891 | −1.653 | 1.00 | 43.58 | C |
| ANISOU | 1173 | C | GLU | A | 382 | 5532 | 5524 | 5502 | 23 | −11 | 78 | C |
| ATOM | 1174 | O | GLU | A | 382 | 20.553 | −10.579 | −2.697 | 1.00 | 42.96 | O |
| ANISOU | 1174 | O | GLU | A | 382 | 5527 | 5460 | 5335 | −5 | −20 | 53 | O |
| ATOM | 1175 | N | SER | A | 383 | 20.946 | −10.360 | −0.445 | 1.00 | 44.09 | N |
| ANISOU | 1175 | N | SER | A | 383 | 5623 | 5628 | 5499 | 25 | 18 | 122 | N |
| ATOM | 1176 | CA | SER | A | 383 | 21.216 | −11.777 | −0.161 | 1.00 | 44.79 | C |
| ANISOU | 1176 | CA | SER | A | 383 | 5700 | 5676 | 5639 | 6 | 37 | 118 | C |
| ATOM | 1177 | CB | SER | A | 383 | 22.699 | −12.113 | −0.341 | 1.00 | 44.80 | C |
| ANISOU | 1177 | CB | SER | A | 383 | 5702 | 5678 | 5642 | 31 | 37 | 101 | C |
| ATOM | 1178 | OG | SER | A | 383 | 22.882 | −13.478 | −0.685 | 1.00 | 45.36 | O |
| ANISOU | 1178 | OG | SER | A | 383 | 5763 | 5641 | 5831 | −6 | 83 | 127 | O |

TABLE 7-continued

| | | | | | | | | | | | |
|---|---|---|---|---|---|---|---|---|---|---|---|
| \multicolumn{12}{|c|}{The atomic structure coordinates of Fc-TM} |
| ATOM | 1179 | C | SER | A | 383 | 20.796 | −12.028 | 1.283 | 1.00 | 45.26 | C |
| ANISOU | 1179 | C | SER | A | 383 | 5775 | 5768 | 5653 | −9 | 11 | 120 | C |
| ATOM | 1180 | O | SER | A | 383 | 20.992 | −11.161 | 2.160 | 1.00 | 45.04 | O |
| ANISOU | 1180 | O | SER | A | 383 | 5758 | 5784 | 5569 | 19 | 43 | 149 | O |
| ATOM | 1181 | N | ASN | A | 384 | 20.208 | −13.202 | 1.518 | 1.00 | 46.24 | N |
| ANISOU | 1181 | N | ASN | A | 384 | 5912 | 5856 | 5798 | 7 | −6 | 130 | N |
| ATOM | 1182 | CA | ASN | A | 384 | 19.541 | −13.516 | 2.797 | 1.00 | 47.30 | C |
| ANISOU | 1182 | CA | ASN | A | 384 | 5994 | 6002 | 5973 | 9 | 40 | 89 | C |
| ATOM | 1183 | CB | ASN | A | 384 | 20.223 | −14.686 | 3.546 | 1.00 | 47.81 | C |
| ANISOU | 1183 | CB | ASN | A | 384 | 6076 | 6055 | 6032 | 50 | 28 | 85 | C |
| ATOM | 1184 | CG | ASN | A | 384 | 21.711 | −14.835 | 3.202 | 1.00 | 49.23 | C |
| ANISOU | 1184 | CG | ASN | A | 384 | 6239 | 6244 | 6220 | 11 | −19 | 15 | C |
| ATOM | 1185 | OD1 | ASN | A | 384 | 22.561 | −14.139 | 3.771 | 1.00 | 51.62 | O |
| ANISOU | 1185 | OD1 | ASN | A | 384 | 6694 | 6509 | 6407 | −81 | −122 | −51 | O |
| ATOM | 1186 | ND2 | ASN | A | 384 | 22.030 | −15.768 | 2.276 | 1.00 | 50.24 | N |
| ANISOU | 1186 | ND2 | ASN | A | 384 | 6461 | 6386 | 6242 | 154 | −7 | 90 | N |
| ATOM | 1187 | C | ASN | A | 384 | 19.305 | −12.315 | 3.720 | 1.00 | 47.46 | C |
| ANISOU | 1187 | C | ASN | A | 384 | 6002 | 5998 | 6034 | 3 | 30 | 68 | C |
| ATOM | 1188 | O | ASN | A | 384 | 19.988 | −12.138 | 4.745 | 1.00 | 47.50 | O |
| ANISOU | 1188 | O | ASN | A | 384 | 5997 | 6046 | 6002 | −31 | 14 | 128 | O |
| ATOM | 1189 | N | GLY | A | 385 | 18.354 | −11.468 | 3.321 | 1.00 | 48.01 | N |
| ANISOU | 1189 | N | GLY | A | 385 | 6027 | 6061 | 6150 | −4 | 39 | 51 | N |
| ATOM | 1190 | CA | GLY | A | 385 | 17.871 | −10.396 | 4.198 | 1.00 | 48.23 | C |
| ANISOU | 1190 | CA | GLY | A | 385 | 6064 | 6061 | 6200 | 13 | 51 | 19 | C |
| ATOM | 1191 | C | GLY | A | 385 | 18.621 | −9.098 | 4.087 | 1.00 | 48.46 | C |
| ANISOU | 1191 | C | GLY | A | 385 | 6080 | 6127 | 6205 | −3 | 47 | 15 | C |
| ATOM | 1192 | O | GLY | A | 385 | 18.014 | −8.041 | 3.849 | 1.00 | 49.13 | O |
| ANISOU | 1192 | O | GLY | A | 385 | 6172 | 6193 | 6300 | 0 | 74 | −4 | O |
| ATOM | 1193 | N | GLN | A | 386 | 19.938 | −9.186 | 4.258 | 1.00 | 48.32 | N |
| ANISOU | 1193 | N | GLN | A | 386 | 6069 | 6151 | 6136 | −3 | −15 | 14 | N |
| ATOM | 1194 | CA | GLN | A | 386 | 20.841 | −8.054 | 4.091 | 1.00 | 48.32 | C |
| ANISOU | 1194 | CA | GLN | A | 386 | 6053 | 6229 | 6077 | −28 | −15 | 30 | C |
| ATOM | 1195 | CB | GLN | A | 386 | 22.184 | −8.360 | 4.790 | 1.00 | 48.91 | C |
| ANISOU | 1195 | CB | GLN | A | 386 | 6138 | 6313 | 6130 | −23 | −19 | 49 | C |
| ATOM | 1196 | CG | GLN | A | 386 | 22.173 | −8.184 | 6.332 | 1.00 | 49.93 | C |
| ANISOU | 1196 | CG | GLN | A | 386 | 6349 | 6323 | 6297 | 12 | 17 | −18 | C |
| ATOM | 1197 | CD | GLN | A | 386 | 21.542 | −6.872 | 6.784 | 1.00 | 53.93 | C |
| ANISOU | 1197 | CD | GLN | A | 386 | 7210 | 6843 | 6437 | 62 | 21 | 77 | C |
| ATOM | 1198 | OE1 | GLN | A | 386 | 22.249 | −5.898 | 7.064 | 1.00 | 52.63 | O |
| ANISOU | 1198 | OE1 | GLN | A | 386 | 6586 | 6564 | 6846 | −191 | −29 | −6 | O |
| ATOM | 1199 | NE2 | GLN | A | 386 | 20.209 | −6.839 | 6.856 | 1.00 | 50.58 | N |
| ANISOU | 1199 | NE2 | GLN | A | 386 | 6207 | 6607 | 6405 | −46 | 59 | 43 | N |
| ATOM | 1200 | C | GLN | A | 386 | 21.064 | −7.587 | 2.620 | 1.00 | 47.59 | C |
| ANISOU | 1200 | C | GLN | A | 386 | 5946 | 6111 | 6025 | −11 | −32 | 25 | C |
| ATOM | 1201 | O | GLN | A | 386 | 20.871 | −8.355 | 1.660 | 1.00 | 47.43 | O |
| ANISOU | 1201 | O | GLN | A | 386 | 5872 | 6171 | 5978 | −14 | 5 | −8 | O |
| ATOM | 1202 | N | PRO | A | 387 | 21.469 | −6.317 | 2.452 | 1.00 | 46.79 | N |
| ANISOU | 1202 | N | PRO | A | 387 | 5884 | 5981 | 5912 | 8 | −30 | 38 | N |
| ATOM | 1203 | CA | PRO | A | 387 | 21.779 | −5.739 | 1.158 | 1.00 | 46.49 | C |
| ANISOU | 1203 | CA | PRO | A | 387 | 5862 | 5936 | 5864 | 6 | −19 | 30 | C |
| ATOM | 1204 | CB | PRO | A | 387 | 21.498 | −4.243 | 1.368 | 1.00 | 46.62 | C |
| ANISOU | 1204 | CB | PRO | A | 387 | 5909 | 5918 | 5886 | −16 | −15 | 26 | C |
| ATOM | 1205 | CG | PRO | A | 387 | 21.249 | −4.046 | 2.854 | 1.00 | 46.58 | C |
| ANISOU | 1205 | CG | PRO | A | 387 | 5910 | 5950 | 5836 | −20 | −43 | 57 | C |
| ATOM | 1206 | CD | PRO | A | 387 | 21.622 | −5.325 | 3.529 | 1.00 | 47.03 | C |
| ANISOU | 1206 | CD | PRO | A | 387 | 5913 | 5996 | 5958 | 15 | −45 | 16 | C |
| ATOM | 1207 | C | PRO | A | 387 | 23.235 | −5.928 | 0.705 | 1.00 | 46.20 | C |
| ANISOU | 1207 | C | PRO | A | 387 | 5849 | 5892 | 5812 | −33 | −23 | 39 | C |
| ATOM | 1208 | O | PRO | A | 387 | 24.173 | −5.617 | 1.452 | 1.00 | 46.11 | O |
| ANISOU | 1208 | O | PRO | A | 387 | 5879 | 5882 | 5758 | −50 | −52 | 64 | O |
| ATOM | 1209 | N | GLU | A | 388 | 23.408 | −6.433 | −0.517 | 1.00 | 45.47 | N |
| ANISOU | 1209 | N | GLU | A | 388 | 5756 | 5801 | 5720 | −47 | −20 | 52 | N |
| ATOM | 1210 | CA | GLU | A | 388 | 24.694 | −6.403 | −1.195 | 1.00 | 44.97 | C |
| ANISOU | 1210 | CA | GLU | A | 388 | 5683 | 5738 | 5662 | −18 | −10 | 44 | C |
| ATOM | 1211 | CB | GLU | A | 388 | 24.706 | −7.402 | −2.338 | 1.00 | 44.97 | C |
| ANISOU | 1211 | CB | GLU | A | 388 | 5665 | 5761 | 5658 | −20 | −28 | 47 | C |
| ATOM | 1212 | CG | GLU | A | 388 | 24.340 | −8.830 | −1.945 | 1.00 | 46.39 | C |
| ANISOU | 1212 | CG | GLU | A | 388 | 5861 | 5872 | 5891 | −63 | −42 | 82 | C |
| ATOM | 1213 | CD | GLU | A | 388 | 25.323 | −9.460 | −0.970 | 1.00 | 48.03 | C |
| ANISOU | 1213 | CD | GLU | A | 388 | 6158 | 6071 | 6019 | −44 | −74 | 23 | C |
| ATOM | 1214 | OE1 | GLU | A | 388 | 26.552 | −9.400 | −1.201 | 1.00 | 47.49 | O |
| ANISOU | 1214 | OE1 | GLU | A | 388 | 6152 | 6000 | 5891 | 0 | 39 | 1 | O |
| ATOM | 1215 | OE2 | GLU | A | 388 | 24.856 | −10.029 | 0.035 | 1.00 | 49.67 | O |
| ANISOU | 1215 | OE2 | GLU | A | 388 | 6394 | 6329 | 6149 | −70 | 29 | 56 | O |
| ATOM | 1216 | C | GLU | A | 388 | 24.879 | −4.998 | −1.738 | 1.00 | 44.67 | C |
| ANISOU | 1216 | C | GLU | A | 388 | 5627 | 5760 | 5582 | −57 | 10 | 43 | C |
| ATOM | 1217 | O | GLU | A | 388 | 24.084 | −4.530 | −2.545 | 1.00 | 45.07 | O |
| ANISOU | 1217 | O | GLU | A | 388 | 5666 | 5799 | 5660 | −63 | 32 | 78 | O |

TABLE 7-continued

| The atomic structure coordinates of Fc-TM | | | | | | | | | | | |
|---|---|---|---|---|---|---|---|---|---|---|---|
| ATOM | 1218 | N | ASN | A | 389 | 25.901 | −4.298 | −1.279 | 1.00 | 44.47 | N |
| ANISOU | 1218 | N | ASN | A | 389 | 5659 | 5699 | 5537 | −59 | 24 | 35 | N |
| ATOM | 1219 | CA | ASN | A | 389 | 26.079 | −2.904 | −1.704 | 1.00 | 44.04 | C |
| ANISOU | 1219 | CA | ASN | A | 389 | 5629 | 5641 | 5462 | −27 | 10 | 35 | C |
| ATOM | 1220 | CB | ASN | A | 389 | 26.024 | −1.961 | −0.492 | 1.00 | 44.59 | C |
| ANISOU | 1220 | CB | ASN | A | 389 | 5722 | 5687 | 5532 | −8 | 38 | 20 | C |
| ATOM | 1221 | CG | ASN | A | 389 | 24.585 | −1.678 | −0.037 | 1.00 | 46.42 | C |
| ANISOU | 1221 | CG | ASN | A | 389 | 5840 | 6045 | 5752 | −29 | −7 | 33 | C |
| ATOM | 1222 | OD1 | ASN | A | 389 | 23.682 | −1.555 | −0.863 | 1.00 | 47.34 | O |
| ANISOU | 1222 | OD1 | ASN | A | 389 | 6045 | 6314 | 5625 | −18 | −114 | −3 | O |
| ATOM | 1223 | ND2 | ASN | A | 389 | 24.374 | −1.565 | 1.288 | 1.00 | 48.67 | N |
| ANISOU | 1223 | ND2 | ASN | A | 389 | 6260 | 6364 | 5865 | −48 | −31 | −51 | N |
| ATOM | 1224 | C | ASN | A | 389 | 27.307 | −2.672 | −2.610 | 1.00 | 43.16 | C |
| ANISOU | 1224 | C | ASN | A | 389 | 5533 | 5513 | 5352 | −26 | 18 | 33 | C |
| ATOM | 1225 | O | ASN | A | 389 | 27.627 | −1.534 | −2.972 | 1.00 | 43.60 | O |
| ANISOU | 1225 | O | ASN | A | 389 | 5592 | 5599 | 5374 | −86 | 14 | 23 | O |
| ATOM | 1226 | N | ASN | A | 390 | 27.945 | −3.773 | −2.997 | 1.00 | 41.86 | N |
| ANISOU | 1226 | N | ASN | A | 390 | 5352 | 5379 | 5173 | 23 | 45 | 56 | N |
| ATOM | 1227 | CA | ASN | A | 390 | 29.083 | −3.793 | −3.919 | 1.00 | 41.00 | C |
| ANISOU | 1227 | CA | ASN | A | 390 | 5220 | 5249 | 5109 | 20 | 7 | 74 | C |
| ATOM | 1228 | CB | ASN | A | 390 | 29.966 | −4.979 | −3.549 | 1.00 | 41.19 | C |
| ANISOU | 1228 | CB | ASN | A | 390 | 5221 | 5310 | 5120 | 45 | 27 | 70 | C |
| ATOM | 1229 | CG | ASN | A | 390 | 31.368 | −4.870 | −4.090 | 1.00 | 41.56 | C |
| ANISOU | 1229 | CG | ASN | A | 390 | 5312 | 5363 | 5115 | −2 | 43 | 34 | C |
| ATOM | 1230 | OD1 | ASN | A | 390 | 31.868 | −3.776 | −4.364 | 1.00 | 41.19 | O |
| ANISOU | 1230 | OD1 | ASN | A | 390 | 5395 | 5253 | 5003 | −42 | 153 | 41 | O |
| ATOM | 1231 | ND2 | ASN | A | 390 | 32.025 | −6.025 | −4.233 | 1.00 | 41.17 | N |
| ANISOU | 1231 | ND2 | ASN | A | 390 | 5229 | 5437 | 4976 | 143 | 37 | 31 | N |
| ATOM | 1232 | C | ASN | A | 390 | 28.594 | −3.918 | −5.382 | 1.00 | 40.10 | C |
| ANISOU | 1232 | C | ASN | A | 390 | 5080 | 5147 | 5009 | 44 | 50 | 76 | C |
| ATOM | 1233 | O | ASN | A | 390 | 28.961 | −4.838 | −6.130 | 1.00 | 39.50 | O |
| ANISOU | 1233 | O | ASN | A | 390 | 5007 | 5028 | 4970 | 3 | 76 | 100 | O |
| ATOM | 1234 | N | TYR | A | 391 | 27.732 | −2.989 | −5.776 | 1.00 | 38.85 | N |
| ANISOU | 1234 | N | TYR | A | 391 | 4892 | 5023 | 4845 | 30 | 31 | 97 | N |
| ATOM | 1235 | CA | TYR | A | 391 | 27.123 | −3.060 | −7.093 | 1.00 | 37.67 | C |
| ANISOU | 1235 | CA | TYR | A | 391 | 4723 | 4859 | 4729 | 39 | 55 | 30 | C |
| ATOM | 1236 | CB | TYR | A | 391 | 25.674 | −3.607 | −7.023 | 1.00 | 37.59 | C |
| ANISOU | 1236 | CB | TYR | A | 391 | 4770 | 4816 | 4693 | 80 | 13 | 10 | C |
| ATOM | 1237 | CG | TYR | A | 391 | 24.671 | −2.674 | −6.375 | 1.00 | 38.73 | C |
| ANISOU | 1237 | CG | TYR | A | 391 | 4872 | 5036 | 4808 | −63 | −19 | 82 | C |
| ATOM | 1238 | CD1 | TYR | A | 391 | 24.362 | −2.780 | −5.014 | 1.00 | 37.63 | C |
| ANISOU | 1238 | CD1 | TYR | A | 391 | 4713 | 4862 | 4722 | 177 | 116 | 46 | C |
| ATOM | 1239 | CE1 | TYR | A | 391 | 23.443 | −1.907 | −4.407 | 1.00 | 38.01 | C |
| ANISOU | 1239 | CE1 | TYR | A | 391 | 4865 | 4872 | 4702 | −18 | 48 | 130 | C |
| ATOM | 1240 | CZ | TYR | A | 391 | 22.846 | −0.928 | −5.185 | 1.00 | 38.97 | C |
| ANISOU | 1240 | CZ | TYR | A | 391 | 4955 | 4954 | 4896 | −4 | −26 | 90 | C |
| ATOM | 1241 | OH | TYR | A | 391 | 21.946 | −0.056 | −4.628 | 1.00 | 37.74 | O |
| ANISOU | 1241 | OH | TYR | A | 391 | 4898 | 4791 | 4649 | 209 | 262 | −75 | O |
| ATOM | 1242 | CE2 | TYR | A | 391 | 23.138 | −0.815 | −6.539 | 1.00 | 35.97 | C |
| ANISOU | 1242 | CE2 | TYR | A | 391 | 4646 | 4399 | 4619 | 38 | 163 | 83 | C |
| ATOM | 1243 | CD2 | TYR | A | 391 | 24.039 | −1.671 | −7.119 | 1.00 | 36.37 | C |
| ANISOU | 1243 | CD2 | TYR | A | 391 | 4651 | 4617 | 4551 | −25 | 77 | 44 | C |
| ATOM | 1244 | C | TYR | A | 391 | 27.200 | −1.701 | −7.765 | 1.00 | 36.92 | C |
| ANISOU | 1244 | C | TYR | A | 391 | 4614 | 4817 | 4594 | 42 | 51 | 55 | C |
| ATOM | 1245 | O | TYR | A | 391 | 27.351 | −0.657 | −7.114 | 1.00 | 36.53 | O |
| ANISOU | 1245 | O | TYR | A | 391 | 4501 | 4815 | 4562 | −50 | −10 | 88 | O |
| ATOM | 1246 | N | LYS | A | 392 | 27.118 | −1.716 | −9.081 | 1.00 | 36.62 | N |
| ANISOU | 1246 | N | LYS | A | 392 | 4561 | 4727 | 4624 | 54 | 58 | 1 | N |
| ATOM | 1247 | CA | LYS | A | 392 | 27.049 | −0.484 | −9.842 | 1.00 | 35.22 | C |
| ANISOU | 1247 | CA | LYS | A | 392 | 4471 | 4551 | 4359 | 25 | 92 | 57 | C |
| ATOM | 1248 | CB | LYS | A | 392 | 28.381 | −0.165 | −10.507 | 1.00 | 34.96 | C |
| ANISOU | 1248 | CB | LYS | A | 392 | 4479 | 4541 | 4263 | 56 | 38 | 59 | C |
| ATOM | 1249 | CG | LYS | A | 392 | 29.467 | 0.393 | −9.610 | 1.00 | 33.97 | C |
| ANISOU | 1249 | CG | LYS | A | 392 | 4364 | 4380 | 4162 | 9 | 118 | 142 | C |
| ATOM | 1250 | CD | LYS | A | 392 | 29.178 | 1.783 | −9.077 | 1.00 | 30.65 | C |
| ANISOU | 1250 | CD | LYS | A | 392 | 3873 | 4093 | 3676 | −50 | −59 | 22 | C |
| ATOM | 1251 | CE | LYS | A | 392 | 30.097 | 2.063 | −7.905 | 1.00 | 34.02 | C |
| ANISOU | 1251 | CE | LYS | A | 392 | 4211 | 4391 | 4322 | 54 | 232 | 178 | C |
| ATOM | 1252 | NZ | LYS | A | 392 | 29.956 | 3.443 | −7.308 | 1.00 | 33.12 | N |
| ANISOU | 1252 | NZ | LYS | A | 392 | 4344 | 4095 | 4143 | 80 | 8 | 56 | N |
| ATOM | 1253 | C | LYS | A | 392 | 25.990 | −0.715 | −10.856 | 1.00 | 34.87 | C |
| ANISOU | 1253 | C | LYS | A | 392 | 4403 | 4536 | 4310 | 11 | 107 | 58 | C |
| ATOM | 1254 | O | LYS | A | 392 | 25.872 | −1.819 | −11.377 | 1.00 | 35.62 | O |
| ANISOU | 1254 | O | LYS | A | 392 | 4423 | 4675 | 4433 | 32 | 181 | 150 | O |
| ATOM | 1255 | N | THR | A | 393 | 25.182 | 0.301 | −11.113 | 1.00 | 34.71 | N |
| ANISOU | 1255 | N | THR | A | 393 | 4367 | 4517 | 4301 | −7 | 76 | 10 | N |
| ATOM | 1256 | CA | THR | A | 393 | 24.148 | 0.202 | −12.152 | 1.00 | 34.16 | C |
| ANISOU | 1256 | CA | THR | A | 393 | 4265 | 4432 | 4281 | 0 | 19 | 3 | C |

TABLE 7-continued

The atomic structure coordinates of Fc-TM

| ATOM | 1257 | CB | THR | A | 393 | 22.709 | 0.335 | −11.564 | 1.00 | 34.10 | | | | C |
|---|---|---|---|---|---|---|---|---|---|---|---|---|---|---|
| ANISOU | 1257 | CB | THR | A | 393 | 4267 | 4421 | 4266 | −9 | 30 | −26 | | | C |
| ATOM | 1258 | OG1 | THR | A | 393 | 22.539 | −0.610 | −10.500 | 1.00 | 33.81 | | | | O |
| ANISOU | 1258 | OG1 | THR | A | 393 | 4259 | 4412 | 4172 | −1 | −82 | −7 | | | O |
| ATOM | 1259 | CG2 | THR | A | 393 | 21.632 | 0.074 | −12.619 | 1.00 | 32.60 | | | | C |
| ANISOU | 1259 | CG2 | THR | A | 393 | 4085 | 4261 | 4038 | 42 | 66 | 47 | | | C |
| ATOM | 1260 | C | THR | A | 393 | 24.399 | 1.248 | −13.221 | 1.00 | 33.43 | | | | C |
| ANISOU | 1260 | C | THR | A | 393 | 4164 | 4382 | 4153 | 14 | 6 | 11 | | | C |
| ATOM | 1261 | O | THR | A | 393 | 24.712 | 2.402 | −12.916 | 1.00 | 32.42 | | | | O |
| ANISOU | 1261 | O | THR | A | 393 | 3933 | 4348 | 4036 | 27 | −28 | 52 | | | O |
| ATOM | 1262 | N | THR | A | 394 | 24.280 | 0.831 | −14.475 | 1.00 | 33.41 | | | | N |
| ANISOU | 1262 | N | THR | A | 394 | 4194 | 4326 | 4173 | −21 | 1 | −3 | | | N |
| ATOM | 1263 | CA | THR | A | 394 | 24.354 | 1.770 | −15.604 | 1.00 | 32.96 | | | | C |
| ANISOU | 1263 | CA | THR | A | 394 | 4273 | 4227 | 4022 | −7 | 8 | −20 | | | C |
| ATOM | 1264 | CB | THR | A | 394 | 24.438 | 1.072 | −17.010 | 1.00 | 32.13 | | | | C |
| ANISOU | 1264 | CB | THR | A | 394 | 4197 | 4083 | 3928 | −5 | 10 | −4 | | | C |
| ATOM | 1265 | OG1 | THR | A | 394 | 23.164 | 0.562 | −17.403 | 1.00 | 30.15 | | | | O |
| ANISOU | 1265 | OG1 | THR | A | 394 | 4301 | 3693 | 3462 | 100 | 189 | −92 | | | O |
| ATOM | 1266 | CG2 | THR | A | 394 | 25.420 | −0.023 | −17.015 | 1.00 | 32.17 | | | | C |
| ANISOU | 1266 | CG2 | THR | A | 394 | 4155 | 4105 | 3960 | 10 | −1 | −49 | | | C |
| ATOM | 1267 | C | THR | A | 394 | 23.180 | 2.745 | −15.578 | 1.00 | 33.10 | | | | C |
| ANISOU | 1267 | C | THR | A | 394 | 4317 | 4262 | 3996 | 22 | −31 | −57 | | | C |
| ATOM | 1268 | O | THR | A | 394 | 22.111 | 2.399 | −15.084 | 1.00 | 31.47 | | | | O |
| ANISOU | 1268 | O | THR | A | 394 | 4242 | 4074 | 3640 | 41 | −14 | −63 | | | O |
| ATOM | 1269 | N | PRO | A | 395 | 23.384 | 3.974 | −16.096 | 1.00 | 33.99 | | | | N |
| ANISOU | 1269 | N | PRO | A | 395 | 4452 | 4367 | 4095 | 17 | 0 | −46 | | | N |
| ATOM | 1270 | CA | PRO | A | 395 | 22.219 | 4.810 | −16.436 | 1.00 | 34.48 | | | | C |
| ANISOU | 1270 | CA | PRO | A | 395 | 4508 | 4400 | 4191 | 5 | 0 | −2 | | | C |
| ATOM | 1271 | CB | PRO | A | 395 | 22.838 | 6.025 | −17.138 | 1.00 | 34.62 | | | | C |
| ANISOU | 1271 | CB | PRO | A | 395 | 4510 | 4435 | 4207 | 39 | 10 | 16 | | | C |
| ATOM | 1272 | CG | PRO | A | 395 | 24.252 | 6.053 | −16.758 | 1.00 | 34.22 | | | | C |
| ANISOU | 1272 | CG | PRO | A | 395 | 4486 | 4452 | 4064 | 2 | −63 | −21 | | | C |
| ATOM | 1273 | CD | PRO | A | 395 | 24.661 | 4.648 | −16.377 | 1.00 | 33.86 | | | | C |
| ANISOU | 1273 | CD | PRO | A | 395 | 4399 | 4344 | 4121 | 12 | −25 | −108 | | | C |
| ATOM | 1274 | C | PRO | A | 395 | 21.270 | 4.066 | −17.399 | 1.00 | 34.85 | | | | C |
| ANISOU | 1274 | C | PRO | A | 395 | 4538 | 4450 | 4251 | −27 | 24 | 75 | | | C |
| ATOM | 1275 | O | PRO | A | 395 | 21.690 | 3.069 | −18.027 | 1.00 | 33.16 | | | | O |
| ANISOU | 1275 | O | PRO | A | 395 | 4370 | 4274 | 3952 | −56 | 11 | 94 | | | O |
| ATOM | 1276 | N | PRO | A | 396 | 19.994 | 4.510 | −17.489 | 1.00 | 35.07 | | | | N |
| ANISOU | 1276 | N | PRO | A | 396 | 4573 | 4414 | 4338 | −15 | 31 | 90 | | | N |
| ATOM | 1277 | CA | PRO | A | 396 | 19.125 | 3.923 | −18.487 | 1.00 | 35.48 | | | | C |
| ANISOU | 1277 | CA | PRO | A | 396 | 4599 | 4477 | 4402 | −4 | 21 | 48 | | | C |
| ATOM | 1278 | CB | PRO | A | 396 | 17.743 | 4.529 | −18.186 | 1.00 | 35.53 | | | | C |
| ANISOU | 1278 | CB | PRO | A | 396 | 4659 | 4433 | 4407 | −25 | 75 | 67 | | | C |
| ATOM | 1279 | CG | PRO | A | 396 | 17.867 | 5.217 | −16.873 | 1.00 | 35.18 | | | | C |
| ANISOU | 1279 | CG | PRO | A | 396 | 4624 | 4408 | 4334 | −59 | 3 | 93 | | | C |
| ATOM | 1280 | CD | PRO | A | 396 | 19.303 | 5.531 | −16.681 | 1.00 | 35.32 | | | | C |
| ANISOU | 1280 | CD | PRO | A | 396 | 4594 | 4469 | 4356 | −36 | 28 | 82 | | | C |
| ATOM | 1281 | C | PRO | A | 396 | 19.586 | 4.324 | −19.886 | 1.00 | 35.60 | | | | C |
| ANISOU | 1281 | C | PRO | A | 396 | 4558 | 4488 | 4477 | −4 | 25 | 45 | | | C |
| ATOM | 1282 | O | PRO | A | 396 | 19.954 | 5.475 | −20.105 | 1.00 | 34.99 | | | | O |
| ANISOU | 1282 | O | PRO | A | 396 | 4438 | 4447 | 4409 | −29 | −6 | −1 | | | O |
| ATOM | 1283 | N | VAL | A | 397 | 19.574 | 3.361 | −20.811 | 1.00 | 35.51 | | | | N |
| ANISOU | 1283 | N | VAL | A | 397 | 4544 | 4506 | 4441 | 17 | 17 | 29 | | | N |
| ATOM | 1284 | CA | VAL | A | 397 | 19.934 | 3.603 | −22.199 | 1.00 | 35.28 | | | | C |
| ANISOU | 1284 | CA | VAL | A | 397 | 4527 | 4479 | 4397 | 49 | 41 | −32 | | | C |
| ATOM | 1285 | CB | VAL | A | 397 | 21.078 | 2.664 | −22.649 | 1.00 | 35.15 | | | | C |
| ANISOU | 1285 | CB | VAL | A | 397 | 4516 | 4432 | 4406 | 15 | −5 | 15 | | | C |
| ATOM | 1286 | CG1 | VAL | A | 397 | 21.631 | 3.022 | −24.077 | 1.00 | 32.51 | | | | C |
| ANISOU | 1286 | CG1 | VAL | A | 397 | 4128 | 4063 | 4159 | 162 | −111 | −9 | | | C |
| ATOM | 1287 | CG2 | VAL | A | 397 | 22.212 | 2.715 | −21.598 | 1.00 | 34.48 | | | | C |
| ANISOU | 1287 | CG2 | VAL | A | 397 | 4490 | 4344 | 4264 | 57 | −19 | 107 | | | C |
| ATOM | 1288 | C | VAL | A | 397 | 18.679 | 3.500 | −23.052 | 1.00 | 35.75 | | | | C |
| ANISOU | 1288 | C | VAL | A | 397 | 4638 | 4562 | 4383 | 61 | 96 | −101 | | | C |
| ATOM | 1289 | O | VAL | A | 397 | 17.902 | 2.554 | −22.928 | 1.00 | 35.03 | | | | O |
| ANISOU | 1289 | O | VAL | A | 397 | 4596 | 4513 | 4200 | 112 | 126 | −186 | | | O |
| ATOM | 1290 | N | LEU | A | 398 | 18.454 | 4.511 | −23.882 | 1.00 | 36.47 | | | | N |
| ANISOU | 1290 | N | LEU | A | 398 | 4739 | 4629 | 4488 | 94 | 73 | −100 | | | N |
| ATOM | 1291 | CA | LEU | A | 398 | 17.325 | 4.490 | −24.793 | 1.00 | 37.45 | | | | C |
| ANISOU | 1291 | CA | LEU | A | 398 | 4793 | 4772 | 4664 | 41 | 20 | −48 | | | C |
| ATOM | 1292 | CB | LEU | A | 398 | 17.122 | 5.874 | −25.398 | 1.00 | 37.18 | | | | C |
| ANISOU | 1292 | CB | LEU | A | 398 | 4747 | 4739 | 4639 | 16 | −9 | −44 | | | C |
| ATOM | 1293 | CG | LEU | A | 398 | 16.080 | 5.972 | −26.506 | 1.00 | 37.09 | | | | C |
| ANISOU | 1293 | CG | LEU | A | 398 | 4734 | 4681 | 4674 | 50 | −12 | 25 | | | C |
| ATOM | 1294 | CD1 | LEU | A | 398 | 14.703 | 6.031 | −25.905 | 1.00 | 33.79 | | | | C |
| ANISOU | 1294 | CD1 | LEU | A | 398 | 4353 | 4255 | 4230 | 41 | −3 | 61 | | | C |
| ATOM | 1295 | CD2 | LEU | A | 398 | 16.370 | 7.193 | −27.347 | 1.00 | 35.57 | | | | C |
| ANISOU | 1295 | CD2 | LEU | A | 398 | 4571 | 4494 | 4446 | −15 | 49 | 72 | | | C |

TABLE 7-continued

The atomic structure coordinates of Fc-TM

| | | | | | | | | | | | | | |
|---|---|---|---|---|---|---|---|---|---|---|---|---|---|
| ATOM | 1296 | C | LEU | A | 398 | 17.556 | 3.429 | −25.888 | 1.00 | 38.23 | | | C |
| ANISOU | 1296 | C | LEU | A | 398 | 4890 | 4908 | 4728 | 11 | 15 | −44 | | C |
| ATOM | 1297 | O | LEU | A | 398 | 18.563 | 3.460 | −26.582 | 1.00 | 38.51 | | | O |
| ANISOU | 1297 | O | LEU | A | 398 | 4999 | 4941 | 4690 | 0 | 55 | −39 | | O |
| ATOM | 1298 | N | ASP | A | 399 | 16.635 | 2.480 | −25.991 | 1.00 | 38.60 | | | N |
| ANISOU | 1298 | N | ASP | A | 399 | 4899 | 4972 | 4792 | −36 | −27 | −45 | | N |
| ATOM | 1299 | CA | ASP | A | 399 | 16.765 | 1.320 | −26.873 | 1.00 | 39.01 | | | C |
| ANISOU | 1299 | CA | ASP | A | 399 | 4912 | 5053 | 4854 | −29 | 24 | −35 | | C |
| ATOM | 1300 | CB | ASP | A | 399 | 16.199 | 0.086 | −26.161 | 1.00 | 38.88 | | | C |
| ANISOU | 1300 | CB | ASP | A | 399 | 4905 | 4978 | 4887 | 15 | −41 | −51 | | C |
| ATOM | 1301 | CG | ASP | A | 399 | 16.844 | −1.192 | −26.597 | 1.00 | 38.32 | | | C |
| ANISOU | 1301 | CG | ASP | A | 399 | 4804 | 4963 | 4792 | −65 | −106 | −121 | | C |
| ATOM | 1302 | OD1 | ASP | A | 399 | 17.484 | −1.181 | −27.654 | 1.00 | 37.78 | | | O |
| ANISOU | 1302 | OD1 | ASP | A | 399 | 4733 | 4944 | 4677 | −131 | 237 | 20 | | O |
| ATOM | 1303 | OD2 | ASP | A | 399 | 16.695 | −2.218 | −25.888 | 1.00 | 34.88 | | | O |
| ANISOU | 1303 | OD2 | ASP | A | 399 | 4527 | 4630 | 4095 | −144 | −197 | −160 | | O |
| ATOM | 1304 | C | ASP | A | 399 | 16.021 | 1.580 | −28.189 | 1.00 | 39.56 | | | C |
| ANISOU | 1304 | C | ASP | A | 399 | 4970 | 5121 | 4940 | −44 | −39 | −55 | | C |
| ATOM | 1305 | O | ASP | A | 399 | 15.173 | 2.463 | −28.256 | 1.00 | 39.73 | | | O |
| ANISOU | 1305 | O | ASP | A | 399 | 4986 | 5183 | 4925 | −115 | −74 | −71 | | O |
| ATOM | 1306 | N | SER | A | 400 | 16.337 | 0.812 | −29.230 | 1.00 | 40.64 | | | N |
| ANISOU | 1306 | N | SER | A | 400 | 5096 | 5273 | 5071 | −57 | −46 | −54 | | N |
| ATOM | 1307 | CA | SER | A | 400 | 15.840 | 1.082 | −30.596 | 1.00 | 41.15 | | | C |
| ANISOU | 1307 | CA | SER | A | 400 | 5251 | 5323 | 5061 | −17 | −32 | −8 | | C |
| ATOM | 1308 | CB | SER | A | 400 | 16.537 | 0.177 | −31.634 | 1.00 | 41.51 | | | C |
| ANISOU | 1308 | CB | SER | A | 400 | 5316 | 5343 | 5111 | −10 | −34 | −7 | | C |
| ATOM | 1309 | OG | SER | A | 400 | 16.267 | −1.193 | −31.421 | 1.00 | 41.13 | | | O |
| ANISOU | 1309 | OG | SER | A | 400 | 5528 | 5227 | 4871 | −68 | −46 | −78 | | O |
| ATOM | 1310 | C | SER | A | 400 | 14.306 | 1.094 | −30.795 | 1.00 | 41.37 | | | C |
| ANISOU | 1310 | C | SER | A | 400 | 5252 | 5362 | 5103 | −45 | −34 | −4 | | C |
| ATOM | 1311 | O | SER | A | 400 | 13.809 | 1.646 | −31.793 | 1.00 | 41.91 | | | O |
| ANISOU | 1311 | O | SER | A | 400 | 5272 | 5451 | 5198 | −42 | −44 | 15 | | O |
| ATOM | 1312 | N | ASP | A | 401 | 13.567 | 0.507 | −29.850 | 1.00 | 40.91 | | | N |
| ANISOU | 1312 | N | ASP | A | 401 | 5201 | 5318 | 5025 | −65 | −57 | −11 | | N |
| ATOM | 1313 | CA | ASP | A | 401 | 12.096 | 0.529 | −29.865 | 1.00 | 40.44 | | | C |
| ANISOU | 1313 | CA | ASP | A | 401 | 5132 | 5251 | 4983 | −27 | −42 | 18 | | C |
| ATOM | 1314 | CB | ASP | A | 401 | 11.534 | −0.798 | −29.335 | 1.00 | 40.38 | | | C |
| ANISOU | 1314 | CB | ASP | A | 401 | 5139 | 5233 | 4968 | −25 | −21 | −7 | | C |
| ATOM | 1315 | CG | ASP | A | 401 | 11.904 | −1.060 | −27.886 | 1.00 | 38.85 | | | C |
| ANISOU | 1315 | CG | ASP | A | 401 | 4987 | 4862 | 4910 | −73 | −13 | 26 | | C |
| ATOM | 1316 | OD1 | ASP | A | 401 | 12.436 | −0.155 | −27.202 | 1.00 | 37.74 | | | O |
| ANISOU | 1316 | OD1 | ASP | A | 401 | 4636 | 5156 | 4545 | 38 | 31 | 174 | | O |
| ATOM | 1317 | OD2 | ASP | A | 401 | 11.649 | −2.183 | −27.431 | 1.00 | 39.72 | | | O |
| ANISOU | 1317 | OD2 | ASP | A | 401 | 5010 | 5104 | 4977 | −4 | 75 | 7 | | O |
| ATOM | 1318 | C | ASP | A | 401 | 11.449 | 1.680 | −29.094 | 1.00 | 39.90 | | | C |
| ANISOU | 1318 | C | ASP | A | 401 | 5041 | 5177 | 4940 | −43 | −37 | 66 | | C |
| ATOM | 1319 | O | ASP | A | 401 | 10.225 | 1.774 | −29.043 | 1.00 | 40.25 | | | O |
| ANISOU | 1319 | O | ASP | A | 401 | 5049 | 5289 | 4953 | −69 | −45 | 118 | | O |
| ATOM | 1320 | N | GLY | A | 402 | 12.250 | 2.543 | −28.477 | 1.00 | 39.08 | | | N |
| ANISOU | 1320 | N | GLY | A | 402 | 4955 | 5065 | 4828 | −36 | −20 | 89 | | N |
| ATOM | 1321 | CA | GLY | A | 402 | 11.704 | 3.649 | −27.704 | 1.00 | 37.86 | | | C |
| ANISOU | 1321 | CA | GLY | A | 402 | 4786 | 4893 | 4704 | −52 | −13 | 78 | | C |
| ATOM | 1322 | C | GLY | A | 402 | 11.595 | 3.341 | −26.218 | 1.00 | 37.33 | | | C |
| ANISOU | 1322 | C | GLY | A | 402 | 4692 | 4826 | 4663 | −63 | −17 | 32 | | C |
| ATOM | 1323 | O | GLY | A | 402 | 11.207 | 4.196 | −25.442 | 1.00 | 36.37 | | | O |
| ANISOU | 1323 | O | GLY | A | 402 | 4563 | 4782 | 4474 | −59 | −1 | 82 | | O |
| ATOM | 1324 | N | SER | A | 403 | 11.926 | 2.109 | −25.833 | 1.00 | 37.09 | | | N |
| ANISOU | 1324 | N | SER | A | 403 | 4673 | 4844 | 4574 | −62 | −36 | 47 | | N |
| ATOM | 1325 | CA | SER | A | 403 | 11.950 | 1.716 | −24.434 | 1.00 | 36.37 | | | C |
| ANISOU | 1325 | CA | SER | A | 403 | 4631 | 4747 | 4437 | −49 | −21 | −12 | | C |
| ATOM | 1326 | CB | SER | A | 403 | 11.448 | 0.278 | −24.256 | 1.00 | 36.02 | | | C |
| ANISOU | 1326 | CB | SER | A | 403 | 4574 | 4762 | 4349 | −7 | −46 | 2 | | C |
| ATOM | 1327 | OG | SER | A | 403 | 12.414 | −0.692 | −24.631 | 1.00 | 33.78 | | | O |
| ANISOU | 1327 | OG | SER | A | 403 | 4447 | 4556 | 3833 | −138 | −49 | 0 | | O |
| ATOM | 1328 | C | SER | A | 403 | 13.386 | 1.883 | −23.941 | 1.00 | 36.54 | | | C |
| ANISOU | 1328 | C | SER | A | 403 | 4660 | 4740 | 4482 | −12 | 25 | −5 | | C |
| ATOM | 1329 | O | SER | A | 403 | 14.295 | 2.067 | −24.761 | 1.00 | 36.38 | | | O |
| ANISOU | 1329 | O | SER | A | 403 | 4672 | 4720 | 4430 | −40 | 37 | 14 | | O |
| ATOM | 1330 | N | PHE | A | 404 | 13.581 | 1.845 | −22.620 | 1.00 | 35.39 | | | N |
| ANISOU | 1330 | N | PHE | A | 404 | 4542 | 4621 | 4282 | −38 | 41 | −73 | | N |
| ATOM | 1331 | CA | PHE | A | 404 | 14.907 | 1.883 | −22.036 | 1.00 | 34.51 | | | C |
| ANISOU | 1331 | CA | PHE | A | 404 | 4526 | 4498 | 4089 | 6 | 74 | −104 | | C |
| ATOM | 1332 | CB | PHE | A | 404 | 14.966 | 2.842 | −20.820 | 1.00 | 33.40 | | | C |
| ANISOU | 1332 | CB | PHE | A | 404 | 4419 | 4290 | 3980 | 33 | 38 | −95 | | C |
| ATOM | 1333 | CG | PHE | A | 404 | 14.744 | 4.276 | −21.166 | 1.00 | 30.44 | | | C |
| ANISOU | 1333 | CG | PHE | A | 404 | 4161 | 4147 | 3255 | −31 | −6 | −191 | | C |
| ATOM | 1334 | CD1 | PHE | A | 404 | 15.823 | 5.101 | −21.466 | 1.00 | 26.60 | | | C |
| ANISOU | 1334 | CD1 | PHE | A | 404 | 3621 | 3887 | 2596 | 99 | −79 | −402 | | C |

TABLE 7-continued

The atomic structure coordinates of Fc-TM

| | | | | | | | | | | | | |
|---|---|---|---|---|---|---|---|---|---|---|---|---|
| ATOM | 1335 | CE1 | PHE | A | 404 | 15.644 | 6.447 | −21.816 | 1.00 | 26.39 | | C |
| ANISOU | 1335 | CE1 | PHE | A | 404 | 3482 | 3882 | 2662 | −15 | 8 | −185 | C |
| ATOM | 1336 | CZ | PHE | A | 404 | 14.347 | 6.978 | −21.858 | 1.00 | 32.27 | | C |
| ANISOU | 1336 | CZ | PHE | A | 404 | 4351 | 4333 | 3573 | 50 | −33 | −132 | C |
| ATOM | 1337 | CE2 | PHE | A | 404 | 13.225 | 6.145 | −21.550 | 1.00 | 29.16 | | C |
| ANISOU | 1337 | CE2 | PHE | A | 404 | 3933 | 3731 | 3415 | −11 | 40 | −51 | C |
| ATOM | 1338 | CD2 | PHE | A | 404 | 13.445 | 4.805 | −21.208 | 1.00 | 30.50 | | C |
| ANISOU | 1338 | CD2 | PHE | A | 404 | 4166 | 4173 | 3248 | −128 | 106 | −201 | C |
| ATOM | 1339 | C | PHE | A | 404 | 15.373 | 0.499 | −21.608 | 1.00 | 34.61 | | C |
| ANISOU | 1339 | C | PHE | A | 404 | 4525 | 4477 | 4146 | 26 | 99 | −204 | C |
| ATOM | 1340 | O | PHE | A | 404 | 14.573 | −0.420 | −21.433 | 1.00 | 33.02 | | O |
| ANISOU | 1340 | O | PHE | A | 404 | 4344 | 4311 | 3889 | 47 | 220 | −276 | O |
| ATOM | 1341 | N | PHE | A | 405 | 16.690 | 0.368 | −21.449 | 1.00 | 34.74 | | N |
| ANISOU | 1341 | N | PHE | A | 405 | 4575 | 4438 | 4184 | 43 | 52 | −212 | N |
| ATOM | 1342 | CA | PHE | A | 405 | 17.272 | −0.759 | −20.737 | 1.00 | 34.42 | | C |
| ANISOU | 1342 | CA | PHE | A | 405 | 4502 | 4382 | 4192 | −2 | 44 | −125 | C |
| ATOM | 1343 | CB | PHE | A | 405 | 17.776 | −1.837 | −21.701 | 1.00 | 32.43 | | C |
| ANISOU | 1343 | CB | PHE | A | 405 | 4151 | 4159 | 4010 | −72 | 155 | −97 | C |
| ATOM | 1344 | CG | PHE | A | 405 | 19.014 | −1.437 | −22.476 | 1.00 | 33.02 | | C |
| ANISOU | 1344 | CG | PHE | A | 405 | 4397 | 3928 | 4220 | 8 | −32 | −287 | C |
| ATOM | 1345 | CD1 | PHE | A | 405 | 20.277 | −1.889 | −22.081 | 1.00 | 29.57 | | C |
| ANISOU | 1345 | CD1 | PHE | A | 405 | 4067 | 3437 | 3730 | −38 | −280 | −316 | C |
| ATOM | 1346 | CE1 | PHE | A | 405 | 21.400 | −1.541 | −22.787 | 1.00 | 25.41 | | C |
| ANISOU | 1346 | CE1 | PHE | A | 405 | 3611 | 3087 | 2955 | −141 | −47 | 125 | C |
| ATOM | 1347 | CZ | PHE | A | 405 | 21.292 | −0.716 | −23.897 | 1.00 | 32.01 | | C |
| ANISOU | 1347 | CZ | PHE | A | 405 | 4279 | 3768 | 4114 | −148 | −68 | −437 | C |
| ATOM | 1348 | CE2 | PHE | A | 405 | 20.048 | −0.245 | −24.310 | 1.00 | 27.60 | | C |
| ANISOU | 1348 | CE2 | PHE | A | 405 | 3778 | 3209 | 3499 | −32 | −193 | −158 | C |
| ATOM | 1349 | CD2 | PHE | A | 405 | 18.915 | −0.607 | −23.606 | 1.00 | 29.13 | | C |
| ANISOU | 1349 | CD2 | PHE | A | 405 | 4022 | 3536 | 3508 | −50 | −6 | −170 | C |
| ATOM | 1350 | C | PHE | A | 405 | 18.415 | −0.275 | −19.858 | 1.00 | 34.59 | | C |
| ANISOU | 1350 | C | PHE | A | 405 | 4492 | 4419 | 4230 | −18 | 50 | −131 | C |
| ATOM | 1351 | O | PHE | A | 405 | 18.909 | 0.844 | −20.028 | 1.00 | 33.97 | | O |
| ANISOU | 1351 | O | PHE | A | 405 | 4478 | 4384 | 4045 | −56 | 30 | −88 | O |
| ATOM | 1352 | N | LEU | A | 406 | 18.811 | −1.132 | −18.922 | 1.00 | 34.15 | | N |
| ANISOU | 1352 | N | LEU | A | 406 | 4406 | 4368 | 4199 | −66 | 89 | −89 | N |
| ATOM | 1353 | CA | LEU | A | 406 | 20.063 | −0.990 | −18.217 | 1.00 | 34.71 | | C |
| ANISOU | 1353 | CA | LEU | A | 406 | 4441 | 4465 | 4282 | −10 | 69 | −40 | C |
| ATOM | 1354 | CB | LEU | A | 406 | 19.973 | 0.066 | −17.112 | 1.00 | 34.26 | | C |
| ANISOU | 1354 | CB | LEU | A | 406 | 4416 | 4403 | 4198 | 0 | 3 | −2 | C |
| ATOM | 1355 | CG | LEU | A | 406 | 19.362 | −0.080 | −15.723 | 1.00 | 32.70 | | C |
| ANISOU | 1355 | CG | LEU | A | 406 | 4113 | 4273 | 4036 | −57 | −11 | 1 | C |
| ATOM | 1356 | CD1 | LEU | A | 406 | 18.140 | 0.758 | −15.580 | 1.00 | 31.62 | | C |
| ANISOU | 1356 | CD1 | LEU | A | 406 | 3956 | 4197 | 3860 | −42 | −51 | 147 | C |
| ATOM | 1357 | CD2 | LEU | A | 406 | 19.149 | −1.480 | −15.240 | 1.00 | 30.79 | | C |
| ANISOU | 1357 | CD2 | LEU | A | 406 | 3828 | 4056 | 3815 | −202 | −43 | −257 | C |
| ATOM | 1358 | C | LEU | A | 406 | 20.593 | −2.310 | −17.687 | 1.00 | 35.03 | | C |
| ANISOU | 1358 | C | LEU | A | 406 | 4496 | 4493 | 4320 | −22 | 88 | −40 | C |
| ATOM | 1359 | O | LEU | A | 406 | 19.908 | −3.316 | −17.763 | 1.00 | 35.15 | | O |
| ANISOU | 1359 | O | LEU | A | 406 | 4419 | 4618 | 4318 | −7 | 134 | −19 | O |
| ATOM | 1360 | N | TYR | A | 407 | 21.835 | −2.297 | −17.198 | 1.00 | 35.31 | | N |
| ANISOU | 1360 | N | TYR | A | 407 | 4535 | 4528 | 4351 | −7 | 40 | −34 | N |
| ATOM | 1361 | CA | TYR | A | 407 | 22.410 | −3.423 | −16.471 | 1.00 | 35.65 | | C |
| ANISOU | 1361 | CA | TYR | A | 407 | 4544 | 4568 | 4430 | −6 | 40 | −15 | C |
| ATOM | 1362 | CB | TYR | A | 407 | 23.581 | −4.065 | −17.216 | 1.00 | 34.84 | | C |
| ANISOU | 1362 | CB | TYR | A | 407 | 4429 | 4478 | 4327 | −14 | 12 | −49 | C |
| ATOM | 1363 | CG | TYR | A | 407 | 23.321 | −4.723 | −18.548 | 1.00 | 34.08 | | C |
| ANISOU | 1363 | CG | TYR | A | 407 | 4249 | 4291 | 4407 | 40 | 57 | 9 | C |
| ATOM | 1364 | CD1 | TYR | A | 407 | 23.139 | −3.959 | −19.694 | 1.00 | 32.26 | | C |
| ANISOU | 1364 | CD1 | TYR | A | 407 | 3966 | 3991 | 4300 | 71 | 69 | −29 | C |
| ATOM | 1365 | CE1 | TYR | A | 407 | 22.945 | −4.551 | −20.936 | 1.00 | 31.35 | | C |
| ANISOU | 1365 | CE1 | TYR | A | 407 | 3804 | 3854 | 4251 | 1 | −7 | 29 | C |
| ATOM | 1366 | CZ | TYR | A | 407 | 22.964 | −5.923 | −21.046 | 1.00 | 32.84 | | C |
| ANISOU | 1366 | CZ | TYR | A | 407 | 3810 | 4228 | 4440 | 0 | 45 | 0 | C |
| ATOM | 1367 | OH | TYR | A | 407 | 22.771 | −6.460 | −22.284 | 1.00 | 34.03 | | O |
| ANISOU | 1367 | OH | TYR | A | 407 | 4198 | 4350 | 4380 | 16 | 61 | 8 | O |
| ATOM | 1368 | CE2 | TYR | A | 407 | 23.163 | −6.726 | −19.925 | 1.00 | 31.27 | | C |
| ANISOU | 1368 | CE2 | TYR | A | 407 | 3774 | 3877 | 4229 | 25 | 90 | −36 | C |
| ATOM | 1369 | CD2 | TYR | A | 407 | 23.354 | −6.119 | −18.681 | 1.00 | 32.21 | | C |
| ANISOU | 1369 | CD2 | TYR | A | 407 | 3878 | 4149 | 4210 | −57 | 57 | 56 | C |
| ATOM | 1370 | C | TYR | A | 407 | 22.935 | −2.988 | −15.099 | 1.00 | 35.88 | | C |
| ANISOU | 1370 | C | TYR | A | 407 | 4601 | 4620 | 4411 | −27 | 26 | −8 | C |
| ATOM | 1371 | O | TYR | A | 407 | 23.460 | −1.890 | −14.934 | 1.00 | 35.29 | | O |
| ANISOU | 1371 | O | TYR | A | 407 | 4616 | 4570 | 4220 | 18 | −14 | −3 | O |
| ATOM | 1372 | N | SER | A | 408 | 22.794 | −3.888 | −14.134 | 1.00 | 36.43 | | N |
| ANISOU | 1372 | N | SER | A | 408 | 4686 | 4700 | 4454 | −17 | 21 | 8 | N |
| ATOM | 1373 | CA | SER | A | 408 | 23.367 | −3.750 | −12.801 | 1.00 | 36.52 | | C |
| ANISOU | 1373 | CA | SER | A | 408 | 4655 | 4722 | 4499 | −22 | 28 | 33 | C |

TABLE 7-continued

The atomic structure coordinates of Fc-TM

| ATOM | 1374 | CB | SER | A | 408 | 22.296 | −3.911 | −11.702 | 1.00 | 36.58 | | C |
|---|---|---|---|---|---|---|---|---|---|---|---|---|
| ANISOU | 1374 | CB | SER | A | 408 | 4665 | 4728 | 4507 | −32 | 27 | 15 | C |
| ATOM | 1375 | OG | SER | A | 408 | 22.782 | −3.508 | −10.426 | 1.00 | 34.60 | | O |
| ANISOU | 1375 | OG | SER | A | 408 | 4359 | 4564 | 4222 | 70 | 111 | 165 | O |
| ATOM | 1376 | C | SER | A | 408 | 24.397 | −4.849 | −12.686 | 1.00 | 36.40 | | C |
| ANISOU | 1376 | C | SER | A | 408 | 4657 | 4704 | 4467 | −12 | 38 | 50 | C |
| ATOM | 1377 | O | SER | A | 408 | 24.159 | −5.985 | −13.121 | 1.00 | 36.21 | | O |
| ANISOU | 1377 | O | SER | A | 408 | 4674 | 4649 | 4435 | −17 | 72 | 98 | O |
| ATOM | 1378 | N | LYS | A | 409 | 25.553 | −4.484 | −12.145 | 1.00 | 36.10 | | N |
| ANISOU | 1378 | N | LYS | A | 409 | 4657 | 4695 | 4362 | 4 | −34 | 66 | N |
| ATOM | 1379 | CA | LYS | A | 409 | 26.659 | −5.409 | −11.944 | 1.00 | 35.94 | | C |
| ANISOU | 1379 | CA | LYS | A | 409 | 4630 | 4629 | 4395 | 7 | −40 | 60 | C |
| ATOM | 1380 | CB | LYS | A | 409 | 27.906 | −4.935 | −12.709 | 1.00 | 35.47 | | C |
| ANISOU | 1380 | CB | LYS | A | 409 | 4588 | 4563 | 4326 | −11 | −12 | 65 | C |
| ATOM | 1381 | CG | LYS | A | 409 | 29.104 | −5.896 | −12.600 | 1.00 | 36.03 | | C |
| ANISOU | 1381 | CG | LYS | A | 409 | 4596 | 4593 | 4500 | −14 | 25 | 105 | C |
| ATOM | 1382 | CD | LYS | A | 409 | 30.197 | −5.695 | −13.673 | 1.00 | 36.06 | | C |
| ANISOU | 1382 | CD | LYS | A | 409 | 4630 | 4581 | 4491 | 54 | −44 | 108 | C |
| ATOM | 1383 | CE | LYS | A | 409 | 31.116 | −4.491 | −13.396 | 1.00 | 33.48 | | C |
| ANISOU | 1383 | CE | LYS | A | 409 | 4373 | 4343 | 4003 | 26 | −214 | 0 | C |
| ATOM | 1384 | NZ | LYS | A | 409 | 31.618 | −4.426 | −11.979 | 1.00 | 34.29 | | N |
| ANISOU | 1384 | NZ | LYS | A | 409 | 4556 | 4113 | 4356 | 53 | 22 | 193 | N |
| ATOM | 1385 | C | LYS | A | 409 | 26.941 | −5.580 | −10.425 | 1.00 | 35.82 | | C |
| ANISOU | 1385 | C | LYS | A | 409 | 4612 | 4607 | 4388 | −8 | −73 | 104 | C |
| ATOM | 1386 | O | LYS | A | 409 | 27.346 | −4.637 | −9.738 | 1.00 | 35.11 | | O |
| ANISOU | 1386 | O | LYS | A | 409 | 4621 | 4589 | 4130 | −13 | −162 | 98 | O |
| ATOM | 1387 | N | LEU | A | 410 | 26.673 | −6.777 | −9.920 | 1.00 | 35.61 | | N |
| ANISOU | 1387 | N | LEU | A | 410 | 4529 | 4579 | 4420 | 14 | −95 | 141 | N |
| ATOM | 1388 | CA | LEU | A | 410 | 26.958 | −7.114 | −8.531 | 1.00 | 35.76 | | C |
| ANISOU | 1388 | CA | LEU | A | 410 | 4598 | 4561 | 4426 | 4 | 1 | 114 | C |
| ATOM | 1389 | CB | LEU | A | 410 | 25.857 | −7.992 | −7.911 | 1.00 | 35.47 | | C |
| ANISOU | 1389 | CB | LEU | A | 410 | 4524 | 4542 | 4409 | −3 | −25 | 72 | C |
| ATOM | 1390 | CG | LEU | A | 410 | 26.145 | −8.413 | −6.445 | 1.00 | 35.65 | | C |
| ANISOU | 1390 | CG | LEU | A | 410 | 4571 | 4520 | 4452 | 10 | 25 | 122 | C |
| ATOM | 1391 | CD1 | LEU | A | 410 | 26.011 | −7.260 | −5.456 | 1.00 | 33.68 | | C |
| ANISOU | 1391 | CD1 | LEU | A | 410 | 4444 | 4388 | 3963 | 51 | 76 | 155 | C |
| ATOM | 1392 | CD2 | LEU | A | 410 | 25.311 | −9.570 | −6.007 | 1.00 | 35.81 | | C |
| ANISOU | 1392 | CD2 | LEU | A | 410 | 4430 | 4679 | 4494 | −71 | 30 | 184 | C |
| ATOM | 1393 | C | LEU | A | 410 | 28.292 | −7.843 | −8.495 | 1.00 | 35.82 | | C |
| ANISOU | 1393 | C | LEU | A | 410 | 4590 | 4560 | 4458 | 39 | −21 | 187 | C |
| ATOM | 1394 | O | LEU | A | 410 | 28.479 | −8.850 | −9.213 | 1.00 | 35.64 | | O |
| ANISOU | 1394 | O | LEU | A | 410 | 4599 | 4489 | 4455 | 42 | −33 | 257 | O |
| ATOM | 1395 | N | THR | A | 411 | 29.225 | −7.315 | −7.707 | 1.00 | 36.06 | | N |
| ANISOU | 1395 | N | THR | A | 411 | 4693 | 4596 | 4410 | 41 | −16 | 193 | N |
| ATOM | 1396 | CA | THR | A | 411 | 30.513 | −7.989 | −7.514 | 1.00 | 37.46 | | C |
| ANISOU | 1396 | CA | THR | A | 411 | 4777 | 4828 | 4625 | 24 | 0 | 147 | C |
| ATOM | 1397 | CB | THR | A | 411 | 31.705 | −7.010 | −7.613 | 1.00 | 37.32 | | C |
| ANISOU | 1397 | CB | THR | A | 411 | 4746 | 4809 | 4625 | 10 | −29 | 154 | C |
| ATOM | 1398 | OG1 | THR | A | 411 | 31.761 | −6.416 | −8.930 | 1.00 | 37.50 | | O |
| ANISOU | 1398 | OG1 | THR | A | 411 | 4710 | 4871 | 4664 | 84 | −11 | 125 | O |
| ATOM | 1399 | CG2 | THR | A | 411 | 33.018 | −7.757 | −7.351 | 1.00 | 36.73 | | C |
| ANISOU | 1399 | CG2 | THR | A | 411 | 4767 | 4595 | 4593 | 3 | 22 | 161 | C |
| ATOM | 1400 | C | THR | A | 411 | 30.540 | −8.758 | −6.171 | 1.00 | 38.50 | | C |
| ANISOU | 1400 | C | THR | A | 411 | 4928 | 4919 | 4780 | 58 | −33 | 132 | C |
| ATOM | 1401 | O | THR | A | 411 | 30.377 | −8.166 | −5.098 | 1.00 | 38.70 | | O |
| ANISOU | 1401 | O | THR | A | 411 | 4944 | 5052 | 4708 | 98 | 23 | 156 | O |
| ATOM | 1402 | N | VAL | A | 412 | 30.733 | −10.070 | −6.231 | 1.00 | 40.03 | | N |
| ANISOU | 1402 | N | VAL | A | 412 | 5107 | 5068 | 5034 | 48 | −15 | 105 | N |
| ATOM | 1403 | CA | VAL | A | 412 | 30.898 | −10.879 | −4.999 | 1.00 | 41.18 | | C |
| ANISOU | 1403 | CA | VAL | A | 412 | 5270 | 5215 | 5159 | 42 | −14 | 107 | C |
| ATOM | 1404 | CB | VAL | A | 412 | 29.671 | −11.783 | −4.715 | 1.00 | 40.91 | | C |
| ANISOU | 1404 | CB | VAL | A | 412 | 5223 | 5145 | 5175 | 45 | −26 | 100 | C |
| ATOM | 1405 | CG1 | VAL | A | 412 | 28.459 | −10.957 | −4.333 | 1.00 | 41.72 | | C |
| ANISOU | 1405 | CG1 | VAL | A | 412 | 5340 | 5253 | 5258 | 8 | 5 | 95 | C |
| ATOM | 1406 | CG2 | VAL | A | 412 | 29.378 | −12.688 | −5.898 | 1.00 | 41.30 | | C |
| ANISOU | 1406 | CG2 | VAL | A | 412 | 5288 | 5262 | 5143 | 56 | −93 | 79 | C |
| ATOM | 1407 | C | VAL | A | 412 | 32.130 | −11.777 | −5.058 | 1.00 | 41.92 | | C |
| ANISOU | 1407 | C | VAL | A | 412 | 5342 | 5298 | 5284 | 55 | 2 | 92 | C |
| ATOM | 1408 | O | VAL | A | 412 | 32.501 | −12.230 | −6.148 | 1.00 | 42.01 | | O |
| ANISOU | 1408 | O | VAL | A | 412 | 5411 | 5272 | 5277 | 51 | −15 | 74 | O |
| ATOM | 1409 | N | ASP | A | 413 | 32.741 | −12.050 | −3.895 | 1.00 | 43.17 | | N |
| ANISOU | 1409 | N | ASP | A | 413 | 5497 | 5486 | 5417 | 25 | −27 | 44 | N |
| ATOM | 1410 | CA | ASP | A | 413 | 33.828 | −13.058 | −3.794 | 1.00 | 44.45 | | C |
| ANISOU | 1410 | CA | ASP | A | 413 | 5685 | 5613 | 5589 | 20 | −20 | 37 | C |
| ATOM | 1411 | CB | ASP | A | 413 | 34.281 | −13.268 | −2.345 | 1.00 | 45.14 | | C |
| ANISOU | 1411 | CB | ASP | A | 413 | 5771 | 5740 | 5638 | 27 | −24 | 76 | C |
| ATOM | 1412 | CG | ASP | A | 413 | 34.976 | −12.041 | −1.745 | 1.00 | 46.83 | | C |
| ANISOU | 1412 | CG | ASP | A | 413 | 6015 | 5966 | 5809 | −56 | −80 | 52 | C |

TABLE 7-continued

| The atomic structure coordinates of Fc-TM | | | | | | | | | | | |
|---|---|---|---|---|---|---|---|---|---|---|---|
| ATOM | 1413 | OD1 | ASP | A | 413 | 35.210 | −11.035 | −2.457 | 1.00 | 48.90 | O |
| ANISOU | 1413 | OD1 | ASP | A | 413 | 6156 | 6319 | 6102 | −40 | 23 | 125 | O |
| ATOM | 1414 | OD2 | ASP | A | 413 | 35.288 | −12.084 | −0.535 | 1.00 | 49.87 | O |
| ANISOU | 1414 | OD2 | ASP | A | 413 | 6489 | 6388 | 6071 | −31 | −24 | 57 | O |
| ATOM | 1415 | C | ASP | A | 413 | 33.345 | −14.385 | −4.372 | 1.00 | 44.46 | C |
| ANISOU | 1415 | C | ASP | A | 413 | 5701 | 5572 | 5620 | −1 | 2 | 46 | C |
| ATOM | 1416 | O | ASP | A | 413 | 32.224 | −14.799 | −4.093 | 1.00 | 44.32 | O |
| ANISOU | 1416 | O | ASP | A | 413 | 5691 | 5550 | 5596 | 4 | 41 | 42 | O |
| ATOM | 1417 | N | LYS | A | 414 | 34.185 | −15.020 | −5.195 | 1.00 | 44.94 | N |
| ANISOU | 1417 | N | LYS | A | 414 | 5770 | 5623 | 5682 | 8 | −7 | 53 | N |
| ATOM | 1418 | CA | LYS | A | 414 | 33.820 | −16.224 | −5.971 | 1.00 | 45.58 | C |
| ANISOU | 1418 | CA | LYS | A | 414 | 5844 | 5751 | 5721 | −21 | −31 | 35 | C |
| ATOM | 1419 | CB | LYS | A | 414 | 34.997 | −16.633 | −6.850 | 1.00 | 45.72 | C |
| ANISOU | 1419 | CB | LYS | A | 414 | 5836 | 5796 | 5740 | −19 | −14 | 37 | C |
| ATOM | 1420 | CG | LYS | A | 414 | 34.725 | −17.758 | −7.819 | 1.00 | 45.82 | C |
| ANISOU | 1420 | CG | LYS | A | 414 | 5880 | 5705 | 5824 | 30 | −23 | 30 | C |
| ATOM | 1421 | CD | LYS | A | 414 | 35.966 | −18.024 | −8.634 | 1.00 | 47.84 | C |
| ANISOU | 1421 | CD | LYS | A | 414 | 6077 | 6009 | 6089 | 18 | 52 | −1 | C |
| ATOM | 1422 | CE | LYS | A | 414 | 35.693 | −18.974 | −9.784 | 1.00 | 48.47 | C |
| ANISOU | 1422 | CE | LYS | A | 414 | 6126 | 6229 | 6062 | 23 | 11 | −100 | C |
| ATOM | 1423 | NZ | LYS | A | 414 | 36.972 | −19.359 | −10.462 | 1.00 | 49.66 | N |
| ANISOU | 1423 | NZ | LYS | A | 414 | 6253 | 6358 | 6256 | 15 | 38 | −89 | N |
| ATOM | 1424 | C | LYS | A | 414 | 33.401 | −17.438 | −5.138 | 1.00 | 46.06 | C |
| ANISOU | 1424 | C | LYS | A | 414 | 5882 | 5808 | 5809 | −53 | −60 | 44 | C |
| ATOM | 1425 | O | LYS | A | 414 | 32.556 | −18.234 | −5.566 | 1.00 | 47.07 | O |
| ANISOU | 1425 | O | LYS | A | 414 | 5999 | 5982 | 5903 | −24 | −123 | 54 | O |
| ATOM | 1426 | N | SER | A | 415 | 34.012 | −17.606 | −3.971 | 1.00 | 46.26 | N |
| ANISOU | 1426 | N | SER | A | 415 | 5896 | 5861 | 5817 | −68 | −56 | 60 | N |
| ATOM | 1427 | CA | SER | A | 415 | 33.679 | −18.728 | −3.088 | 1.00 | 46.61 | C |
| ANISOU | 1427 | CA | SER | A | 415 | 5930 | 5891 | 5888 | −68 | −54 | 52 | C |
| ATOM | 1428 | CB | SER | A | 415 | 34.552 | −18.712 | −1.810 | 1.00 | 46.81 | C |
| ANISOU | 1428 | CB | SER | A | 415 | 5974 | 5905 | 5906 | −59 | −48 | 70 | C |
| ATOM | 1429 | OG | SER | A | 415 | 34.803 | −17.392 | −1.321 | 1.00 | 46.84 | O |
| ANISOU | 1429 | OG | SER | A | 415 | 6000 | 5875 | 5923 | −99 | −111 | 22 | O |
| ATOM | 1430 | C | SER | A | 415 | 32.167 | −18.732 | −2.781 | 1.00 | 46.70 | C |
| ANISOU | 1430 | C | SER | A | 415 | 5922 | 5886 | 5935 | −46 | −18 | 49 | C |
| ATOM | 1431 | O | SER | A | 415 | 31.521 | −19.780 | −2.836 | 1.00 | 47.24 | O |
| ANISOU | 1431 | O | SER | A | 415 | 5992 | 5952 | 6003 | −61 | −44 | 28 | O |
| ATOM | 1432 | N | ARG | A | 416 | 31.617 | −17.544 | −2.512 | 1.00 | 46.83 | N |
| ANISOU | 1432 | N | ARG | A | 416 | 5915 | 5904 | 5972 | −34 | −6 | 62 | N |
| ATOM | 1433 | CA | ARG | A | 416 | 30.171 | −17.325 | −2.328 | 1.00 | 46.36 | C |
| ANISOU | 1433 | CA | ARG | A | 416 | 5861 | 5859 | 5894 | −34 | 0 | 66 | C |
| ATOM | 1434 | CB | ARG | A | 416 | 29.887 | −15.849 | −2.088 | 1.00 | 46.60 | C |
| ANISOU | 1434 | CB | ARG | A | 416 | 5918 | 5875 | 5912 | 0 | 41 | 69 | C |
| ATOM | 1435 | CG | ARG | A | 416 | 29.867 | −15.452 | −0.644 | 1.00 | 47.76 | C |
| ANISOU | 1435 | CG | ARG | A | 416 | 6143 | 6052 | 5950 | −60 | −4 | 53 | C |
| ATOM | 1436 | CD | ARG | A | 416 | 29.723 | −13.956 | −0.492 | 1.00 | 47.81 | C |
| ANISOU | 1436 | CD | ARG | A | 416 | 5941 | 6058 | 6165 | −177 | −24 | 4 | C |
| ATOM | 1437 | NE | ARG | A | 416 | 30.998 | −13.332 | −0.127 | 1.00 | 51.98 | N |
| ANISOU | 1437 | NE | ARG | A | 416 | 6596 | 6580 | 6574 | 64 | 83 | 221 | N |
| ATOM | 1438 | CZ | ARG | A | 416 | 31.182 | −12.562 | 0.945 | 1.00 | 48.85 | C |
| ANISOU | 1438 | CZ | ARG | A | 416 | 5973 | 6438 | 6150 | −125 | 66 | −142 | C |
| ATOM | 1439 | NH1 | ARG | A | 416 | 30.168 | −12.312 | 1.763 | 1.00 | 53.54 | N |
| ANISOU | 1439 | NH1 | ARG | A | 416 | 6843 | 6710 | 6787 | 7 | 1 | 33 | N |
| ATOM | 1440 | NH2 | ARG | A | 416 | 32.379 | −12.028 | 1.196 | 1.00 | 52.19 | N |
| ANISOU | 1440 | NH2 | ARG | A | 416 | 6821 | 6562 | 6445 | 124 | 29 | 86 | N |
| ATOM | 1441 | C | ARG | A | 416 | 29.326 | −17.787 | −3.503 | 1.00 | 46.10 | C |
| ANISOU | 1441 | C | ARG | A | 416 | 5811 | 5841 | 5864 | −26 | −12 | 80 | C |
| ATOM | 1442 | O | ARG | A | 416 | 28.229 | −18.318 | −3.299 | 1.00 | 46.58 | O |
| ANISOU | 1442 | O | ARG | A | 416 | 5912 | 5852 | 5931 | 3 | −22 | 129 | O |
| ATOM | 1443 | N | TRP | A | 417 | 29.814 | −17.566 | −4.727 | 1.00 | 45.76 | N |
| ANISOU | 1443 | N | TRP | A | 417 | 5753 | 5790 | 5841 | −39 | −6 | 47 | N |
| ATOM | 1444 | CA | TRP | A | 417 | 29.109 | −18.028 | −5.933 | 1.00 | 45.44 | C |
| ANISOU | 1444 | CA | TRP | A | 417 | 5708 | 5726 | 5828 | −4 | −12 | 32 | C |
| ATOM | 1445 | CB | TRP | A | 417 | 29.750 | −17.485 | −7.222 | 1.00 | 43.60 | C |
| ANISOU | 1445 | CB | TRP | A | 417 | 5388 | 5589 | 5589 | 11 | −113 | 20 | C |
| ATOM | 1446 | CG | TRP | A | 417 | 29.056 | −17.925 | −8.508 | 1.00 | 43.73 | C |
| ANISOU | 1446 | CG | TRP | A | 417 | 5357 | 5558 | 5700 | 39 | −41 | 38 | C |
| ATOM | 1447 | CD1 | TRP | A | 417 | 29.598 | −18.674 | −9.537 | 1.00 | 41.28 | C |
| ANISOU | 1447 | CD1 | TRP | A | 417 | 4777 | 5490 | 5416 | 116 | −99 | 22 | C |
| ATOM | 1448 | NE1 | TRP | A | 417 | 28.662 | −18.887 | −10.523 | 1.00 | 44.32 | N |
| ANISOU | 1448 | NE1 | TRP | A | 417 | 5725 | 5455 | 5657 | −184 | 23 | 161 | N |
| ATOM | 1449 | CE2 | TRP | A | 417 | 27.488 | −18.279 | −10.152 | 1.00 | 41.66 | C |
| ANISOU | 1449 | CE2 | TRP | A | 417 | 5146 | 5311 | 5372 | 46 | −8 | −11 | C |
| ATOM | 1450 | CD2 | TRP | A | 417 | 27.698 | −17.665 | −8.888 | 1.00 | 43.53 | C |
| ANISOU | 1450 | CD2 | TRP | A | 417 | 5499 | 5455 | 5584 | 22 | 36 | 94 | C |
| ATOM | 1451 | CE3 | TRP | A | 417 | 26.634 | −16.972 | −8.286 | 1.00 | 42.96 | C |
| ANISOU | 1451 | CE3 | TRP | A | 417 | 5359 | 5442 | 5518 | 17 | 14 | 67 | C |

TABLE 7-continued

The atomic structure coordinates of Fc-TM

| | | | | | | | | | | | | |
|---|---|---|---|---|---|---|---|---|---|---|---|---|
| ATOM | 1452 | CZ3 | TRP | A | 417 | 25.417 | −16.905 | −8.962 | 1.00 | 42.84 | | C |
| ANISOU | 1452 | CZ3 | TRP | A | 417 | 5360 | 5442 | 5473 | −41 | 61 | −2 | C |
| ATOM | 1453 | CH2 | TRP | A | 417 | 25.246 | −17.517 | −10.217 | 1.00 | 43.50 | | C |
| ANISOU | 1453 | CH2 | TRP | A | 417 | 5561 | 5399 | 5567 | −97 | 121 | 76 | C |
| ATOM | 1454 | CZ2 | TRP | A | 417 | 26.263 | −18.206 | −10.824 | 1.00 | 42.87 | | C |
| ANISOU | 1454 | CZ2 | TRP | A | 417 | 5358 | 5337 | 5590 | −6 | 99 | 73 | C |
| ATOM | 1455 | C | TRP | A | 417 | 29.072 | −19.558 | −5.927 | 1.00 | 46.18 | | C |
| ANISOU | 1455 | C | TRP | A | 417 | 5795 | 5803 | 5946 | 7 | −35 | 30 | C |
| ATOM | 1456 | O | TRP | A | 417 | 28.009 | −20.167 | −6.166 | 1.00 | 46.90 | | O |
| ANISOU | 1456 | O | TRP | A | 417 | 5817 | 5939 | 6064 | −1 | −68 | 67 | O |
| ATOM | 1457 | N | GLN | A | 418 | 30.217 | −20.167 | −5.598 | 1.00 | 46.23 | | N |
| ANISOU | 1457 | N | GLN | A | 418 | 5783 | 5839 | 5941 | 48 | −14 | 42 | N |
| ATOM | 1458 | CA | GLN | A | 418 | 30.356 | −21.636 | −5.575 | 1.00 | 46.42 | | C |
| ANISOU | 1458 | CA | GLN | A | 418 | 5870 | 5841 | 5926 | 17 | −2 | 41 | C |
| ATOM | 1459 | CB | GLN | A | 418 | 31.842 | −22.049 | −5.700 | 1.00 | 46.09 | | C |
| ANISOU | 1459 | CB | GLN | A | 418 | 5815 | 5825 | 5872 | 36 | 19 | 53 | C |
| ATOM | 1460 | CG | GLN | A | 418 | 32.458 | −21.757 | −7.083 | 1.00 | 46.48 | | C |
| ANISOU | 1460 | CG | GLN | A | 418 | 5847 | 5833 | 5976 | 34 | 73 | −10 | C |
| ATOM | 1461 | CD | GLN | A | 418 | 34.002 | −21.715 | −7.095 | 1.00 | 46.67 | | C |
| ANISOU | 1461 | CD | GLN | A | 418 | 5898 | 5914 | 5920 | 16 | 24 | 20 | C |
| ATOM | 1462 | OE1 | GLN | A | 418 | 34.665 | −21.686 | −6.048 | 1.00 | 47.82 | | O |
| ANISOU | 1462 | OE1 | GLN | A | 418 | 6033 | 6136 | 6000 | 53 | −33 | 66 | O |
| ATOM | 1463 | NE2 | GLN | A | 418 | 34.571 | −21.701 | −8.297 | 1.00 | 47.35 | | N |
| ANISOU | 1463 | NE2 | GLN | A | 418 | 5961 | 6023 | 6004 | 33 | 66 | 26 | N |
| ATOM | 1464 | C | GLN | A | 418 | 29.653 | −22.299 | −4.363 | 1.00 | 46.78 | | C |
| ANISOU | 1464 | C | GLN | A | 418 | 5905 | 5866 | 6002 | −9 | −3 | 20 | C |
| ATOM | 1465 | O | GLN | A | 418 | 29.001 | −23.337 | −4.506 | 1.00 | 47.00 | | O |
| ANISOU | 1465 | O | GLN | A | 418 | 5932 | 5847 | 6078 | −40 | −29 | 35 | O |
| ATOM | 1466 | N | GLN | A | 419 | 29.777 | −21.696 | −3.180 | 1.00 | 47.14 | | N |
| ANISOU | 1466 | N | GLN | A | 419 | 6009 | 5940 | 5961 | −18 | −9 | 36 | N |
| ATOM | 1467 | CA | GLN | A | 419 | 29.014 | −22.148 | −2.017 | 1.00 | 48.11 | | C |
| ANISOU | 1467 | CA | GLN | A | 419 | 6130 | 6033 | 6117 | −16 | −35 | 52 | C |
| ATOM | 1468 | CB | GLN | A | 419 | 29.192 | −21.182 | −0.827 | 1.00 | 47.74 | | C |
| ANISOU | 1468 | CB | GLN | A | 419 | 6122 | 5956 | 6058 | −21 | −65 | 7 | C |
| ATOM | 1469 | CG | GLN | A | 419 | 30.584 | −21.313 | −0.189 | 1.00 | 48.88 | | C |
| ANISOU | 1469 | CG | GLN | A | 419 | 6202 | 6136 | 6231 | −31 | −83 | 18 | C |
| ATOM | 1470 | CD | GLN | A | 419 | 30.835 | −20.383 | 1.010 | 1.00 | 48.22 | | C |
| ANISOU | 1470 | CD | GLN | A | 419 | 6253 | 6005 | 6062 | 61 | −160 | −28 | C |
| ATOM | 1471 | OE1 | GLN | A | 419 | 30.374 | −19.232 | 1.050 | 1.00 | 51.84 | | O |
| ANISOU | 1471 | OE1 | GLN | A | 419 | 6788 | 6288 | 6621 | 72 | −49 | −14 | O |
| ATOM | 1472 | NE2 | GLN | A | 419 | 31.595 | −20.883 | 1.981 | 1.00 | 48.48 | | N |
| ANISOU | 1472 | NE2 | GLN | A | 419 | 6320 | 6025 | 6074 | 22 | −59 | −61 | N |
| ATOM | 1473 | C | GLN | A | 419 | 27.538 | −22.358 | −2.393 | 1.00 | 47.88 | | C |
| ANISOU | 1473 | C | GLN | A | 419 | 6103 | 5976 | 6111 | −20 | −69 | 81 | C |
| ATOM | 1474 | O | GLN | A | 419 | 26.977 | −23.449 | −2.213 | 1.00 | 48.69 | | O |
| ANISOU | 1474 | O | GLN | A | 419 | 6259 | 5993 | 6247 | −19 | −60 | 110 | O |
| ATOM | 1475 | N | GLY | A | 420 | 26.911 | −21.333 | −2.954 | 1.00 | 47.48 | | N |
| ANISOU | 1475 | N | GLY | A | 420 | 6057 | 5915 | 6069 | −12 | −64 | 79 | N |
| ATOM | 1476 | CA | GLY | A | 420 | 25.605 | −21.536 | −3.553 | 1.00 | 46.95 | | C |
| ANISOU | 1476 | CA | GLY | A | 420 | 5936 | 5893 | 6010 | 15 | −32 | 74 | C |
| ATOM | 1477 | C | GLY | A | 420 | 24.588 | −20.527 | −3.120 | 1.00 | 46.55 | | C |
| ANISOU | 1477 | C | GLY | A | 420 | 5880 | 5886 | 5920 | 12 | −26 | 49 | C |
| ATOM | 1478 | O | GLY | A | 420 | 23.394 | −20.701 | −3.397 | 1.00 | 46.93 | | O |
| ANISOU | 1478 | O | GLY | A | 420 | 5889 | 5969 | 5972 | −9 | −8 | 74 | O |
| ATOM | 1479 | N | ASN | A | 421 | 25.070 | −19.488 | −2.433 | 1.00 | 46.34 | | N |
| ANISOU | 1479 | N | ASN | A | 421 | 5839 | 5872 | 5896 | 40 | −50 | 46 | N |
| ATOM | 1480 | CA | ASN | A | 421 | 24.289 | −18.301 | −2.077 | 1.00 | 45.85 | | C |
| ANISOU | 1480 | CA | ASN | A | 421 | 5786 | 5865 | 5770 | 64 | −39 | 9 | C |
| ATOM | 1481 | CB | ASN | A | 421 | 25.211 | −17.091 | −1.903 | 1.00 | 45.59 | | C |
| ANISOU | 1481 | CB | ASN | A | 421 | 5783 | 5824 | 5712 | 51 | −56 | 13 | C |
| ATOM | 1482 | CG | ASN | A | 421 | 25.560 | −16.808 | −0.438 | 1.00 | 46.44 | | C |
| ANISOU | 1482 | CG | ASN | A | 421 | 5950 | 5950 | 5741 | 86 | −2 | −15 | C |
| ATOM | 1483 | OD1 | ASN | A | 421 | 26.110 | −17.659 | 0.284 | 1.00 | 43.48 | | O |
| ANISOU | 1483 | OD1 | ASN | A | 421 | 5884 | 5482 | 5152 | 142 | 48 | 64 | O |
| ATOM | 1484 | ND2 | ASN | A | 421 | 25.277 | −15.577 | −0.009 | 1.00 | 47.25 | | N |
| ANISOU | 1484 | ND2 | ASN | A | 421 | 6145 | 5952 | 5855 | 165 | −93 | −103 | N |
| ATOM | 1485 | C | ASN | A | 421 | 23.213 | −17.924 | −3.095 | 1.00 | 45.79 | | C |
| ANISOU | 1485 | C | ASN | A | 421 | 5772 | 5862 | 5764 | 76 | −20 | 43 | C |
| ATOM | 1486 | O | ASN | A | 421 | 23.401 | −18.062 | −4.327 | 1.00 | 45.60 | | O |
| ANISOU | 1486 | O | ASN | A | 421 | 5768 | 5864 | 5693 | 63 | −16 | 71 | O |
| ATOM | 1487 | N | VAL | A | 422 | 22.089 | −17.454 | −2.553 | 1.00 | 45.55 | | N |
| ANISOU | 1487 | N | VAL | A | 422 | 5739 | 5837 | 5731 | 49 | −11 | 67 | N |
| ATOM | 1488 | CA | VAL | A | 422 | 21.035 | −16.834 | −3.337 | 1.00 | 45.24 | | C |
| ANISOU | 1488 | CA | VAL | A | 422 | 5704 | 5739 | 5744 | 26 | 10 | 70 | C |
| ATOM | 1489 | CB | VAL | A | 422 | 19.661 | −17.027 | −2.690 | 1.00 | 45.54 | | C |
| ANISOU | 1489 | CB | VAL | A | 422 | 5700 | 5790 | 5810 | 24 | 9 | 65 | C |
| ATOM | 1490 | CG1 | VAL | A | 422 | 18.638 | −16.039 | −3.274 | 1.00 | 46.04 | | C |
| ANISOU | 1490 | CG1 | VAL | A | 422 | 5848 | 5757 | 5887 | 73 | 42 | 96 | C |

TABLE 7-continued

| | | | | | | | | | | | |
|---|---|---|---|---|---|---|---|---|---|---|---|
| The atomic structure coordinates of Fc-TM | | | | | | | | | | | |
| ATOM | 1491 | CG2 | VAL | A | 422 | 19.197 | −18.476 | −2.879 | 1.00 | 45.88 | C |
| ANISOU | 1491 | CG2 | VAL | A | 422 | 5756 | 5710 | 5965 | 34 | −24 | 7 | C |
| ATOM | 1492 | C | VAL | A | 422 | 21.346 | −15.357 | −3.459 | 1.00 | 44.78 | C |
| ANISOU | 1492 | C | VAL | A | 422 | 5682 | 5693 | 5638 | 10 | 15 | 94 | C |
| ATOM | 1493 | O | VAL | A | 422 | 21.613 | −14.670 | −2.457 | 1.00 | 44.88 | O |
| ANISOU | 1493 | O | VAL | A | 422 | 5745 | 5738 | 5570 | 0 | 98 | 124 | O |
| ATOM | 1494 | N | PHE | A | 423 | 21.369 | −14.880 | −4.698 | 1.00 | 44.38 | N |
| ANISOU | 1494 | N | PHE | A | 423 | 5592 | 5648 | 5622 | 7 | −27 | 107 | N |
| ATOM | 1495 | CA | PHE | A | 423 | 21.495 | −13.452 | −4.933 | 1.00 | 43.56 | C |
| ANISOU | 1495 | CA | PHE | A | 423 | 5497 | 5571 | 5482 | 0 | −24 | 111 | C |
| ATOM | 1496 | CB | PHE | A | 423 | 22.798 | −13.133 | −5.646 | 1.00 | 43.29 | C |
| ANISOU | 1496 | CB | PHE | A | 423 | 5394 | 5556 | 5497 | −7 | −79 | 107 | C |
| ATOM | 1497 | CG | PHE | A | 423 | 24.008 | −13.224 | −4.759 | 1.00 | 44.33 | C |
| ANISOU | 1497 | CG | PHE | A | 423 | 5633 | 5632 | 5577 | −92 | 29 | 161 | C |
| ATOM | 1498 | CD1 | PHE | A | 423 | 24.936 | −14.249 | −4.937 | 1.00 | 42.42 | C |
| ANISOU | 1498 | CD1 | PHE | A | 423 | 5139 | 5468 | 5509 | 38 | −37 | 193 | C |
| ATOM | 1499 | CE1 | PHE | A | 423 | 26.047 | −14.339 | −4.131 | 1.00 | 42.33 | C |
| ANISOU | 1499 | CE1 | PHE | A | 423 | 5468 | 5273 | 5342 | −127 | 119 | −44 | C |
| ATOM | 1500 | CZ | PHE | A | 423 | 26.245 | −13.401 | −3.133 | 1.00 | 45.72 | C |
| ANISOU | 1500 | CZ | PHE | A | 423 | 5685 | 6031 | 5653 | −193 | 105 | 211 | C |
| ATOM | 1501 | CE2 | PHE | A | 423 | 25.328 | −12.362 | −2.944 | 1.00 | 41.37 | C |
| ANISOU | 1501 | CE2 | PHE | A | 423 | 4978 | 5384 | 5355 | 209 | −92 | 166 | C |
| ATOM | 1502 | CD2 | PHE | A | 423 | 24.217 | −12.288 | −3.751 | 1.00 | 43.86 | C |
| ANISOU | 1502 | CD2 | PHE | A | 423 | 5670 | 5522 | 5470 | −44 | 136 | 92 | C |
| ATOM | 1503 | C | PHE | A | 423 | 20.288 | −12.976 | −5.723 | 1.00 | 43.24 | C |
| ANISOU | 1503 | C | PHE | A | 423 | 5452 | 5530 | 5446 | −1 | −11 | 102 | C |
| ATOM | 1504 | O | PHE | A | 423 | 19.889 | −13.612 | −6.714 | 1.00 | 42.35 | O |
| ANISOU | 1504 | O | PHE | A | 423 | 5366 | 5482 | 5242 | −37 | −48 | 112 | O |
| ATOM | 1505 | N | SER | A | 424 | 19.699 | −11.880 | −5.251 | 1.00 | 42.62 | N |
| ANISOU | 1505 | N | SER | A | 424 | 5361 | 5473 | 5357 | 9 | 17 | 73 | N |
| ATOM | 1506 | CA | SER | A | 424 | 18.502 | −11.336 | −5.875 | 1.00 | 42.62 | C |
| ANISOU | 1506 | CA | SER | A | 424 | 5334 | 5509 | 5350 | 15 | 32 | 50 | C |
| ATOM | 1507 | CB | SER | A | 424 | 17.269 | −11.580 | −4.983 | 1.00 | 42.80 | C |
| ANISOU | 1507 | CB | SER | A | 424 | 5346 | 5561 | 5353 | 30 | 34 | 25 | C |
| ATOM | 1508 | OG | SER | A | 424 | 17.321 | −10.787 | −3.812 | 1.00 | 42.53 | O |
| ANISOU | 1508 | OG | SER | A | 424 | 5276 | 5654 | 5226 | 85 | 74 | 39 | O |
| ATOM | 1509 | C | SER | A | 424 | 18.626 | −9.859 | −6.300 | 1.00 | 42.35 | C |
| ANISOU | 1509 | C | SER | A | 424 | 5296 | 5467 | 5328 | 20 | 18 | 77 | C |
| ATOM | 1510 | O | SER | A | 424 | 19.033 | −8.992 | −5.518 | 1.00 | 41.38 | O |
| ANISOU | 1510 | O | SER | A | 424 | 5174 | 5364 | 5184 | −26 | −2 | 71 | O |
| ATOM | 1511 | N | CYS | A | 425 | 18.282 | −9.603 | −7.563 | 1.00 | 42.32 | N |
| ANISOU | 1511 | N | CYS | A | 425 | 5228 | 5490 | 5359 | 38 | 3 | 113 | N |
| ATOM | 1512 | CA | CYS | A | 425 | 18.182 | −8.238 | −8.086 | 1.00 | 42.32 | C |
| ANISOU | 1512 | CA | CYS | A | 425 | 5236 | 5477 | 5364 | 15 | 4 | 122 | C |
| ATOM | 1513 | CB | CYS | A | 425 | 18.691 | −8.193 | −9.527 | 1.00 | 42.07 | C |
| ANISOU | 1513 | CB | CYS | A | 425 | 5168 | 5425 | 5391 | 5 | −28 | 131 | C |
| ATOM | 1514 | SG | CYS | A | 425 | 18.168 | −6.769 | −10.529 | 1.00 | 41.39 | S |
| ANISOU | 1514 | SG | CYS | A | 425 | 4930 | 5467 | 5327 | 77 | −26 | 166 | S |
| ATOM | 1515 | C | CYS | A | 425 | 16.729 | −7.761 | −7.995 | 1.00 | 42.83 | C |
| ANISOU | 1515 | C | CYS | A | 425 | 5386 | 5497 | 5390 | 14 | 2 | 110 | C |
| ATOM | 1516 | O | CYS | A | 425 | 15.813 | −8.361 | −8.585 | 1.00 | 42.19 | O |
| ANISOU | 1516 | O | CYS | A | 425 | 5252 | 5457 | 5320 | −2 | 48 | 124 | O |
| ATOM | 1517 | N | SER | A | 426 | 16.521 | −6.693 | −7.231 | 1.00 | 43.33 | N |
| ANISOU | 1517 | N | SER | A | 426 | 5489 | 5511 | 5460 | 6 | −17 | 101 | N |
| ATOM | 1518 | CA | SER | A | 426 | 15.185 | −6.185 | −7.025 | 1.00 | 43.91 | C |
| ANISOU | 1518 | CA | SER | A | 426 | 5550 | 5598 | 5534 | −21 | −15 | 67 | C |
| ATOM | 1519 | CB | SER | A | 426 | 14.815 | −6.219 | −5.538 | 1.00 | 44.36 | C |
| ANISOU | 1519 | CB | SER | A | 426 | 5616 | 5660 | 5575 | −47 | −55 | 69 | C |
| ATOM | 1520 | OG | SER | A | 426 | 15.437 | −5.186 | −4.808 | 1.00 | 45.92 | O |
| ANISOU | 1520 | OG | SER | A | 426 | 5898 | 5798 | 5752 | −91 | −95 | 43 | O |
| ATOM | 1521 | C | SER | A | 426 | 14.983 | −4.801 | −7.660 | 1.00 | 43.57 | C |
| ANISOU | 1521 | C | SER | A | 426 | 5506 | 5553 | 5493 | −13 | −31 | 57 | C |
| ATOM | 1522 | O | SER | A | 426 | 15.711 | −3.850 | −7.371 | 1.00 | 43.22 | O |
| ANISOU | 1522 | O | SER | A | 426 | 5456 | 5506 | 5457 | −9 | −46 | 60 | O |
| ATOM | 1523 | N | VAL | A | 427 | 13.976 | −4.725 | −8.528 | 1.00 | 42.97 | N |
| ANISOU | 1523 | N | VAL | A | 427 | 5449 | 5498 | 5380 | −15 | −21 | 49 | N |
| ATOM | 1524 | CA | VAL | A | 427 | 13.734 | −3.579 | −9.400 | 1.00 | 42.05 | C |
| ANISOU | 1524 | CA | VAL | A | 427 | 5340 | 5430 | 5205 | 0 | −15 | 33 | C |
| ATOM | 1525 | CB | VAL | A | 427 | 13.627 | −4.051 | −10.884 | 1.00 | 41.86 | C |
| ANISOU | 1525 | CB | VAL | A | 427 | 5301 | 5420 | 5181 | 17 | −2 | −11 | C |
| ATOM | 1526 | CG1 | VAL | A | 427 | 13.382 | −2.874 | −11.821 | 1.00 | 40.21 | C |
| ANISOU | 1526 | CG1 | VAL | A | 427 | 5056 | 5232 | 4987 | −44 | 57 | −23 | C |
| ATOM | 1527 | CG2 | VAL | A | 427 | 14.872 | −4.811 | −11.296 | 1.00 | 41.53 | C |
| ANISOU | 1527 | CG2 | VAL | A | 427 | 5292 | 5317 | 5170 | 0 | −112 | 30 | C |
| ATOM | 1528 | C | VAL | A | 427 | 12.453 | −2.820 | −9.041 | 1.00 | 41.50 | C |
| ANISOU | 1528 | C | VAL | A | 427 | 5362 | 5341 | 5064 | −13 | 8 | 28 | C |
| ATOM | 1529 | O | VAL | A | 427 | 11.390 | −3.408 | −8.880 | 1.00 | 40.96 | O |
| ANISOU | 1529 | O | VAL | A | 427 | 5279 | 5330 | 4951 | −6 | 48 | 98 | O |

TABLE 7-continued

| The atomic structure coordinates of Fc-TM | | | | | | | | | | | |
|---|---|---|---|---|---|---|---|---|---|---|---|
| ATOM | 1530 | N | MET | A | 428 | 12.559 | −1.500 | −8.969 | 1.00 | 41.12 | N |
| ANISOU | 1530 | N | MET | A | 428 | 5318 | 5327 | 4978 | −22 | 7 | 9 | N |
| ATOM | 1531 | CA | MET | A | 428 | 11.395 | −0.647 | −8.805 | 1.00 | 40.47 | C |
| ANISOU | 1531 | CA | MET | A | 428 | 5291 | 5197 | 4889 | −14 | 60 | −23 | C |
| ATOM | 1532 | CB | MET | A | 428 | 11.585 | 0.281 | −7.620 | 1.00 | 40.36 | C |
| ANISOU | 1532 | CB | MET | A | 428 | 5204 | 5222 | 4908 | −56 | 23 | −2 | C |
| ATOM | 1533 | CG | MET | A | 428 | 12.037 | −0.413 | −6.373 | 1.00 | 41.31 | C |
| ANISOU | 1533 | CG | MET | A | 428 | 5409 | 5218 | 5068 | −29 | 52 | −5 | C |
| ATOM | 1534 | SD | MET | A | 428 | 11.727 | 0.663 | −4.974 | 1.00 | 42.39 | S |
| ANISOU | 1534 | SD | MET | A | 428 | 5767 | 5498 | 4839 | −41 | 119 | −25 | S |
| ATOM | 1535 | CE | MET | A | 428 | 9.947 | 0.788 | −5.114 | 1.00 | 40.75 | C |
| ANISOU | 1535 | CE | MET | A | 428 | 5472 | 5091 | 4920 | 29 | 70 | 102 | C |
| ATOM | 1536 | C | MET | A | 428 | 11.096 | 0.175 | −10.057 | 1.00 | 39.15 | C |
| ANISOU | 1536 | C | MET | A | 428 | 5085 | 5011 | 4777 | 14 | 40 | −108 | C |
| ATOM | 1537 | O | MET | A | 428 | 11.944 | 0.908 | −10.555 | 1.00 | 38.37 | O |
| ANISOU | 1537 | O | MET | A | 428 | 5039 | 4855 | 4683 | 13 | 60 | −72 | O |
| ATOM | 1538 | N | HIS | A | 429 | 9.876 | 0.038 | −10.556 | 1.00 | 37.88 | N |
| ANISOU | 1538 | N | HIS | A | 429 | 4935 | 4841 | 4613 | 56 | 57 | −125 | N |
| ATOM | 1539 | CA | HIS | A | 429 | 9.427 | 0.779 | −11.730 | 1.00 | 36.90 | C |
| ANISOU | 1539 | CA | HIS | A | 429 | 4763 | 4738 | 4517 | 31 | 43 | −119 | C |
| ATOM | 1540 | CB | HIS | A | 429 | 9.829 | 0.086 | −13.033 | 1.00 | 35.73 | C |
| ANISOU | 1540 | CB | HIS | A | 429 | 4590 | 4600 | 4386 | −2 | 24 | −67 | C |
| ATOM | 1541 | CG | HIS | A | 429 | 9.560 | 0.914 | −14.246 | 1.00 | 33.46 | C |
| ANISOU | 1541 | CG | HIS | A | 429 | 4228 | 4253 | 4232 | 12 | 111 | −213 | C |
| ATOM | 1542 | ND1 | HIS | A | 429 | 8.334 | 0.950 | −14.870 | 1.00 | 31.22 | N |
| ANISOU | 1542 | ND1 | HIS | A | 429 | 4260 | 3907 | 3694 | 25 | 43 | −229 | N |
| ATOM | 1543 | CE1 | HIS | A | 429 | 8.385 | 1.778 | −15.894 | 1.00 | 30.83 | C |
| ANISOU | 1543 | CE1 | HIS | A | 429 | 4069 | 3810 | 3833 | −36 | 51 | −163 | C |
| ATOM | 1544 | NE2 | HIS | A | 429 | 9.602 | 2.278 | −15.960 | 1.00 | 31.02 | N |
| ANISOU | 1544 | NE2 | HIS | A | 429 | 4048 | 3977 | 3758 | 10 | −105 | −163 | N |
| ATOM | 1545 | CD2 | HIS | A | 429 | 10.353 | 1.763 | −14.935 | 1.00 | 32.35 | C |
| ANISOU | 1545 | CD2 | HIS | A | 429 | 4277 | 3969 | 4045 | 86 | 47 | −124 | C |
| ATOM | 1546 | C | HIS | A | 429 | 7.929 | 0.843 | −11.664 | 1.00 | 36.82 | C |
| ANISOU | 1546 | C | HIS | A | 429 | 4799 | 4771 | 4418 | 26 | 9 | −122 | C |
| ATOM | 1547 | O | HIS | A | 429 | 7.297 | −0.115 | −11.229 | 1.00 | 36.28 | O |
| ANISOU | 1547 | O | HIS | A | 429 | 4722 | 4796 | 4265 | 10 | −12 | −179 | O |
| ATOM | 1548 | N | GLU | A | 430 | 7.374 | 1.964 | −12.119 | 1.00 | 36.71 | N |
| ANISOU | 1548 | N | GLU | A | 430 | 4815 | 4761 | 4371 | 55 | 19 | −106 | N |
| ATOM | 1549 | CA | GLU | A | 430 | 5.934 | 2.203 | −12.098 | 1.00 | 36.80 | C |
| ANISOU | 1549 | CA | GLU | A | 430 | 4811 | 4731 | 4437 | 41 | 6 | −42 | C |
| ATOM | 1550 | CB | GLU | A | 430 | 5.594 | 3.547 | −12.773 | 1.00 | 36.76 | C |
| ANISOU | 1550 | CB | GLU | A | 430 | 4791 | 4744 | 4430 | −9 | −30 | −31 | C |
| ATOM | 1551 | CG | GLU | A | 430 | 5.694 | 3.553 | −14.307 | 1.00 | 35.19 | C |
| ANISOU | 1551 | CG | GLU | A | 430 | 4490 | 4486 | 4392 | 25 | 72 | 100 | C |
| ATOM | 1552 | CD | GLU | A | 430 | 5.001 | 4.742 | −14.895 | 1.00 | 34.83 | C |
| ANISOU | 1552 | CD | GLU | A | 430 | 4558 | 4546 | 4128 | −71 | 229 | 48 | C |
| ATOM | 1553 | OE1 | GLU | A | 430 | 5.453 | 5.862 | −14.630 | 1.00 | 30.64 | O |
| ANISOU | 1553 | OE1 | GLU | A | 430 | 4122 | 4033 | 3484 | −100 | 187 | 82 | O |
| ATOM | 1554 | OE2 | GLU | A | 430 | 3.991 | 4.560 | −15.606 | 1.00 | 34.10 | O |
| ANISOU | 1554 | OE2 | GLU | A | 430 | 4321 | 4585 | 4048 | −96 | 202 | −27 | O |
| ATOM | 1555 | C | GLU | A | 430 | 5.110 | 1.099 | −12.716 | 1.00 | 36.55 | C |
| ANISOU | 1555 | C | GLU | A | 430 | 4793 | 4631 | 4463 | 48 | −12 | −17 | C |
| ATOM | 1556 | O | GLU | A | 430 | 4.035 | 0.794 | −12.223 | 1.00 | 36.45 | O |
| ANISOU | 1556 | O | GLU | A | 430 | 4876 | 4636 | 4334 | 94 | 23 | −111 | O |
| ATOM | 1557 | N | ALA | A | 431 | 5.613 | 0.513 | −13.803 | 1.00 | 36.85 | N |
| ANISOU | 1557 | N | ALA | A | 431 | 4769 | 4635 | 4595 | 51 | −26 | 26 | N |
| ATOM | 1558 | CA | ALA | A | 431 | 4.836 | −0.427 | −14.622 | 1.00 | 36.97 | C |
| ANISOU | 1558 | CA | ALA | A | 431 | 4763 | 4665 | 4617 | 35 | 0 | −11 | C |
| ATOM | 1559 | CB | ALA | A | 431 | 5.256 | −0.312 | −16.072 | 1.00 | 36.63 | C |
| ANISOU | 1559 | CB | ALA | A | 431 | 4680 | 4637 | 4600 | 53 | −51 | −6 | C |
| ATOM | 1560 | C | ALA | A | 431 | 4.901 | −1.891 | −14.129 | 1.00 | 37.11 | C |
| ANISOU | 1560 | C | ALA | A | 431 | 4752 | 4712 | 4633 | −16 | 12 | −11 | C |
| ATOM | 1561 | O | ALA | A | 431 | 4.366 | −2.798 | −14.764 | 1.00 | 37.32 | O |
| ANISOU | 1561 | O | ALA | A | 431 | 4770 | 4750 | 4656 | −49 | 59 | −15 | O |
| ATOM | 1562 | N | LEU | A | 432 | 5.562 | −2.117 | −13.003 | 1.00 | 36.79 | N |
| ANISOU | 1562 | N | LEU | A | 432 | 4741 | 4648 | 4588 | −2 | 5 | 7 | N |
| ATOM | 1563 | CA | LEU | A | 432 | 5.501 | −3.419 | −12.333 | 1.00 | 37.15 | C |
| ANISOU | 1563 | CA | LEU | A | 432 | 4763 | 4747 | 4605 | −3 | −9 | 8 | C |
| ATOM | 1564 | CB | LEU | A | 432 | 6.813 | −3.728 | −11.587 | 1.00 | 36.16 | C |
| ANISOU | 1564 | CB | LEU | A | 432 | 4697 | 4593 | 4448 | 14 | −19 | 45 | C |
| ATOM | 1565 | CG | LEU | A | 432 | 8.039 | −3.920 | −12.494 | 1.00 | 35.48 | C |
| ANISOU | 1565 | CG | LEU | A | 432 | 4565 | 4483 | 4433 | 11 | −70 | 72 | C |
| ATOM | 1566 | CD1 | LEU | A | 432 | 9.375 | −3.695 | −11.782 | 1.00 | 33.76 | C |
| ANISOU | 1566 | CD1 | LEU | A | 432 | 4494 | 4326 | 4005 | 44 | −80 | 116 | C |
| ATOM | 1567 | CD2 | LEU | A | 432 | 8.019 | −5.273 | −13.221 | 1.00 | 34.94 | C |
| ANISOU | 1567 | CD2 | LEU | A | 432 | 4448 | 4511 | 4315 | 30 | −64 | 152 | C |
| ATOM | 1568 | C | LEU | A | 432 | 4.287 | −3.470 | −11.401 | 1.00 | 37.38 | C |
| ANISOU | 1568 | C | LEU | A | 432 | 4819 | 4804 | 4578 | −12 | −9 | 34 | C |

TABLE 7-continued

| The atomic structure coordinates of Fc-TM | | | | | | | | | | |
|---|---|---|---|---|---|---|---|---|---|---|
| ATOM | 1569 | O | LEU | A | 432 | 3.802 | −2.445 | −10.931 | 1.00 | 37.28 | O |
| ANISOU | 1569 | O | LEU | A | 432 | 4766 | 4889 | 4509 | 32 | 1 | 67 | O |
| ATOM | 1570 | N | HIS | A | 433 | 3.768 | −4.663 | −11.178 | 1.00 | 38.17 | N |
| ANISOU | 1570 | N | HIS | A | 433 | 4911 | 4926 | 4663 | −24 | −11 | 39 | N |
| ATOM | 1571 | CA | HIS | A | 433 | 2.747 | −4.869 | −10.161 | 1.00 | 38.86 | C |
| ANISOU | 1571 | CA | HIS | A | 433 | 4958 | 5015 | 4789 | −27 | −2 | 49 | C |
| ATOM | 1572 | CB | HIS | A | 433 | 2.447 | −6.358 | −10.078 | 1.00 | 39.24 | C |
| ANISOU | 1572 | CB | HIS | A | 433 | 4992 | 5068 | 4847 | −27 | 6 | 41 | C |
| ATOM | 1573 | CG | HIS | A | 433 | 1.480 | −6.722 | −9.003 | 1.00 | 41.29 | C |
| ANISOU | 1573 | CG | HIS | A | 433 | 5182 | 5325 | 5179 | −26 | 27 | 73 | C |
| ATOM | 1574 | ND1 | HIS | A | 433 | 0.117 | −6.574 | −9.150 | 1.00 | 42.44 | N |
| ANISOU | 1574 | ND1 | HIS | A | 433 | 5238 | 5453 | 5433 | −68 | 34 | 41 | N |
| ATOM | 1575 | CE1 | HIS | A | 433 | −0.482 | −6.986 | −8.046 | 1.00 | 42.23 | C |
| ANISOU | 1575 | CE1 | HIS | A | 433 | 5381 | 5485 | 5176 | 10 | −17 | −10 | C |
| ATOM | 1576 | NE2 | HIS | A | 433 | 0.443 | −7.399 | −7.197 | 1.00 | 41.94 | N |
| ANISOU | 1576 | NE2 | HIS | A | 433 | 5411 | 5442 | 5079 | −19 | 12 | −1 | N |
| ATOM | 1577 | CD2 | HIS | A | 433 | 1.678 | −7.241 | −7.769 | 1.00 | 40.89 | C |
| ANISOU | 1577 | CD2 | HIS | A | 433 | 5136 | 5376 | 5025 | −8 | −29 | 20 | C |
| ATOM | 1578 | C | HIS | A | 433 | 3.279 | −4.308 | −8.824 | 1.00 | 38.60 | C |
| ANISOU | 1578 | C | HIS | A | 433 | 4959 | 4969 | 4737 | −33 | 8 | 95 | C |
| ATOM | 1579 | O | HIS | A | 433 | 4.392 | −4.632 | −8.416 | 1.00 | 38.55 | O |
| ANISOU | 1579 | O | HIS | A | 433 | 4974 | 5004 | 4668 | −49 | −28 | 116 | O |
| ATOM | 1580 | N | ASN | A | 434 | 2.522 | −3.420 | −8.187 | 1.00 | 38.26 | N |
| ANISOU | 1580 | N | ASN | A | 434 | 4920 | 4949 | 4665 | −74 | 17 | 108 | N |
| ATOM | 1581 | CA | ASN | A | 434 | 2.994 | −2.709 | −6.994 | 1.00 | 38.50 | C |
| ANISOU | 1581 | CA | ASN | A | 434 | 4948 | 4950 | 4727 | −75 | 13 | 90 | C |
| ATOM | 1582 | CB | ASN | A | 434 | 2.999 | −3.639 | −5.763 | 1.00 | 38.77 | C |
| ANISOU | 1582 | CB | ASN | A | 434 | 4941 | 5054 | 4733 | −120 | 20 | 41 | C |
| ATOM | 1583 | CG | ASN | A | 434 | 1.631 | −4.134 | −5.413 | 1.00 | 38.47 | C |
| ANISOU | 1583 | CG | ASN | A | 434 | 4913 | 5088 | 4614 | −105 | 23 | 7 | C |
| ATOM | 1584 | OD1 | ASN | A | 434 | 1.466 | −5.285 | −5.048 | 1.00 | 38.40 | O |
| ANISOU | 1584 | OD1 | ASN | A | 434 | 5064 | 4785 | 4740 | −130 | −43 | 51 | O |
| ATOM | 1585 | ND2 | ASN | A | 434 | 0.635 | −3.275 | −5.548 | 1.00 | 35.57 | N |
| ANISOU | 1585 | ND2 | ASN | A | 434 | 4416 | 4664 | 4435 | −105 | 161 | −54 | N |
| ATOM | 1586 | C | ASN | A | 434 | 4.372 | −2.064 | −7.143 | 1.00 | 38.65 | C |
| ANISOU | 1586 | C | ASN | A | 434 | 4962 | 4997 | 4727 | −89 | 12 | 73 | C |
| ATOM | 1587 | O | ASN | A | 434 | 5.092 | −1.904 | −6.156 | 1.00 | 38.37 | O |
| ANISOU | 1587 | O | ASN | A | 434 | 4948 | 4953 | 4677 | −158 | 44 | 68 | O |
| ATOM | 1588 | N | HIS | A | 435 | 4.729 | −1.721 | −8.384 | 1.00 | 38.28 | N |
| ANISOU | 1588 | N | HIS | A | 435 | 4930 | 4968 | 4646 | −59 | −13 | 18 | N |
| ATOM | 1589 | CA | HIS | A | 435 | 5.963 | −1.016 | −8.726 | 1.00 | 37.58 | C |
| ANISOU | 1589 | CA | HIS | A | 435 | 4881 | 4891 | 4504 | −25 | 5 | 35 | C |
| ATOM | 1590 | CB | HIS | A | 435 | 5.952 | 0.417 | −8.155 | 1.00 | 37.74 | C |
| ANISOU | 1590 | CB | HIS | A | 435 | 4898 | 4903 | 4537 | −23 | −29 | −1 | C |
| ATOM | 1591 | CG | HIS | A | 435 | 4.584 | 1.032 | −8.082 | 1.00 | 37.92 | C |
| ANISOU | 1591 | CG | HIS | A | 435 | 4873 | 4934 | 4598 | −13 | 14 | −80 | C |
| ATOM | 1592 | ND1 | HIS | A | 435 | 3.749 | 1.135 | −9.174 | 1.00 | 37.42 | N |
| ANISOU | 1592 | ND1 | HIS | A | 435 | 4902 | 4856 | 4459 | 161 | 35 | −122 | N |
| ATOM | 1593 | CE1 | HIS | A | 435 | 2.607 | 1.686 | −8.810 | 1.00 | 38.63 | C |
| ANISOU | 1593 | CE1 | HIS | A | 435 | 4913 | 4743 | 5020 | 62 | 15 | 82 | C |
| ATOM | 1594 | NE2 | HIS | A | 435 | 2.681 | 1.979 | −7.524 | 1.00 | 36.99 | N |
| ANISOU | 1594 | NE2 | HIS | A | 435 | 4821 | 4801 | 4432 | 32 | −57 | 3 | N |
| ATOM | 1595 | CD2 | HIS | A | 435 | 3.903 | 1.573 | −7.044 | 1.00 | 38.62 | C |
| ANISOU | 1595 | CD2 | HIS | A | 435 | 4975 | 4958 | 4739 | −34 | 6 | −67 | C |
| ATOM | 1596 | C | HIS | A | 435 | 7.236 | −1.770 | −8.330 | 1.00 | 37.17 | C |
| ANISOU | 1596 | C | HIS | A | 435 | 4870 | 4880 | 4372 | −25 | 31 | 22 | C |
| ATOM | 1597 | O | HIS | A | 435 | 8.273 | −1.176 | −8.127 | 1.00 | 35.86 | O |
| ANISOU | 1597 | O | HIS | A | 435 | 4733 | 4829 | 4063 | 47 | 22 | 64 | O |
| ATOM | 1598 | N | TYR | A | 436 | 7.153 | −3.088 | −8.248 | 1.00 | 37.91 | N |
| ANISOU | 1598 | N | TYR | A | 436 | 4963 | 4964 | 4476 | 1 | 14 | 15 | N |
| ATOM | 1599 | CA | TYR | A | 436 | 8.235 | −3.873 | −7.684 | 1.00 | 38.88 | C |
| ANISOU | 1599 | CA | TYR | A | 436 | 5029 | 4992 | 4751 | 2 | 12 | −9 | C |
| ATOM | 1600 | CB | TYR | A | 436 | 8.058 | −3.997 | −6.158 | 1.00 | 38.93 | C |
| ANISOU | 1600 | CB | TYR | A | 436 | 5047 | 4980 | 4765 | 8 | −25 | −6 | C |
| ATOM | 1601 | CG | TYR | A | 436 | 9.235 | −4.641 | −5.455 | 1.00 | 39.72 | C |
| ANISOU | 1601 | CG | TYR | A | 436 | 5116 | 5014 | 4959 | 60 | 6 | −69 | C |
| ATOM | 1602 | CD1 | TYR | A | 436 | 9.202 | −5.986 | −5.059 | 1.00 | 40.15 | C |
| ANISOU | 1602 | CD1 | TYR | A | 436 | 5192 | 5178 | 4884 | 57 | 49 | 35 | C |
| ATOM | 1603 | CE1 | TYR | A | 436 | 10.302 | −6.573 | −4.438 | 1.00 | 39.78 | C |
| ANISOU | 1603 | CE1 | TYR | A | 436 | 5150 | 5156 | 4806 | 17 | −21 | 78 | C |
| ATOM | 1604 | CZ | TYR | A | 436 | 11.426 | −5.797 | −4.193 | 1.00 | 40.05 | C |
| ANISOU | 1604 | CZ | TYR | A | 436 | 5151 | 5177 | 4887 | 17 | 10 | 47 | C |
| ATOM | 1605 | OH | TYR | A | 436 | 12.530 | −6.318 | −3.580 | 1.00 | 39.84 | O |
| ANISOU | 1605 | OH | TYR | A | 436 | 5240 | 5038 | 4856 | 63 | −12 | 9 | O |
| ATOM | 1606 | CE2 | TYR | A | 436 | 11.465 | −4.467 | −4.566 | 1.00 | 40.35 | C |
| ANISOU | 1606 | CE2 | TYR | A | 436 | 5160 | 5135 | 5036 | 62 | −59 | 13 | C |
| ATOM | 1607 | CD2 | TYR | A | 436 | 10.389 | −3.905 | −5.195 | 1.00 | 40.97 | C |
| ANISOU | 1607 | CD2 | TYR | A | 436 | 5145 | 5122 | 5300 | 80 | 3 | −58 | C |

TABLE 7-continued

The atomic structure coordinates of Fc-TM

| | | | | | | | | | | | | |
|---|---|---|---|---|---|---|---|---|---|---|---|---|
| ATOM | 1608 | C | TYR | A | 436 | 8.303 | −5.264 | −8.287 | 1.00 | 39.02 | | C |
| ANISOU | 1608 | C | TYR | A | 436 | 5083 | 5005 | 4736 | −49 | −25 | −2 | C |
| ATOM | 1609 | O | TYR | A | 436 | 7.289 | −5.871 | −8.531 | 1.00 | 38.66 | | O |
| ANISOU | 1609 | O | TYR | A | 436 | 5121 | 4885 | 4682 | −64 | −60 | 4 | O |
| ATOM | 1610 | N | THR | A | 437 | 9.514 | −5.755 | −8.503 | 1.00 | 39.50 | | N |
| ANISOU | 1610 | N | THR | A | 437 | 5159 | 5021 | 4828 | −10 | 2 | −25 | N |
| ATOM | 1611 | CA | THR | A | 437 | 9.734 | −7.163 | −8.753 | 1.00 | 40.83 | | C |
| ANISOU | 1611 | CA | THR | A | 437 | 5264 | 5167 | 5080 | −30 | 15 | 33 | C |
| ATOM | 1612 | CB | THR | A | 437 | 9.495 | −7.556 | −10.250 | 1.00 | 40.93 | | C |
| ANISOU | 1612 | CB | THR | A | 437 | 5246 | 5166 | 5137 | −33 | 3 | −17 | C |
| ATOM | 1613 | OG1 | THR | A | 437 | 9.270 | −8.968 | −10.336 | 1.00 | 41.06 | | O |
| ANISOU | 1613 | OG1 | THR | A | 437 | 5236 | 5079 | 5286 | 15 | 103 | −13 | O |
| ATOM | 1614 | CG2 | THR | A | 437 | 10.665 | −7.153 | −11.145 | 1.00 | 39.50 | | C |
| ANISOU | 1614 | CG2 | THR | A | 437 | 5153 | 4957 | 4898 | −9 | 5 | −1 | C |
| ATOM | 1615 | C | THR | A | 437 | 11.121 | −7.579 | −8.248 | 1.00 | 41.64 | | C |
| ANISOU | 1615 | C | THR | A | 437 | 5343 | 5262 | 5214 | −19 | −19 | 68 | C |
| ATOM | 1616 | O | THR | A | 437 | 11.926 | −6.731 | −7.857 | 1.00 | 41.69 | | O |
| ANISOU | 1616 | O | THR | A | 437 | 5358 | 5239 | 5240 | −28 | −17 | 144 | O |
| ATOM | 1617 | N | GLN | A | 438 | 11.371 | −8.886 | −8.250 | 1.00 | 42.72 | | N |
| ANISOU | 1617 | N | GLN | A | 438 | 5471 | 5368 | 5392 | −15 | 17 | 61 | N |
| ATOM | 1618 | CA | GLN | A | 438 | 12.573 | −9.499 | −7.668 | 1.00 | 43.76 | | C |
| ANISOU | 1618 | CA | GLN | A | 438 | 5564 | 5521 | 5541 | 0 | 12 | 72 | C |
| ATOM | 1619 | CB | GLN | A | 438 | 12.260 | −10.041 | −6.266 | 1.00 | 43.80 | | C |
| ANISOU | 1619 | CB | GLN | A | 438 | 5570 | 5515 | 5557 | 21 | −19 | 59 | C |
| ATOM | 1620 | CG | GLN | A | 438 | 13.471 | −10.272 | −5.363 | 1.00 | 45.09 | | C |
| ANISOU | 1620 | CG | GLN | A | 438 | 5780 | 5691 | 5659 | 13 | 21 | 68 | C |
| ATOM | 1621 | CD | GLN | A | 438 | 13.088 | −10.493 | −3.894 | 1.00 | 44.91 | | C |
| ANISOU | 1621 | CD | GLN | A | 438 | 5851 | 5578 | 5634 | 4 | 82 | 72 | C |
| ATOM | 1622 | OE1 | GLN | A | 438 | 12.943 | −11.640 | −3.453 | 1.00 | 46.59 | | O |
| ANISOU | 1622 | OE1 | GLN | A | 438 | 5980 | 5851 | 5871 | −13 | 157 | 97 | O |
| ATOM | 1623 | NE2 | GLN | A | 438 | 12.927 | −9.394 | −3.132 | 1.00 | 45.98 | | N |
| ANISOU | 1623 | NE2 | GLN | A | 438 | 5903 | 5784 | 5783 | −47 | 135 | 46 | N |
| ATOM | 1624 | C | GLN | A | 438 | 12.951 | −10.641 | −8.584 | 1.00 | 43.72 | | C |
| ANISOU | 1624 | C | GLN | A | 438 | 5579 | 5440 | 5593 | 3 | −9 | 94 | C |
| ATOM | 1625 | O | GLN | A | 438 | 12.083 | −11.348 | −9.079 | 1.00 | 43.70 | | O |
| ANISOU | 1625 | O | GLN | A | 438 | 5600 | 5396 | 5605 | −1 | −19 | 100 | O |
| ATOM | 1626 | N | LYS | A | 439 | 14.239 | −10.788 | −8.859 | 1.00 | 44.68 | | N |
| ANISOU | 1626 | N | LYS | A | 439 | 5693 | 5568 | 5715 | −2 | −26 | 96 | N |
| ATOM | 1627 | CA | LYS | A | 439 | 14.741 | −11.933 | −9.615 | 1.00 | 45.43 | | C |
| ANISOU | 1627 | CA | LYS | A | 439 | 5800 | 5662 | 5798 | −16 | −9 | 70 | C |
| ATOM | 1628 | CB | LYS | A | 439 | 15.058 | −11.555 | −11.064 | 1.00 | 45.89 | | C |
| ANISOU | 1628 | CB | LYS | A | 439 | 5825 | 5736 | 5873 | −5 | −9 | 40 | C |
| ATOM | 1629 | CG | LYS | A | 439 | 13.856 | −11.073 | −11.880 | 1.00 | 46.21 | | C |
| ANISOU | 1629 | CG | LYS | A | 439 | 5900 | 5781 | 5874 | 51 | −46 | 49 | C |
| ATOM | 1630 | CD | LYS | A | 439 | 12.907 | −12.194 | −12.253 | 1.00 | 46.24 | | C |
| ANISOU | 1630 | CD | LYS | A | 439 | 5775 | 5776 | 6016 | −18 | −95 | 97 | C |
| ATOM | 1631 | CE | LYS | A | 439 | 11.616 | −11.657 | −12.829 | 1.00 | 47.33 | | C |
| ANISOU | 1631 | CE | LYS | A | 439 | 6039 | 5979 | 5962 | −62 | 19 | 23 | C |
| ATOM | 1632 | NZ | LYS | A | 439 | 10.782 | −12.775 | −13.332 | 1.00 | 47.50 | | N |
| ANISOU | 1632 | NZ | LYS | A | 439 | 6069 | 6016 | 5962 | −55 | −46 | 41 | N |
| ATOM | 1633 | C | LYS | A | 439 | 15.969 | −12.490 | −8.917 | 1.00 | 46.09 | | C |
| ANISOU | 1633 | C | LYS | A | 439 | 5848 | 5746 | 5916 | −7 | −7 | 78 | C |
| ATOM | 1634 | O | LYS | A | 439 | 16.907 | −11.749 | −8.596 | 1.00 | 46.55 | | O |
| ANISOU | 1634 | O | LYS | A | 439 | 5959 | 5751 | 5975 | 6 | −6 | 117 | O |
| ATOM | 1635 | N | SER | A | 440 | 15.946 | −13.796 | −8.655 | 1.00 | 46.72 | | N |
| ANISOU | 1635 | N | SER | A | 440 | 5934 | 5839 | 5979 | −31 | −11 | 81 | N |
| ATOM | 1636 | CA | SER | A | 440 | 17.032 | −14.454 | −7.942 | 1.00 | 46.85 | | C |
| ANISOU | 1636 | CA | SER | A | 440 | 5928 | 5897 | 5975 | −7 | −17 | 88 | C |
| ATOM | 1637 | CB | SER | A | 440 | 16.496 | −15.469 | −6.913 | 1.00 | 47.28 | | C |
| ANISOU | 1637 | CB | SER | A | 440 | 5941 | 6005 | 6016 | −9 | −20 | 46 | C |
| ATOM | 1638 | OG | SER | A | 440 | 16.183 | −14.836 | −5.671 | 1.00 | 48.78 | | O |
| ANISOU | 1638 | OG | SER | A | 440 | 6002 | 6424 | 6105 | −24 | 17 | 60 | O |
| ATOM | 1639 | C | SER | A | 440 | 17.973 | −15.124 | −8.918 | 1.00 | 46.89 | | C |
| ANISOU | 1639 | C | SER | A | 440 | 5980 | 5868 | 5969 | −17 | −17 | 95 | C |
| ATOM | 1640 | O | SER | A | 440 | 17.545 | −15.633 | −9.959 | 1.00 | 47.05 | | O |
| ANISOU | 1640 | O | SER | A | 440 | 6023 | 5846 | 6007 | −34 | −57 | 109 | O |
| ATOM | 1641 | N | LEU | A | 441 | 19.258 | −15.097 | −8.571 | 1.00 | 47.27 | | N |
| ANISOU | 1641 | N | LEU | A | 441 | 6010 | 5908 | 6042 | 16 | −21 | 93 | N |
| ATOM | 1642 | CA | LEU | A | 441 | 20.323 | −15.741 | −9.329 | 1.00 | 47.61 | | C |
| ANISOU | 1642 | CA | LEU | A | 441 | 6027 | 5975 | 6087 | 14 | 1 | 78 | C |
| ATOM | 1643 | CB | LEU | A | 441 | 21.264 | −14.677 | −9.907 | 1.00 | 47.64 | | C |
| ANISOU | 1643 | CB | LEU | A | 441 | 6073 | 5959 | 6066 | 37 | 7 | 102 | C |
| ATOM | 1644 | CG | LEU | A | 441 | 22.391 | −15.101 | −10.862 | 1.00 | 47.04 | | C |
| ANISOU | 1644 | CG | LEU | A | 441 | 5967 | 5906 | 5997 | 40 | 6 | 66 | C |
| ATOM | 1645 | CD1 | LEU | A | 441 | 21.849 | −15.691 | −12.147 | 1.00 | 47.09 | | C |
| ANISOU | 1645 | CD1 | LEU | A | 441 | 6088 | 5875 | 5927 | 76 | 24 | 60 | C |
| ATOM | 1646 | CD2 | LEU | A | 441 | 23.266 | −13.921 | −11.162 | 1.00 | 47.11 | | C |
| ANISOU | 1646 | CD2 | LEU | A | 441 | 5985 | 5891 | 6020 | 25 | −6 | 88 | C |

TABLE 7-continued

| | | | | | | | | | | | | |
|---|---|---|---|---|---|---|---|---|---|---|---|---|
| ATOM | 1647 | C | LEU | A | 441 | 21.101 | −16.740 | −8.437 | 1.00 | 48.31 | | C |
| ANISOU | 1647 | C | LEU | A | 441 | 6136 | 6022 | 6196 | 33 | −7 | 89 | C |
| ATOM | 1648 | O | LEU | A | 441 | 21.434 | −16.440 | −7.269 | 1.00 | 47.92 | | O |
| ANISOU | 1648 | O | LEU | A | 441 | 6026 | 5982 | 6196 | 0 | −72 | 71 | O |
| ATOM | 1649 | N | SER | A | 442 | 21.366 | −17.924 | −8.998 | 1.00 | 49.31 | | N |
| ANISOU | 1649 | N | SER | A | 442 | 6259 | 6162 | 6314 | 38 | 26 | 67 | N |
| ATOM | 1650 | CA | SER | A | 442 | 22.025 | −19.032 | −8.263 | 1.00 | 50.46 | | C |
| ANISOU | 1650 | CA | SER | A | 442 | 6432 | 6297 | 6442 | 43 | 18 | 55 | C |
| ATOM | 1651 | CB | SER | A | 442 | 20.983 | −19.965 | −7.635 | 1.00 | 50.19 | | C |
| ANISOU | 1651 | CB | SER | A | 442 | 6428 | 6217 | 6421 | 34 | 26 | 71 | C |
| ATOM | 1652 | OG | SER | A | 442 | 20.685 | −19.603 | −6.297 | 1.00 | 50.93 | | O |
| ANISOU | 1652 | OG | SER | A | 442 | 6648 | 6207 | 6496 | 55 | −43 | 19 | O |
| ATOM | 1653 | C | SER | A | 442 | 22.947 | −19.865 | −9.145 | 1.00 | 51.22 | | C |
| ANISOU | 1653 | C | SER | A | 442 | 6514 | 6433 | 6515 | 40 | 21 | 51 | C |
| ATOM | 1654 | O | SER | A | 442 | 22.689 | −20.034 | −10.346 | 1.00 | 51.69 | | O |
| ANISOU | 1654 | O | SER | A | 442 | 6550 | 6551 | 6539 | 26 | −4 | 45 | O |
| ATOM | 1655 | N | LEU | A | 443 | 24.012 | −20.392 | −8.537 | 1.00 | 52.28 | | N |
| ANISOU | 1655 | N | LEU | A | 443 | 6616 | 6628 | 6619 | 21 | 5 | 55 | N |
| ATOM | 1656 | CA | LEU | A | 443 | 24.886 | −21.388 | −9.174 | 1.00 | 53.25 | | C |
| ANISOU | 1656 | CA | LEU | A | 443 | 6742 | 6744 | 6746 | 33 | 0 | 26 | C |
| ATOM | 1657 | CB | LEU | A | 443 | 25.940 | −21.890 | −8.178 | 1.00 | 53.57 | | C |
| ANISOU | 1657 | CB | LEU | A | 443 | 6795 | 6808 | 6748 | 31 | −4 | 40 | C |
| ATOM | 1658 | CG | LEU | A | 443 | 27.061 | −22.777 | −8.734 | 1.00 | 53.94 | | C |
| ANISOU | 1658 | CG | LEU | A | 443 | 6821 | 6927 | 6747 | 71 | 10 | 64 | C |
| ATOM | 1659 | CD1 | LEU | A | 443 | 27.662 | −22.226 | −10.044 | 1.00 | 55.71 | | C |
| ANISOU | 1659 | CD1 | LEU | A | 443 | 7063 | 7076 | 7027 | −4 | 40 | 67 | C |
| ATOM | 1660 | CD2 | LEU | A | 443 | 28.135 | −22.952 | −7.702 | 1.00 | 55.22 | | C |
| ANISOU | 1660 | CD2 | LEU | A | 443 | 6963 | 7124 | 6892 | 17 | 6 | −2 | C |
| ATOM | 1661 | C | LEU | A | 443 | 24.112 | −22.576 | −9.771 | 1.00 | 53.71 | | C |
| ANISOU | 1661 | C | LEU | A | 443 | 6819 | 6793 | 6792 | 4 | 2 | 27 | C |
| ATOM | 1662 | O | LEU | A | 443 | 23.550 | −23.410 | −9.032 | 1.00 | 53.76 | | O |
| ANISOU | 1662 | O | LEU | A | 443 | 6815 | 6847 | 6764 | 25 | 9 | 84 | O |
| ATOM | 1663 | N | SER | A | 444 | 24.103 | −22.645 | −11.106 | 1.00 | 54.22 | | N |
| ANISOU | 1663 | N | SER | A | 444 | 6928 | 6846 | 6826 | −17 | 15 | 25 | N |
| ATOM | 1664 | CA | SER | A | 444 | 23.320 | −23.649 | −11.835 | 1.00 | 54.89 | | C |
| ANISOU | 1664 | CA | SER | A | 444 | 6984 | 6928 | 6940 | −35 | 12 | 13 | C |
| ATOM | 1665 | CB | SER | A | 444 | 23.149 | −23.261 | −13.303 | 1.00 | 54.86 | | C |
| ANISOU | 1665 | CB | SER | A | 444 | 6962 | 6941 | 6939 | −49 | 23 | 16 | C |
| ATOM | 1666 | OG | SER | A | 444 | 22.201 | −24.103 | −13.928 | 1.00 | 54.82 | | O |
| ANISOU | 1666 | OG | SER | A | 444 | 7079 | 6949 | 6799 | −69 | 14 | −88 | O |
| ATOM | 1667 | C | SER | A | 444 | 23.919 | −25.055 | −11.752 | 1.00 | 55.51 | | C |
| ANISOU | 1667 | C | SER | A | 444 | 7024 | 6992 | 7072 | −18 | 33 | 3 | C |
| ATOM | 1668 | O | SER | A | 444 | 25.131 | −25.226 | −11.969 | 1.00 | 55.87 | | O |
| ANISOU | 1668 | O | SER | A | 444 | 7048 | 7066 | 7112 | −44 | 54 | −23 | O |
| ATOM | 1669 | N | PRO | A | 445 | 23.069 | −26.066 | −11.448 | 1.00 | 55.87 | | N |
| ANISOU | 1669 | N | PRO | A | 445 | 7077 | 7024 | 7123 | −21 | 55 | 28 | N |
| ATOM | 1670 | CA | PRO | A | 445 | 23.527 | −27.447 | −11.334 | 1.00 | 56.18 | | C |
| ANISOU | 1670 | CA | PRO | A | 445 | 7138 | 7066 | 7139 | −14 | 43 | 20 | C |
| ATOM | 1671 | CB | PRO | A | 445 | 22.634 | −28.013 | −10.213 | 1.00 | 56.09 | | C |
| ANISOU | 1671 | CB | PRO | A | 445 | 7127 | 7062 | 7121 | −19 | 38 | 43 | C |
| ATOM | 1672 | CG | PRO | A | 445 | 21.374 | −27.115 | −10.201 | 1.00 | 55.99 | | C |
| ANISOU | 1672 | CG | PRO | A | 445 | 7107 | 7028 | 7136 | −18 | 60 | 17 | C |
| ATOM | 1673 | CD | PRO | A | 445 | 21.619 | −25.973 | −11.182 | 1.00 | 55.94 | | C |
| ANISOU | 1673 | CD | PRO | A | 445 | 7068 | 7042 | 7143 | −13 | 32 | 27 | C |
| ATOM | 1674 | C | PRO | A | 445 | 23.313 | −28.224 | −12.636 | 1.00 | 56.28 | | C |
| ANISOU | 1674 | C | PRO | A | 445 | 7162 | 7119 | 7100 | −20 | 5 | 9 | C |
| ATOM | 1675 | O | PRO | A | 445 | 22.773 | −27.671 | −13.598 | 1.00 | 56.74 | | O |
| ANISOU | 1675 | O | PRO | A | 445 | 7250 | 7159 | 7148 | −40 | −2 | 46 | O |
| ATOM | 1676 | C1 | NAG | C | 1 | 23.582 | 33.784 | −6.381 | 1.00 | 62.40 | | C |
| ANISOU | 1676 | C1 | NAG | C | 1 | 7883 | 7954 | 7870 | −44 | −8 | −30 | C |
| ATOM | 1677 | C2 | NAG | C | 1 | 23.462 | 33.722 | −7.905 | 1.00 | 65.49 | | C |
| ANISOU | 1677 | C2 | NAG | C | 1 | 8282 | 8330 | 8269 | −28 | 6 | −4 | C |
| ATOM | 1678 | N2 | NAG | C | 1 | 23.093 | 35.025 | −8.441 | 1.00 | 66.24 | | N |
| ANISOU | 1678 | N2 | NAG | C | 1 | 8456 | 8344 | 8368 | 18 | 29 | 25 | N |
| ATOM | 1679 | C7 | NAG | C | 1 | 23.585 | 35.522 | −9.579 | 1.00 | 67.45 | | C |
| ANISOU | 1679 | C7 | NAG | C | 1 | 8530 | 8535 | 8561 | −1 | −2 | 14 | C |
| ATOM | 1680 | O7 | NAG | C | 1 | 23.964 | 34.827 | −10.522 | 1.00 | 67.51 | | O |
| ANISOU | 1680 | O7 | NAG | C | 1 | 8538 | 8539 | 8571 | 59 | 54 | −2 | O |
| ATOM | 1681 | C8 | NAG | C | 1 | 23.648 | 37.017 | −9.676 | 1.00 | 66.89 | | C |
| ANISOU | 1681 | C8 | NAG | C | 1 | 8466 | 8432 | 8517 | −1 | 16 | 31 | C |
| ATOM | 1682 | C3 | NAG | C | 1 | 22.443 | 32.665 | −8.344 | 1.00 | 65.88 | | C |
| ANISOU | 1682 | C3 | NAG | C | 1 | 8333 | 8317 | 8379 | −25 | 6 | −44 | C |
| ATOM | 1683 | O3 | NAG | C | 1 | 22.590 | 32.483 | −9.734 | 1.00 | 66.07 | | O |
| ANISOU | 1683 | O3 | NAG | C | 1 | 8394 | 8322 | 8385 | −34 | 33 | −29 | O |
| ATOM | 1684 | C4 | NAG | C | 1 | 22.599 | 31.331 | −7.598 | 1.00 | 65.99 | | C |
| ANISOU | 1684 | C4 | NAG | C | 1 | 8321 | 8333 | 8418 | 5 | 7 | −11 | C |
| ATOM | 1685 | O4 | NAG | C | 1 | 21.474 | 30.499 | −7.821 | 1.00 | 66.44 | | O |
| ANISOU | 1685 | O4 | NAG | C | 1 | 8287 | 8408 | 8547 | 13 | 31 | 9 | O |

TABLE 7-continued

The atomic structure coordinates of Fc-TM

| | | | | | | | | | | | | |
|---|---|---|---|---|---|---|---|---|---|---|---|---|
| ATOM | 1686 | C5 | NAG | C | 1 | 22.752 | 31.577 | −6.097 | 1.00 | 66.41 | | C |
| ANISOU | 1686 | C5 | NAG | C | 1 | 8343 | 8413 | 8474 | −27 | 15 | −25 | C |
| ATOM | 1687 | C6 | NAG | C | 1 | 22.991 | 30.280 | −5.319 | 1.00 | 70.02 | | C |
| ANISOU | 1687 | C6 | NAG | C | 1 | 8892 | 8745 | 8966 | 21 | 22 | 38 | C |
| ATOM | 1688 | O6 | NAG | C | 1 | 23.519 | 30.524 | −4.020 | 1.00 | 73.85 | | O |
| ANISOU | 1688 | O6 | NAG | C | 1 | 9391 | 9317 | 9349 | −6 | −44 | −16 | O |
| ATOM | 1689 | O5 | NAG | C | 1 | 23.817 | 32.482 | −5.871 | 1.00 | 63.94 | | O |
| ANISOU | 1689 | O5 | NAG | C | 1 | 8161 | 8050 | 8084 | 80 | 50 | 57 | O |
| ATOM | 1690 | C1 | NAG | C | 2 | 21.730 | 29.460 | −8.798 | 1.00 | 65.34 | | C |
| ANISOU | 1690 | C1 | NAG | C | 2 | 8142 | 8275 | 8407 | 44 | 10 | 1 | C |
| ATOM | 1691 | C2 | NAG | C | 2 | 21.096 | 28.144 | −8.338 | 1.00 | 65.73 | | C |
| ANISOU | 1691 | C2 | NAG | C | 2 | 8184 | 8346 | 8442 | 35 | −16 | −3 | C |
| ATOM | 1692 | N2 | NAG | C | 2 | 21.683 | 27.718 | −7.084 | 1.00 | 64.89 | | N |
| ANISOU | 1692 | N2 | NAG | C | 2 | 8185 | 8149 | 8320 | −5 | 14 | −2 | N |
| ATOM | 1693 | C7 | NAG | C | 2 | 20.978 | 27.261 | −6.059 | 1.00 | 63.76 | | C |
| ANISOU | 1693 | C7 | NAG | C | 2 | 8044 | 7955 | 8225 | −2 | 10 | −19 | C |
| ATOM | 1694 | O7 | NAG | C | 2 | 19.755 | 27.237 | −6.045 | 1.00 | 64.27 | | O |
| ANISOU | 1694 | O7 | NAG | C | 2 | 8126 | 7933 | 8360 | 58 | −45 | −18 | O |
| ATOM | 1695 | C8 | NAG | C | 2 | 21.759 | 26.753 | −4.886 | 1.00 | 63.17 | | C |
| ANISOU | 1695 | C8 | NAG | C | 2 | 8009 | 7902 | 8089 | −43 | 0 | −70 | C |
| ATOM | 1696 | C3 | NAG | C | 2 | 21.272 | 27.045 | −9.384 | 1.00 | 66.30 | | C |
| ANISOU | 1696 | C3 | NAG | C | 2 | 8307 | 8391 | 8490 | −9 | 39 | −16 | C |
| ATOM | 1697 | O3 | NAG | C | 2 | 20.552 | 25.897 | −9.004 | 1.00 | 66.84 | | O |
| ANISOU | 1697 | O3 | NAG | C | 2 | 8376 | 8464 | 8554 | 36 | 21 | −17 | O |
| ATOM | 1698 | C4 | NAG | C | 2 | 20.804 | 27.518 | −10.758 | 1.00 | 67.01 | | C |
| ANISOU | 1698 | C4 | NAG | C | 2 | 8356 | 8544 | 8559 | 11 | 6 | 16 | C |
| ATOM | 1699 | O4 | NAG | C | 2 | 21.178 | 26.580 | −11.745 | 1.00 | 68.38 | | O |
| ANISOU | 1699 | O4 | NAG | C | 2 | 8536 | 8661 | 8781 | 48 | 1 | −50 | O |
| ATOM | 1700 | C5 | NAG | C | 2 | 21.470 | 28.857 | −11.105 | 1.00 | 66.52 | | C |
| ANISOU | 1700 | C5 | NAG | C | 2 | 8316 | 8433 | 8524 | 47 | 10 | −29 | C |
| ATOM | 1701 | C6 | NAG | C | 2 | 20.959 | 29.383 | −12.447 | 1.00 | 65.54 | | C |
| ANISOU | 1701 | C6 | NAG | C | 2 | 8421 | 8024 | 8454 | 24 | 13 | 40 | C |
| ATOM | 1702 | O6 | NAG | C | 2 | 20.896 | 30.794 | −12.448 | 1.00 | 66.76 | | O |
| ANISOU | 1702 | O6 | NAG | C | 2 | 8300 | 8669 | 8396 | −35 | 74 | −46 | O |
| ATOM | 1703 | O5 | NAG | C | 2 | 21.262 | 29.813 | −10.083 | 1.00 | 65.04 | | O |
| ANISOU | 1703 | O5 | NAG | C | 2 | 8097 | 8260 | 8355 | 41 | 32 | 14 | O |
| ATOM | 1704 | C1 | BMA | C | 3 | 20.170 | 25.602 | −12.036 | 1.00 | 69.16 | | C |
| ANISOU | 1704 | C1 | BMA | C | 3 | 8600 | 8769 | 8908 | 4 | 18 | 7 | C |
| ATOM | 1705 | C2 | BMA | C | 3 | 20.218 | 25.313 | −13.529 | 1.00 | 70.30 | | C |
| ANISOU | 1705 | C2 | BMA | C | 3 | 8850 | 8920 | 8938 | 19 | 27 | −8 | C |
| ATOM | 1706 | O2 | BMA | C | 3 | 21.569 | 24.990 | −13.866 | 1.00 | 70.44 | | O |
| ANISOU | 1706 | O2 | BMA | C | 3 | 8922 | 8873 | 8967 | −10 | 1 | −5 | O |
| ATOM | 1707 | C3 | BMA | C | 3 | 19.301 | 24.146 | −13.887 | 1.00 | 71.64 | | C |
| ANISOU | 1707 | C3 | BMA | C | 3 | 8983 | 9046 | 9190 | 8 | 23 | 33 | C |
| ATOM | 1708 | O3 | BMA | C | 3 | 19.431 | 23.763 | −15.259 | 1.00 | 75.50 | | O |
| ANISOU | 1708 | O3 | BMA | C | 3 | 9547 | 9570 | 9568 | −21 | 91 | −86 | O |
| ATOM | 1709 | C4 | BMA | C | 3 | 19.635 | 22.931 | −13.035 | 1.00 | 69.90 | | C |
| ANISOU | 1709 | C4 | BMA | C | 3 | 8765 | 8895 | 8898 | 29 | 63 | −28 | C |
| ATOM | 1710 | O4 | BMA | C | 3 | 18.694 | 21.909 | −13.353 | 1.00 | 69.61 | | O |
| ANISOU | 1710 | O4 | BMA | C | 3 | 8791 | 8790 | 8869 | −4 | 63 | 40 | O |
| ATOM | 1711 | C5 | BMA | C | 3 | 19.565 | 23.304 | −11.562 | 1.00 | 68.25 | | C |
| ANISOU | 1711 | C5 | BMA | C | 3 | 8529 | 8638 | 8763 | 43 | 25 | 26 | C |
| ATOM | 1712 | C6 | BMA | C | 3 | 19.992 | 22.163 | −10.656 | 1.00 | 66.92 | | C |
| ANISOU | 1712 | C6 | BMA | C | 3 | 8364 | 8482 | 8579 | 9 | 30 | −59 | C |
| ATOM | 1713 | O6 | BMA | C | 3 | 20.187 | 22.675 | −9.336 | 1.00 | 64.81 | | O |
| ANISOU | 1713 | O6 | BMA | C | 3 | 8159 | 8199 | 8264 | 28 | −14 | −16 | O |
| ATOM | 1714 | O5 | BMA | C | 3 | 20.426 | 24.412 | −11.292 | 1.00 | 68.53 | | O |
| ANISOU | 1714 | O5 | BMA | C | 3 | 8472 | 8748 | 8818 | 3 | −2 | 14 | O |
| ATOM | 1715 | C1 | MAN | C | 4 | 18.485 | 24.451 | −16.100 | 1.00 | 80.48 | | C |
| ANISOU | 1715 | C1 | MAN | C | 4 | 10175 | 10231 | 10170 | 54 | −11 | 39 | C |
| ATOM | 1716 | C2 | MAN | C | 4 | 17.857 | 23.471 | −17.095 | 1.00 | 83.30 | | C |
| ANISOU | 1716 | C2 | MAN | C | 4 | 10595 | 10536 | 10515 | −34 | 3 | −45 | C |
| ATOM | 1717 | O2 | MAN | C | 4 | 16.758 | 24.059 | −17.785 | 1.00 | 86.66 | | O |
| ANISOU | 1717 | O2 | MAN | C | 4 | 10987 | 10961 | 10976 | 56 | −72 | 11 | O |
| ATOM | 1718 | C3 | MAN | C | 4 | 18.909 | 22.950 | −18.097 | 1.00 | 83.50 | | C |
| ANISOU | 1718 | C3 | MAN | C | 4 | 10571 | 10594 | 10570 | −3 | −6 | −16 | C |
| ATOM | 1719 | O3 | MAN | C | 4 | 18.291 | 22.361 | −19.225 | 1.00 | 83.93 | | O |
| ANISOU | 1719 | O3 | MAN | C | 4 | 10617 | 10659 | 10610 | 21 | 0 | −35 | O |
| ATOM | 1720 | C4 | MAN | C | 4 | 19.916 | 24.011 | −18.569 | 1.00 | 83.25 | | C |
| ANISOU | 1720 | C4 | MAN | C | 4 | 10531 | 10556 | 10544 | 0 | 21 | −13 | C |
| ATOM | 1721 | O4 | MAN | C | 4 | 21.086 | 23.342 | −18.983 | 1.00 | 82.77 | | O |
| ANISOU | 1721 | O4 | MAN | C | 4 | 10525 | 10482 | 10441 | −7 | 36 | −14 | O |
| ATOM | 1722 | C5 | MAN | C | 4 | 20.281 | 25.007 | −17.461 | 1.00 | 82.93 | | C |
| ANISOU | 1722 | C5 | MAN | C | 4 | 10477 | 10508 | 10524 | 23 | 16 | −3 | C |
| ATOM | 1723 | C6 | MAN | C | 4 | 21.110 | 26.187 | −17.945 | 1.00 | 82.33 | | C |
| ANISOU | 1723 | C6 | MAN | C | 4 | 10560 | 10453 | 10268 | −61 | −54 | −113 | C |
| ATOM | 1724 | O6 | MAN | C | 4 | 21.526 | 26.916 | −16.808 | 1.00 | 84.80 | | O |
| ANISOU | 1724 | O6 | MAN | C | 4 | 10612 | 10772 | 10835 | 71 | 57 | 111 | O |

TABLE 7-continued

The atomic structure coordinates of Fc-TM

| | | | | | | | | | | | | |
|---|---|---|---|---|---|---|---|---|---|---|---|---|
| ATOM | 1725 | O5 | MAN | C | 4 | 19.111 | 25.485 | −16.823 | 1.00 | 81.69 | | O |
| ANISOU | 1725 | O5 | MAN | C | 4 | 10367 | 10342 | 10328 | −38 | 18 | 6 | O |
| ATOM | 1726 | C1 | NAG | C | 5 | 15.457 | 23.728 | −17.226 | 1.00 | 89.09 | | C |
| ANISOU | 1726 | C1 | NAG | C | 5 | 11237 | 11320 | 11293 | −16 | 29 | −14 | C |
| ATOM | 1727 | C2 | NAG | C | 5 | 14.333 | 24.200 | −18.167 | 1.00 | 90.32 | | C |
| ANISOU | 1727 | C2 | NAG | C | 5 | 11439 | 11436 | 11441 | 8 | −17 | 15 | C |
| ATOM | 1728 | N2 | NAG | C | 5 | 13.146 | 24.596 | −17.413 | 1.00 | 90.36 | | N |
| ANISOU | 1728 | N2 | NAG | C | 5 | 11463 | 11426 | 11444 | 5 | 8 | −13 | N |
| ATOM | 1729 | C7 | NAG | C | 5 | 12.233 | 25.470 | −17.860 | 1.00 | 91.03 | | C |
| ANISOU | 1729 | C7 | NAG | C | 5 | 11565 | 11585 | 11434 | −4 | 21 | −26 | C |
| ATOM | 1730 | O7 | NAG | C | 5 | 12.477 | 26.652 | −18.106 | 1.00 | 90.45 | | O |
| ANISOU | 1730 | O7 | NAG | C | 5 | 11527 | 11441 | 11396 | −12 | 27 | −5 | O |
| ATOM | 1731 | C8 | NAG | C | 5 | 10.835 | 24.956 | −18.055 | 1.00 | 90.77 | | C |
| ANISOU | 1731 | C8 | NAG | C | 5 | 11519 | 11492 | 11476 | −12 | −1 | −20 | C |
| ATOM | 1732 | C3 | NAG | C | 5 | 13.944 | 23.170 | −19.237 | 1.00 | 91.25 | | C |
| ANISOU | 1732 | C3 | NAG | C | 5 | 11585 | 11552 | 11533 | 1 | −6 | −9 | C |
| ATOM | 1733 | O3 | NAG | C | 5 | 14.135 | 23.730 | −20.517 | 1.00 | 91.88 | | O |
| ANISOU | 1733 | O3 | NAG | C | 5 | 11692 | 11628 | 11590 | −8 | 8 | −1 | O |
| ATOM | 1734 | C4 | NAG | C | 5 | 14.713 | 21.851 | −19.167 | 1.00 | 91.47 | | C |
| ANISOU | 1734 | C4 | NAG | C | 5 | 11616 | 11584 | 11554 | 13 | −11 | −4 | C |
| ATOM | 1735 | O4 | NAG | C | 5 | 13.982 | 20.876 | −19.882 | 1.00 | 91.95 | | O |
| ANISOU | 1735 | O4 | NAG | C | 5 | 11633 | 11671 | 11632 | −13 | −47 | −33 | O |
| ATOM | 1736 | C5 | NAG | C | 5 | 14.961 | 21.352 | −17.736 | 1.00 | 91.25 | | C |
| ANISOU | 1736 | C5 | NAG | C | 5 | 11588 | 11546 | 11537 | 9 | −15 | −10 | C |
| ATOM | 1737 | C6 | NAG | C | 5 | 16.052 | 20.276 | −17.726 | 1.00 | 92.24 | | C |
| ANISOU | 1737 | C6 | NAG | C | 5 | 11575 | 11579 | 11891 | 0 | −46 | −137 | C |
| ATOM | 1738 | O6 | NAG | C | 5 | 16.007 | 19.560 | −16.510 | 1.00 | 90.72 | | O |
| ANISOU | 1738 | O6 | NAG | C | 5 | 11735 | 11388 | 11344 | −24 | −54 | 91 | O |
| ATOM | 1739 | O5 | NAG | C | 5 | 15.297 | 22.377 | −16.797 | 1.00 | 90.15 | | O |
| ANISOU | 1739 | O5 | NAG | C | 5 | 11430 | 11414 | 11406 | 5 | −15 | 26 | O |
| ATOM | 1740 | C1 | MAN | C | 7 | 20.272 | 21.548 | −8.453 | 1.00 | 64.56 | | C |
| ANISOU | 1740 | C1 | MAN | C | 7 | 8141 | 8188 | 8199 | −9 | −4 | −47 | C |
| ATOM | 1741 | C2 | MAN | C | 7 | 19.819 | 21.886 | −7.041 | 1.00 | 64.34 | | C |
| ANISOU | 1741 | C2 | MAN | C | 7 | 8131 | 8140 | 8175 | 3 | 1 | −13 | C |
| ATOM | 1742 | O2 | MAN | C | 7 | 19.851 | 20.689 | −6.290 | 1.00 | 64.37 | | O |
| ANISOU | 1742 | O2 | MAN | C | 7 | 8170 | 8136 | 8152 | 13 | 14 | −72 | O |
| ATOM | 1743 | C3 | MAN | C | 7 | 20.773 | 22.900 | −6.390 | 1.00 | 64.46 | | C |
| ANISOU | 1743 | C3 | MAN | C | 7 | 8127 | 8187 | 8177 | −25 | 13 | −19 | C |
| ATOM | 1744 | O3 | MAN | C | 7 | 20.410 | 23.129 | −5.037 | 1.00 | 63.53 | | O |
| ANISOU | 1744 | O3 | MAN | C | 7 | 7975 | 8057 | 8105 | −67 | −15 | −101 | O |
| ATOM | 1745 | C4 | MAN | C | 7 | 22.239 | 22.434 | −6.476 | 1.00 | 64.50 | | C |
| ANISOU | 1745 | C4 | MAN | C | 7 | 8179 | 8148 | 8180 | 7 | 13 | −40 | C |
| ATOM | 1746 | O4 | MAN | C | 7 | 23.132 | 23.509 | −6.221 | 1.00 | 64.35 | | O |
| ANISOU | 1746 | O4 | MAN | C | 7 | 8206 | 8105 | 8139 | 46 | −5 | −78 | O |
| ATOM | 1747 | C5 | MAN | C | 7 | 22.602 | 21.790 | −7.827 | 1.00 | 64.16 | | C |
| ANISOU | 1747 | C5 | MAN | C | 7 | 8159 | 8123 | 8096 | −6 | 0 | −11 | C |
| ATOM | 1748 | C6 | MAN | C | 7 | 23.842 | 20.915 | −7.667 | 1.00 | 63.34 | | C |
| ANISOU | 1748 | C6 | MAN | C | 7 | 7929 | 7985 | 8151 | −24 | −13 | 57 | C |
| ATOM | 1749 | O6 | MAN | C | 7 | 24.053 | 20.180 | −8.846 | 1.00 | 61.06 | | O |
| ANISOU | 1749 | O6 | MAN | C | 7 | 7751 | 7711 | 7737 | 40 | −16 | −78 | O |
| ATOM | 1750 | O5 | MAN | C | 7 | 21.565 | 20.982 | −8.380 | 1.00 | 64.42 | | O |
| ANISOU | 1750 | O5 | MAN | C | 7 | 8221 | 8144 | 8112 | −36 | 17 | −13 | O |
| ATOM | 1751 | C1 | NAG | C | 8 | 18.593 | 20.003 | −6.270 | 1.00 | 63.46 | | C |
| ANISOU | 1751 | C1 | NAG | C | 8 | 8070 | 8012 | 8030 | −5 | −1 | −34 | C |
| ATOM | 1752 | C2 | NAG | C | 8 | 18.856 | 18.592 | −5.766 | 1.00 | 64.09 | | C |
| ANISOU | 1752 | C2 | NAG | C | 8 | 8169 | 8111 | 8072 | −6 | −10 | 14 | C |
| ATOM | 1753 | N2 | NAG | C | 8 | 19.889 | 17.946 | −6.563 | 1.00 | 63.96 | | N |
| ANISOU | 1753 | N2 | NAG | C | 8 | 8038 | 8176 | 8088 | 48 | −11 | 12 | N |
| ATOM | 1754 | C7 | NAG | C | 8 | 21.157 | 17.831 | −6.142 | 1.00 | 67.85 | | C |
| ANISOU | 1754 | C7 | NAG | C | 8 | 8475 | 8217 | 9086 | −90 | 51 | 262 | C |
| ATOM | 1755 | O7 | NAG | C | 8 | 21.540 | 18.162 | −5.017 | 1.00 | 63.54 | | O |
| ANISOU | 1755 | O7 | NAG | C | 8 | 8084 | 8252 | 7806 | −67 | −148 | −118 | O |
| ATOM | 1756 | C8 | NAG | C | 8 | 22.133 | 17.253 | −7.129 | 1.00 | 63.31 | | C |
| ANISOU | 1756 | C8 | NAG | C | 8 | 8014 | 8140 | 7899 | 131 | 171 | −31 | C |
| ATOM | 1757 | C3 | NAG | C | 8 | 17.561 | 17.785 | −5.725 | 1.00 | 63.80 | | C |
| ANISOU | 1757 | C3 | NAG | C | 8 | 8109 | 8055 | 8075 | 0 | −8 | −41 | C |
| ATOM | 1758 | O3 | NAG | C | 8 | 17.802 | 16.564 | −5.040 | 1.00 | 64.18 | | O |
| ANISOU | 1758 | O3 | NAG | C | 8 | 8158 | 8167 | 8059 | 20 | −18 | −53 | O |
| ATOM | 1759 | C4 | NAG | C | 8 | 16.450 | 18.562 | −4.999 | 1.00 | 62.99 | | C |
| ANISOU | 1759 | C4 | NAG | C | 8 | 8022 | 7934 | 7977 | 24 | −38 | −22 | C |
| ATOM | 1760 | O4 | NAG | C | 8 | 15.194 | 17.950 | −5.229 | 1.00 | 63.13 | | O |
| ANISOU | 1760 | O4 | NAG | C | 8 | 8044 | 7901 | 8038 | 54 | −37 | −48 | O |
| ATOM | 1761 | C5 | NAG | C | 8 | 16.391 | 20.062 | −5.340 | 1.00 | 62.31 | | C |
| ANISOU | 1761 | C5 | NAG | C | 8 | 7922 | 7895 | 7856 | 3 | 2 | −21 | C |
| ATOM | 1762 | C6 | NAG | C | 8 | 15.637 | 20.861 | −4.271 | 1.00 | 61.45 | | C |
| ANISOU | 1762 | C6 | NAG | C | 8 | 7823 | 7770 | 7755 | −29 | −23 | −11 | C |
| ATOM | 1763 | O6 | NAG | C | 8 | 16.235 | 20.685 | −2.999 | 1.00 | 59.23 | | O |
| ANISOU | 1763 | O6 | NAG | C | 8 | 7510 | 7497 | 7498 | 24 | 71 | −106 | O |

TABLE 7-continued

| | | | | | The atomic structure coordinates of Fc-TM | | | | | | |
|---|---|---|---|---|---|---|---|---|---|---|---|
| ATOM | 1764 | O5 | NAG | C | 8 | 17.675 | 20.637 | −5.415 | 1.00 | 62.28 | O |
| ANISOU | 1764 | O5 | NAG | C | 8 | 7944 | 7849 | 7870 | −26 | −26 | 4 | O |
| ATOM | 1765 | C1 | GAL | C | 9 | 14.603 | 17.561 | −3.972 | 1.00 | 62.63 | C |
| ANISOU | 1765 | C1 | GAL | C | 9 | 7968 | 7907 | 7920 | −3 | −4 | −28 | C |
| ATOM | 1766 | C2 | GAL | C | 9 | 13.290 | 16.787 | −4.178 | 1.00 | 62.38 | C |
| ANISOU | 1766 | C2 | GAL | C | 9 | 7981 | 7842 | 7878 | 19 | −5 | −33 | C |
| ATOM | 1767 | O2 | GAL | C | 9 | 12.274 | 17.622 | −4.709 | 1.00 | 60.03 | O |
| ANISOU | 1767 | O2 | GAL | C | 9 | 7846 | 7411 | 7550 | −14 | 6 | −131 | O |
| ATOM | 1768 | C3 | GAL | C | 9 | 12.818 | 16.148 | −2.860 | 1.00 | 62.73 | C |
| ANISOU | 1768 | C3 | GAL | C | 9 | 8016 | 7945 | 7872 | 38 | 8 | −36 | C |
| ATOM | 1769 | O3 | GAL | C | 9 | 11.849 | 15.158 | −3.102 | 1.00 | 62.97 | O |
| ANISOU | 1769 | O3 | GAL | C | 9 | 7994 | 7990 | 7941 | −25 | 39 | 8 | O |
| ATOM | 1770 | C4 | GAL | C | 9 | 13.958 | 15.500 | −2.082 | 1.00 | 63.15 | C |
| ANISOU | 1770 | C4 | GAL | C | 9 | 8053 | 7994 | 7944 | 4 | 6 | 44 | C |
| ATOM | 1771 | O4 | GAL | C | 9 | 14.499 | 14.420 | −2.818 | 1.00 | 61.84 | O |
| ANISOU | 1771 | O4 | GAL | C | 9 | 7873 | 7903 | 7720 | 12 | 9 | 65 | O |
| ATOM | 1772 | C5 | GAL | C | 9 | 15.022 | 16.559 | −1.867 | 1.00 | 63.69 | C |
| ANISOU | 1772 | C5 | GAL | C | 9 | 8052 | 8039 | 8108 | −2 | −14 | 28 | C |
| ATOM | 1773 | C6 | GAL | C | 9 | 16.117 | 16.112 | −0.903 | 1.00 | 64.97 | C |
| ANISOU | 1773 | C6 | GAL | C | 9 | 8268 | 8195 | 8220 | 44 | −44 | 59 | C |
| ATOM | 1774 | O6 | GAL | C | 9 | 17.286 | 16.891 | −1.077 | 1.00 | 65.24 | O |
| ANISOU | 1774 | O6 | GAL | C | 9 | 8290 | 8153 | 8345 | −73 | −89 | 82 | O |
| ATOM | 1775 | O5 | GAL | C | 9 | 15.525 | 16.843 | −3.157 | 1.00 | 64.20 | O |
| ANISOU | 1775 | O5 | GAL | C | 9 | 8132 | 8127 | 8132 | 15 | −28 | −36 | O |
| ATOM | 1776 | C1 | FUC | C | 11 | 24.736 | 29.847 | −3.954 | 1.00 | 77.44 | C |
| ANISOU | 1776 | C1 | FUC | C | 11 | 9759 | 9799 | 9837 | 29 | −9 | 1 | C |
| ATOM | 1777 | C2 | FUC | C | 11 | 26.080 | 30.499 | −4.293 | 1.00 | 78.54 | C |
| ANISOU | 1777 | C2 | FUC | C | 11 | 9883 | 9910 | 10014 | −7 | 4 | 2 | C |
| ATOM | 1778 | O2 | FUC | C | 11 | 26.808 | 30.755 | −3.112 | 1.00 | 79.77 | O |
| ANISOU | 1778 | O2 | FUC | C | 11 | 9917 | 10007 | 10050 | 72 | −20 | −34 | O |
| ATOM | 1779 | C3 | FUC | C | 11 | 26.977 | 29.696 | −5.231 | 1.00 | 78.25 | C |
| ANISOU | 1779 | C3 | FUC | C | 11 | 9972 | 9993 | 10072 | −6 | 44 | −18 | C |
| ATOM | 1780 | O3 | FUC | C | 11 | 26.852 | 30.264 | −6.510 | 1.00 | 79.46 | O |
| ANISOU | 1780 | O3 | FUC | C | 11 | 10023 | 10064 | 10081 | −17 | 58 | 20 | O |
| ATOM | 1781 | C4 | FUC | C | 11 | 26.769 | 28.174 | −5.286 | 1.00 | 77.45 | C |
| ANISOU | 1781 | C4 | FUC | C | 11 | 10020 | 10011 | 10048 | −23 | 33 | −20 | C |
| ATOM | 1782 | O4 | FUC | C | 11 | 26.880 | 27.703 | −6.627 | 1.00 | 78.56 | O |
| ANISOU | 1782 | O4 | FUC | C | 11 | 10076 | 9967 | 9991 | −28 | 42 | −26 | O |
| ATOM | 1783 | C5 | FUC | C | 11 | 25.463 | 27.641 | −4.693 | 1.00 | 77.17 | C |
| ANISOU | 1783 | C5 | FUC | C | 11 | 10016 | 10033 | 10124 | 13 | 23 | −2 | C |
| ATOM | 1784 | C6 | FUC | C | 11 | 24.460 | 27.240 | −5.783 | 1.00 | 78.48 | C |
| ANISOU | 1784 | C6 | FUC | C | 11 | 10059 | 9937 | 10067 | 0 | 46 | −62 | C |
| ATOM | 1785 | O5 | FUC | C | 11 | 24.873 | 28.467 | −3.681 | 1.00 | 79.38 | O |
| ANISOU | 1785 | O5 | FUC | C | 11 | 9928 | 9876 | 10085 | −4 | 13 | −44 | O |
| ATOM | 1786 | ZN | ZN | I | 1 | 1.011 | 2.625 | −6.522 | 1.00 | 37.90 | ZN |
| ANISOU | 1786 | ZN | ZN | I | 1 | 5916 | 5645 | 2837 | −109 | −134 | −300 | ZN |
| ATOM | 1787 | ZN | ZN | I | 2 | −2.850 | 29.288 | 0.411 | 1.00 | 66.11 | ZN |
| ANISOU | 1787 | ZN | ZN | I | 2 | 8310 | 7792 | 9014 | 476 | 23 | −269 | ZN |
| ATOM | 1788 | ZN | ZN | I | 3 | 0.081 | 21.125 | −18.851 | 0.50 | 60.89 | ZN |
| ANISOU | 1788 | ZN | ZN | I | 3 | 7926 | 7551 | 7656 | 24 | −73 | 15 | ZN |
| ATOM | 1789 | ZN | ZN | I | 4 | 4.094 | −7.924 | −14.198 | 0.50 | 63.49 | ZN |
| ANISOU | 1789 | ZN | ZN | I | 4 | 7915 | 7950 | 8259 | −54 | 190 | −25 | ZN |
| ATOM | 1790 | OW | HOH | W | 1 | −2.686 | −4.705 | −7.680 | 1.00 | 51.42 | O |
| ANISOU | 1790 | OW | HOH | W | 1 | 6584 | 6695 | 6258 | 169 | −102 | 48 | O |
| ATOM | 1791 | OW | HOH | W | 2 | 15.326 | 7.920 | −11.915 | 1.00 | 41.62 | O |
| ANISOU | 1791 | OW | HOH | W | 2 | 5180 | 5671 | 4961 | −35 | −220 | −272 | O |
| ATOM | 1792 | OW | HOH | W | 3 | 11.705 | 21.084 | −15.919 | 1.00 | 53.41 | O |
| ANISOU | 1792 | OW | HOH | W | 3 | 6696 | 6842 | 6755 | 76 | −83 | 53 | O |
| ATOM | 1793 | OW | HOH | W | 4 | 4.028 | 8.613 | −6.717 | 1.00 | 24.34 | O |
| ANISOU | 1793 | OW | HOH | W | 4 | 3616 | 2379 | 3251 | 0 | −336 | 632 | O |
| ATOM | 1794 | OW | HOH | W | 5 | 4.904 | 7.310 | −3.564 | 1.00 | 23.00 | O |
| ANISOU | 1794 | OW | HOH | W | 5 | 3808 | 3315 | 1615 | −69 | 307 | −476 | O |
| ATOM | 1795 | OW | HOH | W | 6 | 2.707 | 2.220 | −14.972 | 1.00 | 23.50 | O |
| ANISOU | 1795 | OW | HOH | W | 6 | 3794 | 2827 | 2306 | 91 | −630 | 374 | O |
| ATOM | 1796 | OW | HOH | W | 7 | 0.086 | 8.821 | −15.891 | 1.00 | 13.87 | O |
| ANISOU | 1796 | OW | HOH | W | 7 | 2598 | 1403 | 1268 | 195 | 51 | −373 | O |
| ATOM | 1797 | OW | HOH | W | 8 | 23.163 | 6.265 | −13.153 | 1.00 | 41.03 | O |
| ANISOU | 1797 | OW | HOH | W | 8 | 5402 | 4550 | 5636 | 147 | 229 | 45 | O |
| ATOM | 1798 | OW | HOH | W | 9 | 20.619 | 3.699 | −13.114 | 1.00 | 23.85 | O |
| ANISOU | 1798 | OW | HOH | W | 9 | 3742 | 2526 | 2794 | −240 | −69 | −539 | O |
| ATOM | 1799 | OW | HOH | W | 10 | −2.466 | −6.638 | −5.878 | 1.00 | 44.21 | O |
| ANISOU | 1799 | OW | HOH | W | 10 | 5803 | 5719 | 5275 | −213 | 103 | 100 | O |
| ATOM | 1800 | OW | HOH | W | 11 | 12.642 | −1.804 | −2.353 | 1.00 | 63.47 | O |
| ANISOU | 1800 | OW | HOH | W | 11 | 8214 | 7905 | 7995 | −35 | −45 | −9 | O |
| ATOM | 1801 | OW | HOH | W | 12 | 22.639 | 6.534 | −20.972 | 1.00 | 33.47 | O |
| ANISOU | 1801 | OW | HOH | W | 12 | 3867 | 4337 | 4510 | −144 | 129 | −236 | O |
| ATOM | 1802 | OW | HOH | W | 13 | 21.422 | 1.104 | −8.987 | 1.00 | 24.16 | O |
| ANISOU | 1802 | OW | HOH | W | 13 | 3539 | 3414 | 2226 | −145 | 221 | 76 | O |

TABLE 7-continued

The atomic structure coordinates of Fc-TM

| | | | | | | | | | | | | |
|---|---|---|---|---|---|---|---|---|---|---|---|---|
| ATOM   | 1803 | OW | HOH | W | 14 | 8.879  | 4.061   | -13.080 | 1.00 | 24.97 |      | O |
| ANISOU | 1803 | OW | HOH | W | 14 | 3170   | 3239    | 3075    | 162  | -18   | -220 | O |
| ATOM   | 1804 | OW | HOH | W | 15 | 11.288 | 6.795   | -26.054 | 1.00 | 45.90 |      | O |
| ANISOU | 1804 | OW | HOH | W | 15 | 5829   | 5389    | 6220    | -13  | 40    | 27   | O |
| ATOM   | 1805 | OW | HOH | W | 16 | 14.749 | -1.980  | -24.051 | 1.00 | 16.53 |      | O |
| ANISOU | 1805 | OW | HOH | W | 16 | 3271   | 2274    | 735     | 26   | 224   | -273 | O |
| ATOM   | 1806 | OW | HOH | W | 17 | -0.444 | 6.851   | -20.367 | 1.00 | 17.75 |      | O |
| ANISOU | 1806 | OW | HOH | W | 17 | 2576   | 1988    | 2179    | 732  | 234   | 28   | O |
| ATOM   | 1807 | OW | HOH | W | 18 | 2.245  | 11.930  | -0.120  | 1.00 | 32.42 |      | O |
| ANISOU | 1807 | OW | HOH | W | 18 | 4359   | 4213    | 3746    | -160 | 29    | -125 | O |
| ATOM   | 1808 | OW | HOH | W | 19 | 5.162  | 7.718   | -18.328 | 1.00 | 25.83 |      | O |
| ANISOU | 1808 | OW | HOH | W | 19 | 3497   | 3439    | 2878    | 96   | -375  | -584 | O |
| ATOM   | 1809 | OW | HOH | W | 20 | 0.796  | 0.967   | -5.140  | 1.00 | 21.38 |      | O |
| ANISOU | 1809 | OW | HOH | W | 20 | 3124   | 2654    | 2344    | 142  | 186   | -165 | O |
| ATOM   | 1810 | OW | HOH | W | 21 | -2.715 | 28.725  | 2.415   | 1.00 | 36.34 |      | O |
| ANISOU | 1810 | OW | HOH | W | 21 | 4766   | 4654    | 4387    | -175 | 10    | 163  | O |
| ATOM   | 1811 | OW | HOH | W | 22 | 30.225 | -4.400  | -9.331  | 1.00 | 25.40 |      | O |
| ANISOU | 1811 | OW | HOH | W | 22 | 3794   | 3473    | 2383    | -207 | 171   | 921  | O |
| ATOM   | 1812 | OW | HOH | W | 23 | 7.961  | 6.779   | -13.116 | 1.00 | 20.66 |      | O |
| ANISOU | 1812 | OW | HOH | W | 23 | 2905   | 2729    | 2214    | -3   | 224   | -281 | O |
| ATOM   | 1813 | OW | HOH | W | 24 | 7.734  | 8.056   | -10.907 | 1.00 | 11.86 |      | O |
| ANISOU | 1813 | OW | HOH | W | 24 | 2940   | 1037    | 527     | 120  | -14   | -462 | O |
| ATOM   | 1814 | OW | HOH | W | 25 | -0.824 | -8.657  | -5.241  | 1.00 | 50.76 |      | O |
| ANISOU | 1814 | OW | HOH | W | 25 | 6516   | 6602    | 6166    | -193 | 254   | 42   | O |
| ATOM   | 1815 | OW | HOH | W | 26 | -5.085 | 12.307  | -13.493 | 1.00 | 33.94 |      | O |
| ANISOU | 1815 | OW | HOH | W | 26 | 4426   | 4303    | 4165    | 0    | -23   | -112 | O |
| ATOM   | 1816 | OW | HOH | W | 27 | 21.117 | -3.680  | -2.105  | 1.00 | 36.56 |      | O |
| ANISOU | 1816 | OW | HOH | W | 27 | 4582   | 4997    | 4310    | -135 | 5     | 141  | O |
| ATOM   | 1817 | OW | HOH | W | 28 | 26.199 | 1.780   | -6.259  | 1.00 | 42.44 |      | O |
| ANISOU | 1817 | OW | HOH | W | 28 | 5350   | 5564    | 5209    | -205 | 54    | -69  | O |
| ATOM   | 1818 | OW | HOH | W | 29 | 25.352 | 2.736   | -9.492  | 1.00 | 26.64 |      | O |
| ANISOU | 1818 | OW | HOH | W | 29 | 2921   | 3682    | 3517    | -164 | -195  | 80   | O |
| ATOM   | 1819 | OW | HOH | W | 30 | 2.621  | 13.373  | -12.530 | 1.00 | 27.62 |      | O |
| ANISOU | 1819 | OW | HOH | W | 30 | 3212   | 3716    | 3565    | -15  | 69    | 381  | O |
| ATOM   | 1820 | OW | HOH | W | 31 | 1.676  | -5.459  | -13.242 | 1.00 | 40.05 |      | O |
| ANISOU | 1820 | OW | HOH | W | 31 | 5122   | 5075    | 5018    | -150 | -104  | -138 | O |
| ATOM   | 1821 | OW | HOH | W | 32 | 5.616  | -7.649  | -12.054 | 1.00 | 25.11 |      | O |
| ANISOU | 1821 | OW | HOH | W | 32 | 3700   | 2636    | 3203    | 249  | 375   | 178  | O |
| ATOM   | 1822 | OW | HOH | W | 33 | 0.073  | 12.268  | -18.854 | 0.50 | 29.68 |      | O |
| ANISOU | 1822 | OW | HOH | W | 33 | 4084   | 3873    | 3317    | 5    | 87    | -2   | O |
| ATOM   | 1823 | OW | HOH | W | 34 | -0.277 | 3.231   | -8.278  | 1.00 | 36.13 |      | O |
| ANISOU | 1823 | OW | HOH | W | 34 | 4577   | 4672    | 4477    | -7   | -155  | -157 | O |
| ATOM   | 1824 | OW | HOH | W | 35 | 19.204 | 7.619   | -19.539 | 1.00 | 41.16 |      | O |
| ANISOU | 1824 | OW | HOH | W | 35 | 5228   | 5167    | 5241    | 76   | 175   | -195 | O |
| ATOM   | 1825 | OW | HOH | W | 36 | 21.318 | 8.586   | -18.968 | 1.00 | 51.27 |      | O |
| ANISOU | 1825 | OW | HOH | W | 36 | 6874   | 6589    | 6015    | -17  | -36   | -19  | O |
| ATOM   | 1826 | OW | HOH | W | 37 | 20.898 | 9.827   | -16.899 | 1.00 | 40.21 |      | O |
| ANISOU | 1826 | OW | HOH | W | 37 | 5588   | 4786    | 4901    | -99  | 37    | 53   | O |
| ATOM   | 1827 | OW | HOH | W | 38 | 19.991 | 12.076  | -17.304 | 1.00 | 40.03 |      | O |
| ANISOU | 1827 | OW | HOH | W | 38 | 5127   | 5018    | 5064    | -96  | 287   | 75   | O |
| ATOM   | 1828 | OW | HOH | W | 39 | 22.786 | 6.524   | -23.584 | 1.00 | 29.46 |      | O |
| ANISOU | 1828 | OW | HOH | W | 39 | 4105   | 3167    | 3919    | -272 | 63    | -315 | O |
| ATOM   | 1829 | OW | HOH | W | 40 | 12.659 | 7.843   | -28.830 | 1.00 | 40.36 |      | O |
| ANISOU | 1829 | OW | HOH | W | 40 | 5338   | 4722    | 5272    | -206 | -20   | 69   | O |
| ATOM   | 1830 | OW | HOH | W | 41 | 12.960 | 24.065  | -13.045 | 1.00 | 46.62 |      | O |
| ANISOU | 1830 | OW | HOH | W | 41 | 5904   | 6077    | 5733    | 92   | 33    | -161 | O |
| ATOM   | 1831 | OW | HOH | W | 42 | 11.135 | 11.754  | -10.185 | 1.00 | 30.37 |      | O |
| ANISOU | 1831 | OW | HOH | W | 42 | 4271   | 4163    | 3103    | 204  | -349  | 187  | O |
| ATOM   | 1832 | OW | HOH | W | 43 | 13.202 | 12.031  | -11.515 | 1.00 | 36.35 |      | O |
| ANISOU | 1832 | OW | HOH | W | 43 | 4845   | 3955    | 5010    | 28   | -111  | -34  | O |
| ATOM   | 1833 | OW | HOH | W | 44 | 10.537 | 13.629  | -2.714  | 1.00 | 36.03 |      | O |
| ANISOU | 1833 | OW | HOH | W | 44 | 4892   | 4473    | 4324    | -219 | -62   | -316 | O |
| ATOM   | 1834 | OW | HOH | W | 45 | 13.983 | -0.137  | 1.252   | 0.50 | 26.99 |      | O |
| ANISOU | 1834 | OW | HOH | W | 45 | 3481   | 3502    | 3270    | -79  | -42   | -87  | O |
| ATOM   | 1835 | OW | HOH | W | 46 | 13.547 | 11.524  | 0.333   | 1.00 | 50.26 |      | O |
| ANISOU | 1835 | OW | HOH | W | 46 | 6295   | 6703    | 6097    | 45   | -125  | 13   | O |
| ATOM   | 1836 | OW | HOH | W | 47 | -3.193 | 30.208  | -1.659  | 1.00 | 52.68 |      | O |
| ANISOU | 1836 | OW | HOH | W | 47 | 6778   | 6676    | 6562    | -56  | 51    | -22  | O |
| ATOM   | 1837 | OW | HOH | W | 48 | 2.590  | 0.640   | -3.975  | 1.00 | 38.51 |      | O |
| ANISOU | 1837 | OW | HOH | W | 48 | 4885   | 5274    | 4470    | 286  | 140   | -394 | O |
| ATOM   | 1838 | OW | HOH | W | 49 | -4.829 | 10.389  | -8.743  | 1.00 | 30.98 |      | O |
| ANISOU | 1838 | OW | HOH | W | 49 | 4328   | 4157    | 3286    | -6   | 85    | 54   | O |
| ATOM   | 1839 | OW | HOH | W | 50 | -5.682 | 15.166  | -5.147  | 1.00 | 62.12 |      | O |
| ANISOU | 1839 | OW | HOH | W | 50 | 7854   | 7808    | 7937    | 93   | -68   | -65  | O |
| ATOM   | 1840 | OW | HOH | W | 51 | 9.256  | 11.495  | -13.968 | 1.00 | 24.43 |      | O |
| ANISOU | 1840 | OW | HOH | W | 51 | 3144   | 3093    | 3042    | 17   | -92   | -182 | O |
| ATOM   | 1841 | OW | HOH | W | 52 | 10.348 | 13.858  | -13.762 | 1.00 | 31.05 |      | O |
| ANISOU | 1841 | OW | HOH | W | 52 | 3599   | 3978    | 4219    | -257 | -125  | 70   | O |

TABLE 7-continued

The atomic structure coordinates of Fc-TM

| ATOM | 1842 | OW | HOH | W | 53 | 1.049 | 14.118 | −17.122 | 1.00 | 31.08 | | O |
|---|---|---|---|---|---|---|---|---|---|---|---|---|
| ANISOU | 1842 | OW | HOH | W | 53 | 3973 | 4342 | 3492 | −11 | −363 | −196 | O |
| ATOM | 1843 | OW | HOH | W | 54 | 1.515 | 10.299 | −19.955 | 1.00 | 35.99 | | O |
| ANISOU | 1843 | OW | HOH | W | 54 | 4519 | 4385 | 4770 | 160 | 52 | 168 | O |
| ATOM | 1844 | OW | HOH | W | 55 | 2.150 | 9.713 | −17.242 | 1.00 | 38.39 | | O |
| ANISOU | 1844 | OW | HOH | W | 55 | 4625 | 5500 | 4461 | 81 | −84 | 35 | O |
| ATOM | 1845 | OW | HOH | W | 56 | 3.020 | 6.247 | −17.374 | 1.00 | 18.01 | | O |
| ANISOU | 1845 | OW | HOH | W | 56 | 3197 | 2872 | 774 | 149 | −339 | −801 | O |
| ATOM | 1846 | OW | HOH | W | 57 | 7.330 | 25.213 | −16.752 | 1.00 | 49.75 | | O |
| ANISOU | 1846 | OW | HOH | W | 57 | 6292 | 6287 | 6321 | −124 | −65 | 56 | O |
| ATOM | 1847 | OW | HOH | W | 58 | 6.140 | 4.420 | −24.421 | 1.00 | 31.76 | | O |
| ANISOU | 1847 | OW | HOH | W | 58 | 4147 | 4290 | 3628 | 107 | 5 | 22 | O |
| ATOM | 1848 | OW | HOH | W | 59 | 6.934 | 6.415 | −25.965 | 1.00 | 48.06 | | O |
| ANISOU | 1848 | OW | HOH | W | 59 | 6126 | 6215 | 5917 | 104 | −184 | 125 | O |
| ATOM | 1849 | OW | HOH | W | 60 | 2.789 | −10.262 | −14.281 | 1.00 | 52.27 | | O |
| ANISOU | 1849 | OW | HOH | W | 60 | 6829 | 6640 | 6389 | −85 | 61 | −132 | O |
| ATOM | 1850 | OW | HOH | W | 61 | 10.173 | −11.474 | −17.131 | 1.00 | 43.89 | | O |
| ANISOU | 1850 | OW | HOH | W | 61 | 5243 | 5991 | 5441 | −19 | 145 | −51 | O |
| ATOM | 1851 | OW | HOH | W | 62 | 10.423 | −9.588 | −15.301 | 1.00 | 41.60 | | O |
| ANISOU | 1851 | OW | HOH | W | 62 | 4910 | 5490 | 5403 | −299 | −111 | 149 | O |
| ATOM | 1852 | OW | HOH | W | 63 | 12.562 | 10.469 | −16.760 | 1.00 | 47.26 | | O |
| ANISOU | 1852 | OW | HOH | W | 63 | 6061 | 6168 | 5726 | 54 | −119 | 90 | O |
| ATOM | 1853 | OW | HOH | W | 64 | 25.207 | 4.876 | −13.048 | 1.00 | 43.98 | | O |
| ANISOU | 1853 | OW | HOH | W | 64 | 5382 | 5861 | 5465 | 4 | 11 | −150 | O |
| ATOM | 1854 | OW | HOH | W | 65 | 20.403 | 6.945 | −24.246 | 1.00 | 31.68 | | O |
| ANISOU | 1854 | OW | HOH | W | 65 | 4456 | 4465 | 3114 | −263 | −194 | −229 | O |
| ATOM | 1855 | OW | HOH | W | 66 | 16.219 | 5.833 | −30.699 | 1.00 | 53.61 | | O |
| ANISOU | 1855 | OW | HOH | W | 66 | 6744 | 6870 | 6754 | −31 | −25 | −174 | O |
| ATOM | 1856 | OW | HOH | W | 67 | 15.439 | −3.579 | −28.825 | 1.00 | 50.26 | | O |
| ANISOU | 1856 | OW | HOH | W | 67 | 6356 | 6649 | 6091 | 19 | −89 | −6 | O |
| ATOM | 1857 | OW | HOH | W | 68 | 0.448 | −2.007 | −9.703 | 1.00 | 47.76 | | O |
| ANISOU | 1857 | OW | HOH | W | 68 | 5769 | 6029 | 6348 | −118 | −41 | 33 | O |
| ATOM | 1858 | OW | HOH | W | 69 | 9.088 | 10.333 | −11.458 | 1.00 | 45.89 | | O |
| ANISOU | 1858 | OW | HOH | W | 69 | 5637 | 5868 | 5931 | 55 | 174 | 101 | O |
| ATOM | 1859 | OW | HOH | W | 70 | 2.301 | 8.833 | 3.077 | 1.00 | 41.79 | | O |
| ANISOU | 1859 | OW | HOH | W | 70 | 5409 | 5255 | 5212 | 66 | −371 | −158 | O |
| ATOM | 1860 | OW | HOH | W | 71 | 19.184 | 33.621 | −4.885 | 1.00 | 59.40 | | O |
| ANISOU | 1860 | OW | HOH | W | 71 | 7601 | 7341 | 7625 | −69 | −45 | −52 | O |
| ATOM | 1861 | OW | HOH | W | 72 | 11.411 | 47.589 | −7.153 | 1.00 | 50.72 | | O |
| ANISOU | 1861 | OW | HOH | W | 72 | 6739 | 6215 | 6314 | −100 | −123 | −98 | O |
| ATOM | 1862 | OW | HOH | W | 73 | −2.721 | 22.353 | −19.060 | 1.00 | 50.88 | | O |
| ANISOU | 1862 | OW | HOH | W | 73 | 6801 | 6612 | 5916 | 38 | 18 | −78 | O |
| ATOM | 1863 | OW | HOH | W | 74 | −2.520 | 30.795 | −12.887 | 1.00 | 44.98 | | O |
| ANISOU | 1863 | OW | HOH | W | 74 | 5923 | 5326 | 5838 | −14 | 57 | 136 | O |
| ATOM | 1864 | OW | HOH | W | 75 | 35.811 | −10.347 | −12.530 | 1.00 | 32.21 | | O |
| ANISOU | 1864 | OW | HOH | W | 75 | 4854 | 4402 | 2979 | 196 | 130 | 6 | O |
| END | | | | | | | | | | | | |

Conclusion: The three-dimensional structure of Fc/TM was found to be very similar to that of other unliganded, unmutated human Fc regions. The dramatic, broad-ranging functional effects of the TM set of substitutions were not caused by major structural rearrangements in the Fc structure, but rather by the localized loss of a few interactions at the mutation sites.

6.34 Example 34: Internalization of Anti-IFNAR1 Antibodies

Purpose: To investigate the ability of anti-IFNAR1 antibodies to internalize in cells.

Methods: THP-1 cells were cultured in RPM1-1640 media containing 0.05 mM 2-mercaptoethanol and 10% fetal bovine serum at 37° C. in 5% $CO_2$ incubator. THP-1 cells were seeded at $2 \times 10^5$ cells/ml in fresh growth media one day prior to experiments. At the day of the experiment, cells were washed, counted and resuspended in PBS at $3 \times 10^6$ cells/ml. The cells were stained with 1 μM CFSE in 37° C. $CO_2$ incubator for 10 min. Following additional two washes with PBS, the cells were placed on ice and incubated with FcR block using 20 μl per $10^6$ cells on ice for 5 min and then stained with 1 μg/ml of Alexa647-9D4-TM or Alexa 647-R347 (non-specific control antibody) on ice for 1 h. After removal of unbound mAb by 3 washes with PBS, cells were resuspended in PBS containing 2% BSA and sodium azide. The internalization was initiated by transferring the cells to an environmentally controlled chamber under 37° C., 5% $CO_2$ and 70% humidity and the internalization kinetics of Alexa647-9D4-TM was recorded over time by imaging the fluorescence of cells.

The fluorescence images of cells were analyzed using an algorithm. The algorithm used CFSE cytosolic dye to identify the boundary of a cell and a membrane region. The algorithm quantified the 9D4-TM associated fluorescence inside cells as well as on membrane. Rate of fluorescence accumulated inside the cells was calculated by model fitting of the data using SAAMII software.

Results: Alexa647-9D4-TM bound to THP-1 cells. No binding of Alexa647-R347, the isotype control of 9D4-TM, was observed on the same cells. This result demonstrated specific binding to THP-1 cells by 9D4-TM (FIG. 33). At 4° C., 9D4-TM binding was predominately located at cell surface (0 min—FIG. 33). Once the cells were incubated at 37° C., the fluorescence signal for 9D4-TM staining was significantly decreased from cell surface and accumulated in cytosolic compartment as punctuated spots. Kinetic images recorded over 60 min indicated gradual migration of fluorescence from cell surface to punctuated spots located at cytosolic compartment (15, 30 and 50 min time points, FIG. 33). The result clearly demonstrated internalization of 9D4-TM on THP-1 cells.

6.35 Example 35: Absence of 9D4-TM Mediated CDC Activity

Purpose: To determine if 9D4-TM is unable to induce CDC activity a series of experiments were conducted.

Methods: Freshly isolated human blood from healthy, human donors was collected (approximately 100 ml) and spun down for 10 minutes at 3000G to separate serum from cells. The serum fraction was separated into two tubes. The first tube was diluted with phenol-free RPMI 1640 to a final concentration of 10% serum (non-heat inactivated or NHI). The second tube was placed in a 56° C. water bath for 30 minutes to heat inactivate the complement components. Subsequently, the second tube was diluted with phenol-free RPMI-1640 media to a final concentration of 10% heat-inactivated (HI) human serum.

Daudi B cells were used as target cells as they express CD20 (target for positive control antibody) and IFNAR1. Target cells were washed and resuspended in either phenol-free RPMI media with 10% non-heat inactivated serum or in phenol-free RPMI media with 10% heat inactivated serum at a final concentration of $0.4 \times 10^6$ cells/mL. Antibody solutions were prepared as a 3× dilution series with the concentrations ranging from 50 ug/mL-$1.3 \times 10^{-6}$ µg/mL. Replicate preparations of antibody dilutions were made in either media with heat-inactivated or non-heat-inactivated human serum. The CDC assay was prepared by adding 50 µL of NHI or HI media to appropriate wells of a 96 well, round bottom plate. 50 µL of antibody dilution series were added to the appropriate wells. Subsequently, 500 µL of the target cell preparation was added to the wells, including extra wells with target cells alone for controls. The plates were incubated for 37° C. for 4 hours in 5% $CO_2$. After 3.5 hour incubation, 20 uL lysis buffer was added to appropriate control wells designated for determination of maximum lysis signal. The Quantitate™ LDH release assay was performed using protocols defined in Promega non-radioactive cytotoxicity assay, #G1780. Absorbance was measured at 490 nM and Kd values were generated using GraphPad Prism 4 analysis software.

Results: Presented in FIG. 34 are the results from the CDC performed as described above. The modified anti-IFNAR1 antibody, 9D4-TM exhibited no detectable CDC activity on target Daudi B cells over that observed with the R347 antibody. In contrast, the positive control antibody, which binds CD20 expressed on Daudi B cells, caused a dose-dependent increase in cytotoxicity over background levels. These results confirm that 9D4-TM cannot mediate CDC on IFNAR1 expressing target cells.

6.36 Example 36: The Modified Anti-IFNAR1 Antibody, 9D4-TM does not Display any Adverse Toxicity Purpose: To establish that 9D4-TM does not elicit any adverse toxicity, a single-dose toxicity study was performed in cynomolgus monkeys.

Methods: In this study, 4 groups of 10 animals each (5/sex/group) received a single dose of 0, 5, 30, or 100 mg/kg of 9D4-TM on Day 1. After dosing, 2 animals/sex/group were assigned to necropsy on Day 3 with all remaining animals monitored until Day 70 and then removed from study without necropsy. Toxicity was assessed based on mortality, clinical signs (including menses), immunophenotyping, body weights, physical examinations (including heart rate, respiration rate, and body temperature), clinical pathology, organ weights, and microscopic data.

Results: Under the conditions outlined above, there were no 9D4-TM-related adverse changes in mortality, clinical signs (including menses), body weight, physical examinations (heart rate, respiration rate and body temperature), clinical pathology, organ weights and microscopic data. These results suggest that the modified anti-IFNAR1 antibody, 9D4-TM does not elicity any adverse toxicity.

Whereas, particular embodiments of the invention have been described above for purposes of description, it will be appreciated by those skilled in the art that numerous variations of the details may be made without departing from the invention as described in the appended claims.

All publications, patents and patent applications mentioned in this specification are herein incorporated by reference into the specification to the same extent as if each individual publication, patent or patent application was specifically and individually indicated to be incorporated herein by reference.

We claim:

1. An isolated nucleic acid comprising a polynucleotide sequence encoding a modified IgG1 class human monoclonal antibody specific for IFNAR1, wherein said antibody comprises:
   (i) a human heavy chain variable region comprising the amino acid sequence of SEQ ID NO: 38;
   (ii) a human light chain variable region comprising the amino acid sequence of SEQ ID NO: 40;
   (iii) a human light chain constant region comprising the amino acid sequence of SEQ ID NO: 41;
   (iv) a human heavy chain constant region comprising the amino acid sequence of SEQ ID NO: 42.

2. The nucleic acid of claim 1 wherein, said nucleic acid is a replicable vector.

3. The nucleic acid of claim 2 wherein, said polynucleotide sequence is operably linked to a promoter.

\* \* \* \* \*